US012037345B2

(12) United States Patent
Shimamura et al.

(10) Patent No.: US 12,037,345 B2
(45) Date of Patent: Jul. 16, 2024

(54) HETEROBICYCLIC COMPOUNDS FOR INHIBITING THE ACTIVITY OF SHP2

(71) Applicants: TAIHO PHARMACEUTICAL CO., LTD., Tokyo (JP); OTSUKA PHARMACEUTICAL CO., LTD., Tokyo (JP)

(72) Inventors: Tadashi Shimamura, Ibaraki (JP); Ryo Kato, Ibaraki (JP); Risako Miura, Ibaraki (JP); Takashi Mita, Ibaraki (JP); Takahiro Ogawa, Ibaraki (JP); Yufu Sagara, Ibaraki (JP); Christopher Norbert Johnson, Cambridge (GB); Steven Howard, Cambridge (GB); James Edward Harvey Day, Cambridge (GB); Jeffrey David St. Denis, Cambridge (GB); John Walter Liebeschuetz, Cambridge (GB)

(73) Assignees: TAIHO PHARMACEUTICAL CO., LTD., Tokyo (JP); OTSUKA PHARMACEUTICAL CO., LTD., Tokyo (JP)

( * ) Notice: Subject to any disclaimer, the term of this patent is extended or adjusted under 35 U.S.C. 154(b) by 715 days.

(21) Appl. No.: 17/262,341

(22) PCT Filed: Jul. 23, 2019

(86) PCT No.: PCT/JP2019/028822
§ 371 (c)(1),
(2) Date: Jan. 22, 2021

(87) PCT Pub. No.: WO2020/022323
PCT Pub. Date: Jan. 30, 2020

(65) Prior Publication Data
US 2022/0363693 A1    Nov. 17, 2022

(30) Foreign Application Priority Data
Jul. 24, 2018    (JP) ................................. 2018-138244

(51) Int. Cl.
*C07D 519/00* (2006.01)
*A61K 31/519* (2006.01)
*A61P 35/00* (2006.01)
*A61P 43/00* (2006.01)
*C07D 487/04* (2006.01)

(52) U.S. Cl.
CPC .......... *C07D 519/00* (2013.01); *A61K 31/519* (2013.01); *A61P 35/00* (2018.01); *A61P 43/00* (2018.01); *C07D 487/04* (2013.01)

(58) Field of Classification Search
CPC .. C07D 519/00; C07D 487/04; C07D 487/02; C07D 487/00; C07F 7/0812; C07F 7/081; C07F 7/0803; C07F 7/08; C07F 7/02; C07F 7/00; A61K 31/519; A61P 35/00; A61P 43/00
See application file for complete search history.

(56) References Cited

U.S. PATENT DOCUMENTS 10,975,080 B2 *    4/2021    Bagdanoff ........... C07D 471/04
11,466,016 B2    10/2022    Johnson et al.
2019/0343836 A1    11/2019    Alghalandis et al.
(Continued)

FOREIGN PATENT DOCUMENTS

CL    202100843    4/2021
CL    202200404    2/2022
(Continued)

OTHER PUBLICATIONS

Patani et. al. (Dec. 19, 1996) Bioisosterism A rational approach in drug design, Chem. Rev., 96, 3147-3176 (Year: 1996).*
Bagdanoff, Jeffrey et al., "Optimization of Fused Bicyclic Allosteric SHP2 Inhibitors" J. Med. Chem. 2019, 62, pp. 1781-1792.
V.G. Belikov, Pharmaceutical Chemistry, Chapter 2.6 "Relationship between the chemical structure, the properties of substances and their actions in an organism"—M.: MEDpress-inform, 2007, pp. 27-29.
Himiceskij, Chemical Encyclopedic dictionary, Chief editor I, L. Knunanc, Moscow, Soviet Encyclopedia, 1983, pp. 130-131.
(Continued)

*Primary Examiner* — Kortney L. Klinkel
*Assistant Examiner* — Dawanna Shar-Day White
(74) *Attorney, Agent, or Firm* — Heslin Rothenberg Farley & Mesiti P.C.

(57) ABSTRACT

The invention provides a compound of formula (I):

[Chem. 1]

wherein Ring A, Q, $R^1$, $R^2$, $R^3$, $R^4$, $R^5$, $R^6$, $R^7$, $R^8$, $R^9$, $R^{10}$, $R^{11}$, X, a, b, c and d are as defined in the specification, useful for inhibiting the activity of SHP2.

19 Claims, No Drawings

(56) References Cited

U.S. PATENT DOCUMENTS

| | | |
|---|---|---|
| 2021/0107908 A1 | 4/2021 | Johnson et al. |
| 2023/0049719 A1 | 2/2023 | Howard et al. |
| 2023/0146795 A1 | 5/2023 | Hoshino et al. |

FOREIGN PATENT DOCUMENTS

| | | |
|---|---|---|
| CN | 102311447 B | 11/2013 |
| JP | 2021/506776 A | 2/2021 |
| JP | 2021/514962 A | 6/2021 |
| RU | 2635917 C2 | 11/2017 |
| WO | 2005/099688 A2 | 10/2005 |
| WO | 2006/058074 A1 | 6/2006 |
| WO | 2013/063214 A1 | 5/2013 |
| WO | 2015/107493 A1 | 7/2015 |
| WO | 2015/107494 A1 | 7/2015 |
| WO | 2015/107495 A1 | 7/2015 |
| WO | 2016/203404 A1 | 12/2016 |
| WO | 2016/203405 A1 | 12/2016 |
| WO | 2016/203406 A1 | 12/2016 |
| WO | 2016/208595 A1 | 12/2016 |
| WO | 2017/156397 A1 | 9/2017 |
| WO | 2017/210134 A1 | 12/2017 |
| WO | 2017/211303 A1 | 12/2017 |
| WO | 2017/216706 A1 | 12/2017 |
| WO | 2018/057884 A1 | 3/2018 |
| WO | 2018/081091 A1 | 5/2018 |
| WO | 2018/130928 A1 | 7/2018 |
| WO | 2018/193410 A1 | 10/2018 |
| WO | 2018/218133 A1 | 11/2018 |
| WO | 2019/051084 A1 | 3/2019 |
| WO | 2019/118909 A1 | 6/2019 |
| WO | 2019/165073 A1 | 8/2019 |
| WO | 2019/167000 A1 | 9/2019 |
| WO | 2019/182960 A1 | 9/2019 |
| WO | 2019/183364 A1 | 9/2019 |
| WO | 2019/213318 A1 | 11/2019 |
| WO | 2020/065452 A1 | 4/2020 |
| WO | 2020/065453 A1 | 4/2020 |
| WO | 2021/033153 A1 | 2/2021 |
| WO | 2021/149817 A1 | 7/2021 |

OTHER PUBLICATIONS

Harkevic D.A., Pharmacology—textbook, 10th edition, M.LGEOTAR-Media, 2010, pp. 72-82.
K. Kummerer, Pharmaceuticals in the environment, Annual Review of Environment and Resources, 2010, V.35, p. 57-75, doi: 10.1146/annurev-environ-052809-161223.
P. V. Sergeeva, Short course on molecular pharmacology, M., 1975, p. 10.
L. E. Holodov et al. Clinical pharmacokinetics, M., "Medicine", 1985, pp. 83-98, 134-138, 160, 378-380.
Smit V., Bochkov A., Caple R., Organic synthesis, the science behind the art: Translation from English Language—M.:Mir, 2001, 573 pages, figures, p. 64.
Pokrovsky, Small medical encyclopedia, vol. 5, Moscow, "Medicine", 1996, pp. 90-96.
M. D. Maskovskij Medicaments, 14th edition, vol. 1, Moscow, 2001, p. 11.
Kubasov A. A., Chemical Kinetics and catalysis. Part 1, Moscow, Publisher of the University of Moscow, 2004, pp. 2-3.
Bagdanoff, et al., "Optimization of Fused Bicyclic Allosteric SHP2 Inhibitors," J. Med. Chem. 2019, 62, 1781-1792.
Yuan, et al., "Recent Advances of SHP2 Inhibitors in Cancer Therapy: Current Development and Clinical Application," J. Med. Chem. 2020, 63, 11368-11396.
Lamarche, et al., "Identification of TNO155, an Allosteric SHP2 Inhibitor for the Treatment of Cancer," J. Med. Chem. 2020, 63, 13578-13594.
Nichols, et al., "RAS Nucleotide Cycling Underlies the SHP2 Phosphatase Dependence of Mutant BRAF-NF1- and RAS-Driven Cancers," Nature Cell Biology, 2018, 20, 1064-1073.
Caira, Mino R., "Crystalline Polymorphism of Organic Compounds", Springer, Berlin, 198, 1998, 163-208.
International Search Report and Written Opinion of the International Searching Authority for International Application No. PCT/JP2019/028822 mailed on Oct. 8, 2019.
Chen, Y.P., et al., "Allosteric inhibition of SHP2 phosphatase inhibits cancers driven by receptor tyrosine kinases", Nature, vol. 535, pp. 148-152 (2016).
Himiceskaa enciklopedia [Encyclopedia of Chemistry], vol. 4, pp. 499-501, Academic Publisher "Bol'saa rossijskaa enciklopedia" [The Great Russian Encyclopedia], Moscow, 1995.
V.V. Boltromeuk "Obsaa himia" [General Chemistry], Minsk, Vysejsaa skola, 2012, p. 65.
J. R. Riggs et al., The Discovery of a Dual TTK Protein Kinase/CDC-2 Like Kinase (CLK2) Inhibitor for the Treatment of Triple Negative Breast Cancer Initiated from a Phenotypic Screen, Journal of Medicinal Chemistry, 2017, vol. 60, No. 21, pp. 8989-9002.
Meng, Fanhao, "Pharmaceutical Chemistry" pp. 385-387, Jan. 2016.

* cited by examiner

HETEROBICYCLIC COMPOUNDS FOR INHIBITING THE ACTIVITY OF SHP2

CROSS REFERENCE TO RELATED APPLICATIONS

This application is a national stage filing under section 371 of International Application No. PCT/JP2019/028822, filed on Jul. 23, 2019, and published on Jan. 30, 2020 as WO 2020/022323, which claims priority to Japanese Application No. 2018-138244, filed on Jul. 24, 2018. The entire contents of WO 2020/022323 are hereby incorporated herein by reference.

TECHNICAL FIELD

The present invention relates to novel heterobicyclic compounds for inhibiting the activity of SHP2, pharmaceutical compositions comprising the compound and uses of the compounds.

BACKGROUND ART

Src homology region 2 (SH2)-containing protein tyrosine phosphatase 2 (SHP2) is a ubiquitously expressed protein tyrosine phosphatase encoded by the PTPN11 gene. SHP2 contains two N-terminal tandem SH2 domains (N—SH2, C—SH2), a catalytic phosphatase (PTP) domain and a C-terminal tail with 2 tyrosine phosphorylation sites.

SHP2 switches between "open" active and "closed" inactive forms due to autoinhibitory interactions between the N—SH2 and the PTP domain. This naturally occurring autoinhibition is released when bis-tyrosylphosphorylated peptides bind to the N—SH2 domains and SHP2 adopts an "open" conformation, resulting in activation of the enzyme and exposure of the PTP domain for substrate recognition and catalysis.

PTPN11 mutations have been linked to several human diseases including cancer. Germline PTPN11 mutations are associated with developmental disorders such as Noonan Syndrome and Leopard Syndrome, whilst somatic mutations occur in several types of hematologic malignancies, such as JMML and more rarely in solid tumours.

SHP2 is required for signalling downstream of receptor tyrosine kinases (e.g. EGFR, ALK, PDGFR) and plays a positive role in regulating many cellular processes such as proliferation in response to growth factor and cytokine stimulation. Previous studies have shown that SHP2 acts upstream of Ras and is required for full, sustained activation of the MAPK pathway. RTK deregulation often leads to a wide range of cancers, making SHP2 a valuable target in RTK-activated cancers. SHP2 is also reported to play a role in regulating immune responses by mediating immune checkpoint pathways (e.g. PD-1) as immunoreceptor tyrosine-based inhibitory motifs (ITIMs) bind to the SH2 domains of SHP2 to mediate a negative signal.

It has been reported that some SHP2 inhibitor compound show inhibitory effect on proliferation of in vitro cancer cells and on increase in tumour volume in a mouse xenograft model (Nature (2016) 535: 148-152).

CITATION LIST

Non Patent Literature

[NPL 1]
Nature (2016) 535: 148-152

SUMMARY OF INVENTION

Technical Problem

An object of the present invention is to provide a novel series of compounds which selectively inhibit SHP2 and which can be used to treat a disease or condition mediated by SHP2.

Solution to Problem

The present inventors conducted extensive research to achieve the above object, and consequently found that a compound group represented by Formulas (I) below showed excellent inhibitory activity against SHP2, and was useful as a pharmaceutical preparation for treating SHP2 mediated diseases such as cancer. Thus, the present invention has been completed.

The present invention comprises the following items.

Item 1. A compound of formula (I):

[Chem. 1]

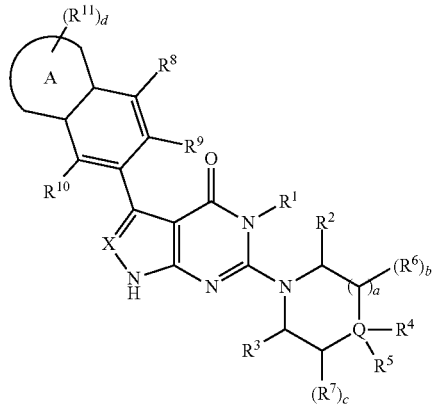

(I)

or a tautomer or a solvate or a pharmaceutically acceptable salt thereof, wherein:

X is CH or N;
$R^1$ is —$CH_3$;
$R^2$ and $R^3$ are independently selected from hydrogen and $C_{1-4}$alkyl;
Q is C or N;
  wherein when Q is C then either:
    (i) $R^4$ is amino, amino$C_{1-4}$alkyl or mono$C_{1-4}$alkylamino;
    $R^5$ is hydrogen, $C_{1-4}$alkyl, halogen, hydroxy$C_{1-4}$alkyl, $C_{1-4}$alkoxy, halo$C_{1-4}$alkyl or $C_{1-4}$alkoxy$C_{1-4}$alkyl;
    or
    (ii) $R^4$ and $R^5$ together with Q form a four- to six-membered ring that can optionally contain 1 to 3 heteroatoms or groups independently selected from N, O, S, NH, C(O) and S(O)$_m$, and said ring formed by $R^4$ and $R^5$ can be unsubstituted or substituted with 1 to 4 groups independently selected from amino, halogen, halo$C_{1-4}$alkyl, hydroxyl, methoxy, methylamino, and $C_{1-4}$alkyl, and m is selected from 1 and 2; and
  wherein when Q is N then:
    $R^4$ is absent; and
    $R^5$ is hydrogen;

R$^6$ and R$^7$ are independently selected from halogen, C$_{1-4}$alkyl, hydroxyC$_{1-4}$alkyl and hydroxyl provided that when Q is N then R$^6$ or R$^7$ are not halogen or hydroxyl;

Or, any two groups selected from R$^2$, R$^3$, R$^6$ and R$^7$ together form a one- to three-membered bridge group selected from C$_{1-3}$alkylene, C$_{2-3}$alkenylene, methylene-NR$^q$-methylene and methylene-O-methylene, wherein the bridge group is optionally substituted by a group selected from C$_{1-4}$alkyl, hydroxyl and halogen and R$^q$ is selected from hydrogen and C$_{1-4}$alkyl;

Or, R$^4$ and R$^7$ form a four- to six-membered ring containing a N atom;

Or, R$^5$ and R$^7$ form a three- to six-membered ring;

Or, R$^6$ and R$^7$ form a direct bond;

a is selected from 0, 1 and 2;

b is selected from 0, 1 and 2;

c is selected from 0, 1 and 2;

Or, Q is C, c is 2, R$^4$ is hydrogen and the two R$^7$ join to form a 4 to 6 membered nitrogen containing ring;

Ring A is either:
(i) a five-membered nitrogen-containing heterocyclic ring wherein the heterocyclic ring optionally contains one or two additional heteroatoms selected from N, O and S, or
(ii) a six-membered aromatic nitrogen-containing heterocyclic ring, wherein the heterocyclic ring optionally contains one or two additional heteroatoms selected from N, O and S; or
(iii) a six-membered non-aromatic nitrogen-containing heterocyclic ring, wherein the heterocyclic ring optionally contains one or two additional heteroatoms selected from N and S;

R$^8$ is selected from hydrogen, C$_{1-4}$alkyl, haloC$_{1-4}$alkyl and halogen;

R$^9$ is selected from hydrogen and halogen;

R$^{10}$ is selected from haloC$_{1-4}$alkyl, C$_{1-4}$alkyl, halogen, hydrogen or C$_{1-4}$alkoxy;

R$^{11}$ are independently selected from halogen, cyano, cyanoC$_{1-4}$alkyl, hydroxyl, oxo (=O), C$_{1-4}$alkyl optionally substituted with five- or six-membered heterocyclic group containing 1 or 2 heteroatoms selected from O, N, or S, haloC$_{1-4}$alkyl, C$_{1-4}$alkoxy, hydroxylC$_{1-4}$alkyl, C$_{1-4}$alkoxyC$_{1-4}$alkyl, C$_{1-4}$alkylsulfone, amino, monoC$_{1-4}$alkylamino, diC$_{1-4}$alkylamino, aminoC$_{1-4}$alkyl, —C$_{1-4}$alkylene-C(=O)NH$_{(2-q)}$(C$_{1-6}$alkyl)$_q$), —C$_{1-4}$alkylene-NHC(=O)C$_{1-6}$alkyl, sulfonamide, sulfonamideC$_{1-4}$alkyl, 3 to 6 membered cycloalkyl, C$_{1-4}$alkyl substituted with 3 to 6 membered cycloalkyl, five- or six-membered unsaturated heterocyclic group containing 1, 2, 3 or 4 heteroatoms selected from O, N, or S, and optionally substituted four- to six-membered saturated heterocyclic group containing 1 or 2 heteroatoms selected from O, N, or S where the optional substituent is selected from C$_{1-4}$alkyl;

q is selected from 0, 1 or 2; and d is selected from 0, 1 and 2.

Item 2. A compound according to item 1 or a tautomer or a solvate or a pharmaceutically acceptable salt thereof, wherein:

Ring A is a five-membered or six-membered nitrogen-containing heteroaromatic ring wherein the ring optionally contains one or two additional heteroatoms selected from N, O and S.

Item 3. A compound according to item 1 or 2, or a tautomer or a solvate or a pharmaceutically acceptable salt thereof, wherein any two groups selected from R$^2$, R$^3$, R$^6$ and R$^7$ together form a one to three-membered bridge group selected from C$_{1-3}$alkylene, C$_{2-3}$alkenylene, methylene-NR$^q$-methylene and methylene-O-methylene, wherein the bridge group is optionally substituted by a group selected from C$_{1-4}$alkyl, hydroxyl and halogen and R$^q$ is selected from hydrogen and C$_{1-4}$alkyl.

Item 4. A compound according to any one of items 1 to 3, or a tautomer or a solvate or a pharmaceutically acceptable salt thereof, wherein Q is C.

Item 5. A compound according to any one of items 1 to 4, or a tautomer or a solvate or a pharmaceutically acceptable salt thereof, wherein R$^4$ is amino, aminoC$_{1-4}$alkyl or monoC$_{1-4}$alkylamino;

R$^5$ is hydrogen, C$_{1-4}$alkyl, halogen, hydroxyC$_{1-4}$alkyl, C$_{1-4}$alkoxy, haloC$_{1-4}$alkyl or C$_{1-4}$alkoxyC$_{1-4}$alkyl Item 6. A compound according to any one of items 1 to 4, or a tautomer or a solvate or a pharmaceutically acceptable salt thereof, wherein R$^4$ and R$^5$ together with Q form a four- to six-membered ring that can optionally contain 1 to 3 heteroatoms or groups independently selected from N, O, S, NH, C(O) and S(O)$_m$, and said ring formed by R$^4$ and R$^5$ can be unsubstituted or substituted with 1 to 4 groups independently selected from amino, halogen, haloC$_{1-4}$alkyl, hydroxyl, methoxy, methylamino, and C$_{1-4}$alkyl, and m is selected from 1 and 2

Item 7. A compound according to any one of items 1 to 5, or a tautomer or a solvate or a pharmaceutically acceptable salt thereof, wherein Q is N.

Item 8. A compound according to any one of items 1 to 7, or a tautomer or a solvate or a pharmaceutically acceptable salt thereof, wherein X is CH.

Item 9. A compound according to any one of items 1 to 7, or a tautomer or a solvate or a pharmaceutically acceptable salt thereof, wherein X is N.

Item 10. A compound according to item 1, or a tautomer or a solvate or a pharmaceutically acceptable salt thereof, wherein the compound is selected from:

2-(3,8-diazabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one, 2-(4-(aminomethyl)-4-methylpiperidin-1-yl)-5-(4-chloro-2-ethyl-2H-indazol-5-yl)-3-methyl-3,7-dihydro-4H-pyrrolo[2,3-d]pyrimidin-4-one, 2-(4-amino-4-methylpiperidin-1-yl)-5-(4-chloro-2-ethyl-2H-indazol-5-yl)-3-methyl-3,7-dihydro-4H-pyrrolo[2,3-d]pyrimidin-4-one, 2-(exo-3-amino-8-azabicyclo[3.2.1]octan-8-yl)-5-(4-chloro-2-ethyl-2H-indazol-5-yl)-3-methyl-3,7-dihydro-4H-pyrrolo[2,3-d]pyrimidin-4-one, 2-(endo-3-amino-8-azabicyclo[3.2.1]octan-8-yl)-5-(4-chloro-2-ethyl-2H-indazol-5-yl)-3-methyl-3,7-dihydro-4H-pyrrolo[2,3-d]pyrimidin-4-one, 2-(endo-3-amino-8-azabicyclo[3.2.1]octan-8-yl)-5-(7-chloro-2-ethylbenzo[d]thiazol-6-yl)-3-methyl-3,7-dihydro-4H-pyrrolo[2,3-d]pyrimidin-4-one, 2-(endo-3-amino-8-azabicyclo[3.2.1]octan-8-yl)-5-(7-chloro-2-methylbenzo[d]thiazol-6-yl)-3-methyl-3,7-dihydro-4H-pyrrolo[2,3-d]pyrimidin-4-one, 2-(endo-3-amino-8-azabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one, 2-(endo-3-Amino-8-azabicyclo[3.2.1]octan-8-yl)-5-(2-(tert-butyl)-4-chloro-2H-indazol-5-yl)-3-methyl-3,7-dihydro-4H-pyrrolo[2,3-d]pyrimidin-4-one, 2-(exo-3-amino-8-azabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one, (R)-2-(1-amino-8-azaspiro[4.5]decan-8-yl)-5-(4-chloro-2-ethyl-2H-indazol-5-yl)-3-methyl-3,7-dihydro-4H-pyrrolo[2,3-d]pyrimidin-4-one, (S)-2-(4-amino-2-oxa-8-azaspiro[4.5]decan-8-yl)-5-(4-chloro-2-ethyl-2H-indazol-5-yl)-3-methyl-3,7-dihydro-4H-pyrrolo[2,3-d]pyrimidin-4-one, 5-(4-chloro-2-ethyl-2H-indazol-5-yl)-3-methyl-2-(endo-3-(methylamino)-8-azabicyclo[3.2.1]octan-8-yl)-3,7-dihydro-4H-pyrrolo[2,3-d]pyrimidin-4-one, 5-(4-chloro-2-methyl-2H-indazol-5-yl)-3-methyl-2-(endo-3-(methylamino)-8-azabicyclo[3.2.1]octan-8-yl)-3,7-dihydro-4H-pyrrolo[2,3-d]pyrimidin-4-one, 2-(endo-3-amino-3-methyl-8-azabicyclo[3.2.1]octan-8-yl)-5-(4-chloro-2-ethyl-2H-indazol-5-yl)-3-methyl-3,7-dihydro-4H-pyrrolo[2,3-d]pyrimidin-4-one, 2-(endo-3-amino-3-methyl-8-azabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one, 2-(3-oxa-7,9-diazabicyclo[3.3.1]nonan-7-yl)-5-(4-chloro-2-methyl-2H-indazol-5-yl)-3-methyl-3,7-dihydro-4H-pyrrolo[2,3-d]pyrimidin-4-one, (R)-5-(4-chloro-2-methyl-2H-indazol-5-yl)-3-methyl-2-(3-methylpiperazin-1-yl)-3,7-dihydro-4H-pyrrolo[2,3-d]pyrimidin-4-one, (S)-5-(4-chloro-2-methyl-2H-indazol-5-yl)-2-(3-(hydroxymethyl)piperazin-1-yl)-3-methyl-3,7-dihydro-4H-pyrrolo[2,3-d]pyrimidin-4-one, (R)-5-(4-chloro-2-methyl-2H-indazol-5-yl)-2-(3-(2-hydroxyethyl)piperazin-1-yl)-3-methyl-3,7-dihydro-4H-pyrrolo[2,3-d]pyrimidin-4-one, 2-((1S,4S)-2,5-diazabicyclo[2.2.1]heptan-2-yl)-5-(4-chloro-2-methyl-2H-indazol-5-yl)-3-methyl-3,7-dihydro-4H-pyrrolo[2,3-d]pyrimidin-4-one, 2-(7-amino-3-oxa-9-azabicyclo[3.3.1]nonan-9-yl)-5-(4-chloro-2-methyl-2H-indazol-5-yl)-3-methyl-3,7-dihydro-4H-pyrrolo[2,3-d]pyrimidin-4-one, 2-((1R,4R)-2,5-diazabicyclo[2.2.1]heptan-2-yl)-5-(4-chloro-2-methyl-2H-indazol-5-yl)-3-methyl-3,7-dihydro-4H-pyrrolo[2,3-d]pyrimidin-4-one, 2-(exo-8-amino-3-azabicyclo[3.2.1]octan-3-yl)-5-(4-chloro-2-methyl-2H-indazol-5-yl)-3-methyl-3,7-dihydro-4H-pyrrolo[2,3-d]pyrimidin-4-one, 2-(endo-8-amino-3-azabicyclo[3.2.1]octan-3-yl)-5-(4-chloro-2-methyl-2H-indazol-5-yl)-3-methyl-3,7-dihydro-4H-pyrrolo[2,3-d]pyrimidin-4-one, rac-2-((1S,2R,3R,5R)-3-amino-2-fluoro-8-azabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one, 2-(3,9-diazabicyclo[3.3.1]nonan-9-yl)-5-(4-chloro-2-methyl-2H-indazol-5-yl)-3-methyl-3,7-dihydro-4H-pyrrolo[2,3-d]pyrimidin-4-one, 2-(3,8-diazabicyclo[3.2.1]octan-3-yl)-5-(4-chloro-2-methyl-2H-indazol-5-yl)-3-methyl-3,7-dihydro-4H-pyrrolo[2,3-d]pyrimidin-4-one, 2-(3,6-diazabicyclo[3.1.1]heptan-6-yl)-5-(4-chloro-2-methyl-2H-indazol-5-yl)-3-methyl-3,7-dihydro-4H-pyrrolo[2,3-d]pyrimidin-4-one, 2-(3,9-diazabicyclo[3.3.1]nonan-3-yl)-5-(4-chloro-2-methyl-2H-indazol-5-yl)-3-methyl-3,7-dihydro-4H-pyrrolo[2,3-d]pyrimidin-4-one, 2-(3,6-diazabicyclo[3.1.1]heptan-3-yl)-5-(4-chloro-2-methyl-2H-indazol-5-yl)-3-methyl-3,7-dihydro-4H-pyrrolo[2,3-d]pyrimidin-4-one, 2-(2,5-diazabicyclo[2.2.2]octan-2-yl)-5-(4-chloro-2-methyl-2H-indazol-5-yl)-3-methyl-3,7-dihydro-4H-pyrrolo[2,3-d]pyrimidin-4-one, 2-(exo-6-amino-3-azabicyclo[3.1.1]heptan-3-yl)-5-(4-chloro-2-methyl-2H-indazol-5-yl)-3-methyl-3,7-dihydro-4H-pyrrolo[2,3-d]pyrimidin-4-one, 2-(endo-6-amino-3-azabicyclo[3.1.1]heptan-3-yl)-5-(4-chloro-2-methyl-2H-indazol-5-yl)-3-methyl-3,7-dihydro-4H-pyrrolo[2,3-d]pyrimidin-4-one, 2-(5-amino-2-azabicyclo[2.2.1]heptan-2-yl)-5-(4-chloro-2-methyl-2H-indazol-5-yl)-3-methyl-3,7-dihydro-4H-pyrrolo[2,3-d]pyrimidin-4-one, 2-(exo-3-amino-9-azabicyclo[3.3.1]nonan-9-yl)-5-(4-chloro-2-methyl-2H-indazol-5-yl)-3-methyl-3,7-dihydro-4H-pyrrolo[2,3-d]pyrimidin-4-one, 2-(endo-3-amino-9-azabicyclo[3.3.1]nonan-9-yl)-5-(4-chloro-2-methyl-2H-indazol-5-yl)-3-methyl-3,7-dihydro-4H-pyrrolo[2,3-d]pyrimidin-4-one, 5-(4-chloro-2-methyl-2H-indazol-5-yl)-3-methyl-2-(1,8-diazaspiro[4.5]decan-8-yl)-3,7-dihydro-4H-pyrrolo[2,3-d]pyrimidin-4-one, 5-(4-chloro-2-methyl-2H-indazol-5-yl)-3-methyl-2-(piperazin-1-yl)-3,7-dihydro-4H-pyrrolo[2,3-d]pyrimidin-4-one, 2-(3,7-diazabicyclo[4.2.0]octan-3-yl)-5-(4-chloro-2-methyl-2H-indazol-5-yl)-3-methyl-3,7-dihydro-4H-pyrrolo[2,3-d]pyrimidin-4-one, 5-(4-chloro-2-methyl-2H-indazol-5-yl)-3-methyl-2-(1,9-diazaspiro[5.5]undecan-9-yl)-3,7-dihydro-4H-pyrrolo[2,3-d]pyrimidin-4-one, 5-(4-chloro-2-methyl-2H-indazol-5-yl)-3-methyl-2-(1,7-diazaspiro[3.5]nonan-7-yl)-3,7-dihydro-4H-pyrrolo[2,3-d]pyrimidin-4-one, (S)-2-(3-aminopyrrolidin-1-yl)-5-(4-chloro-2-methyl-2H-indazol-5-yl)-3-methyl-3,7-dihydro-4H-pyrrolo[2,3-d]pyrimidin-4-one, (R)-2-(3-aminopyrrolidin-1-yl)-5-(4-chloro-2-methyl-2H-indazol-5-yl)-3-methyl-3,7-dihydro-4H-pyrrolo[2,3-d]pyrimidin-4-one, (S)-5-(4-chloro-2-methyl-2H-indazol-5-yl)-3-methyl-2-(3-methylpiperazin-1-yl)-3,7-dihydro-4H-pyrrolo[2,3-d]pyrimidin-4-one, 2-((1S,2S,4R)-2-amino-7-azabicyclo[2.2.1]heptan-7-yl)-5-(4-chloro-2-methyl-2H-indazol-5-yl)-3-methyl-3,7-dihydro-4H-pyrrolo[2,3-d]pyrimidin-4-one, (R)-5-(4-chloro-2-methyl-2H-indazol-5-yl)-3-methyl-2-(2-methylpiperazin-1-yl)-3,7-dihydro-4H-pyrrolo[2,3-d]pyrimidin-4-one, (S)-5-(4-chloro-2-methyl-2H-indazol-5-yl)-3-methyl-2-(2-methylpiperazin-1-yl)-3,7-dihydro-4H-pyrrolo[2,3-d]pyrimidin-4-one, 2-((1R,2R,4S)-2-amino-7-azabicyclo[2.2.1]heptan-7-yl)-5-(4-chloro-2-methyl-2H-indazol-5-yl)-3-methyl-3,7-dihydro-4H-pyrrolo[2,3-d]pyrimidin-4-one, 2-((3R,4S)-3-amino-4-fluoropyrrolidin-1-yl)-5-(4-chloro-2-methyl-2H-indazol-5-yl)-3-methyl-3,7-dihydro-4H-pyrrolo[2,3-d]pyrimidin-4-one, rac-2-((1S,4S,7S)-7-amino-2-azabicyclo[2.2.1]heptan-2-yl)-5-(4-chloro-2-methyl-2H-indazol-5-yl)-3-methyl-3,7-dihydro-4H-pyrrolo[2,3-d]pyrimidin-4-one, 2-((3S,4S)-3-amino-4-fluoropyrrolidin-1-yl)-5-(4-chloro-2-methyl-2H-indazol-5-yl)-3-methyl-3,7-dihydro-4H-pyrrolo[2,3-d]pyrimidin-4-one, 2-(4-amino-3,3-difluoropyrrolidin-1-yl)-5-(4-chloro-2-methyl-2H-indazol-5-yl)-3-methyl-3,7-dihydro-4H-pyrrolo[2,3-d]pyrimidin-4-one, (S)-2-(3-amino-3-methylpyrrolidin-1-yl)-5-(4-chloro-2-methyl-2H-indazol-5-yl)-3-methyl-3,7-dihydro-4H-pyrrolo[2,3-d]pyrimidin-4-one,
(R)-2-(3-amino-3-methylpyrrolidin-1-yl)-5-(4-chloro-2-methyl-2H-indazol-5-yl)-3-methyl-3,7-dihydro-4H-pyrrolo[2,3-d]pyrimidin-4-one,
2-((3R,4R)-3-amino-4-methylpyrrolidin-1-yl)-5-(4-chloro-2-methyl-2H-indazol-5-yl)-3-methyl-3,7-dihydro-4H-pyrrolo[2,3-d]pyrimidin-4-one,
2-((3R,4S)-3-amino-4-methylpyrrolidin-1-yl)-5-(4-chloro-2-methyl-2H-indazol-5-yl)-3-methyl-3,7-dihydro-4H-pyrrolo[2,3-d]pyrimidin-4-one,
2-(3-amino-3-(hydroxymethyl)pyrrolidin-1-yl)-5-(4-chloro-2-methyl-2H-indazol-5-yl)-3-methyl-3,7-dihydro-4H-pyrrolo[2,3-d]pyrimidin-4-one,
2-((3S,4S)-4-amino-3-methyl-2-oxa-8-azaspiro[4.5]decan-8-yl)-5-(4-chloro-2-methyl-2H-indazol-5-yl)-3-methyl-3,7-dihydro-4H-pyrrolo[2,3-d]pyrimidin-4-one,
(R)-2-(3-(aminomethyl)pyrrolidin-1-yl)-5-(4-chloro-2-methyl-2H-indazol-5-yl)-3-methyl-3,7-dihydro-4H-pyrrolo[2,3-d]pyrimidin-4-one,
2-(1-amino-3-azabicyclo[3.1.0]hexan-3-yl)-5-(4-chloro-2-methyl-2H-indazol-5-yl)-3-methyl-3,7-dihydro-4H-pyrrolo[2,3-d]pyrimidin-4-one,
2-(6-amino-3-azabicyclo[3.1.0]hexan-3-yl)-5-(4-chloro-2-methyl-2H-indazol-5-yl)-3-methyl-3,7-dihydro-4H-pyrrolo[2,3-d]pyrimidin-4-one,
(S)-2-(3-(aminomethyl)pyrrolidin-1-yl)-5-(4-chloro-2-methyl-2H-indazol-5-yl)-3-methyl-3,7-dihydro-4H-pyrrolo[2,3-d]pyrimidin-4-one,
2-(4-(aminomethyl)-4-methoxypiperidin-1-yl)-5-(4-chloro-2-methyl-2H-indazol-5-yl)-3-methyl-3,7-dihydro-4H-pyrrolo[2,3-d]pyrimidin-4-one,
2-(4-(aminomethyl)-4-fluoropiperidin-1-yl)-5-(4-chloro-2-methyl-2H-indazol-5-yl)-3-methyl-3,7-dihydro-4H-pyrrolo[2,3-d]pyrimidin-4-one,
2-(3,9-diazabicyclo[3.3.1]nonan-9-yl)-5-(4-chloro-2-ethyl-2H-indazol-5-yl)-3-methyl-3,7-dihydro-4H-pyrrolo[2,3-d]pyrimidin-4-one,
2-(endo-3-amino-8-azabicyclo[3.2.1]octan-8-yl)-3-methyl-5-(2-methyl-2H-indazol-5-yl)-3,7-dihydro-4H-pyrrolo[2,3-d]pyrimidin-4-one,
2-(endo-3-amino-8-azabicyclo[3.2.1]octan-8-yl)-5-(7-chloro-2-methylbenzo[d]oxazol-6-yl)-3-methyl-3,7-dihydro-4H-pyrrolo[2,3-d]pyrimidin-4-one,
2-(endo-3-amino-8-azabicyclo[3.2.1]octan-8-yl)-5-(7-chloro-2-ethylbenzo[d]oxazol-6-yl)-3-methyl-3,7-dihydro-4H-pyrrolo[2,3-d]pyrimidin-4-one,
2-(endo-3-amino-8-azabicyclo[3.2.1]octan-8-yl)-5-(4-fluoro-2-methyl-2H-indazol-5-yl)-3-methyl-3,7-dihydro-4H-pyrrolo[2,3-d]pyrimidin-4-one,
2-(endo-3-amino-8-azabicyclo[3.2.1]octan-8-yl)-5-(6,7-difluoro-1-methyl-1H-benzo[d][1,2,3]triazol-5-yl)-3-methyl-3,7-dihydro-4H-pyrrolo[2,3-d]pyrimidin-4-one,
2-(endo-3-amino-8-azabicyclo[3.2.1]octan-8-yl)-5-(6-fluoro-2-methyl-2H-indazol-5-yl)-3-methyl-3,7-dihydro-4H-pyrrolo[2,3-d]pyrimidin-4-one,
2-(endo-3-amino-8-azabicyclo[3.2.1]octan-8-yl)-5-(4-methoxy-2-methyl-2H-indazol-5-yl)-3-methyl-3,7-dihydro-4H-pyrrolo[2,3-d]pyrimidin-4-one,
2-(endo-3-amino-8-azabicyclo[3.2.1]octan-8-yl)-5-(7-chloro-1-methyl-1H-benzo[d][1,2,3]triazol-6-yl)-3-methyl-3,7-dihydro-4H-pyrrolo[2,3-d]pyrimidin-4-one,
2-(endo-3-amino-8-azabicyclo[3.2.1]octan-8-yl)-5-(4-chloro-2-(2-hydroxy-2-methylpropyl)-2H-indazol-5-yl)-3-methyl-3,7-dihydro-4H-pyrrolo[2,3-d]pyrimidin-4-one,
2-(endo-3-amino-8-azabicyclo[3.2.1]octan-8-yl)-5-(4-chloro-2,7-dimethyl-2H-indazol-5-yl)-3-methyl-3,7-dihydro-4H-pyrrolo[2,3-d]pyrimidin-4-one,
2-(endo-3-amino-8-azabicyclo[3.2.1]octan-8-yl)-5-(1H-indazol-5-yl)-3-methyl-3,7-dihydro-4H-pyrrolo[2,3-d]pyrimidin-4-one,
2-(endo-3-amino-8-azabicyclo[3.2.1]octan-8-yl)-5-(3,4-dichloro-2-methyl-2H-indazol-5-yl)-3-methyl-3,7-dihydro-4H-pyrrolo[2,3-d]pyrimidin-4-one,
2-(endo-3-amino-3-methyl-8-azabicyclo[3.2.1]octan-8-yl)-5-(3,4-dichloro-2-methyl-2H-indazol-5-yl)-3-methyl-3,7-dihydro-4H-pyrrolo[2,3-d]pyrimidin-4-one,
2-(3-oxa-7,9-diazabicyclo[3.3.1]nonan-7-yl)-5-(3,4-dichloro-2-methyl-2H-indazol-5-yl)-3-methyl-3,7-dihydro-4H-pyrrolo[2,3-d]pyrimidin-4-one,
2-(3-oxa-7,9-diazabicyclo[3.3.1]nonan-7-yl)-5-(7-chloro-2-methylbenzo[d]thiazol-6-yl)-3-methyl-3,7-dihydro-4H-pyrrolo[2,3-d]pyrimidin-4-one,
2-(5-(2-(3,9-diazabicyclo[3.3.1]nonan-9-yl)-3-methyl-4-oxo-4,7-dihydro-3H-pyrrolo[2,3-d]pyrimidin-5-yl)-3,4-dichloro-2H-indazol-2-yl)-N,N-dimethylacetamide,
3-(5-(2-(3,9-diazabicyclo[3.3.1]nonan-9-yl)-3-methyl-4-oxo-4,7-dihydro-3H-pyrrolo[2,3-d]pyrimidin-5-yl)-3,4-dichloro-2H-indazol-2-yl)-N,N-dimethylpropanamide,
2-(6-(2-(3,9-diazabicyclo[3.3.1]nonan-9-yl)-3-methyl-4-oxo-4,7-dihydro-3H-pyrrolo[2,3-d]pyrimidin-5-yl)-7-chlorobenzo[d]thiazol-2-yl)-N,N-dimethylacetamide,
2-(3-oxa-7,9-diazabicyclo[3.3.1]nonan-9-yl)-5-(4-chloro-2-methyl-2H-indazol-5-yl)-3-methyl-3,7-dihydro-4H-pyrrolo[2,3-d]pyrimidin-4-one,
2-(5-(2-(3,8-diazabicyclo[3.2.1]octan-8-yl)-3-methyl-4-oxo-4,7-dihydro-3H-pyrrolo[2,3-d]pyrimidin-5-yl)-4-chloro-2H-indazol-2-yl)-N,N-dimethylacetamide,
2-(3,8-diazabicyclo[3.2.1]octan-8-yl)-5-(4-chloro-2-methyl-2H-benzo[d][1,2,3]triazol-5-yl)-3-methyl-3,7-dihydro-4H-pyrrolo[2,3-d]pyrimidin-4-one,
3-(5-(2-(3,8-diazabicyclo[3.2.1]octan-8-yl)-3-methyl-4-oxo-4,7-dihydro-3H-pyrrolo[2,3-d]pyrimidin-5-yl)-4-chloro-2H-indazol-2-yl)-N,N-dimethylpropanamide,
3-(5-(2-(3,8-diazabicyclo[3.2.1]octan-8-yl)-3-methyl-4-oxo-4,7-dihydro-3H-pyrrolo[2,3-d]pyrimidin-5-yl)-3,4-dichloro-2H-indazol-2-yl)-N,N-dimethylpropanamide,
2-(3,8-diazabicyclo[3.2.1]octan-8-yl)-5-(7-chloro-2-methylbenzo[d]thiazol-6-yl)-3-methyl-3,7-dihydro-4H-pyrrolo[2,3-d]pyrimidin-4-one,
2-(3,8-diazabicyclo[3.2.1]octan-8-yl)-5-(4-chloro-2-ethyl-2H-indazol-5-yl)-3-methyl-3,7-dihydro-4H-pyrrolo[2,3-d]pyrimidin-4-one,
2-((1R,2R,4S)-2-amino-7-azabicyclo[2.2.1]heptan-7-yl)-5-(4-chloro-2-ethyl-2H-indazol-5-yl)-3-methyl-3,7-dihydro-4H-pyrrolo[2,3-d]pyrimidin-4-one,
2-((1R,2R,4S)-2-amino-7-azabicyclo[2.2.1]heptan-7-yl)-5-(3,4-dichloro-2-methyl-2H-indazol-5-yl)-3-methyl-3,7-dihydro-4H-pyrrolo[2,3-d]pyrimidin-4-one,
2-((1R,2R,4S)-2-amino-7-azabicyclo[2.2.1]heptan-7-yl)-5-(4-chloro-2,3-dimethyl-2H-indazol-5-yl)-3-methyl-3,7-dihydro-4H-pyrrolo[2,3-d]pyrimidin-4-one,
2-((1R,2R,4S)-2-amino-7-azabicyclo[2.2.1]heptan-7-yl)-5-(7-chloro-2-methylbenzo[d]thiazol-6-yl)-3-methyl-3,7-dihydro-4H-pyrrolo[2,3-d]pyrimidin-4-one,
2-((1R,2R,4S)-2-amino-7-azabicyclo[2.2.1]heptan-7-yl)-5-(3-chloro-4-fluoro-2-methyl-2H-indazol-5-yl)-3-methyl-3,7-dihydro-4H-pyrrolo[2,3-d]pyrimidin-4-one,
5-(4-chloro-2-methyl-2H-indazol-5-yl)-3-methyl-2-((1R,2R,4S)-2-(methylamino)-7-azabicyclo[2.2.1]heptan-7-yl)-3,7-dihydro-4H-pyrrolo[2,3-d]pyrimidin-4-one, 5-(4-chloro-2-ethyl-2H-indazol-5-yl)-3-methyl-2-((1R,2R,4S)-2-(methylamino)-7-azabicyclo[2.2.1]heptan-7-yl)-3,7-dihydro-4H-pyrrolo[2,3-d]pyrimidin-4-one, 2-(3,9-diazabicyclo[3.3.1]nonan-9-yl)-5-(3,4-dichloro-2-methyl-2H-indazol-5-yl)-3-methyl-3,7-dihydro-4H-pyrrolo[2,3-d]pyrimidin-4-one, 2-(3,9-diazabicyclo[3.3.1]nonan-9-yl)-5-(3-chloro-4-fluoro-2-methyl-2H-indazol-5-yl)-3-methyl-3,7-dihydro-4H-pyrrolo[2,3-d]pyrimidin-4-one, 2-((1R,2R,4S)-2-amino-7-azabicyclo[2.2.1]heptan-7-yl)-5-(7-chlorobenzo[d]thiazol-6-yl)-3-methyl-3,7-dihydro-4H-pyrrolo[2,3-d]pyrimidin-4-one, 2-((1R,2R,4S)-2-amino-7-azabicyclo[2.2.1]heptan-7-yl)-5-(4-chloro-2-ethyl-3-methoxy-2H-indazol-5-yl)-3-methyl-3,7-dihydro-4H-pyrrolo[2,3-d]pyrimidin-4-one, 2-((1R,2R,4S)-2-amino-7-azabicyclo[2.2.1]heptan-7-yl)-5-(3,4-dichloro-2-(fluoromethyl)-2H-indazol-5-yl)-3-methyl-3,7-dihydro-4H-pyrrolo[2,3-d]pyrimidin-4-one, 5-(3,4-dichloro-2-methyl-2H-indazol-5-yl)-3-methyl-2-((1R,2R,4S)-2-(methylamino)-7-azabicyclo[2.2.1]heptan-7-yl)-3,7-dihydro-4H-pyrrolo[2,3-d]pyrimidin-4-one, 5-(7-chlorobenzo[d]thiazol-6-yl)-3-methyl-2-((1R,2R,4S)-2-(methylamino)-7-azabicyclo[2.2.1]heptan-7-yl)-3,7-dihydro-4H-pyrrolo[2,3-d]pyrimidin-4-one, 5-(3-chloro-4-fluoro-2-methyl-2H-indazol-5-yl)-3-methyl-2-((1R,2R,4S)-2-(methylamino)-7-azabicyclo[2.2.1]heptan-7-yl)-3,7-dihydro-4H-pyrrolo[2,3-d]pyrimidin-4-one, 5-(7-chloro-2-methylbenzo[d]thiazol-6-yl)-3-methyl-2-((1R,2R,4S)-2-(methylamino)-7-azabicyclo[2.2.1]heptan-7-yl)-3,7-dihydro-4H-pyrrolo[2,3-d]pyrimidin-4-one, 2-(3,9-diazabicyclo[3.3.1]nonan-9-yl)-5-(7-chlorobenzo[d]thiazol-6-yl)-3-methyl-3,7-dihydro-4H-pyrrolo[2,3-d]pyrimidin-4-one, 2-((1R,2R,4S)-2-amino-7-azabicyclo[2.2.1]heptan-7-yl)-5-(4-chloro-3-(difluoromethyl)-2-ethyl-2H-indazol-5-yl)-3-methyl-3,7-dihydro-4H-pyrrolo[2,3-d]pyrimidin-4-one, 2-((1R,2R,4S)-2-amino-7-azabicyclo[2.2.1]heptan-7-yl)-5-(4-chloro-2-ethyl-3-(hydroxymethyl)-2H-indazol-5-yl)-3-methyl-3,7-dihydro-4H-pyrrolo[2,3-d]pyrimidin-4-one, 6-(3,9-diazabicyclo[3.3.1]nonan-9-yl)-3-(4-chloro-2-ethyl-2H-indazol-5-yl)-5-methyl-1,5-dihydro-4H-pyrazolo[3,4-d]pyrimidin-4-one, 6-((1R,2R,4S)-2-amino-7-azabicyclo[2.2.1]heptan-7-yl)-3-(4-chloro-2-ethyl-2H-indazol-5-yl)-5-methyl-1,5-dihydro-4H-pyrazolo[3,4-d]pyrimidin-4-one, 6-((1R,2R,4S)-2-amino-7-azabicyclo[2.2.1]heptan-7-yl)-3-(7-chloro-2-methylbenzo[d]thiazol-6-yl)-5-methyl-1,5-dihydro-4H-pyrazolo[3,4-d]pyrimidin-4-one, 6-((1R,2R,4S)-2-amino-7-azabicyclo[2.2.1]heptan-7-yl)-3-(3,4-dichloro-2-methyl-2H-indazol-5-yl)-5-methyl-1,5-dihydro-4H-pyrazolo[3,4-d]pyrimidin-4-one, 6-(endo-3-amino-3-methyl-8-azabicyclo[3.2.1]octan-8-yl)-3-(4-chloro-2-ethyl-2H-indazol-5-yl)-5-methyl-1,5-dihydro-4H-pyrazolo[3,4-d]pyrimidin-4-one, 6-(3,9-diazabicyclo[3.3.1]nonan-9-yl)-3-(3,4-dichloro-2-methyl-2H-indazol-5-yl)-5-methyl-1,5-dihydro-4H-pyrazolo[3,4-d]pyrimidin-4-one, 6-(3,9-diazabicyclo[3.3.1]nonan-9-yl)-3-(4-chloro-2-methyl-2H-indazol-5-yl)-5-methyl-1,5-dihydro-4H-pyrazolo[3,4-d]pyrimidin-4-one, 3-(4-chloro-2-ethyl-2H-indazol-5-yl)-5-methyl-6-((1R,2R,4S)-2-(methylamino)-7-azabicyclo[2.2.1]heptan-7-yl)-1,5-dihydro-4H-pyrazolo[3,4-d]pyrimidin-4-one, 3-(3,4-dichloro-2-methyl-2H-indazol-5-yl)-5-methyl-6-((1R,2R,4S)-2-(methylamino)-7-azabicyclo[2.2.1]heptan-7-yl)-1,5-dihydro-4H-pyrazolo[3,4-d]pyrimidin-4-one, 3-(4-chloro-2-methyl-2H-indazol-5-yl)-5-methyl-6-((1R,2R,4S)-2-(methylamino)-7-azabicyclo[2.2.1]heptan-7-yl)-1,5-dihydro-4H-pyrazolo[3,4-d]pyrimidin-4-one, 3-(3-chloro-4-fluoro-2-methyl-2H-indazol-5-yl)-5-methyl-6-((1R,2R,4S)-2-(methylamino)-7-azabicyclo[2.2.1]heptan-7-yl)-1,5-dihydro-4H-pyrazolo[3,4-d]pyrimidin-4-one, 6-(3,9-diazabicyclo[3.3.1]nonan-9-yl)-3-(7-chlorobenzo[d]thiazol-6-yl)-5-methyl-1,5-dihydro-4H-pyrazolo[3,4-d]pyrimidin-4-one, 3-(7-chlorobenzo[d]thiazol-6-yl)-5-methyl-6-((1R,2R,4S)-2-(methylamino)-7-azabicyclo[2.2.1]heptan-7-yl)-1,5-dihydro-4H-pyrazolo[3,4-d]pyrimidin-4-one, 3-(7-chloro-2-methylbenzo[d]thiazol-6-yl)-5-methyl-6-((1R,2R,4S)-2-(methylamino)-7-azabicyclo[2.2.1]heptan-7-yl)-1,5-dihydro-4H-pyrazolo[3,4-d]pyrimidin-4-one, rac-6-((1S,4S,7S)-7-amino-2-azabicyclo[2.2.1]heptan-2-yl)-3-(4-chloro-2-ethyl-2H-indazol-5-yl)-5-methyl-1,5-dihydro-4H-pyrazolo[3,4-d]pyrimidin-4-one, rac-6-((1S,4S,7S)-7-amino-2-azabicyclo[2.2.1]heptan-2-yl)-3-(3,4-dichloro-2-methyl-2H-indazol-5-yl)-5-methyl-1,5-dihydro-4H-pyrazolo[3,4-d]pyrimidin-4-one, 6-((1R,2R,4S)-2-amino-7-azabicyclo[2.2.1]heptan-7-yl)-3-(3,4-dichloro-2-ethyl-2H-indazol-5-yl)-5-methyl-1,5-dihydro-4H-pyrazolo[3,4-d]pyrimidin-4-one, 3-(3,4-dichloro-2-ethyl-2H-indazol-5-yl)-5-methyl-6-((1R,2R,4S)-2-(methylamino)-7-azabicyclo[2.2.1]heptan-7-yl)-1,5-dihydro-4H-pyrazolo[3,4-d]pyrimidin-4-one, 2-((1R,2S,3R,5S)-3-amino-2-fluoro-8-azabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one, 2-((1S,2R,3S,5R)-3-amino-2-fluoro-8-azabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one, 2-((1R,2R,3R,5S)-3-amino-2-fluoro-8-azabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one, 2-((1S,2S,3S,5R)-3-amino-2-fluoro-8-azabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one, rac-2-((1S,4S,7S)-7-amino-2-azabicyclo[2.2.1]heptan-2-yl)-5-(4-chloro-2-ethyl-2H-indazol-5-yl)-3-methyl-3,7-dihydro-4H-pyrrolo[2,3-d]pyrimidin-4-one, rac-((1S,4S,7S)-7-amino-2-azabicyclo[2.2.1]heptan-2-yl)-3-(7-chlorobenzo[d]thiazol-6-yl)-5-methyl-1,5-dihydro-4H-pyrazolo[3,4-d]pyrimidin-4-one, rac-5-(4-chloro-2-methyl-2H-indazol-5-yl)-3-methyl-2-((1S,4S,7S)-7-(methylamino)-2-azabicyclo[2.2.1]heptan-2-yl)-3,7-dihydro-4H-pyrrolo[2,3-d]pyrimidin-4-one, endo-6-[3-amino-8-azabicyclo[3.2.1]octan-8-yl]-3-(4-chloro-2-methyl-2H-indazol-5-yl)-5-methyl-1H,4H,5H-pyrazolo[3,4-d]pyrimidin-4-one, 3-(4-chloro-2-methyl-2H-indazol-5-yl)-6-{3,8-diazabicyclo[3.2.1]octan-8-yl}-5-methyl-1H,4H,5H-pyrazolo[3,4-d]pyrimidin-4-one, 6-[(1R,3S)-1-amino-3-hydroxy-8-azaspiro[4.5]decan-8-yl]-3-(4-chloro-2-methyl-2H-indazol-5-yl)-5-methyl-1H,4H,5H-pyrazolo[3,4-d]pyrimidin-4-one, 6-[(4S)-4-amino-2-oxa-8-azaspiro[4.5]decan-8-yl]-3-(4-chloro-2-methyl-2H-indazol-5-yl)-5-methyl-1H,4H,5H-pyrazolo[3,4-d]pyrimidin-4-one, exo-6-[3-amino-8-azabicyclo[3.2.1]octan-8-yl]-3-(4-chloro-2-methyl-2H-indazol-5-yl)-5-methyl-1H,4H,5H-pyrazolo[3,4-d]pyrimidin-4-one, 3-(4-chloro-2-methyl-2H-indazol-5-yl)-6-{2,7-diazaspiro[3.5]nonan-7-yl}-5-methyl-1H,4H,5H-pyrazolo[3,4-d]pyrimidin-4-one, 6-[(1R)-1-amino-8-azaspiro[4.5]decan-8-yl]-3-(4-chloro-2-methyl-2H-indazol-5-yl)-5-methyl-1H,4H,5H-pyrazolo[3,4-d]pyrimidin-4-one, 6-[(3S,4S)-4-amino-3-methyl-2-oxa-8-azaspiro[4.5]decan-8-yl]-3-(4-chloro-2-methyl-2H-indazol-5-yl)-5-methyl-1H,4H,5H-pyrazolo[3,4-d]pyrimidin-4-one, 6-[(1R,3R)-1-amino-3-fluoro-8-azaspiro[4.5]decan-8-yl]-3-(4-chloro-2-methyl-2H-indazol-5-yl)-5-methyl-1H,4H,5H-pyrazolo[3,4-d]pyrimidin-4-one, 3-(4-chloro-2-methyl-2H-indazol-5-yl)-5-methyl-6-{3-oxa-7,9-diazabicyclo[3.3.1]nonan-7-yl}-1H,4H,5H-pyrazolo[3,4-d]pyrimidin-4-one, 3-(3,4-dichloro-2-methyl-2H-indazol-5-yl)-5-methyl-6-{3-oxa-7,9-diazabicyclo[3.3.1]nonan-7-yl}-1H,4H,5H-pyrazolo[3,4-d]pyrimidin-4-one, 6-[(3S,4S)-4-amino-3-methyl-2-oxa-8-azaspiro[4.5]decan-8-yl]-3-(3,4-dichloro-2-methyl-2H-indazol-5-yl)-5-methyl-1H,4H,5H-pyrazolo[3,4-d]pyrimidin-4-one, 6-[(3S,4S)-4-amino-3-methyl-2-oxa-8-azaspiro[4.5]decan-8-yl]-3-(4-chloro-2-ethyl-2H-indazol-5-yl)-5-methyl-1H,4H,5H-pyrazolo[3,4-d]pyrimidin-4-one, 6-[(1S,2R,3S,5R)-3-amino-2-fluoro-8-azabicyclo[3.2.1]octan-8-yl]-3-(4-chloro-2-methyl-2H-indazol-5-yl)-5-methyl-1H,4H,5H-pyrazolo[3,4-d]pyrimidin-4-one, 2-[(3S,4S)-4-amino-3-methyl-2-oxa-8-azaspiro[4.5]decan-8-yl]-5-(4-chloro-2-ethyl-2H-indazol-5-yl)-3-methyl-3H,4H,7H-pyrrolo[2,3-d]pyrimidin-4-one, 5-(4-chloro-2-ethyl-2H-indazol-5-yl)-2-(1,4-diazepan-1-yl)-3-methyl-3H,4H,7H-pyrrolo[2,3-d]pyrimidin-4-one, rac-2-[(1R,2R,5R)-2-amino-8-azabicyclo[3.2.1]octan-8-yl]-5-(4-chloro-2-methyl-2H-indazol-5-yl)-3-methyl-3H,4H,7H-pyrrolo[2,3-d]pyrimidin-4-one, rac-5-(4-chloro-2-methyl-2H-indazol-5-yl)-2-[(1R,6S)-3,9-diazabicyclo[4.2.1]nonan-9-yl]-3-methyl-3H,4H,7H-pyrrolo[2,3-d]pyrimidin-4-one, rac-2-(4-aminoazepan-1-yl)-5-(4-chloro-2-ethyl-2H-indazol-5-yl)-3-methyl-3H,4H,7H-pyrrolo[2,3-d]pyrimidin-4-one, rel-2-((1R,4R,7R)-7-amino-2-azabicyclo[2.2.1]heptan-2-yl)-5-(4-chloro-2-ethyl-2H-indazol-5-yl)-3-methyl-3,7-dihydro-4H-pyrrolo[2,3-d]pyrimidin-4-one, rel-2-((1S,4S,7S)-7-amino-2-azabicyclo[2.2.1]heptan-2-yl)-5-(4-chloro-2-ethyl-2H-indazol-5-yl)-3-methyl-3,7-dihydro-4H-pyrrolo[2,3-d]pyrimidin-4-one, rel-2-((1R,4R,7R)-7-amino-2-azabicyclo[2.2.1]heptan-2-yl)-5-(4-chloro-2-methyl-2H-indazol-5-yl)-3-methyl-3,7-dihydro-4H-pyrrolo[2,3-d]pyrimidin-4-one, rel-2-((1S,4S,7S)-7-Amino-2-azabicyclo[2.2.1]heptan-2-yl)-5-(4-chloro-2-methyl-2H-indazol-5-yl)-3-methyl-3,7-dihydro-4H-pyrrolo[2,3-d]pyrimidin-4-one, 5-(2-((1R,2R,4S)-2-amino-7-azabicyclo[2.2.1]heptan-7-yl)-3-methyl-4-oxo-4,7-dihydro-3H-pyrrolo[2,3-d]pyrimidin-5-yl)-4-chloro-2-ethyl-2H-indazole-3-carbonitrile, 6-(endo-3-amino-8-azabicyclo[3.2.1]octan-8-yl)-3-(3,4-dichloro-2-methyl-2H-indazol-5-yl)-5-methyl-1,5-dihydro-4H-pyrazolo[3,4-d]pyrimidin-4-one, 6-(endo-3-amino-3-methyl-8-azabicyclo[3.2.1]octan-8-yl)-3-(3,4-dichloro-2-methyl-2H-indazol-5-yl)-5-methyl-1,5-dihydro-4H-pyrazolo[3,4-d]pyrimidin-4-one, 6-((3R,4S)-4-amino-3-fluoropiperidin-1-yl)-3-(3,4-dichloro-2-methyl-2H-indazol-5-yl)-5-methyl-1,5-dihydro-4H-pyrazolo[3,4-d]pyrimidin-4-one, 2-((1R,2S,3S,5S)-3-amino-2-fluoro-8-azabicyclo[3.2.1]octan-8-yl)-5-(3,4-dichloro-2-methyl-2H-indazol-5-yl)-3-methyl-3,7-dihydro-4H-pyrrolo[2,3-d]pyrimidin-4-one, 2-(rac-(1R,2S,4S)-2-amino-7-azabicyclo[2.2.1]heptan-7-yl)-5-(4-chloro-2-methyl-2H-indazol-5-yl)-3-methyl-3,7-dihydro-4H-pyrrolo[2,3-d]pyrimidin-4-one, 5-(4-chloro-2-methyl-2H-indazol-5-yl)-3-methyl-2-((1S,2S,4R)-2-(methylamino)-7-azabicyclo[2.2.1]heptan-7-yl)-3,7-dihydro-4H-pyrrolo[2,3-d]pyrimidin-4-one, 2-((1R,2S,4S)-2-amino-7-azabicyclo[2.2.1]heptan-7-yl)-5-(3,4-dichloro-2-methyl-2H-indazol-5-yl)-3-methyl-3,7-dihydro-4H-pyrrolo[2,3-d]pyrimidin-4-one, 2-((1R,2R,4S)-2-amino-7-azabicyclo[2.2.1]heptan-7-yl)-5-(3-chloro-2-methyl-2H-indazol-5-yl)-3-methyl-3,7-dihydro-4H-pyrrolo[2,3-d]pyrimidin-4-one, 2-((1R,2S,4S)-2-amino-7-azabicyclo[2.2.1]heptan-7-yl)-3-methyl-5-(3,4,7-trichloro-2-methyl-2H-indazol-5-yl)-3,7-dihydro-4H-pyrrolo[2,3-d]pyrimidin-4-one, 2-((1R,2R,4S)-2-amino-7-azabicyclo[2.2.1]heptan-7-yl)-5-(5-chloro-3-methoxyquinoxalin-6-yl)-3-methyl-3,7-dihydro-4H-pyrrolo[2,3-d]pyrimidin-4-one, 2-((1R,2R,4S)-2-amino-7-azabicyclo[2.2.1]heptan-7-yl)-5-(5-chloro-3-(dimethylamino)quinoxalin-6-yl)-3-methyl-3,7-dihydro-4H-pyrrolo[2,3-d]pyrimidin-4-one, 6-((1R,4R,7R)-7-amino-2-azabicyclo[2.2.1]heptan-2-yl)-3-(3,4-dichloro-2-methyl-2H-indazol-5-yl)-5-methyl-1,5-dihydro-4H-pyrazolo[3,4-d]pyrimidin-4-one, 2-((1R,4R,7R)-7-amino-2-azabicyclo[2.2.1]heptan-2-yl)-5-(3,4-dichloro-2-methyl-2H-indazol-5-yl)-3-methyl-3,7-dihydro-4H-pyrrolo[2,3-d]pyrimidin-4-one, rac-2-((1R,2R,4S)-2-amino-2-methyl-7-azabicyclo[2.2.1]heptan-7-yl)-5-(3,4-dichloro-2-methyl-2H-indazol-5-yl)-3-methyl-3,7-dihydro-4H-pyrrolo[2,3-d]pyrimidin-4-one, 2-((1R,4R,7R)-7-amino-2-azabicyclo[2.2.1]heptan-2-yl)-5-(3-chloro-4-fluoro-2-methyl-2H-indazol-5-yl)-3-methyl-3,7-dihydro-4H-pyrrolo[2,3-d]pyrimidin-4-one, rac-6-((1R,2R,4S)-2-amino-2-methyl-7-azabicyclo[2.2.1]heptan-7-yl)-3-(3,4-dichloro-2-methyl-2H-indazol-5-yl)-5-methyl-1,5-dihydro-4H-pyrazolo[3,4-d]pyrimidin-4-one, 2-(endo-3-amino-8-azabicyclo[3.2.1]octan-8-yl)-5-(5-chloroquinoxalin-6-yl)-3-methyl-3,7-dihydro-4H-pyrrolo[2,3-d]pyrimidin-4-one, 3-(3,4-dichloro-2-methyl-2H-indazol-5-yl)-6-((1R,2R,4S)-2-(ethylamino)-7-azabicyclo[2.2.1]heptan-7-yl)-5-methyl-1,5-dihydro-4H-pyrazolo[3,4-d]pyrimidin-4-one, 2-((1R,2R,4S)-2-amino-7-azabicyclo[2.2.1]heptan-7-yl)-5-(4-chloro-2-(2-methoxyethyl)-2H-indazol-5-yl)-3-methyl-3,7-dihydro-4H-pyrrolo[2,3-d]pyrimidin-4-one, 3-(3,4-dichloro-2-methyl-2H-indazol-5-yl)-6-((1R,2R,4S)-2-(isopropylamino)-7-azabicyclo[2.2.1]heptan-7-yl)-5-methyl-1,5-dihydro-4H-pyrazolo[3,4-d]pyrimidin-4-one, 2-[(4S)-4-amino-2-oxa-8-azaspiro[4.5]decan-8-yl]-5-(2-ethyl-2H-indazol-5-yl)-3-methyl-3H,4H,7H-pyrrolo[2,3-d]pyrimidin-4-one, 2-[(4S)-4-amino-2-oxa-8-azaspiro[4.5]decan-8-yl]-5-(2-ethyl-4-fluoro-2H-indazol-5-yl)-3-methyl-3H,4H,7H-pyrrolo[2,3-d]pyrimidin-4-one, 2-[(4S)-4-amino-2-oxa-8-azaspiro[4.5]decan-8-yl]-5-(7-chloro-2-ethyl-2H-indazol-6-yl)-3-methyl-3H,4H,7H-pyrrolo[2,3-d]pyrimidin-4-one, 2-[(4S)-4-amino-2-oxa-8-azaspiro[4.5]decan-8-yl]-5-(2-ethyl-2H-indazol-6-yl)-3-methyl-3H,4H,7H-pyrrolo[2,3-d]pyrimidin-4-one, 2-[(4S)-4-amino-2-oxa-8-azaspiro[4.5]decan-8-yl]-5-(2-ethyl-7-fluoro-2H-indazol-6-yl)-3-methyl-3H,4H,7H-pyrrolo[2,3-d]pyrimidin-4-one, 2-[(endo)-3-amino-3-(difluoromethyl)-8-azabicyclo[3.2.1]octan-8-yl]-5-(4-chloro-2-methyl-2H-indazol-5-yl)-3-methyl-3H,4H,7H-pyrrolo[2,3-d]pyrimidin-4-one, 2-[(4S)-4-amino-2-oxa-8-azaspiro[4.5]decan-8-yl]-5-(2-ethyl-7-fluoro-2H-indazol-5-yl)-3-methyl-3H,4H,7H-pyrrolo[2,3-d]pyrimidin-4-one, 2-[(3R,4S)-4-amino-3-fluoropiperidin-1-yl]-5-(7-chloro-1,3-benzothiazol-6-yl)-3-methyl-3H,4H,7H-pyrrolo[2,3-d]pyrimidin-4-one, 5-(4-chloro-2-methyl-2H-indazol-5-yl)-2-[(1S,6R)-3,9-diazabicyclo[4.2.1]nonan-9-yl]-3-methyl-3H,4H,7H-pyrrolo[2,3-d]pyrimidin-4-one, 5-(4-chloro-2-methyl-2H-indazol-5-yl)-2-[(1R,6S)-3,9-diazabicyclo[4.2.1]nonan-9-yl]-3-methyl-3H,4H,7H-pyrrolo[2,3-d]pyrimidin-4-one, 5-(4-chloro-2-ethyl-2H-indazol-5-yl)-2-{(1R,5R)-3,6-diazabicyclo[3.2.1]octan-3-yl}-3-methyl-3H,4H,7H-pyrrolo[2,3-d]pyrimidin-4-one, 5-(4-chloro-2-ethyl-2H-indazol-5-yl)-2-{(1S,5S)-3,6-diazabicyclo[3.2.1]octan-3-yl}-3-methyl-3H,4H,7H-pyrrolo[2,3-d]pyrimidin-4-one, 5-(4-chloro-2-ethyl-2H-indazol-5-yl)-2-[(1S,5R)-3,6-diazabicyclo[3.2.1]octan-6-yl]-3-methyl-3H,4H,7H-pyrrolo[2,3-d]pyrimidin-4-one 5-(4-chloro-2-ethyl-2H-indazol-5-yl)-2-[(1R,5S)-3,6-diazabicyclo[3.2.1]octan-6-yl]-3-methyl-3H,4H,7H-pyrrolo[2,3-d]pyrimidin-4-one 2-[(3S,4S)-4-amino-3-methyl-2-oxa-8-azaspiro[4.5]decan-8-yl]-5-(4-chloro-7-fluoro-2-methyl-2H-indazol-5-yl)-3-methyl-3H,4H,7H-pyrrolo[2,3-d]pyrimidin-4-one, 2-[(endo)-2-amino-2-methyl-7-azabicyclo[2.2.1]heptan-7-yl]-5-(4-chloro-2-methyl-2H-indazol-5-yl)-3-methyl-3H,4H,7H-pyrrolo[2,3-d]pyrimidin-4-one, Rac-5-(4-chloro-2-ethyl-2H-indazol-5-yl)-2-{2,6-diazaspiro[3.4]octan-6-yl}-3-methyl-3H,4H,7H-pyrrolo[2,3-d]pyrimidin-4-one, 2-[(1R,2S,3S,5S)-3-amino-2-fluoro-8-azabicyclo[3.2.1]octan-8-yl]-5-(4-chloro-2-ethyl-2H-indazol-5-yl)-3-methyl-3H,4H,7H-pyrrolo[2,3-d]pyrimidin-4-one, 2-[(1R,2R,4S)-2-amino-7-azabicyclo[2.2.1]heptan-7-yl]-5-[8-chloro-2-(dimethylamino)quinolin-7-yl]-3-methyl-3H,4H,7H-pyrrolo[2,3-d]pyrimidin-4-one, and 2-[(1R,2R,4S)-2-amino-7-azabicyclo[2.2.1]heptan-7-yl]-5-[8-chloro-2-(methylamino)quinolin-7-yl]-3-methyl-3H,4H,7H-pyrrolo[2,3-d]pyrimidin-4-one.

Item 11. A pharmaceutical composition comprising a compound according to any one of items 1 to 10 and a pharmaceutically acceptable carrier.

Item 12. A pharmaceutical composition according to item 11 for the prophylaxis or treatment of a disease or condition mediated by SHP2.

Item 13. A compound according to any one of items 1 to 10 for use in therapy.

Item 14. A compound according to any one of items 1 to 10 for use in the prophylaxis or treatment of a disease or condition mediated by SHP2.

Item 15. A use of a compound according to any one of items 1 to 10 for the manufacture of a medicament for use in the prophylaxis or treatment of a disease or condition mediated by SHP2.

Item 16. A method for the prophylaxis or treatment of a disease or condition mediated by SHP2 comprising administering to a patient a compound according to any one of items 1 to 10.

Item 17. A pharmaceutical composition of items 11 and 12, a compound of items 13 and 14, a use of item 15 or a method of item 16, wherein the subject of therapy or the disease or condition mediated by SHP2 is cancer.

It is understood that "a compound" in a pharmaceutical composition, a compound, a use or a method of items 11 to 17 encompasses a tautomer or a solvate or a pharmaceutically acceptable salt of the corresponding compound.

rac-2-[(1R,2R,5R)-2-amino-8-azabicyclo[3.2.1]octan-8-yl]-5-(4-chloro-2-methyl-2H-indazol-5-yl)-3-methyl-3H,4H,7H-pyrrolo[2,3-d]pyrimidin-4-one, herein referred as Compound 152, which is outside the scope of Item 1, can be independently claimed as a compound or a tautomer or a solvate or a pharmaceutically acceptable salt thereof. A pharmaceutical composition, a compound, a use or a method wherein Compound 152 is comprised, used or administered can be claimed similarly as Items 11 to 17.

Advantageous Effects of Invention

It has been revealed that the compound of the formula (I) or a tautomer or a solvate or a pharmaceutically acceptable salt thereof has excellent SHP2 inhibitory activity. Therefore, the compound of the present invention or a derivative thereof is useful as an agent for preventing and/or treating SHP2 mediated diseases such as cancer.

The compound of the formula (I) or a tautomer or a solvate or a pharmaceutically acceptable salt thereof have superior properties in some aspects, for example, potency, selectivity, pharmacokinetics e.g., ADME properties, oral bioavailability, ability to cross the blood brain barrier, duration of action, physicochemical properties, hERG activity, QT prolongation, etc.

DESCRIPTION OF EMBODIMENTS

The compound represented by Formula (I) of the present invention is a novel pyrrolopyrimidone or pyrazolopyrimidone compound comprising (i) a monocyclic, bicyclic, bridged cyclic or spirocyclic nitrogen-containing saturated five to seven-membered heterocyclic group and (ii) an aromatic or non-aromatic fused ring containing a benzo-ring, and a five or six-membered nitrogen containing heterocyclic ring.

In the present specification, * represents a bonding position, unless otherwise specified.

In the present specification, examples of the "halogen" include fluorine, chlorine, bromine, iodine, and the like, with fluorine, chlorine, bromine, or iodine being preferable, and fluorine or chlorine being more preferable.

In the present specification, the "alkyl" may be straight or branched. Examples of $C_{1-6}$alkyl include methyl, ethyl, n-propyl, isopropyl, n-butyl, isobutyl, sec-butyl, tert-butyl, n-pentyl, isopentyl, tert-pentyl, and n-hexyl. Examples of $C_{1-4}$alkyl include methyl, ethyl, n-propyl, isopropyl, n-butyl, isobutyl, sec-butyl, tert-butyl.

In the present specification, "alkylene" is a divalent group where one hydrogen is removed from above-listed alkyl groups. Examples of $C_{1-4}$alkylene include straight $C_{1-4}$alkylene such as methylene, ethylene, propylene, butylene, and branched $C_{1-4}$alkylene such as

[Chem. 2]

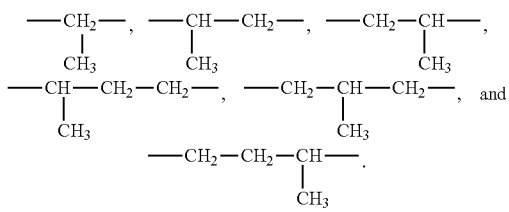

In the present specification, "heterocyclic ring" includes any monocyclic or polycyclic, saturated or unsaturated ring system comprising carbon atoms and at least one hetero atom. "heterocyclic ring" covers aromatic and non-aromatic groups.

In the present specification, examples of "$C_{2-3}$alkenylene" include vinylene and allylene.

In the present specification, the "3 to 6 membered cycloalkyl" includes cyclopropyl, cyclobutyl, cyclopentyl and cyclohexyl.

In the present specification, "amino$C_{1-4}$alkyl" is the above-listed straight or branched $C_{1-4}$ alkyl having one amino group and refers to a group represented by —$C_{1-4}$alkylene-NH$_2$. Examples include -methylene-amino, -ethylene-amino, -propylene-amino, -butylene-amino, and the like.

Examples of "mono$C_{1-4}$alkylamino" include amino monosubstituted with straight or branched $C_{1-4}$alkyl, such as methylamino, ethylamino, n-propylamino, isopropylamino, n-butylamino, isobutylamino, tert-butylamino, and the like.

Examples of "di$C_{1-4}$alkylamino" include amino disubstituted with the same or different straight or branched $C_{1-4}$alkyl groups, such as dimethylamino, diethylamino, di(n-propyl)amino, diisopropylamino, di(n-butyl)amino, diisobutylamino, di(tert-butyl)amino, and the like.

In the present specification, examples of the "hydroxy$C_{1-4}$alkyl" include the above-listed straight or branched alkyl groups that have at least one hydroxy group (e.g., one or two hydroxy groups). Specific examples include hydroxymethyl, 2-hydroxyethyl, 1-hydroxyethyl, 3-hydroxypropyl, 2-hydroxypropyl, 1-methyl-2-hydroxyethyl, 4-hydroxybutyl, 2,2-dimethyl-2-hydroxyethyl, and the like, with hydroxyalkyl having one hydroxy group being preferable.

In the present specification, the "$C_{1-4}$alkoxy" refers to oxy(—O—) to which the above-listed straight or branched $C_{1-4}$alkyl is bonded. Examples include methoxy, ethoxy, n-propoxy, isopropoxy, n-butoxy, isobutoxy, tert-butoxy etc.

In the present specification, examples of the "cyano$C_{1-4}$alkyl" include the above-listed straight or branched $C_{1-4}$alkyl groups that have at least one cyano group (e.g., one or two cyano groups). Specific examples include cyanomethyl, 2-cyanoethyl, 1-cyanoethyl, 3-cyanopropyl, 2-cyanopropyl, 1-methyl-2-cyanoethyl, 4-cyanobutyl, 2,2-dimethyl-2-cyanoethyl, and the like, with cyanoalkyl having one cyano group being preferable.

In the present specification, the "halo$C_{1-4}$alkyl" is the above-listed straight or branched $C_{1-4}$ alkyl having 1 to 7 halogen atoms (halogeno $C_{1-4}$alkyl). Examples include fluoromethyl, difluoromethyl, trifluoromethyl, trichloromethyl, fluoroethyl, 1,1,1-trifluoroethyl, monofluoro-n-propyl, perfluoro-n-propyl, and perfluoroisopropyl.

In the present specification, "$C_{1-4}$alkoxy$C_{1-4}$alkyl" is the above-listed straight or branched $C_{1-4}$ having one of the above listed $C_{1-4}$alkoxy and refers to a group represented by —$C_{1-4}$alkylene-$C_{1-4}$alkoxy (—$C_{1-4}$alkylene-O—$C_{1-4}$alkyl). Examples of $C_{1-4}$alkylene, $C_{1-4}$alkoxy and $C_{1-4}$alkyl are above listed.

In the present specification, "$C_{1-4}$alkylsulfone" refers to a group represented by —SO$_2$—$C_{1-4}$alkyl. Examples include methylsulfone, ethylsulfone, propylsulfone, butylsulfone, and the like.

In the present specification, examples of "—$C_{1-4}$alkylene-C(=O)NH$_{(2-q)}$(C$_{1-6}$alkyl)$_q$" wherein q is an integer of 0, 1 or 2, include —$C_{1-4}$alkylene-C(=O)NH$_2$, —$C_{1-4}$alkylene-C(=O)NH(C$_{1-8}$alkyl), and —$C_{1-4}$alkylene-C(=O)N(C$_{1-8}$alkyl)$_2$. Examples of $C_{1-4}$alkylene and $C_{1-8}$alkyl are above listed.

In the present specification, "—$C_{1-4}$alkylene-NHC(=O)$C_{1-8}$alkyl," refers to a group where the above-mentioned $C_{1-4}$alkylene and $C_{1-8}$alkyl, are joined by an amide bond (—NHC(=O)—). Examples of $C_{1-4}$alkylene and $C_{1-8}$alkyl are above listed.

In the present specification, "sulfonamide$C_{1-4}$alkyl" refers to a group represented by —$C_{1-4}$alkylene-SO$_2$—NH$_2$. Examples include —SO$_2$—NH$_2$, -methylene-SO$_2$—NH$_2$, -ethylene-SO$_2$—NH$_2$, -propylene-SO$_2$—NH$_2$, -butylene-SO$_2$—NH$_2$, and the like.

In the compound represented by formula (I) of the present invention, X represents CH or N. When X represents CH, the compound represented by formula (I) is a pyrrolopyrimidone compound, and when X represents N, the compound represented by formula (I) is a pyrazolopyrimidone compound.

In the compound represented by formula (I) of the present invention, $R^1$ represents methyl (—CH$_3$).

In the compound represented by formula (I) of the present invention, the following portion (hereafter referred to as portion Z):

[Chem. 3]

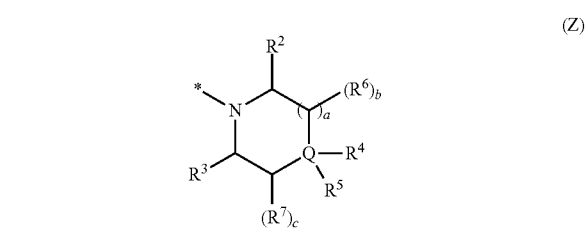

wherein Q, $R^2$, $R^3$, $R^4$, $R^5$, $R^6$ and $R^7$, a, b and c are as defined above;
is a monocyclic, bicyclic, bridged cyclic or spirocyclic nitrogen-containing saturated heterocyclic group.

In the compound represented by formula (I) of the present invention, $R^2$ and $R^3$ independently represent any one selected from hydrogen and $C_{1-4}$alkyl.

In the compound represented by formula (I) of the present invention, $R^6$ and $R^7$ independently represent any one selected from halogen, $C_{1-4}$alkyl, hydroxy$C_{1-4}$alkyl, and hydroxyl. When Q is N, then $R^6$ or $R^7$ do not represent halogen or hydroxyl, thus represents $C_{1-4}$alkyl.

In the compound represented by formula (I) of the present invention, Q represents C or N.

In one embodiment when Q represents C, $R^4$ is amino, amino$C_{1-4}$alkyl or mono$C_{1-4}$alkylamino; $R^5$ is hydrogen, $C_{1-4}$alkyl, halogen, hydroxy$C_{1-4}$alkyl, $C_{1-4}$alkoxy, halo$C_{1-4}$alkyl or $C_{1-4}$alkoxy$C_{1-4}$alkyl. In one embodiment when $R^4$ is amino then $R^5$ is selected from hydrogen, $C_{1-4}$alkyl, hydroxy$C_{1-4}$alkyl, $C_{1-4}$alkoxy, halo$C_{1-4}$alkyl and $C_{1-4}$alkoxy$C_{1-4}$alkyl.

In such embodiment, the portion Z is a monocyclic nitrogen-containing saturated five to seven-membered heterocyclic group containing one nitrogen, represented by the formula below:

[Chem. 4]

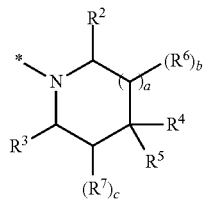

wherein $R^2$, $R^3$, $R^4$, $R^5$, $R^6$ and $R^7$, a, b and c are as defined above;

In another embodiment when Q represents C, $R^4$ and $R^5$ together with Q form a four- to six-membered ring that can optionally contain 1 to 3 heteroatoms or groups independently selected from N, O, S, NH, C(O) and S(O)$_m$, and said ring formed by $R^4$ and $R^5$ can be unsubstituted or substituted with 1 to 4 groups independently selected from amino, halogen, halo$C_{1-4}$alkyl, hydroxyl, methoxy, methylamino, $C_{1-4}$alkyl, and m is selected from 1 and 2.

In such embodiment, the portion Z is a spirocyclic nitrogen-containing saturated heterocyclic group containing eight to twelve members including Q, one to four among the members being nitrogen, and one to four among the members optionally being identical or different heteroatoms selected from oxygen, and sulfur. In such embodiment, the portion Z is represented by the formula below:

[Chem. 5]

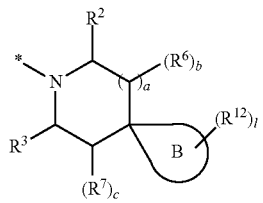

wherein $R^2$, $R^3$, $R^6$, $R^7$, a, b and c are as defined above;
wherein Ring B is a saturated four- to six-membered ring that can optionally contain 1 to 3 heteroatoms or groups independently selected from N, O, S, NH, C(O) and S(O)$_m$,
$R^{12}$ is independently selected from amino, halogen, halo$C_{1-4}$alkyl, hydroxyl, methoxy, methylamino, $C_{1-4}$alkyl,
l is a integer selected from 0, 1, 2, 3 and 4,
m is a integer selected from 1 and 2.

Examples of the four- to six-membered ring that can optionally contain 1 to 3 heteroatoms or groups independently selected from N, O, C(O) and S(O)$_m$ include

[Chem. 6]

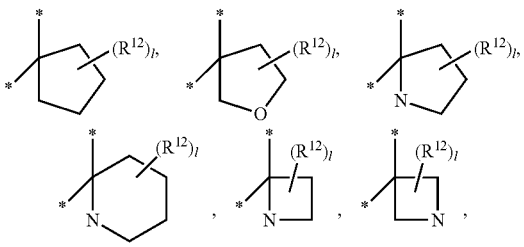

wherein $R^{12}$ and l are as defined above.

In one embodiment when Q represents N, then $R^4$ is absent and $R^5$ is hydrogen.

In such embodiment, the portion Z may be represented by the formula below:

[Chem. 7]

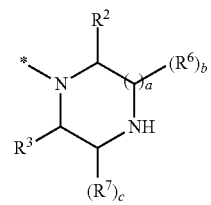

wherein $R^2$, $R^3$, a, b and c are as defined above; $R^6$ and $R^7$ independently selected from hydroxy$C_{1-4}$alkyl and $C_{1-4}$alkyl, provided a is not zero;
and is a monocyclic nitrogen-containing saturated five to seven-membered heterocyclic group containing two nitrogen.

In the compound represented by formula (I) of the present invention, $R^2$, $R^3$, $R^6$ and $R^7$ may alternatively have the following structure wherein any two groups selected from $R^2$, $R^3$, $R^6$ and $R^7$ together form a one- to three-membered bridge group selected from $C_{1-3}$alkylene, $C_{2-3}$alkenylene, methylene-NR$^q$-methylene and methylene-O-methylene, wherein the bridge group is optionally substituted by a group selected from $C_{1-4}$alkyl, hydroxyl and halogen and $R^q$ is selected from hydrogen, and $C_{1-4}$alkyl.

Examples of such embodiment includes the portion Z being represented by any one of the formulas below:

[Chem. 8]

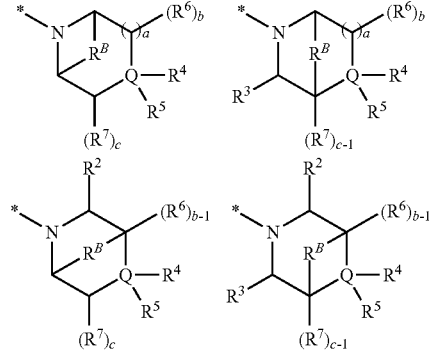

wherein Q, $R^2$, $R^3$, $R^4$, $R^5$, $R^6$ and $R^7$, a, b and c are as defined above, with the provisio that in the formulas containing "b-1" and/or "c-1", "b-1" (can be referred to as b') and "c-1" (can be referred to as c') are independently selected from 0 and 1.

$R^B$ represents a one- to three-membered bridge group selected from straight $C_{1-3}$alkylene, $C_{2-3}$alkenylene, methylene-$NR^q$-methylene and methylene-O-methylene, wherein the bridge group is optionally substituted by a group selected from $C_{1-4}$alkyl, hydroxyl and halogen and $R^q$ is selected from hydrogen and $C_{1-4}$alkyl.

In another embodiment of the compound represented by formula (I) of the present invention, Q is C, c is 2, $R^4$ is hydrogen and the two $R^7$ join to form a 4 to 6 membered nitrogen containing ring. Examples of such embodiment includes the portion Z being represented by any one of the formulas below:

[Chem. 9]

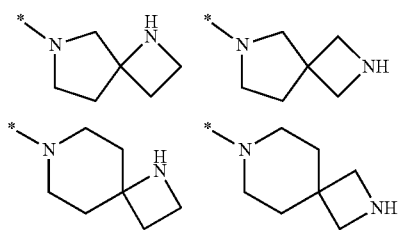

In the compound represented by formula (I) of the present invention, $R^4$ and $R^7$ may alternatively form a four- to six-membered ring containing one N atom. Examples of such embodiment where includes the portion Z being represented by any one of the formulas below:

[Chem. 10]

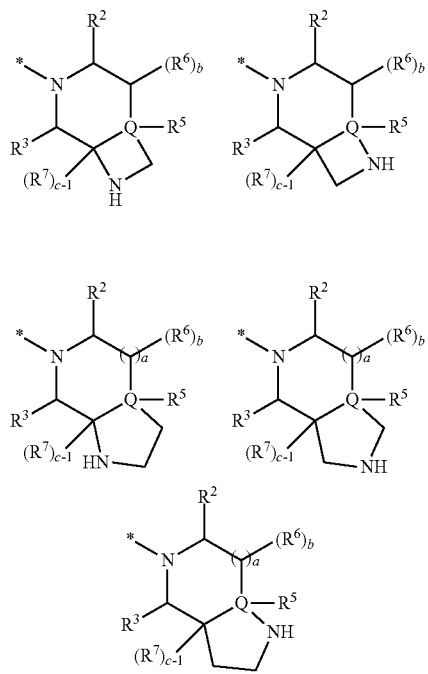

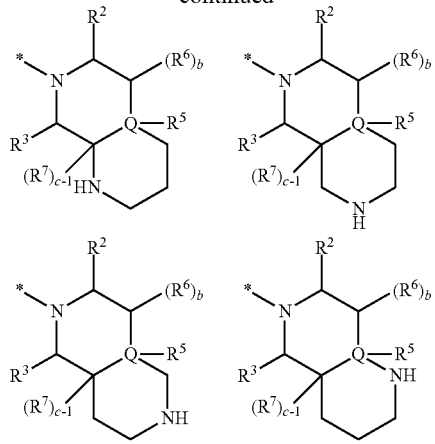

wherein Q, $R^2$, $R^3$, $R^5$, $R^6$ and $R^7$, a, b and c are as defined above, with the provisio that "c-1" (can be referred to as c') is selected from 0 and 1.

In the compound represented by formula (I) of the present invention, $R^5$ and $R^7$ may alternatively form a three- to six-membered ring. Examples of such embodiment includes the portion Z being represented by any one of the formulas below:

[Chem. 11]

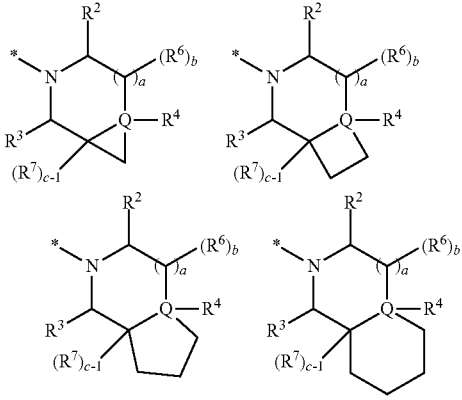

wherein Q, $R^2$, $R^3$, $R^4$, $R^6$ and $R^7$, a, b and c are as defined above, with the provisio that "c-1" (can be referred to as c') is selected from 0 and 1.

In one alternative embodiment, $R^6$ and $R^7$ alternatively form a direct bond. Examples of such embodiment includes the portion Z being represented by formula below:

[Chem. 12]

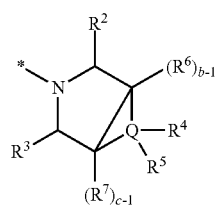

wherein Q, $R^2$, $R^3$, $R^4$, $R^5$, $R^6$, $R^7$, b and c are as defined above, with the provisio that "b-1" (can be referred to as b') and "c-1" (can be referred to as c') are independently selected from 0 and 1.

In the compound represented by formula (I), a is an integer selected from 0, 1 and 2.

In the compound represented by formula (I), b is an integer selected from 0, 1 and 2.

In the compound represented by formula (I), c is an integer selected from 0, 1 and 2;

Preferable embodiments includes the portion Z being represented by any one of the formulas below:

[Chem.13]

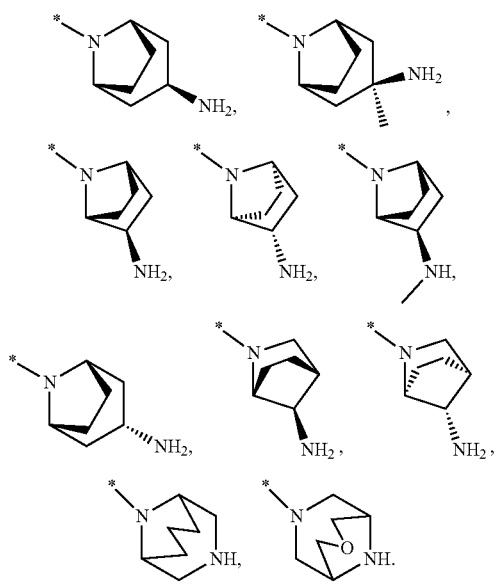

Another preferable embodiments includes the portion Z being represented by any one of the formulas below:

[Chem. 14]

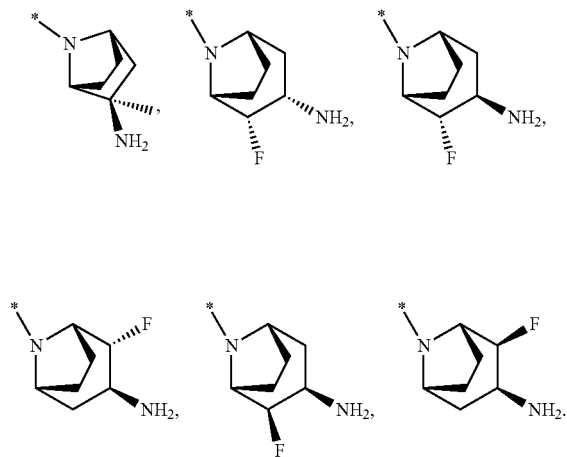

In the compound represented by formula (I) of the present invention, the following portion (hereafter referred to as portion Y):

[Chem. 15]

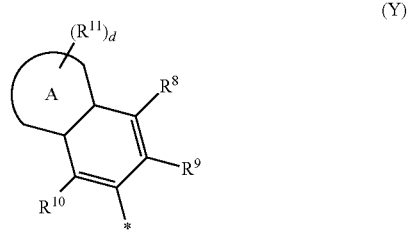

wherein Ring A, $R^8$, $R^9$, $R^{10}$, $R^{11}$ and d are as defined above;
is an aromatic or non-aromatic fused ring containing a benzo-ring, and a five or six-membered nitrogen containing heterocyclic ring.

In the compound represented by formula (I), Ring A represented below

[Chem. 16]

forms, together with the benzo-ring to which this group is bonded, a five or six-membered nitrogen containing heterocyclic ring.

Specifically, Ring A is either:
(i) a five-membered nitrogen-containing heterocyclic ring wherein the heterocyclic ring optionally contains one or two additional heteroatoms selected from N, O and S, or
(ii) a six-membered aromatic nitrogen-containing heterocyclic ring, wherein the heterocyclic ring optionally contains one or two additional heteroatoms selected from N, O and S; or
(iii) a six-membered non-aromatic nitrogen-containing heterocyclic ring, wherein the heterocyclic ring optionally contains one or two additional heteroatoms selected from N and S.

The five-membered nitrogen-containing heterocyclic ring wherein the heterocyclic ring optionally contains one or two additional heteroatoms selected from N, O and S may be a five-membered aromatic nitrogen-containing heterocyclic ring or a five-membered non-aromatic nitrogen-containing heterocyclic ring. Such heterocyclic ring contains two to four carbon atoms including the two carbon atoms that is shared with the benzo-ring to which this group is bonded, one to three nitrogen atoms, and the carbon atoms that is not shared with the benzo ring (one or two carbon atoms) replaced with an oxygen atom or a sulfur atom.

Examples of five-membered aromatic nitrogen-containing heterocyclic rings include pyrrole, imidazole, pyrazole, oxazole, isoxazole, thiazole, isothiazole, and the like.

Examples of five-membered non-aromatic nitrogen-containing heterocyclic rings include pyrrolidine, pyrazolidine, triazolidine, oxazolidine, isoxazolidine, thiazolidine, isothiazolidine, and the like.

The six-membered aromatic nitrogen-containing heterocyclic ring, wherein the heterocyclic ring optionally contains one or two additional heteroatoms selected from N, O and S. Such heterocyclic ring contains two to five carbon atoms including the two carbon atoms that is shared with the benzo-ring to which this group is bonded, one to three nitrogen atoms, and the carbon atoms that is not shared with the benzo-ring (one, two or three carbon atoms) replaced with an oxygen atom or a sulfur atom.

Examples of six-membered aromatic nitrogen-containing heterocyclic ring include pyridine, pyrazine, pyrimidine, pyridazine, triazine, oxazine, thiazine, and the like.

The six-membered non-aromatic nitrogen-containing heterocyclic ring, wherein the heterocyclic ring optionally contains one or two additional heteroatoms selected from N and S. Such heterocyclic ring contains two to five carbon atoms including the two carbon atoms that is shared with the benzo-ring to which this group is bonded, one to three nitrogen atoms, and the carbon atoms that is not shared with the benzo-ring (one, two or three carbon atoms) replaced with a sulfur atom.

Examples of six-membered non-aromatic nitrogen-containing heterocyclic ring include piperidine, piperazine, morpholine, and the like.

In the compound represented by formula (I), $R^8$ represents one selected from hydrogen, $C_{1-4}$alkyl, halo$C_{1-4}$alkyl and halogen.

In the compound represented by formula (I), $R^9$ represents one selected from hydrogen and halogen.

In the compound represented by formula (I), $R^{10}$ represents one selected from halo$C_{1-4}$alkyl, $C_{1-4}$alkyl, halogen, hydrogen and $C_{1-4}$alkoxy.

In the compound represented by formula (I), each $R^{11}$ independently represents one selected from halogen, cyano, cyano$C_{1-4}$alkyl, hydroxyl, oxo (=O), $C_{1-4}$alkyl optionally substituted with five- or six-membered heterocyclic group containing 1 or 2 heteroatoms selected from O, N, or S, halo$C_{1-4}$alkyl, $C_{1-4}$alkoxy, hydroxyl$C_{1-4}$alkyl, $C_{1-4}$alkoxy$C_{1-4}$alkyl, $C_{1-4}$alkylsulfone, amino, mono$C_{1-4}$alkylamino, di$C_{1-4}$alkylamino, amino$C_{1-4}$alkyl, —$C_{1-4}$alkylene-C(=O)NH$_{(2-q)}$($C_{1-6}$alkyl)$_q$), —$C_{1-4}$alkylene-NHC(=O)$C_{1-8}$alkyl, sulfonamide, sulfonamide$C_{1-4}$alkyl, 3 to 6 membered cycloalkyl, $C_{1-4}$alkyl substituted with 3 to 6 membered cycloalkyl, five- or six-membered unsaturated heterocyclic group containing 1, 2, 3 or 4 heteroatoms selected from O, N, or S, and optionally substituted four- to six-membered saturated heterocyclic group containing 1 or 2 heteroatoms selected from O, N, or S where the optional substituent is selected from $C_{1-4}$alkyl.

When $R^{11}$ is oxo (=O), the atomic bonding between $R^{11}$ and Ring A is a double bond. In other cases where $R^{11}$ is a monovalent group, the atomic bonding between $R^{11}$ and Ring A is a single bond.

In the compound represented by formula (I), q is an integer selected from 0, 1 and 2.

In the compound represented by formula (I), d is an integer selected from 0, 1 and 2.

Preferable embodiments includes the portion Y being represented by any one of the formulas below:

[Chem. 17]

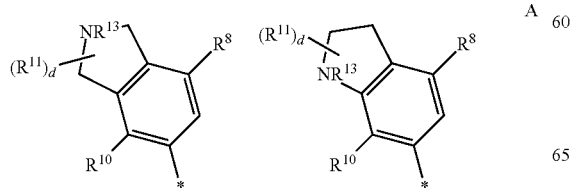
A

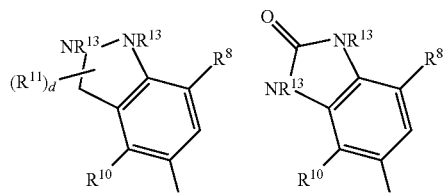
B

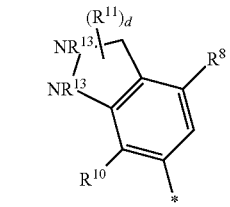

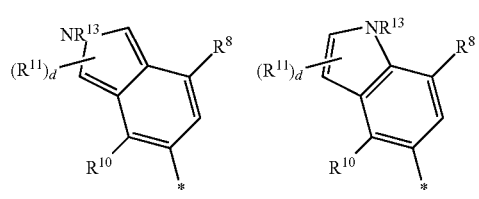
C

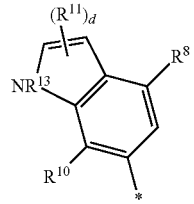

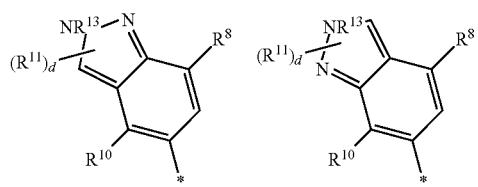
D

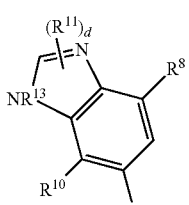
E

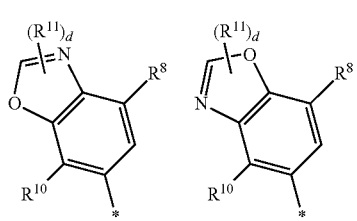
F

-continued

[Chem. 18]

G

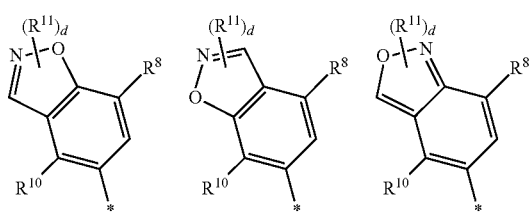

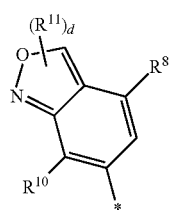

H

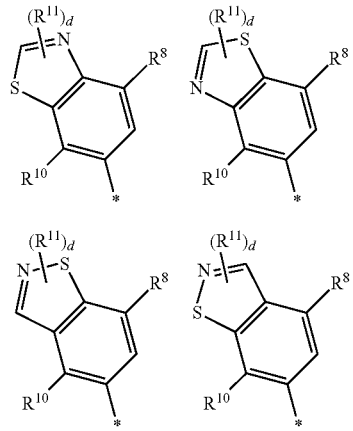

I

J

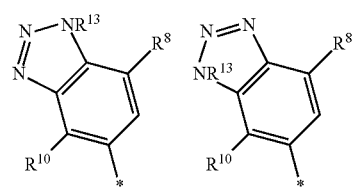

K

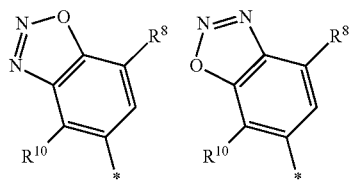

L

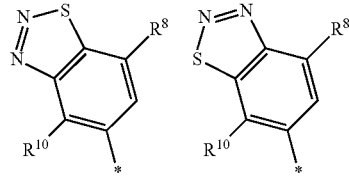

-continued

[Chem. 19]

M

N

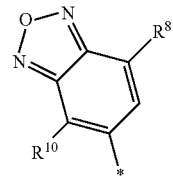

O

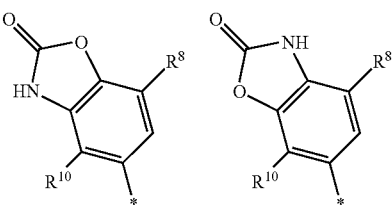

P

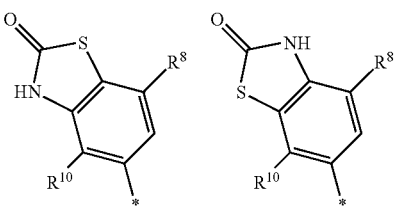

Q

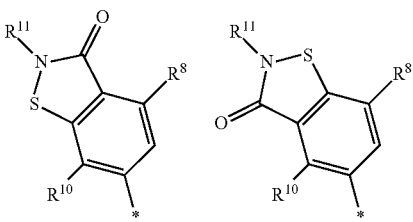

wherein $R^8$, $R^{10}$, $R^{11}$ and d are as defined above;

$R^{13}$ are independently selected from hydrogen, cyano, cyano$C_{1-4}$alkyl, $C_{1-4}$alkyl optionally substituted with five- or six-membered heterocyclic group containing 1 or 2 heteroatoms selected from O, N, or S, halo$C_{1-4}$alkyl, $C_{1-4}$alkoxy, hydroxyl$C_{1-4}$alkyl, $C_{1-4}$alkoxy$C_{1-4}$alkyl, $C_{1-4}$alkylsulfone, amino$C_{2-4}$alkyl, —$C_{1-4}$alkylene-C(=O)NH$_{(2-q)}$($C_{1-6}$alkyl)$_q$), —$C_{1-4}$alkylene-NHC(=O)$C_{1-6}$alkyl, sulfoneamide$C_{1-4}$alkyl, 3 to 6 membered cycloalkyl, $C_{1-4}$alkyl substituted with 3 to 6 membered cycloalkyl, five- or six-membered unsaturated heterocyclic group containing 1, 2, 3 or 4 heteroatoms selected from O, N, or S, and optionally substituted four- to six-membered saturated heterocyclic group containing 1 or 2 heteroatoms selected from O, N, or S where the optional substituent is selected from $C_{1-4}$alkyl.

Other preferable embodiments include the portion Y being represented by any one of the formulas below:

[Chem. 20]

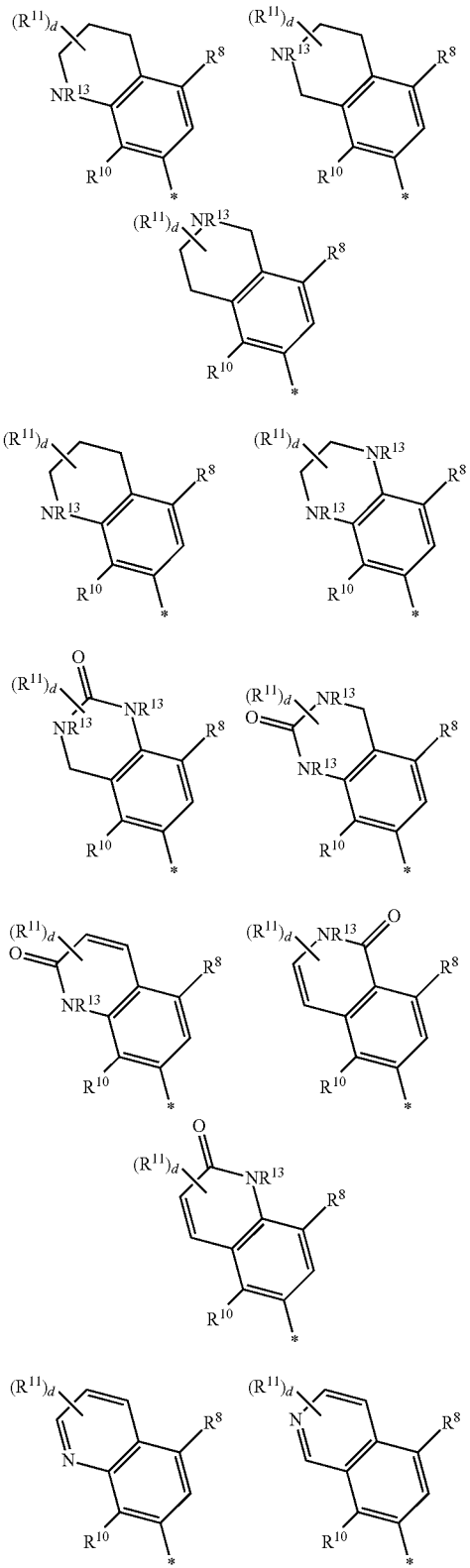

[Chem. 21]

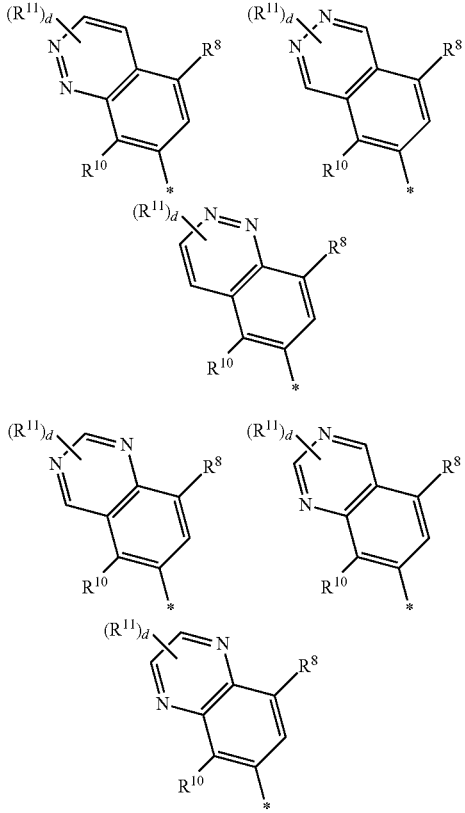

wherein $R^8$, $R^{10}$, $R^{11}$ and d are as defined above;
$R^{13}$ are independently selected from hydrogen, cyano, cyano$C_{1-4}$alkyl, $C_{1-4}$alkyl optionally substituted with five- or six-membered heterocyclic group containing 1 or 2 heteroatoms selected from O, N, or S, halo$C_{1-4}$ alkyl, $C_{1-4}$alkoxy, hydroxyl$C_{1-4}$alkyl, $C_{1-4}$alkoxy$C_{1-4}$ alkyl, $C_{1-4}$alkylsulfone, amino$C_{2-4}$alkyl, —$C_{1-4}$alkylene-C(=O)NH$_{(2-q)}$(C$_{1-6}$alkyl)$_q$), —C$_{1-4}$alkylene-NHC(=O)C$_{1-6}$alkyl, sulfoneamideC$_{1-4}$alkyl, 3 to 6 membered cycloalkyl, C$_{1-4}$alkyl substituted with 3 to 6 membered cycloalkyl, five- or six-membered unsaturated heterocyclic group containing 1, 2, 3 or 4 heteroatoms selected from O, N, or S, and optionally substituted four- to six-membered saturated heterocyclic group containing 1 or 2 heteroatoms selected from O, N, or S where the optional substituent is selected from C$_{1-4}$alkyl.

Other preferable embodiments include the portion Y being represented by any one of the formulas below:

[Chem. 22]

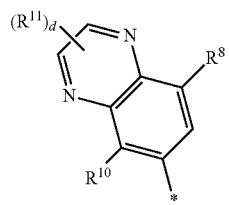

wherein R$^8$, R$^{10}$, R$^{11}$ and d are as defined above;

More preferable embodiments includes the portion Y being represented by any one of the formulas below:

[Chem. 23]

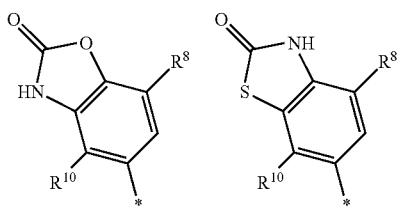

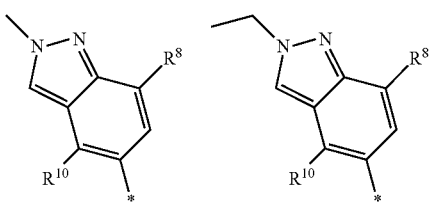

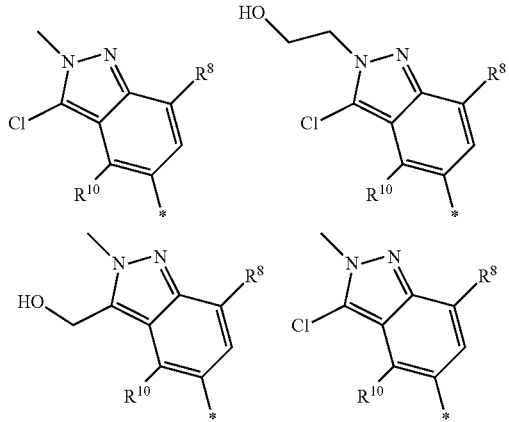

-continued

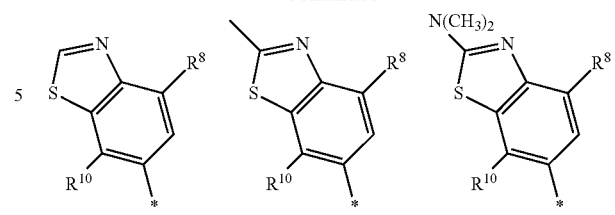

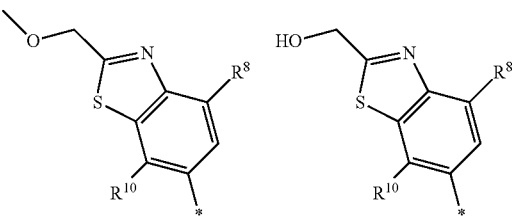

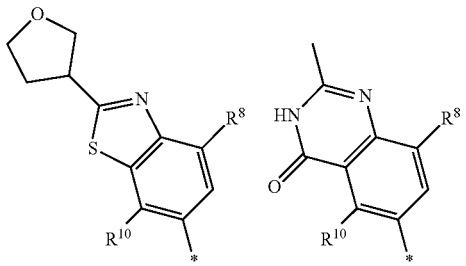

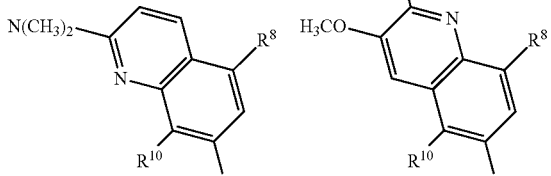

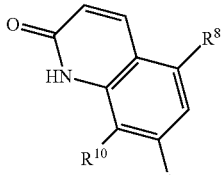

wherein R$^8$ and R$^{10}$ are as defined above.

More preferable embodiments includes the portion Y being represented by any one of the formulas below:

[Chem. 24]

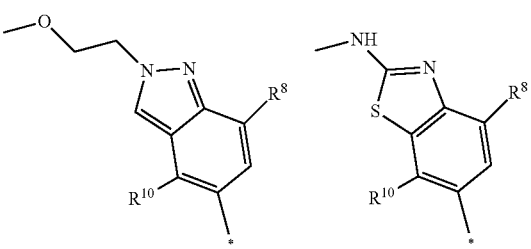

-continued

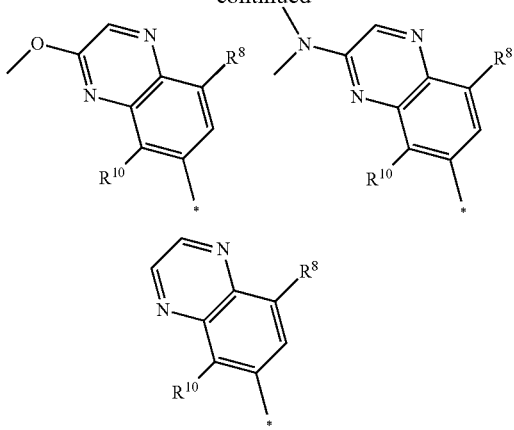

More preferable embodiments include the portion Y being represented by any one of the formulas below:

[Chem. 25]

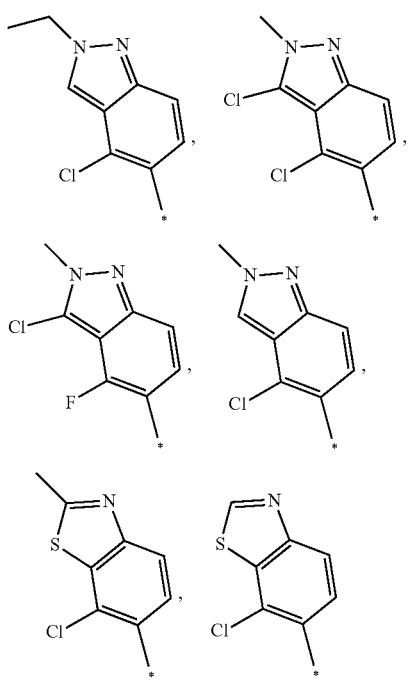

Particularly preferable embodiments include the portion Y being represented by any one of the formulas below:

[Chem. 26]

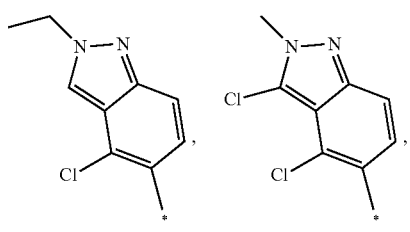

-continued

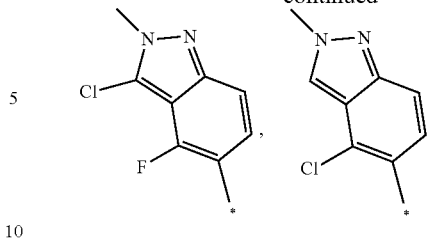

The following are examples of preferable compounds of the present invention:

2-(3,8-diazabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one, 2-(4-(aminomethyl)-4-methylpiperidin-1-yl)-5-(4-chloro-2-ethyl-2H-indazol-5-yl)-3-methyl-3,7-dihydro-4H-pyrrolo[2,3-d]pyrimidin-4-one, 2-(4-amino-4-methylpiperidin-1-yl)-5-(4-chloro-2-ethyl-2H-indazol-5-yl)-3-methyl-3,7-dihydro-4H-pyrrolo[2,3-d]pyrimidin-4-one, 2-(exo-3-amino-8-azabicyclo[3.2.1]octan-8-yl)-5-(4-chloro-2-ethyl-2H-indazol-5-yl)-3-methyl-3,7-dihydro-4H-pyrrolo[2,3-d]pyrimidin-4-one, 2-(endo-3-amino-8-azabicyclo[3.2.1]octan-8-yl)-5-(4-chloro-2-ethyl-2H-indazol-5-yl)-3-methyl-3,7-dihydro-4H-pyrrolo[2,3-d]pyrimidin-4-one, 2-(endo-3-amino-8-azabicyclo[3.2.1]octan-8-yl)-5-(7-chloro-2-ethylbenzo[d]thiazol-6-yl)-3-methyl-3,7-dihydro-4H-pyrrolo[2,3-d]pyrimidin-4-one, 2-(endo-3-amino-8-azabicyclo[3.2.1]octan-8-yl)-5-(7-chloro-2-methylbenzo[d]thiazol-6-yl)-3-methyl-3,7-dihydro-4H-pyrrolo[2,3-d]pyrimidin-4-one, 2-(endo-3-amino-8-azabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one, 2-(endo-3-amino-8-azabicyclo[3.2.1]octan-8-yl)-5-(2-(tert-butyl)-4-chloro-2H-indazol-5-yl)-3-methyl-3,7-dihydro-4H-pyrrolo[2,3-d]pyrimidin-4-one, 2-(exo-3-amino-8-azabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one, (R)-2-(1-amino-8-azaspiro[4.5]decan-8-yl)-5-(4-chloro-2-ethyl-2H-indazol-5-yl)-3-methyl-3,7-dihydro-4H-pyrrolo[2,3-d]pyrimidin-4-one, (S)-2-(4-amino-2-oxa-8-azaspiro[4.5]decan-8-yl)-5-(4-chloro-2-ethyl-2H-indazol-5-yl)-3-methyl-3,7-dihydro-4H-pyrrolo[2,3-d]pyrimidin-4-one, 5-(4-chloro-2-ethyl-2H-indazol-5-yl)-3-methyl-2-(endo-3-(methylamino)-8-azabicyclo[3.2.1]octan-8-yl)-3,7-dihydro-4H-pyrrolo[2,3-d]pyrimidin-4-one, 5-(4-chloro-2-methyl-2H-indazol-5-yl)-3-methyl-2-(endo-3-(methylamino)-8-azabicyclo[3.2.1]octan-8-yl)-3,7-dihydro-4H-pyrrolo[2,3-d]pyrimidin-4-one, 2-(endo-3-amino-3-methyl-8-azabicyclo[3.2.1]octan-8-yl)-5-(4-chloro-2-ethyl-2H-indazol-5-yl)-3-methyl-3,7-dihydro-4H-pyrrolo[2,3-d]pyrimidin-4-one, 2-(endo-3-amino-3-methyl-8-azabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one, 2-(3-oxa-7,9-diazabicyclo[3.3.1]nonan-7-yl)-5-(4-chloro-2-methyl-2H-indazol-5-yl)-3-methyl-3,7-dihydro-4H-pyrrolo[2,3-d]pyrimidin-4-one, (R)-5-(4-chloro-2-methyl-2H-indazol-5-yl)-3-methyl-2-(3-methylpiperazin-1-yl)-3,7-dihydro-4H-pyrrolo[2,3-d]pyrimidin-4-one, (S)-5-(4-chloro-2-methyl-2H-indazol-5-yl)-2-(3-(hydroxymethyl)piperazin-1-yl)-3-methyl-3,7-dihydro-4H-pyrrolo[2,3-d]pyrimidin-4-one,
(R)-5-(4-chloro-2-methyl-2H-indazol-5-yl)-2-(3-(2-hydroxyethyl)piperazin-1-yl)-3-methyl-3,7-dihydro-4H-pyrrolo[2,3-d]pyrimidin-4-one,
2-((1S,4S)-2,5-diazabicyclo[2.2.1]heptan-2-yl)-5-(4-chloro-2-methyl-2H-indazol-5-yl)-3-methyl-3,7-dihydro-4H-pyrrolo[2,3-d]pyrimidin-4-one,
2-(7-amino-3-oxa-9-azabicyclo[3.3.1]nonan-9-yl)-5-(4-chloro-2-methyl-2H-indazol-5-yl)-3-methyl-3,7-dihydro-4H-pyrrolo[2,3-d]pyrimidin-4-one,
2-((1R,4R)-2,5-diazabicyclo[2.2.1]heptan-2-yl)-5-(4-chloro-2-methyl-2H-indazol-5-yl)-3-methyl-3,7-dihydro-4H-pyrrolo[2,3-d]pyrimidin-4-one,
2-(exo-8-amino-3-azabicyclo[3.2.1]octan-3-yl)-5-(4-chloro-2-methyl-2H-indazol-5-yl)-3-methyl-3,7-dihydro-4H-pyrrolo[2,3-d]pyrimidin-4-one,
2-(endo-8-amino-3-azabicyclo[3.2.1]octan-3-yl)-5-(4-chloro-2-methyl-2H-indazol-5-yl)-3-methyl-3,7-dihydro-4H-pyrrolo[2,3-d]pyrimidin-4-one,
rac-2-((1S,2R,3R,5R)-3-amino-2-fluoro-8-azabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one,
2-(3,9-diazabicyclo[3.3.1]nonan-9-yl)-5-(4-chloro-2-methyl-2H-indazol-5-yl)-3-methyl-3,7-dihydro-4H-pyrrolo[2,3-d]pyrimidin-4-one,
2-(3,8-diazabicyclo[3.2.1]octan-3-yl)-5-(4-chloro-2-methyl-2H-indazol-5-yl)-3-methyl-3,7-dihydro-4H-pyrrolo[2,3-d]pyrimidin-4-one,
2-(3,6-diazabicyclo[3.1.1]heptan-6-yl)-5-(4-chloro-2-methyl-2H-indazol-5-yl)-3-methyl-3,7-dihydro-4H-pyrrolo[2,3-d]pyrimidin-4-one,
2-(3,9-diazabicyclo[3.3.1]nonan-3-yl)-5-(4-chloro-2-methyl-2H-indazol-5-yl)-3-methyl-3,7-dihydro-4H-pyrrolo[2,3-d]pyrimidin-4-one,
2-(3,6-diazabicyclo[3.1.1]heptan-3-yl)-5-(4-chloro-2-methyl-2H-indazol-5-yl)-3-methyl-3,7-dihydro-4H-pyrrolo[2,3-d]pyrimidin-4-one,
2-(2,5-diazabicyclo[2.2.2]octan-2-yl)-5-(4-chloro-2-methyl-2H-indazol-5-yl)-3-methyl-3,7-dihydro-4H-pyrrolo[2,3-d]pyrimidin-4-one,
2-(exo-6-amino-3-azabicyclo[3.1.1]heptan-3-yl)-5-(4-chloro-2-methyl-2H-indazol-5-yl)-3-methyl-3,7-dihydro-4H-pyrrolo[2,3-d]pyrimidin-4-one,
2-(endo-6-amino-3-azabicyclo[3.1.1]heptan-3-yl)-5-(4-chloro-2-methyl-2H-indazol-5-yl)-3-methyl-3,7-dihydro-4H-pyrrolo[2,3-d]pyrimidin-4-one,
2-(5-amino-2-azabicyclo[2.2.1]heptan-2-yl)-5-(4-chloro-2-methyl-2H-indazol-5-yl)-3-methyl-3,7-dihydro-4H-pyrrolo[2,3-d]pyrimidin-4-one,
2-(exo-3-amino-9-azabicyclo[3.3.1]nonan-9-yl)-5-(4-chloro-2-methyl-2H-indazol-5-yl)-3-methyl-3,7-dihydro-4H-pyrrolo[2,3-d]pyrimidin-4-one,
2-(endo-3-amino-9-azabicyclo[3.3.1]nonan-9-yl)-5-(4-chloro-2-methyl-2H-indazol-5-yl)-3-methyl-3,7-dihydro-4H-pyrrolo[2,3-d]pyrimidin-4-one,
5-(4-chloro-2-methyl-2H-indazol-5-yl)-3-methyl-2-(1,8-diazaspiro[4.5]decan-8-yl)-3,7-dihydro-4H-pyrrolo[2,3-d]pyrimidin-4-one,
5-(4-chloro-2-methyl-2H-indazol-5-yl)-3-methyl-2-(piperazin-1-yl)-3,7-dihydro-4H-pyrrolo[2,3-d]pyrimidin-4-one,
2-(3,7-diazabicyclo[4.2.0]octan-3-yl)-5-(4-chloro-2-methyl-2H-indazol-5-yl)-3-methyl-3,7-dihydro-4H-pyrrolo[2,3-d]pyrimidin-4-one,
5-(4-chloro-2-methyl-2H-indazol-5-yl)-3-methyl-2-(1,9-diazaspiro[5.5]undecan-9-yl)-3,7-dihydro-4H-pyrrolo[2,3-d]pyrimidin-4-one,
5-(4-chloro-2-methyl-2H-indazol-5-yl)-3-methyl-2-(1,7-diazaspiro[3.5]nonan-7-yl)-3,7-dihydro-4H-pyrrolo[2,3-d]pyrimidin-4-one,
(S)-2-(3-aminopyrrolidin-1-yl)-5-(4-chloro-2-methyl-2H-indazol-5-yl)-3-methyl-3,7-dihydro-4H-pyrrolo[2,3-d]pyrimidin-4-one,
(R)-2-(3-aminopyrrolidin-1-yl)-5-(4-chloro-2-methyl-2H-indazol-5-yl)-3-methyl-3,7-dihydro-4H-pyrrolo[2,3-d]pyrimidin-4-one,
(S)-5-(4-chloro-2-methyl-2H-indazol-5-yl)-3-methyl-2-(3-methylpiperazin-1-yl)-3,7-dihydro-4H-pyrrolo[2,3-d]pyrimidin-4-one,
2-((1S,2S,4R)-2-amino-7-azabicyclo[2.2.1]heptan-7-yl)-5-(4-chloro-2-methyl-2H-indazol-5-yl)-3-methyl-3,7-dihydro-4H-pyrrolo[2,3-d]pyrimidin-4-one,
(R)-5-(4-chloro-2-methyl-2H-indazol-5-yl)-3-methyl-2-(2-methylpiperazin-1-yl)-3,7-dihydro-4H-pyrrolo[2,3-d]pyrimidin-4-one,
(S)-5-(4-chloro-2-methyl-2H-indazol-5-yl)-3-methyl-2-(2-methylpiperazin-1-yl)-3,7-dihydro-4H-pyrrolo[2,3-d]pyrimidin-4-one,
2-((1R,2R,4S)-2-amino-7-azabicyclo[2.2.1]heptan-7-yl)-5-(4-chloro-2-methyl-2H-indazol-5-yl)-3-methyl-3,7-dihydro-4H-pyrrolo[2,3-d]pyrimidin-4-one,
2-((3R,4S)-3-amino-4-fluoropyrrolidin-1-yl)-5-(4-chloro-2-methyl-2H-indazol-5-yl)-3-methyl-3,7-dihydro-4H-pyrrolo[2,3-d]pyrimidin-4-one,
rac-2-((1S,4S,7S)-7-amino-2-azabicyclo[2.2.1]heptan-2-yl)-5-(4-chloro-2-methyl-2H-indazol-5-yl)-3-methyl-3,7-dihydro-4H-pyrrolo[2,3-d]pyrimidin-4-one,
2-((3S,4S)-3-amino-4-fluoropyrrolidin-1-yl)-5-(4-chloro-2-methyl-2H-indazol-5-yl)-3-methyl-3,7-dihydro-4H-pyrrolo[2,3-d]pyrimidin-4-one,
2-(4-amino-3,3-difluoropyrrolidin-1-yl)-5-(4-chloro-2-methyl-2H-indazol-5-yl)-3-methyl-3,7-dihydro-4H-pyrrolo[2,3-d]pyrimidin-4-one,
(S)-2-(3-amino-3-methylpyrrolidin-1-yl)-5-(4-chloro-2-methyl-2H-indazol-5-yl)-3-methyl-3,7-dihydro-4H-pyrrolo[2,3-d]pyrimidin-4-one,
(R)-2-(3-amino-3-methylpyrrolidin-1-yl)-5-(4-chloro-2-methyl-2H-indazol-5-yl)-3-methyl-3,7-dihydro-4H-pyrrolo[2,3-d]pyrimidin-4-one,
2-((3R,4R)-3-amino-4-methylpyrrolidin-1-yl)-5-(4-chloro-2-methyl-2H-indazol-5-yl)-3-methyl-3,7-dihydro-4H-pyrrolo[2,3-d]pyrimidin-4-one,
2-((3R,4S)-3-amino-4-methylpyrrolidin-1-yl)-5-(4-chloro-2-methyl-2H-indazol-5-yl)-3-methyl-3,7-dihydro-4H-pyrrolo[2,3-d]pyrimidin-4-one,
2-(3-amino-3-(hydroxymethyl)pyrrolidin-1-yl)-5-(4-chloro-2-methyl-2H-indazol-5-yl)-3-methyl-3,7-dihydro-4H-pyrrolo[2,3-d]pyrimidin-4-one,
2-((3S,4S)-4-amino-3-methyl-2-oxa-8-azaspiro[4.5]decan-8-yl)-5-(4-chloro-2-methyl-2H-indazol-5-yl)-3-methyl-3,7-dihydro-4H-pyrrolo[2,3-d]pyrimidin-4-one,
(R)-2-(3-(aminomethyl)pyrrolidin-1-yl)-5-(4-chloro-2-methyl-2H-indazol-5-yl)-3-methyl-3,7-dihydro-4H-pyrrolo[2,3-d]pyrimidin-4-one,
2-(1-amino-3-azabicyclo[3.1.0]hexan-3-yl)-5-(4-chloro-2-methyl-2H-indazol-5-yl)-3-methyl-3,7-dihydro-4H-pyrrolo[2,3-d]pyrimidin-4-one,
2-(6-amino-3-azabicyclo[3.1.0]hexan-3-yl)-5-(4-chloro-2-methyl-2H-indazol-5-yl)-3-methyl-3,7-dihydro-4H-pyrrolo[2,3-d]pyrimidin-4-one, (S)-2-(3-(aminomethyl)pyrrolidin-1-yl)-5-(4-chloro-2-methyl-2H-indazol-5-yl)-3-methyl-3,7-dihydro-4H-pyrrolo[2,3-d]pyrimidin-4-one,
2-(4-(aminomethyl)-4-methoxypiperidin-1-yl)-5-(4-chloro-2-methyl-2H-indazol-5-yl)-3-methyl-3,7-dihydro-4H-pyrrolo[2,3-d]pyrimidin-4-one,
2-(4-(aminomethyl)-4-fluoropiperidin-1-yl)-5-(4-chloro-2-methyl-2H-indazol-5-yl)-3-methyl-3,7-dihydro-4H-pyrrolo[2,3-d]pyrimidin-4-one,
2-(3,9-diazabicyclo[3.3.1]nonan-9-yl)-5-(4-chloro-2-ethyl-2H-indazol-5-yl)-3-methyl-3,7-dihydro-4H-pyrrolo[2,3-d]pyrimidin-4-one,
2-(endo-3-amino-8-azabicyclo[3.2.1]octan-8-yl)-3-methyl-5-(2-methyl-2H-indazol-5-yl)-3,7-dihydro-4H-pyrrolo[2,3-d]pyrimidin-4-one,
2-(endo-3-amino-8-azabicyclo[3.2.1]octan-8-yl)-5-(7-chloro-2-methylbenzo[d]oxazol-6-yl)-3-methyl-3,7-dihydro-4H-pyrrolo[2,3-d]pyrimidin-4-one,
2-(endo-3-amino-8-azabicyclo[3.2.1]octan-8-yl)-5-(7-chloro-2-ethylbenzo[d]oxazol-6-yl)-3-methyl-3,7-dihydro-4H-pyrrolo[2,3-d]pyrimidin-4-one,
2-(endo-3-amino-8-azabicyclo[3.2.1]octan-8-yl)-5-(4-fluoro-2-methyl-2H-indazol-5-yl)-3-methyl-3,7-dihydro-4H-pyrrolo[2,3-d]pyrimidin-4-one,
2-(endo-3-amino-8-azabicyclo[3.2.1]octan-8-yl)-5-(6,7-difluoro-1-methyl-1H-benzo[d][1,2,3]triazol-5-yl)-3-methyl-3,7-dihydro-4H-pyrrolo[2,3-d]pyrimidin-4-one,
2-(endo-3-amino-8-azabicyclo[3.2.1]octan-8-yl)-5-(6-fluoro-2-methyl-2H-indazol-5-yl)-3-methyl-3,7-dihydro-4H-pyrrolo[2,3-d]pyrimidin-4-one,
2-(endo-3-amino-8-azabicyclo[3.2.1]octan-8-yl)-5-(4-methoxy-2-methyl-2H-indazol-5-yl)-3-methyl-3,7-dihydro-4H-pyrrolo[2,3-d]pyrimidin-4-one,
2-(endo-3-amino-8-azabicyclo[3.2.1]octan-8-yl)-5-(7-chloro-1-methyl-1H-benzo[d][1,2,3]triazol-6-yl)-3-methyl-3,7-dihydro-4H-pyrrolo[2,3-d]pyrimidin-4-one,
2-(endo-3-amino-8-azabicyclo[3.2.1]octan-8-yl)-5-(4-chloro-2-(2-hydroxy-2-methylpropyl)-2H-indazol-5-yl)-3-methyl-3,7-dihydro-4H-pyrrolo[2,3-d]pyrimidin-4-one,
2-(endo-3-amino-8-azabicyclo[3.2.1]octan-8-yl)-5-(4-chloro-2,7-dimethyl-2H-indazol-5-yl)-3-methyl-3,7-dihydro-4H-pyrrolo[2,3-d]pyrimidin-4-one,
2-(endo-3-amino-8-azabicyclo[3.2.1]octan-8-yl)-5-(1H-indazol-5-yl)-3-methyl-3,7-dihydro-4H-pyrrolo[2,3-d]pyrimidin-4-one,
2-(endo-3-amino-8-azabicyclo[3.2.1]octan-8-yl)-5-(3,4-dichloro-2-methyl-2H-indazol-5-yl)-3-methyl-3,7-dihydro-4H-pyrrolo[2,3-d]pyrimidin-4-one,
2-(endo-3-amino-3-methyl-8-azabicyclo[3.2.1]octan-8-yl)-5-(3,4-dichloro-2-methyl-2H-indazol-5-yl)-3-methyl-3,7-dihydro-4H-pyrrolo[2,3-d]pyrimidin-4-one,
2-(3-oxa-7,9-diazabicyclo[3.3.1]nonan-7-yl)-5-(3,4-dichloro-2-methyl-2H-indazol-5-yl)-3-methyl-3,7-dihydro-4H-pyrrolo[2,3-d]pyrimidin-4-one,
2-(3-oxa-7,9-diazabicyclo[3.3.1]nonan-7-yl)-5-(7-chloro-2-methylbenzo[d]thiazol-6-yl)-3-methyl-3,7-dihydro-4H-pyrrolo[2,3-d]pyrimidin-4-one,
2-(5-(2-(3,9-diazabicyclo[3.3.1]nonan-9-yl)-3-methyl-4-oxo-4,7-dihydro-3H-pyrrolo[2,3-d]pyrimidin-5-yl)-3,4-dichloro-2H-indazol-2-yl)-N,N-dimethylacetamide,
3-(5-(2-(3,9-diazabicyclo[3.3.1]nonan-9-yl)-3-methyl-4-oxo-4,7-dihydro-3H-pyrrolo[2,3-d]pyrimidin-5-yl)-3,4-dichloro-2H-indazol-2-yl)-N,N-dimethylpropanamide,
2-(6-(2-(3,9-diazabicyclo[3.3.1]nonan-9-yl)-3-methyl-4-oxo-4,7-dihydro-3H-pyrrolo[2,3-d]pyrimidin-5-yl)-7-chlorobenzo[d]thiazol-2-yl)-N,N-dimethylacetamide,
2-(3-oxa-7,9-diazabicyclo[3.3.1]nonan-9-yl)-5-(4-chloro-2-methyl-2H-indazol-5-yl)-3-methyl-3,7-dihydro-4H-pyrrolo[2,3-d]pyrimidin-4-one,
2-(5-(2-(3,8-diazabicyclo[3.2.1]octan-8-yl)-3-methyl-4-oxo-4,7-dihydro-3H-pyrrolo[2,3-d]pyrimidin-5-yl)-4-chloro-2H-indazol-2-yl)-N,N-dimethylacetamide,
2-(3,8-diazabicyclo[3.2.1]octan-8-yl)-5-(4-chloro-2-methyl-2H-benzo[d][1,2,3]triazol-5-yl)-3-methyl-3,7-dihydro-4H-pyrrolo[2,3-d]pyrimidin-4-one,
3-(5-(2-(3,8-diazabicyclo[3.2.1]octan-8-yl)-3-methyl-4-oxo-4,7-dihydro-3H-pyrrolo[2,3-d]pyrimidin-5-yl)-4-chloro-2H-indazol-2-yl)-N,N-dimethylpropanamide,
3-(5-(2-(3,8-diazabicyclo[3.2.1]octan-8-yl)-3-methyl-4-oxo-4,7-dihydro-3H-pyrrolo[2,3-d]pyrimidin-5-yl)-3,4-dichloro-2H-indazol-2-yl)-N,N-dimethylpropanamide,
2-(3,8-diazabicyclo[3.2.1]octan-8-yl)-5-(7-chloro-2-methylbenzo[d]thiazol-6-yl)-3-methyl-3,7-dihydro-4H-pyrrolo[2,3-d]pyrimidin-4-one,
2-(3,8-diazabicyclo[3.2.1]octan-8-yl)-5-(4-chloro-2-ethyl-2H-indazol-5-yl)-3-methyl-3,7-dihydro-4H-pyrrolo[2,3-d]pyrimidin-4-one,
2-((1R,2R,4S)-2-amino-7-azabicyclo[2.2.1]heptan-7-yl)-5-(4-chloro-2-ethyl-2H-indazol-5-yl)-3-methyl-3,7-dihydro-4H-pyrrolo[2,3-d]pyrimidin-4-one,
2-((1R,2R,4S)-2-amino-7-azabicyclo[2.2.1]heptan-7-yl)-5-(3,4-dichloro-2-methyl-2H-indazol-5-yl)-3-methyl-3,7-dihydro-4H-pyrrolo[2,3-d]pyrimidin-4-one,
2-((1R,2R,4S)-2-amino-7-azabicyclo[2.2.1]heptan-7-yl)-5-(4-chloro-2,3-dimethyl-2H-indazol-5-yl)-3-methyl-3,7-dihydro-4H-pyrrolo[2,3-d]pyrimidin-4-one,
2-((1R,2R,4S)-2-amino-7-azabicyclo[2.2.1]heptan-7-yl)-5-(7-chloro-2-methylbenzo[d]thiazol-6-yl)-3-methyl-3,7-dihydro-4H-pyrrolo[2,3-d]pyrimidin-4-one,
2-((1R,2R,4S)-2-amino-7-azabicyclo[2.2.1]heptan-7-yl)-5-(3-chloro-4-fluoro-2-methyl-2H-indazol-5-yl)-3-methyl-3,7-dihydro-4H-pyrrolo[2,3-d]pyrimidin-4-one,
5-(4-chloro-2-methyl-2H-indazol-5-yl)-3-methyl-2-((1R,2R,4S)-2-(methylamino)-7-azabicyclo[2.2.1]heptan-7-yl)-3,7-dihydro-4H-pyrrolo[2,3-d]pyrimidin-4-one,
5-(4-chloro-2-ethyl-2H-indazol-5-yl)-3-methyl-2-((1R,2R,4S)-2-(methylamino)-7-azabicyclo[2.2.1]heptan-7-yl)-3,7-dihydro-4H-pyrrolo[2,3-d]pyrimidin-4-one,
2-(3,9-diazabicyclo[3.3.1]nonan-9-yl)-5-(3,4-dichloro-2-methyl-2H-indazol-5-yl)-3-methyl-3,7-dihydro-4H-pyrrolo[2,3-d]pyrimidin-4-one,
2-(3,9-diazabicyclo[3.3.1]nonan-9-yl)-5-(3-chloro-4-fluoro-2-methyl-2H-indazol-5-yl)-3-methyl-3,7-dihydro-4H-pyrrolo[2,3-d]pyrimidin-4-one,
2-((1R,2R,4S)-2-amino-7-azabicyclo[2.2.1]heptan-7-yl)-5-(7-chlorobenzo[d]thiazol-6-yl)-3-methyl-3,7-dihydro-4H-pyrrolo[2,3-d]pyrimidin-4-one,
2-((1R,2R,4S)-2-amino-7-azabicyclo[2.2.1]heptan-7-yl)-5-(4-chloro-2-ethyl-3-methoxy-2H-indazol-5-yl)-3-methyl-3,7-dihydro-4H-pyrrolo[2,3-d]pyrimidin-4-one,
2-((1R,2R,4S)-2-amino-7-azabicyclo[2.2.1]heptan-7-yl)-5-(3,4-dichloro-2-(fluoromethyl)-2H-indazol-5-yl)-3-methyl-3,7-dihydro-4H-pyrrolo[2,3-d]pyrimidin-4-one,
5-(3,4-dichloro-2-methyl-2H-indazol-5-yl)-3-methyl-2-((1R,2R,4S)-2-(methylamino)-7-azabicyclo[2.2.1]heptan-7-yl)-3,7-dihydro-4H-pyrrolo[2,3-d]pyrimidin-4-one,
5-(7-chlorobenzo[d]thiazol-6-yl)-3-methyl-2-((1R,2R,4S)-2-(methylamino)-7-azabicyclo[2.2.1]heptan-7-yl)-3,7-dihydro-4H-pyrrolo[2,3-d]pyrimidin-4-one,
5-(3-chloro-4-fluoro-2-methyl-2H-indazol-5-yl)-3-methyl-2-((1R,2R,4S)-2-(methylamino)-7-azabicyclo[2.2.1]heptan-7-yl)-3,7-dihydro-4H-pyrrolo[2,3-d]pyrimidin-4-one, 5-(7-chloro-2-methylbenzo[d]thiazol-6-yl)-3-methyl-2-((1R,2R,4S)-2-(methylamino)-7-azabicyclo[2.2.1]heptan-7-yl)-3,7-dihydro-4H-pyrrolo[2,3-d]pyrimidin-4-one, 2-(3,9-diazabicyclo[3.3.1]nonan-9-yl)-5-(7-chlorobenzo[d]thiazol-6-yl)-3-methyl-3,7-dihydro-4H-pyrrolo[2,3-d]pyrimidin-4-one, 2-((1R,2R,4S)-2-amino-7-azabicyclo[2.2.1]heptan-7-yl)-5-(4-chloro-3-(difluoromethyl)-2-ethyl-2H-indazol-5-yl)-3-methyl-3,7-dihydro-4H-pyrrolo[2,3-d]pyrimidin-4-one, 2-((1R,2R,4S)-2-amino-7-azabicyclo[2.2.1]heptan-7-yl)-5-(4-chloro-2-ethyl-3-(hydroxymethyl)-2H-indazol-5-yl)-3-methyl-3,7-dihydro-4H-pyrrolo[2,3-d]pyrimidin-4-one, 6-(3,9-diazabicyclo[3.3.1]nonan-9-yl)-3-(4-chloro-2-ethyl-2H-indazol-5-yl)-5-methyl-1,5-dihydro-4H-pyrazolo[3,4-d]pyrimidin-4-one, 6-((1R,2R,4S)-2-amino-7-azabicyclo[2.2.1]heptan-7-yl)-3-(4-chloro-2-ethyl-2H-indazol-5-yl)-5-methyl-1,5-dihydro-4H-pyrazolo[3,4-d]pyrimidin-4-one, 6-((1R,2R,4S)-2-amino-7-azabicyclo[2.2.1]heptan-7-yl)-3-(7-chloro-2-methylbenzo[d]thiazol-6-yl)-5-methyl-1,5-dihydro-4H-pyrazolo[3,4-d]pyrimidin-4-one, 6-((1R,2R,4S)-2-amino-7-azabicyclo[2.2.1]heptan-7-yl)-3-(3,4-dichloro-2-methyl-2H-indazol-5-yl)-5-methyl-1,5-dihydro-4H-pyrazolo[3,4-d]pyrimidin-4-one, 6-(endo-3-amino-3-methyl-8-azabicyclo[3.2.1]octan-8-yl)-3-(4-chloro-2-ethyl-2H-indazol-5-yl)-5-methyl-1,5-dihydro-4H-pyrazolo[3,4-d]pyrimidin-4-one, 6-(3,9-diazabicyclo[3.3.1]nonan-9-yl)-3-(3,4-dichloro-2-methyl-2H-indazol-5-yl)-5-methyl-1,5-dihydro-4H-pyrazolo[3,4-d]pyrimidin-4-one, 6-(3,9-diazabicyclo[3.3.1]nonan-9-yl)-3-(4-chloro-2-methyl-2H-indazol-5-yl)-5-methyl-1,5-dihydro-4H-pyrazolo[3,4-d]pyrimidin-4-one, 3-(4-chloro-2-ethyl-2H-indazol-5-yl)-5-methyl-6-((1R,2R,4S)-2-(methylamino)-7-azabicyclo[2.2.1]heptan-7-yl)-1,5-dihydro-4H-pyrazolo[3,4-d]pyrimidin-4-one, 3-(3,4-dichloro-2-methyl-2H-indazol-5-yl)-5-methyl-6-((1R,2R,4S)-2-(methylamino)-7-azabicyclo[2.2.1]heptan-7-yl)-1,5-dihydro-4H-pyrazolo[3,4-d]pyrimidin-4-one, 3-(4-chloro-2-methyl-2H-indazol-5-yl)-5-methyl-6-((1R,2R,4S)-2-(methylamino)-7-azabicyclo[2.2.1]heptan-7-yl)-1,5-dihydro-4H-pyrazolo[3,4-d]pyrimidin-4-one, 3-(3-chloro-4-fluoro-2-methyl-2H-indazol-5-yl)-5-methyl-6-((1R,2R,4S)-2-(methylamino)-7-azabicyclo[2.2.1]heptan-7-yl)-1,5-dihydro-4H-pyrazolo[3,4-d]pyrimidin-4-one, 6-(3,9-diazabicyclo[3.3.1]nonan-9-yl)-3-(7-chlorobenzo[d]thiazol-6-yl)-5-methyl-1,5-dihydro-4H-pyrazolo[3,4-d]pyrimidin-4-one, 3-(7-chlorobenzo[d]thiazol-6-yl)-5-methyl-6-((1R,2R,4S)-2-(methylamino)-7-azabicyclo[2.2.1]heptan-7-yl)-1,5-dihydro-4H-pyrazolo[3,4-d]pyrimidin-4-one, 3-(7-chloro-2-methylbenzo[d]thiazol-6-yl)-5-methyl-6-((1R,2R,4S)-2-(methylamino)-7-azabicyclo[2.2.1]heptan-7-yl)-1,5-dihydro-4H-pyrazolo[3,4-d]pyrimidin-4-one, rac-6-((1S,4S,7S)-7-amino-2-azabicyclo[2.2.1]heptan-2-yl)-3-(4-chloro-2-ethyl-2H-indazol-5-yl)-5-methyl-1,5-dihydro-4H-pyrazolo[3,4-d]pyrimidin-4-one, rac-6-((1S,4S,7S)-7-amino-2-azabicyclo[2.2.1]heptan-2-yl)-3-(3,4-dichloro-2-methyl-2H-indazol-5-yl)-5-methyl-1,5-dihydro-4H-pyrazolo[3,4-d]pyrimidin-4-one, 6-((1R,2R,4S)-2-amino-7-azabicyclo[2.2.1]heptan-7-yl)-3-(3,4-dichloro-2-ethyl-2H-indazol-5-yl)-5-methyl-1,5-dihydro-4H-pyrazolo[3,4-d]pyrimidin-4-one, 3-(3,4-dichloro-2-ethyl-2H-indazol-5-yl)-5-methyl-6-((1R,2R,4S)-2-(methylamino)-7-azabicyclo[2.2.1]heptan-7-yl)-1,5-dihydro-4H-pyrazolo[3,4-d]pyrimidin-4-one, 2-((1R,2S,3R,5S)-3-amino-2-fluoro-8-azabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one, 2-((1S,2R,3S,5R)-3-amino-2-fluoro-8-azabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one, 2-((1R,2R,3R,5S)-3-amino-2-fluoro-8-azabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one, 2-((1S,2S,3S,5R)-3-amino-2-fluoro-8-azabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one, rac-2-((1S,4S,7S)-7-amino-2-azabicyclo[2.2.1]heptan-2-yl)-5-(4-chloro-2-ethyl-2H-indazol-5-yl)-3-methyl-3,7-dihydro-4H-pyrrolo[2,3-d]pyrimidin-4-one, rac-((1S,4S,7S)-7-amino-2-azabicyclo[2.2.1]heptan-2-yl)-3-(7-chlorobenzo[d]thiazol-6-yl)-5-methyl-1,5-dihydro-4H-pyrazolo[3,4-d]pyrimidin-4-one, rac-5-(4-chloro-2-methyl-2H-indazol-5-yl)-3-methyl-2-((1S,4S,7S)-7-(methylamino)-2-azabicyclo[2.2.1]heptan-2-yl)-3,7-dihydro-4H-pyrrolo[2,3-d]pyrimidin-4-one, endo-6-[3-amino-8-azabicyclo[3.2.1]octan-8-yl]-3-(4-chloro-2-methyl-2H-indazol-5-yl)-5-methyl-1H,4H,5H-pyrazolo[3,4-d]pyrimidin-4-one, 3-(4-chloro-2-methyl-2H-indazol-5-yl)-6-{3,8-diazabicyclo[3.2.1]octan-8-yl}-5-methyl-1H,4H,5H-pyrazolo[3,4-d]pyrimidin-4-one, 6-[(1R,3S)-1-amino-3-hydroxy-8-azaspiro[4.5]decan-8-yl]-3-(4-chloro-2-methyl-2H-indazol-5-yl)-5-methyl-1H,4H,5H-pyrazolo[3,4-d]pyrimidin-4-one, 6-[(4S)-4-amino-2-oxa-8-azaspiro[4.5]decan-8-yl]-3-(4-chloro-2-methyl-2H-indazol-5-yl)-5-methyl-1H,4H,5H-pyrazolo[3,4-d]pyrimidin-4-one, exo-6-[3-amino-8-azabicyclo[3.2.1]octan-8-yl]-3-(4-chloro-2-methyl-2H-indazol-5-yl)-5-methyl-1H,4H,5H-pyrazolo[3,4-d]pyrimidin-4-one, 3-(4-chloro-2-methyl-2H-indazol-5-yl)-6-{2,7-diazaspiro[3.5]nonan-7-yl}-5-methyl-1H,4H,5H-pyrazolo[3,4-d]pyrimidin-4-one, 6-[(1R)-1-amino-8-azaspiro[4.5]decan-8-yl]-3-(4-chloro-2-methyl-2H-indazol-5-yl)-5-methyl-1H,4H,5H-pyrazolo[3,4-d]pyrimidin-4-one, 6-[(3S,4S)-4-amino-3-methyl-2-oxa-8-azaspiro[4.5]decan-8-yl]-3-(4-chloro-2-methyl-2H-indazol-5-yl)-5-methyl-1H,4H,5H-pyrazolo[3,4-d]pyrimidin-4-one, 6-[(1R,3R)-1-amino-3-fluoro-8-azaspiro[4.5]decan-8-yl]-3-(4-chloro-2-methyl-2H-indazol-5-yl)-5-methyl-1H,4H,5H-pyrazolo[3,4-d]pyrimidin-4-one, 3-(4-chloro-2-methyl-2H-indazol-5-yl)-5-methyl-6-{3-oxa-7,9-diazabicyclo[3.3.1]nonan-7-yl}-1H,4H,5H-pyrazolo[3,4-d]pyrimidin-4-one, 3-(3,4-dichloro-2-methyl-2H-indazol-5-yl)-5-methyl-6-{3-oxa-7,9-diazabicyclo[3.3.1]nonan-7-yl}-1H,4H,5H-pyrazolo[3,4-d]pyrimidin-4-one, 6-[(3S,4S)-4-amino-3-methyl-2-oxa-8-azaspiro[4.5]decan-8-yl]-3-(3,4-dichloro-2-methyl-2H-indazol-5-yl)-5-methyl-1H,4H,5H-pyrazolo[3,4-d]pyrimidin-4-one, 6-[(3S,4S)-4-amino-3-methyl-2-oxa-8-azaspiro[4.5]decan-8-yl]-3-(4-chloro-2-ethyl-2H-indazol-5-yl)-5-methyl-1H,4H,5H-pyrazolo[3,4-d]pyrimidin-4-one, 6-[(1S,2R,3S,5R)-3-amino-2-fluoro-8-azabicyclo[3.2.1]octan-8-yl]-3-(4-chloro-2-methyl-2H-indazol-5-yl)-5-methyl-1H,4H,5H-pyrazolo[3,4-d]pyrimidin-4-one, 2-[(3S,4S)-4-amino-3-methyl-2-oxa-8-azaspiro[4.5]decan-8-yl]-5-(4-chloro-2-ethyl-2H-indazol-5-yl)-3-methyl-3H,4H,7H-pyrrolo[2,3-d]pyrimidin-4-one, 5-(4-chloro-2-ethyl-2H-indazol-5-yl)-2-(1,4-diazepan-1-yl)-3-methyl-3H,4H,7H-pyrrolo[2,3-d]pyrimidin-4-one, rac-2-[(1R,2R,5R)-2-amino-8-azabicyclo[3.2.1]octan-8-yl]-5-(4-chloro-2-methyl-2H-indazol-5-yl)-3-methyl-3H,4H,7H-pyrrolo[2,3-d]pyrimidin-4-one, rac-5-(4-chloro-2-methyl-2H-indazol-5-yl)-2-[(1R,6S)-3,9-diazabicyclo[4.2.1]nonan-9-yl]-3-methyl-3H,4H,7H-pyrrolo[2,3-d]pyrimidin-4-one, rac-2-(4-aminoazepan-1-yl)-5-(4-chloro-2-ethyl-2H-indazol-5-yl)-3-methyl-3H,4H,7H-pyrrolo[2,3-d]pyrimidin-4-one, rel-2-((1R,4R,7R)-7-amino-2-azabicyclo[2.2.1]heptan-2-yl)-5-(4-chloro-2-ethyl-2H-indazol-5-yl)-3-methyl-3,7-dihydro-4H-pyrrolo[2,3-d]pyrimidin-4-one, rel-2-((1S,4S,7S)-7-amino-2-azabicyclo[2.2.1]heptan-2-yl)-5-(4-chloro-2-ethyl-2H-indazol-5-yl)-3-methyl-3,7-dihydro-4H-pyrrolo[2,3-d]pyrimidin-4-one, rel-2-((1R,4R,7R)-7-amino-2-azabicyclo[2.2.1]heptan-2-yl)-5-(4-chloro-2-methyl-2H-indazol-5-yl)-3-methyl-3,7-dihydro-4H-pyrrolo[2,3-d]pyrimidin-4-one, rel-2-((1S,4S,7S)-7-Amino-2-azabicyclo[2.2.1]heptan-2-yl)-5-(4-chloro-2-methyl-2H-indazol-5-yl)-3-methyl-3,7-dihydro-4H-pyrrolo[2,3-d]pyrimidin-4-one, 5-(2-((1R,2R,4S)-2-amino-7-azabicyclo[2.2.1]heptan-7-yl)-3-methyl-4-oxo-4,7-dihydro-3H-pyrrolo[2,3-d]pyrimidin-5-yl)-4-chloro-2-ethyl-2H-indazole-3-carbonitrile, 6-(endo-3-amino-8-azabicyclo[3.2.1]octan-8-yl)-3-(3,4-dichloro-2-methyl-2H-indazol-5-yl)-5-methyl-1,5-dihydro-4H-pyrazolo[3,4-d]pyrimidin-4-one, 6-(endo-3-amino-3-methyl-8-azabicyclo[3.2.1]octan-8-yl)-3-(3,4-dichloro-2-methyl-2H-indazol-5-yl)-5-methyl-1,5-dihydro-4H-pyrazolo[3,4-d]pyrimidin-4-one, 6-((3R,4S)-4-amino-3-fluoropiperidin-1-yl)-3-(3,4-dichloro-2-methyl-2H-indazol-5-yl)-5-methyl-1,5-dihydro-4H-pyrazolo[3,4-d]pyrimidin-4-one, 2-((1R,2S,3S,5S)-3-amino-2-fluoro-8-azabicyclo[3.2.1]octan-8-yl)-5-(3,4-dichloro-2-methyl-2H-indazol-5-yl)-3-methyl-3,7-dihydro-4H-pyrrolo[2,3-d]pyrimidin-4-one, 2-(rac-(1R,2S,4S)-2-amino-7-azabicyclo[2.2.1]heptan-7-yl)-5-(4-chloro-2-methyl-2H-indazol-5-yl)-3-methyl-3,7-dihydro-4H-pyrrolo[2,3-d]pyrimidin-4-one, 5-(4-chloro-2-methyl-2H-indazol-5-yl)-3-methyl-2-((1S,2S,4R)-2-(methylamino)-7-azabicyclo[2.2.1]heptan-7-yl)-3,7-dihydro-4H-pyrrolo[2,3-d]pyrimidin-4-one, 2-((1R,2S,4S)-2-amino-7-azabicyclo[2.2.1]heptan-7-yl)-5-(3,4-dichloro-2-methyl-2H-indazol-5-yl)-3-methyl-3,7-dihydro-4H-pyrrolo[2,3-d]pyrimidin-4-one, 2-((1R,2R,4S)-2-amino-7-azabicyclo[2.2.1]heptan-7-yl)-5-(3-chloro-2-methyl-2H-indazol-5-yl)-3-methyl-3,7-dihydro-4H-pyrrolo[2,3-d]pyrimidin-4-one, 2-((1R,2S,4S)-2-amino-7-azabicyclo[2.2.1]heptan-7-yl)-3-methyl-5-(3,4,7-trichloro-2-methyl-2H-indazol-5-yl)-3,7-dihydro-4H-pyrrolo[2,3-d]pyrimidin-4-one, 2-((1R,2R,4S)-2-amino-7-azabicyclo[2.2.1]heptan-7-yl)-5-(5-chloro-3-methoxyquinoxalin-6-yl)-3-methyl-3,7-dihydro-4H-pyrrolo[2,3-d]pyrimidin-4-one, 2-((1R,2R,4S)-2-amino-7-azabicyclo[2.2.1]heptan-7-yl)-5-(5-chloro-3-(dimethylamino)quinoxalin-6-yl)-3-methyl-3,7-dihydro-4H-pyrrolo[2,3-d]pyrimidin-4-one, 6-((1R,4R,7R)-7-amino-2-azabicyclo[2.2.1]heptan-2-yl)-3-(3,4-dichloro-2-methyl-2H-indazol-5-yl)-5-methyl-1,5-dihydro-4H-pyrazolo[3,4-d]pyrimidin-4-one, 2-((1R,4R,7R)-7-amino-2-azabicyclo[2.2.1]heptan-2-yl)-5-(3,4-dichloro-2-methyl-2H-indazol-5-yl)-3-methyl-3,7-dihydro-4H-pyrrolo[2,3-d]pyrimidin-4-one, rac-2-((1R,2R,4S)-2-amino-2-methyl-7-azabicyclo[2.2.1]heptan-7-yl)-5-(3,4-dichloro-2-methyl-2H-indazol-5-yl)-3-methyl-3,7-dihydro-4H-pyrrolo[2,3-d]pyrimidin-4-one, 2-((1R,4R,7R)-7-amino-2-azabicyclo[2.2.1]heptan-2-yl)-5-(3-chloro-4-fluoro-2-methyl-2H-indazol-5-yl)-3-methyl-3,7-dihydro-4H-pyrrolo[2,3-d]pyrimidin-4-one, rac-6-((1R,2R,4S)-2-amino-2-methyl-7-azabicyclo[2.2.1]heptan-7-yl)-3-(3,4-dichloro-2-methyl-2H-indazol-5-yl)-5-methyl-1,5-dihydro-4H-pyrazolo[3,4-d]pyrimidin-4-one, 2-(endo-3-amino-8-azabicyclo[3.2.1]octan-8-yl)-5-(5-chloroquinoxalin-6-yl)-3-methyl-3,7-dihydro-4H-pyrrolo[2,3-d]pyrimidin-4-one, 3-(3,4-dichloro-2-methyl-2H-indazol-5-yl)-6-((1R,2R,4S)-2-(ethylamino)-7-azabicyclo[2.2.1]heptan-7-yl)-5-methyl-1,5-dihydro-4H-pyrazolo[3,4-d]pyrimidin-4-one, 2-((1R,2R,4S)-2-amino-7-azabicyclo[2.2.1]heptan-7-yl)-5-(4-chloro-2-(2-methoxyethyl)-2H-indazol-5-yl)-3-methyl-3,7-dihydro-4H-pyrrolo[2,3-d]pyrimidin-4-one, 3-(3,4-dichloro-2-methyl-2H-indazol-5-yl)-6-((1R,2R,4S)-2-(isopropylamino)-7-azabicyclo[2.2.1]heptan-7-yl)-5-methyl-1,5-dihydro-4H-pyrazolo[3,4-d]pyrimidin-4-one, 2-[(4S)-4-amino-2-oxa-8-azaspiro[4.5]decan-8-yl]-5-(2-ethyl-2H-indazol-5-yl)-3-methyl-3H,4H,7H-pyrrolo[2,3-d]pyrimidin-4-one, 2-[(4S)-4-amino-2-oxa-8-azaspiro[4.5]decan-8-yl]-5-(2-ethyl-4-fluoro-2H-indazol-5-yl)-3-methyl-3H,4H,7H-pyrrolo[2,3-d]pyrimidin-4-one, 2-[(4S)-4-amino-2-oxa-8-azaspiro[4.5]decan-8-yl]-5-(7-chloro-2-ethyl-2H-indazol-6-yl)-3-methyl-3H,4H,7H-pyrrolo[2,3-d]pyrimidin-4-one, 2-[(4S)-4-amino-2-oxa-8-azaspiro[4.5]decan-8-yl]-5-(2-ethyl-2H-indazol-6-yl)-3-methyl-3H,4H,7H-pyrrolo[2,3-d]pyrimidin-4-one, 2-[(4S)-4-amino-2-oxa-8-azaspiro[4.5]decan-8-yl]-5-(2-ethyl-7-fluoro-2H-indazol-6-yl)-3-methyl-3H,4H,7H-pyrrolo[2,3-d]pyrimidin-4-one, 2-[(endo)-3-amino-3-(difluoromethyl)-8-azabicyclo[3.2.1]octan-8-yl]-5-(4-chloro-2-methyl-2H-indazol-5-yl)-3-methyl-3H,4H,7H-pyrrolo[2,3-d]pyrimidin-4-one, 2-[(4S)-4-amino-2-oxa-8-azaspiro[4.5]decan-8-yl]-5-(2-ethyl-7-fluoro-2H-indazol-5-yl)-3-methyl-3H,4H,7H-pyrrolo[2,3-d]pyrimidin-4-one, 2-[(3R,4S)-4-amino-3-fluoropiperidin-1-yl]-5-(7-chloro-1,3-benzothiazol-6-yl)-3-methyl-3H,4H,7H-pyrrolo[2,3-d]pyrimidin-4-one, 5-(4-chloro-2-methyl-2H-indazol-5-yl)-2-[(1S,6R)-3,9-diazabicyclo[4.2.1]nonan-9-yl]-3-methyl-3H,4H,7H-pyrrolo[2,3-d]pyrimidin-4-one, 5-(4-chloro-2-methyl-2H-indazol-5-yl)-2-[(1R,6S)-3,9-diazabicyclo[4.2.1]nonan-9-yl]-3-methyl-3H,4H,7H-pyrrolo[2,3-d]pyrimidin-4-one, 5-(4-chloro-2-ethyl-2H-indazol-5-yl)-2-{(1R,5R)-3,6-diazabicyclo[3.2.1]octan-3-yl}-3-methyl-3H,4H,7H-pyrrolo[2,3-d]pyrimidin-4-one, 5-(4-chloro-2-ethyl-2H-indazol-5-yl)-2-{(1S,5S)-3,6-diazabicyclo[3.2.1]octan-3-yl}-3-methyl-3H,4H,7H-pyrrolo[2,3-d]pyrimidin-4-one, 5-(4-chloro-2-ethyl-2H-indazol-5-yl)-2-[(1S,5R)-3,6-diazabicyclo[3.2.1]octan-6-yl]-3-methyl-3H,4H,7H-pyrrolo[2,3-d]pyrimidin-4-one, 5-(4-chloro-2-ethyl-2H-indazol-5-yl)-2-[(1R,5S)-3,6-diazabicyclo[3.2.1]octan-6-yl]-3-methyl-3H,4H,7H-pyrrolo[2,3-d]pyrimidin-4-one 2-[(3S,4S)-4-amino-3-methyl-2-oxa-8-azaspiro[4.5]decan-8-yl]-5-(4-chloro-7-fluoro-2-methyl-2H-indazol-5-yl)-3-methyl-3H,4H,7H-pyrrolo[2,3-d]pyrimidin-4-one, 2-[(endo)-2-amino-2-methyl-7-azabicyclo[2.2.1]heptan-7-yl]-5-(4-chloro-2-methyl-2H-indazol-5-yl)-3-methyl-3H,4H,7H-pyrrolo[2,3-d]pyrimidin-4-one, rac-5-(4-chloro-2-ethyl-2H-indazol-5-yl)-2-{2,6-diazaspiro[3.4]octan-6-yl}-3-methyl-3H,4H,7H-pyrrolo[2,3-d]pyrimidin-4-one, 2-[(1R,2S,3S,5S)-3-amino-2-fluoro-8-azabicyclo[3.2.1]octan-8-yl]-5-(4-chloro-2-ethyl-2H-indazol-5-yl)-3-methyl-3H,4H,7H-pyrrolo[2,3-d]pyrimidin-4-one, 2-[(1R,2R,4S)-2-amino-7-azabicyclo[2.2.1]heptan-7-yl]-5-[8-chloro-2-(dimethylamino)quinolin-7-yl]-3-methyl-3H,4H,7H-pyrrolo[2,3-d]pyrimidin-4-one, and 2-[(1R,2R,4S)-2-amino-7-azabicyclo[2.2.1]heptan-7-yl]-5-[8-chloro-2-(methylamino)quinolin-7-yl]-3-methyl-3H,4H,7H-pyrrolo[2,3-d]pyrimidin-4-one.

Methods for the Preparation of Compounds of Formula (I)

Compounds of the formula (I) can be prepared in accordance with synthetic methods well known to the skilled person.

According to a further aspect of the invention there is provided a process for preparing a compound of formula (I), or a tautomer, stereoisomer, pharmaceutically acceptable salt, or solvate thereof, which comprises:

[Chem. 27]

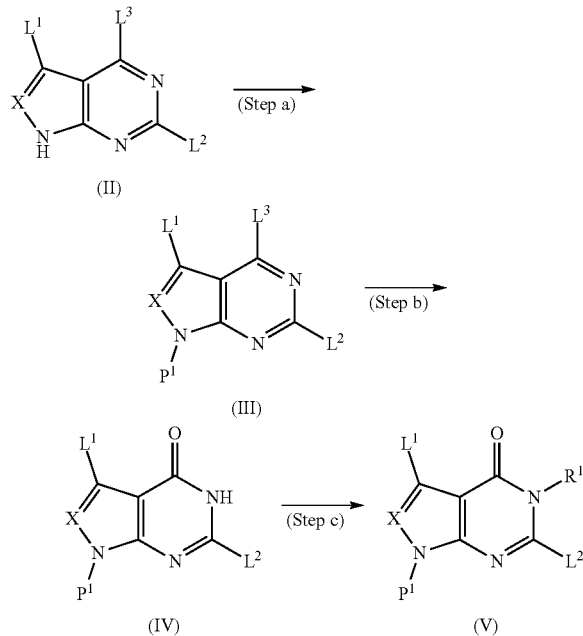

(wherein $P^1$ is a protecting group, $L^1$, $L^2$ and $L^3$ are leaving groups, $R^1$ and X are as defined above). $L^1$, $L^2$, and $L^3$ can be, for example, any of chrolide, bromide and iodide.

Step a

In this step, the compound of formula (II) is protected to produce the compound of formula (III).

The compounds of formula (II) were either commercially available, or are prepared using methods analogous to those described in the examples.

Examples of the protecting group represented by $P^1$ in the compound of formula (III) include ((2-trimethylsilyl)ethoxy)methyl (SEM) or tetrahydro-2H-pyran-2-yl (THP).

The process typically comprises, reacting a compound of formula (II) with ((2-trimethylsilyl)ethoxy)methylchloride (SEMCl) in a suitable solvent, a suitable base at a suitable temperature. Examples of suitable bases are sodium hydride, triethylamine or N,N-diisopropylethylamine. Examples of suitable solvents are tetrahydrofuran or N,N-dimethylformamide. The amount of SEMCl used is usually 1 to 10 moles, and preferably 1 to 5 moles, per mole of the compound represented by formula (II). The amount of the base used is generally 1 to 100 moles, preferably 1 to 10 moles, per mole of the compound represented by formula (II).

The process typically comprises, reacting a compound of formula (II) with 3,4-dihydro-2H-pyran in a suitable solvent, a suitable acid at a suitable temperature. Examples of suitable acids are p-toluenesufonic acid monohydrate or camphorsulfonic acid. Examples of suitable solvents are tetrahydrofuran or methylene chloride. The amount of 3,4-dihydro-2H-pyran used is usually 1 to 10 moles, and preferably 1 to 5 moles, per mole of the compound represented by formula (II). The amount of the acid used is generally 0.001 to 100 moles, preferably 0.01 to 10 moles, per mole of the compound represented by formula (II).

The reaction temperature generally ranges from 0 to 200° C., preferably room temperature to 150° C. The reaction time generally ranges from 5 minutes to 7 days, preferably 30 minutes to 4 days. The thus-obtained compound of formula (III) can be subjected to the subsequent step after or without isolation or purification by known separation and purification means, such as concentration, vacuum concentration, crystallization, solvent extraction, reprecipitation, and chromatography.

Step b

In this step, the compound of formula (III) is hydroxylated to produce the compound of formula (IV).

The process typically comprises, reacting a compound of formula (III) with a suitable base in a suitable solvent at a suitable temperature. Examples of suitable base are sodium hydroxide or potassium hydroxide. Examples of suitable solvents are tetrahydrofuran, 1,2-dimethoxyethane or 1,4-dioxane with water.

The amount of the base used is usually 0.1 to 100 moles, and preferably 1 to 20 moles, per mole of the compound represented by formula (III).

The reaction temperature generally ranges from 0 to 200° C., preferably room temperature to 150° C. The reaction time generally ranges from 5 minutes to 7 days, preferably 30 min to 4 days.

The thus-obtained compound of formula (IV) can be subjected to the subsequent step after or without isolation or purification by known separation and purification means, such as concentration, vacuum concentration, crystallization, solvent extraction, reprecipitation, and chromatography.

Step c

In this step, the compound of formula (IV) is reacting with an alkylating agent such as iodomethane to produce the compound of formula (V).

The process typically comprises, reacting a compound of formula (IV) with iodomethane and a suitable base in a suitable solvent at a suitable temperature. Examples of suitable base are potassium carbonate or cesium carbonate. Examples of suitable solvents are N,N-dimethylformamide or N-methyl-2-pyrrolidinone.

The amount of iodomethane used is usually 1 to 100 moles, and preferably 1 to 20 moles, per mole of the compound represented by formula (IV). The amount of the base used is usually 1 to 100 moles, and preferably 1 to 20 moles, per mole of the compound represented by formula (IV).

The reaction temperature generally ranges from 0 to 200° C., preferably 0 to 100° C. The reaction time generally ranges from 5 minutes to 7 days, preferably 30 min to 4 days.

The thus-obtained compound of formula (V) can be subjected to the subsequent step after or without isolation or purification by known separation and purification means, such as concentration, vacuum concentration, crystallization, solvent extraction, reprecipitation, and chromatography.

[Chem. 28]

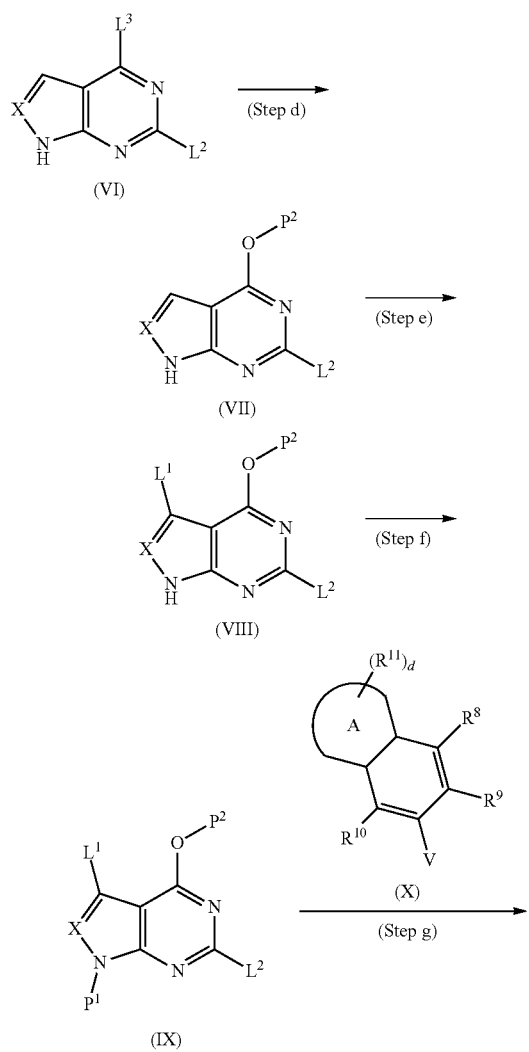

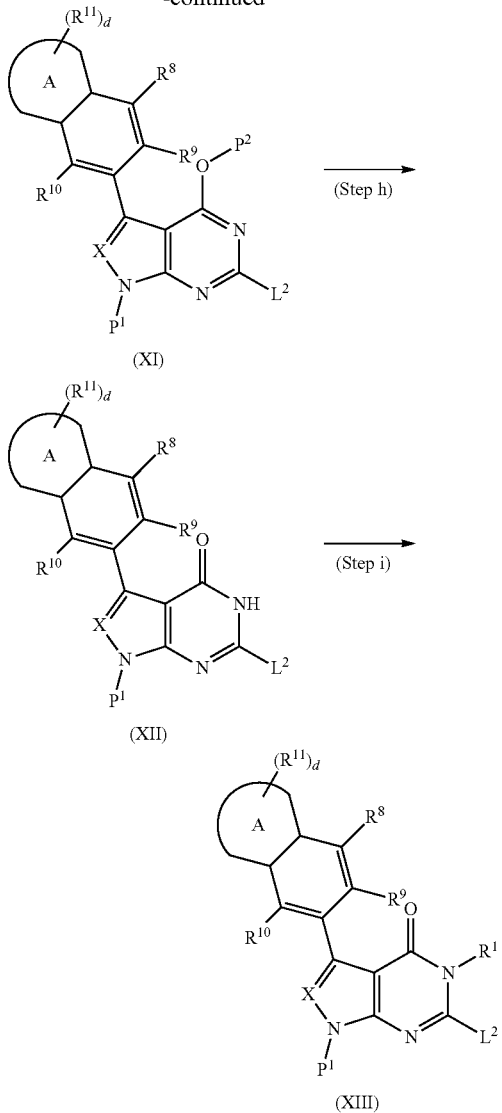

(wherein $P^1$, $P^2$ are protecting groups, $L^1$, $L^2$ and $L^3$ are leaving groups, V represents a metal or metaloid residue (such as boronic acid, pinacol boronate), Ring A, $R^7$, $R^8$, $R^9$, $R^{10}$, $R^{11}$, X and d are as defined above).

Step d

In this step, the compound of formula (VI) is reacting with an alcohol $P^2$—OH to produce the compound of formula (VII).

The compounds of formula (VI) were either commercially available, or are prepared using methods analogous to those described in the examples.

The process typically comprises, reacting a compound of formula (VI) with an alcohol such as 4-methoxybenzyl alcohol and a suitable base in a suitable solvent at a suitable temperature. Examples of suitable base are potassium tert-butoxide or sodium tert-butoxide. Examples of suitable solvents are tetrahydrofuran or 1,4-dioxane.

The amount of the alcohol used is usually 1 to 100 moles, and preferably 1 to 20 moles, per mole of the compound represented by formula (VI). The amount of the base used is usually 1 to 100 moles, and preferably 1 to 20 moles, per mole of the compound represented by formula (VI).

The reaction temperature generally ranges from 0 to 200° C., preferably 0 to 100° C. The reaction time generally ranges from 5 minutes to 7 days, preferably 30 min to 4 days.

The thus-obtained compound of formula (VII) can be subjected to the subsequent step after or without isolation or purification by known separation and purification means, such as concentration, vacuum concentration, crystallization, solvent extraction, reprecipitation, and chromatography.

Step e

In this step, the compound of formula (VII) is halogenated to produce the compound of formula (VIII) where $L^1$ is halogen.

The process typically comprises, reacting a compound of formula (VII) with a halogenating reagent in a suitable solvent at a suitable temperature. Examples of halogenating reagents are N-bromosuccinimide or N-iodosuccinimide. Examples of suitable solvents are tetrahydrofuran or N,N-dimethylformamide.

The amount of the halogenating reagent used is usually 1 to 100 moles, and preferably 1 to 20 moles, per mole of the compound represented by formula (VII).

The reaction temperature generally ranges from −78 to 100° C., preferably −20 to 100° C. The reaction time generally ranges from 5 minutes to 7 days, preferably 30 min to 4 days.

The thus-obtained compound of formula (VIII) can be subjected to the subsequent step after or without isolation or purification by known separation and purification means, such as concentration, vacuum concentration, crystallization, solvent extraction, reprecipitation, and chromatography.

Step f

This step can be performed in a similar manner as in step a.

Step g

In this step, the compound of formula (IX) is subjected to a coupling reaction with the compound of formula (X) to produce the compound of formula (XI).

The compounds of formula (X) were either commercially available, or are prepared using methods analogous to those described in the examples.

The process typically comprises, reacting a compound of formula (IX) with a compound of formula (X) with a suitable catalyst, a suitable base in a suitable solvent at a suitable temperature.

Examples of suitable catalysts are [1,1'-bis(diphenylphosphino)ferrocene]palladium(II) dichloride, tetrakistriphenylphosphine palladium or tris(dibenzylideneacetone)dipalladium(0) with a suitable ligand (such as triphenylphosphine, tri-tert-butylphosphine, 2-dicyclohexylphosphino-2',4',6'-triisopropylbiphenyl). Another example of a suitable catalyst is (di-tert-butyl(4-dimethylaminophenyl)phosphine)dichloropalladium(ii). Examples of suitable base are sodium carbonate, potassium carbonate or potassium phosphate. Examples of suitable solvents are tetrahydrofuran, 1,2-dimethoxyethane or 1,4-dioxane with water).

The amount of a compound of formula (X) used is usually 1 to 100 moles, and preferably 1 to 20 moles, per mole of the compound represented by formula (IX). The amount of the catalyst used is usually 0.0001 to 1 moles, and preferably 0.001 to 0.5 moles, per mole of the compound represented by formula (IX). The amount of the ligand used is usually 0.0001 to 4 moles, and preferably 0.001 to 2 moles, per mole of the compound represented by formula (IX). The amount of the base used is usually 0.1 to 10 moles, and preferably 1 to 5 moles, per mole of the compound represented by formula (IX).

The reaction temperature generally ranges from 0 to 200° C., preferably room temperature to 150° C. The reaction time generally ranges from 5 minutes to 7 days, preferably 30 min to 4 days.

The thus-obtained compound of formula (XI) can be subjected to the subsequent step after or without isolation or purification by known separation and purification means, such as concentration, vacuum concentration, crystallization, solvent extraction, reprecipitation, and chromatography.

Step h

In this step, the compound of formula (XI) is deprotected to produce the compound of formula (XII).

The process typically comprises, reacting a compound of formula (XI) with 2,3-dichloro-5,6-dicyano-p-benzoquinone in a suitable solvent at a suitable temperature. Example of suitable solvent is dichloromethane.

The amount of 2,3-dichloro-5,6-dicyano-p-benzoquinone used is usually 1 to 100 moles, and preferably 1 to 20 moles, per mole of the compound represented by formula (XI).

The reaction temperature generally ranges from 0 to 200° C., preferably room temperature to 100° C. The reaction time generally ranges from 5 minutes to 7 days, preferably 30 min to 4 days.

The thus-obtained compound of formula (XII) can be subjected to the subsequent step after or without isolation or purification by known separation and purification means, such as concentration, vacuum concentration, crystallization, solvent extraction, reprecipitation, and chromatography.

Step i

This step can be performed in a similar manner as in step c.

[Chem. 29]

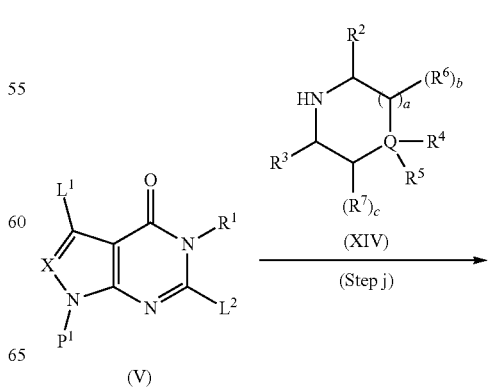

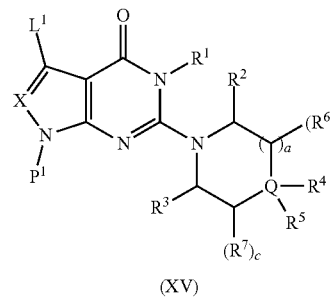

(XV)

(wherein P¹ is a protecting group, L¹, L² are leaving groups, R¹, R², R³, R⁴, R⁵, R⁶, R⁷, Q, X, a, b and c are as defined above).

Step j

In this step, the compound of formula (V) is subjected to a coupling reaction with the compound of formula (XIV) to produce the compound of formula (XV).

Optionally this is performed in the presence of an activating agent.

The compounds of formula (XIV) were either commercially available, or are prepared using methods analogous to those described in the examples.

The process typically comprises, reacting a compound of formula (V) with a compound of formula (XIV) and suitable base in a suitable solvent at a suitable temperature. Example of a suitable base is N,N-diisopropylethylamine. Examples of suitable solvents are N-methyl-2-pyrrolidinone or N,N-dimethylformamide.

The amount of a compound of formula (XIV) used is usually 1 to 100 moles, and preferably 1 to 10 moles, per mole of the compound represented by formula (V). The amount of the base used is usually 1 to 100 moles, and preferably 1 to 20 moles, per mole of the compound represented by formula (V).

The reaction temperature generally ranges from room temperature to 200° C., preferably room temperature to 150° C. The reaction time generally ranges from 5 minutes to 7 days, preferably 30 min to 4 days.

The thus-obtained compound of formula (XV) can be subjected to the subsequent step after or without isolation or purification by known separation and purification means, such as concentration, vacuum concentration, crystallization, solvent extraction, reprecipitation, and chromatography.

[Chem. 30]

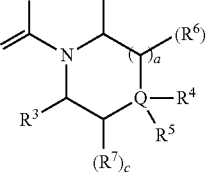

(XV)

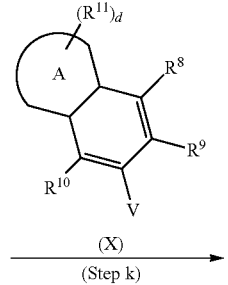

(XVI)

(wherein P¹ is a protecting group, L¹ is a leaving group, V represents a metal or metaloid residue (such as boronic acid or pinacol boronate), Ring A, R¹, R², R³, R⁴, R⁵, R⁶, R⁷, R⁸, R⁹, R¹⁰, R¹¹, Q, X, a, b, c and d are as defined above).

Step k

This step can be performed in a similar manner as in step g.

[Chem. 31]

(XIII)

-continued

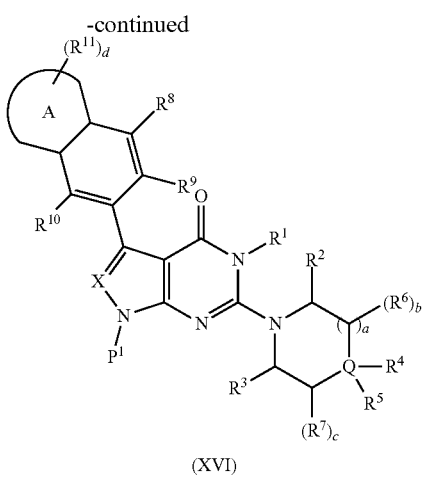

(XVI)

(wherein P¹ is a protecting group, L² is a leaving group, Ring A, R¹, R², R³, R⁴, R⁵, R⁶, R⁷, R⁸, R⁹, R¹⁰, R¹¹, Q, X, a, b, c and d are as defined above).

Step l

This step can be performed in a similar manner as in step j.

[Chem. 32]

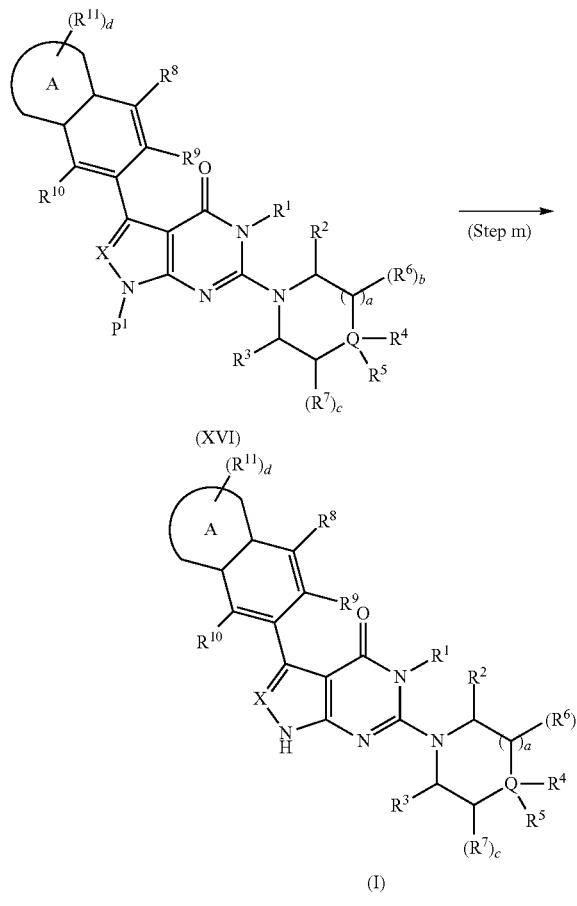

(wherein P¹ is a protecting group, Ring A, R¹, R², R³, R⁴, R⁵, R⁶, R⁷, R⁸, R⁹, R¹⁰, R¹¹, Q, X, a, b, c and d are as defined above).

Step m

In this step, the compound of formula (XVI) is deprotected to produce the compound of formula (I).

Process typically comprises any suitable deprotection reaction, the conditions of which will depend upon the nature of the protecting group. When the protecting group P¹ represents ((2-trimethylsilyl)ethoxy)methyl group (SEM), such a deprotection reaction will typically comprise the use of a suitable acid in a suitable solvent, followed by removal of the hydroxymethyl adduct formed during the acid deprotection of the SEM protecting group with ethylenediamine or sodium hydroxide. For example, the acid may suitably comprise of trifluoroacetic acid or hydrogen chloride and the solvent may suitably comprise dichloromethane, chloroform, N,N-dimethylformamide or methanol. Optionally a mixture of solvents may be used, for example water and methanol. The second step involves concentration in vacuo, followed by dissolving the crude material in a suitable solvent such as methanol and treatment with a suitable scavenging reagent such as ethylenediamine or sodium hydroxide.

The amount of the acid used is usually 1 to 100 moles, and preferably 1 to 20 moles, per mole of the compound represented by formula (XVI). The amount of the scavenging reagent used is usually 1 to 100 moles, and preferably 1 to 20 moles, per mole of the compound represented by formula (XVI).

The reaction temperature generally ranges from 0 to 200° C., preferably room temperature to 100° C. The reaction time generally ranges from 5 minutes to 7 days, preferably 30 min to 4 days.

Where the protecting group is a tetrahydro-2H-pyran-2-yl group (THP), a strong acid such as hydrochloric acid may be used in a suitable solvents such as methanol at a suitable temperature.

The amount of the acid used is usually 1 to 100 moles, and preferably 1 to 20 moles, per mole of the compound represented by formula (XVI).

The reaction temperature generally ranges from 0 to 200° C., preferably room temperature to 100° C. The reaction time generally ranges from 5 minutes to 7 days, preferably 30 min to 4 days.

The thus-obtained compound of Formula (I) can be isolated and purified by known separation and purification means, such as concentration, vacuum concentration, crystallization, solvent extraction, reprecipitation, and chromatography.

The deprotection may be carried out in accordance with the procedures described herein as general procedures for preparation of compounds of formula (I).

[Chem. 33]

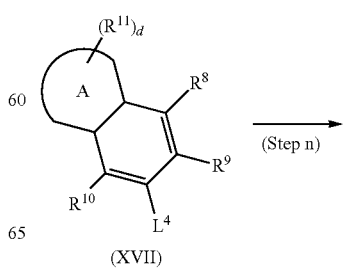

(XVII)

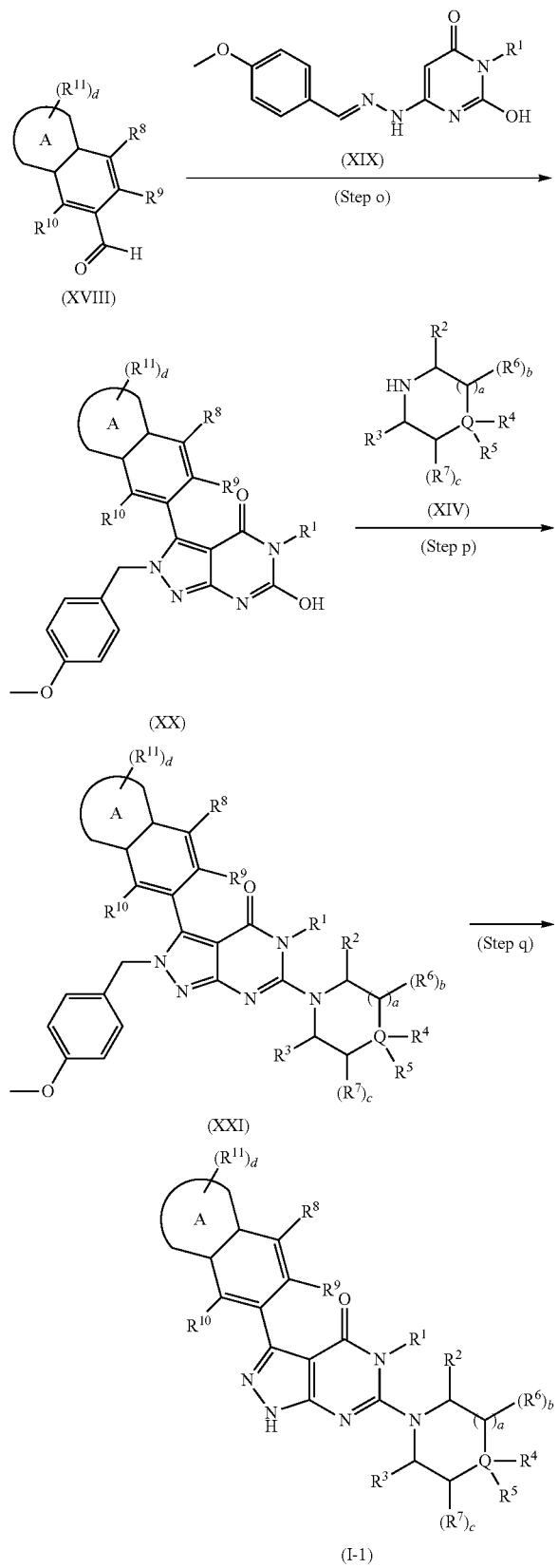

(wherein L⁴ is a leaving group, R¹, R², R³, R⁴, R⁵, R⁶, R⁷, R⁸, R⁹, R¹⁰, R¹¹, Ring A, Q, a, b, c and d are as defined above). L⁴ can be, for example, any of bromide, iodide and trifluoromethanesulfonate.

Step n

In this step, the compound of formula (XVII) is subjected to a formylation to produce the compound of formula (XVIII).

The process typically comprises, reacting a compound of formula (XVII) with an organometallic reagent such as i-PrMgCl and a formylating agent such as N,N-dimethylformamide in a suitable solvent at a suitable temperature. Example of a suitable solvent is tetrahydrofuran.

The amount of i-PrMgCl used is usually 1 to 10 moles, and preferably 1 to 5 moles, per mole of the compound represented by formula (XVII). The amount of N,N-dimethylformamide used is usually 1 to 20 moles, and preferably 1 to 10 moles, per mole of the compound represented by formula (XVII).

The reaction temperature generally ranges from 0 to 100° C., preferably 0 to 60° C. The reaction time generally ranges from 5 minutes to 7 days, preferably 30 min to 4 days.

The thus-obtained compound of formula (XVIII) can be subjected to the subsequent step after or without isolation or purification by known separation and purification means, such as concentration, vacuum concentration, crystallization, solvent extraction, reprecipitation, and chromatography.

Step o

In this step, the compound of formula (XVIII) is subjected to a cyclization reaction with the compound of formula (XIX) to produce the compound of formula (XX).

The process typically comprises, reacting a compound of formula (XVIII) and a compound of formula (XIX) with a suitable base in a suitable solvent at a suitable temperature. Example of a suitable base is piperidine. Examples of suitable solvents are N,N-dimethylformamide and isopropanol.

The amount of a compound of formula (XVIII) used is usually 1 to 10 moles, and preferably 1 to 5 moles, per mole of the compound represented by formula (XIX). The amount of the base used is usually 1 to 10 moles, and preferably 1 to 5 moles, per mole of the compound represented by formula (XIX).

The reaction temperature generally ranges from 0 to 100° C., preferably 0 to 60° C. The reaction time generally ranges from 5 minutes to 7 days, preferably 30 min to 4 days.

The thus-obtained compound of formula (XX) can be subjected to the subsequent step after or without isolation or purification by known separation and purification means, such as concentration, vacuum concentration, crystallization, solvent extraction, reprecipitation, and chromatography.

Compounds of formula (XIX) are known or prepared my methods analogous to those described in the literature.

Step p

In this step, the compound of formula (XX) is subjected to a coupling reaction with the compound of formula (XIV) to produce the compound of formula (XXI).

The compounds of formula (XIV) were either commercially available, or are prepared using methods analogous to those described in the examples.

The process typically comprises, reacting a compound of formula (XX) with a compound of formula (XIV), an activating agent such as PyBOP and suitable base in a suitable solvent at a suitable temperature. Examples of suitable bases are DBU or N,N-diisopropylethylamine. Examples of suitable solvents are N-methyl-2-pyrrolidinone or N,N-dimethylformamide.

The amount of a compound of formula (XVIII) used is usually 1 to 10 moles, and preferably 1 to 5 moles, per mole of the compound represented by formula (XX). The amount of PyBOP used is usually 1 to 10 moles, and preferably 1 to 5 moles, per mole of the compound represented by formula (XX). The amount of the base used is usually 1 to 20 moles, and preferably 1 to 10 moles, per mole of the compound represented by formula (XX).

The reaction temperature generally ranges from 0 to 100° C., preferably 0 to 60° C. The reaction time generally ranges from 5 minutes to 7 days, preferably 30 min to 4 days.

The thus-obtained compound of formula (XXI) can be subjected to the subsequent step after or without isolation or purification by known separation and purification means, such as concentration, vacuum concentration, crystallization, solvent extraction, reprecipitation, and chromatography.

Step q

In this step, the compound of formula (XXI) is deprotected to produce the compound of formula (I-1).

The process typically comprises, reacting a compound of formula (XXI) with a suitable acid in a suitable solvent at a suitable temperature. Example of a suitable acid is trifluoromethanesulfonic acid. Examples of suitable solvents are dichloromethane or chloroform.

The amount of trifluoromethanesulfonic acid used is usually 1 to 100 moles, and preferably 1 to 20 moles, per mole of the compound represented by formula (XXI).

The reaction temperature generally ranges from 0 to 200° C., preferably 0 to 100° C. The reaction time generally ranges from 5 minutes to 7 days, preferably 30 min to 4 days.

The thus-obtained compound of Formula (I-1) can be isolated and purified by known separation and purification means, such as concentration, vacuum concentration, crystallization, solvent extraction, reprecipitation, and chromatography.

The deprotection may be carried out in accordance with the procedures described herein as general procedures for preparation of compounds of formula (I-1).

In any of the above steps, protection of a substituent, and removal or conversion of the protecting group, can be suitably performed. For example, for functional groups such as amino, imino, hydroxy, carboxy, carbonyl, and amide groups, as well as functional groups having an active proton, such as indole, protected reagents can be used, or a protecting group can be introduced into such a functional group according to a usual method; afterward, the protecting group can be removed in an appropriate step in each production method.

The protecting group of an amino group or protecting group of an imino group is not particularly limited, insofar as it has a protecting function. Examples of such protecting groups include aralkyl groups, such as benzyl, p-methoxybenzyl, 3,4-dimethoxybenzyl, o-nitrobenzyl, p-nitrobenzyl, benzhydryl, trityl, and cumyl; lower alkanoyl groups, such as formyl, acetyl, propionyl, butyryl, pivaloyl, trifluoroacetyl, and trichloroacetyl; benzoyl; arylalkanoyl groups, such as phenylacetyl and phenoxyacetyl; lower alkoxycarbonyl groups, such as methoxycarbonyl, ethoxycarbonyl, propyloxycarbonyl, and tert-butoxycarbonyl; aralkyloxycarbonyl groups, such as p-nitrobenzyloxycarbonyl and phenethyloxycarbonyl; lower alkylsilyl groups, such as trimethylsilyl and tert-butyldimethylsilyl; tetrahydropyranyl; trimethylsilylethoxymethyl; lower alkylsulfonyl groups, such as methylsulfonyl, ethylsulfonyl, and tert-butylsulfonyl; lower alkylsulfinyl groups, such as tert-butylsulfinyl; arylsulfonyl groups, such as benzenesulfonyl and toluenesulfonyl; and imido groups, such as phthalimido. In particular, trifluoroacetyl, acetyl, tert-butoxycarbonyl, benzyloxycarbonyl, trimethylsilylethoxymethyl, cumyl, and the like are preferable.

The protecting group of a hydroxy group is not particularly limited insofar as it has a protecting function. Examples of such protecting groups include lower alkyl groups, such as methyl, ethyl, propyl, isopropyl, and tert-butyl; lower alkylsilyl groups, such as trimethylsilyl and tert-butyldimethylsilyl; lower alkoxymethyl groups, such as methoxymethyl and 2-methoxyethoxymethyl; tetrahydropyranyl; trimethylsilylethoxymethyl; aralkyl groups, such as benzyl, p-methoxybenzyl, 2,3-dimethoxybenzyl, o-nitrobenzyl, p-nitrobenzyl, and trityl; and acyl groups, such as formyl, acetyl, and trifluoroacetyl. In particular, methyl, methoxymethyl, tetrahydropyranyl, trimethylsilylethoxymethyl, tert-butyldimethylsilyl, and acetyl are preferable.

The protecting group of a carboxy group is not particularly limited insofar as it has a protecting function. Examples of such protecting groups include lower alkyl groups, such as methyl, ethyl, propyl, isopropyl, and tert-butyl; halo-lower-alkyl groups, such as 2,2,2-trichloroethyl; lower alkenyl groups, such as allyl; trimethylsilylethoxymethyl; and aralkyl groups, such as benzyl, p-methoxybenzyl, p-nitrobenzyl, benzhydryl, and trityl. In particular, methyl, ethyl, tert-butyl, allyl, benzyl, p-methoxybenzyl, trimethylsilylethoxymethyl, and the like are preferable.

The protecting group of a carbonyl group is not particularly limited insofar as it has a protecting function. Examples of such protecting groups include ethylene ketal, trimethylene ketal, dimethyl ketal, ethylene acetal, trimethylene acetal, dimethyl acetal, and like ketals and acetals.

The protecting group of an amide group or the protecting group of a functional group having an active proton, such as indole, is not particularly limited, insofar as it has a protecting function. Examples of such protecting groups include lower alkyl groups, such as methyl, ethyl, propyl, isopropyl, and tert-butyl; lower alkylsilyl groups, such as trimethylsilyl and tert-butyldimethylsilyl; lower alkoxymethyl groups, such as methoxymethyl and 2-methoxyethoxymethyl; tetrahydropyranyl; trimethylsilylethoxymethyl; aralkyl groups, such as benzyl, p-methoxybenzyl, 2,3-dimethoxybenzyl, o-nitrobenzyl, p-nitrobenzyl, and trityl; and acyl groups, such as formyl, acetyl, and trifluoroacetyl. In particular, methyl, methoxymethyl, tetrahydropyranyl, trimethylsilylethoxymethyl, tert-butyldimethylsilyl, and acetyl are preferable.

The method for removing such a protecting group may vary depending on the type of protecting group, stability of the target compound (I), etc. For example, the following methods can be used: solvolysis using an acid or a base according to the method disclosed in a publication (Protective Groups in Organic Synthesis, third edition, T. W. Green, John Wiley & Sons (1999)) or a similar method, i.e., a method comprising reacting with 0.01 moles or a large excess of an acid, preferably trifluoroacetic acid, formic acid, or hydrochloric acid, or an equimolar to large excessive molar amount of a base, preferably potassium hydroxide or calcium hydroxide; chemical reduction using a metal hydride complex etc.; or catalytic reduction using a palladium-carbon catalyst, Raney nickel catalyst, etc.

The compound of the present invention can be easily isolated and purified by common isolation and purification means. Examples of such means include solvent extraction, recrystallization, preparative reversed-phase high-performance liquid chromatography, column chromatography, preparative thin-layer chromatography, and the like.

When the compound of the present invention has isomers such as optical isomers, stereoisomers, rotational isomers, and tautomers, any of the isomers and mixtures thereof is included within the scope of the compound of the present invention, unless otherwise specified. For example, when the compound of the present invention has optical isomers, the optical isomer separated from a racemic mixture is also included within the scope of the compound of the present invention, unless otherwise specified. Each of such isomers can be obtained as a single compound by known synthesis and separation means (e.g., concentration, solvent extraction, and column chromatography, recrystallization).

As stated above, unless otherwise specified, the compound of the present invention includes all of the enantiomers and mixtures thereof. The compound of the present invention may be a mixture of R and S enantiomers. Such a mixture may be a mixture comprising 55% or more, 60% or more, 65% or more, 70% or more, 75% or more, 80% or more, 85% or more, 90% or more, 95% or more, or 99% or more of R enantiomer; a mixture comprising 55% or more, 60% or more, 65% or more, 70% or more, 75% or more, 80% or more, 85% or more, 90% or more, 95% or more, or 99% or more of S enantiomer; or the like.

Methods for chiral resolution include, for example: a diastereomer method of causing a chiral resolving agent to act on the compound of the present invention to form a salt, and resolving one of the enantiomers using a solubility difference etc. of the obtained salt; a preferential crystallization method of adding one of the enantiomers to a supersaturated solution of a racemate as a seed for crystallization; and column chromatography such as HPLC using a chiral column. A chiral resolving agent that can be used in the diastereomer method can be appropriately selected from, for example, acid resolving agents such as tartaric acid, malic acid, lactic acid, mandelic acid, 10-camphorsulfonic acid, and derivatives thereof; and basic resolving agents such as brucine, strychnine, quinine, and like alkaloid compounds, amino acid derivatives, cinchonidine, and α-methylbenzylamine. One of the enantiomers of the compound of the present invention alone can be obtained not only by obtaining the compound of the present invention as a mixture of enantiomers and then conducting chiral resolution as above, but also by obtaining one enantiomer of the compound of the present invention through chiral resolution as above or by other methods, and using it as a synthetic raw material of the compound of the present invention. Furthermore, methods for obtaining one of the enantiomers of the compound of the present invention or its raw material compound include a method of preferentially obtaining one of the enantiomers by adjusting reaction conditions for a catalyst or the like in a reaction step of generating asymmetric carbon.

Compounds of formula (I) may optionally be converted to a pharmacologically acceptable salt. The compound of the present invention or a salt thereof may be in the form of crystals. Single crystals and polymorphic crystal mixtures are included within the scope of the compound of the present invention or a salt thereof. Such crystals can be produced by crystallization according to a crystallization method known per se in the art. The compound of the present invention or a salt thereof may be a solvate (e.g., a hydrate) or a non-solvate. Any of such forms are included within the scope of the compound of the present invention or a salt thereof. Compounds labeled with one or more isotopes (e.g., $^2H$, $^3H$, $^{14}C$, $^{35}S$, and $^{125}I$) are also included within the scope of the compound of the present invention or a salt thereof.

The salts of the compounds of the present invention or of the intermediates thereof refer to common salts used in the field of organic chemistry. Examples of such salts include base addition salts to a carboxy group when the compound has a carboxy group, and acid addition salts to an amino or basic heterocyclic group when the compound has an amino or basic heterocyclic group.

Examples of base addition salts include alkali metal salts, such as sodium salts and potassium salts; alkaline earth metal salts, such as calcium salts and magnesium salts; ammonium salts; and organic amine salts, such as trimethylamine salts, triethylamine salts, dicyclohexylamine salts, ethanolamine salts, diethanolamine salts, triethanolamine salts, procaine salts, and N,N'-dibenzylethylenediamine salts.

Examples of acid addition salts include inorganic acid salts, such as hydrochloride, sulfate, nitrate, phosphate, and perchlorate; organic acid salts, such as acetate, formate, maleate, fumarate, tartrate, citrate, ascorbate, and trifluoroacetate; and sulfonates such as methanesulfonate, isethionate, benzenesulfonate, and p-toluenesulfonate.

Also encompassed by formula (I) are any pro-drugs of the compounds of the formula (I). By "prodrugs" is meant for example any compound that is converted in vivo into a biologically active compound of the formula (I). Such prodrugs can, for example, be produced by replacing appropriate functionalities present in the compounds of the formula (I) with certain moieties known to those skilled in the art. In one embodiment, certain compounds of the formula (I) may themselves act as prodrugs of other of the compounds of the formula (I). In one embodiment formula (I) does not include prodrugs of the compounds of the formula (I) within its scope.

Due to their excellent SHP2 inhibitory activity, the compounds of the present invention or salts thereof are useful as a pharmaceutical preparation for prophylaxsis or treatment of a disease or condition mediated by SHP2.

Examples of the "a disease or condition mediated by SHP2" include diseases or condition whose incidence can be reduced, and whose symptoms can be remitted, relieved, and/or completely cured by eliminating, suppressing, and/or inhibiting SHP2 function. Such diseases may encompass diseases in which SHP2 activity/existence/status is abnormal associated with aberrant RAS-ERK signalling pathway or receptor tyrosine kinase signalling pathway status, or diseases in which SHP2 activity/existence/status is abnormal associated with aberrant immune response status. Examples of "a disease or condition mediated by SHP2" include, but are not limited to, malignant tumors etc.

The type of malignant tumor to be treated by the compound or a salt thereof of the present invention is not particularly limited. Examples of such malignant tumors include head and neck cancers, esophagus cancer, gastric cancer, colon cancer, rectum cancer, liver cancer, gallbladder cancer, cholangiocarcinoma, biliary tract cancer, pancreatic cancer, lung cancer, breast cancer, ovarian cancer, cervical cancer, endometrial cancer, renal cancer, bladder cancer, prostate cancer, testicular tumor, osteosarcoma, soft-tissue sarcoma, leukemia, myelodysplastic syndrome, chronic myeloproliferative disease, malignant lymphoma, multiple myeloma, skin cancer, brain tumor, mesothelioma, and the like.

When the compounds or salts thereof of the present invention are used as pharmaceutical preparations, a pharmaceutically acceptable carrier can be added, if required, thereby forming a suitable dosage form according to prevention and treatment purposes. Examples of the dosage form include oral preparations, injections, suppositories, ointments, patches, and the like; preferably oral preparations. Such dosage forms can be formed by methods conventionally known to persons skilled in the art.

As the pharmaceutically acceptable carrier, various conventional organic or inorganic carrier materials used as preparation materials may be blended as an excipient, binder, disintegrant, lubricant, or coating agent in solid preparations; or as a solvent, solubilizing agent, suspending agent, isotonizing agent, pH adjuster/buffer, or soothing agent in liquid preparations. Moreover, pharmaceutical preparation additives, such as antiseptics, antioxidants, colorants, sweeteners, and stabilizers, may also be used, if required.

When a solid preparation for oral administration is prepared, optionally an excipient, a binder, a disintegrator, a lubricant, a colorant, a sweetener, and the like may be added to the compound of the present invention; and the resulting mixture may be formulated into tablets, coated tablets, granules, powders, capsules, etc., according to an ordinary method.

When an injection is prepared, a pH adjuster, a buffer, a stabilizer, an isotonizing agent, a local anesthetic, and the like may be added, as necessary, to the compound of the present invention; and the resulting mixture may be formulated into subcutaneous, intramuscular, and intravenous injections according to an ordinary method.

The amount of the compound of the present invention to be incorporated in each of such dosage unit forms depends on the condition of the patient to whom the compound is administered, the dosage form, etc. In general, in the case of an oral agent, an injection, and a suppository, the amount of the compound of the present invention is preferably 0.05 to 1000 mg, 0.01 to 500 mg, and 1 to 1000 mg, respectively, per dosage unit form.

The amount of the active compound administered will be dependent on the mammal being treated, the severity of the disorder or condition, the rate of administration, the disposition of the compound and the discretion of the prescribing physician. An effective dosage is typically in the range of about 0.001 to about 100 mg per kg body weight per day, preferably about 0.01 to about 40 mg/kg/day, in single or divided doses. For example, the daily dose of the compound of the present invention for an adult (body weight: 50 kg) may be generally about 0.05 to about 5000 mg, and preferably about 0.5 to about 2000 mg. In some instances, dosage levels below the lower limit of the aforesaid range may be more than adequate, while in other cases still larger doses may be used without causing any harmful side effect. Such larger doses typically may be divided into several smaller doses for administration throughout the day. The total daily dose may be administered in single or divided doses. At the physician's discretion, the total daily dose may fall outside of the typical range based on an average human subject e.g., those having a weight of about 50 to about 70 kg. The physician will readily be able to determine doses for subjects whose weight falls outside this range, such as infants and the elderly.

EXAMPLES

Synthetic Methods

By following methods similar and/or analogous to general procedures below, the compounds set out below were prepared.

The following synthetic procedures are provided for illustration of the methods used; for a given preparation or step the precursor used may not necessarily derive from the individual batch synthesised according to the step in the description given.

Where a compound is described as a mixture of two diastereoisomers/epimers, the configuration of the stereocentre is not specified and is represented by straight lines.

As understood by a person skilled in the art, compounds synthesised using the protocols as indicated may exist as a solvate e.g. hydrate, and/or contain residual solvent or minor impurities. Compounds isolated as a salt form, may be integer stoichiometric i.e. mono- or di-salts, or of intermediate stoichiometry.

Some of the compounds below are isolated as the salt, for example depending on the acid used in the purification method. Some compounds are isolated as the free base.

Compounds containing a single stereocentre are typically isolated as a single isomer using preparative chiral HPLC (as described in general methods); at (or towards) the final stage of the synthetic sequence. In these cases the stereochemistry is designated in accordance with IUPAC, using 'hashed' or 'solid' wedged lines. Unless stated otherwise, a straight line at a stereocentre indicates the compound exists as a mixture of both isomers.

Compounds containing a second stereocentre are typically isolated as a single isomer by preparative achiral and/or chiral HPLC.

The optical isomers may be characterised by their optical activity (i.e. as + and − isomers, or d and l isomers). The stereocentre can also assigned as "R or S" according to the nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog, *Angew. Chem. Int. Ed. Engl.*, 1966, 5, 385-415.

Optical isomers can be separated by a number of techniques including chiral chromatography (chromatography on a chiral support) and such techniques are well known to the person skilled in the art.

As an alternative to chiral chromatography, optical isomers of basic compounds can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulfonic acid, separating the diastereoisomeric salts by preferential crystallisation, and then dissociating the salts to give the individual enantiomer of the free base. Likewise, optical iomers of acidic compounds can be separated by forming diastereoisomeric salts with chiral amines such as Brucine, Cinchonidine, quinine etc.

Additionally enantiomeric separation can be achieved by covalently linking a enantiomerically pure chiral auxiliary onto the compound and then performing diastereoisomer separation using conventional methods such as chromatography. This is then followed by cleavage of the aforementioned covalent linkage to generate the appropriate enantiomerically pure product. Examples could include making menthol esters of an acidic compound.

Where compounds of the formula (I) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers.

Accordingly, the invention provides compositions containing a compound of the formula (I) having one or more chiral centres, wherein at least 55% (e.g. at least 60%, 65%, 70%, 75%, 80%, 85%, 90% or 95%) of the compound of the formula (I) is present as a single optical isomer (e.g. enantiomer or diastereoisomer). In one general embodiment, 99% or more (e.g. substantially all) of the total amount of the compound of the formula (I) may be present as a single optical isomer (e.g. enantiomer or diastereoisomer).

Compounds encompassing double bonds can have an E (entgegen) or Z (zusammen) stereochemistry at said double bond. Substituents on bivalent cyclic or (partially) saturated radicals may have either the cis- or trans-configuration. The terms cis and trans when used herein are in accordance with Chemical Abstracts nomenclature (J. Org. Chem. 1970, 35 (9), 2849-2867), and refer to the position of the substituents on a ring moiety.

Of special interest are those compounds of formula (I) which are stereochemically pure. When a compound of formula (I) is for instance specified as R, this means that the compound is substantially free of the S isomer. If a compound of formula (I) is for instance specified as E, this means that the compound is substantially free of the Z isomer. The terms cis, trans, R, S, E and Z are well known to a person skilled in the art.

The terms exo and endo refer to the stereochemistry of a bridged bicycloalkane, such as a substituted tropane, described in PAC, 1996, 68, 2193, basic terminology of stereochemistry (IUPAC Recommendations 1996). If a substituent, e.g. the amino group, is orientated towards the highest numbered bridge it is given the description exo; if it is orientated away from the highest numbered bridge it is given the description endo. Where there are two substituents on the same carbon atom, the terms exo and endo refer to the higher priority substituent. The FIGURE below illustrates the pictorial representation of how the amino tropane is defined in this patent.

[Chem. 34]

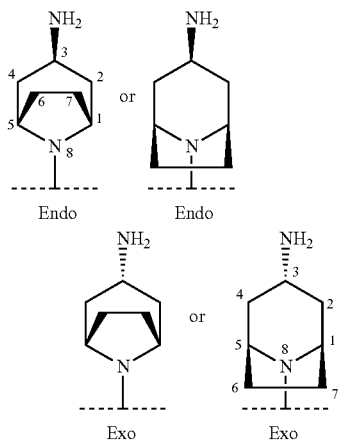

EXAMPLES

The invention will now be illustrated, but not limited, by reference to the specific embodiments described in the following examples. Compounds are named, for example, using an automated naming package such as AutoNom (MDL), using IUPAC rules or are as named by the chemical supplier. In the examples, the following abbreviations are used.

[Math. 1]
Ac acetyl
aq. aqueous
Boc tert-butyloxycarbonyl
Boc$_2$O di-tert-butyl dicarbonate
BuLi butyllithium
t-BuOK potassium tert-butoxide
t-BuONa sodium tert-butoxide
Cbz carboxybenzyl
DBU 1,8-diazabicyclo[5.4.0]undec-7-ene
DCM dichloromethane
DIAD diisopropyl azodicarboxylate
DIBAL-H diisobutylaluminum hydride
DIPEA N,N-diisopropylethylamine
DMA N,N-dimethylacetamide
DME 1,2-dimethoxyethane
DMEAD di-2-methoxyethyl azodicarboxylate
DMF N,N-dimethylformamide
DMSO dimethyl sulfoxide
Et$_2$O diethyl ether
EtOAc ethyl acetate
EtOH ethanol
h hour
HATU O-(7-azabenzotriazol-1-yl)-N,N,N',N'-tetramethyluronium hexafluorophosphate
HPLC high performance liquid chromatography
IPA isopropyl alcohol
LDA lithium diisopropylamide
i-PrMgCl isopropylmagnesium chloride
MeCN acetonitrile
[Math. 2]
MeOH methanol
min. minutes
MS mass spectrometry
MTBE tert-butyl methyl ether
NaOMe sodium methoxide
NBS N-bromosuccinimde
NCS N-chlorosuccinimide
NMP N-methyl-2-pyrrolidinone
NMR nuclear magnetic resonance spectroscopy
PMB p-methoxybenzyl
PyBOP (benzotriazol-1-yloxy)tripyrrolidinophosphonium hexafluorophosphate
RT room temperature
Sat. saturated
SEM (2-(trimethylsilyl)ethoxy)methyl
SEMCl 2-(trimethylsilyl)ethoxymethyl chloride
TBAF tetrabutylammonium fluoride
TBSCl tert-butyldimethylsilyl chloride
TEA triethylamine
TBME tert-butyl methyl ether
TFA trifluoroacetic acid
TH F tetrahydrofuran
TLC thin layer chromatography
TsCl p-toluenesulfonyl chloride
Z-chloride benzyl chloroformate
Synthetic Methods All starting materials and solvents were obtained either from commercial sources or prepared according to the literature citation. Unless otherwise stated all reactions were stirred. Organic solutions were routinely dried over anhydrous magnesium sulfate. Hydrogenations were performed on a Parr hydrogenator, a Thales H-cube flow reactor under the conditions stated or under a balloon of hydrogen. Microwave reactions were performed in Biotage(Registered Trademark) Initiator, a CEM Discover and Smithcreator microwave reactor, heating to a constant temperature using variable power microwave irradiation. Normal phase column chromatography was routinely carried out on an automated flash chromatography system such as CombiFlash Companion or CombiFlash RF system using pre-packed silica (230-400 mesh, 40-63 μm) cartridges. SCX was purchased from Supelco and treated with 1 M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with a solvent such as 1% $NH_3$ in MeOH. $NH_2$ ion exchange silica gel purification was done with Strata $NH_2$ (55 μm, 70 Å) columns, loaded directly onto the $NH_2$ column and eluting with a solvent such as methanol. Biotage(Registered Trademark) SNAP Ultra silica gel columns and Biotage(Registered Trademark) KP-NH SNAP silica gel columns were purchased from Biotage(Registered Trademark). Reverse phase purification was done using Biotage(Registered Trademark) SNAP Ultra C18 silica gel columns and were purchased from Biotage(Registered Trademark).

NMR Data $^1$H NMR spectra were acquired on a Bruker Avance III spectrometer at 400 MHz, an AL400 (400 MHz; produced by JEOL), a Mercury 400 (400 MHz; produced by Agilent Technologies, Inc.), a 500 MHz Bruker Avance III HD NMR Spectrometer or a Bruker Avance NEO NMR spectrometer (400 MHz) Either the central peaks of chloroform-d, dimethylsulfoxide-$d_6$ or an internal standard of tetramethylsilane were used as references. For NMR data, where the number of protons assigned is less than the theoretical number of protons in the molecule, it is assumed that the apparently missing signal(s) is/are obscured by solvent and/or water peaks. In addition, where spectra were obtained in protic NMR solvents, exchange of NH and/or OH protons with solvent occurs and hence such signals are normally not observed.

Analytical and Preparative LC-MS Systems

Analytical LC-MS System and Method Description

In the following examples, compounds were characterised by mass spectroscopy using the systems and operating conditions set out below. Where atoms with different isotopes are present and a single mass quoted, the mass quoted for the compound is the monoisotopic mass (i.e. $^{35}$Cl; $^{79}$Br etc.).

[Math. 3]
Shimadzu Nexera
HPLC System: Shimadzu SIL-30AC autosampler/2× Shimadzu LC-30AD pumps
Mass Spec Detector: Shimadzu LCMS-2020 single quadrupole MS
Second Detector: Shimadzu SPD-M20A diode array detector
MS Operating Conditions
Qarray DC voltage: 20V on ES Pos (−20V on ES Neg)
Drying gas flow: 20.0 L/min
DL Temperature: 300° C.
Heat Block Temperature: 350° C.
Nebulising Gas Flow: 1.5 L/min
Scan Range: 100-750 amu
Ionisation Mode: ElectroSpray Positive-Negative switching

[Math. 4]
Agilent 1290 Infinity II—6130 LC-MS System
HPLC System: Agilent 1290 Infinity II
Mass Spec Detector: Agilent 6130 single quadrupole
Second Detector: Agilent 1290 Infinity II Diode Array Detector
MS Operating Conditions
Capillary voltage: 3000V
Fragmentor/Gain: 70
Gain: 1
Drying gas flow: 13.0 L/min
Gas Temperature: 350° C.
Nebuliser Pressure: 40 psig
Scan Range: 150-1000 amu
Sheath Gas Temperature: 360° C.
Sheath Gas Flow: 10.0 L/min
Nozzle Voltage: 300 (+ve mode)/1750 (−ve mode)
Ionisation Mode: Agilent Jet Stream Electrospray Positive-Negative switching
LCMS spectra were alternatively measured with an SQD manufactured by Waters Corporation under the following two conditions, and the [M+H]$^+$ values were shown.

[Math. 5]
MS detection: ESI positive
UV detection: 254 nm
Column flow rate: 0.5 mL/min
Mobile phase: water/acetonitrile (0.1% formic acid)
Injection volume: 1 μL
Method
Column: Acguity BEH, 2.1×50 mm, 1.7 μm
Gradient:

| Time (min) | water/acetonitrile (0.1% formic acid) |
|---|---|
| 0 | 95/5 |
| 0.1 | 95/5 |
| 2.1 | 5/95 |
| 3.0 | STOP |

Preparative LC-MS System and Method Description

Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC-MS; *J Comb Chem.;* 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb Chem.;* 2003; 5(3); 322-9.

Several systems for purifying compounds via preparative LC-MS are described below although a person skilled in the art will appreciate that alternative systems and methods to those described could be used. From the information provided herein, or employing alternative chromatographic systems, a person skilled in the art could purify the compounds described herein by preparative LC-MS.

Mass Directed Purification LC-MS System

Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; J Comb Chem.; 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; J Comb Chem.; 2003; 5(3); 322-9.

One such system for purifying compounds via preparative LC-MS is described below although a person skilled in the art will appreciate that alternative systems and methods to those described could be used. In particular, normal phase preparative LC based methods might be used in place of the reverse phase methods described here. Most preparative LC-MS systems utilise reverse phase LC and volatile acidic modifiers, since the approach is very effective for the purification of small molecules and because the eluents are compatible with positive ion electrospray mass spectrometry. Employing other chromatographic solutions e.g. normal phase LC, alternatively buffered mobile phase, basic modifiers etc as outlined in the analytical methods described above could alternatively be used to purify the compounds.

[Math. 6]
Agilent 1260 LC-MS Preparative System
Hardware:
Autosampler: G2260A Prep ALS
Pumps: 2× G1361A Prep Pumps for preparative flow gradient, G1311C Quat Pump VL for pumping modifier in prep flow and G1310B Iso Pump for make-up pump flow
UV detector: G1365C 1260 MWD
MS detector: G6120B Quadrupole LC-MS
Fraction Collector: 2× G1364B 1260 FC-PS
G1968D Active Splitter
Software:
Agilent OpenLab C01.06
Agilent MS Operating Conditions:
Capillary voltage: 3000 V
Fragmentor/Gain: 70/1
Drying gas flow: 12.0 L/min
Drying Gas Temperature: 275° C.
Nebuliser Pressure: 40 psig
Vaporizer Temperature: 200° C.
Scan Range: 125-800 amu
Ionisation Mode: ElectroSpray Positive
[Math. 7]
Columns:
1. Waters XBridge Prep C18 5 m OBD 100×19 mm
    Typically used for ammonium bicarbonate-based methods
2. Waters SunFire Prep C18 OBD 5 m 100×19 mm
    Typically used for TFA-based methods
3. Waters XBridge Prep Phenyl 5 m OBD 100×19 mm
    Typically used for neutral pH ammonium acetate-based methods
4. Supelco Ascentis RP-Amide 5 m 100×21.2 mm
    Typically used for formic acid-based methods
5. Phenomenex Synergi Fusion-RP 4 m 100×21.2 mm
    Typically used for formic acid-based methods
Eluents:
Solvent A: Water
Solvent B: Acetonitrile
Solvent C: Choice of available modifiers:
    2.5% Trifluoroacetic acid in water
    2.5% Formic acid in water
    250 mM ammonium bicarbonate in water pH 9.4
    250 mM ammonium acetate
Make Up Solvent:
90:10 Methanol:Water+0.2% Formic Acid (for all chromatography types)
Methods:

According to the analytical trace the most appropriate preparative chromatography type was chosen. A typical routine was to run an analytical LC-MS using the type of chromatography (low or high pH) most suited for compound structure. Once the analytical trace showed good chromatography a suitable preparative method of the same type was chosen. Typical running conditions for both low and high pH chromatography methods were:

Flow rate: 25 mL/min
Gradient: Generally all gradients had an initial 0.4 min step with 95% A+5% B (with additional modifier C). Then according to analytical trace a 6.6 min gradient was chosen in order to achieve good separation (e.g. from 5% to 50% B for early retaining compounds; from 35% to 80% B for middle retaining compounds and so on)
Wash: 1.6 minute wash step was performed at the end of the gradient
Make Up flow rate: 0.8 mL/min
Solvent:
All compounds were usually dissolved in 100% MeOH or 100% DMSO From the information provided someone skilled in the art could purify the compounds described herein by preparative LC-MS.

[Math. 8]
Waters Fractionlynx System
Hardware:
2767 Dual Loop Autosampler/Fraction Collector
2525 preparative pump
CFO (column fluidic organiser) for column selection
RMA (Waters reagent manager) as make up pump
Waters ZQ Mass Spectrometer
Waters 2996 Photo Diode Array detector
Waters ZQ Mass Spectrometer
Software:
Masslynx 4.1
Waters MS Running Conditions:
Capillary voltage: 3.5 kV (3.2 kV on ES Negative)
Cone voltage: 25 V
Source Temperature: 120° C.
Multiplier: 500 V
Scan Range: 125-800 amu
Ionisation Mode: ElectroSpray Positive or ElectroSpray Negative Alternatively Reverse phase preparative HPLC column chromatography was performed at the following conditions.

[Math. 9]
Column: CAPCELL PAK C18 AQ manufactured by SHISEIDO, 30×50 mm, 5 μm
UV detection: 254 nm
Column flow rate: 40 mL/min
Mobile phase: water/acetonitrile (0.1% formic acid)

Injection volume: 1.0 mL

Basic gradient method: water/acetonitrile 0%-50% (8 minutes)

Achiral Preparative Chromatography

The compound examples described have undergone HPLC purification, where indicated, using methods developed following recommendations as described in Snyder L. R., Dolan J. W., High-Performance Gradient Elution The Practical Application of the Linear-Solvent-Strength Model, Wiley, Hoboken, 2007.

Chiral Preparative Chromatography

Preparative separations using Chiral Stationary Phases (CSPs) are the natural technique to apply to the resolution of enantiomeric mixtures. Equally, it can be applied to the separation of diastereomers and achiral molecules. Methods are well known in the art for optimising preparative chiral separations on CSPs and then using them to purify compounds. Such methods are described in Beesley T. E., Scott R. P. W.; Chiral Chromatography; Wiley, Chichester, 1998.

Preparation 1: 2-Chloro-4-((4-methoxybenzyl)oxy)-7H-pyrrolo[2,3-d]pyrimidine

[Chem. 35]

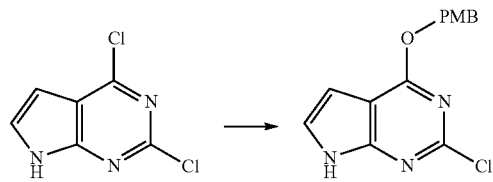

To a solution of 2,4-dichloro-7H-pyrrolo[2,3-d]pyrimidine (2.5 g, 13.3 mmol) and 4-methoxybenzyl alcohol (1.99 mL, 16.0 mmol) in 1,4-dioxane (37.5 mL) was added potassium tert-butoxide (5.97 g, 53.2 mmol) at RT. The mixture was stirred at RT for 1 h. Sat. NH$_4$Cl was added at RT. The precipitate was collected, washed with water and EtOAc, and dried at 50° C. overnight under reduced pressure to give the title compound (3.14 g). MS: [M+H]$^+$=290, 292.

Preparation 2: 5-Bromo-2-chloro-4-((4-methoxybenzyl)oxy)-7H-pyrrolo[2,3-d]pyrimidine

[Chem. 36]

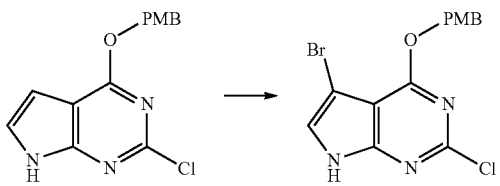

To a solution of 2-chloro-4-((4-methoxybenzyl)oxy)-7H-pyrrolo[2,3-d]pyrimidine (3.14 g, 10.8 mmol) in DMF (31.4 mL) was added NBS (2.12 g, 11.9 mmol) at −20° C. The mixture was stirred at −20° C. for 30 min. Sat. sodium thiosulfate (30 mL) and EtOAc (15 mL) were added. The mixture was stirred at RT for 30 min. The precipitate was collected, washed with water, and dried at 50° C. overnight under reduced pressure to give the title compound (3.78 g). MS: [M+H]$^+$=368, 370.

Preparation 3: 5-Bromo-2-chloro-4-((4-methoxybenzyl)oxy)-7-((2-(trimethylsilyl)ethoxy)methyl)-7H-pyrrolo[2,3-d]pyrimidine

[Chem. 37]

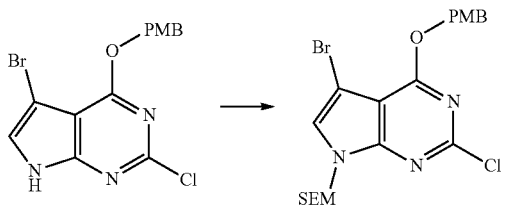

To a solution of 5-bromo-2-chloro-4-((4-methoxybenzyl)oxy)-7H-pyrrolo[2,3-d]pyrimidine (2.0 g, 5.43 mmol) in DMF (40 mL) were added sodium hydride (60% in mineral oil, 0.26 g, 6.51 mmol) and SEMCl (1.14 mL, 6.51 mmol) at 0° C. The mixture was stirred at 0° C. for 1 h. Sat. NH$_4$Cl was added and the mixture was extracted with EtOAc. The organic layer was washed with water and brine, dried over anhydrous Na$_2$SO$_4$, filtered, and concentrated in vacuo. The residue was purified by column chromatography on silica gel (gradient elution, 20-60% EtOAc/hexane) to give the title compound (2.68 g). MS: [M+H]$^+$=498, 500.

Preparation 4: 5-Bromo-2-chloro-7-((2-(trimethylsilyl)ethoxy)methyl)-3,7-dihydro-4H-pyrrolo[2,3-d]pyrimidin-4-one

[Chem. 38]

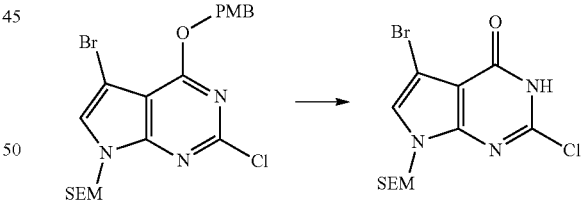

To a solution of 5-bromo-2-chloro-4-((4-methoxybenzyl)oxy)-7-((2-(trimethylsilyl)ethoxy)methyl)-7H-pyrrolo[2,3-d]pyrimidine (1.6 g, 3.21 mmol) in DCM (30.4 mL) were added 2,3-dichloro-5,6-dicyano-p-benzoquinone (2.18 g, 9.62 mmol) and water (1.6 mL) at RT. The mixture was stirred at RT for 3 days. CHCl$_3$ and sat. NaHCO$_3$ were added at RT. The mixture was filtered through a pad of Celite, and washed with CHCl$_3$ and water. The filtrate was extracted with CHCl$_3$, dried over anhydrous Na$_2$SO$_4$, filtered, and concentrated in vacuo. The residue was purified by column chromatography on silica gel (gradient elution, 0-60% EtOAc/hexane) to give the title compound (0.746 g). MS: [M+H]$^+$=378, 380.

Preparation 5: 5-Bromo-2-chloro-3-methyl-7-((2-(trimethylsilyl)ethoxy)methyl)-3,7-dihydro-4H-pyrrolo[2,3-d]pyrimidin-4-one

[Chem. 39]

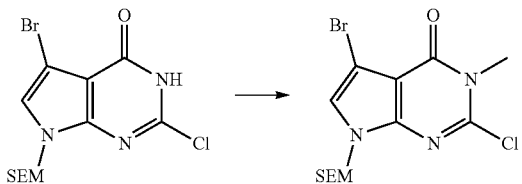

To a solution of 5-bromo-2-chloro-7-((2-(trimethylsilyl)ethoxy)methyl)-3,7-dihydro-4H-pyrrolo[2,3-d]pyrimidin-4-one (0.746 g, 1.97 mmol) in DMF (7.46 mL) were added $K_2CO_3$ (0.544 g, 3.94 mmol) and iodomethane (0.245 mL, 3.94 mmol) at RT. The mixture was stirred at RT for 30 min, poured into water, and extracted with EtOAc. The organic layer was washed with water and brine, dried over anhydrous $Na_2SO_4$, filtered, and concentrated in vacuo. The residue was purified by column chromatography on silica gel (gradient elution, 0-60% EtOAc/hexane) to give the title compound (0.7 g). MS: $[M+H]^+$=392, 394.

Preparation 6: 2,4-Dichloro-5-iodo-7-((2-(trimethylsilyl)ethoxy)methyl)-7H-pyrrolo[2,3-d]pyrimidine

[Chem. 40]

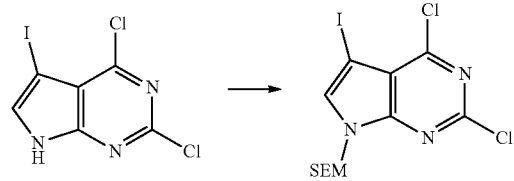

To a mixture of 2,4-dichloro-5-iodo-7H-pyrrolo[2,3-d]pyrimidine (1 g, 3.18 mmol) and DIPEA (1.66 mL, 9.55 mmol) in THF (10 mL) were added SEMCl (1.13 mL, 6.37 mmol) at RT. The mixture was stirred at RT for 2 h, and concentrated in vacuo. The residue was purified by column chromatography on silica gel (gradient elution, 0-30% EtOAc/hexane) to give the title compound (1.5 g). MS: $[M+H]^+$=444, 446.

Preparation 7: 2-Chloro-5-iodo-7-((2-(trimethylsilyl)ethoxy)methyl)-3,7-dihydro-4H-pyrrolo[2,3-d]pyrimidin-4-one

[Chem. 41]

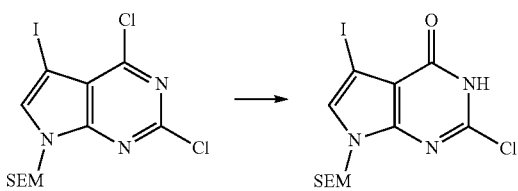

To a mixture of 2,4-dichloro-5-iodo-7-((2-(trimethylsilyl)ethoxy)methyl)-7H-pyrrolo[2,3-d]pyrimidine (0.3 g, 0.67 mmol) in 1,4-dioxane (4 mL) was added 4 M KOH (1 mL, 4 mmol) at RT. The mixture was stirred at 60° C. overnight, cooled to RT, acidified with aq. HCl, and extracted with EtOAc. The organic layer was washed with brine, dried over anhydrous $Na_2SO_4$, filtered, and concentrated in vacuo. The residue was purified by column chromatography on silica gel (gradient elution, 0-70% EtOAc/hexane) to give the title compound (0.17 g). MS: $[M+H]^+$=426, 428.

Preparation 8: 2-Chloro-5-iodo-3-methyl-7-((2-(trimethylsilyl)ethoxy)methyl)-3,7-dihydro-4H-pyrrolo[2,3-d]pyrimidin-4-one

[Chem. 42]

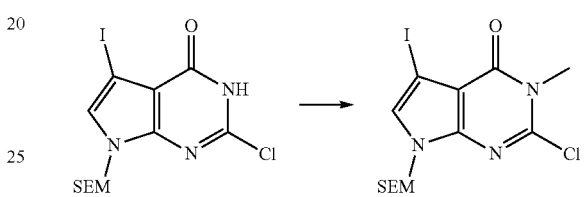

To a mixture of 2-chloro-5-iodo-7-((2-(trimethylsilyl)ethoxy)methyl)-3,7-dihydro-4H-pyrrolo[2,3-d]pyrimidin-4-one (0.17 g, 0.40 mmol) and $K_2CO_3$ (0.11 g, 0.79 mmol) in NMP (1 mL) was added iodomethane (0.05 mL, 0.79 mmol) at RT. The mixture was stirred at RT for 3 h, diluted with EtOAc, washed with water and brine, dried over anhydrous $Na_2SO_4$, filtered, and concentrated in vacuo. The residue was purified by column chromatography on silica gel (gradient elution, 0-50% EtOAc/hexane) to give the title compound (0.15 g). MS: $[M+H]^+$=440, 442.

Preparation 9: Benzyl [endo-3-(tert-butoxycarbonyl)amino]-8-azabicyclo[3.2.1]octane-8-carboxylate

[Chem. 43]

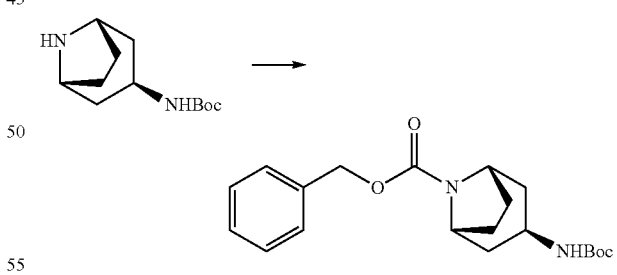

To a suspension of tert-butyl (endo-8-azabicyclo[3.2.1]octan-3-yl)carbamate (1.0 g, 4.4 mmol) and TEA (1.2 equiv., 5.3 mmol) in THF (5.0 mL) and DCM (3.0 mL) was added Z-chloride (0.69 mL, 4.9 mmol) at 0° C. in an ice bath. The ice bath was removed and the mixture was stirred at RT for 1 h. Z-chloride (0.13 mL, 0.88 mmol) was added to the mixture at RT and the mixture was stirred at RT for additional 3 h. To the mixture were added dil. HCl aq. and EtOAc, and the mixture was extracted with EtOAc (×3). The organic extracts were washed with water and brine, dried over anhydrous $Na_2SO_4$, filtered, and concentrated in vacuo.

The residue (a pale yellow oil, 1.7 g) was purified by column chromatography on silica gel (gradient elution, 0-8% MeOH/CHCl₃) to give the title compound (1.4 g, 4.0 mmol, 91% Yield) as a colorless solid. MS: [M+H]⁺=361.

Preparation 10: Benzyl [endo-3-(tert-butoxycarbonyl)(methyl)amino]-8-azabicyclo[3.2.1]octane-8-carboxylate

[Chem. 44]

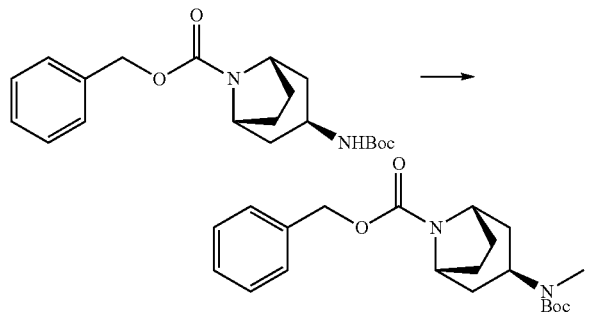

To benzyl [endo-3-(tert-butoxycarbonyl)amino]-8-azabicyclo[3.2.1]octane-8-carboxylate (1.4 g, 4.0 mmol) in DMF (5.0 mL) was added sodium hydride (60% in mineral oil, 0.24 g, 5.99 mmol) at 0° C. and the mixture was stirred at 0° C. for 40 min. Iodomethane (0.50 mL, 7.99 mmol) was added to the mixture at 0° C. and the ice bath was removed in 5 min. After stirred at RT for 30 min, sodium hydride (60% in mineral oil, 32 mg, 0.799 mmol) and iodomethane (0.12 mL, 2.00 mmol) were added to the mixture and the mixture was stirred at RT for additional 30 min. To the mixture were added dil. aqueous citric acid solution and EtOAc, and the mixture was extracted with EtOAc. The organic extracts were washed with water and brine, and dried over Na₂SO₄. Concentration of the filtrate gave the crude product (a yellow oil, 1.7 g), which was purified by column chromatography on silica gel (gradient elution, 0-70% EtOAc/hexane) to give the title compound (879 mg, 2.3 mmol, 58% Yield) as a colorless oil. MS: [M+H]⁺=375.

Preparation 11: tert-Butyl (endo-8-azabicyclo[3.2.1]octan-3-yl)(methyl)carbamate

[Chem. 45]

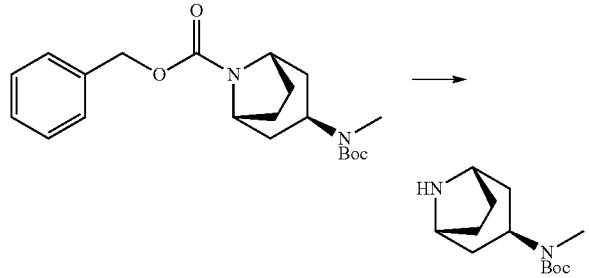

Benzyl [endo-3-(tert-butoxycarbonyl)(methyl)amino]-8-azabicyclo[3.2.1]octane-8-carboxylate (875 mg, 2.3 mmol) and 10% Pd—C(M) Wet (500 mg) was suspended in MeOH (5.0 mL) and the mixture was substituted with H₂. The mixture was stirred at RT for 3 h. The reaction mixture was applied to a pad of Celite and the filtrate was concentrated. The residue was dissolved in MeOH and was again applied to a pad of Celite and the filtrate was concentrated to give the title compound (556 mg, 2.3 mmol, 99% Yield) as a pale yellow oil-solid. MS: [M+H]⁺=241.

Preparation 12: 8-Benzyl-3-methyl-8-azabicyclo[3.2.1]octan-3-ol

[Chem. 46]

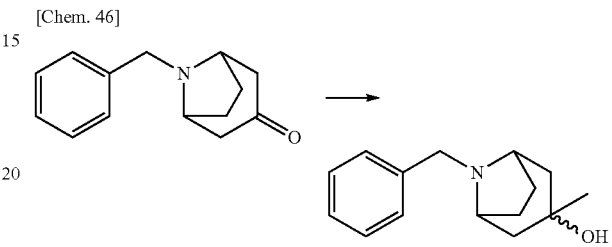

To a solution of 8-benzyl-8-azabicyclo[3.2.1]octan-3-one (4.28 g, 19.9 mmol) in THF (47.0 mL) was added 3.0 mol/L methylmagnesium chloride in THF solution (29.4 mL, 88.4 mmol) under MeCN-dry ice bath, and the reaction was stirred for 30 min at this temperature and then 20 h at RT. Sat. NH₄Cl solution was added at 0° C. and the mixture was extracted with EtOAc. The combined organic layers were washed with water and sat. sodium chloride solution, and dried over anhydrous sodium sulfate. After the desiccant was filtered off, the solvent was removed at reduced pressure. The residue was purified by column chromatography on silica gel (NH silica gel, gradient elution, 20-50% CHCl₃/hexane), to give the title compound (4.50 g). MS: [M+H]⁺=232.

Preparation 13: N-(endo-8-Benzyl-3-methyl-8-azabicyclo[3.2.1]octan-3-yl)acetamide

[Chem. 47]

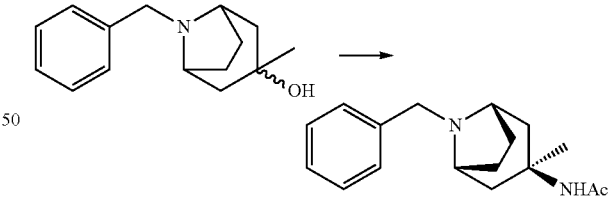

To a solution of 8-benzyl-3-methyl-8-azabicyclo[3.2.1]octan-3-ol (4.28 g, 18.48 mmol) in acetonitrile (26 mL) was added conc. sulfuric acid (18 mL) dropwise over 15 min. at 0° C., and stirred for 18 h at RT. The reaction mixture was poured into ice (ca. 200 g), and basified (ca pH 10) with 5 mol/L sodium hydroxide solution (ca. 100 mL). The reaction mixture was extracted with EtOAc. The combined organic layers were washed with water and sat. sodium chloride solution, and dried over anhydrous sodium sulfate. After the desiccant was filtered off, the solvent was removed at reduced pressure. The residue was washed with diethylether and petrol, to give the title compound (2.45 g). MS: [M+H]⁺= 273.

Preparation 14: tert-Butyl N-(endo-8-benzyl-3-methyl-8-azabicyclo[3.2.1]octan-3-yl)carbamate

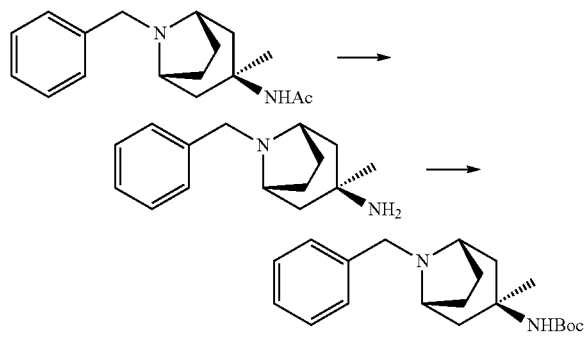

[Chem. 48]

To N-(endo-8-benzyl-3-methyl-8-azabicyclo[3.2.1]octan-3-yl)acetamide was added 6 mol/L hydrochloric acid (80 mL) and the mixture was stirred for 11 days at 140° C. The reaction mixture was basified with 4 mol/L sodium hydroxide solution at 0° C., and 1,4-dioxane (20 mL), and di-tert-butyl dicarbonate (3.93 g, 18.0 mmol) was added. The reaction was stirred for 1 h at 0° C., and for 18 h at RT. The reaction mixture was extracted with EtOAc. The combined organic layers were washed with water and sat. sodium chloride solution, and dried over anhydrous sodium sulfate. After the desiccant was filtered off, the solvent was removed at reduced pressure. The residue was purified by column chromatography on silica gel (gradient elution, 0-10% MeOH/DCM) to give the title compound (3.05 g). MS: [M+H]$^+$=331.

Preparation 15: tert-Butyl N-(endo-3-methyl-8-azabicyclo[3.2.1]octan-3-yl)carbamate

[Chem. 49]

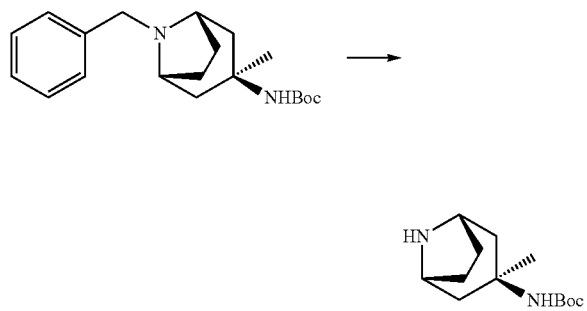

Pd(OH)$_2$/C (10 wt % Pd, 637 mg, 0.454 mmol) was added to a solution of tert-butyl N-(endo-8-benzyl-3-methyl-8-azabicyclo[3.2.1]octan-3-yl)carbamate (3.0 g, 9.08 mmol) in MeOH (20 mL) and the reaction was subjected to hydrogenation at ambient pressure and RT for 24 h. The reaction was filtered through Celite and the filtrate evaporated. The residue was triturated with diethyl ether to give the title compound (1.86 g). MS: [M+H]$^+$=241.

Preparation 16: rac-tert-Butyl (1S,2R,3S,5R)-3-(benzylamino)-2-fluoro-8-azabicyclo[3.2.1]octane-8-carboxylate

[Chem. 50]

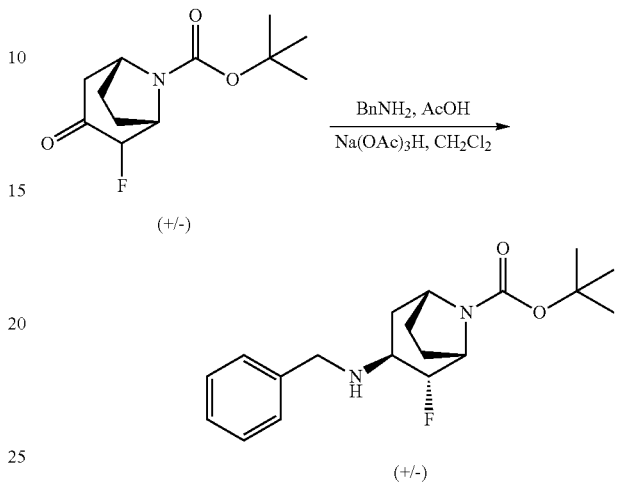

Sodium triacetoxyborohydride (41 g, 193 mmol) was added portion wise to a solution of (±)-tert-butyl 2-fluoro-3-oxo-8-azabicyclo[3.2.1]octane-8-carboxylate (34.8 g, 129 mmol), acetic acid (11.0 ml, 192 mmol) and benzylamine (20 ml, 183 mmol) in dichloromethane (500 mL) then stirred at room temperature overnight. The mixture was diluted with 10% sodium hydrogen carbonate (500 mL) then extracted with dichloromethane (3×500 mL). The combined organic phases were dried (MgSO$_4$), filtered and concentrated under reduced pressure. The crude material was recrystallised from ethyl acetate:isohexane (800 mL, 1:3), to give the title compound (11.6 g). $^1$H NMR (500 MHz, DMSO-d$_6$) δ: 7.39-7.27 (m, 4H), 7.27-7.19 (m, 1H), 4.51 (br d, 1H), 4.38-4.21 (m, 1H), 4.13-4.04 (m, 1H), 3.83-3.65 (m, 2H), 2.80 (dd, 1H), 2.48-2.33 (m, 1H), 2.09 (s, 1H), 2.03-1.88 (m, 2H), 1.86-1.69 (m, 2H), 1.56 (d, 1H), 1.37 (s, 9H).

The filtrate was concentrated under reduced pressure then purified by column chromatography on silica gel (gradient elution, 0-50% EtOAc/isohexane), to afford the following compounds:

Preparation 17: rac-tert-Butyl (1S,2S,3S,5R)-3-(benzylamino)-2-fluoro-8-azabicyclo[3.2.1]octane-8-carboxylate

[Chem. 51]

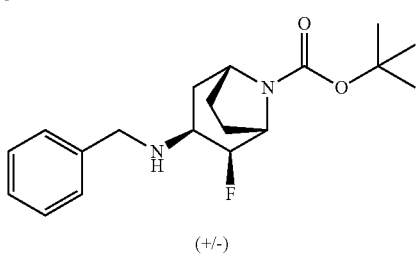

To give the title compound (3.8 g). ¹H NMR (500 MHz, DMSO-d₆) δ: 7.42-7.28 (m, 4H), 7.29-7.18 (m, 1H), 4.68 (dt, 1H), 4.16-4.04 (m, 1H), 4.05-3.94 (m, 1H), 3.82 (dd, 1H), 3.63 (dd, 1H), 3.29-3.20 (m, 1H), 2.44-2.31 (m, 1H), 2.21-2.04 (m, 2H), 1.97-1.87 (m, 1H), 1.89-1.61 (m, 3H), 1.39 (s, 9H).

Preparation 18: rac-tert-Butyl (1S,2R,3R,5R)-3-(benzylamino)-2-fluoro-8-azabicyclo[3.2.1]octane-8-carboxylate

[Chem. 52]

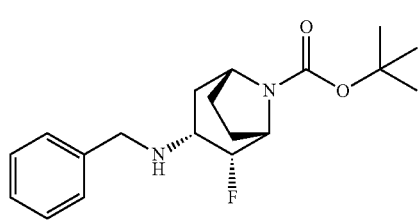

(+/-)

To give 14 g of a colourless oil which was purified by column chromatography on silica gel (gradient elution, 0-50% EtOAc/isohexane), to give the title compound (11.9 g). ¹H NMR (500 MHz, DMSO-d₆) δ: 7.38-7.26 (m, 4H), 7.26-7.15 (m, 1H), 4.66 (dt, 1H), 4.48-4.24 (m, 1H), 4.19-4.06 (m, 1H), 3.77 (d, 1H), 3.72 (d, 1H), 2.96-2.72 (m, 1H), 1.95-1.64 (m, 4H), 1.61-1.43 (m, 3H), 1.38 (s, 9H).

Preparation 19: rac-tert-Butyl (1S,2R,3S,5R)-3-amino-2-fluoro-8-azabicyclo[3.2.1]octane-8-carboxylate

[Chem. 53]

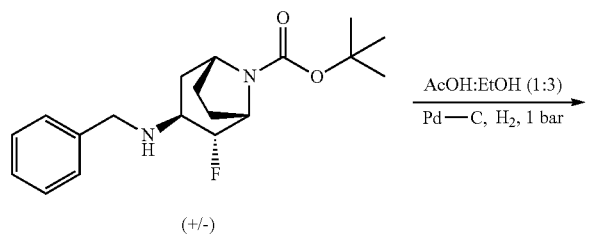

(+/-)

rac-tert-Butyl (1S,2R,3S,5R)-3-(benzylamino)-2-fluoro-8-azabicyclo[3.2.1]octane-8-carboxylate (18.5 g, 55.3 mmol) and 10% palladium on carbon (JM Type 39, 57.3% moisture) (4.0 g, 1.605 mmol) were dissolved in acetic acid/ethanol (1:3, 200 mL) and stirred under hydrogen at 1 bar for 2 h. The catalyst was removed by filtration and the filtrate was concentrated under reduced pressure. The residue was treated with sodium bicarbonate slurry (10 g in 100 mL) then extracted with chloroform/IPA (9:1, 3×100 mL). The combined organic phases were concentrated under reduced pressure, to give the title compound (13.5 g). ¹H NMR (500 MHz, DMSO-d₆) δ: 4.39-4.15 (m, 2H), 4.07 (m, 1H), 3.11 (dd, 1H), 2.12-1.88 (m, 4H), 1.83-1.65 (m, 4H), 1.37 (s, 9H).

Preparation 20: rac-tert-Butyl (1S,2R,3R,5R)-3-amino-2-fluoro-8-azabicyclo[3.2.1]octane-8-carboxylate

[Chem. 54]

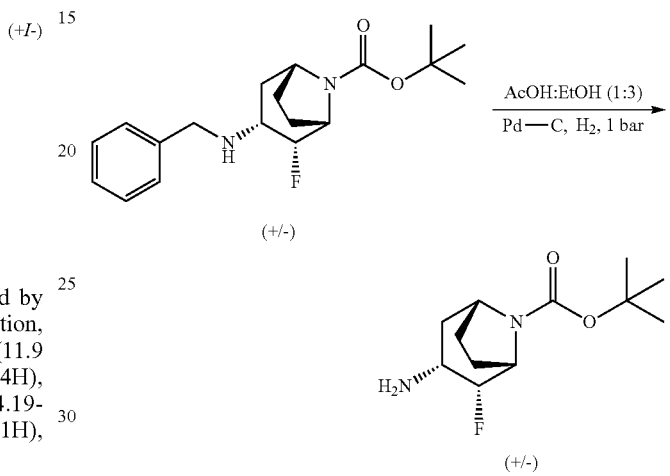

The title compound was prepared similar fashion to rac-tert-butyl (1S,2R,3S,5R)-3-amino-2-fluoro-8-azabicyclo[3.2.1]octane-8-carboxylate using rac-tert-butyl (1S,2R,3R,5R)-3-(benzylamino)-2-fluoro-8-azabicyclo[3.2.1]octane-8-carboxylate (11 g, 32.9 mmol), to give the title compound (8.25 g). ¹H NMR (500 MHz, DMSO-d₆) δ: 4.37 (dt, 2H), 4.38-4.33 (m, 1H), 4.16-4.09 (m, 1H), 2.95 (dddd, 1H), 1.88-1.76 (m, 3H), 1.66-1.46 (m, 4H), 1.41 (d, J=0.5 Hz, 9H).

Preparation 21: rac-tert-Butyl (1S,2S,3S,5R)-3-amino-2-fluoro-8-azabicyclo[3.2.1]octane-8-carboxylate

[Chem. 55]

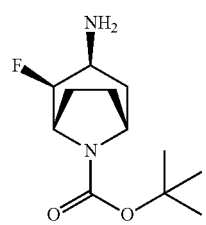

(+/-)

The title compound was prepared similar fashion to rac-tert-butyl (1S,2R,3S,5R)-3-amino-2-fluoro-8-azabicyclo[3.2.1]octane-8-carboxylate using rac-tert-butyl (1S,2S,3S,5R)-3-(benzylamino)-2-fluoro-8-azabicyclo[3.2.1]octane-8-carboxylate (6.0 g, 17.0 mmol), to give the title compound (4.0 g). ¹H NMR (500 MHz, DMSO-d₆) δ: 4.53

(dt, 1H), 4.13-4.03 (m, 1H), 4.03-3.91 (m, 1H), 3.64-3.53 (m, 1H), 2.50-2.40 (m, 1H), 2.22-2.05 (m, 1H), 1.97-1.49 (m, 6H), 1.39 (d, 9H).

Preparation 22: rac-tert-Butyl (1S,2R,3S,5R)-3-{[(benzyloxy)carbonyl]amino}-2-fluoro-8-azabicyclo[3.2.1]octane-8-carboxylate

[Chem. 56]

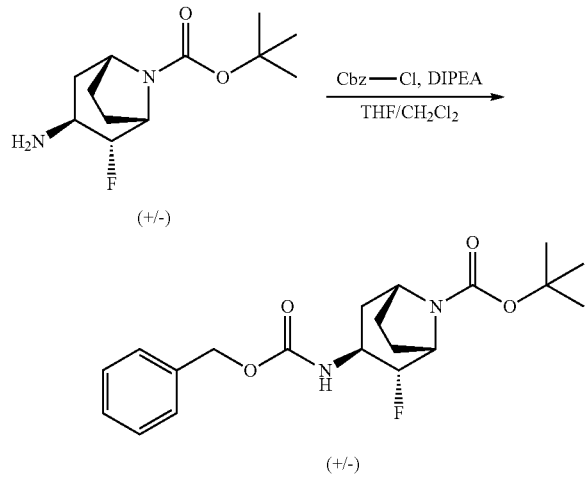

Benzyl chloroformate (10 mL, 70.0 mmol) was added to a cooled (0° C.) solution of rac-tert-butyl (1S,2R,3S,5R)-3-amino-2-fluoro-8-azabicyclo[3.2.1]octane-8-carboxylate (13.5 g, 52.5 mmol) and DIPEA (27 mL, 155 mmol) in THF/DCM (375 mL: 1:4) then stirred at room temperature overnight. Water (400 mL) was added then the mixture was extracted with dichloromethane (3×400 mL) and combined organic phases were concentrated under reduced pressure. The crude product was purified by chromatography on silica gel (0-30% EtOAc/isohexane). The purified oil was purified again by column chromatography on silica gel (gradient elution, 0-10% EtOAc/DCM), to give the title compound (19.5 g). $^1$H NMR (500 MHz, DMSO-$d_6$) δ: 7.46-7.39 (m, 1H), 7.39-7.34 (m, 4H), 7.34-7.29 (m, 1H), 5.07 (d, 1H), 5.02 (d, 1H), 4.51 (br d, 1H), 4.38-4.20 (m, 1H), 4.16-4.06 (m, 1H), 3.64-3.49 (m, 1H), 2.23-2.11 (m, 1H), 1.94-1.79 (m, 2H), 1.78-1.66 (m, 2H), 1.49-1.43 (m, 1H), 1.38 (s, 9H).

Preparation 23: rac-tert-Butyl (1S,2R,3R,5R)-3-{[(benzyloxy)carbonyl]amino}-2-fluoro-8-azabicyclo[3.2.1]octane-8-carboxylate

[Chem. 57]

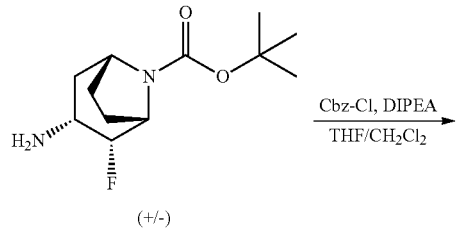

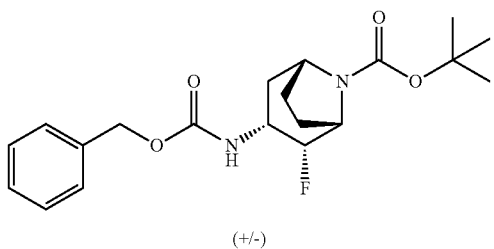

The title compound was prepared similar fashion to rac-tert-butyl (1S,2R,3S,5R)-3-{[(benzyloxy)carbonyl]amino}-2-fluoro-8-azabicyclo[3.2.1]octane-8-carboxylate using rac-tert-butyl (1S,2R,3R,5R)-3-amino-2-fluoro-8-azabicyclo[3.2.1]octane-8-carboxylate (8.25 g, 32.1 mmol), to give the title compound (10.9 g). $^1$H NMR (500 MHz, DMSO-$d_6$) δ: 7.46-7.26 (m, 6H), 5.11-4.94 (m, 2H), 4.54 (dt, 1H), 4.43-4.26 (m, 1H), 4.20-4.06 (m, 1H), 3.92-3.72 (m, 1H), 1.99-1.69 (m, 3H), 1.70-1.48 (m, 3H), 1.38 (s, 9H).

Preparation 24: rac-tert-Butyl (1S,2S,3S,5R)-3-{[(benzyloxy)carbonyl]amino}-2-fluoro-8-azabicyclo[3.2.1]octane-8-carboxylate

[Chem. 58]

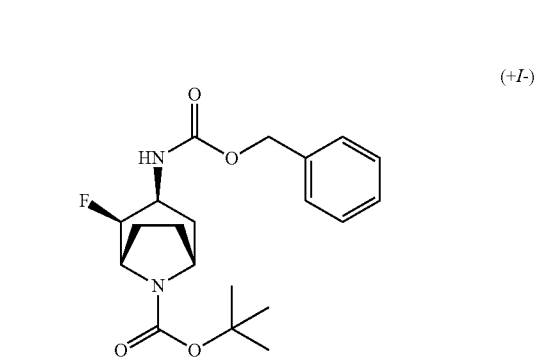

The title compound was prepared similar fashion to rac-tert-butyl (1S,2R,3S,5R)-3-{[(benzyloxy)carbonyl]amino}-2-fluoro-8-azabicyclo[3.2.1]octane-8-carboxylate using rac-tert-butyl (1S,2S,3S,5R)-3-amino-2-fluoro-8-azabicyclo[3.2.1]octane-8-carboxylate (4.0 g, 15.5 mmol), to give the title compound (5.45 g). $^1$H NMR (500 MHz, DMSO-$d_6$) δ: 7.41-7.35 (m, 4H), 7.35-7.28 (m, 1H), 7.14-6.93 (m, 1H), 5.23-4.89 (m, 2H), 4.85-4.65 (m, 1H), 4.22-4.07 (m, 2H), 4.07-3.97 (m, 1H), 2.29-2.17 (m, 1H), 2.08-2.02 (m, 1H), 1.99-1.79 (m, 2H), 1.80-1.64 (m, 2H), 1.40 (s, 9H).

Preparation 25: rac-Benzyl N-[(1S,2S,3S,5R)-2-fluoro-8-azabicyclo[3.2.1]octan-3-yl]carbamate

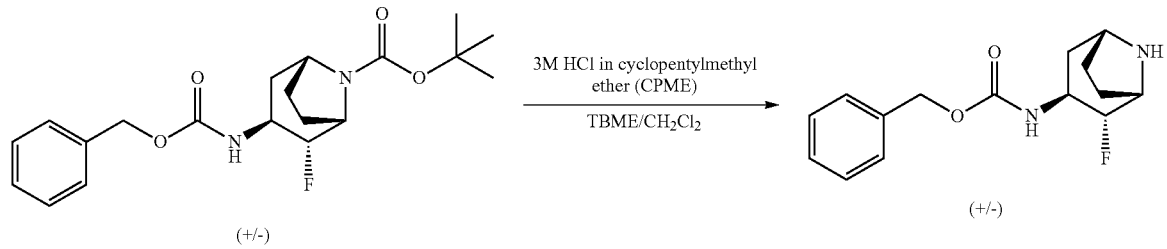

3.0 M hydrogen chloride in cyclopentyl methyl ether (130 mL, 390 mmol) was added to a solution of rac-tert-butyl (1S,2R,3S,5R)-3-{[(benzyloxy)carbonyl]amino}-2-fluoro-8-azabicyclo[3.2.1]octane-8-carboxylate (14.5 g, 36.4 mmol) in tert-butyl methyl ether (15 mL) then stirred at room temperature for 18 h. The mixture was concentrated under reduced pressure then partitioned between dichloromethane (200 mL) and saturated sodium hydrogen carbonate solution (200 mL). The organic layer was concentrated under reduced pressure then purified by column chromatography on silica gel (gradient elution, 0-10% (0.7 M Ammonia/MeOH)/DCM), to give the title compound (6.0 g). $^1$H NMR (500 MHz, DMSO-d$_6$) δ: 7.41-7.28 (m, 5H), 7.28-7.20 (m, 1H), 5.10-4.97 (m, 2H), 4.29 (ddd, 1H), 3.69-3.51 (m, 1H), 3.41 (dd, 1H), 3.37-3.29 (m, 1H), 2.30-2.09 (m, 1H), 2.10-1.97 (m, 1H), 1.77-1.63 (m, 2H), 1.64-1.47 (m, 2H), 1.30-1.14 (m, 1H).

Preparation 26: rac-Benzyl N-[(1S,2S,3R,5R)-2-fluoro-8-azabicyclo[3.2.1]octan-3-yl]carbamate hydrochloride

[Chem. 60]

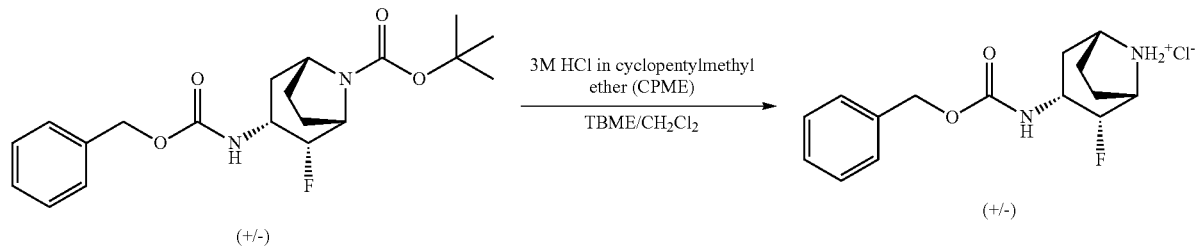

3.0 M hydrogen chloride in cyclopentyl methyl ether (100 mL, 300 mmol) was added to a suspension of (±)-tert-butyl (1S,2S,3R,5R)-3-(((benzyloxy)carbonyl)amino)-2-fluoro-8-azabicyclo[3.2.1]octane-8-carboxylate (10.9 g, 27.4 mmol) in tert-butyl methyl ether (15 mL) and dichloromethane (10 mL) then stirred at room temperature for 18 h. The resulting precipitate was collected by filtration to give the title compound (8.8 g). $^1$H NMR (500 MHz, DMSO-d$_6$) δ: 10.28-9.22 (m, 1H), 9.22-8.29 (m, 1H), 7.74-7.59 (m, 1H), 7.42-7.35 (m, 4H), 7.35-7.29 (m, 1H), 5.07 (d, 1H), 5.04 (d, 1H), 4.83 (dt, 1H), 4.22-4.12 (m, 1H), 3.99-3.92 (m, 1H), 3.92-3.75 (m, 1H), 2.08-1.86 (m, 4H), 1.86-1.68 (m, 2H).

Preparation 27: rac-Benzyl N-[(1S,2R,3S,5R)-2-fluoro-8-azabicyclo[3.2.1]octan-3-yl]carbamate hydrochloride

[Chem. 61]

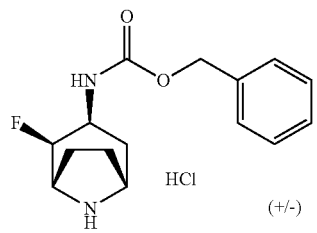

rac-tert-Butyl (1S,2S,3S,5R)-3-{[(benzyloxy)carbonyl]amino}-2-fluoro-8-azabicyclo[3.2.1]octane-8-carboxylate (5.45 g, 14.26 mmol) was dissolved in dichloromethane (5 mL) then stirred with 3.0 M hydrogen chloride in cyclopentyl methyl ether (50 mL) at room temperature for 4 h. TBME (c.a. 10 mL) was added dropwise whilst still stirring until the turbidity persisted, then the mixture was stirred overnight. The resulting precipitate was collected by filtration then washed with TBME (10 mL) and isohexane (10 mL), to give the title compound (3.9 g). $^1$H NMR (500 MHz, DMSO-d$_6$) δ: 10.08-9.28 (m, 2H), 7.46-7.14 (m, 6H), 5.21-5.00 (m, 3H), 4.27-4.15 (m, 1H), 4.13-4.04 (m, 1H), 3.96-3.88 (m, 1H), 2.42 (ddd, 1H), 2.36-2.26 (m, 1H), 2.16 (ddd, 1H), 2.04-1.90 (m, 2H), 1.89-1.78 (m, 1H).

Preparation 28: Benzyl N-[(1S,2S,3S,5R)-2-fluoro-8-azabicyclo[3.2.1]octan-3-yl]carbamate (Fast eluting isomer)

[Chem. 62]

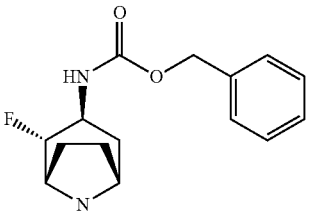

rac-Benzyl N-[(1S,2S,3S,5R)-2-fluoro-8-azabicyclo[3.2.1]octan-3-yl]carbamate (5.82 g) was dissolved in methanol (150 mL) then purified by chiral preparative supercritical fluid chromatography (Lux A1 column, (21.2 mm×250 mm, 5 um); 40° C., Flow Rate 50 mL/min, BPR 100 BarG, Detection at 210 nm, Injection Volume 200 uL (30 mg), 35:65 MeOH:$CO_2$ (0.2% v/v $NH_3$)). Pure fractions were combined then evaporated, to give the title compound (2.58 g) as the faster eluting enantiomer. $^1$H NMR (500 MHz, DMSO-$d_6$) δ: 7.41-7.28 (m, 5H), 7.28-7.20 (m, 1H), 5.10-4.97 (m, 2H), 4.29 (ddd, 1H), 3.69-3.51 (m, 1H), 3.41 (dd, 1H), 3.37-3.29 (m, 1H), 2.30-2.09 (m, 1H), 2.10-1.97 (m, 1H), 1.77-1.63 (m, 2H), 1.64-1.47 (m, 2H), 1.30-1.14 (m, 1H).

Preparation 29: Benzyl N-[(1R,2R,3R,5S)-2-fluoro-8-azabicyclo[3.2.1]octan-3-yl]carbamate (Slow eluting isomer)

[Chem. 63]

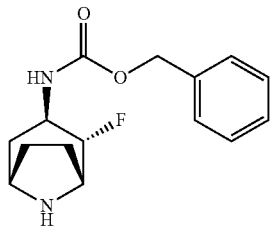

rac-Benzyl N-[(1S,2S,3S,5R)-2-fluoro-8-azabicyclo[3.2.1]octan-3-yl]carbamate (5.82 g) was dissolved in methanol (150 mL) then purified by chiral preparative supercritical fluid chromatography (Lux A1 column, (21.2 mm×250 mm, 5 um); 40° C., Flow Rate 50 mL/min, BPR 100 BarG, Detection at 210 nm, Injection Volume 200 uL (30 mg), 35:65 MeOH:$CO_2$ (0.2% v/v $NH_3$)). Pure fractions were combined then evaporated, to give the title compound (2.99 g). $^1$H NMR (500 MHz, DMSO-$d_6$) δ: 7.41-7.28 (m, 5H), 7.28-7.20 (m, 1H), 5.10-4.97 (m, 2H), 4.29 (ddd, 1H), 3.69-3.51 (m, 1H), 3.41 (dd, 1H), 3.37-3.29 (m, 1H), 2.30-2.09 (m, 1H), 2.10-1.97 (m, 1H), 1.77-1.63 (m, 2H), 1.64-1.47 (m, 2H), 1.30-1.14 (m, 1H).

Preparation 30: Benzyl N-[(1S,2S,3S,5R)-2-fluoro-8-azabicyclo[3.2.1]octan-3-yl]carbamate hydrochloride

[Chem. 64]

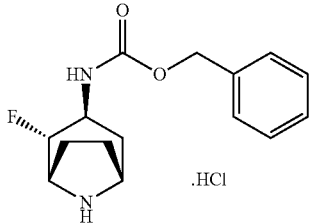

Fast eluting isomer benzyl N-[(1S,2S,3S,5R)-2-fluoro-8-azabicyclo[3.2.1]octan-3-yl]carbamate (3.8 g) was dissolved in dichloromethane (10 mL) then treated with 3.0 M hydrogen chloride in cyclopentyl methyl ether (10 ml, 30.0 mmol), to give a white solid which was recrystallised in acetonitrile (50 mL), to give the title compound (2.2 g). $^1$H NMR (500 MHz, DMSO-$d_6$) δ: 9.34 (br s, 2H), 7.76-7.56 (m, 1H), 7.45-7.27 (m, 5H), 5.09 (d, 1H), 5.04 (d, 1H), 4.95-4.77 (m, 1H), 4.17-4.06 (m, 1H), 3.98-3.87 (m, 1H), 3.77-3.60 (m, 1H), 2.33 (ddd, 1H), 2.18 (q, 1H), 2.03-1.89 (m, 3H), 1.79 (d, 1H).

Preparation 31: Benzyl N-[(1R,2R,3R,5S)-2-fluoro-8-azabicyclo[3.2.1]octan-3-yl]carbamate hydrochloride

[Chem. 65]

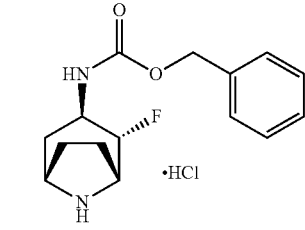

Slow eluting isomer benzyl N-[(1R,2R,3R,5S)-2-fluoro-8-azabicyclo[3.2.1]octan-3-yl]carbamate (3.8 g) was dissolved in dichloromethane (10 mL) then treated with 3.0 M hydrogen chloride in cyclopentyl methyl ether (10 ml, 30.0 mmol), to give a white solid which was recrystallised in acetonitrile (50 mL), to give the title compound (3.2 g). $^1$H NMR (500 MHz, DMSO-$d_6$) δ: 9.34 (br s, 2H), 7.76-7.56 (m, 1H), 7.45-7.27 (m, 5H), 5.09 (d, 1H), 5.04 (d, 1H), 4.95-4.77 (m, 1H), 4.17-4.06 (m, 1H), 3.98-3.87 (m, 1H), 3.77-3.60 (m, 1H), 2.33 (ddd, 1H), 2.18 (q, 1H), 2.03-1.89 (m, 3H), 1.79 (d, 1H).

Preparation 32: Benzyl N-[(1S,2S,3R,5R)-2-fluoro-8-azabicyclo[3.2.1]octan-3-yl]carbamate (Fast eluting isomer)

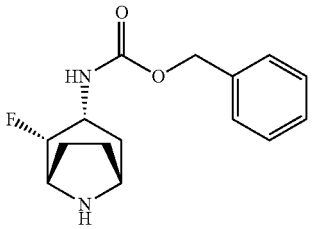

rac-Benzyl N-[(1S,2S,3R,5R)-2-fluoro-8-azabicyclo[3.2.1]octan-3-yl]carbamate (8.8 g) was dissolved in methanol (50 mg mL$^{-1}$) then purified by chiral preparative supercritical fluid chromatography (Lux C2 (4.6 mm×250 mm, 5 um); 40° C., Flow Rate 50 mL/min, BPR 100 BarG, Detection at 210 nm, Injection Volume 500 uL (25 mg), 35:65 EtOH:CO$_2$ (0.2% v/v NH3)). Pure fractions were combined then evaporated, to give the title compound (4.04 g) as the faster eluting enantiomer. $^1$H NMR (500 MHz, DMSO-d$_6$) δ: 8.08-7.57 (m, 2), 7.53 (d, 1H), 7.41-7.28 (m, 5H), 5.04 (d, 1H), 5.02 (d, 1H), 4.67 (dt, 1H), 3.99-3.89 (m, 1H), 3.85-3.67 (m, 2H), 1.97-1.59 (m, 6H). (compound isolated as a partial hydrochloride salt)

Preparation 33: Benzyl N-[(1R,2R,3S,5S)-2-fluoro-8-azabicyclo[3.2.1]octan-3-yl]carbamate (Slow eluting isomer)

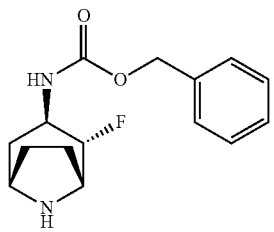

rac-Benzyl N-[(1S,2S,3R,5R)-2-fluoro-8-azabicyclo[3.2.1]octan-3-yl]carbamate (8.8 g) was dissolved in methanol (50 mg mL$^{-1}$) then purified by chiral preparative supercritical fluid chromatography (Lux C2 (4.6 mm×250 mm, 5 um); 40° C., Flow Rate 50 mL/min, BPR 100 BarG, Detection at 210 nm, Injection Volume 500 uL (25 mg), 35:65 EtOH:CO$_2$ (0.2% v/v NH3)). Pure fractions were combined then evaporated, to give the title compound (4.01 g) as the slower eluting enantiomer. $^1$H NMR (500 MHz, DMSO-d$_6$) δ: 7.47-7.28 (m, 6H), 5.97-4.75 (m, 2H), 5.08-4.99 (m, 2H), 4.52 (dt, 1H), 3.82-3.72 (m, 1H), 3.73-3.65 (m, 2H), 3.59-3.51 (m, 1H), 1.85-1.72 (m, 2H), 1.72-1.50 (m, 3H). (compound isolated as a partial hydrochloride salt)

Preparation 34: Benzyl N-[(1S,2S,3R,5R)-2-fluoro-8-azabicyclo[3.2.1]octan-3-yl]carbamate, hydrochloride salt

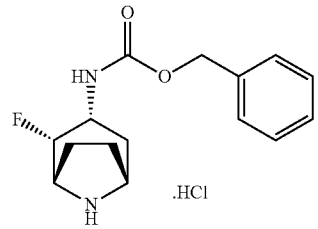

Partial HCl salt of benzyl ((1S,2S,3R,5R)-2-fluoro-8-azabicyclo[3.2.1]octan-3-yl)carbamate (faster eluting enantiomer) (4.0 g, 13.65 mmol) was slurried in a minimal amount of dichloromethane (10 mL) and tert-butyl methyl ether (50 mL) then treated with 3M hydrogen chloride solution in cyclopentyl methyl ether (7 ml, 21.00 mmol). The mixture was slurried overnight then collected by filtration, to give the title compound (4.19 g). $^1$H NMR (500 MHz, DMSO-d$_6$) δ: 10.3-8.10 (br m, 2H), 7.65 (d, 1H), 7.46-7.24 (m, 5H), 5.18-4.94 (m, 2H), 4.82 (d, J=47.7 Hz, 1H), 4.25-4.09 (m, 1H), 3.99-3.90 (m, 1H), 3.90-3.75 (m, 1H), 2.08-1.73 (m, 6H). [α]$^{20}_D$=15.47° (c 1.00, MeOH).

Preparation 35: Benzyl N-[(1R,2R,3S,5S)-2-fluoro-8-azabicyclo[3.2.1]octan-3-yl]carbamate, hydrochloride salt

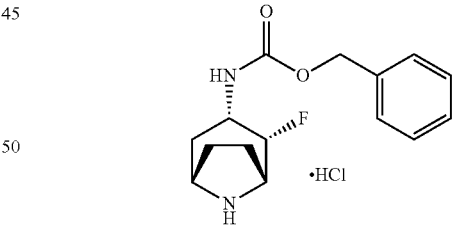

Benzyl N-[(1R,2R,3S,5S)-2-fluoro-8-azabicyclo[3.2.1]octan-3-yl]carbamate (slow eluting isomer) (4.0 g, 13.65 mmol) was slurried in a minimal amount of dichloromethane (10 mL) and tert-butyl methyl ether (50 mL) then treated with 3M hydrogen chloride solution in cyclopentyl methyl ether (7 mL, 21.00 mmol). The mixture was slurried overnight then collected by filtration, to give the title compound (4.23 g). $^1$H NMR (500 MHz, DMSO-d$_6$) δ: 10.3-8.10 (br m, 2H), 7.65 (d, 1H), 7.46-7.24 (m, 5H), 5.18-4.94 (m, 2H), 4.82 (d, J=47.7 Hz, 1H), 4.25-4.09 (m, 1H), 3.99-3.90 (m, 1H), 3.90-3.75 (m, 1H), 2.08-1.73 (m, 6H). [α]$^{20}_D$=−11.88° (c 1.05, MeOH).

Preparation 36: Benzyl N-[(1S,2R,3S,5R)-2-fluoro-8-azabicyclo[3.2.1]octan-3-yl]carbamate hydrochloride (Fast eluting isomer)

[Chem. 70]

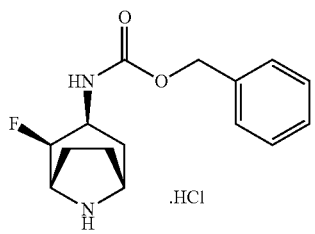

rac-Benzyl N-[(1S,2R,3S,5R)-2-fluoro-8-azabicyclo[3.2.1]octan-3-yl]carbamate (3.83 g) was dissolved in methanol (50 mg mL$^{-1}$) then purified by chiral preparative supercritical fluid chromatography (Lux A1 (4.6 mm×250 mm, 5 um), 40° C., Flow Rate 50 mL/min, BPR 125 BarG, Detection at 210 nm, Injection Volume 1000 uL (50 mg), 50:50 MeOH:CO$_2$ (0.7% v/v DEA)). Benzyl N-[(1S,2R,3S,5R)-2-fluoro-8-azabicyclo[3.2.1]octan-3-yl]carbamate was isolated as the faster eluting enantiomer). Pure fractions were combined then evaporated. The residue was then dissolved in dichloromethane (5 mL) then added dropwise to a stirred mixture of tert-butyl methyl ether (20 mL), isohexane (20 mL) and 3.0 M hydrogen chloride in cyclopentyl methyl ether (2 mL, 6.00 mmol) to give a solid which was recrystallised in acetonitrile (15 mL), to give the title compound (1.15 g). $^1$H NMR (500 MHz, DMSO-d$_6$) δ: 9.82-9.29 (m, 2H), 7.62-6.86 (m, 6H), 5.25-4.87 (m, 3H), 4.29-4.13 (m, 1H), 4.13-4.00 (m, 1H), 3.98-3.85 (m, 1H), 2.42 (ddd, J=14.1, 9.7, 4.7 Hz, 1H), 2.33-2.23 (m, 1H), 2.22-2.11 (m, 1H), 2.03-1.86 (m, 2H), 1.87-1.73 (m, 1H).

Preparation 37: Benzyl N-[(1R,2S,3R,5S)-2-fluoro-8-azabicyclo[3.2.1]octan-3-yl]carbamate hydrochloride (Slow eluting isomer)

[Chem. 71]

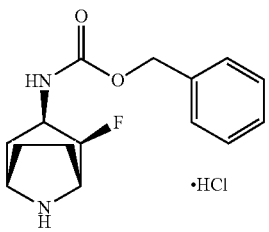

rac-Benzyl N-[(1S,2R,3S,5R)-2-fluoro-8-azabicyclo[3.2.1]octan-3-yl]carbamate was subjected to chiral preparative supercritical fluid chromatography (as above) and isolated as the slow eluting enantiomer. Pure fractions were combined then evaporated. The residue was then dissolved in dichloromethane (5 mL) then diluted with tert-butyl methyl ether (20 mL) and treated with 3.0 M hydrogen chloride in cyclopentyl methyl ether (2 ml, 6.00 mmol) to give a sticky suspension. The suspension was diluted with isohexane (30 mL) stirred for 18 h and collected by filtration, to give the title compound (1.5 g). $^1$H NMR (500 MHz, DMSO-d$_6$) δ: 9.82-9.29 (m, 2H), 7.62-6.86 (m, 6H), 5.25-4.87 (m, 3H), 4.29-4.13 (m, 1H), 4.13-4.00 (m, 1H), 3.98-3.85 (m, 1H), 2.42 (ddd, J=14.1, 9.7, 4.7 Hz, 1H), 2.33-2.23 (m, 1H), 2.22-2.11 (m, 1H), 2.03-1.86 (m, 2H), 1.87-1.73 (m, 1H).

Preparation 38: tert-Butyl ((1R,2R,4S)-7-azabicyclo[2.2.1]heptan-2-yl)carbamate

[Chem. 72]

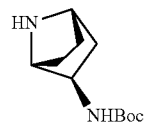

Step 1 rac-tert-Butyl ((1S,2S,4R)-7-azabicyclo[2.2.1]heptan-2-yl)carbamate hydrochloride (36 mg) was dissolved in DCM (2.89 mL). TEA (0.040 mL) and benzyl chloroformate (0.025 mL) were added thereto at RT, followed by stirring at RT for 1 h. The solvent was distilled off, and chloroform and water were added thereto. The mixture was extracted twice with chloroform and washed with water and saturated saline. The solvent was distilled off, and the residue was purified by silica gel column chromatography (gradient elution:hexane/EtOAc) to give benzyl rac-(1S,2S,4R)-2-((tert-butoxycarbonyl)amino)-7-azabicyclo[2.2.1]heptane-7-carboxylate.

rac-Benzyl (1S,2S,4R)-2-((tert-butoxycarbonyl)amino)-7-azabicyclo[2.2.1]heptane-7-carboxylate was obtained as a 10 mg/mL ethanol solution, and separation was performed under the following conditions.

Column: Daicel CHIRALPAK IC 2.0×25 cm
Mobile phase:hexane/2-propanol=85/15
Flow rate: 12.5 mL/min
Retention Time of Each Isomer:
Benzyl (1R,2R,4S)-2-((tert-butoxycarbonyl)amino)-7-azabicyclo[2.2.1]heptane-7-carboxylate: 16.93 minutes
Benzyl (1S,2S,4R)-2-((tert-butoxycarbonyl)amino)-7-azabicyclo[2.2.1]heptane-7-carboxylate: 23.82 minutes.
Chiral Analysis Conditions:
Column: CHIRALPAK IC 4.6×150 mm
Mobile phase:hexane/2-propanol=85/15
Flow rate: 1.0 mL/min
Retention Time of Each Isomer:
Benzyl (1R,2R,4S)-2-((tert-butoxycarbonyl)amino)-7-azabicyclo[2.2.1]heptane-7-carboxylate: 6.972 minutes
Benzyl (1S,2S,4R)-2-((tert-butoxycarbonyl)amino)-7-azabicyclo[2.2.1]heptane-7-carboxylate: 9.895 minutes.

Step 2

Benzyl (1R,2R,4S)-2-((tert-butoxycarbonyl)amino)-7-azabicyclo[2.2.1]heptane-7-carboxylate (93 g) and 10% Pd/C (10 g) were suspended in methanol (1.0 L). The mixture was stirred at RT for 5 h under a hydrogen atmosphere (50 psi). The reaction solution was filtrated, and the filtrate was concentrated to give the title compound. MS: [M+H]$^+$=213. $^1$H-NMR (DMSO-d$_6$) δ: 6.96-6.92 (1H, m), 3.63-3.56 (1H, m), 3.41-3.38 (1H, m), 3.35-3.32 (1H, m), 1.79-1.72 (1H, m), 1.67-1.61 (1H, m), 1.42-1.30 (11H, m), 1.27-1.19 (1H, m), 0.98-0.93 (1H, m).

Preparation 39: tert-Butyl ((1S,2S,4R)-7-azabicyclo[2.2.1]heptan-2-yl)carbamate

[Chem. 73]

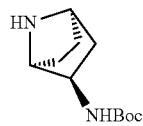

In accordance with Step 2 of Preparation 38, except that benzyl (1S,2S,4R)-2-((tert-butoxycarbonyl)amino)-7-azabicyclo[2.2.1]heptane-7-carboxylate obtained in Step 1 of Preparation 38 was used in place of benzyl (1R,2R,4S)-2-((tert-butoxycarbonyl)amino)-7-azabicyclo[2.2.1]heptane-7-carboxylate, the title compound was obtained. MS: [M+H]$^+$=213. $^1$H-NMR (DMSO-d$_6$) δ: 6.97-6.93 (1H, m), 3.63-3.57 (1H, m), 3.42-3.38 (1H, m), 3.36-3.32 (1H, m), 1.79-1.72 (1H, m), 1.67-1.61 (1H, m), 1.43-1.30 (11H, m), 1.28-1.20 (1H, m), 0.99-0.92 (1H, m).

Preparation 40: Benzyl 1-oxa-6-azaspiro[2.5]octane-6-carboxylate

[Chem. 74]

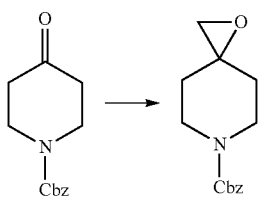

To a mixture of benzyl 4-oxopiperidine-1-carboxylate (11.7 g, 50 mmol) and trimethylsulfoxonium iodide (12.1 g, 55 mmol) in DME (200 mL) was added potassium tert-butoxide (6.17 g, 55 mmol), and stirred at 100° C. for 5 h. Water was added at RT and the mixture was extracted with EtOAc. The organic layer was washed with water and brine, and dried over anhydrous Na$_2$SO$_4$, filtered, and concentrated in vacuo, The residue was purified by column chromatography on silica gel (gradient elution, EtOAc:hexane=1:5 to 1:2) to give the title compound (7.58 g). MS: [M+H]$^+$=248.

Preparation 41: Benzyl 4-(azidomethyl)-4-methoxypiperidine-1-carboxylate

[Chem. 75]

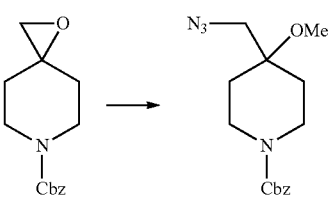

To a solution of benzyl 1-oxa-6-azaspiro[2.5]octane-6-carboxylate (1.24 g, 5.0 mmol) in MeOH (30 mL) and water (6 ml) were added sodium azide (1.63 g., 25 mmol) and NH$_4$Cl (535 mg, 10 mmol) and stirred at 90° C. for 14 h. The solvent was removed under reduced pressure, and the mixture was extracted with EtOAc. The organic layer was washed with water and brine, and dried over anhydrous Na$_2$SO$_4$, filtered, and concentrated in vacuo. The residue in THF (15 mL) was added sodium hydride (55% in mineral oil, 262 mg, 6.0 mmol) at 0° C., and stirred for 15 min., and added iodomethane (0.40 mL, 6.5 mmol) and stirred at RT for 15 h. Sat. NH$_4$Cl was added at 0° C., the mixture was extracted with EtOAc. The organic layer was washed with water and brine, and dried over anhydrous Na$_2$SO$_4$, filtered, and concentrated in vacuo. The residue was purified by column chromatography on silica gel (gradient elution, EtOAc:hexane=1:5 to 1:2) to give the title compound (1.16 g). MS: [M+H]$^+$=305.

Preparation 42: Benzyl 4-(((tert-butoxycarbonyl)amino)methyl)-4-methoxypiperidine-1-carboxylate

[Chem. 76]

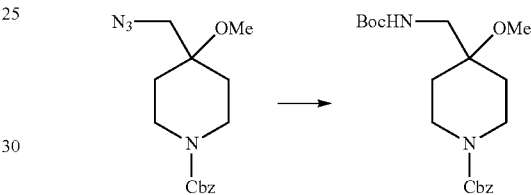

To a solution of benzyl 4-(azidomethyl)-4-methoxypiperidine-1-carboxylate (1.07 g, 3.5 mmol) in THF (15 mL) and water (0.63 mL, 35 mmol) was added triphenylphosphine (1.84 g, 7.0 mmol) at RT, and stirred at 45° C. for 15 h. The mixture was added 2 M NaOH (3.5 mL, 7.0 mmol) and di-tert-butyl dicarbonate (918 mg, 4.2 mmol) at 0° C. and stirred at RT for 2 h. The mixture was extracted with EtOAc. The organic layer was washed with water and brine, and dried over anhydrous Na$_2$SO$_4$, filtered, and concentrated in vacuo. The residue was purified by column chromatography on silica gel (gradient elution, EtOAc:hexane=1:3 to 2:3) to give the title compound (1.32 g). MS: [M+H]$^+$=379.

Preparation 43: tert-Butyl ((4-methoxypiperidin-4-yl)methyl)carbamate

[Chem. 77]

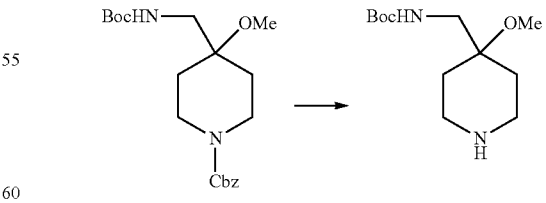

To a solution of benzyl 4-(((tert-butoxycarbonyl)amino)methyl)-4-methoxypiperidine-1-carboxylate (1.14 g, 3.0 mmol) in THF (15 mL) was added 10% palladium on carbon (46.7% wet, 280 mg, 0.12 mmol) and stirred for 1 h under hydrogen atmosphere. The mixture was added MeOH (15 mL) and stirred for 6 h under hydrogen atmosphere. After

Preparation 44: Benzyl 4-fluoro-4-(hydroxymethyl)piperidine-1-carboxylate

[Chem. 78]

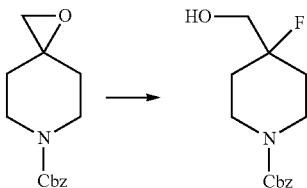

To a solution of benzyl 1-oxa-6-azaspiro[2.5]octane-6-carboxylate (2.47 g, 10.0 mmol) in DCM (15 mL) was added pyridine polyfluoride hydrofluoride (2.0 mL, 14 mmol) in DCM (5 mL) at −10° C. and stirred at RT for 2 h. Sat. NaHCO$_3$ was added at 0° C., and the mixture was extracted with EtOAc. The organic layer was washed with water and brine, and dried over anhydrous Na$_2$SO$_4$, filtered, and concentrated in vacuo. The residue was purified by column chromatography on silica gel (gradient elution, EtOAc:CHCl$_3$=1:10 to 1:3) to give the title compound (1.71 g). MS: [M+H]$^+$=268.

Preparation 45: Benzyl 4-(azidomethyl)-4-fluoropiperidine-1-carboxylate

[Chem. 79]

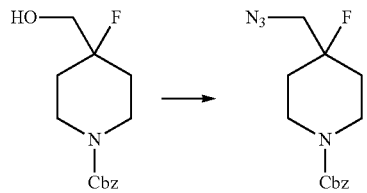

To a solution of benzyl 4-fluoro-4-(hydroxymethyl)piperidine-1-carboxylate (1.60 g, 6.0 mmol) in DCM (20 mL) were added Et$_3$N (1.68 mL, 12 mmol) and methanesulfonyl chloride (0.56 mL, 7.2 mmol) at RT, and stirred for 1 h. Water was added at 0° C., and the mixture was extracted with EtOAc. The organic layer was washed with water and brine, and dried over anhydrous Na$_2$SO$_4$, filtered, and concentrated in vacuo. The residue in DMF (15 mL) was added sodium azide (1.94 g, 30 mmol) and stirred at 110° C. for 48 h. Water was added at RT, and the mixture was extracted with EtOAc. The organic layer was washed with water and brine, and dried over anhydrous Na$_2$SO$_4$, filtered, and concentrated in vacuo. The residue was purified by column chromatography on silica gel (gradient elution, EtOAc:hexane=1:5 to 1:2) to give the title compound (1.20 g). MS: [M+H]$^+$=293.

Preparation 46: Benzyl 4-(((tert-butoxycarbonyl)amino)methyl)-4-fluoropiperidine-1-carboxylate

[Chem. 80]

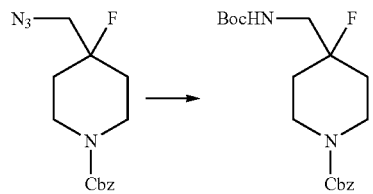

To a solution of benzyl 4-(azidomethyl)-4-fluoropiperidine-1-carboxylate (1.02 g, 3.5 mmol) in THF (15 mL) and water (0.63 mL, 35 mmol) was added triphenylphosphine (1.84 g, 7.0 mmol) at RT, and stirred at 45° C. for 15 h. To the mixture were added 2 M NaOH (3.5 mL, 7.0 mmol) and di-tert-butyl dicarbonate (918 mg, 4.2 mmol) at 0° C. and stirred at RT for 6 h. The mixture was extracted with EtOAc. The organic layer was washed with water and brine, and dried over anhydrous Na$_2$SO$_4$, filtered, and concentrated in vacuo. The residue was purified by column chromatography on silica gel (gradient elution, EtOAc:hexane=1:3 to 2:3) to give the title compound (1.24 g). MS: [M+H]$^+$=367.

Preparation 47: tert-Butyl ((4-fluoropiperidin-4-yl)methyl)carbamate

[Chem. 81]

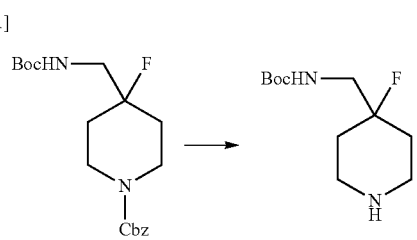

To a solution of benzyl 4-(((tert-butoxycarbonyl)amino)methyl)-4-fluoropiperidine-1-carboxylate (1.10 g, 3.0 mmol) in THF (15 mL) and MeOH (15 mL) was added 10% palladium on carbon (46.7% wet, 345 mg, 0.15 mmol) and stirred for 8 h under hydrogen atmosphere. After the reaction mixture was filtered by celite, the solvent was removed at reduced pressure to give the title compound (718 mg). MS: [M+H]$^+$=233.

Preparation 48: 2-Methyl-N—((R)-8-azaspiro[4.5]decan-1-yl)propane-2-sulfinamide

[Chem. 82]

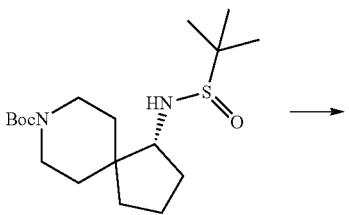

-continued

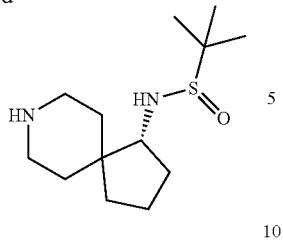

To a solution of tert-butyl (1R)-1-((tert-butylsulfinyl)amino)-8-azaspiro[4.5]decane-8-carboxylate (0.10 g, 0.28 mmol) prepared by the method as described in WO2016203405 in CHCl₃ (1 mL) was added TFA (0.20 mL, 2.6 mmol) at RT. The mixture was stirred at RT for 2 h. The volatiles were removed under reduced pressure, and the resulting crude 2-methyl-N—((R)-8-azaspiro[4.5]decan-1-yl)propane-2-sulfinamide salt was used without further purification. MS: [M+H]⁺=259.

Preparation 49:
(S)-2-oxa-8-azaspiro[4.5]decan-4-amine

[Chem. 83]

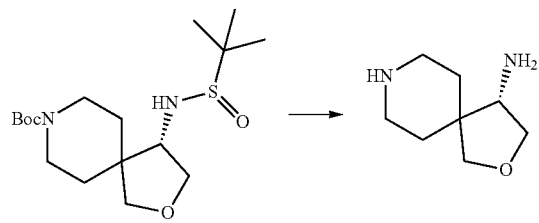

To a solution of tert-butyl (4S)-4-((tert-butylsulfinyl)amino)-2-oxa-8-azaspiro[4.5]decane-8-carboxylate (0.10 g, 0.28 mmol) prepared by the method as described in WO2016203405 in MeOH (1 mL) was added 4M HCl in 1,4-dioxane (0.70 mL, 2.8 mmol) at RT. The mixture was stirred at 50° C. for 30 min, and cooled to RT. The volatiles were removed under reduced pressure, the residue was azeotroped with toluene and the resulting crude (S)-2-oxa-8-azaspiro[4.5]decan-4-amine salt was used without further purification. MS: [M+H]⁺=157.

Preparation 50: (1R,3R)-3-Fluoro-8-azaspiro[4.5]decan-1-amine dihydrochloride

[Chem. 84]

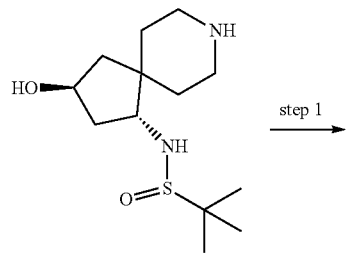

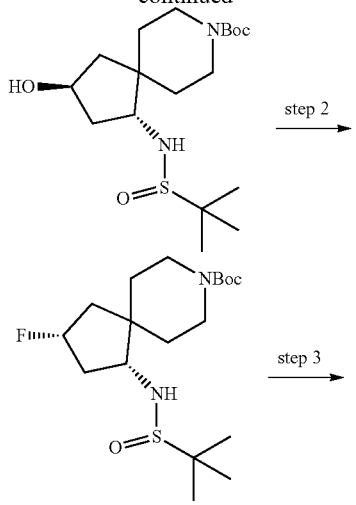

Step 1: (1R,3S)-tert-Butyl 1-(1,1-dimethylethylsulfinamido)-3-hydroxy-8-azaspiro[4.5]decane-8-carboxylate N-((1R,3S)-3-Hydroxy-8-azaspiro[4.5]decan-1-yl)-2-methylpropane-2-sulfinamide (950 mg, 3.46 mmol) was dissolved in THF (5 mL) and Boc₂O (754 mg, 3.46 mmol) was added. The solution was stirred at 50° C. for 4 hours before being concentrated. The crude material was purified by chromatography on silica gel (12 g cartridge, 0-10% MeOH/DCM) to afford (1R,3S)-tert-butyl 1-(1,1-dimethylethylsulfinamido)-3-hydroxy-8-azaspiro[4.5]decane-8-carboxylate (210 mg, 0.53 mmol, 15% yield) as a colourless solid. MS: [M+Na]⁺=397.

Step 2: (1R,3R)-tert-Butyl 1-(1,1-dimethylethylsulfinamido)-3-fluoro-8-azaspiro[4.5]decane-8-carboxylate (1R,3S)-tert-Butyl 1-(1,1-dimethylethylsulfinamido)-3-hydroxy-8-azaspiro[4.5]decane-8-carboxylate (200 mg, 0.53 mmol) was dissolved in DCM (2.5 mL) and the solution cooled to 0° C. Deoxofluor (50% wt in toluene) (0.35 mL, 0.934 mmol) was added dropwise and the mixture stirred at room temperature for 3 hours. A further portion of deoxofluor (50% wt in toluene) (0.35 mL, 0.934 mmol) was added and the reaction was stirred at 0° C. for 3 hours and then ambient temperature for 30 minutes. The reaction was quenched with sat. aq. NaHCO₃ (5 mL) and the mixture stirred for 15 minutes. The organic phase was isolated and the aqueous phase was further extracted with DCM (2×10 mL). The combined organic phases were dried (MgSO₄), filtered, and concentrated to give the crude material as an orange oil. The crude product was purified by chromatography on silica gel (4 g cartridge, 0-10% MeOH/DCM) to afford (1R,3R)-tert-butyl 1-(1,1-dimethylethylsulfinamido)-3-fluoro-8-azaspiro[4.5]decane-8-carboxylate (135 mg, 0.32 mmol, 60% yield) as a pale orange gum. MS: [M+Na]⁺=399.

Step 3: (1R,3R)-3-Fluoro-8-azaspiro[4.5]decan-1-amine dihydrochloride

HCl (4M in dioxane) (1.0 mL) was added to (1R,3R)-tert-butyl 1-(1,1-dimethylethylsulfinamido)-3-fluoro-8-azaspiro[4.5]decane-8-carboxylate (130 mg, 0.345 mmol) and the mixture stirred at room temperature. A further portion of HCl (4M in dioxane) (1.0 mL) was added and the reaction was stirred at room temperature for 1 hour 30 minutes. The mixture was concentrated to give orange solids. The crude material was used directly in subsequent steps.

Preparation 51: (3S,4S)-3-Methyl-2-oxa-8-azaspiro[4.5]decan-4-amine hydrochloride

[Chem. 85]

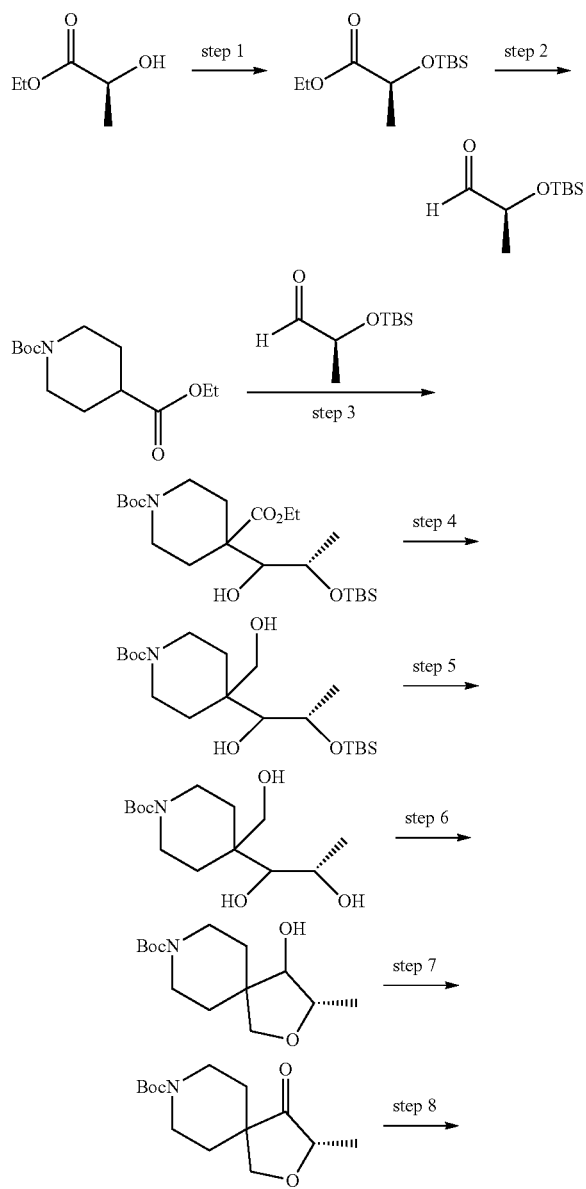

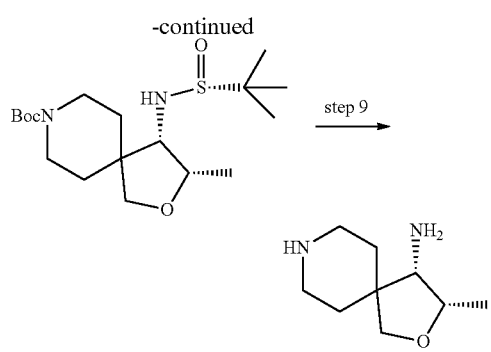

Step 1: Ethyl (2S)-2-[(tert-butyldimethylsilyl)oxy]propanoate

The reaction mixture of ethyl (2S)-2-hydroxypropanoate (95.0 g, 0.8 mol) in DCM (1 L) was cooled to 0° C., then imidazole (81.6 g, 1.2 mol) and TBSCl (133.3 g, 0.88 mol) were added, stirred at ambient temperature for about 1.5 h. The reaction mixture was poured into water (1.0 L), extracted with DCM (2×500 mL), then washed with brine, dried over $Na_2SO_4$, concentrated in vacuo, purified by silica column (pet.ether/EtOAc=50/1 to 20/1) to give the product (180.0 g, 97%) as a colourless oil. $^1$H NMR (500 MHz, $CDCl_3$) δ: 4.33 (s, 1H), 4.22 (s, 2H), 1.44 (d, 3H), 1.32 (t, 3H), 0.97 (s, 9H), 0.15 (s, 6H).

Step 2: (2S)-2-[(tert-Butyldimethylsilyl)oxy]propanal

A solution of ethyl (2S)-2-[(tert-butyldimethylsilyl)oxy]propanoate (131.0 g, 0.56 mol) in toluene (800 mL) was cooled to −60° C., DIBAL-H (1.5 M, 560 mL, 0.85 mol) was dropwise added, then stirred at −60° C. for 2 h. The reaction mixture was poured into water (800 mL), extracted with EtOAc (2×500 mL), washed with brine, dried over $Na_2SO_4$, concentrated in vacuo to give the crude product. It was used in the next step without purification.

Step 3: 1-tert-Butyl 4-ethyl 4-[(2S)-2-[(tert-butyldimethylsilyl)oxy]-1-hydroxypropyl]piperidine-1,4-dicarboxylate A solution of diisopropylamine (65.0 g, 0.64 mol) in THF (400 mL) was cooled to −20° C. n-BuLi (2.5 M, 224 mL, 0.56 mol) was added dropwise, then stirred at −10° C. for 1 h. 1-tert-Butyl 4-ethyl piperidine-1,4-dicarboxylate (110.0 g, 0.43 mol) in THF (200 mL) was added dropwise at −10° C., then stirred at −10° C. to ambient temperature for 1 h under N2. (2S)-2-[(tert-Butyldimethylsilyl)oxy]propanal (120.0 g, 0.64 mol) in THF (200 mL) was added dropwise at −10° C., then stirred at −10° C. to 0° C. for 2 h. The reaction mixture was poured into sat. $NH_4Cl$ (1 L), extracted with EtOAc (2×500 mL), the combined EtOAc phase was washed with brine, dried over $Na_2SO_4$, concentrated in vacuo, purified by silica column (pet.ether/EtOAc=50/1 to 30/1 to 20/1) to give the product (70.0 g, 37%) as a yellow oil. $^1$H NMR (400 MHz, $CDCl_3$) δ: 4.29-4.09 (m, 2H), 4.06-3.88 (m, 2H), 3.79 (d, 1H), 3.60-3.48 (m, 1H), 2.78 (s, 2H), 2.66-2.25 (m, 1H), 2.24-1.94 (m, 2H), 1.74 (m, 2H), 1.50-1.37 (m, 9H), 1.34-1.18 (m, 5H), 1.12 (d, 3H), 0.91 (s, 10H), 0.04 (s, 6H).

Step 4: tert-Butyl 4-[(2S)-2-[(tert-butyldimethylsilyl)oxy]-1-hydroxypropyl]-4-(hydroxymethyl)piperidine-1-carboxylate To the solution of 1-tert-butyl 4-ethyl 4-[(2S)-2-[(tert-butyldimethylsilyl)oxy]-1-hydroxypropyl]piperidine-1,4-dicarboxylate (70.0 g, 0.157 mol) in THF (700 mL) was added LiBH$_4$ (2 M, 118 mL, 0.236 mol) at 0° C., then stirred at ambient temperature overnight. The mixture was poured into water (500 mL), stirred at ambient temperature for 20 min, extracted with EtOAc (2×300 mL), washed with brine, dried over Na$_2$SO$_4$, concentrated in vacuo to give the crude product (60.0 g). It was used in the next step without purification.

Step 5: tert-Butyl 4-[(2S)-1,2-dihydroxypropyl]-4-(hydroxymethyl)piperidine-1-carboxylate To a cooled (0° C.) solution of tert-butyl 4-[(2S)-2-[(tert-butyldimethylsilyl)oxy]-1-hydroxypropyl]-4-(hydroxymethyl)piperidine-1-carboxylate (60.0 g, 0.149 mol) in THF (600 mL), TBAF (1 M, 223 mL, 0.223 mol) was added, and stirred at ambient temperature for 2 h. NaHCO$_3$ (aq. 600 mL) was added, stirred at ambient temperature for 10 min, extracted with EtOAc (2×300 mL), washed with brine, dried over Na$_2$SO$_4$, concentrated in vacuo, purified by silica column (DCM/MeOH=100/1 to 50/1 to 30/1) to give the product (37.0 g, 86%) as a yellow oil. $^1$H NMR (400 MHz, CDCl$_3$) δ: 4.02-3.87 (m, 1H), 3.74 (m, 4H), 3.36 (d, 4H), 3.10 (s, 2H), 1.66 (s, 3H), 1.40 (s, 10H), 1.31 (s, 3H).

Step 6: tert-Butyl (3S)-4-hydroxy-3-methyl-2-oxa-8-azaspiro[4.5]decane-8-carboxylate To an ice cooled solution of tert-butyl 4-[(2S)-1,2-dihydroxypropyl]-4-(hydroxymethyl)piperidine-1-carboxylate (37.0 g, 0.127 mol) in THF (400 mL) was added NaH (17.8 g, 0.44 mol) in portions, then a solution of TsCl (25.5 g, 0.134 mol) in THF (200 mL) was added and the reaction mixture was stirred at 0° C. for 2 h. The reaction mixture was poured into ice and NH$_4$Cl (aq. 600 mL), extracted with EtOAc (3×400 mL), washed with brine, dried over Na$_2$SO$_4$, concentrated in vacuo, purified by silica column (DCM/MeOH=100/1 to 50/1 to 30/1) to give the product (20.0 g, 58%) as a yellow oil. $^1$H NMR (400 MHz, CDCl$_3$) δ: 3.94-3.57 (m, 4H), 3.45 (d, 1H), 2.96 (s, 2H), 1.70 (s, 3H), 1.42 (s, 10H), 1.29 (m, 4H).

Step 7: tert-Butyl (3S)-3-methyl-4-oxo-2-oxa-8-azaspiro[4.5]decane-8-carboxylate To an ice cooled solution of tert-butyl (3S)-4-hydroxy-3-methyl-2-oxa-8-azaspiro[4.5]decane-8-carboxylate (20.0 g, 0.074 mol) in DCM (200 mL) was added DMP (37.5 g, 0.088 mol) in portions. The reaction mixture was stirred at ambient temperature for 1 h, poured into NaHCO$_3$ (aq.), extracted with DCM, washed with brine, dried over Na$_2$SO$_4$, concentrated in vacuo to give the product (19.0 g, 95%) as a yellow oil. It was used in the next step directly.

Step 8: tert-Butyl (3S,4S)-3-methyl-4-[(2-methylpropane-2-sulfinyl)amino]-2-oxa-8-azaspiro[4.5]decane-8-carboxylate To the solution of tert-butyl (3S)-3-methyl-4-oxo-2-oxa-8-azaspiro[4.5]decane-8-carboxylate (11.0 g, 0.04 mol) in THF (250 mL) was added (R)-2-methylpropane-2-sulfinamide (9.9 g, 0.08 mol), Ti(OEt)$_4$ (36.5 g, 0.16 mol) and the reaction mixture was stirred at 75° C. for overnight. The reaction mixture was cooled to −10° C., LiBH$_4$ (2 M, 30 mL, 0.06 mol) was dropwise added, then stirred at −10° C. for 1 h. The reaction mixture was poured into ice and NH$_4$Cl (aq. 300 mL) and EtOAc (300 mL), stirred at ambient temperature for 20 min, then filtered through celite. The reaction mixture was extracted with EtOAc (2×300 mL), washed with brine, dried over Na$_2$SO$_4$, concentrated in vacuo, purified by silica column (pet. ether/EtOAc=10/1 to 5/1 to 3/1 to 2/1) to give the product (7.0 g, 47%). $^1$H NMR (400 MHz, DMSO-d$_6$) δ: 5.07 (d, J=11.0 Hz, 1H), 4.06 (s, 1H), 3.74 (m, 3H), 3.37 (d, 3H), 2.84 (s, 2H), 1.69-1.50 (m, 2H), 1.39 (s, 11H), 1.15 (s, 9H), 1.06 (m, 3H).

Step 9: (3S,4S)-3-Methyl-2-oxa-8-azaspiro[4.5]decan-4-amine hydrochloride

To the solution of tert-butyl (3S,4S)-3-methyl-4-[(2-methylpropane-2-sulfinyl)amino]-2-oxa-8-azaspiro[4.5]decane-8-carboxylate (5.8 g, 15.5 mmol) in MeOH (20 mL) was added HCl/dioxane (4M, 39 mL, 155 mmol), then stirred at 50° C. for 2 h. The reaction mixture was cooled to ambient temperature and concentrated in vacuo. The crude product was dissolved in water (50 mL), extracted with EtOAc (3×40 mL). The aqueous phase was freeze dried to give the HCl salt of the product (4.0 g) as a yellow solid. MS: [M+H]$^+$=171. $^1$H NMR (400 MHz, DMSO-de) δ: 4.44 (m, 1H), 4.05-3.88 (m, 2H), 3.67 (s, 1H), 3.58-3.39 (m, 2H), 3.22-3.01 (m, 2H), 1.98 (m, 4H), 1.34 (s, 3H).

Preparation 52: N-((1R,3S)-3-Hydroxy-8-azaspiro[4.5]decan-1-yl)-2-methylpropane-2-sulfinamide

[Chem. 86]

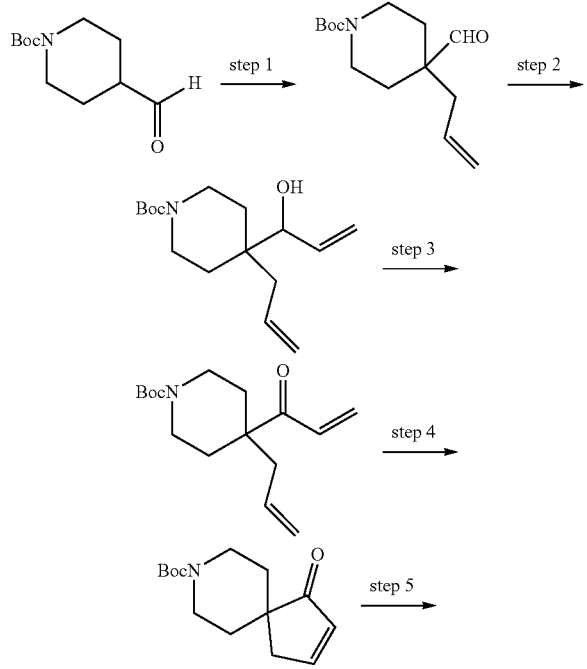

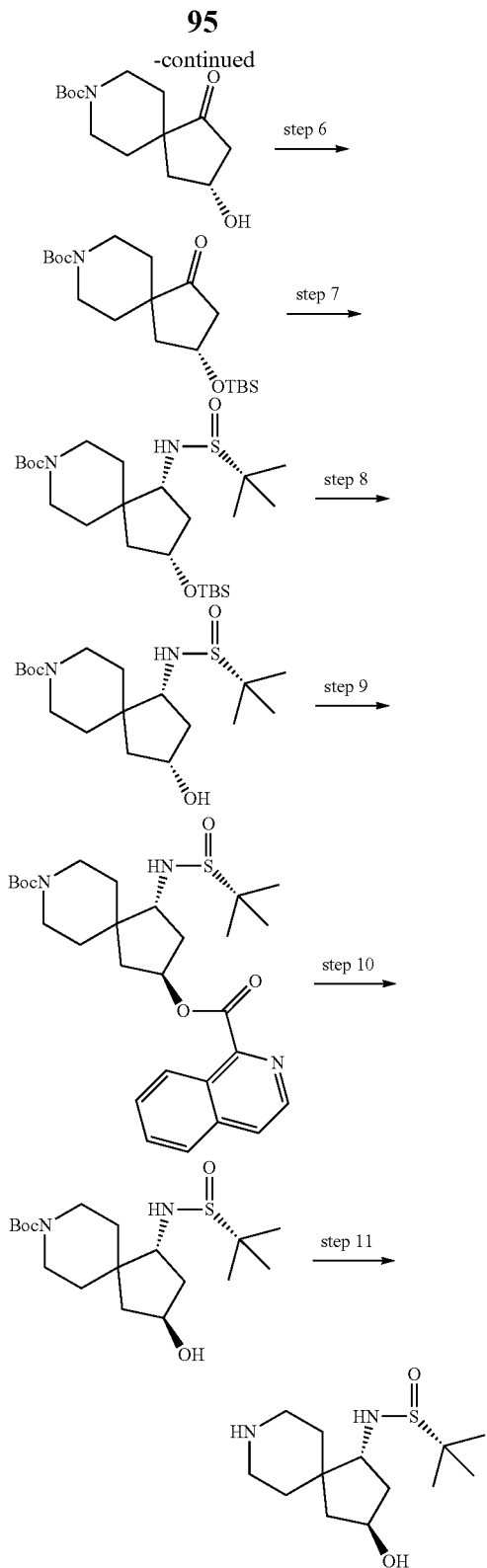

(173.0 g, 1.55 mol) in portions, then stirred at −25° C.~−15° C. for 45 min. The reaction mixture was poured into ice and NH₄Cl (aq. 3 L), extracted with EtOAc (2×2 L), washed with brine, dried over Na₂SO₄, concentrated in vacuo, purified by silica column (pet.ether/EtOAc=50/1 to 20/1 to 10/1) to give the product (210.0 g, 60%) as a colorless oil. $^1$H NMR (400 MHz, CDCl₃) δ: 9.48 (s, 1H), 5.58 (s, 1H), 5.03 (s, 2H), 3.76 (s, 2H), 2.90 (s, 2H), 2.21 (s, 2H), 1.89 (s, 2H), 1.43 (s, 9H).

Step 2: tert-Butyl 4-(1-hydroxyprop-2-en-1-yl)-4-(prop-2-en-1-yl)piperidine-1-carboxylate A solution of tert-butyl 4-formyl-4-(prop-2-en-1-yl)piperidine-1-carboxylate (250.0 g, 0.99 mol) in THF (2.5 L) was cooled to −60° C., vinylmagnesium bromide (1.18 L, 1.18 mol) was added, then stirred at ambient temperature for 1 h. The mixture was poured into NH₄Cl (aq. 3 L), extracted with EtOAc (2×2 L), washed with brine, dried over Na₂SO₄, concentrated in vacuo to give the product (270.0 g, 97%) as a brown oil. $^1$H NMR (400 MHz, CDCl₃) δ: 6.00-5.78 (m, 2H), 5.28-5.15 (m, 2H), 5.11-4.99 (m, 2H), 3.98 (d, 1H), 3.79-3.56 (m, 2H), 3.09 (s, 2H), 2.24 (ddd, 7.5 Hz, 2H), 1.86 (d, 1H), 1.65-1.49 (m, 2H), 1.45-1.38 (m, 11H).

Step 3: tert-Butyl 4-(prop-2-en-1-yl)-4-(prop-2-enoyl)piperidine-1-carboxylate

A solution of tert-butyl 4-(1-hydroxyprop-2-en-1-yl)-4-(prop-2-en-1-yl)piperidine-1-carboxylate (286.0 g, 1.01 mol) in DCM (1.5 L) was cooled to 0° C., DMP (471.0 g, 1.1 mol) was added and stirred at ambient temperature for 2 h. The reaction mixture was poured into NaHCO₃/Na₂SO₃ (1:1, 2 L), extracted with DCM (1 L), the combined DCM phase was washed with brine, dried over Na₂SO₄, concentrated in vacuo to give the crude product (840.0 g) as a yellow oil. $^1$H NMR (400 MHz, CDCl3) δ: 6.88-6.70 (m, 1H), 6.37 (d, 1H), 5.68 (d, 1H), 5.55 (d, 1H), 5.02 (t, 2H), 3.74 (s, 2H), 2.93 (s, 2H), 2.28 (s, 2H), 2.06 (s, 2H), 1.43 (s, 11H).

Step 4: tert-Butyl 1-oxo-8-azaspiro[4.5]dec-2-ene-8-carboxylate

To a solution of tert-butyl 4-(prop-2-en-1-yl)-4-(prop-2-enoyl)piperidine-1-carboxylate (256.0 g, 0.91 mol) in toluene (3 L) was added dichloro[1,3-bis(2,4,6-trimethylphenyl)-2-imidazolidinylidene](benzylidene)(tricyclohexylphosphine)ruthenium(II) (31.1 g, 0.037 mol) and stirred at 85° C. for 3 h. The reaction mixture was concentrated in vacuo, purified by silica column (pet.ether/EtOAc=50/1 to 30/1 to 15/1) to give the product (370.0 g) as a brown solid. $^1$H NMR (400 MHz, CDCl₃) δ: 7.64 (s, 1H), 6.16 (s, 1H), 4.08 (s, 2H), 2.90 (s, 2H), 2.60 (s, 2H), 1.72 (m, 2H), 1.46 (s, 9H), 1.25 (s, 2H).

Step 5: tert-Butyl (3R)-3-hydroxy-1-oxo-8-azaspiro[4.5]decane-8-carboxylate

A mixture of CuCl (1.55 g, 0.0156 mol), (S)-TolBINAP (10.6 g, 0.0156 mol), t-BuONa (1.5 g, 0.0156 mol) in THF (900 mL) was stirred at ambient temperature for 30 min. Bis(pinacolato)diboron (145.3 g, 0.572 mol) in THF (400 mL) was added and stirred at ambient temperature for 15 min. tert-Butyl 1-oxo-8-azaspiro[4.5]dec-2-ene-8-carboxylate (130.0 g, 0.52 mol) in (THF 200 mL) and MeOH (33.3 g, 1.04 mol) were added and the reaction mixture was stirred Step 1: tert-Butyl 4-formyl-4-(prop-2-en-1-yl)piperidine-1-carboxylate A solution of tert-butyl 4-formylpiperidine-1-carboxylate (300.0 g, 1.40 mol) in THF (3 L) was cooled to −25° C., allylbromide (187.7 g, 1.55 mol) was added, then t-BuOK at ambient temperature overnight. Water (1.6 L) and NaBO$_3$ (400.0 g, 2.6 mol) were added and the reaction mixture was stirred at ambient temperature for 1 h. The mixture was filtered, extracted with EtOAc, washed with brine, dried over Na$_2$SO$_4$, concentrated in vacuo and purified by silica column (pet. ether/EtOAc=20/1 to 10/1 to 3/1) to give the product (100.0 g, 71%) as a brown solid. $^1$H NMR (400 MHz, CDCl$_3$) δ: 4.61 (s, 1H), 3.88 (s, 2H), 3.03 (m, 2H), 2.65 (s, 1H), 2.38 (s, 1H), 2.19 (s, 3H), 1.73 (m, 4H), 1.44 (s, 9H).

Step 6: tert-Butyl (3R)-3-[(tert-butyldimethylsilyl)oxy]-1-oxo-8-azaspiro[4.5]decane-8-carboxylate To a solution of tert-butyl (3R)-3-hydroxy-1-oxo-8-azaspiro[4.5]decane-8-carboxylate (110.0 g, 0.4 mol) in DMF (1.0 L) were added imidazole (41.0 g, 0.6 mol), TBSCl (73.3 g, 0.48 mol) and the reaction mixture was stirred at ambient temperature overnight. The reaction mixture was poured into water (5 L), extracted with EtOAc (2×2 L) washed with brine, dried over Na$_2$SO$_4$, concentrated in vacuo, purified by silica column (pet.ether/EtOAc=20/1 to 10/1 to 3/1) to give the product (120.0 g, 78%) as a yellow oil. $^1$H NMR (400 MHz, CDCl$_3$) δ: 4.49 (s, 1H), 3.88 (s, 2H), 2.97 (s, 2H), 2.52 (s, 1H), 2.21 (s, 2H), 2.06 (s, 2H), 1.66 (s, 4H), 1.43 (s, 9H), 0.87 (s, 9H), 0.03 (s, 6H).

Step 7: tert-Butyl (1R,3R)-3-[(tert-butyldimethylsilyl)oxy]-1-[(2-methylpropane-2-sulfinyl)amino]-8-azaspiro[4.5]decane-8-carboxylate To the solution of tert-butyl (3R)-3-[(tert-butyldimethylsilyl)oxy]-1-oxo-8-azaspiro[4.5]decane-8-carboxylate (80.0 g, 0.2 mol) in THF (1.3 L) was added (R)-2-methylpropane-2-sulfinamide (50.6 g, 0.4 mol), Ti(OEt)$_4$ (182.5 g, 0.8 mol), then stirred at 65° C. overnight. The reaction mixture was cooled to −60° C., LiBH$_4$ (2 M, 300 mL, 0.6 mol) was added dropwise, stirred at −60° C. overnight. The reaction mixture was poured into NH$_4$Cl (aq. 2 L), extracted with EtOAc (2×1 L), washed with brine, dried over Na$_2$SO$_4$, concentrated in vacuo, purified by silica column (pet.ether/EtOAc=10/1 to 3/1) to give the product (120.0 g) as a yellow oil. 1H NMR (400 MHz, CDCl$_3$) δ: 4.30 (s, 1H), 3.94 (s, 2H), 3.58 (s, 1H), 3.28 (s, 1H), 2.82 (s, 2H), 2.30 (s, 1H), 1.76 (m, 7H), 1.38 (s, 9H), 1.19 (s, 9H), 0.85 (s, 9H), 0.01 (s, 6H).

Step 8: tert-Butyl (1R,3R)-3-hydroxy-1-[(2-methylpropane-2-sulfinyl)amino]-8-azaspiro[4.5]decane-8-carboxylate To the solution of tert-butyl (1R,3R)-3-[(tert-butyldimethylsilyl)oxy]-1-[(2-methylpropane-2-sulfinyl)amino]-8-azaspiro[4.5]decane-8-carboxylate (135.0 g, 0.276 mol) in THF (800 mL) was added TBAF (553 mL, 0.553 mol) and stirred at ambient temperature for 4 h. The reaction mixture was poured into water (1 L), extracted with EtOAc (2×500 mL), washed with brine, dried over Na$_2$SO$_4$, concentrated in vacuo to give the crude product (100.0 g, 97%) as a yellow oil. It was used in the next step without purification. $^1$H NMR (400 MHz, DMSO-d$_6$) δ: 5.05 (s, 1H), 4.67 (s, 1H), 4.04 (s, 1H), 3.82 (s, 2H), 3.05 (s, 1H), 2.74 (br, s, 2H), 2.10 (m, 1H), 1.67 (m, 4H), 1.42 (m, 11H), 1.24 (s, 2H), 1.09 (m, 9H).

Step 9: tert-Butyl (1R,3S)-3-(isoquinoline-1-carbonyloxy)-1-[(2-methylpropane-2-sulfinyl)amino]-8-azaspiro[4.5]decane-8-carboxylate To the solution of tert-butyl (1R,3R)-3-hydroxy-1-[(2-methylpropane-2-sulfinyl)amino]-8-azaspiro[4.5]decane-8-carboxylate (120.0 g, 0.32 mol) in THF (1 L) was added isoquinoline-1-carboxylic acid (166.6 g, 0.96 mol), DIAD (97.1 g, 0.48 mol), TPP (125.9 g, 0.48 mol) and the reaction mixture was stirred at ambient temperature for 2 h. The reaction mixture was poured into NaHCO$_3$ (aq. 2 L), extracted with EtOAc (2×1 L), washed with brine, dried over Na$_2$SO4, concentrated in vacuo to give the crude product, which was purified by silica column (DCM/EtOAc=50/1 to 20/1 to DCM/MeOH=20/1) to give the product (120.0 g, 71%) as a yellow solid. MS: [M+H]$^+$=530. $^1$H NMR (400 MHz, DMSO-d$_6$) δ: 8.59 (s, 1H), 8.40 (s, 1H), 8.04 (s, 2H), 7.83 (d, 2H), 5.48 (s, 1H), 5.23 (s, 1H), 3.85 (s, 2H), 3.50 (s, 1H), 2.77 (s, 2H), 2.49-2.38 (m, 1H), 2.14 (d, 2H), 1.73 (s, 2H), 1.47 (s, 1H), 1.38 (s, 9H), 1.25 (s, 3H), 1.15-1.11 (m, 9H).

Step 10: tert-Butyl (1R,3S)-3-hydroxy-1-[(2-methylpropane-2-sulfinyl)amino]-8-azaspiro[4.5]decane-8-carboxylate To the solution of tert-butyl (1R,3S)-3-(isoquinoline-1-carbonyloxy)-1-[(2-methylpropane-2-sulfinyl)amino]-8-azaspiro[4.5]decane-8-carboxylate (120.0 g, 0.227 mol) in THF/H$_2$O (1/1, 1 L) was added LiOH·H$_2$O (92.9 g, 2.27 mol) and stirred at ambient temperature for 2 h. The reaction mixture was poured into NH$_4$Cl (aq. 2 L), extracted with EtOAc (2×1 L), washed with brine, dried over Na$_2$SO$_4$, concentrated in vacuo to give the crude product, which was purified by crystallization from EtOAc/hexane to give the product (64.0 g, 75%) as a white solid. MS: [M+H-Boc]$^+$=275. $^1$H NMR (400 MHz, DMSO-d$_6$) δ: 4.97 (s, 1H), 4.51 (s, 1H), 4.06 (s, 1H), 3.82 (s, 2H), 3.39 (s, 1H), 2.74 (s, 2H), 1.99 (s, 1H), 1.81 (s, 3H), 1.39 (s, 11H), 1.28-1.16 (m, 1H), 1.11 (s, 9H).

Step 11: N-[(1R,3S)-3-Hydroxy-8-azaspiro[4.5]decan-1-yl]-2-methylpropane-2-sulfinamide To the solution of tert-butyl (1R,3S)-3-hydroxy-1-[(2-methylpropane-2-sulfinyl)amino]-8-azaspiro[4.5]decane-8-carboxylate (64.0 g, 0.171 mol) in DCM (600 mL) was added TFA (195.3 g, 1.71 mol), stirred at ambient temperature for 2 h. The reaction mixture was poured into water (2 L), extracted with Et$_2$O (5×300 mL) to remove impurities, then the pH was adjusted pH=8 with NaHCO$_3$ (aq.), the water was freeze dried to give the product (50.0 g) as a colourless oil. MS: [M+H]$^+$=275. $^1$H NMR (400 MHz, DMSO-d$_6$) δ: 5.13 (d, 1H), 4.83 (br, s, 3H), 4.08 (s, 1H), 3.44 (m, 1H), 3.15 (m, 2H), 2.78 (m, 2H), 2.01-1.64 (m, 4H), 1.40 (m, 2H), 1.25 (m, 1H), 1.15 (s, 9H).

Preparation 53:
5-Bromo-4-chloro-2-methyl-2H-indazole

[Chem. 87]

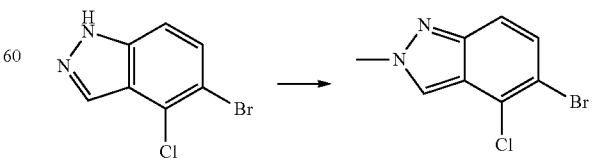

To a suspension of 5-bromo-4-chloro-1H-indazole (10.0 g, 43.2 mmol) in EtOAc (200 mL) was added trimethyloxonium tetrafluoroborate (9.58 g, 64.8 mmol) at RT. The mixture was stirred at RT for 20 h, quenched with sat. NaHCO$_3$, and extracted with EtOAc. The organic layer was washed with brine, dried over anhydrous Na$_2$SO$_4$, filtered, and concentrated in vacuo. The residue was purified by column chromatography on silica gel (gradient elution, 0-50% EtOAc/hexane) to give the title compound (9.16 g). MS: [M+H]$^+$=245, 247.

Preparation 54:
5-Bromo-4-chloro-2-ethyl-2H-indazole

[Chem. 88]

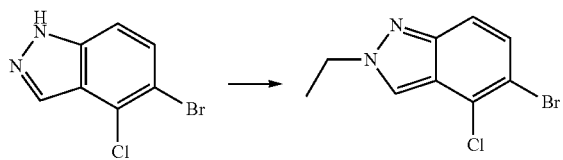

To a suspension of 5-bromo-4-chloro-1H-indazole (5.0 g, 21.6 mmol) in EtOAc (100 mL) was added triethyloxonium hexafluorophosphate (8.04 g, 32.4 mmol) at RT. The mixture was stirred at RT overnight, quenched with sat. NaHCO$_3$, and extracted with EtOAc. The organic layer was washed with brine, dried over anhydrous Na$_2$SO$_4$, filtered, and concentrated in vacuo. The residue was purified by column chromatography on silica gel (gradient elution, 0-50% EtOAc/hexane) to give the title compound (5.05 g). MS: [M+H]$^+$=259, 261.

Preparation 55:
5-Bromo-2-(tert-butyl)-4-chloro-2H-indazole

[Chem. 89]

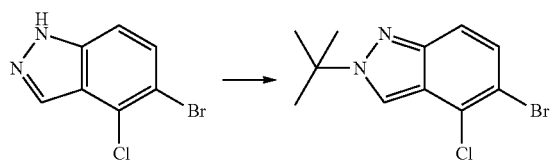

To a suspension of 5-bromo-4-chloro-1H-indazole (0.93 g, 4.0 mmol) in toluene (8.0 mL) were added tert-butyl acetate (4.7 g, 40 mmol) and methanesulfonic acid (0.38 g, 4.0 mmol) at RT. The mixture was stirred at 95° C. for 1 d. To the mixture was added tert-butyl acetate (4.7 g, 40 mmol) and methanesulfonic acid (0.38 g, 4.0 mmol) and stirred for another 1 d. The mixture was diluted with EtOAc, and washed with water and brine. The organic layer was concentrated in vacuo. The residue was purified by column chromatography on silica gel (gradient elution, 0-20% EtOAc/hexane) to give the title compound (1.1 g). MS: [M+H]$^+$=287, 289.

Preparation 56: 5-Bromo-2-methyl-2H-indazole

[Chem. 90]

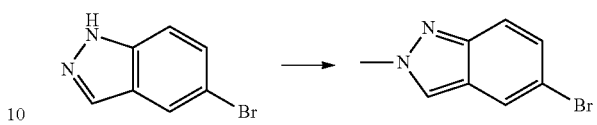

Prepared from 5-bromo-1H-indazole using similar procedure for the preparation of 5-bromo-4-chloro-2-methyl-2H-indazole, to give the title compound. MS: [M+H]$^+$=211, 213.

Preparation 57:
5-Bromo-4-fluoro-2-methyl-2H-indazole

[Chem. 91]

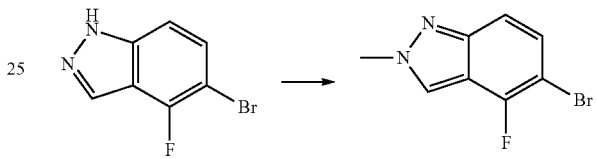

Prepared from 5-bromo-4-fluoro-1H-indazole using similar procedure for the preparation of 5-bromo-4-chloro-2-methyl-2H-indazole, to give the title compound. MS: [M+H]$^+$=229, 231.

Preparation 58:
5-Bromo-6-fluoro-2-methyl-2H-indazole

[Chem. 92]

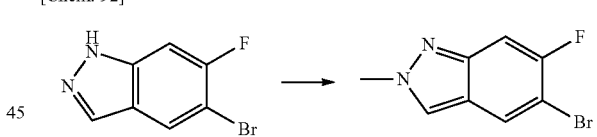

Prepared from 5-bromo-6-fluoro-1H-indazole using similar procedure for the preparation of 5-bromo-4-chloro-2-methyl-2H-indazole, to give the title compound. MS: [M+H]$^+$=229, 231.

Preparation 59:
5-Bromo-4-methoxy-2-methyl-2H-indazole

[Chem. 93]

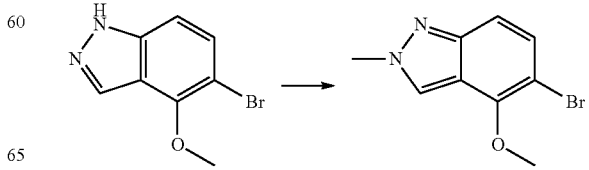

Prepared from 5-bromo-4-methoxy-1H-indazole using similar procedure for the preparation of 5-bromo-4-chloro-2-methyl-2H-indazole, to give the title compound. MS: [M+H]$^+$=241, 243.

Preparation 60: 1-(5-Bromo-4-chloro-2H-indazol-2-yl)-2-methylpropan-2-ol

[Chem. 94]

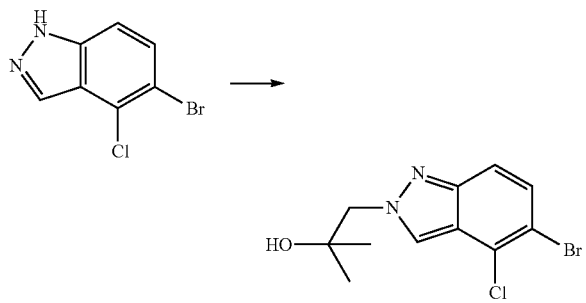

To a solution of 5-bromo-4-chloro-1H-indazole (1.0 g, 4.32 mmol) in DMF (10 mL) was added K$_2$CO$_3$ (1.19 g, 8.64 mmol) and isobutylene oxide (0.58 mL, 6.48 mmol) at RT. The mixture was stirred at 100° C. for 2 h, diluted with water, and extracted with EtOAc. The organic layer was washed with brine, dried over anhydrous Na$_2$SO$_4$, filtered, and concentrated in vacuo. The residue was purified by column chromatography on silica gel (gradient elution, 10-20% EtOAc/hexane) to give the title compound (0.55 g). MS: [M+H]$^+$=303, 305.

Preparation 61: 5-Bromo-4-chloro-2,7-dimethyl-2H-indazole

[Chem. 95]

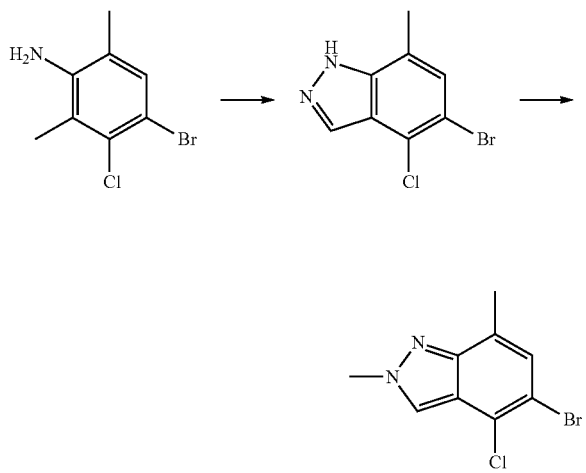

To a mixture of 4-bromo-3-chloro-2,6-dimethylaniline (4.8 g, 20 mmol), potassium acetate (3.1 g, 31 mmol), acetic acid (1.8 g, 29 mmol) and toluene (61 mL) was added tert-butyl nitrite (2.5 g, 25 mmol) at RT. The mixture was stirred at 45° C. overnight. To the mixture was added EtOAc (40 mL) and 1 M NaOH aq. (40 mL). The separated organic layer was washed with brine, and concentrated in vacuo. The residue was suspended in toluene and heptane. The precipitate was collected and dried at 50° C. under reduced pressure to give a mixture of 5-bromo-4-chloro-7-methyl-1H-indazole and 5-bromo-6-chloro-7-methyl-1H-indazole (3.4 g). MS: [M+H]$^+$=245, 247.

Prepared from a mixture of 5-bromo-4-chloro-7-methyl-1H-indazole and 5-bromo-6-chloro-7-methyl-1H-indazole using similar procedure for the preparation of 5-bromo-4-chloro-2-methyl-2H-indazole, to give the title compound. MS: [M+H]$^+$=259, 261

Preparation 62: 5-Bromo-3,4-dichloro-2-methyl-2H-indazole

[Chem. 96]

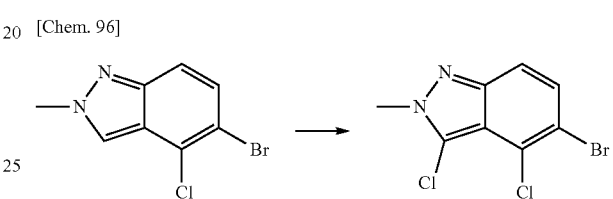

To a solution of 5-bromo-4-chloro-2-methyl-2H-indazole (5 g, 20.3 mmol) in DMF (50 mL) was added NCS (2.99 g, 22.4 mmol) at 0° C. The mixture was stirred at RT overnight. Water (150 mL) was added at RT. The mixture was stirred at RT for 1 h. The precipitate was collected, washed with water, and dried at 60° C. for 3 h under reduced pressure to give the title compound (5.63 g). MS: [M+H]$^+$=279, 281.

Preparation 63: 5-Bromo-4-chloro-2,3-dimethyl-2H-indazole

[Chem. 97]

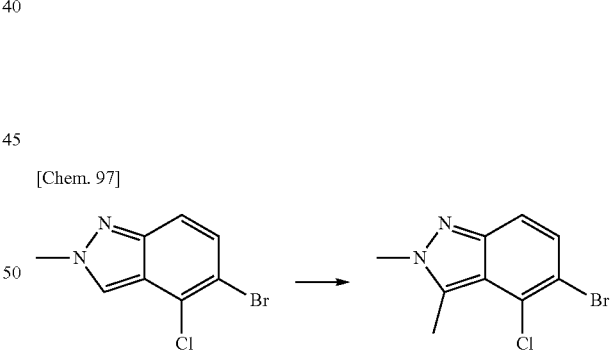

To a solution of 5-bromo-4-chloro-2-methyl-2H-indazole (500 mg, 2.03 mmol) in THF (10 mL) was added LDA (1.08 M in THF, 2.26 mL, 2.44 mmol) at −78° C. The mixture was stirred at 0° C. for 30 min, and cooled to −78° C. Iodomethane (0.190 mL, 3.05 mmol) was added at −78° C. The mixture was stirred at −78° C. for 2 h, quenched with sat. NH$_4$Cl, and extracted with EtOAc. The organic layer was washed with brine, dried over anhydrous Na$_2$SO$_4$, filtered, and concentrated in vacuo. The residue was purified by column chromatography on silica gel (gradient elution, 0-60% EtOAc/hexane) to give the title compound (442 mg). MS: [M+H]$^+$=259, 261.

Preparation 64: 2-(5-Bromo-4-chloro-2H-indazol-2-yl)-N,N-dimethylacetamide

[Chem. 98]

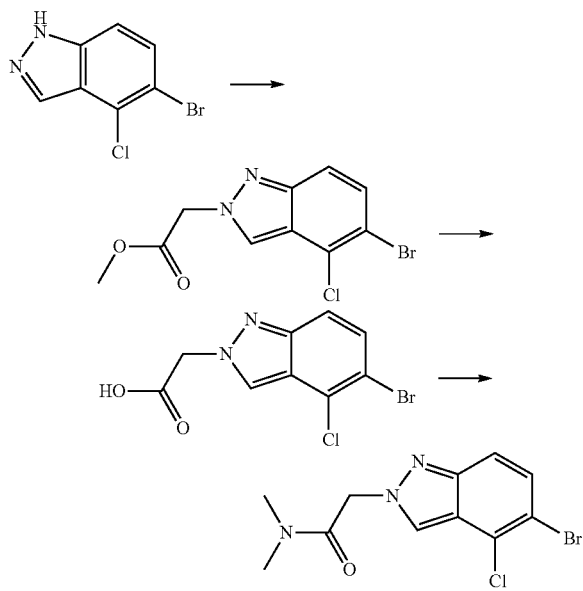

Step 1

To a solution of 5-bromo-4-chloro-1H-indazole (500 mg, 2.16 mmol) and methyl glycolate (0.25 mL, 3.24 mmol) in THF (10 mL) was added DMEAD (759 mg, 3.24 mmol) and triphenylphosphine (850 mg, 3.24 mmol) at RT. The mixture was stirred at RT for 2 h. The reaction solution was concentrated in vacuo, and the residue was purified by column chromatography on silica gel (gradient elution, 20-40% EtOAc/hexane) to give methyl 2-(5-bromo-4-chloro-2H-indazol-2-yl)acetate (190 mg). MS: [M+H]$^+$=303, 305.

Step 2

To a solution of methyl 2-(5-bromo-4-chloro-2H-indazol-2-yl)acetate (190 mg, 0.63 mmol) in THF (1.9 mL) was added a solution of LiOH (90 mg, 3.76 mmol) in water (0.95 mL) at RT. The mixture was stirred at RT for 20 min, diluted with MTBE and added 2 M NaOH. The aqueous layer was added 6 M HCl and extracted with CHCl$_3$ three times. The organic layer was washed with brine, dried over anhydrous Na$_2$SO$_4$, filtered, and concentrated in vacuo to give 2-(5-bromo-4-chloro-2H-indazol-2-yl)acetic acid (140 mg). MS: [M+H]$^+$=289, 291.

Step 3

2-(5-Bromo-4-chloro-2H-indazol-2-yl)acetic acid (140 mg, 0.48 mmol) in THF (1.4 mL) was added TEA (0.27 mL, 1.93 mmol), HATU (276 mg, 0.73 mmol) and dimethylamine hydrochloride (59 mg, 0.73 mmol) at RT. The mixture was stirred at 50° C. for 1 h. The reaction solution was concentrated in vacuo, and the residue was purified by column chromatography on silica gel (gradient elution, 40-100% EtOAc/hexane) to give the title compound (125 mg). MS: [M+H]$^+$=316, 318.

Preparation 65: 6-Bromo-7-chloro-2,3-dihydro-1,3-benzothiazole-2-thione

[Chem. 99]

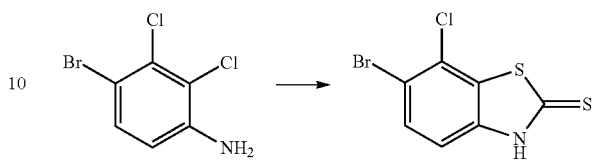

A mixture of 4-bromo-2,3-dichloroaniline (10.0 g, 41.5 mmol) and potassium ethyl xanthate (15.0 g, 93.4 mmol) in DMF (100 mL) was stirred at 120° C. for 18 h. The mixture was quenched with 2 M aq. HCl (80 ml) and water (400 mL). The mixture was filtered and washed with water to give the title compound (1.13 g). $^1$H-NMR (400 MHz, DMSO-d$_6$) δ: 14.10 (1H, s), 7.78 (1H, d), 7.19 (1H, d).

Preparation 66: 6-Bromo-7-chloro-1,3-benzothiazole

[Chem. 100]

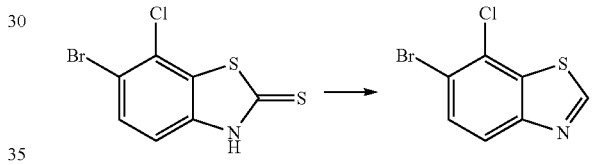

A round bottomed flask charged with 6-bromo-7-chloro-2,3-dihydro-1,3-benzothiazole-2-thione (1.13 g, 40.3 mmol), iron powder (12.4 g, 221.5 mmol) and acetic acid (200 mL) at RT was stirred (with mechanical stirrer) at 120° C. for 2 h. Further iron powder (24.8 g, 443.0 mmol) was added and the mixture was stirred at 120° C. for 2 h. Additional iron powder (12.4 g, 221.5 mmol) was added and the reaction was stirred at 120° C. for 15 h. The mixture was filtered and the filtrate concentrated under reduced pressure. The residue was purified by recrystallization from EtOAc and then by column chromatography on silica gel (10% EtOAc/petrol) to give the title compound (0.27 g). MS: [M+H]$^+$=248.

Preparation 67: N-(4-Bromo-3-chloro-2-fluorophenyl)acetamide

[Chem. 101]

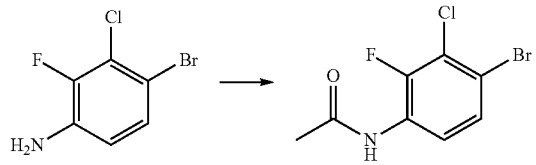

To a solution of 4-bromo-3-chloro-2-fluoroaniline (25 g, 111 mmol) and DIPEA (48.5 ml, 278 mmol) in DCM (250 mL) cooled in an ice bath was added acetic anhydride (11.05 ml, 117 mmol) over 1.5 h. The reaction was warmed to RT and stirred for 24 h. The reaction was washed with HCl (1 M, 250 mL), NaHCO$_3$ (150 mL) and water (100 mL). The organic phase was dried (MgSO$_4$) and concentrated under reduced pressure. The residue was purified by column chromatography on silica gel (gradient elution, 0-40% EtOAc/petrol) to give the title compound (23.8 g). $^1$H-NMR (500 MHz, DMSO-d$_6$) δ: 9.97 (s, 1H), 7.95-7.77 (m, 1H), 7.56 (dd, 1H), 2.10 (s, 3H).

Preparation 68:
6-Bromo-7-chloro-2-methyl-1,3-benzothiazole

[Chem. 102]

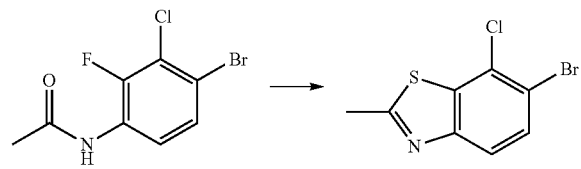

To a solution of N-(4-bromo-3-chloro-2-fluorophenyl)acetamide (1.0 g, 3.77 mmol) in xylene (9.86 mL) was added Lawesson's Reagent (1.53 g, 2.26 mmol). The reaction was heated to 110° C. for 18 h. Cesium carbonate (4.11 g, 7.55 mmol) was added and the mixture was stirred at 110° C. for 18 h. The reaction was cooled to RT and the reaction was diluted with water (500 mL) and ethyl acetate. The organic layer was separated and washed with sat. brine solution, then dried over anhydrous Na$_2$SO$_4$, filtered and concentrated under reduced pressure. The residue was purified by column chromatography on silica (gradient elution, 0-20% EtOAc/petrol), to give the title compound (0.97 g). $^1$H-NMR (400 MHz, DMSO-d$_6$) δ: 7.85 (2H, d), 2.83 (3H, s).

Preparation 69:
6-Bromo-7-chloro-2-ethylbenzo[d]thiazole

[Chem. 103]

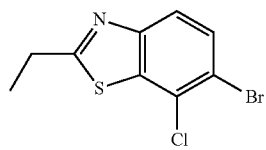

Prepared from propionyl chloride using similar procedure for the preparation of 6-bromo-7-chloro-2-methyl-1,3-benzothiazole, to give the title compound. MS: [M+H]$^+$=211, 213.

Preparation 70: 2-(6-Bromo-7-chlorobenzo[d]thiazol-2-yl)-N,N-dimethylacetamide

[Chem. 104]

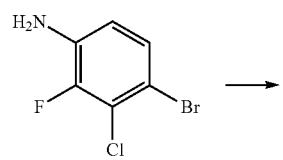

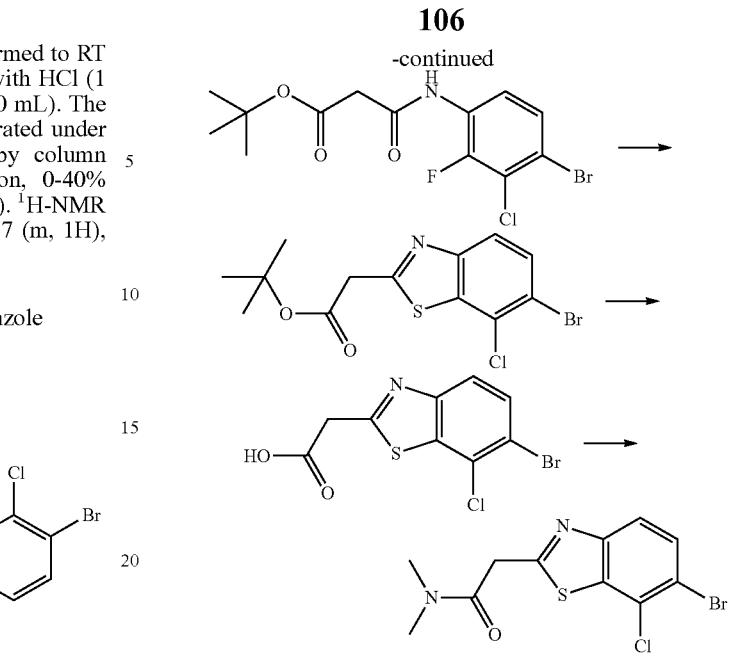

Step 1

To a solution of 4-bromo-3-chloro-2-fluoro-aniline (3 g, 13.4 mmol) and HATU (10.2 g, 26.7 mmol) in DMA (30 mL) was added TEA (5.58 mL, 40.1 mmol) and 3-tert-butoxy-3-oxopropanoic acid (3.09 mL, 20.0 mmol) at RT. The mixture was stirred at 50° C. for 1 h, diluted with water, and extracted with EtOAc. The organic layer was washed with brine, dried over anhydrous Na$_2$SO$_4$, filtered, and concentrated in vacuo. The residue was purified by column chromatography on silica gel (gradient elution, 30-70% EtOAc/hexane) to give tert-butyl 3-(4-bromo-3-chloro-2-fluoro-anilino)-3-oxo-propanoate (3.35 g).

Step 2

To a suspension of tert-butyl 3-(4-bromo-3-chloro-2-fluoro-anilino)-3-oxo-propanoate (2 g, 5.47 mmol) in toluene (20 mL) was added LAWESSON'S REAGENT (1.32 g, 3.27 mmol) at RT. The mixture was stirred at 110° C. for 3 h. Cs$_2$CO$_3$ (3.56 g, 10.9 mmol) was added. The mixture was stirred at 110° C. for 19 h, cooled to RT, and filtered. The filtrate was concentrated in vacuo. The residue was purified by column chromatography on silica gel (gradient elution, 0-20% EtOAc/CHCl$_3$) to give tert-butyl 2-(6-bromo-7-chlorobenzo[d]thiazol-2-yl)acetate (983 mg).

Step 3

To a solution of tert-butyl 2-(6-bromo-7-chlorobenzo[d]thiazol-2-yl)acetate (500 mg, 1.38 mmol) in CHCl$_3$ (5 mL) was added TFA (2.5 mL, 32 mmol) at RT. The mixture was stirred at 60° C. for 1 h. The reaction solution was concentrated in vacuo, and the residue was suspended with hexane. The precipitate was collected, washed with hexane, and dried at 60° C. for 3 h under reduced pressure to give 2-(6-bromo-7-chlorobenzo[d]thiazol-2-yl)acetic acid (200 mg). MS: [M+H]$^+$=306, 308.

Step 4

To a solution of 2-(6-bromo-7-chlorobenzo[d]thiazol-2-yl)acetic acid (200 mg, 0.65 mmol) in THF (4 mL) was added TEA (0.45 mL, 3.26 mmol), propylphosphonic anhydride (1.6 M in THF, 0.82 mL, 1.30 mmol), and dimethylamine (2.0 M in THF, 0.65 mL, 1.30 mmol) at RT. The mixture was stirred at RT for 10 min. The reaction solution was concentrated in vacuo, and the residue was purified by column chromatography on silica gel (gradient elution, 80-100% EtOAc/hexane) to give the title compound (168 mg). MS: [M+H]$^+$=333, 335.

Preparation 71:
N-(4-Bromo-3-chloro-2-hydroxyphenyl)acetamide

[Chem. 105]

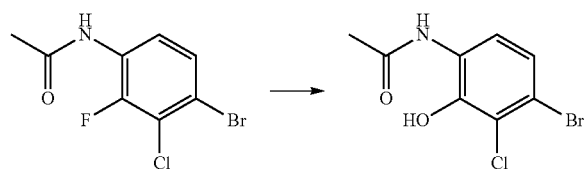

The suspension of N-(4-bromo-3-chloro-2-fluoro-phenyl)acetamide (1.0 g, 3.8 mmol), cesium carbonate (2.0 equiv., 7.5 mmol) in NMP (6.0 mL) was irradiated by microwave (Initiator, Biotage) at 150° C. for 5 h. To the mixture was added NMP (15 mL) and the mixture was again irradiated at 150° C. by microwave for 5 h. The reaction mixture was diluted by EtOAc and water and acidified with 5 N HCl aq. to adjust its pH to 1-2. The mixture was extracted with EtOAc (×3), and the organic extracts were washed with brine and dried over Na$_2$SO$_4$. Concentration gave the crude mixture (1.20 g, a brown oil), which was subjected to column chromatography purification (gradient elution, 5-70% EtOAc/hexane) to give the title compound (425 mg, 1.61 mmol, 43% Yield) as a yellow solid. MS: [M+H]$^+$=264, 266.

Preparation 72:
6-Bromo-7-chloro-2-methylbenzo[d]oxazole

[Chem. 106]

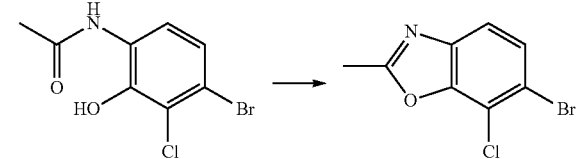

To the solution of N-(4-bromo-3-chloro-2-hydroxyphenyl)acetamide (1.09 g, 4.12 mmol), triphenylphosphine (1.62 g, 6.18 mmol) in THF (30 mL) was added diisopropyl azodicarboxylate (1.21 mL, 6.18 mmol) and the mixture was heated in an oil bath at 50° C. for 2 h 45 min. The reaction mixture was concentrated to give the crude oil (4.30 g, a brown oil), which was subjected to column chromatography purification (gradient elution, 5-70% EtOAc/hexane), successively suspended in hexane and collected by filtration to give the title compound (908 mg, 3.68 mmol, 89% Yield) as a colorless solid. MS: [M+H]$^+$=246, 248.

Preparation 73:
N-(4-Bromo-3-chloro-2-fluorophenyl)propionamide

[Chem. 107]

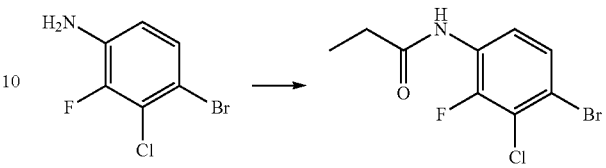

To the solution of 4-bromo-3-chloro-2-fluoroaniline (5.00 g, 22.3 mmol) in DCM (40 mL) were added TEA (2.0 equiv., 44.6 mmol) and propionyl chloride (2.34 mL, 26.7 mmol) at 0° C. The ice water bath was removed and the mixture was stirred at RT for 17 h. Propionyl chloride (0.779 mL, 8.92 mmol) was added to the mixture at RT. After 45 min stirring at RT, water was added to the mixture. The mixture was extracted with EtOAc (×2) and the organic extracts were washed with water, dil. NH$_4$Cl aq., NaHCO$_3$ aq., and brine and dried over Na$_2$SO$_4$. The concentrated crude mixture was suspended in hexane-EtOAc (4/1) and collected by a Kiriyama-roshi (No. 4) to give the title compound (4.22 g, 15.0 mmol, 67% Yield) as a colorless needle. The filterate (an orange solid, 2.23 g) was subjected to column chromatography purification (gradient elution, 5-40% EtOAc/hexane) to give the title compound (1.33 g, 4.74 mmol, 21% Yield) as a colorless needle. MS: [M+H]$^+$=280, 282.

Preparation 74:
N-(4-Bromo-3-chloro-2-hydroxyphenyl)propionamide

[Chem. 108]

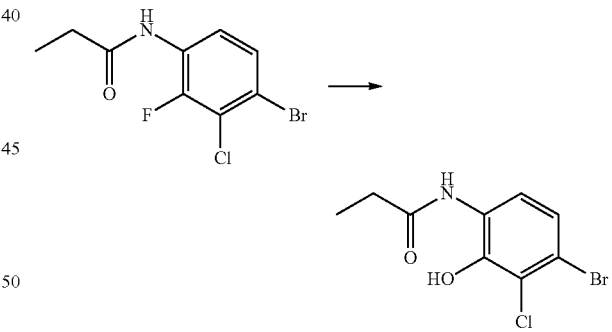

The suspension of N-(4-bromo-3-chloro-2-fluoro-phenyl)propanamide (2.50 g, 8.91 mmol), cesium carbonate (5.80 g, 17.8 mmol) in NMP (15 mL) was irradiated by microwave (Initiator, Biotage) at 150° C. for 5 h. To the mixture was added NMP (15 mL) and the mixture was again irradiated at 150° C. by microwave for 5 h. The reaction mixture was diluted by EtOAc and water and acidified with 5 N HCl aq. to adjust its pH to 1-2. The mixture was extracted with EtOAc (×3), and the organic extracts were washed with brine and dried over Na$_2$SO$_4$. Concentration gave the crude mixture (5.90 g, a brown oil), which was subjected to column chromatography purification (gradient elution, 5-100% EtOAc/hexane) to give the title compound (1.27 g, 4.56 mmol, 51% Yield). MS: [M+H]$^+$=278, 280.

Preparation 75: 6-Bromo-7-chloro-2-ethylbenzo[d]oxazole

[Chem. 109]

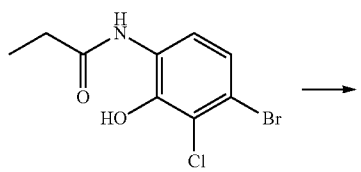

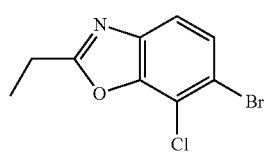

To the solution of N-(4-bromo-3-chloro-2-hydroxyphenyl)propanamide (607 mg, 2.18 mmol), triphenylphosphine (857 mg, 3.27 mmol) in THF (10 mL) was added diisopropyl azodicarboxylate (0.642 mL, 3.27 mmol) and the mixture was heated in an oil bath at 50° C. for 1 h 45 min. The reaction mixture was concentrated to give the crude oil (2.38 g, a brown oil), which was subjected to column chromatography purification (gradient elution, 5-50% EtOAc/hexane) to give the title compound (525 mg, 2.02 mmol, 92% Yield) as a pale yellow solid. MS: [M+H]$^+$=260, 262.

Preparation 76: 6-Bromo-7-chloro-1-methyl-1H-benzo[d][1,2,3]triazole

[Chem. 110]

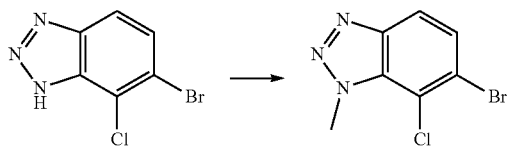

To a solution of 6-bromo-7-chloro-1H-benzo[d][1,2,3]triazole (400 mg, 1.72 mmol) in THF (8 mL) was added triphenylphosphine (542 mg, 2.06 mmol), MeOH (0.084 mL, 2.06 mmol) and DMEAD (484 mg, 2.06 mmol) at RT. The mixture was stirred at RT for 2 h. The reaction solution was then concentrated in vacuo, and the residue was purified by column chromatography on silica gel (gradient elution, 10-40% EtOAc/hexane). The fractions containing target product were collected, and concentrated in vacuo. The residue was purified by column chromatography on NH silica gel (gradient elution, 0-20% EtOAc/hexane) to give the title compound (152 mg). $^1$H-NMR (CDCl$_3$) δ: 7.82 (1H, d, J=8.8 Hz), 7.58 (1H, d, J=8.8 Hz), 4.57 (3H, s). MS: [M+H]$^+$=246, 248.

Preparation 77: 5-Bromo-4-chloro-2-methyl-2H-benzo[d][1,2,3]triazole

[Chem. 111]

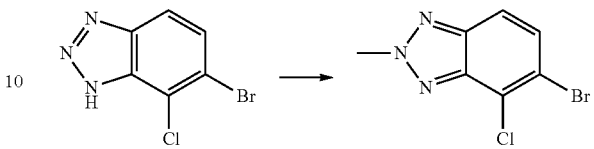

To a solution of 6-bromo-7-chloro-1H-benzo[d][1,2,3]triazole (400 mg, 1.72 mmol) in THF (8 mL) was added triphenylphosphine (542 mg, 2.06 mmol), MeOH (0.084 mL, 2.06 mmol) and DMEAD (484 mg, 2.06 mmol) at RT. The mixture was stirred at RT for 2 h. The reaction solution was then concentrated in vacuo, and the residue was purified by column chromatography on silica gel (gradient elution, 10-40% EtOAc/hexane). The fractions containing target product were collected, and concentrated in vacuo. The residue was purified by column chromatography on NH silica gel (gradient elution, 0-20% EtOAc/hexane) to give the title compound (160 mg). $^1$H-NMR (CDCl$_3$) δ: 7.66 (1H, d, J=9.0 Hz), 7.57 (1H, d, J=9.0 Hz), 4.54 (3H, s). MS: [M+H]$^+$=246, 248.

Preparation 78: 5-Bromo-3-chloro-4-fluoro-2-methyl-2H-indazole

[Chem. 112]

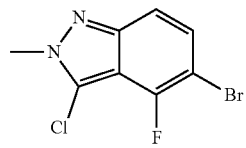

Prepared from 5-bromo-4-fluoro-2-methyl-2H-indazole using similar procedure for the preparation of 5-bromo-3,4-dichloro-2-methyl-2H-indazole, to give the title compound. MS: [M+H]$^+$=263, 265.

Preparation 79: 5-Bromo-4-chloro-2-ethyl-2H-indazole-3-carbaldehyde

[Chem. 113]

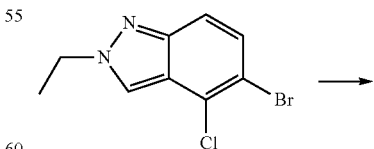

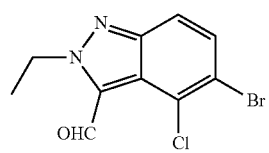

To a solution of 5-bromo-4-chloro-2-ethyl-2H-indazole (1.1 g, 4.1 mmol) in THF (8.3 mL) was added LDA (1.08 M in hexane-THF, 5.8 mL, 6.3 mmol) at −78° C. The mixture was stirred at 0° C. for 30 min. N,N-dimethylformamide (0.61 g, 8.3 mmol) was added at 0° C. The mixture was stirred at RT overnight, quenched with sat. NH$_4$Cl aq., and extracted with EtOAc. The organic layer was washed with brine and concentrated in vacuo. The residue was purified by column chromatography on silica gel (gradient elution, 0-40% EtOAc/hexane) to give the title compound (772 mg). MS: [M+H]$^+$=287, 289.

Preparation 80:
5-Bromo-4-chloro-2-ethyl-3-methoxy-2H-indazole

[Chem. 114]

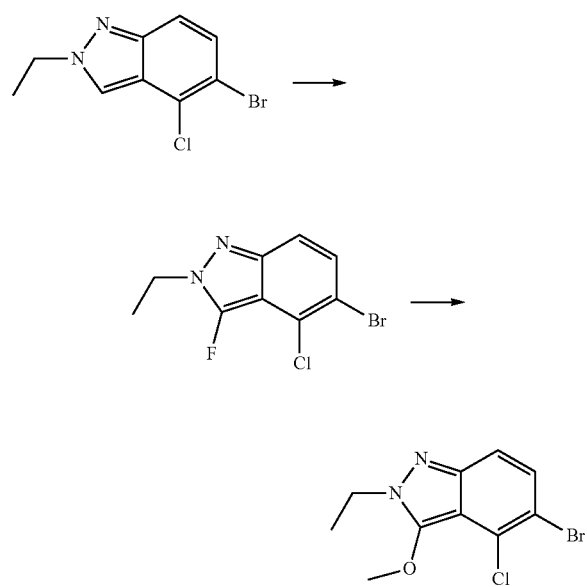

To a solution of 5-bromo-4-chloro-2-ethyl-2H-indazole (500 mg, 1.92 mmol) in THF (10 mL) was added LDA (1.08 M in THF, 2.14 mL, 2.31 mmol) at −78° C. The mixture was stirred at 0° C. for 30 min. N-Fluorobenzenesulfonimide (850 mg, 2.69 mmol) was added at 0° C. The mixture was stirred at 0° C. for 1 h, quenched with water, and extracted with EtOAc. The organic layer was washed with brine, dried over anhydrous Na$_2$SO$_4$, filtered, and concentrated in vacuo. The residue was purified by column chromatography on silica gel (gradient elution, 0-60% EtOAc/hexane) to give 5-bromo-4-chloro-2-ethyl-3-fluoro-2H-indazole (185 mg). MS: [M+H]$^+$=277, 279.

To a solution of 5-bromo-4-chloro-2-ethyl-3-fluoro-2H-indazole (183 mg, 0.659 mmol) in THF (3 mL) was added NaOMe (28% in MeOH, 0.472 mL, 1.97 mmol) at RT. The mixture was stirred at 60° C. for 4 h, cooled to RT, poured into water, and extracted with EtOAc. The organic layer was washed with brine, dried over anhydrous Na$_2$SO$_4$, filtered, and concentrated in vacuo. The residue was purified by column chromatography on silica gel (gradient elution, 0-60% EtOAc/hexane) to give the title compound (166 mg). MS: [M+H]$^+$=289, 291.

Preparation 81:
5-Bromo-3,4-dichloro-2-(fluoromethyl)-2H-indazole

[Chem. 115]

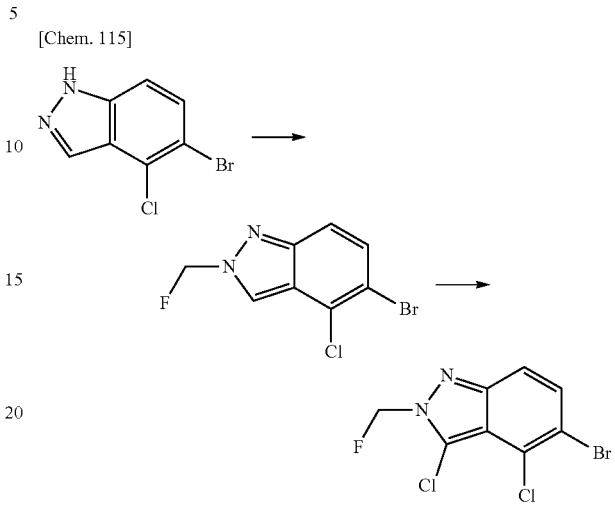

The mixture of 5-bromo-4-chloro-1H-indazole (1.00 g, 4.32 mmol), fluoromethyl p-toluenesulfonate (0.970 g, 4.75 mmol), Cs$_2$CO$_3$ (1.68 g, 5.18 mmol) and NMP (10 mL) was stirred at 60° C. for 11 h, cooled to RT, poured into water, and extracted with EtOAc. The organic layer was washed with water and brine, dried over anhydrous Na$_2$SO$_4$, filtered, and concentrated in vacuo. The residue was purified by column chromatography on silica gel (gradient elution, 0-60% EtOAc/hexane) to give 5-bromo-4-chloro-2-(fluoromethyl)-2H-indazole (346 mg). MS: [M+H]$^+$=263, 265.

To a solution of 5-bromo-4-chloro-2-(fluoromethyl)-2H-indazole (378 mg, 1.43 mmol) in DMF (4 mL) was added NCS (210 mg, 1.57 mmol) at 0° C. The mixture was stirred at RT for 44 h. NCS (40 mg, 0.299 mmol) was added at RT. The mixture was stirred at RT for 24 h, poured into water, and extracted with EtOAc. The organic layer was washed with water and brine, dried over anhydrous Na$_2$SO$_4$, filtered, and concentrated in vacuo. The residue was purified by column chromatography on silica gel (gradient elution, 10-35% EtOAc/hexane) to give the title compound (401 mg). MS: [M+H]$^+$=297, 299.

Preparation 82: 4-Chloro-2-methyl-5-(4,4,5,5-tetramethyl-1,3,2-dioxaborolan-2-yl)-2H-indazole

[Chem. 116]

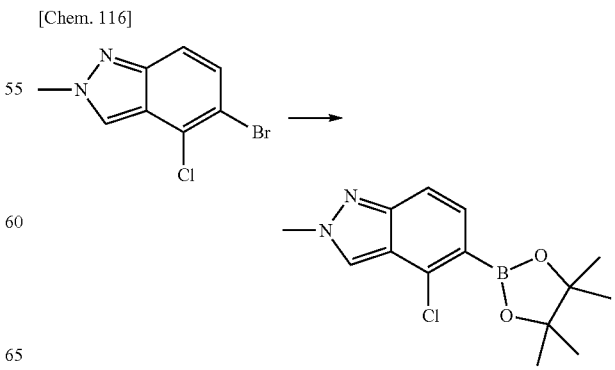

The mixture of 5-bromo-4-chloro-2-methyl-2H-indazole (12.14 g, 49.45 mmol), bis(pinacolato)diboron (18.83 g, 74.18 mmol), [1,1'-bis(diphenylphosphino)ferrocene]dichloropalladium(II) complex with dichloromethane (4.038 g, 4.945 mmol) and potassium acetate (9.706 g, 98.90 mmol) in 1,4-dioxane (120 mL) was degassed, purged with nitrogen, and stirred at 120° C. for 5 h. The reaction was cooled to RT, filtered through a pad of Celite, and washed with EtOAc. The filtrate was concentrated in vacuo. The residue was purified by column chromatography on NH silica gel (gradient elution, 0-70% EtOAc/hexane) to give the title compound (14.36 g). MS: [M+H]$^+$=293, 295.

Compounds of Table 1 below were prepared using procedures analogous to that described in preparation 82, starting from the appropriate substituted aryl halide (synthesised as described above with any significant variations indicated below).

TABLE 1

| Compound | Compound name | MS: [M + H]$^+$ m/z | Procedure |
|---|---|---|---|
| (structure) | 4-Chloro-2-ethyl-5-(4,4,5,5-tetramethyl-1,3,2-dioxaborolan-2-yl)-2H-indazole | 307, 309 | Prepared as preparation 82 above using 5-bromo-4-chloro-2-ethyl-2H-indazole |
| (structure) | 2-(tert-Butyl)-4-chloro-5-(4,4,5,5-tetramethyl-1,3,2-dioxaborolan-2-yl)-2H-indazole | 335, 337 | Prepared as preparation 82 above using 5-bromo-2-(tert-butyl)-4-chloro-2H-indazole |
| (structure) | 2-Methyl-5-(4,4,5,5-tetramethyl-1,3,2-dioxaborolan-2-yl)-2H-indazole | 259 | Prepared as preparation 82 above using 5-bromo-2-methyl-2H-indazole |
| (structure) | 4-Fluoro-2-methyl-5-(4,4,5,5-tetramethyl-1,3,2-dioxaborolan-2-yl)-2H-indazole | 277 | Prepared as preparation 82 above using 5-bromo-4-fluoro-2-methyl-2H-indazole |
| (structure) | 6-Fluoro-2-methyl-5-(4,4,5,5-tetramethyl-1,3,2-dioxaborolan-2-yl)-2H-indazole | 277 | Prepared as preparation 82 above using 5-bromo-6-fluoro-2-methyl-2H-indazole |
| (structure) | 4-Methoxy-2-methyl-5-(4,4,5,5-tetramethyl-1,3,2-dioxaborolan-2-yl)-2H-indazole | 289 | Prepared as preparation 82 above using 5-bromo-4-methoxy-2-methyl-2H-indazole |

TABLE 1-continued

| Compound | Compound name | MS: [M + H]+ m/z | Procedure |
|---|---|---|---|
| | 1-(4-Chloro-5-(4,4,5,5-tetramethyl-1,3,2-dioxaborolan-2-yl)-2H-indazol-2-yl)-2-methylpropan-2-ol | 351, 353 | Prepared as preparation 82 above using 1-(5-bromo-4-chloro-2H-indazol-2-yl)-2-methylpropan-2-ol |
| | 4-Chloro-2,7-dimethyl-5-(4,4,5,5-tetramethyl-1,3,2-dioxaborolan-2-yl)-2H-indazole | 307, 309 | Prepared as preparation 82 above using 5-bromo-4-chloro-2,7-dimethyl-2H-indazole |
| | 4-Chloro-5-(4,4,5,5-tetramethyl-1,3,2-dioxaborolan-2-yl)-1H-indazole | 279, 281 | Prepared as preparation 82 above using 5-bromo-4-chloro-1H-indazole |
| | 4-Chloro-2,3-dimethyl-5-(4,4,5,5-tetramethyl-1,3,2-dioxaborolan-2-yl)-2H-indazole | 307, 309 | Prepared as preparation 82 above using 5-bromo-4-chloro-2,3-dimethyl-2H-indazole |
| | 3,4-Dichloro-2-methyl-5-(4,4,5,5-tetramethyl-1,3,2-dioxaborolan-2-yl)-2H-indazole | 327, 329 | Prepared as preparation 82 above using 5-bromo-3,4-dichloro-2-methyl-2H-indazole |
| | 2-(4-Chloro-5-(4,4,5,5-tetramethyl-1,3,2-dioxaborolan-2-yl)-2H-indazol-2-yl)-N,N-dimethylacetamide | 364, 366 | Prepared as preparation 82 above using 2-(5-bromo-4-chloro-2H-indazol-2-yl)-N,N-dimethylacetamide |
| | 7-Chloro-6-(4,4,5,5-tetramethyl-1,3,2-dioxaborolan-2-yl)benzo[d]thiazole | 296, 298 | Prepared as preparation 82 above using 6-bromo-7-chlorobenzo[d]thiazole |

TABLE 1-continued

| Compound | Compound name | MS: [M + H]+ m/z | Procedure |
|---|---|---|---|
| | 7-Chloro-2-methyl-6-(4,4,5,5-tetramethyl-1,3,2-dioxaborolan-2-yl)benzo[d]thiazole | 310, 312 | Prepared as preparation 82 above using 6-bromo-7-chloro-2-methylbenzo[d]thiazole |
| | 7-Chloro-2-ethyl-6-(4,4,5,5-tetramethyl-1,3,2-dioxaborolan-2-yl)benzo[d]thiazole | 324, 326 | Prepared as preparation 82 above using 6-bromo-7-chloro-2-ethylbenzo[d]thiazole |
| | 2-(7-Chloro-6-(4,4,5,5-tetramethyl-1,3,2-dioxaborolan-2-yl)benzo[d]thiazol-2-yl)-N,N-dimethylacetamide | 381, 383 | Prepared as preparation 82 above using 2-(6-bromo-7-chlorobenzo[d]thiazol-2-yl)-N,N-dimethylacetamide |
| | 7-Chloro-2-methyl-6-(4,4,5,5-tetramethyl-1,3,2-dioxaborolan-2-yl)benzo[d]oxazole | 294, 296 | Prepared as preparation 82 above using 6-bromo-7-chloro-2-methylbenzo[d]oxazole |
| | 7-Chloro-2-ethyl-6-(4,4,5,5-tetramethyl-1,3,2-dioxaborolan-2-yl)benzo[d]oxazole | 308, 310 | Prepared as preparation 82 above using 6-bromo-7-chloro-2-ethylbenzo[d]oxazole |
| | 6,7-Difluoro-1-methyl-5-(4,4,5,5-tetramethyl-1,3,2-dioxaborolan-2-yl)-1H-benzo[d][1,2,3]triazole | 296 | Prepared as preparation 82 above using 5-bromo-6,7-difluoro-1-methyl-1H-benzo[d][1,2,3]triazole |
| | 7-Chloro-1-methyl-6-(4,4,5,5-tetramethyl-1,3,2-dioxaborolan-2-yl)-1H-benzo[d][1,2,3]triazole | 294, 296 | Prepared as preparation 82 above using 6-bromo-7-chloro-1-methyl-1H-benzo[d][1,2,3]triazole |

TABLE 1-continued

| Compound | Compound name | MS: [M + H]+ m/z | Procedure |
|---|---|---|---|
| (structure) | 4-Chloro-2-methyl-5-(4,4,5,5-tetramethyl-1,3,2-dioxaborolan-2-yl)-2H-benzo[d][1,2,3]triazole | 294, 296 | Prepared as preparation 82 above using 5-bromo-4-chloro-2-methyl-2H-benzo[d][1,2,3]triazole |
| (structure) | 3-Chloro-4-fluoro-2-methyl-5-(4,4,5,5-tetramethyl-1,3,2-dioxaborolan-2-yl)-2H-indazole | 311, 313 | Prepared as preparation 82 above using 5-bromo-3-chloro-4-fluoro-2-methyl-2H-indazole |
| (structure) | 4-Chloro-2-ethyl-5-(4,4,5,5-tetramethyl-1,3,2-dioxaborolan-2-yl)-2H-indazole-3-carbaldehyde | 335, 337 | Prepared as preparation 82 above using 5-bromo-4-chloro-2-ethyl-2H-indazole-3-carbaldehyde |
| (structure) | 4-Chloro-2-ethyl-3-methoxy-5-(4,4,5,5-tetramethyl-1,3,2-dioxaborolan-2-yl)-2H-indazole | 337, 339 | Prepared as preparation 82 above using 5-bromo-4-chloro-2-ethyl-3-methoxy-2H-indazole |
| (structure) | 3,4-Dichloro-2-(fluoromethyl)-5-(4,4,5,5-tetramethyl-1,3,2-dioxaborolan-2-yl)-2H-indazole | 345, 347 | Prepared as preparation 82 above using 5-bromo-3,4-dichloro-2-(fluoromethyl)-2H-indazole |

Preparation 83: 2-(3,4-Dichloro-5-(4,4,5,5-tetramethyl-1,3,2-dioxaborolan-2-yl)-2H-indazol-2-yl)-N,N-dimethylacetamide

[Chem. 117]

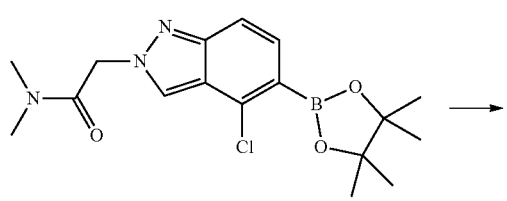
→
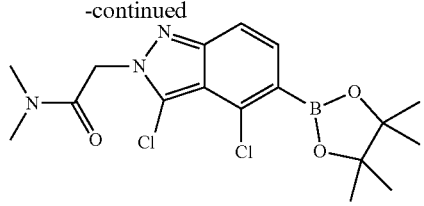

To a solution of 2-(4-chloro-5-(4,4,5,5-tetramethyl-1,3,2-dioxaborolan-2-yl)-2H-indazol-2-yl)-N,N-dimethylacetamide (109 mg, 0.30 mmol) in MeCN (2.18 mL) was added NCS (48 mg, 0.36 mmol) at RT. The mixture was stirred at 50° C. for 18 h. The reaction solution was then concentrated in vacuo, and the residue was purified by column chromatography on silica gel (gradient elution, 0-20% MeOH/CHCl$_3$) to give the title compound (71 mg). MS: [M+H]+= 398, 400.

121

Preparation 84: 3-(4-Chloro-5-(4,4,5,5-tetramethyl-1,3,2-dioxaborolan-2-yl)-2H-indazol-2-yl)-N,N-dimethylpropanamide

[Chem. 118]

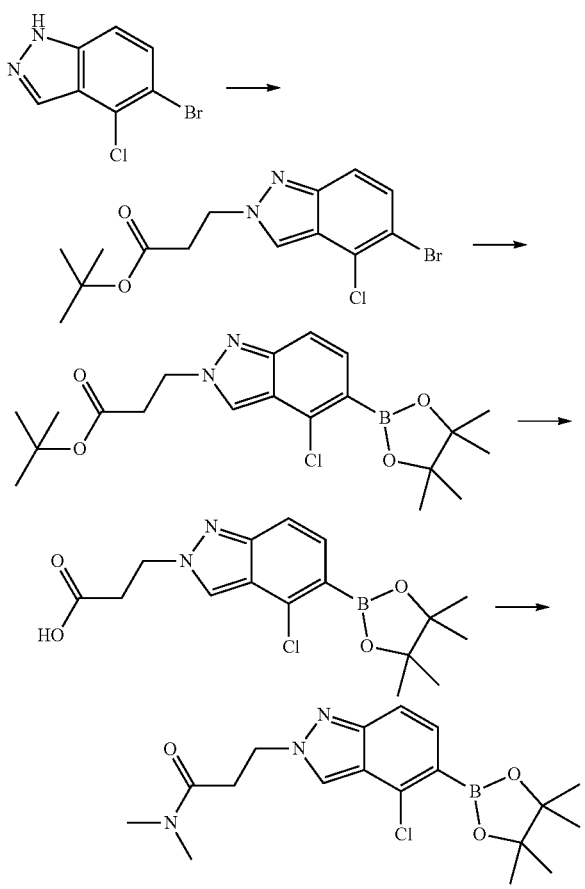

Step 1

To a solution of 5-bromo-4-chloro-1H-indazole (1 g, 4.32 mmol) in DMF (10 mL) was added $K_2CO_3$ (1.19 g, 8.64 mmol) and tert-butyl 3-bromopropanoate (1.44 mL, 8.64 mmol) at RT. The mixture was stirred at 100° C. for 2 h, diluted with water, and extracted with EtOAc. The organic layer was washed with brine, dried over anhydrous $Na_2SO_4$, filtered, and concentrated in vacuo. The residue was purified by column chromatography on silica gel (gradient elution, 5-30% EtOAc/hexane) to give tert-butyl 3-(5-bromo-4-chloro-2H-indazol-2-yl)propanoate (599 mg). MS: $[M+H]^+= 361, 363$.

Step 2

The mixture of tert-butyl 3-(5-bromo-4-chloro-2H-indazol-2-yl)propanoate (599 mg, 1.67 mmol), bis(pinacolato)diboron (634 mg, 2.50 mmol), [1,1'-bis(diphenylphosphino)ferrocene]dichloropalladium(II) complex with dichloromethane (109 mg, 0.133 mmol) and potassium acetate (327 g, 3.33 mmol) in 1,4-dioxane (6 mL) was degassed, purged with nitrogen, and stirred at 120° C. for 5 h. The reaction was cooled to RT, filtered through a pad of Celite, and washed with EtOAc. The filtrate was concentrated in vacuo. The residue was purified by column chromatography on NH silica gel (gradient elution, 10-30% EtOAc/hexane) to give tert-butyl 3-(4-chloro-5-(4,4,5,5-tetramethyl-1,3,2-dioxaborolan-2-yl)-2H-indazol-2-yl)propanoate (553 g). MS: $[M+H]^+=406, 408$.

Step 3

To a solution of tert-butyl 3-(4-chloro-5-(4,4,5,5-tetramethyl-1,3,2-dioxaborolan-2-yl)-2H-indazol-2-yl)propanoate (200 mg, 0.492 mmol) in $CHCl_3$ (2 mL) was added TFA (1 mL, 13.0 mmol) at RT. The mixture was stirred at 60° C. for 1 h, diluted with water, and extracted with $CHCl_3$. The organic layer was washed with brine, dried over anhydrous $Na_2SO_4$, filtered, and concentrated in vacuo. The residue was diluted with THF (4 mL). The mixture was added TEA (0.685 mL, 4.92 mmol), propylphosphonic anhydride (1.6 M in THF, 0.92 mL, 1.48 mmol), and dimethylamine (2.0 M in THF, 0.98 mL, 1.97 mmol) at RT. The mixture was stirred at RT for 30 min. The reaction solution was then concentrated in vacuo, and the residue was purified by column chromatography on silica gel (gradient elution, 0-10% MeOH/CHCl_3) to give the title compound (116 mg). MS: $[M+H]^+=378, 380$.

Preparation 85: 3,4-Dichloro-2-ethyl-5-(4,4,5,5-tetramethyl-1,3,2-dioxaborolan-2-yl)-2H-indazole

[Chem. 119]

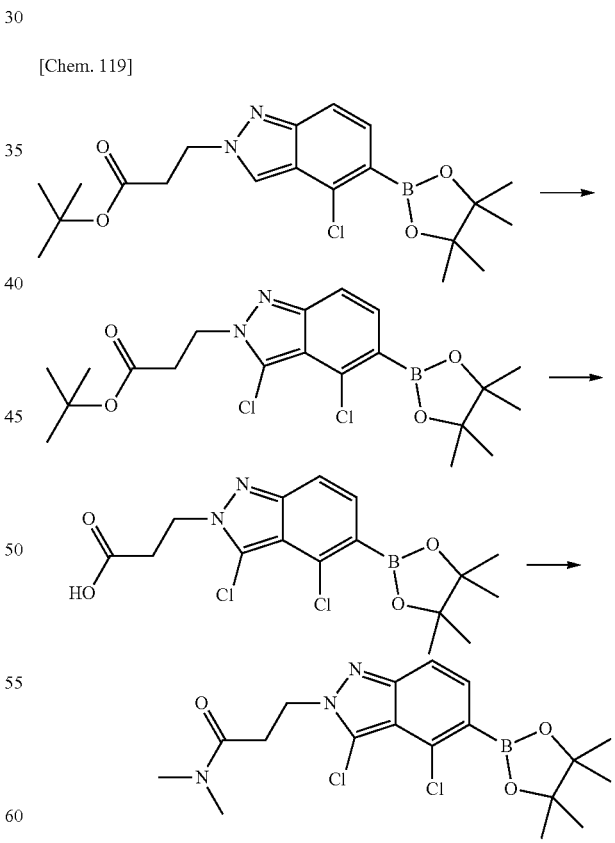

Step 1

To a solution of tert-butyl 3-(4-chloro-5-(4,4,5,5-tetramethyl-1,3,2-dioxaborolan-2-yl)-2H-indazol-2-yl)propanoate (250 mg, 0.615 mmol) in MeCN (5 mL) was added NCS (99 mg, 0.738 mmol) at RT. The mixture was stirred at 60° C. for 12 h. The reaction solution was then concentrated in vacuo, and the residue was purified by column chromatography on silica gel (gradient elution, 10-20% EtOAc/hexane) to give tert-butyl 3-(3,4-dichloro-5-(4,4,5,5-tetramethyl-1,3,2-dioxaborolan-2-yl)-2H-indazol-2-yl)propanoate (164 mg). MS: [M+H]$^+$=441, 443.

Step 2

To a solution of tert-butyl 3-(3,4-dichloro-5-(4,4,5,5-tetramethyl-1,3,2-dioxaborolan-2-yl)-2H-indazol-2-yl)propanoate (164 mg, 0.372 mmol) in CHCl$_3$ (1 mL) was added TFA (1 mL, 13.0 mmol) at RT. The mixture was stirred at 70° C. for 10 min, diluted with water, and extracted with CHCl$_3$. The organic layer was washed with brine, dried over anhydrous Na$_2$SO$_4$, filtered, and concentrated in vacuo. The residue was diluted with THF (2.58 mL). The mixture was added TEA (0.233 mL, 1.68 mmol), propylphosphonic anhydride (1.6 M in THF, 0.420 mL, 0.670 mmol), and dimethylamine (2.0 M in THF, 0.34 mL, 0.670 mmol) at RT. The mixture was stirred at RT for 30 min. The reaction solution was then concentrated in vacuo, and the residue was purified by column chromatography on silica gel (gradient elution, 0-10% MeOH/CHCl$_3$) to give the title compound (128 mg). MS: [M+H]$^+$=412, 414.

Preparation 86: 2-Chloro-5-(4-chloro-2-ethyl-2H-indazol-5-yl)-4-((4-methoxybenzyl)oxy)-7-((2-(trimethylsilyl)ethoxy)methyl)-7H-pyrrolo[2,3-d]pyrimidine

[Chem. 120]

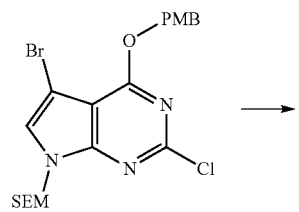

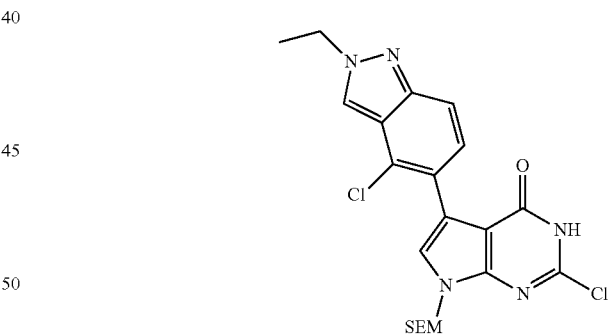

The mixture of 5-bromo-2-chloro-4-((4-methoxybenzyl)oxy)-7-((2-(trimethylsilyl)ethoxy)methyl)-7H-pyrrolo[2,3-d]pyrimidine (2.68 g, 5.37 mmol), 4-chloro-2-ethyl-5-(4,4,5,5-tetramethyl-1,3,2-dioxaborolan-2-yl)-2H-indazole (2.47 g, 6.45 mmol), K$_3$PO$_4$ (2.28 g, 10.7 mmol), [1,1'-bis(diphenylphosphino)ferrocene]dichloropalladium(II) complex with dichloromethane (0.439 g, 0.537 mmol), 1,4-dioxane (53.6 mL) and water (5.36 mL) was stirred at 120° C. for 1 h, cooled to RT, poured into water, and extracted with EtOAc. The organic layer was washed with brine, dried over anhydrous Na$_2$SO$_4$, filtered, and concentrated in vacuo. The residue was purified by column chromatography on silica gel (gradient elution, 0-100% EtOAc/hexane) to give the title compound (1.7 g). MS: [M+H]$^+$=598, 600.

Preparation 87: 2-Chloro-5-(4-chloro-2-ethyl-2H-indazol-5-yl)-7-((2-(trimethylsilyl)ethoxy)methyl)-3,7-dihydro-4H-pyrrolo[2,3-d]pyrimidin-4-one

[Chem. 121]

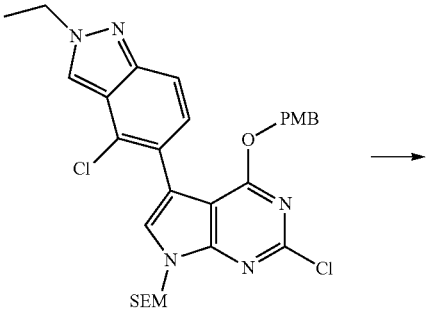

To a solution of 2-chloro-5-(4-chloro-2-ethyl-2H-indazol-5-yl)-4-((4-methoxybenzyl)oxy)-7-((2-(trimethylsilyl)ethoxy)methyl)-7H-pyrrolo[2,3-d]pyrimidine (1.7 g, 2.84 mmol) in DCM (32.3 mL) were added 2,3-dichloro-5,6-dicyano-p-benzoquinone (1.93 g, 8.52 mmol) and water (1.7 mL) at RT. The mixture was stirred at RT overnight. CHCl$_3$ and sat. NaHCO$_3$ were added at RT. The mixture was filtered through a pad of Celite, and washed with CHCl$_3$ and water. The filtrate was extracted with CHCl$_3$, dried over anhydrous Na$_2$SO$_4$, filtered, and concentrated in vacuo. The residue was purified by column chromatography on silica gel (gradient elution, 0-100% EtOAc/hexane) to give the title compound (0.713 g). MS: [M+H]$^+$=478, 480.

Preparation 88: 2-Chloro-5-(4-chloro-2-ethyl-2H-indazol-5-yl)-3-methyl-7-((2-(trimethylsilyl)ethoxy)methyl)-3,7-dihydro-4H-pyrrolo[2,3-d]pyrimidin-4-one

[Chem. 122]

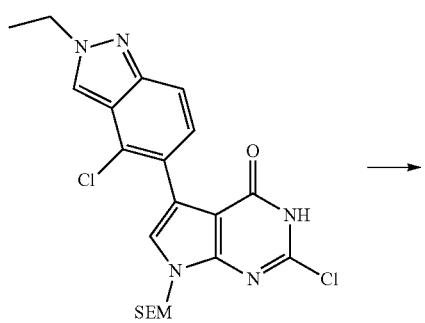

→

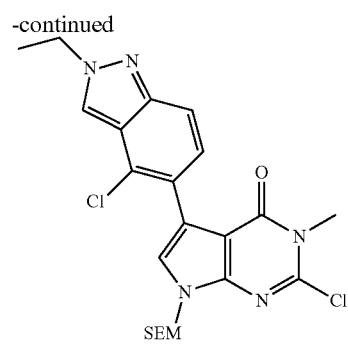

To a solution of 2-chloro-5-(4-chloro-2-ethyl-2H-indazol-5-yl)-7-((2-(trimethylsilyl)ethoxy)methyl)-3,7-dihydro-4H-pyrrolo[2,3-d]pyrimidin-4-one (0.713 g, 1.49 mmol) in DMF (7.13 mL) were added $K_2CO_3$ (0.412 g, 2.98 mmol) and iodomethane (0.186 mL, 2.98 mmol) at RT. The mixture was stirred at RT for 30 min, poured into water, and extracted with EtOAc. The organic layer was washed with water and brine, dried over anhydrous $Na_2SO_4$, filtered, and concentrated in vacuo. The residue was purified by column chromatography on silica gel (gradient elution, 0-100% EtOAc/hexane) to give the title compound (0.717 g). MS: $[M+H]^+$=492, 494.

Compounds of Table 2 below were prepared using procedures analogous to that described in preparation 86-88, starting from the appropriate substituted aryl boronate (synthesised as described above with any significant variations indicated below).

TABLE 2

| Compound | Compound name | MS: [M + H]+ m/z | Procedure |
|---|---|---|---|
| | 2-Chloro-5-(7-chloro-2-methylbenzo[d]thiazol-6-yl)-3-methyl-7-((2-(trimethylsilyl)ethoxy)methyl)-3,7-dihydro-4H-pyrrolo[2,3-d]pyrimidin-4-one | 495, 497 | Prepared as preparation 86 above using 7-chloro-2-methyl-6-(4,4,5,5-tetramethyl-1,3,2-dioxaborolan-2-yl)benzo[d]thiazole |
| | 2-Chloro-5-(7-chloro-2-ethylbenzo[d]thiazol-6-yl)-3-methyl-7-((2-(trimethylsilyl)ethoxy)methyl)-3,7-dihydro-4H-pyrrolo[2,3-d]pyrimidin-4-one | 509, 511 | Prepared as preparation 86 above using 7-chloro-2-ethyl-6-(4,4,5,5-tetramethyl-1,3,2-dioxaborolan-2-yl)benzo[d]thiazole |

TABLE 2-continued

| Compound | Compound name | MS: [M + H]+ m/z | Procedure |
|---|---|---|---|
| 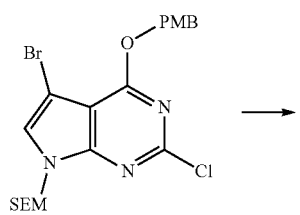 | 5-(2-(tert-Butyl)-4-chloro-2H-indazol-5-yl)-2-chloro-3-methyl-7-((2-(trimethylsilyl)ethoxy)methyl)-3,7-dihydro-4H-pyrrolo[2,3-d]pyrimidin-4-one | 520, 522 | Prepared as preparation 86 above using 2-(tert-butyl)-4-chloro-5-(4,4,5,5-tetramethyl-1,3,2-dioxaborolan-2-yl)-2H-indazole |

Preparation 89: 2-Chloro-5-(4-chloro-2-methyl-2H-indazol-5-yl)-4-((4-methoxybenzyl)oxy)-7-((2-(trimethylsilyl)ethoxy)methyl)-7H-pyrrolo[2,3-d]pyrimidine

[Chem. 123]

Preparation 90: 2-Chloro-5-(4-chloro-2-methyl-2H-indazol-5-yl)-7-((2-(trimethylsilyl)ethoxy)methyl)-3,7-dihydro-4H-pyrrolo[2,3-d]pyrimidin-4-one

[Chem. 124]

Prepared from 4-chloro-2-methyl-5-(4,4,5,5-tetramethyl-1,3,2-dioxaborolan-2-yl)-2H-indazole using similar procedure for the preparation of 2-chloro-5-(4-chloro-2-ethyl-2H-indazol-5-yl)-4-((4-methoxybenzyl)oxy)-7-((2-(trimethylsilyl)ethoxy)methyl)-7H-pyrrolo[2,3-d]pyrimidine, to give the title compound. MS: [M+H]+=584, 586.

Prepared from 2-chloro-5-(4-chloro-2-methyl-2H-indazol-5-yl)-4-((4-methoxybenzyl)oxy)-7-((2-(trimethylsilyl)ethoxy)methyl)-7H-pyrrolo[2,3-d]pyrimidine using similar procedure for the preparation of 2-chloro-5-(4-chloro-2-ethyl-2H-indazol-5-yl)-7-((2-(trimethylsilyl)ethoxy)methyl)-3,7-dihydro-4H-pyrrolo[2,3-d]pyrimidin-4-one, to give the title compound. MS: [M+H]+=464, 466.

Preparation 91: 2-Chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one

[Chem. 125]

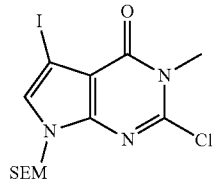

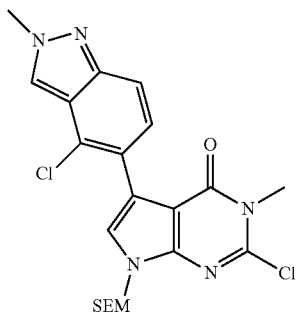

The mixture of 2-chloro-5-iodo-3-methyl-7-((2-(trimethylsilyl)ethoxy)methyl)-3,7-dihydro-4H-pyrrolo[2,3-d]pyrimidin-4-one (150 mg, 0.341 mmol), 4-chloro-2-methyl-5-(4,4,5,5-tetramethyl-1,3,2-dioxaborolan-2-yl)-2H-indazole (171 mg, 0.409 mmol), K$_2$CO$_3$ (110 mg, 0.798 mmol), [1,1'-bis(diphenylphosphino)ferrocene]dichloropalladium (II) complex with dichloromethane (27.8 mg, 0.0341 mmol), 1,4-dioxane (2.5 mL) and water (0.5 mL) was stirred at 70° C. for 2 h, cooled to RT, poured into water, and extracted with EtOAc. The organic layer was washed with brine, dried over anhydrous Na$_2$SO$_4$, filtered, and concentrated in vacuo. The residue was purified by column chromatography on silica gel (gradient elution, 0-100% EtOAc/hexane) to give the title compound (90 mg). MS: [M+H]$^+$=478, 480.

Preparation 92: tert-Butyl (endo-8-(5-bromo-3-methyl-4-oxo-7-((2-(trimethylsilyl)ethoxy)methyl)-4,7-dihydro-3H-pyrrolo[2,3-d]pyrimidin-2-yl)-8-azabicyclo[3.2.1]octan-3-yl)carbamate

[Chem. 126]

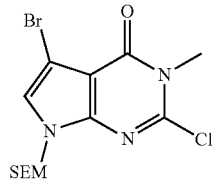

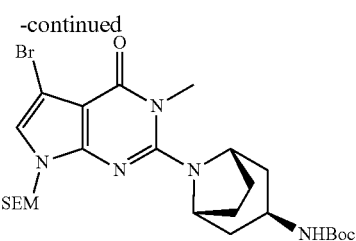

The mixture of 5-bromo-2-chloro-3-methyl-7-((2-(trimethylsilyl)ethoxy)methyl)-3,7-dihydro-4H-pyrrolo[2,3-d]pyrimidin-4-one (0.700 g, 1.78 mmol), tert-butyl endo-(8-azabicyclo[3.2.1]octan-3-yl)carbamate (1.21 g, 5.34 mmol), DIPEA (3.10 mL, 17.8 mmol) and NMP (1 mL) was stirred at 120° C. for 30 min, and cooled to RT. Water was added and the mixture was extracted with EtOAc. The organic layer was washed with water and brine, dried over anhydrous Na$_2$SO$_4$, filtered, and concentrated in vacuo. The residue was purified by column chromatography on silica gel (gradient elution, 0-100% EtOAc/hexane) to give the title compound. MS: [M+H]$^+$=581, 583.

Preparation 93: tert-Butyl (endo-8-(5-iodo-3-methyl-4-oxo-7-((2-(trimethylsilyl)ethoxy)methyl)-4,7-dihydro-3H-pyrrolo[2,3-d]pyrimidin-2-yl)-8-azabicyclo[3.2.1]octan-3-yl)carbamate

[Chem. 127]

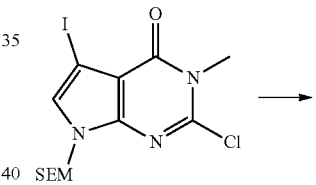

The mixture of 5-iodo-2-chloro-3-methyl-7-((2-(trimethylsilyl)ethoxy)methyl)-3,7-dihydro-4H-pyrrolo[2,3-d]pyrimidin-4-one (2.00 g, 4.55 mmol), tert-butyl endo-(8-azabicyclo[3.2.1]octan-3-yl)carbamate (1.24 g, 5.46 mmol), DIPEA (1.58 mL, 9.10 mmol) and NMP (10 mL) was stirred at 120° C. for 8 h, and cooled to RT. Water was added and the mixture was extracted with EtOAc. The organic layer was washed with water and brine, dried over anhydrous Na$_2$SO$_4$, filtered, and concentrated in vacuo. The residue was purified by column chromatography on silica gel (gradient elution, 0-80% EtOAc/hexane) to give the title compound (2.41 g). MS: [M+H]$^+$=630.

Compounds of Table 3 below were prepared using procedures analogous to that described in preparation 93, starting from the appropriate substituted amine (synthesised as described above with any significant variations indicated below).

TABLE 3

| Compound | Compound name | MS: [M + H]+ m/z | Procedure |
|---|---|---|---|
| 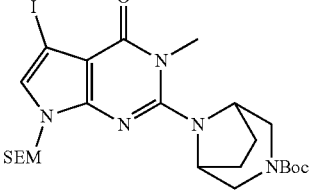 | tert-Butyl 8-(5-iodo-3-methyl-4-oxo-7-((2-(trimethylsilyl)ethoxy)methyl)-4,7-dihydro-3H-pyrrolo[2,3-d]pyrimidin-2-yl)-3,8-diazabicyclo[3.2.1]octane-3-carboxylate | 616 | Prepared as preparation 93 above using tert-butyl 3,8-diazabicyclo[3.2.1]octane-3-carboxylate |
| 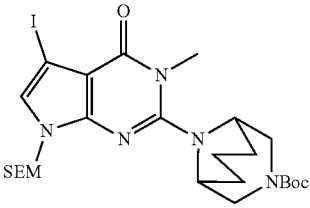 [SMILES: Cn1c(N2C3CCCC2CN(C(=O)OC(C)(C)C)C3)nc2c(c(I)cn2COCC[Si](C)(C)C)c1=O] | tert-Butyl 9-(5-iodo-3-methyl-4-oxo-7-((2-(trimethylsilyl)ethoxy)methyl)-4,7-dihydro-3H-pyrrolo[2,3-d]pyrimidin-2-yl)-3,9-diazabicyclo[3.3.1]nonane-3-carboxylate | 630 | Prepared as preparation 93 above using tert-butyl 3,9-diazabicyclo[3.3.1]nonane-3-carboxylate |
| 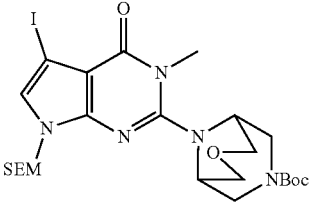 [SMILES: Cn1c(N2C3COCC2CN(C(=O)OC(C)(C)C)C3)nc2c(c(I)cn2COCC[Si](C)(C)C)c1=O] | tert-Butyl 9-(5-iodo-3-methyl-4-oxo-7-((2-(trimethylsilyl)ethoxy)methyl)-4,7-dihydro-3H-pyrrolo[2,3-d]pyrimidin-2-yl)-3-oxa-7,9-diazabicyclo[3.3.1]nonane-7-carboxylate | 632 | Prepared as preparation 93 above using tert-butyl 3-oxa-7,9-diazabicyclo[3.3.1]nonane-7-carboxylate |
| 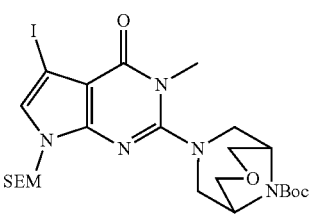 [SMILES: Cn1c(N2CC3COCC(C2)N3C(=O)OC(C)(C)C)nc2c(c(I)cn2COCC[Si](C)(C)C)c1=O] | tert-Butyl 7-(5-iodo-3-methyl-4-oxo-7-((2-(trimethylsilyl)ethoxy)methyl)-4,7-dihydro-3H-pyrrolo[2,3-d]pyrimidin-2-yl)-3-oxa-7,9-diazabicyclo[3.3.1]nonane-9-carboxylate | 632 | Prepared as preparation 93 above using tert-butyl 3-oxa-7,9-diazabicyclo[3.3.1]nonane-9-carboxylate |
| 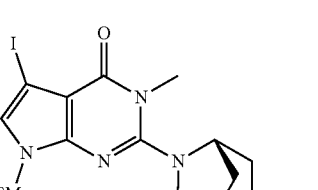 | tert-Butyl (endo-8-(5-iodo-3-methyl-4-oxo-7-((2-(trimethylsilyl)ethoxy)methyl)-4,7-dihydro-3H-pyrrolo[2,3-d]pyrimidin-2-yl)-3-methyl-8-azabicyclo[3.2.1]octan-3-yl)carbamate | 644 | Prepared as preparation 93 above using tert-butyl (endo-3-methyl-8-azabicyclo[3.2.1]octan-3-yl)carbamate |
| 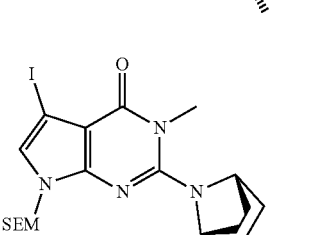 | tert-Butyl ((1R,2R,4S)-7-(5-iodo-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)carbamate | 616 | Prepared as preparation 93 above using tert-butyl ((1R,2R,4S)-7-azabicyclo[2.2.1]heptan-2-yl)carbamate |

TABLE 3-continued

| Compound | Compound name | MS: [M + H]⁺ m/z | Procedure |
|---|---|---|---|
| 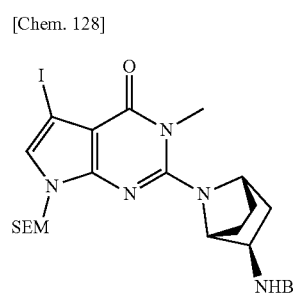 | rac-tert-butyl ((1S,4S,7S)-2-(5-iodo-3-methyl-4-oxo-7-((2-(trimethylsilyl)ethoxy)methyl)-4,7-dihydro-3H-pyrrolo[2,3-d]pyrimidin-2-yl)-2-azabicyclo[2.2.1]heptan-7-yl)carbamate | 616 | Prepared as preparation 93 above using rac-tert-butyl ((1S,4S,7S)-2-azabicyclo[2.2.1]heptan-7-yl)carbamate |

Preparation 94: tert-Butyl ((1R,2R,4S)-7-(5-iodo-3-methyl-4-oxo-7-((2-trimethylsilyl)ethoxy)methyl)-4,7-dihydro-3H-pyrrolo[2,3-d]pyrimidin-2-yl)-7-azabicyclo[2.2.1]heptan-2-yl)(methyl)carbamate Preparation 95: 3-Bromo-4,6-dichloro-1-((2-(trimethylsilyl)ethoxy)methyl)-1H-pyrazolo[3,4-d]pyrimidine

[Chem. 128]

[Chem. 129]

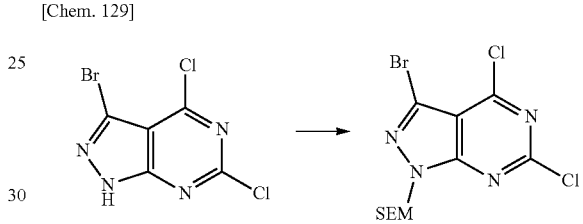

To a mixture of 3-bromo-4,6-dichloro-1H-pyrazolo[3,4-d]pyrimidine (1.00 g, 3.73 mmol) and DIPEA (1.95 mL, 11.2 mmol) in DCM (10 mL) was added SEMCl (0.794 mL, 4.47 mmol) at RT. The mixture was stirred at RT for 1 h and purified by column chromatography on silica gel (gradient elution, 0-15% EtOAc/hexane) to give the title compound (1.12 g). MS: [M+H]⁺=397, 399.

Preparation 96: 3-Bromo-6-chloro-1-((2-(trimethylsilyl)ethoxy)methyl)-1,5-dihydro-4H-pyrazolo[3,4-d]pyrimidin-4-one

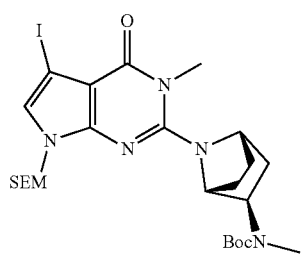

[Chem. 130]

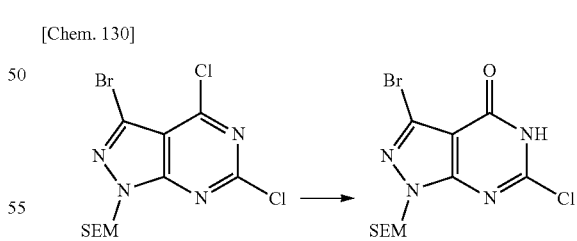

To a solution of tert-butyl ((1R,2R,4S)-7-(5-iodo-3-methyl-4-oxo-7-((2-trimethylsilyl)ethoxy)methyl)-4,7-dihydro-3H-pyrrolo[2,3-d]pyrimidin-2-yl)-7-azabicyclo[2.2.1]heptan-2-yl)carbamate (500 mg, 0.812 mmol) in THF (15 mL) was added NaH (60% in mineral oil, 64.9 mg, 1.62 mmol) at 0° C. The mixture was stirred at 0° C. for 15 min. Iodomethane (0.101 mL, 1.62 mmol) was added at 0° C. The mixture was stirred at RT overnight, poured into sat. NH₄Cl, and extracted with EtOAc. The organic layer was washed with water and brine, dried over anhydrous Na₂SO₄, filtered, and concentrated in vacuo. The residue was purified by column chromatography on silica gel (gradient elution, 30-50% EtOAc/hexane) to give the title compound (493 mg). MS: [M+H]⁺=630.

To a solution of 3-bromo-4,6-dichloro-1-((2-(trimethylsilyl)ethoxy)methyl)-1H-pyrazolo[3,4-d]pyrimidine (1.12 g, 2.81 mmol) in THF (10 mL) was added 5 M NaOH (5.06 mL, 25.3 mmol) at RT. The mixture was stirred at RT for 7 h, diluted with 2-methyltetrahydrofuran, acidified with 6 M HCl, and extracted with EtOAc. The organic layer was washed with brine, dried over anhydrous Na₂SO₄, filtered, and concentrated in vacuo to give the title compound (1.05 g). MS: [M+H]⁺=379, 381.

Preparation 97: 3-Bromo-6-chloro-5-methyl-1-((2-(trimethylsilyl)ethoxy)methyl)-1,5-dihydro-4H-pyrazolo[3,4-d]pyrimidin-4-one

[Chem. 131]

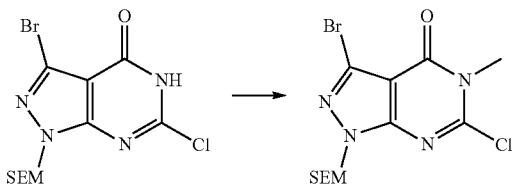

To a mixture of 3-bromo-6-chloro-1-((2-(trimethylsilyl)ethoxy)methyl)-1,5-dihydro-4H-pyrazolo[3,4-d]pyrimidin-4-one (1.05 g, 2.77 mmol) and $K_2CO_3$ (0.764 g, 5.53 mmol) in DMF (10 mL) was added iodomethane (0.344 mL, 5.53 mmol) at RT. The mixture was stirred at RT for 30 min, diluted with EtOAc, washed with water and brine, dried over anhydrous $Na_2SO_4$, filtered, and concentrated in vacuo. The residue was purified by column chromatography on silica gel (gradient elution, 0-50% EtOAc/hexane) to give the title compound (0.780 g). MS: $[M+H]^+=393, 395$.

Preparation 98: 3-Bromo-4,6-dichloro-1-(tetrahydro-2H-pyran-2-yl)-1H-pyrazolo[3,4-d]pyrimidine

[Chem. 132]

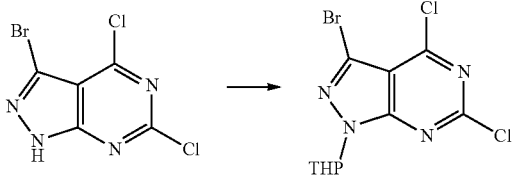

3-Bromo-4,6-dichloro-1H-pyrazolo[3,4-d]pyrimidine (4.55 g, 17.0 mmol), 3,4-dihydro-2H-pyran (4.62 mL, 51.0 mmol) and p-toluenesulfonic acid monohydrate (0.646 g, 3.40 mmol) were dissolved in THE (74 mL) and heated at 70° C. for 2 h. The solvent was removed under vacuum and the solid residue triturated in $Et_2O$ (30 mL) at 40° C. for 2 h. The resulting suspension was allowed to slowly cool down to RT. The solid was collected by filtration and washed with $Et_2O$. This wet solid was dried in a vacuum oven at 50° C. to give the title compound (4.8 g). MS: $[M+H]^+=353, 355$.

Preparation 99: 3-Bromo-6-chloro-1-(tetrahydro-2H-pyran-2-yl)-1,5-dihydro-4H-pyrazolo[3,4-d]pyrimidin-4-one

[Chem. 133]

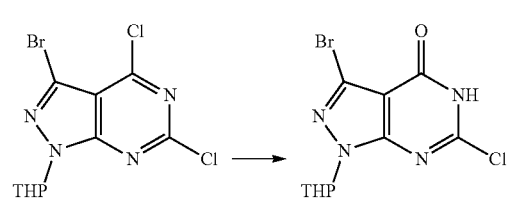

To a solution of 3-bromo-4,6-dichloro-1-(tetrahydro-2H-pyran-2-yl)-1H-pyrazolo[3,4-d]pyrimidine (5.42 g, 15.4 mmol) in THE (54 mL) was added 5 M NaOH (27 mL) at 0° C. The mixture was stirred at RT overnight. The mixture was diluted with 2-methyltetrahydrofuran, acidified with 6 M HCl, and extracted with 2-methyltetrahydrofuran. The organic layer was washed with brine, dried over $Na_2SO_4$, filtered, and concentrated in vacuo to give the the title compound (5.14 g). MS: $[M+H]^+=333, 335$.

Preparation 100: 3-Bromo-6-chloro-5-methyl-1-(tetrahydro-2H-pyran-2-yl)-1,5-dihydro-4H-pyrazolo[3,4-d]pyrimidin-4-one

[Chem. 134]

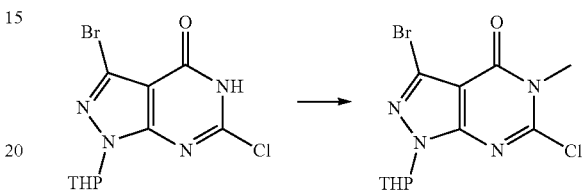

To a mixture of 3-bromo-6-chloro-1-(tetrahydro-2H-pyran-2-yl)-1,5-dihydro-4H-pyrazolo[3,4-d]pyrimidin-4-one (12.8 g, 38.4 mmol) and $K_2CO_3$ (10.6 g, 76.7 mmol) in NMP (256 mL) was added iodomethane (4.78 mL, 76.7 mmol) at RT. The mixture was stirred at RT for 1 h, diluted with EtOAc, washed with water (×2) and brine, dried over $Na_2SO_4$, filtered and then concentrated in vacuo to give the title compound (9.08 g). MS: $[M+H]^+=347, 349$.

Preparation 101: tert-Butyl 9-(3-bromo-5-methyl-4-oxo-1-((2-(trimethylsilyl)ethoxy)methyl)-4,5-dihydro-1H-pyrazolo[3,4-d]pyrimidin-6-yl)-3,9-diazabicyclo[3.3.1]nonane-3-carboxylate

[Chem. 135]

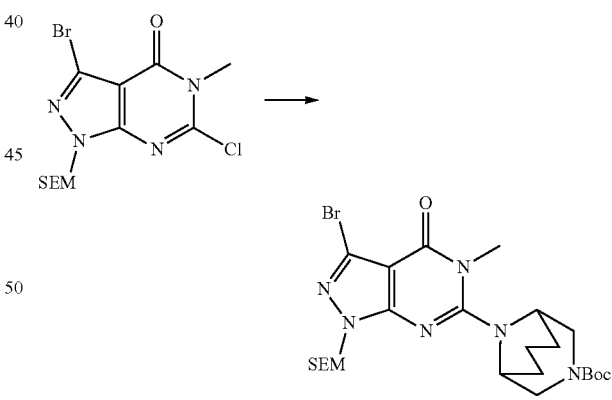

The mixture of 3-bromo-6-chloro-5-methyl-1-((2-(trimethylsilyl)ethoxy)methyl)-1,5-dihydro-4H-pyrazolo[3,4-d]pyrimidin-4-one (780 mg, 1.981 mmol), tert-butyl 3,9-diazabicyclo[3.3.1]nonane-3-carboxylate (0.89 g, 3.9620 mmol), DIPEA (1.72 mL, 9.90 mmol) and NMP (8 mL) was stirred at 120° C. for 5 h, cooled to RT, poured in to water, and extracted with EtOAc. The organic layer was washed with water and brine, dried over anhydrous $Na_2SO_4$, filtered, and concentrated in vacuo. The residue was purified by column chromatography on silica gel (gradient elution, 0-100% EtOAc/hexane) to give the title compound (1.10 g). MS: $[M+H]^+=583, 585$.

Compounds of Table 4 below were prepared using procedures analogous to that described in preparation 101, starting from the appropriate substituted amine (synthesised as described above with any significant variations indicated below).

TABLE 4

| Compound | Compound name | MS: [M + H]+ m/z | Procedure |
|---|---|---|---|
| 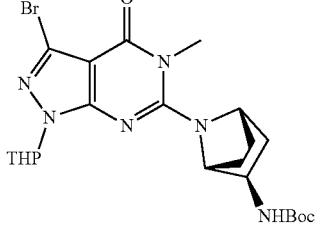 | tert-Butyl ((1R,2R,4S)-7-(3-bromo-5-methyl-4-oxo-1-(tetrahydro-2H-pyran-2-yl)-4,5-dihydro-1H-pyrazolo[3,4-d]pyrimidin-6-yl)-7-azabicyclo[2.2.1]heptan-2-yl)carbamate | 523, 525 | Prepared as preparation 101 above using 3-bromo-6-chloro-5-methyl-1-(tetrahydro-2H-pyran-2-yl)-1,5-dihydro-4H-pyrazolo[3,4-d]pyrimidin-4-one and tert-butyl ((1R,2R,4S)-7-azabicyclo[2.2.1]heptan-2-yl)carbamate |
| 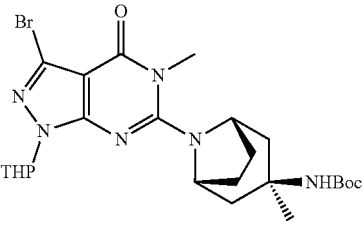 | tert-Butyl (endo-8-(3-bromo-5-methyl-4-oxo-1-(tetrahydro-2H-pyran-2-yl)-4,5-dihydro-1H-pyrazolo[3,4-d]pyrimidin-6-yl)-3-methyl-8-azabicyclo[3.2.1]octan-3-yl)carbamate | 551, 553 | Prepared as preparation 101 above using 3-bromo-6-chloro-5-methyl-1-(tetrahydro-2H-pyran-2-yl)-1,5-dihydro-4H-pyrazolo[3,4-d]pyrimidin-4-one and tert-butyl (endo-3-methyl-8-azabicyclo[3.2.1]octan-3-yl)carbamate |
| 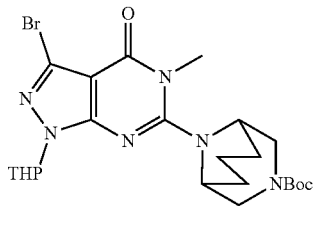 | tert-Butyl 9-(3-bromo-5-methyl-4-oxo-1-(tetrahydro-2H-pyran-2-yl)-4,5-dihydro-1H-pyrazolo[3,4-d]pyrimidin-6-yl)-3,9-diazabicyclo[3.3.1]nonane-3-carboxylate | 537, 539 | Prepared as preparation 101 above using 3-bromo-6-chloro-5-methyl-1-(tetrahydro-2H-pyran-2-yl)-1,5-dihydro-4H-pyrazolo[3,4-d]pyrimidin-4-one and tert-butyl 3,9-diazabicyclo[3.3.1]nonane-3-carboxylate |
| 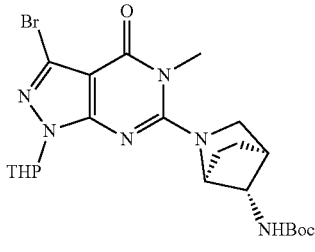 | rac-tert-Butyl ((1S,4S,7S)-2-(3-bromo-5-methyl-4-oxo-1-(tetrahydro-2H-pyran-2-yl)-4,5-dihydro-1H-pyrazolo[3,4-d]pyrimidin-6-yl)-2-azabicyclo[2.2.1]heptan-7-yl)carbamate | 523, 525 | Prepared as preparation 101 above using 3-bromo-6-chloro-5-methyl-1-(tetrahydro-2H-pyran-2-yl)-1,5-dihydro-4H-pyrazolo[3,4-d]pyrimidin-4-one and rac-tert-butyl ((1S,4S,7S)-2-azabicyclo[2.2.1]heptan-7-yl)carbamate |

Preparation 102: rac-tert-butyl ((1S,4S,7S)-2-(5-iodo-3-methyl-4-oxo-7-((2-(trimethylsilyl)ethoxy)methyl)-4,7-dihydro-3H-pyrrolo[2,3-d]pyrimidin-2-yl)-2-azabicyclo[2.2.1]heptan-7-yl)(methyl)carbamate)

[Chem. 136]

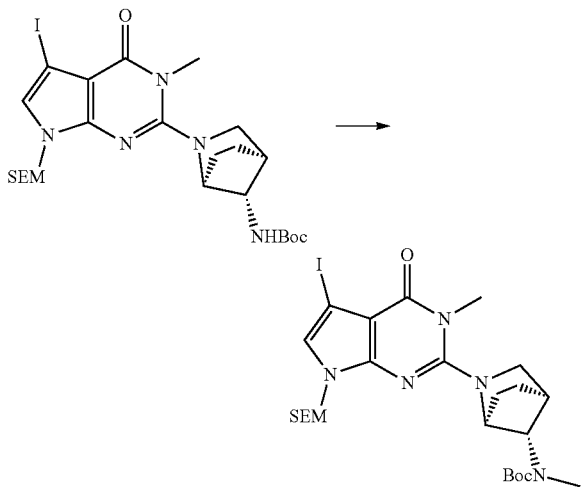

rac-tert-Butyl ((1S,4S,7S)-2-(5-iodo-3-methyl-4-oxo-7-((2-(trimethylsilyl)ethoxy)methyl)-4,7-dihydro-3H-pyrrolo[2,3-d]pyrimidin-2-yl)-2-azabicyclo[2.2.1]heptan-7-yl)(methyl)carbamate was prepared from rac-tert-butyl ((1S,4S,7S)-2-(5-iodo-3-methyl-4-oxo-7-((2-(trimethylsilyl)ethoxy)methyl)-4,7-dihydro-3H-pyrrolo[2,3-d]pyrimidin-2-yl)-2-azabicyclo[2.2.1]heptan-7-yl)carbamate using procedures analogous to that described in Preparation 94. MS: [M+H]⁺=630.

Preparation 103: tert-Butyl ((1R,2R,4S)-7-(3-bromo-5-methyl-4-oxo-1-(tetrahydro-2H-pyran-2-yl)-4,5-dihydro-1H-pyrazolo[3,4-d]pyrimidin-6-yl)-7-azabicyclo[2.2.1]heptan-2-yl)(methyl)carbamate

[Chem. 137]

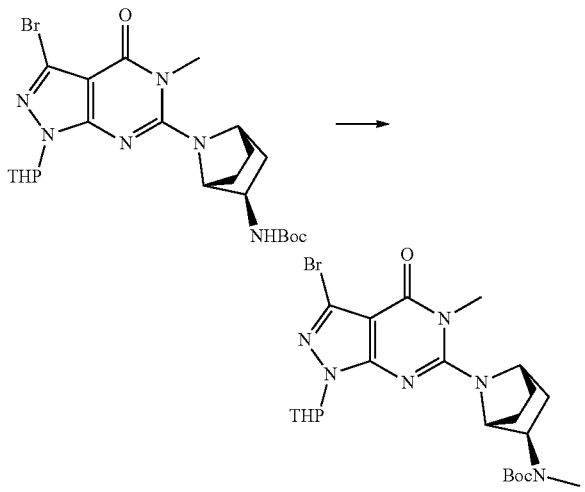

To a solution of tert-butyl ((1R,2R,4S)-7-(3-bromo-5-methyl-4-oxo-1-(tetrahydro-2H-pyran-2-yl)-4,5-dihydro-1H-pyrazolo[3,4-d]pyrimidin-6-yl)-7-azabicyclo[2.2.1]heptan-2-yl)carbamate (1.5 g, 2.90 mmol) in THF (30 mL) was added NaH (60% in mineral oil, 230 mg, 5.70 mmol) at 0° C. The mixture was stirred at 0° C. for 15 min. Iodomethane (0.360 mL, 5.70 mmol) was added at 0° C. The mixture was stirred at RT overnight, poured into sat. NH₄Cl, and extracted with EtOAc. The organic layer was washed with water and brine, dried over anhydrous Na₂SO₄, filtered, and concentrated in vacuo. The residue was purified by column chromatography on silica gel (gradient elution, 20-50% EtOAc/hexane) to give the title compound (1.37 g). MS: [M+H]⁺=537, 539.

Preparation 104: 6-Hydrazinyl-2-hydroxy-3-methyl-3,4-dihydropyrimidin-4-one

[Chem. 138]

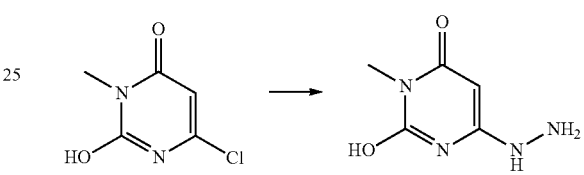

To a suspension of 6-chloro-2-hydroxy-3-methylpyrimidin-4(3H)-one (27.15 g, 169 mmol) in EtOH (250 mL), was added hydrazine-H₂O (49.7 mL, 507 mmol) at room temperature. The resulting suspension was allowed to stir at 80° C. for 18 h. The reaction was allowed to cool to room temperature and then at 0° C. in an ice bath for 1 h. The off-white precipitate was collected and washed with cold EtOH (2×100 mL). MS: [M+H]⁺=157.

Preparation 105: 2-Hydroxy-6-[(E)-2-[(4-methoxyphenyl)methylidene]hydrazin-1-yl]-3-methyl-3,4-dihydropyrimidin-4-one

[Chem. 139]

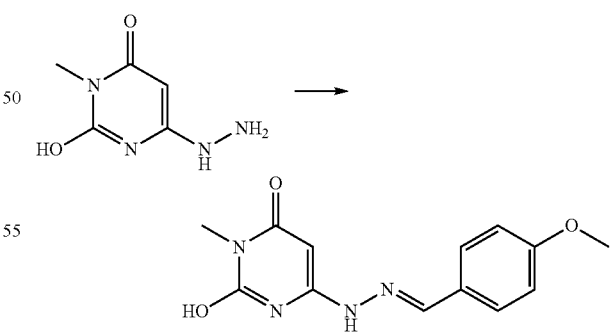

4-Methoxybenzaldehyde (11.68 mL, 96 mmol) was added slowly to a suspension of 6-hydrazinyl-2-hydroxy-3-methyl-3,4-dihydropyrimidin-4-one (10 g, 64.0 mmol) in methanol (250 mL) and the mixture was stirred for 3 hours before being filtered. The precipitate was washed with MeOH (3×100 mL) before being transferred to a flask and stirred with 3:1 DCM/EtOAc (400 mL) overnight. The precipitate was filtered and dried on a sinter to give the title compound (9.56 g, 31.7 mmol, 49.5% yield) as a colourless solid. MS: [M+H]$^+$=275.

Preparation 106:
4-Chloro-2-methyl-2H-indazole-5-carbaldehyde

[Chem. 140]

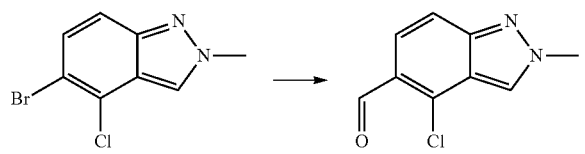

A solution of 5-bromo-4-chloro-2-methyl-2H-indazole (8.78 g, 35.8 mmol) in THF (60 mL) was added slowly over 10 minutes to a three-necked flask containing i-PrMgCl·LiCl (55 mL, 71.5 mmol) under nitrogen. The reaction was stirred at 30° C. for 4 hours before DMF (13.84 mL, 179 mmol) was added slowly. The reaction was stirred at 30° C. for 1 hour before MeOH (40 mL) was added over 10 minutes. The mixture was allowed to stand at room temperature overnight. The mixture was concentrated under vacuum and the residue taken up in a mixture of EtOAc (150 mL), DCM (10 mL), and MeOH (10 mL). This solution was washed with water (100 mL) and brine (100 mL). The organic phase was isolated and the aqueous phase was further extracted with EtOAc (100 mL). The combined organic phases were then washed with water (2×100 mL) then dried (MgSO4), filtered, and concentrated to give the crude material. This was triturated with 4:1 isohexane/EtOAc (4×25 mL) and the solids filtered. They were then further triturated with 4:1 isohexane/EtOAc (2×25 mL) to give 4-chloro-2-methyl-2H-indazole-5-carbaldehyde (1.17 g, 5.89 mmol, 16.48% yield) as a pale brown solid. MS: [M+H]$^+$=195.

Preparation 107:
4-Chloro-2-ethyl-2H-indazole-5-carbaldehyde

[Chem. 141]

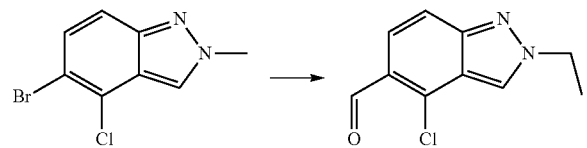

4-Chloro-2-ethyl-2H-indazole-5-carbaldehyde was prepared from 5-bromo-4-chloro-2-ethyl-2H-indazole using procedures analogous to that described in preparation 106. MS: [M+H]$^+$=209.

Preparation 108:
3,4-Dichloro-2-methyl-2H-indazole-5-carbaldehyde

[Chem. 142]

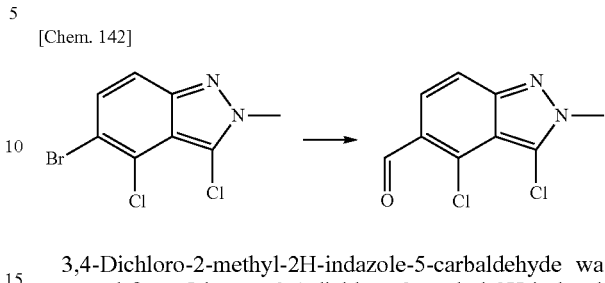

3,4-Dichloro-2-methyl-2H-indazole-5-carbaldehyde was prepared from 5-bromo-3,4-dichloro-2-methyl-2H-indazole using procedures analogous to that described in preparation 106. MS: [M+H]$^+$=229.

Preparation 109: 3-(4-Chloro-2-methyl-2H-indazol-5-yl)-6-hydroxy-2-[(4-methoxyphenyl)methyl]-5-methyl-2H,4H,5H-pyrazolo[3,4-d]pyrimidin-4-one

[Chem. 143]

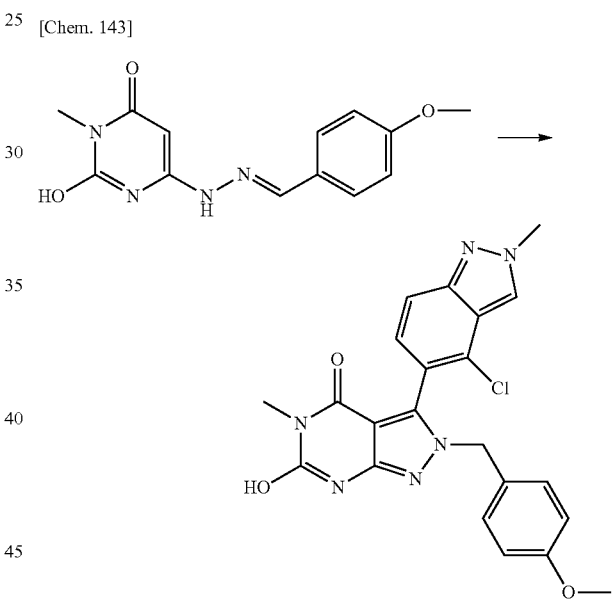

A suspension of 2-hydroxy-6-[(E)-2-[(4-methoxyphenyl)methylidene]hydrazin-1-yl]-3-methyl-3,4-dihydropyrimidin-4-one (2.013 g, 7.34 mmol) and 4-chloro-2-methyl-2H-indazole-5-carbaldehyde (1.5 g, 7.71 mmol) was stirred in DMF/IPA (2:1, 55 mL) at room temperature. Piperidine (0.763 mL, 7.71 mmol) was added in one portion and the reaction was stirred at 35° C. overnight. The reaction mixture was poured into water (200 mL) and extracted with EtOAc (2×100 mL) and 10% MeOH in DCM (2×100 mL). The combined organic phases were dried (MgSO$_4$), filtered, and concentrated to give the crude material. The crude product was purified by chromatography on silica gel (80 g cartridge, 0-3% MeOH/DCM) to afford the title compound (932 mg, 2.0 mmol, 27.3% yield) as a pale orange solid.
MS: [M+H]$^+$=451. $^1$H NMR (500 MHz, DMSO-d$_6$) δ: 11.74 (s, 1H), 8.65 (s, 1H), 7.70 (dd, J=8.8, 1.0 Hz, 1H), 7.23 (d, J=8.8 Hz, 1H), 6.94 (d, J=8.7 Hz, 2H), 6.80 (d, J=8.7 Hz, 2H), 5.08 (d, J=15.1 Hz, 1H), 4.99 (d, J=15.1 Hz, 1H), 4.25 (s, 3H), 3.69 (s, 3H), 3.10 (s, 3H).

Preparation 110: 3-(4-Chloro-2-ethyl-2H-indazol-5-yl)-6-hydroxy-2-[(4-methoxyphenyl)methyl]-5-methyl-2H,4H,5H-pyrazolo[3,4-d]pyrimidin-4-one

[Chem. 144]

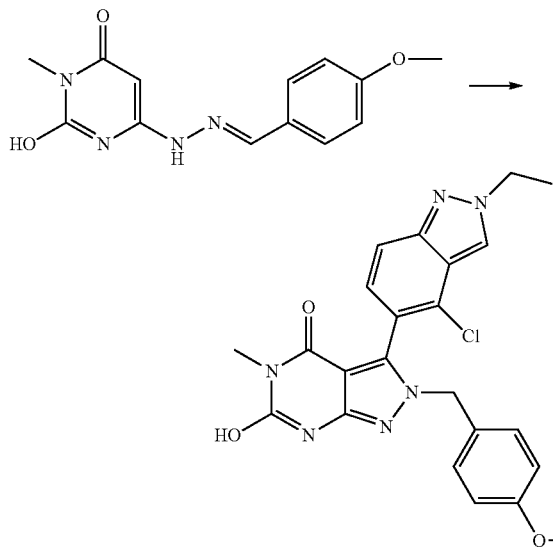

3-(4-Chloro-2-ethyl-2H-indazol-5-yl)-6-hydroxy-2-[(4-methoxyphenyl)methyl]-5-methyl-2H,4H,5H-pyrazolo[3,4-d]pyrimidin-4-one was prepared using procedures analogous to that described in preparation 109, starting from 2-hydroxy-6-[(E)-2-[(4-methoxyphenyl)methylidene]hydrazin-1-yl]-3-methyl-3,4-dihydropyrimidin-4-one and 4-chloro-2-ethyl-2H-indazole-5-carbaldehyde. MS: $[M+H]^+= 465$. $^1$H NMR (500 MHz, DMSO-d$_6$) δ: 11.73 (s, 1H), 8.70 (s, 1H), 7.71 (dd, J=8.8, 0.7 Hz, 1H), 7.23 (d, J=8.8 Hz, 1H), 6.96 (d, J=8.7 Hz, 2H), 6.81 (d, J=8.7 Hz, 2H), 5.09 (d, J=15.1 Hz, 1H), 5.00 (d, J=15.1 Hz, 1H), 4.54 (q, J=7.3 Hz, 2H), 3.69 (s, 3H), 3.10 (s, 3H), 1.55 (t, J=7.3 Hz, 3H).

Preparation 111: 3-(3,4-Dichloro-2-methyl-2H-indazol-5-yl)-6-hydroxy-2-[(4-methoxyphenyl)methyl]-5-methyl-2H,4H,5H-pyrazolo[3,4-d]pyrimidin-4-one

[Chem. 145]

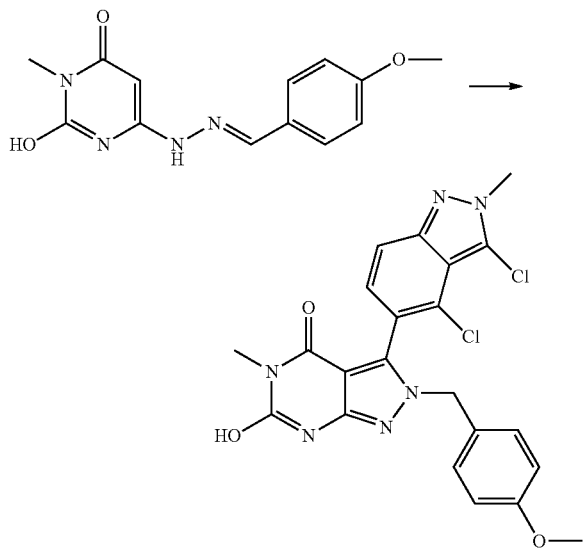

3-(3,4-Dichloro-2-methyl-2H-indazol-5-yl)-6-hydroxy-2-[(4-methoxyphenyl)methyl]-5-methyl-2H,4H,5H-pyrazolo[3,4-d]pyrimidin-4-one was prepared using procedures analogous to that described in preparation 109, starting from 2-hydroxy-6-[(E)-2-[(4-methoxyphenyl)methylidene]hydrazin-1-yl]-3-methyl-3,4-dihydropyrimidin-4-one and 3,4-dichloro-2-methyl-2H-indazole-5-carbaldehyde. MS: $[M+H]^+=485$.

$^1$H NMR (500 MHz, DMSO-d$_6$) δ: 11.76 (s, 1H), 7.72 (d, J=8.8 Hz, 1H), 7.26 (d, J=8.8 Hz, 1H), 6.96 (d, J=8.7 Hz, 2H), 6.81 (d, J=8.7 Hz, 2H), 5.08 (d, J=15.1 Hz, 1H), 5.01 (d, J=15.1 Hz, 1H), 4.19 (s, 3H), 3.69 (s, 3H), 3.10 (s, 3H).

General procedure 1: tert-Butyl 8-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-3,8-diazabicyclo[3.2.1]octane-3-carboxylate

[Chem. 146]

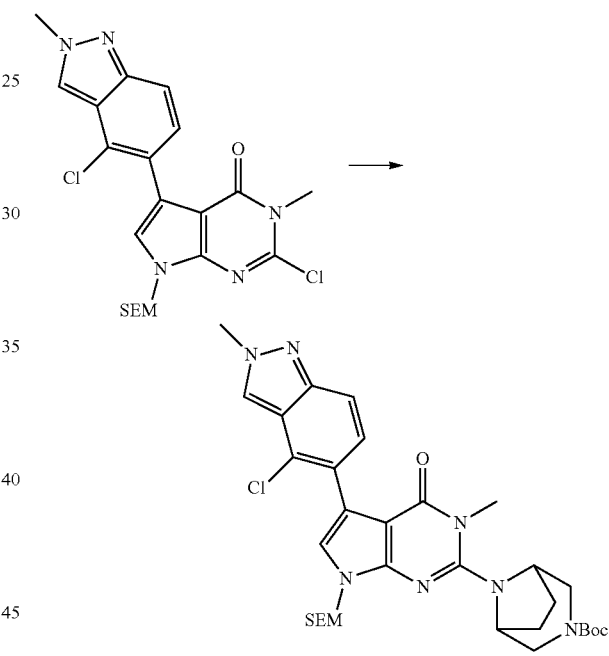

The mixture of 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one (100 mg, 0.209 mmol), tert-butyl 3,8-diazabicyclo[3.2.1]octane-3-carboxylate (88.7 mg, 0.418 mmol), DIPEA (0.109 mL, 0.627 mmol) and NMP (2 mL) was stirred at 120° C. for 8 h, cooled to RT, diluted with EtOAc, washed with water and brine, dried over anhydrous Na$_2$SO$_4$, filtered, and concentrated in vacuo. The residue was purified by column chromatography on silica gel (gradient elution, 0-100% EtOAc/hexane) to give the title compound (140 mg). MS: $[M+H]^+= 654, 656$.

Compounds of Table 5 below were prepared using procedures analogous to that described in general procedure 1 starting from the appropriate substituted protected pyrrolopyrimidinone and varying the amine (synthesised as described above with any significant variations indicated below).

TABLE 5

| Compound | Compound name | MS: [M + H]+ m/z | Procedure |
|---|---|---|---|
| | tert-Butyl ((1-(5-(4-chloro-2-ethyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-4-methylpiperidin-4-yl)methyl)carbamate | 684, 686 | Prepared as general procedure 1 above using 2-chloro-5-(4-chloro-2-ethyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl ((4-methylpiperidin-4-yl)methyl)carbamate |
| | tert-Butyl (1-(5-(4-chloro-2-ethyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-4-methylpiperidin-4-yl)carbamate | 670, 672 | Prepared as general procedure 1 above using 2-chloro-5-(4-chloro-2-ethyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl (4-methylpiperidin-4-yl)carbamate |
| | tert-Butyl (endo-8-(5-(4-chloro-2-ethyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-8-azabicyclo[3.2.1]octan-3-yl)carbamate | 682, 684 | Prepared as general procedure 1 above using 2-chloro-5-(4-chloro-2-ethyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl (endo-8-azabicyclo[3.2.1]octan-3-yl)carbamate |
| | tert-Butyl (endo-8-(5-(7-chloro-2-ethylbenzo[d]thiazol-6-yl)-3-methyl-4-oxo-7-((2-(trimethylsilyl)ethoxy)methyl)-4,7-dihydro-3H-pyrrolo[2,3-d]pyrimidin-2-yl)-8-azabicyclo[3.2.1]octan-3-yl)carbamate | 699, 701 | Prepared as general procedure 1 above using 2-chloro-5-(7-chloro-2-ethylbenzo[d]thiazol-6-yl)-3-methyl-7-((2-(trimethylsilyl)ethoxy)methyl)-3,7-dihydro-4H-pyrrolo[2,3-d]pyrimidin-4-one and tert-butyl (endo-8-azabicyclo[3.2.1]octan-3-yl)carbamate |
| | tert-Butyl (endo-8-(5-(7-chloro-2-methylbenzo[d]thiazol-6-yl)-3-methyl-4-oxo-7-((2-(trimethylsilyl)ethoxy)methyl)-4,7-dihydro-3H-pyrrolo[2,3-d]pyrimidin-2-yl)-8-azabicyclo[3.2.1]octan-3-yl)carbamate | 685, 687 | Prepared as general procedure 1 above using 2-chloro-5-(7-chloro-2-methylbenzo[d]thiazol-6-yl)-3-methyl-7-((2-(trimethylsilyl)ethoxy)methyl)-3,7-dihydro-4H-pyrrolo[2,3-d]pyrimidin-4-one and tert-butyl (endo-8-azabicyclo[3.2.1]octan-3-yl)carbamate |

TABLE 5-continued

| Compound | Compound name | MS: [M + H]+ m/z | Procedure |
|---|---|---|---|
| | tert-Butyl (endo-8-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-8-azabicyclo[3.2.1]octan-3-yl)carbamate | 668, 670 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl (endo-8-azabicyclo[3.2.1]octan-3-yl)carbamate |
| | tert-Butyl (endo-8-(5-(2-(tert-buty)-4-chloro-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-8-azabicyclo[3.2.1]octan-3-yl)carbamate | 710, 712 | Prepared as general procedure 1 above using 5-(2-(tert-butyl)-4-chloro-2H-indazol-5-yl)-2-chloro-3-methyl-7-((2-(trimethylsilyl)ethoxy)methyl)-3,7-dihydro-4H-pyrrolo[2,3-d]pyrimidin-4-one and tert-butyl (endo-8-azabicyclo[3.2.1]octan-3-yl)carbamate |
| | tert-Butyl (exo-8-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-8-azabicyclo[3.2.1]octan-3-yl)carbamate | 668, 670 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl (exo-8-azabicyclo[3.2.1]octan-3-yl)carbamate |
| | N-((R)-8-(5-(4-Chloro-2-ethyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-8-azaspiro[4.5]decan-1-yl)-2-methylpropane-2-sulfinamide | 714, 716 | Prepared as general procedure 1 above using 2-chloro-5-(4-chloro-2-ethyl-2H-indazol-5-yl)-3-methyl-7-((2-(trimethylsilyl)ethoxy)methyl)-3,7-dihydro-4H-pyrrolo[2,3-d]pyrimidin-4-one and 2-methyl-N-((R)-8-azaspiro[4.5]decan-1-yl)propane-2-sulfinamide |
| | (S)-2-(4-Amino-2-oxa-8-azaspiro[4.5]decan-8-yl)-5-(4-chloro-2-ethyl-2H-indazol-5-yl)-3-methyl-7-((2-(trimethylsilyl)ethoxy)methyl)-3,7-dihydro-4H-pyrrolo[2,3-d]pyrimidin-4-one | 612, 614 | Prepared as general procedure 1 above using 2-chloro-5-(4-chloro-2-ethyl-2H-indazol-5-yl)-3-methyl-7-((2-(trimethylsilyl)ethoxy)methyl)-3,7-dihydro-4H-pyrrolo[2,3-d]pyrimidin-4-one and (S)-2-oxa-8-azaspiro[4.5]decan-4-amine dihydrochloride |

TABLE 5-continued

| Compound | Compound name | MS: [M + H]+ m/z | Procedure |
|---|---|---|---|
| (structure) | tert-Butyl (endo-8-(5-(4-chloro-2-ethyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-8-azabicyclo[3.2.1]octan-3-yl)(methyl)carbamate | 696, 698 | Prepared as general procedure 1 above using 2-chloro-5-(4-chloro-2-ethyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl (endo-8-azabicyclo[3.2.1]octan-3-yl)(methyl)carbamate |
| (structure) | tert-Butyl (endo-8-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-8-azabicyclo[3.2.1]octan-3-yl)(methyl)carbamate | 682, 684 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl (endo-8-azabicyclo[3.2.1]octan-3-yl)(methyl)carbamate |
| (structure) | tert-Buty (endo-8-(5-(4-chloro-2-ethyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-3-methyl-8-azabicyclo[3.2.1]octan-3-yl)carbamate | 696, 698 | Prepared as general procedure 1 above using 2-chloro-5-(4-chloro-2-ethyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl (endo-3-methyl-8-azabicyclo[3.2.1]octan-3-yl)carbamate |
| (structure) | tert-Butyl (endo-8-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-3-methyl-8-azabicyclo[3.2.1]octan-3-yl)carbamate | 682, 684 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl (endo-3-methyl-8-azabicyclo[3.2.1]octan-3-yl)carbamate |
| (structure) | tert-Butyl 7-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-3-oxa-7,9-diazabicyclo[3.3.1]nonane-9-carboxylate | 670, 672 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl 3-oxa-7,9-diazabicyclo[3.3.1]nonane-9-carboxylate |

TABLE 5-continued

| Compound | Compound name | MS: [M + H]+ m/z | Procedure |
|---|---|---|---|
| 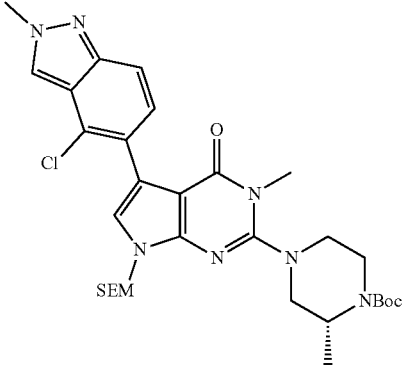 [SMILES: C[C@@H]1CN(c2nc3c(c(-c4ccc5nn(C)cc5c4Cl)cn3COCC[Si](C)(C)C)c(=O)n2C)CCN1C(=O)OC(C)(C)C] | tert-Butyl (R)-4-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-2-methylpiperazine-1-carboxylate | 642, 644 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl (R)-2-methylpiperazine-1-carboxylate. |
| 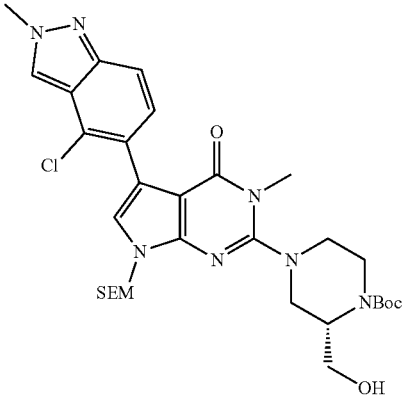 [SMILES: Cn1cc2c(Cl)c(-c3cn(COCC[Si](C)(C)C)c4nc(N5CCN(C(=O)OC(C)(C)C)[C@H](CO)C5)n(C)c(=O)c34)ccc2n1] | tert-Butyl (S)-4-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-2-(hydroxymethyl)piperazine-1-carboxylate | 658, 660 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl (S)-2-(hydroxymethyl)piperazine-1-carboxylate. |
| 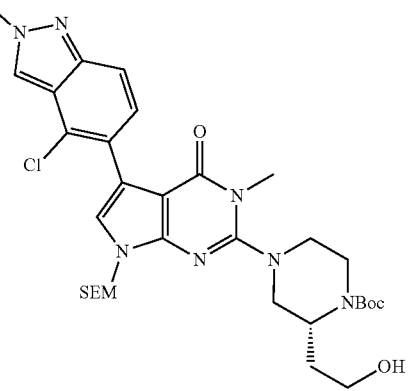 | tert-Butyl (R)-4-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-2-(2-hydroxyethyl)piperazine-1-carboxylate | 672, 674 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl (R)-2-(2-hydroxyethyl)piperazine-1-carboxylate. |
| 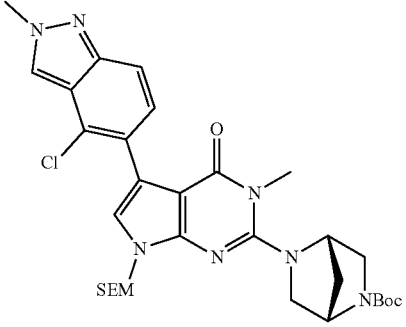 [SMILES: Cn1cc2c(Cl)c(-c3cn(COCC[Si](C)(C)C)c4nc(N5C[C@@H]6C[C@H]5CN6C(=O)OC(C)(C)C)n(C)c(=O)c34)ccc2n1] | tert-Buty (1S,4S)-5-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-2,5-diazabicyclo[2.2.1]heptane-2-carboxylate | 640, 642 | Prepared as general procedure 1 above using 2-chloro-5-(4-chloro-2-methyl-2H-indazol-5-yl)-7-((2-(trimethylsilyl)ethoxy)methyl)-3,7-dihydro-4H-pyrrolo[2,3-d]pyrimidin-4-one and tert-butyl (1S,4S)-2,5-diazabicyclo[2.2.1]heptane-2-carboxylate |

TABLE 5-continued

| Compound | Compound name | MS: [M + H]+ m/z | Procedure |
|---|---|---|---|
| | tert-Butyl (9-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-3-oxa-9-azabicyclo[3.3.1]nonan-7-yl)carbamate | 684, 686 | Prepared as general procedure 1 above using 2-chloro-5-(4-chloro-2-methyl-2H-indazol-5-yl)-7-((2-(trimethylsilyl)ethoxy)methyl)-3,7-dihydro-4H-pyrrolo[2,3-d]pyrimidin-4-one and tert-butyl (3-oxa-9-azabicyclo[3.3.1]nonan-7-yl)carbamate |
| | tert-Butyl (1R,4R)-5-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-2,5-diazabicyclo[2.2.1]heptane-2-carboxylate | 640, 642 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl (1R,4R)-2,5-diazabicyclo[2.2.1]heptane-2-carboxylate |
| | tert-Butyl (exo-3-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-3-azabicyclo[3.2.1]octan-8-yl)carbamate | 668, 670 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl (exo-3-azabicyclo[3.2.1]octan-8-yl)carbamate |
| | tert-Butyl (endo-3-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-3-azabicyclo[3.2.1]octan-8-yl)carbamate | 668, 670 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl (endo-3-azabicyclo[3.2.1]octan-8-yl)carbamate |

TABLE 5-continued

| Compound | Compound name | MS: [M + H]+ m/z | Procedure |
|---|---|---|---|
|  | rac-Benzyl ((1S,2R,3R,5R)-8-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-2-fluoro-8-azabicyclo[3.2.1]octan-3-yl)carbamate | 720, 722 | Prepared as general procedure 1 above using 2-chloro-5-(4-chloro-2-methyl-2H-indazol-5-yl)-7-((2-(trimethylsilyl)ethoxy)methyl)-3,7-dihydro-4H-pyrrolo[2,3-d]pyrimidin-4-one and rac-benzyl ((1S,2S,3R,5R)-2-fluoro-8-azabicyclo[3.2.1]octan-3-yl)carbamate hydrochloride |
|  | tert-Butyl 9-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-3,9-diazabicyclo[3.3.1]nonane-3-carboxylate | 668, 670 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl 3,9-diazabicyclo[3.3.1]nonane-3-carboxylate |
|  | tert-Butyl 3-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-3,8-diazabicyclo[3.2.1]octane-8-carboxylate | 654, 656 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl 3,8-diazabicyclo[3.2.1]octane-8-carboxylate |
|  | tert-Butyl 6-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-3,6-diazabicyclo[3.1.1]heptane-3-carboxylate | 640, 642 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl 3,6-diazabicyclo[3.1.1]heptane-3-carboxylate |

TABLE 5-continued

| Compound | Compound name | MS: [M + H]+ m/z | Procedure |
|---|---|---|---|
| | tert-Butyl 3-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-3,9-diazabicyclo[3.3.1]nonane-9-carboxylate | 668, 670 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl 3,9-diazabicyclo[3.3.1]nonane-9-carboxylate |
| | tert-Butyl 3-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-3,6-diazabicyclo[3.1.1]heptane-6-carboxylate | 640, 642 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl 3,6-diazabicyclo[3.1.1]heptane-6-carboxylate |
| | tert-Butyl 5-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-2,5-diazabicyclo[2.2.2]octane-2-carboxylate | 654, 656 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl 2,5-diazabicyclo[2.2.2]octane-2-carboxylate |
| | tert-Butyl (exo-3-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-3-azabicyclo[3.1.1]heptan-6-yl)carbamate | 654, 656 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl (exo-3-azabicyclo[3.1.1]heptan-6-yl)carbamate. |

TABLE 5-continued

| Compound | Compound name | MS: [M + H]+ m/z | Procedure |
|---|---|---|---|
| | tert-Butyl (endo-3-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-3-azabicyclo[3.1.1]heptan-6-yl)carbamate | 654, 656 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl (endo-3-azabicyclo[3.1.1]heptan-6-yl)carbamate |
| | tert-Butyl (2-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-2-azabicyclo[2.2.1]heptan-5-yl)carbamate | 654, 656 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl (2-azabicyclo[2.2.1]heptan-5-yl)carbamate |
| | tert-Buty (exo-9-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-9-azabicyclo[3.3.1]nonan-3-yl)carbamate | 682, 684 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl (exo-9-azabicyclo[3.3.1]nonan-3-yl)carbamate. |
| | tert-Butyl (endo-9-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-9-azabicyclo[3.3.1]nonan-3-yl)carbamate | 682, 684 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl (endo-9-azabicyclo[3.3.1]nonan-3-yl)carbamate. |

TABLE 5-continued

| Compound | Compound name | MS: [M + H]+ m/z | Procedure |
|---|---|---|---|
| | tert-Butyl 8-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-1,8-diazaspiro[4.5]decane-1-carboxylate | 682, 684 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl 1,8-diazaspiro[4.5]decane-1-carboxylate. |
| | tert-Butyl 4-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)piperazine-1-carboxylate | 628, 630 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl piperazine-1-carboxylate |
| | tert-Butyl 3-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-3,7-diazabicyclo[4.2.0]octane-7-carboxylate | 654, 656 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl 3,7-diazabicyclo[4.2.0]octane-7-carboxylate |
| | tert-Butyl 9-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-1,9-diazaspiro[5.5]undecane-1-carboxylate | 696, 698 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl 1,9-diazaspiro[5.5]undecane-1-carboxylate |

TABLE 5-continued

| Compound | Compound name | MS: [M + H]+ m/z | Procedure |
|---|---|---|---|
| (structure) | tert-Butyl 7-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-1,7-diazaspiro[3.5]nonane-1-carboxylate | 668, 670 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl 1,7-diazaspiro[3.5]nonane-1-carboxylate |
| (structure) | tert-Butyl (S)-(1-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)pyrrolidin-3-yl)carbamate | 628, 630 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl (S)-pyrrolidin-3-ylcarbamate |
| (structure) | tert-Butyl (R)-(1-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)pyrrolidin-3-yl)carbamate | 628, 630 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl (R)-pyrrolidin-3-ylcarbamate |
| (structure) | tert-Butyl (S)-4-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-2-methylpiperazine-1-carboxylate | 642, 644 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl (S)-2-methylpiperazine-1-carboxylate |

TABLE 5-continued

| Compound | Compound name | MS: [M + H]+ m/z | Procedure |
|---|---|---|---|
| (structure) | tert-Butyl ((1S,2S,4R)-7-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)carbamate | 654, 656 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl ((1S,2S,4R)-7-azabicyclo[2.2.1]heptan-2-yl)carbamate |
| (structure) | tert-Butyl (R)-4-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-3-methylpiperazine-1-carboxylate | 642, 644 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl (R)-3-methylpiperazine-1-carboxylate |
| (structure) | tert-Butyl (S)-4-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-3-methylpiperazine-1-carboxylate | 642, 644 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl (S)-3-methylpiperazine-1-carboxylate |
| (structure) | tert-Butyl ((1R,2R,4S)-7-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)carbamate | 654, 656 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl ((1R,2R,4S)-7-azabicyclo[2.2.1]heptan-2-yl)carbamate |

TABLE 5-continued

| Compound | Compound name | MS: [M + H]+ m/z | Procedure |
|---|---|---|---|
| (structure) | tert-Butyl ((3R,4S)-1-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-4-fluoropyrrolidin-3-yl)carbamate | 646, 648 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl ((3R,4S)-4-fluoropyrrolidin-3-yl)carbamate |
| (structure) | rac-tert-Butyl ((1S,4S,7S)-2-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-2-azabicyclo[2.2.1]heptan-7-yl)carbamate | 654, 656 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and rac-tert-butyl ((1S,4S,7S)-2-azabicyclo[2.2.1]heptan-7-yl)carbamate |
| (structure) | tert-Butyl ((3S,4S)-1-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-4-fluoropyrrolidin-3-yl)carbamate | 646, 648 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl ((3S,4S)-4-fluoropyrrolidin-3-yl)carbamate |
| (structure) | tert-Butyl (1-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-4,4-difluoropyrrolidin-3-yl)carbamate | 664, 666 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl (4,4-difluoropyrrolidin-3-yl)carbamate |

TABLE 5-continued

| Compound | Compound name | MS: [M + H]+ m/z | Procedure |
|---|---|---|---|
| | tert-Butyl (S)-(1-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-3-methylpyrrolidin-3-yl)carbamate | 642, 644 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl (S)-(3-methylpyrrolidin-3-yl)carbamate |
| | tert-Butyl (R)-(1-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-3-methylpyrrolidin-3-yl)carbamate | 642, 644 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl (R)-(3-methylpyrrolidin-3-yl)carbamate |
| | tert-Butyl ((3R,4R)-1-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-4-methylpyrrolidin-3-yl)carbamate | 642, 644 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl ((3R,4R)-4-methylpyrrolidin-3-yl)carbamate |
| | tert-Butyl ((3R,4S)-1-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-4-methylpyrrolidin-3-yl)carbamate | 642, 644 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl ((3R,4S)-4-methylpyrrolidin-3-yl)carbamate |

TABLE 5-continued

| Compound | Compound name | MS: [M + H]+ m/z | Procedure |
|---|---|---|---|
|  | tert-Butyl (1-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-3-(hydroxymethyl)pyrrolidin-3-yl)carbamate | 658, 660 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl (3-(hydroxymethyl)pyrrolidin-3-yl)carbamate |
|  | 2-((3S,4S)-4-Amino-3-methyl-2-oxa-8-azaspiro[4.5]decan-8-yl)-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one | 612, 614 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and (3S,4S)-3-methyl-2-oxa-8-azaspiro[4.5]decan-4-amine dihydrochloride |
|  | tert-Butyl (R)-((1-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)pyrrolidin-3-yl)methyl)carbamate | 642, 644 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl (S)-(pyrrolidin-3-ylmethyl)carbamate |
|  | tert-Butyl (3-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-3-azabicyclo[3.1.0]hexan-1-yl)carbamate | 640, 642 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl (3-azabicyclo[3.1.0]hexan-1-yl)carbamate |

TABLE 5-continued

| Compound | Compound name | MS: [M + H]+ m/z | Procedure |
|---|---|---|---|
|  | tert-Butyl (3-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-3-azabicyclo[3.1.0]hexan-6-yl)carbamate | 640, 642 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl (3-azabicyclo[3.1.0]hexan-6-yl)carbamate |
|  | tert-Butyl (S)-((1-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)pyrrolidin-3-yl)methyl)carbamate | 642, 644 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl (R)-(pyrrolidin-3-ylmethyl)carbamate |
|  | tert-Butyl ((1-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-4-methoxypiperidin-4-yl)methyl)carbamate | 686, 688 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl ((4-methoxypiperidin-4-yl)methyl)carbamate |
|  | tert-Butyl ((1-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-4-fluoropiperidin-4-yl)methyl)carbamate | 674, 676 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl ((4-fluoropiperidin-4-yl)methyl)carbamate |
|  | Benzyl ((1S,2R,3S,5R)-8-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-2-fluoro-8-azabicyclo[3.2.1]octan-3-yl)carbamate | 720, 722 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and benzyl ((1S,2S,3S,5R)-2-fluoro-8-azabicyclo[3.2.1]octan-3-yl)carbamate |

TABLE 5-continued

| Compound | Compound name | MS: [M + H]+ m/z | Procedure |
|---|---|---|---|
| (structure) | Benzyl ((1R,2S,3R,5S)-8-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-2-fluoro-8-azabicyclo[3.2.1]octan-3-yl)carbamate | 720, 722 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and benzyl ((1R,2R,3R,5S)-2-fluoro-8-azabicyclo[3.2.1]octan-3-yl)carbamate |
| (structure) | Benzyl ((1S,2S,3S,5R)-8-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-2-fluoro-8-azabicyclo[3.2.1]octan-3-yl)carbamate | 720, 722 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and benzyl ((1S,2R,3S,5R)-2-fluoro-8-azabicyclo[3.2.1]octan-3-yl)carbamate |
| (structure) | Benzyl ((1R,2R,3R,5S)-8-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-2-fluoro-8-azabicyclo[3.2.1]octan-3-yl)carbamate | 720, 722 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and benzyl ((1R,2S,3R,5S)-2-fluoro-8-azabicyclo[3.2.1]octan-3-yl)carbamate |

General procedure 2: tert-Butyl 9-(5-(4-chloro-2-ethyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-3,9-diazabicyclo[3.3.1]nonane-3-carboxylate

[Chem. 147]

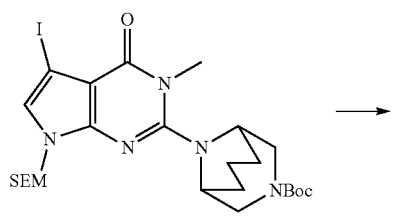

→

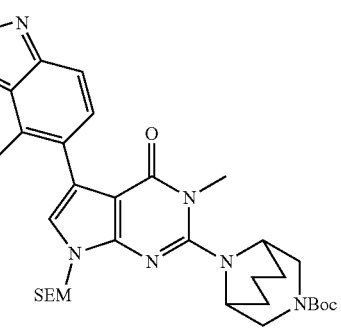

The mixture of tert-butyl 9-(5-iodo-3-methyl-4-oxo-7-((2-trimethylsilyl)ethoxy)methyl)-4,7-dihydro-3H-pyrrolo[2,3-d]pyrimidin-2-yl)-3,9-diazabicyclo[3.3.1]nonane-3-carboxylate (500 mg, 0.794 mmol), 4-chloro-2-ethyl-5-(4,4,5,5-tetramethyl-1,3,2-dioxaborolan-2-yl)-2H-indazole (365 mg, 1.19 mmol), $K_3PO_4$ (337 mg, 1.58 mmol), [1,1'-bis(diphenylphosphino)ferrocene]dichloropalladium(II) complex with dichloromethane (64.8 mg, 0.0794 mmol), 1,4-dioxane (8 mL) and water (2 mL) was stirred at 70° C. for 2 h, cooled to RT, poured into water, and extracted with EtOAc. The organic layer was washed with brine, dried over anhydrous $Na_2SO_4$, filtered, and concentrated in vacuo. The residue was purified by column chromatography on silica gel (gradient elution, 0-100% EtOAc/hexane) to give the title compound (375 mg). MS: $[M+H]^+=682, 684$.

Compounds of Table 6 below were prepared using procedures analogous to that described in general procedure 2 starting from the appropriate substituted protected pyrrolopyrimidinone and varying the boronate or boronic acid (synthesised as described above with any significant variations indicated below).

TABLE 6

| Compound | Compound name | MS: $[M+H]^+$ m/z | Procedure |
|---|---|---|---|
| (structure) | tert-Butyl (endo-8-(3-methyl-5-(2-methyl-2H-indazol-5-yl)-4-oxo-7-((2-(trimethylsilyl)ethoxy)methyl)-4,7-dihydro-3H-pyrrolo[2,3-d]pyrimidin-2-yl)-8-azabicyclo[3.2.1]octan-3-yl)carbamate | 634 | Prepared as general procedure 2 above using tert-Butyl (endo-8-(5-iodo-3-methyl-4-oxo-7-((2-(trimethylsilyl)ethoxy)methyl)-4,7-dihydro-3H-pyrrolo[2,3-d]pyrimidin-2-yl)-8-azabicyclo[3.2.1]octan-3-yl)carbamate and 2-methyl-5-(4,4,5,5-tetramethyl-1,3,2-dioxaborolan-2-yl)-2H-indazole |
| (structure) | tert-Butyl (endo-8-[5-(7-chloro-2-methylbenzo[d]oxazol-6-yl)-3-methyl-4-oxo-7-((2-(trimethylsilyl)ethoxy)methyl)pyrrolo[2,3-d]pyrimidin-2-yl]-8-azabicyclo[3.2.1]octan-3-yl]carbamate | 669, 671 | Prepared as general procedure 2 above using tert-butyl (endo-8-(5-iodo-3-methyl-4-oxo-7-((2-(trimethylsilyl)ethoxy)methyl)-4,7-dihydro-3H-pyrrolo[2,3-d]pyrimidin-2-yl)bicyclo[3.2.1]octan-3-yl)carbamate and 7-chloro-2-methyl-6-(4,4,5,5-tetramethyl-1,3,2-dioxaborolan-2-yl)benzo[d]oxazole |

TABLE 6-continued

| Compound | Compound name | MS: [M + H]+ m/z | Procedure |
|---|---|---|---|
| | tert-Butyl (endo-8-(5-(7-chloro-2-ethylbenzo[d]oxazol-6-yl)-3-methyl-4-oxo-7-((2-(trimethylsilyl)ethoxy)methyl)-4,7-dihydro-3H-pyrrolo[2,3-d]pyrimidin-2-yl)-8-azabicyclo[3.2.1]octan-3-yl)carbamate | 683, 685 | Prepared as general procedure 2 above using tert-butyl (endo-8-(5-bromo-3-methyl-4-oxo-7-((2-(trimethylsilyl)ethoxy)methyl)-4,7-dihydro-3H-pyrrolo[2,3-d]pyrimidin-2-yl)-8-azabicyclo[3.2.1]octan-3-yl)carbamate and 7-chloro-2-ethyl-6-(4,4,5,5-tetramethyl-1,3,2-dioxaborolan-2-yl)benzo[d]oxazole |
| | tert-Butyl (endo-8-(5-(4-fluoro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-8-azabicyclo[3.2.1]octan-3-yl)carbamate | 652 | Prepared as general procedure 2 above using tert-butyl (endo-8-(5-iodo-3-methyl-4-oxo-7-((2-(trimethylsilyl)ethoxy)methyl)-4,7-dihydro-3H-pyrrolo[2,3-d]pyrimidin-2-yl)bicyclo[3.2.1]octan-3-yl)carbamate and 4-fluoro-2-methyl-5-(4,4,5,5-tetramethyl-1,3,2-dioxaborolan-2-yl)-2H-indazole |
| | tert-Butyl (endo-8-(5-(6,7-difluoro-1-methyl-1H-benzo[d][1,2,3]triazol-5-yl)-3-methyl-4-oxo-7-((2-(trimethylsilyl)ethoxy)methyl)-4,7-dihydro-3H-pyrrolo[2,3-d]pyrimidin-2-yl)-8-azabicyclo[3.2.1]octan-3-yl)carbamate | 671 | Prepared as general procedure 2 above using tert-butyl endo-(8-(5-iodo-3-methyl-4-oxo-7-((2-(trimethylsilyl)ethoxy)methyl)-4,7-dihydro-3H-pyrrolo[2,3-d]pyrimidin-2-yl)bicyclo[3.2.1]octan-3-yl)carbamate and 6,7-difluoro-1-methyl-5-(4,4,5,5-tetramethyl-1,3,2-dioxaborolan-2-yl)-1H-benzo[d][1,2,3]triazole |
| | tert-Butyl (endo-8-(5-(6-fluoro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-8-azabicyclo[3.2.1]octan-3-yl)carbamate | 652 | Prepared as general procedure 2 above using tert-butyl endo-(8-(5-iodo-3-methyl-4-oxo-7-((2-(trimethylsilyl)ethoxy)methyl)-4,7-dihydro-3H-pyrrolo[2,3-d]pyrimidin-2-yl)bicyclo[3.2.1]octan-3-yl)carbamate and 6-fluoro-2-methyl-5-(4,4,5,5-tetramethyl-1,3,2-dioxaborolan-2-yl)-2H-indazole |
| | tert-Butyl (endo-8-(5-(4-methoxy-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-8-azabicyclo[3.2.1]octan-3-yl)carbamate | 664 | Prepared as general procedure 2 above using tert-butyl endo-(8-(5-iodo-3-methyl-4-oxo-7-((2-(trimethylsilyl)ethoxy)methyl)-4,7-dihydro-3H-pyrrolo[2,3-d]pyrimidin-2-yl)bicyclo[3.2.1]octan-3-yl)carbamate and 4-methoxy-2-methyl-5-(4,4,5,5-tetramethyl-1,3,2-dioxaborolan-2-yl)-2H-indazole |

TABLE 6-continued

| Compound | Compound name | MS: [M + H]+ m/z | Procedure |
|---|---|---|---|
| | tert-Butyl (endo-8-(5-(7-chloro-1-methyl-1H-benzo[d][1,2,3]triazol-6-yl)-3-methyl-4-oxo-7-((2-(trimethylsilyl)ethoxy)methyl)-4,7-dihydro-3H-pyrrolo[2,3-d]pyrimidin-2-yl)-8-azabicyclo[3.2.1]octan-3-yl)carbamate | 669, 671 | Prepared as general procedure 2 above using tert-butyl endo-(8-(5-iodo-3-methyl-4-oxo-7-((2-(trimethylsilyl)ethoxy)methyl)-4,7-dihydro-3H-pyrrolo[2,3-d]pyrimidin-2-yl)bicyclo[3.2.1]octan-3-yl)carbamate and 7-chloro-1-methyl-6-(4,4,5,5-tetramethyl-1,3,2-dioxaborolan-2-yl)-1H-benzo[d][1,2,3]triazole |
| | tert-Butyl (endo-8-(5-(4-chloro-2-(2-hydroxy-2-methylpropyl)-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-8-azabicyclo[3.2.1]octan-3-yl)carbamate | 726, 728 | Prepared as general procedure 2 above using tert-butyl endo-(8-(5-iodo-3-methyl-4-oxo-7-((2-(trimethylsilyl)ethoxy)methyl)-4,7-dihydro-3H-pyrrolo[2,3-d]pyrimidin-2-yl)bicyclo[3.2.1]octan-3-yl)carbamate and 1-(4-chloro-5-(4,4,5,5-tetramethyl-1,3,2-dioxaborolan-2-yl)-2H-indazol-2-yl)-2-methylpropan-2-ol |
| | tert-Butyl (endo-8-(5-(4-chloro-2,7-dimethyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-8-azabicyclo[3.2.1]octan-3-yl)carbamate | 682, 684 | Prepared as general procedure 2 above using tert-butyl (endo-8-(5-iodo-3-methyl-4-oxo-7-((2-(trimethylsilyl)ethoxy)methyl)-4,7-dihydro-3H-pyrrolo[2,3-d]pyrimidin-2-yl)-8-azabicyclo[3.2.1]octan-3-yl)carbamate and 4-chloro-2,7-dimethyl-5-(4,4,5,5-tetramethyl-1,3,2-dioxaborolan-2-yl)-2H-indazole |
| | tert-Butyl (endo-8-(5-(4-chloro-1H-indazol-5-yl)-3-methyl-4-oxo-7-((2-(trimethylsilyl)ethoxy)methyl)-4,7-dihydro-3H-pyrrolo[2,3-d]pyrimidin-2-yl)-8-azabicyclo[3.2.1]octan-3-yl)carbamate | 654, 656 | Prepared as general procedure 2 above using tert-butyl endo-(8-(5-iodo-3-methyl-4-oxo-7-((2-(trimethylsilyl)ethoxy)methyl)-4,7-dihydro-3H-pyrrolo[2,3-d]pyrimidin-2-yl)bicyclo[3.2.1]octan-3-yl)carbamate and 4-chloro-5-(4,4,5,5-tetramethyl-1,3,2-dioxaborolan-2-yl)-1H-indazole |
| | tert-Butyl (endo-8-(5-(3,4-dichloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-8-azabicyclo[3.2.1]octan-3-yl)carbamate | 702, 704 | Prepared as general procedure 2 above using tert-butyl (endo-8-(5-iodo-3-methyl-4-oxo-7-((2-(trimethylsilyl)ethoxy)methyl)-4,7-dihydro-3H-pyrrolo[2,3-d]pyrimidin-2-yl)-8-azabicyclo[3.2.1]octan-3-yl)carbamate and 3,4-dichloro-2-methyl-5-(4,4,5,5-tetramethyl-1,3,2-dioxaborolan-2-yl)-2H-indazole |

TABLE 6-continued

| Compound | Compound name | MS: [M + H]+ m/z | Procedure |
|---|---|---|---|
| | tert-Butyl (endo-8-(5-(3,4-dichloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-3-methyl-8-azabicyclo[3.2.1]octan-3-yl)carbamate | 716, 718 | Prepared as general procedure 2 above using tert-butyl (endo-8-(5-iodo-3-methyl-4-oxo-7-((2-(trimethylsilyl)ethoxy)methyl)-4,7-dihydro-3H-pyrrolo[2,3-d]pyrimidin-2-yl)-3-methyl-8-azabicyclo[3.2.1]octan-3-yl)carbamate and 3,4-dichloro-2-methyl-5-(4,4,5,5-tetramethyl-1,3,2-dioxaborolan-2-yl)-2H-indazole |
| | tert-Butyl 7-(5-(3,4-dichloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-3-oxa-7,9-diazabicyclo[3.3.1]nonane-9-carboxylate | 704, 706 | Prepared as general procedure 2 above using tert-butyl 7-[5-iodo-3-methyl-4-oxo-7-(2-trimethylsilylethoxymethyl)pyrrolo[2,3-d]pyrimidin-2-yl]-3-oxa-7,9-diazabicyclo[3.3.1]nonane-9-carboxylate and 3,4-dichloro-2-methyl-5-(4,4,5,5-tetramethyl-1,3,2-dioxaborolan-2-yl)-2H-indazole |
| | tert-Butyl 7-(5-(7-chloro-2-methylbenzo[d]thiazol-6-yl)-3-methyl-4-oxo-7-((2-(trimethylsilyl)ethoxy)methyl)-4,7-dihydro-3H-pyrrolo[2,3-d]pyrimidin-2-yl)-3-oxa-7,9-diazabicyclo[3.3.1]nonane-9-carboxylate | 687, 689 | Prepared as general procedure 2 above using tert-butyl 7-[5-iodo-3-methyl-4-oxo-7-(2-trimethylsilylethoxymethyl)pyrrolo[2,3-d]pyrimidin-2-yl]-3-oxa-7,9-diazabicyclo[3.3.1]nonane-9-carboxylate and 7-chloro-2-methyl-6-(4,4,5,5-tetramethyl-1,3,2-dioxaborolan-2-yl)-1,3-benzothiazole |
| | tert-Butyl 9-(5-(3,4-dichloro-2-(2-(dimethylamino)-2-oxoethyl)-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-3,9-diazabicyclo[3.3.1]nonane-3-carboxylate | 773, 775 | Prepared as general procedure 2 above using 2-(3,4-dichloro-5-(4,4,5,5-tetramethyl-1,3,2-dioxaborolan-2-yl)-2H-indazol-2-yl)-N,N-dimethylacetamide |
| | tert-Butyl 9-(5-(3,4-dichloro-2-(3-(dimethylamino)-3-oxopropyl)-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-3,9-diazabicyclo[3.3.1]nonane-3-carboxylate | 787, 789 | Prepared as general procedure 2 above using 3-(3,4-dichloro-5-(4,4,5,5-tetramethyl-1,3,2-dioxaborolan-2-yl)-2H-indazol-2-yl)-N,N-dimethylpropanamide |

TABLE 6-continued

| Compound | Compound name | MS: [M + H]+ m/z | Procedure |
|---|---|---|---|
| | tert-Butyl 9-(5-(7-chloro-2-(2-(dimethylamino)-2-oxoethyl)benzo[d]thiazol-6-yl)-3-methyl-4-oxo-7-((2-(trimethylsilyl)ethoxy)methyl)-4,7-dihydro-3H-pyrrolo[2,3-d]pyrimidin-2-yl)-3,9-diazabicyclo[3.3.1]nonane-3-carboxylate | 756, 758 | Prepared as general procedure 2 above using 2-(7-chloro-6-(4,4,5,5-tetramethyl-1,3,2-dioxaborolan-2-yl)benzo[d]thiazol-2-yl)-N,N-dimethylacetamide |
| | tert-Butyl 9-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-3-oxa-7,9-diazabicyclo[3.3.1]nonane-7-carboxylate | 670, 672 | Prepared as general procedure 2 above using tert-butyl 9-(5-iodo-3-methyl-4-oxo-7-((2-(trimethylsilyl)ethoxy)methyl)-4,7-dihydro-3H-pyrrolo[2,3-d]pyrimidin-2-yl)-3-oxa-7,9-diazabicyclo[3.3.1]nonane-7-carboxylate and 4-chloro-2-methyl-5-(4,4,5,5-tetramethyl-1,3,2-dioxaborolan-2-yl)-2H-indazole |
| | tert-Butyl 8-(5-(4-chloro-2-(2-(dimethylamino)-2-oxoethyl)-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-3,8-diazabicyclo[3.2.1]octane-3-carboxylate | 725, 727 | Prepared as general procedure 2 above using tert-butyl 8-(5-iodo-3-methyl-4-oxo-7-((2-(trimethylsilyl)ethoxy)methyl)-4,7-dihydro-3H-pyrrolo[2,3-d]pyrimidin-2-yl)-3,8-diazabicyclo[3.2.1]octane-3-carboxylate and 2-(4-chloro-5-(4,4,5,5-tetramethyl-1,3,2-dioxaborolan-2-yl)-2H-indazol-2-yl)-N,N-dimethylacetamide |
| | tert-Butyl 8-(5-(4-chloro-2-methyl-2H-benzo[d][1,2,3]triazol-5-yl)-3-methyl-4-oxo-7-((2-(trimethylsilyl)ethoxy)methyl)-4,7-dihydro-3H-pyrrolo[2,3-d]pyrimidin-2-yl)-3,8-diazabicyclo[3.2.1]octane-3-carboxylate | 655, 657 | Prepared as general procedure 2 above using tert-butyl 8-(5-iodo-3-methyl-4-oxo-7-((2-(trimethylsilyl)ethoxy)methyl)-4,7-dihydro-3H-pyrrolo[2,3-d]pyrimidin-2-yl)-3,8-diazabicyclo[3.2.1]octane-3-carboxylate and 4-chloro-2-methyl-5-(4,4,5,5-tetramethyl-1,3,2-dioxaborolan-2-yl)-2H-benzo[d][1,2,3]triazole |

TABLE 6-continued

| Compound | Compound name | MS: [M + H]+ m/z | Procedure |
|---|---|---|---|
| | tert-Butyl 8-(5-(4-chloro-2-(3-(dimethylamino)-3-oxopropyl)-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-3,8-diazabicyclo[3.2.1]octane-3-carboxylate | 739, 741 | Prepared as general procedure 2 above using tert-butyl 8-(5-iodo-3-methyl-4-oxo-7-((2-(trimethylsilyl)ethoxy)methyl)-4,7-dihydro-3H-pyrrolo[2,3-d]pyrimidin-2-yl)-3,8-diazabicyclo[3.2.1]octane-3-carboxylate and 3-(4-chloro-5-(4,4,5,5-tetramethyl-1,3,2-dioxaborolan-2-yl)-2H-indazol-2-yl)-N,N-dimethylpropanamide |
| | tert-Butyl 8-(5-(3,4-dichloro-2-(3-(dimethylamino)-3-oxopropyl)-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-3,8-diazabicyclo[3.2.1]octane-3-carboxylate | 773, 775 | Prepared as general procedure 2 above using tert-butyl 8-(5-iodo-3-methyl-4-oxo-7-((2-(trimethylsilyl)ethoxy)methyl)-4,7-dihydro-3H-pyrrolo[2,3-d]pyrimidin-2-yl)-3,8-diazabicyclo[3.2.1]octane-3-carboxylate and 3-(3,4-dichloro-5-(4,4,5,5-tetramethyl-1,3,2-dioxaborolan-2-yl)-2H-indazol-2-yl)-N,N-dimethylpropanamide |
| | tert-Butyl 8-(5-(7-chloro-2-methylbenzo[d]thiazol-6-yl)-3-methyl-4-oxo-7-((2-(trimethylsilyl)ethoxy)methyl)-4,7-dihydro-3H-pyrrolo[2,3-d]pyrimidin-2-yl)-3,8-diazabicyclo[3.2.1]octane-3-carboxylate | 671, 673 | Prepared as general procedure 2 above using tert-butyl 8-(5-iodo-3-methyl-4-oxo-7-((2-(trimethylsilyl)ethoxy)methyl)-4,7-dihydro-3H-pyrrolo[2,3-d]pyrimidin-2-yl)-3,8-diazabicyclo[3.2.1]octane-3-carboxylate and 7-chloro-2-methyl-6-(4,4,5,5-tetramethyl-1,3,2-dioxaborolan-2-yl)benzo[d]thiazole |
| | tert-Butyl 8-(5-(4-chloro-2-ethyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-3,8-diazabicyclo[3.2.1]octane-3-carboxylate | 668, 670 | Prepared as general procedure 2 above using tert-butyl 8-(5-iodo-3-methyl-4-oxo-7-((2-(trimethylsilyl)ethoxy)methyl)-4,7-dihydro-3H-pyrrolo[2,3-d]pyrimidin-2-yl)-3,8-diazabicyclo[3.2.1]octane-3-carboxylate and 4-chloro-2-ethyl-5-(4,4,5,5-tetramethyl-1,3,2-dioxaborolan-2-yl)-2H-indazole |
| | tert-Butyl ((1R,2R,4S)-7-(5-(4-chloro-2-ethyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)carbamate | 668, 670 | Prepared as general procedure 2 above using tert-butyl ((1R,2R,4S)-7-(5-iodo-3-methyl-4-oxo-7-((2-trimethylsilyl)ethoxy)methyl)-4,7-dihydro-3H-pyrrolo[2,3-d]pyrimidin-2-yl)-7-azabicyclo[2.2.1]heptan-2-yl)carbamate and 4-chloro-2-ethyl-5-(4,4,5,5-tetramethyl-1,3,2-dioxaborolan-2-yl)-2H-indazole |

TABLE 6-continued

| Compound | Compound name | MS: [M + H]⁺ m/z | Procedure |
|---|---|---|---|
| | tert-Butyl ((1R,2R,4S)-7-(5-(3,4-dichloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)carbamate | 688, 690 | Prepared as general procedure 2 above using tert-butyl ((1R,2R,4S)-7-(5-iodo-3-methyl-4-oxo-7-((2-trimethylsilyl)ethoxy)methyl)-4,7-dihydro-3H-pyrrolo[2,3-d]pyrimidin-2-yl)-7-azabicyclo[2.2.1]heptan-2-yl)carbamate and 3,4-dichloro-2-methyl-5-(4,4,5,5-tetramethyl-1,3,2-dioxaborolan-2-yl)-2H-indazole |
| | tert-Buty ((1R,2R,4S)-7-(5-(4-chloro-2,3-dimethyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)carbamate | 668, 670 | Prepared as general procedure 2 above using tert-butyl ((1R,2R,4S)-7-(5-iodo-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)carbamate and 4-chloro-2,3-dimethyl-5-(4,4,5,5-tetramethyl-1,3,2-dioxaborolan-2-yl)-2H-indazole |
| | tert-Butyl ((1R,2R,4S)-7-(5-(7-chloro-2-methylbenzo[d]thiazol-6-yl)-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)carbamate | 671, 673 | Prepared as general procedure 2 above using tert-butyl ((1R,2R,4S)-7-(5-iodo-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)carbamate and 7-chloro-2-methyl-6-(4,4,5,5-tetramethyl-1,3,2-dioxaborolan-2-yl)benzo[d]thiazole |
| | tert-Butyl ((1R,2R,4S)-7-(5-(3-chloro-4-fluoro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)carbamate | 672, 674 | Prepared as general procedure 2 above using tert-butyl ((1R,2R,4S)-7-(5-iodo-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)carbamate and 3-chloro-4-fluoro-2-methyl-5-(4,4,5,5-tetramethyl-1,3,2-dioxaborolan-2-yl)-2H-indazole |

TABLE 6-continued

| Compound | Compound name | MS: [M + H]+ m/z | Procedure |
|---|---|---|---|
| | tert-Buty ((1R,2R,4S)-7-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)(methyl)carbamate | 668, 670 | Prepared as general procedure 2 above using tert-butyl ((1R,2R,4S)-7-(5-iodo-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)(methyl)carbamate and 4-chloro-2-methyl-5-(4,4,5,5-tetramethyl-1,3,2-dioxaborolan-2-yl)-2H-indazole |
| | tert-Butyl ((1R,2R,4S)-7-(5-(4-chloro-2-ethyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)(methyl)carbamate | 682, 684 | Prepared as general procedure 2 above using tert-butyl ((1R,2R,4S)-7-(5-iodo-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)(methyl)carbamate |
| | tert-Butyl 9-(5-(3,4-dichloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-3,9-diazabicyclo[3.3.1]nonane-3-carboxylate | 702, 704 | Prepared as general procedure 2 above using tert-butyl 9-(5-iodo-3-methyl-4-oxo-7-((2-(trimethylsilyl)ethoxy)methyl)-4,7-dihydro-3H-pyrrolo[2,3-d]pyrimidin-2-yl)-3,9-diazabicyclo[3.3.1]nonane-3-carboxylate and 3,4-dichloro-2-methyl-5-(4,4,5,5-tetramethyl-1,3,2-dioxaborolan-2-yl)-2H-indazole |
| | tert-Butyl 9-(5-(3-chloro-4-fluoro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-3,9-diazabicyclo[3.3.1]nonane-3-carboxylate | 686, 688 | Prepared as general procedure 2 above using tert-butyl 9-(5-iodo-3-methyl-4-oxo-7-((2-(trimethylsilyl)ethoxy)methyl)-4,7-dihydro-3H-pyrrolo[2,3-d]pyrimidin-2-yl)-3,9-diazabicyclo[3.3.1]nonane-3-carboxylate and 3-chloro-4-fluoro-2-methyl-5-(4,4,5,5-tetramethyl-1,3,2-dioxaborolan-2-yl)-2H-indazole |

TABLE 6-continued

| Compound | Compound name | MS: [M + H]+ m/z | Procedure |
|---|---|---|---|
| | tert-Butyl ((1R,2R,4S)-7-(5-(7-chlorobenzo[d]thiazol-6-yl)-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)carbamate | 657, 659 | Prepared as general procedure 2 above using tert-butyl ((1R,2R,4S)-7-(5-iodo-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)carbamate and 7-chloro-6-(4,4,5,5-tetramethyl-1,3,2-dioxaborolan-2-yl)benzo[d]thiazole |
| | tert-Butyl ((1R,2R,4S)-7-(5-(4-chloro-2-ethyl-3-methoxy-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)carbamate | 698, 700 | Prepared as general procedure 2 above using tert-butyl ((1R,2R,4S)-7-(5-iodo-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)carbamate and 4-chloro-2-ethyl-3-methoxy-5-(4,4,5,5-tetramethyl-1,3,2-dioxaborolan-2-yl)-2H-indazole |
| | tert-Butyl ((1R,2R,4S)-7-(5-(3,4-dichloro-2-(fluoromethyl)-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)carbamate | 706, 708 | Prepared as general procedure 2 above using tert-butyl ((1R,2R,4S)-7-(5-iodo-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)carbamate and 3,4-dichloro-2-(fluoromethyl)-5-(4,4,5,5-tetramethyl-1,3,2-dioxaborolan-2-yl)-2H-indazole |
| | tert-Butyl ((1R,2R,4S)-7-(5-(3,4-dichloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)(methyl)carbamate | 702, 704 | Prepared as general procedure 2 above using tert-butyl ((1R,2R,4S)-7-(5-iodo-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)(methyl)carbamate and 3,4-dichloro-2-methyl-5-(4,4,5,5-tetramethyl-1,3,2-dioxaborolan-2-yl)-2H-indazole |

TABLE 6-continued

| Compound | Compound name | MS: [M + H]+ m/z | Procedure |
|---|---|---|---|
| (structure) | tert-Butyl ((1R,2R,4S)-7-(5-(7-chlorobenzo[d]thiazol-6-yl)-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)(methyl)carbamate | 671, 673 | Prepared as general procedure 2 above using tert-butyl ((1R,2R,4S)-7-(5-iodo-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)(methyl)carbamate and 7-chloro-6-(4,4,5,5-tetramethyl-1,3,2-dioxaborolan-2-yl)benzo[d]thiazole |
| (structure) | tert-Butyl ((1R,2R,4S)-7-(5-(3-chloro-4-fluoro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)(methyl)carbamate | 686, 688 | Prepared as general procedure 2 above using tert-butyl ((1R,2R,4S)-7-(5-iodo-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)(methyl)carbamate and 3-chloro-4-fluoro-2-methyl-5-(4,4,5,5-tetramethyl-1,3,2-dioxaborolan-2-yl)-2H-indazole |
| (structure) | tert-Butyl ((1R,2R,4S)-7-(5-(7-chloro-2-methylbenzo[d]thiazol-6-yl)-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)(methyl)carbamate | 685, 687 | Prepared as general procedure 2 above using tert-butyl ((1R,2R,4S)-7-(5-iodo-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)(methyl)carbamate and 7-chloro-2-methyl-6-(4,4,5,5-tetramethyl-1,3,2-dioxaborolan-2-yl)benzo[d]thiazole |
| (structure) | tert-Butyl 9-(5-(benzo[d]thiazol-6-yl)-3-methyl-4-oxo-7-((2-(trimethylsilyl)ethoxy)methyl)-4,7-dihydro-3H-pyrrolo[2,3-d]pyrimidin-2-yl)-3,9-diazabicyclo[3.3.1]nonane-3-carboxylate | 685, 687 | Prepared as general procedure 2 above using tert-butyl 9-(5-iodo-3-methyl-4-oxo-7-((2-(trimethylsilyl)ethoxy)methyl)-4,7-dihydro-3H-pyrrolo[2,3-d]pyrimidin-2-yl)-3,9-diazabicyclo[3.3.1]nonane-3-carboxylate and 7-chloro-6-(4,4,5,5-tetramethyl-1,3,2-dioxaborolan-2-yl)benzo[d]thiazole |

| Compound | Compound name | MS: [M + H]⁺ m/z | Procedure |
|---|---|---|---|
|  | tert-Butyl ((1R,2R,4S)-7-(5-(4-chloro-2-ethyl-3-formyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)carbamate | 696, 698 | Prepared as general procedure 2 above using tert-butyl ((1R,2R,4S)-7-(5-iodo-3-methyl-4-oxo-7-((2-(trimethylsilyl)ethoxy)methyl)-4,7-dihydro-3H-pyrrolo[2,3-cy]pyrimidin-2-yl)-7-azabicyclo[2.2.1]heptan-2-yl)(methyl)carbamate and 4-chloro-2-ethyl-5-(4,4,5,5-tetramethyl-1,3,2-dioxaborolan-2-yl)-2H-indazole-3-carbaldehyde |
|  | rac-tert-Butyl ((1S,4S,7S)-2-(5-(4-chloro-2-ethyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-2-azabicyclo[2.2.1]heptan-7-yl)carbamate | 668, 670 | Prepared as general procedure 2 above using rac-tert-butyl ((1S,4S,7S)-2-(5-iodo-3-methyl-4-oxo-7-((2-(trimethylsilyl)ethoxy)methyl)-4,7-dihydro-3H-pyrrolo[2,3-d]pyrimidin-2-yl)-2-azabicyclo[2.2.1]heptan-7-yl)carbamate and 4-chloro-2-ethyl-5-(4,4,5,5-tetramethyl-1,3,2-dioxaborolan-2-yl)-2H-indazole |
|  | rac-tert-butyl ((1S,4S,7S)-2-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-2-azabicyclo[2.2.1]heptan-7-yl)(methyl)carbamate | 668, 670 | Prepared as general procedure 2 above using rac-tert-butyl ((1S,4S,7S)-2-(5-iodo-3-methyl-4-oxo-7-((2-(trimethylsilyl)ethoxy)methyl)-4,7-dihydro-3H-pyrrolo[2,3-d]pyrimidin-2-yl)-2-azabicyclo[2.2.1]heptan-7-yl)(methyl)carbamate and 2-methyl-5-(4,4,5,5-tetramethyl-1,3,2-dioxaborolan-2-yl)-2H-indazole |

199

Preparation 112: tert-Butyl ((1R,2R,4S)-7-(5-(4-chloro-3-(difluoromethyl)-2-ethyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)carbamate

[Chem. 148]

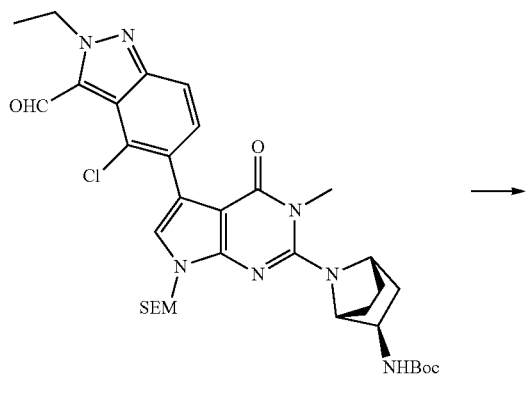

To a solution of tert-butyl ((1R,2R,4S)-7-(5-(4-chloro-2-ethyl-3-formyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)carbamate (220 mg, 0.32 mmol) in 1,2-dichloroethane (1.3 mL) was added bis(2-methoxyethyl)aminosulfur trifluoride (290 mg, 1.3 mmol). The mixture was stirred at 50° C. overnight. The mixture was quenched with sat. NaHCO₃, and extracted with EtOAc. The organic layer was concentrated in vacuo. The residue was purified by column chromatography on silica gel (gradient elution, 0-80% EtOAc/hexane) to give the title compound (54 mg). MS: [M+H]⁺= 718, 720.

200

Preparation 113: tert-Butyl ((1R,2R,4S)-7-(5-(4-chloro-2-ethyl-3-(hydroxymethyl)-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)carbamate

[Chem. 149]

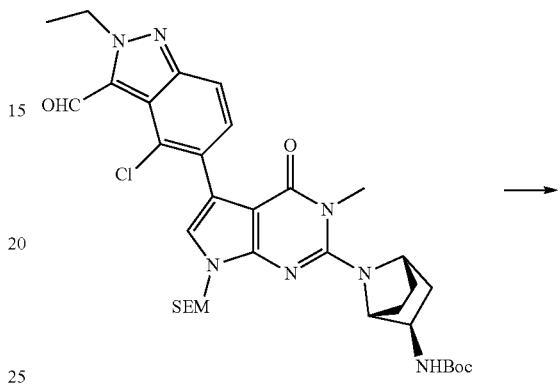

To a solution of tert-butyl ((1R,2R,4S)-7-(5-(4-chloro-2-ethyl-3-formyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)carbamate (240 mg, 0.34 mmol) in methanol (3.0 mL) was added sodium borohydride (21 mg, 0.56 mmol). The mixture was stirred at RT for 1 h. The mixture was quenched with sat. NH₄Cl aq., extracted with EtOAc. The organic layer was washed with water and brine, and concentrated in vacuo. The residue was purified by column chromatography on silica gel (gradient elution, 0-10% MeOH/CHCl₃) to give the title compound (215 mg). MS: [M+H]⁺=698, 700.

201

Preparation 114: tert-butyl ((1R,2R,4S)-7-(5-(4-chloro-3-cyano-2-ethyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)carbamate

[Chem. 150]

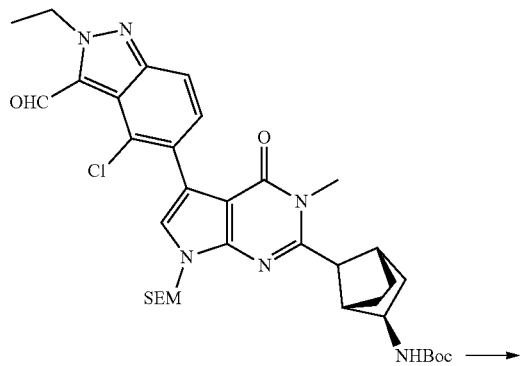

To a mixture of tert-butyl ((1R,2R,4S)-7-(5-(4-chloro-2-ethyl-3-formyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)carbamate (314 mg, 0.45 mmol) and sodium carbonate (75 mg, 0.71 mmol) in ethanol (0.9 mL) was added hydroxylamine hydrochloride (49 mg, 0.71 mmol). The mixture was stirred at RT overnight. The mixture was diluted with EtOAc, washed with water and brine, and concentrated in vacuo. To the residue was added acetonitrile (2.4 ml) and copper(II) acetate (8.1 mg, 0.045 mmol). The mixture was stirred at 80° C. for 5 h, and then concentrated in vacuo. The residue was purified by column chromatography on NH-silica gel (gradient elution, 0-10% MeOH/CHCl$_3$) to give the title compound (245 mg). MS: [M+H]$^+$=693, 695.

202

General procedure 3: tert-Butyl 9-(3-(4-chloro-2-ethyl-2H-indazol-5-yl)-5-methyl-4-oxo-1-((2-(trimethylsilyl)ethoxy)methyl)-4,5-dihydro-1H-pyrazolo[3,4-d]pyrimidin-6-yl)-3,9-diazabicyclo[3.3.1]nonane-3-carboxylate

[Chem. 151]

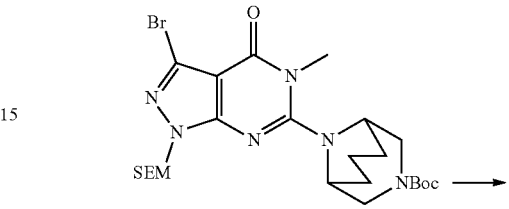

The mixture of tert-butyl 9-(3-bromo-5-methyl-4-oxo-1-((2-(trimethylsilyl)ethoxy)methyl)-4,5-dihydro-1H-pyrazolo[3,4-d]pyrimidin-6-yl)-3,9-diazabicyclo[3.3.1]nonane-3-carboxylate (300 mg, 0.475 mmol), 4-chloro-2-ethyl-5-(4,4,5,5-tetramethyl-1,3,2-dioxaborolan-2-yl)-2H-indazole (315 mg, 1.02 mmol), K$_3$PO$_4$ (327 mg, 1.54 mmol), [1,1'-bis(diphenylphosphino)ferrocene]dichloropalladium(II) complex with dichloromethane (41.9 mg, 0.0514 mmol), 1,4-dioxane (6 mL) and water (1.5 mL) was stirred at 90° C. for 2 h, cooled to RT, poured into water, and extracted with EtOAc. The organic layer was washed with brine, dried over anhydrous Na$_2$SO$_4$, filtered, and concentrated in vacuo. The residue was purified by column chromatography on silica gel (gradient elution, 0-100% EtOAc/hexane) to give the title compound (200 mg). MS: [M+H]$^+$=683, 685.

Compounds of Table 7 below were prepared using procedures analogous to that described in general procedure 3 starting from the appropriate the appropriate substituted protected pyrazolopyrimidinone and varying the boronate or boronic acid (synthesised as described above with any significant variations indicated below).

TABLE 7

| Compound | Compound name | MS: [M + H]+ m/z | Procedure |
|---|---|---|---|
| | tert-Butyl ((1R,2R,4S)-7-(3-(4-chloro-2-ethyl-2H-indazol-5-yl)-5-methyl-4-oxo-1-(tetrahydro-2H-pyran-2-yl)-4,5-dihydro-1H-pyrazolo[3,4-d]pyrimidin-6-yl)-7-azabicyclo[2.2.1]heptan-2-yl)carbamate | 623, 625 | Prepared as general procedure 3 above using tert-Butyl ((1R,2R,4S)-7-(3-bromo-5-methyl-4-oxo-1-(tetrahydro-2H-pyran-2-yl)-4,5-dihydro-1H-pyrazolo[3,4-d]pyrimidin-6-yl)-7-azabicyclo[2.2.1]heptan-2-yl)carbamate |
| | tert-Butyl ((1R,2R,4S)-7-(3-(7-chloro-2-methylbenzo[d]thiazol-6-yl)-5-methyl-4-oxo-1-(tetrahydro-2H-pyran-2-yl)-4,5-dihydro-1H-pyrazolo[3,4-d]pyrimidin-6-yl)-7-azabicyclo[2.2.1]heptan-2-yl)carbamate | 626, 628 | Prepared as general procedure 3 above using tert-butyl ((1R,2R,4S)-7-(3-bromo-5-methyl-4-oxo-1-(tetrahydro-2H-pyran-2-yl)-4,5-dihydro-1H-pyrazolo[3,4-d]pyrimidin-6-yl)-7-azabicyclo[2.2.1]heptan-2-yl)carbamate and 7-chloro-2-methyl-6-(4,4,5,5-tetramethyl-1,3,2-dioxaborolan-2-yl)benzo[d]thiazole |
| | tert-Butyl ((1R,2R,4S)-7-(3-(3,4-dichloro-2-methyl-2H-indazol-5-yl)-5-methyl-4-oxo-1-(tetrahydro-2H-pyran-2-yl)-4,5-dihydro-1H-pyrazolo[3,4-d]pyrimidin-6-yl)-7-azabicyclo[2.2.1]heptan-2-yl)carbamate | 643, 645 | Prepared as general procedure 3 above using tert-butyl ((1R,2R,4S)-7-(3-bromo-5-methyl-4-oxo-1-(tetrahydro-2H-pyran-2-yl)-4,5-dihydro-1H-pyrazolo[3,4-d]pyrimidin-6-yl)-7-azabicyclo[2.2.1]heptan-2-yl)carbamate and 3,4-dichloro-2-methyl-5-(4,4,5,5-tetramethyl-1,3,2-dioxaborolan-2-yl)-2H-indazole |
| | tert-Butyl (endo-8-(3-(4-chloro-2-ethyl-2H-indazol-5-yl)-5-methyl-4-oxo-1-(tetrahydro-2H-pyran-2-yl)-4,5-dihydro-1H-pyrazolo[3,4-d]pyrimidin-6-yl)-3-methyl-8-azabicyclo[3.2.1]octan-3-yl)carbamate | 651, 653 | Prepared as general procedure 3 above using tert-butyl (endo-8-(3-bromo-5-methyl-4-oxo-1-(tetrahydro-2H-pyran-2-yl)-4,5-dihydro-1H-pyrazolo[3,4-d]pyrimidin-6-yl)-3-methyl-8-azabicyclo[3.2.1]octan-3-yl)carbamate and 4-chloro-2-ethyl-5-(4,4,5,5-tetramethyl-1,3,2-dioxaborolan-2-yl)-2H-indazole. |

TABLE 7-continued

| Compound | Compound name | MS: [M + H]+ m/z | Procedure |
|---|---|---|---|
| 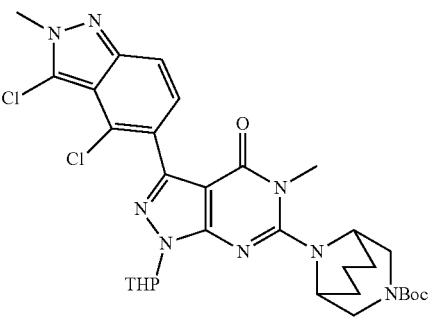 | tert-Butyl 9-(3-(3,4-dichloro-2-methyl-2H-indazol-5-yl)-5-methyl-4-oxo-1-(tetrahydro-2H-pyran-2-yl)-4,5-dihydro-1H-pyrazolo[3,4-d]pyrimidin-6-yl)-3,9-diazabicyclo[3.3.1]nonane-3-carboxylate | 657, 659 | Prepared as general procedure 3 above using tert-butyl 9-(3-bromo-5-methyl-4-oxo-1-(tetrahydro-2H-pyran-2-yl)-4,5-dihydro-1H-pyrazolo[3,4-d]pyrimidin-6-yl)-3,9-diazabicyclo[3.3.1]nonane-3-carboxylate and 3,4-dichloro-2-methyl-5-(4,4,5,5-tetramethyl-1,3,2-dioxaborolan-2-yl)-2H-indazole |
| 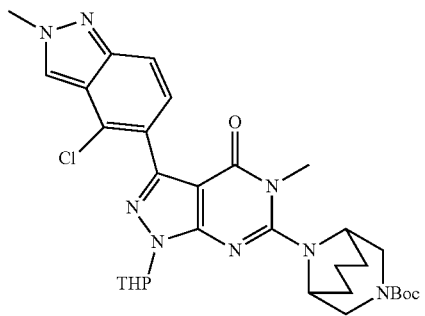 | tert-Butyl 9-(3-(4-chloro-2-methyl-2H-indazol-5-yl)-5-methyl-4-oxo-1-(tetrahydro-2H-pyran-2-yl)-4,5-dihydro-1H-pyrazolo[3,4-d]pyrimidin-6-yl)-3,9-diazabicyclo[3.3.1]nonane-3-carboxylate | 623, 625 | Prepared as general procedure 3 above using tert-butyl 9-(3-bromo-5-methyl-4-oxo-1-(tetrahydro-2H-pyran-2-yl)-4,5-dihydro-1H-pyrazolo[3,4-d]pyrimidin-6-yl)-3,9-diazabicyclo[3.3.1]nonane-3-carboxylate and 4-chloro-2-methyl-5-(4,4,5,5-tetramethyl-1,3,2-dioxaborolan-2-yl)-2H-indazole. |
| 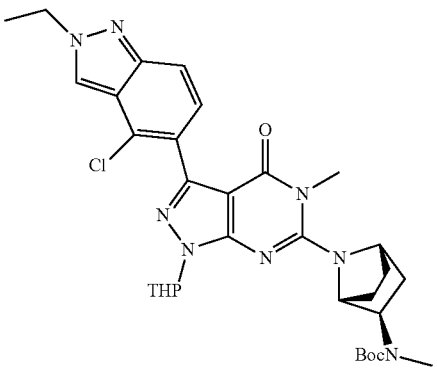 | tert-Butyl ((1R,2R,4S)-7-(3-(4-chloro-2-ethyl-2H-indazol-5-yl)-5-methyl-4-oxo-1-(tetrahydro-2H-pyran-2-yl)-4,5-dihydro-1H-pyrazolo[3,4-d]pyrimidin-6-yl)-7-azabicyclo[2.2.1]heptan-2-yl)(methyl)carbamate | 637, 639 | Prepared as general procedure 3 above using tert-butyl ((1R,2R,4S)-7-(3-bromo-5-methyl-4-oxo-1-(tetrahydro-2H-pyran-2-yl)-4,5-dihydro-1H-pyrazolo[3,4-d]pyrimidin-6-yl)-7-azabicyclo[2.2.1]heptan-2-yl)(methyl)carbamate |
| 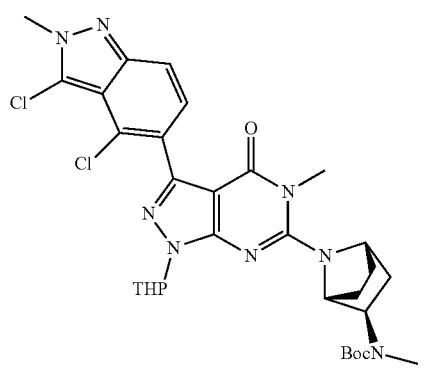 | tert-Butyl ((1R,2R,4S)-7-(3-(3,4-dichloro-2-methyl-2H-indazol-5-yl)-5-methyl-4-oxo-1-(tetrahydro-2H-pyran-2-yl)-4,5-dihydro-1H-pyrazolo[3,4-d]pyrimidin-6-yl)-7-azabicyclo[2.2.1]heptan-2-yl)(methyl)carbamate | 657, 659 | Prepared as general procedure 3 above using tert-butyl ((1R,2R,4S)-7-(3-bromo-5-methyl-4-oxo-1-(tetrahydro-2H-pyran-2-yl)-4,5-dihydro-1H-pyrazolo[3,4-d]pyrimidin-6-yl)-7-azabicyclo[2.2.1]heptan-2-yl)(methyl)carbamate and 3,4-dichloro-2-methyl-5-(4,4,5,5-tetramethyl-1,3,2-dioxaborolan-2-yl)-2H-indazole |

TABLE 7-continued

| Compound | Compound name | MS: [M + H]+ m/z | Procedure |
|---|---|---|---|
| | tert-Butyl ((1R,2R,4S)-7-(3-(4-chloro-2-methyl-2H-indazol-5-yl)-5-methyl-4-oxo-1-(tetrahydro-2H-pyran-2-yl)-4,5-dihydro-1H-pyrazolo[3,4-d]pyrimidin-6-yl)-7-azabicyclo[2.2.1]heptan-2-yl)(methyl)carbamate | 623, 625 | Prepared as general procedure 3 above using tert-butyl ((1R,2R,4S)-7-(3-bromo-5-methyl-4-oxo-1-(tetrahydro-2H-pyran-2-yl)-4,5-dihydro-1H-pyrazolo[3,4-d]pyrimidin-6-yl)-7-azabicyclo[2.2.1]heptan-2-yl)(methyl)carbamate and 4-chloro-2-methyl-5-(4,4,5,5-tetramethyl-1,3,2-dioxaborolan-2-yl)-2H-indazole |
| | tert-Butyl ((1R,2R,4S)-7-(3-(3-chloro-4-fluoro-2-methyl-2H-indazol-5-yl)-5-methyl-4-oxo-1-(tetrahydro-2H-pyran-2-yl)-4,5-dihydro-1H-pyrazolo[3,4-d]pyrimidin-6-yl)-7-azabicyclo[2.2.1]heptan-2-yl)(methyl)carbamate | 642, 644 | Prepared as general procedure 3 above using tert-butyl ((1R,2R,4S)-7-(3-bromo-5-methyl-4-oxo-1-(tetra-hydro-2H-pyran-2-yl)-4,5-dihydro-1H-pyrazolo[3,4-d]pyrimidin-6-yl)-7-azabicyclo[2.2.1]heptan-2-yl)(methyl)carbamate and 3-chloro-4-fluoro-2-methyl-5-(4,4,5,5-tetramethyl-1,3,2-dioxaborolan-2-yl)-2H-indazole |
| | tert-Butyl 9-(3-(7-chlorobenzo[d]thiazol-6-yl)-5-methyl-4-oxo-1-(tetrahydro-2H-pyran-2-yl)-4,5-dihydro-1H-pyrazolo[3,4-d]pyrimidin-6-yl)-3,9-diazabicyclo[3.3.1]nonane-3-carboxylate | 626, 628 | Prepared as general procedure 3 above using tert-butyl 9-(3-bromo-5-methyl-4-oxo-1-(tetrahydro-2H-pyran-2-yl)-4,5-dihydro-1H-pyrazolo[3,4-d]pyrimidin-6-yl)-3,9-diazabicyclo[3.3.1]nonane-3-carboxylate and 7-chloro-6-(4,4,5,5-tetramethyl-1,3,2-dioxaborolan-2-yl)benzo[d]thiazole |
| | tert-Butyl ((1R,2R,4S)-7-(3-(7-chlorobenzo[d]thiazol-6-yl)-5-methyl-4-oxo-1-(tetrahydro-2H-pyran-2-yl)-4,5-dihydro-1H-pyrazolo[3,4-d]pyrimidin-6-yl)-7-azabicyclo[2.2.1]heptan-2-yl)(methyl)carbamate | 626, 628 | Prepared as general procedure 3 above using tert-butyl ((1R,2R,4S)-7-(3-bromo-5-methyl-4-oxo-1-(tetrahydro-2H-pyran-2-yl)-4,5-dihydro-1H-pyrazolo[3,4-d]pyrimidin-6-yl)-7-azabicyclo[2.2.1]heptan-2-yl)(methyl)carbamate and 7-chloro-6-(4,4,5,5-tetra-methyl-1,3,2-dioxaborolan-2-yl)benzo[d]thiazole |

TABLE 7-continued

| Compound | Compound name | MS: [M + H]+ m/z | Procedure |
|---|---|---|---|
| (structure) | tert-Butyl ((1R,2R,4S)-7-(3-(7-chloro-2-methylbenzo[d]thiazol-6-yl)-5-methyl-4-oxo-1-(tetrahydro-2H-pyran-2-yl)-4,5-dihydro-1H-pyrazolo[3,4-d]pyrimidin-6-yl)-7-azabicyclo[2.2.1]heptan-2-yl)(methyl)carbamate | 640, 642 | Prepared as general procedure 3 above using tert-butyl ((1R,2R,4S)-7-(3-bromo-5-methyl-4-oxo-1-(tetrahydro-2H-pyran-2-yl)-4,5-dihydro-1H-pyrazolo[3,4-d]pyrimidin-6-yl)-7-azabicyclo[2.2.1]heptan-2-yl)(methyl)carbamate and 7-chloro-2-methyl-6-(4,4,5,5-tetramethyl-1,3,2-dioxaborolan-2-yl)benzo[d]thiazole |
| (structure) | rac-tert-Butyl ((1S,4S,7S)-2-(3-(4-chloro-2-ethyl-2H-indazol-5-yl)-5-methyl-4-oxo-1-(tetrahydro-2H-pyran-2-yl)-4,5-dihydro-1H-pyrazolo[3,4-d]pyrimidin-6-yl)-2-azabicyclo[2.2.1]heptan-7-yl)carbamate | 623, 625 | Prepared as general procedure 3 above using rac-tert-butyl ((1S,4S,7S)-2-(3-bromo-5-methyl-4-oxo-1-(tetrahydro-2H-pyran-2-yl)-4,5-dihydro-1H-pyrazolo[3,4-d]pyrimidin-6-yl)-2-azabicyclo[2.2.1]heptan-7-yl)carbamate and 4-chloro-2-ethyl-5-(4,4,5,5-tetramethyl-1,3,2-dioxaborolan-2-yl)-2H-indazole |
| (structure) | rac-tert-Butyl ((1S,4S,7S)-2-(3-(3,4-dichloro-2-methyl-2H-indazol-5-yl)-5-methyl-4-oxo-1-(tetrahydro-2H-pyran-2-yl)-4,5-dihydro-1H-pyrazolo[3,4-d]pyrimidin-6-yl)-2-azabicyclo[2.2.1]heptan-7-yl)carbamate | 643, 645 | Prepared as general procedure 3 above using rac-tert-butyl ((1S,4S,7S)-2-(3-bromo-5-methyl-4-oxo-1-(tetrahydro-2H-pyran-2-yl)-4,5-dihydro-1H-pyrazolo[3,4-d]pyrimidin-6-yl)-2-azabicyclo[2.2.1]heptan-7-yl)carbamate and 3,4-dichloro-2-methyl-5-(4,4,5,5-tetramethyl-1,3,2-dioxaborolan-2-yl)-2H-indazole |
| (structure) | rac-tert-Butyl ((1S,4S,7S)-2-(3-(7-chlorobenzo[d]thiazol-6-yl)-5-methyl-4-oxo-1-((2-(trimethylsilyl)ethoxy)methyl)-4,5-dihydro-1H-pyrazolo[3,4-d]pyrimidin-6-yl)-2-azabicyclo[2.2.1]heptan-7-yl)carbamate | 612, 614 | Prepared as general procedure 3 above using rac-tert-butyl ((1S,4S,7S)-2-(3-bromo-5-methyl-4-oxo-1-(tetrahydro-2H-pyran-2-yl)-4,5-dihydro-1H-pyrazolo[3,4-d]pyrimidin-6-yl)-2-azabicyclo[2.2.1]heptan-7-yl)carbamate and 7-chloro-6-(4,4,5,5-tetramethyl-1,3,2-dioxaborolan-2-yl)benzo[d]thiazole |

211

Preparation 115: tert-Butyl ((1R,2R,4S)-7-(3-(3,4-dichloro-2-ethyl-2H-indazol-5-yl)-5-methyl-4-oxo-1-(tetrahydro-2H-pyran-2-yl)-4,5-dihydro-1H-pyrazolo[3,4-d]pyrimidin-6-yl)-7-azabicyclo[2.2.1]heptan-2-yl)carbamate

[Chem. 152]

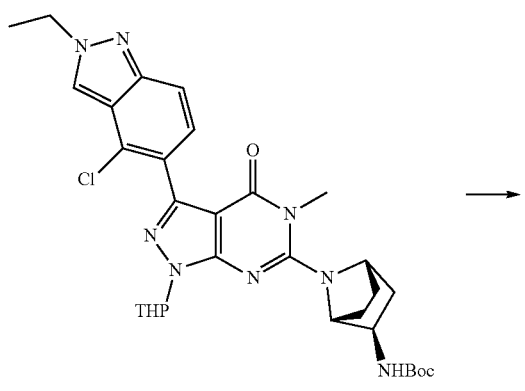

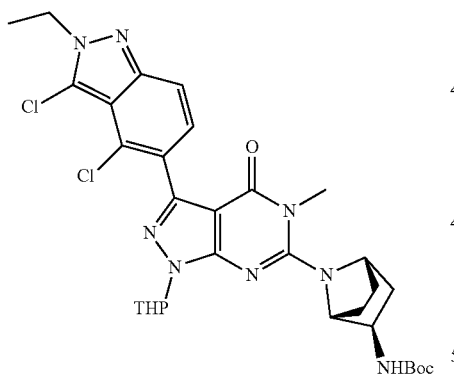

To a solution of tert-butyl ((1R,2R,4S)-7-(3-(4-chloro-2-ethyl-2H-indazol-5-yl)-5-methyl-4-oxo-1-(tetrahydro-2H-pyran-2-yl)-4,5-dihydro-1H-pyrazolo[3,4-d]pyrimidin-6-yl)-7-azabicyclo[2.2.1]heptan-2-yl)carbamate (140 mg, 0.225 mmol) in DMF (1.4 mL) was added NCS (36 mg, 0.270 mmol) at RT. The mixture was stirred at 60° C. for 5 h. The reaction mixture was cooled to RT and treated with NCS (15 mg, 0.112 mmol) at RT. The mixture was stirred at 60° C. for 1 h, diluted with water, and extracted with EtOAc. The organic layer was washed with water (×3) and brine, dried over anhydrous Na$_2$SO$_4$, filtered, and concentrated in vacuo. The residue was purified by column chromatography on silica gel (gradient elution, 50-80% EtOAc/hexane) to give the title compound (81 mg). MS: [M+H]$^+$=657, 659.

212

Preparation 116: tert-Butyl ((1R,2R,4S)-7-(3-(3,4-dichloro-2-ethyl-2H-indazol-5-yl)-5-methyl-4-oxo-1-(tetrahydro-2H-pyran-2-yl)-4,5-dihydro-1H-pyrazolo[3,4-d]pyrimidin-6-yl)-7-azabicyclo[2.2.1]heptan-2-yl)(methyl)carbamate

[Chem. 153]

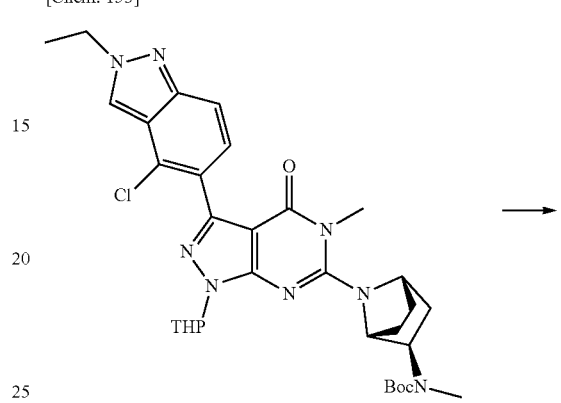

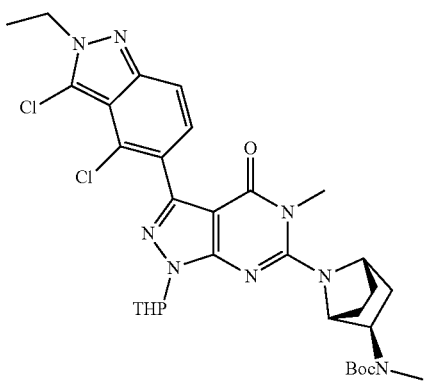

To a solution of tert-butyl ((1R,2R,4S)-7-(3-(4-chloro-2-ethyl-2H-indazol-5-yl)-5-methyl-4-oxo-1-(tetrahydro-2H-pyran-2-yl)-4,5-dihydro-1H-pyrazolo[3,4-d]pyrimidin-6-yl)-7-azabicyclo[2.2.1]heptan-2-yl)(methyl)carbamate (177 mg, 0.278 mmol) in DMF (1.4 mL) was added NCS (55.6 mg, 0.417 mmol) at RT. The mixture was stirred at 60° C. for 30 min, diluted with water, and extracted with EtOAc. The organic layer was washed with water (×3) and brine, dried over anhydrous Na$_2$SO$_4$, filtered, and concentrated in vacuo. The residue was purified by column chromatography on silica gel (gradient elution, 40-80% EtOAc/hexane) to give the title compound (115 mg). MS: [M+H]$^+$=671, 673.

General Procedure 4: tert-Butyl N-[endo-8-[3-(4-chloro-2-methyl-2H-indazol-5-yl)-2-[(4-methoxyphenyl)methyl]-5-methyl-4-oxo-2H,4H,5H-pyrazolo[3,4-d]pyrimidin-6-yl]-8-azabicyclo[3.2.1]octan-3-yl]carbamate

[Chem. 154]

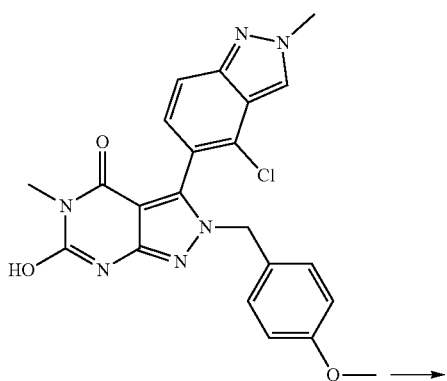

→

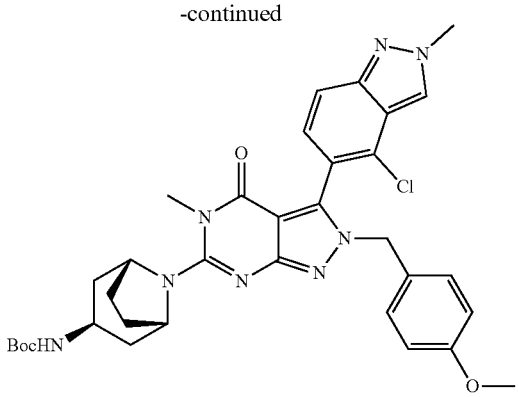

-continued

DBU (0.0677 mL, 0.45 mmol) was added dropwise at ambient temperature to 3-(4-chloro-2-methyl-2H-indazol-5-yl)-6-hydroxy-2-[(4-methoxyphenyl)methyl]-5-methyl-2H,4H,5H-pyrazolo[3,4-d]pyrimidin-4-one (135 mg, 0.3 mmol) and PyBOP (172 mg, 0.33 mmol) in DMF (2.5 mL). The mixture was stirred for 10 minutes, then treated with tert-butyl N-(endo-8-azabicyclo[3.2.1]octan-3-yl)carbamate (102 mg, 0.45 mmol). The mixture was left to stirring overnight for 20 hours—some starting material remaining. The mixture was treated with water (40 mL). The fine precipitate was then extracted into EtOAc (50 mL), then the organic layer was washed with water (2×20 mL), dried ($Na_2SO_4$) and evaporated in vacuo. The crude product was purified by chromatography on silica gel (12 g cartridge, 0-100% EtOAc/isohexane) to afford the title compound (128 mg, 0.19 mmol, 65% yield) as a clear colourless glass. MS: $[M+H]^+=659$.

Compounds of Table 8 below were prepared using procedures analogous to that described in general Procedure 4, starting from the appropriate substituted protected pyrazolopyrimidinone and varying the amine (synthesised as described above with any significant variations indicated below).

TABLE 8

| Compound | Compound Name | MS: $[M + H]^+$ m/z | Procedure |
|---|---|---|---|
| | tert-Butyl 8-[3-(4-chloro-2-methyl-2H-indazol-5-yl)-2-[(4-methoxyphenyl)methyl]-5-methyl-4-oxo-2H,4H,5H-pyrazolo[3,4-d]pyrimidin-6-yl]-3,8-diazabicyclo[3.2.1]octane-3-carboxylate | 645 | Prepared as general procedure 4 using 3-(4-chloro-2-methyl-2H-indazol-5-yl)-6-hydroxy-2-[(4-methoxyphenyl)methyl]-5-methyl-2H,4H,5H-pyrazolo[3,4-d]pyrimidin-4-one and tert-butyl 3,8-diazabicyclo[3.2.1]octane-3-carboxylate, stirring for 48 h. |

TABLE 8-continued

| Compound | Compound Name | MS: [M + H]+ m/z | Procedure |
|---|---|---|---|
| (structure) | N-[(1R,3S)-8-[3-(4-Chloro-2-methyl-2H-indazol-5-yl)-2-[(4-methoxyphenyl)methyl]-5-methyl-4-oxo-2H,4H,5H-pyrazolo[3,4-d]pyrimidin-6-yl]-3-hydroxy-8-azaspiro[4.5]decan-1-yl]-2-methylpropane-2-sulfinamide | 707 | Prepared as general procedure 4 using 3-(4-chloro-2-methyl-2H-indazol-5-yl)-6-hydroxy-2-[(4-methoxyphenyl)methyl]-5-methyl-2H,4H,5H-pyrazolo[3,4-d]pyrimidin-4-one and N-((1R,3S)-3-hydroxy-8-azaspiro[4.5]decan-1-yl)-2-methylpropane-2-sulfinamide, stirring for 24 h at room temperature, 24 h at 40° C. and 24 h at 50° C. |
| (structure) | 6-[(4S)-4-Amino-2-oxa-8-azaspiro[4.5]decan-8-yl]-3-(4-chloro-2-methyl-2H-indazol-5-yl)-2-[(4-methoxyphenyl)methyl]-5-methyl-2H,4H,5H-pyrazolo[3,4-d]pyrimidin-4-one | 589 | Prepared as general procedure 4 from 3-(4-chloro-2-methyl-2H-indazol-5-yl)-6-hydroxy-2-[(4-methoxyphenyl)methyl]-5-methyl-2H,4H,5H-pyrazolo[3,4-d]pyrimidin-4-one and (S)-2-oxa-8-azaspiro[4.5]decan-4-amine dihydrochloride using 3.5 eq. of DBU and stirring for 2 h. |
| (structure) | tert-Butyl N-[exo-8-[3-(4-chloro-2-methyl-2H-indazol-5-yl)-2-[(4-methoxyphenyl)methyl]-5-methyl-4-oxo-2H,4H,5H-pyrazolo[3,4-d]pyrimidin-6-yl]-8-azabicyclo[3.2.1]octan-3-yl]carbamate | 659 | Prepared as general procedure 4 using 3-(4-chloro-2-methyl-2H-indazol-5-yl)-6-hydroxy-2-[(4-methoxyphenyl)methyl]-5-methyl-2H,4H,5H-pyrazolo[3,4-d]pyrimidin-4-one and tert-butyl N-(exo-8-azabicyclo[3.2.1]octan-3-yl)carbamate. |

TABLE 8-continued

| Compound | Compound Name | MS: [M + H]+ m/z | Procedure |
|---|---|---|---|
| (structure) | tert-Butyl 7-[3-(4-chloro-2-methyl-2H-indazol-5-yl)-2-[(4-methoxyphenyl)methyl]-5-methyl-4-oxo-2H,4H,5H-pyrazolo[3,4-d]pyrimidin-6-yl]-2,7-diazaspiro[3.5]nonane-2-carboxylate | 659 | Prepared as general procedure 4 using 3-(4-chloro-2-methyl-2H-indazol-5-yl)-6-hydroxy-2-[(4-methoxyphenyl)methyl]-5-methyl-2H,4H,5H-pyrazolo[3,4-d]pyrimidin-4-one and tert-butyl 2,7-diazaspiro[3.5]nonane-2-carboxylate, stirring for 48 h. |
| (structure) | 6-[(1R)-1-Amino-8-azaspiro[4.5]decan-8-yl]-3-(4-chloro-2-methyl-2H-indazol-5-yl)-2-[(4-methoxyphenyl)methyl]-5-methyl-2H,4H,5H-pyrazolo[3,4-d]pyrimidin-4-one | 587 | Prepared as general procedure 4 from 3-(4-chloro-2-methyl-2H-indazol-5-yl)-6-hydroxy-2-[(4-methoxyphenyl)methyl]-5-methyl-2H,4H,5H-pyrazolo[3,4-d]pyrimidin-4-one and (R)-8-azaspiro[4.5]decan-1-amine dihydrochloride using 3.5 eq. DBU. |
| (structure) | 6-[(3S,4S)-4-Amino-3-methyl-2-oxa-8-azaspiro[4.5]decan-8-yl]-3-(4-chloro-2-methyl-2H-indazol-5-yl)-2-[(4-methoxyphenyl)methyl]-5-methyl-2H,4H,5H-pyrazolo[3,4-d]pyrimidin-4-one | 603 | Prepared as general procedure 4 from 3-(4-chloro-2-methyl-2H-indazol-5-yl)-6-hydroxy-2-[(4-methoxyphenyl)methyl]-5-methyl-2H,4H,5H-pyrazolo[3,4-d]pyrimidin-4-one and (3S,4S)-3-methyl-2-oxa-8-azaspiro[4.5]decan-4-amine dihydrochloride using 4.5 eq. DBU. |

TABLE 8-continued

| Compound | Compound Name | MS: [M + H]+ m/z | Procedure |
|---|---|---|---|
| | 6-[(1R,3R)-1-Amino-3-fluoro-8-azaspiro[4.5]decan-8-yl]-3-(4-chloro-2-methyl-2H-indazol-5-yl)-2-[(4-methoxyphenyl)methyl]-5-methyl-2H,4H,5H-pyrazolo[3,4-d]pyrimidin-4-one | 605 | Prepared as general procedure 4 from 3-(4-chloro-2-methyl-2H-indazol-5-yl)-6-hydroxy-2-[(4-methoxyphenyl)methyl]-5-methyl-2H,4H,5H-pyrazolo[3,4-d]pyrimidin-4-one and (1R,3R)-3-fluoro-8-azaspiro[4.5]decan-1-amine dihydrochloride using 4.5 eq. DBU. |
| | tert-Butyl 7-[3-(4-chloro-2-methyl-2H-indazol-5-yl)-2-[(4-methoxyphenyl)methyl]-5-methyl-4-oxo-2H,4H,5H-pyrazolo[3,4-d]pyrimidin-6-yl]-3-oxa-7,9-diazabicyclo[3.3.1]nonane-9-carboxylate | 661 | Prepared as general procedure 4 from 3-(4-chloro-2-methyl-2H-indazol-5-yl)-6-hydroxy-2-[(4-methoxyphenyl)methyl]-5-methyl-2H,4H,5H-pyrazolo[3,4-d]pyrimidin-4-one and tert-butyl 3-oxa-7,9-diazabicyclo[3.3.1]nonane-9-carboxylate. |
| | tert-Butyl 7-[3-(3,4-dichloro-2-methyl-2H-indazol-5-yl)-2-[(4-methoxyphenyl)methyl]-5-methyl-4-oxo-2H,4H,5H-pyrazolo[3,4-d]pyrimidin-6-yl]-3-oxa-7,9-diazabicyclo[3.3.1]nonane-9-carboxylate | 695 | Prepared as general procedure 4 from 3-(3,4-dichloro-2-methyl-2H-indazol-5-yl)-6-hydroxy-2-[(4-methoxyphenyl)methyl]-5-methyl-2H,4H,5H-pyrazolo[3,4-d]pyrimidin-4-one and tert-butyl 3-oxa-7,9-diazabicyclo[3.3.1]nonane-9-carboxylate. |

TABLE 8-continued

| Compound | Compound Name | MS: [M + H]+ m/z | Procedure |
|---|---|---|---|
| | 6-[(3S,4S)-4-Amino-3-methyl-2-oxa-8-azaspiro[4.5]decan-8-yl]-3-(3,4-dichloro-2-methyl-2H-indazol-5-yl)-2-[(4-methoxyphenyl)methyl]-5-methyl-2H,4H,5H-pyrazolo[3,4-d]pyrimidin-4-one | 637 | Prepared as general procedure 4 from 3-(3,4-dichloro-2-methyl-2H-indazol-5-yl)-6-hydroxy-2-[(4-methoxyphenyl)methyl]-5-methyl-2H,4H,5H-pyrazolo[3,4-d]pyrimidin-4-one and (3S,4S)-3-methyl-2-oxa-8-azaspiro[4.5]decan-4-amine dihydrochloride using 4.5 eq. DBU. |
| | 6-[(3S,4S)-4-Amino-3-methyl-2-oxa-8-azaspiro[4.5]decan-8-yl]-3-(4-chloro-2-ethyl-2H-indazol-5-yl)-2-[(4-methoxyphenyl)methyl]-5-methyl-2H,4H,5H-pyrazolo[3,4-d]pyrimidin-4-one | 617 | Prepared as general procedure 4 from 3-(4-chloro-2-ethyl-2H-indazol-5-yl)-6-hydroxy-2-[(4-methoxyphenyl)methyl]-5-methyl-2H,4H,5H-pyrazolo[3,4-d]pyrimidin-4-one and (3S,4S)-3-methyl-2-oxa-8-azaspiro[4.5]decan-4-amine dihydrochloride using 4.5 eq. DBU. |

General Procedure 5: 2-[(3S,4S)-4-Amino-3-methyl-2-oxa-8-azaspiro[4.5]decan-8-yl]-5-(4-chloro-2-ethyl-2H-indazol-5-yl)-3-methyl-7-{[2-(trimethylsilyl)ethoxy]methyl}-3H,4H,7H-pyrrolo[2,3-d]pyrimidin-4-one

[Chem. 155]

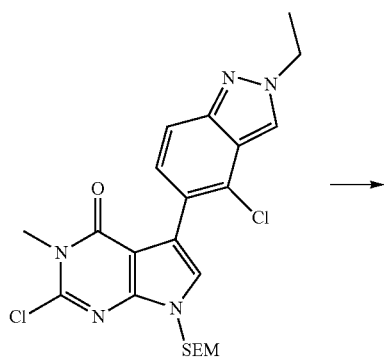

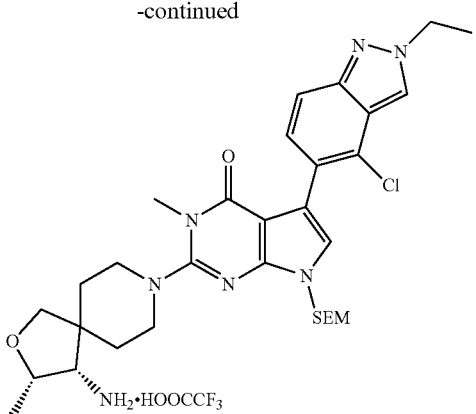

A mixture of 2-chloro-5-(4-chloro-2-ethyl-2H-indazol-5-yl)-3-methyl-7-{[2-(trimethylsilyl)ethoxy]methyl}-3H,4H,7H-pyrrolo[2,3-d]pyrimidin-4-one (250 mg, 0.51 mmol), (3S,4S)-3-methyl-2-oxa-8-azaspiro[4.5]decan-4-amine dihydrochloride (148 mg, 0.61 mmol) and triethylamine (0.21 mL, 1.52 mmol) in NMP (1 mL) was heated to 100° C. for 2 h. Cooled to ambient temperature and partitioned between EtOAc and water, phases separated and aq. phase extracted with EtOAc. Combined organic phases washed with 50% sat. brine, then brine, dried (MgSO₄+hydrophobic frit) and concentrated. The residue was purified by reverse phase chromatography on C18 silica, eluted with 5-100% MeCN/H₂O with 0.1% TFA added to afford the title compound as the TFA salt (256 mg, 0.346 mmol, 68%). ¹H NMR (400 MHz, DMSO-d₆) δ: 8.48 (1H, s), 7.98 (3H, s), 7.54 (1H, dd), 7.31 (1H, d), 7.25 (1H, s), 5.48 (2H, s), 4.50 (2H, q), 4.29-4.18 (1H, m), 3.70-3.66 (1H, m), 3.62 (2H, t), 3.53-3.33 (7H, m), 3.03-2.73 (2H, m), 1.98-1.86 (2H, m), 1.82-1.77 (1H, m), 1.66 (1H, d), 1.53 (3H, t), 1.24 (3H, d), 0.93-0.82 (2H, m), 0.02-0.08 (9H, m). MS: [M+H]⁺=626.

Compounds of Table 9 below were prepared using procedures analogous to that described in general Procedure 5, starting from the appropriate substituted protected pyrrolopyrimidinone and varying the amine (synthesised as described above with any significant variations indicated below).

TABLE 9

| Compound | Compound Name | MS: [M + H]⁺ m/z | Procedure |
|---|---|---|---|
|  | tert-Butyl 4-[5-(4-chloro-2-ethyl-2H-indazol-5-yl)-3-methyl-4-oxo-7-{[2-(trimethylsilyl)ethoxy]methyl}-3H,4H,7H-pyrrolo[2,3-d]pyrimidin-2-yl]-1,4-diazepane-1-carboxylate | 656 | Prepared as general procedure 5 using 2-chloro-5-(4-chloro-2-ethyl-2H-indazol-5-yl)-3-methyl-7-{[2-(trimethylsilyl)ethoxy]methyl}-3H,4H,7H-pyrrolo[2,3-d]pyrimidin-4-one and tert-butyl 1,4-diazepane-1-carboxylate, purified by normal phase chromatography on silica gel. |
|  | tert-Butyl N-{1-[5-(4-chloro-2-ethyl-2H-indazol-5-yl)-3-methyl-4-oxo-7-{[2-(trimethylsilyl)ethoxy]methyl}-3H,4H,7H-pyrrolo[2,3-d]pyrimidin-2-yl]azepan-4-yl}carbamate | 670 | Prepared as general procedure 5 using 2-chloro-5-(4-chloro-2-ethyl-2H-indazol-5-yl)-3-methyl-7-{[2-(trimethylsilyl)ethoxy]methyl}-3H,4H,7H-pyrrolo[2,3-d]pyrimidin-4-one and tert-butyl N-(azepan-4-yl)carbamate, purified by normal phase chromatography on silica gel. |
|  | rac-tert-Butyl N-[(1R,2R,5R)-8-[5-(4-chloro-2-methyl-2H-indazol-5-yl)-3-methyl-4-oxo-7-{[2-(trimethylsilyl)ethoxy]methyl}-3H,4H,7H-pyrrolo[2,3-d]pyrimidin-2-yl]-8-azabicyclo[3.2.1]octan-2-yl]carbamate | 668 | Prepared as general procedure 5 from 2-chloro-5-(4-chloro-2-methyl-2H-indazol-5-yl)-3-methyl-7-{[(trimethylsilyl)ethoxy]methyl}-3H,4H,7H-pyrrolo[2,3-d]pyrimidin-4-one and rac-tert-butyl N-[(1R,2R,5S)-8-azabicyclo[3.2.1]octan-2-yl]carbamate using DIPEA and heating for 16 h. The crude product was purified by normal phase chromatography on silica gel. |

TABLE 9-continued

| Compound | Compound Name | MS: [M + H]+ m/z | Procedure |
|---|---|---|---|
| 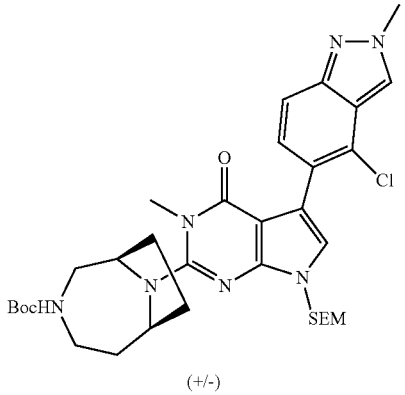 (+/-) | rac-tert-Butyl (1R,6S)-9-[5-(4-chloro-2-methyl-2H-indazol-5-yl)-3-methyl-4-oxo-7-{[2-(trimethylsilyl)ethoxy]methyl}-3H,4H,7H-pyrrolo[2,3-d]pyrimidin-2-yl]-3,9-diazabicyclo[4.2.1]nonane-3-carboxylate | 668 | Prepared as general procedure 5 from 2-chloro-5-(4-chloro-2-methyl-2H-indazol-5-yl)-3-methyl-7-{[(trimethylsilyl)methoxy]methyl}-3H,4H,7H-pyrrolo[2,3-d]pyrimidin-4-one and rac-tert-butyl (1R,6S)-3,9-diazabicyclo[4.2.1]nonane-3-carboxylate using DIPEA and heating for 16 h. The crude product was purified by normal phase chromatography on silica gel. |

General Procedures for Preparations of Compounds of Formula (I)

The following procedures are illustrative for general methods used in the preparation of Examples 1-135 listed in Table 10 below.

Method 1: 2-(3,8-Diazabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one

[Chem. 156]

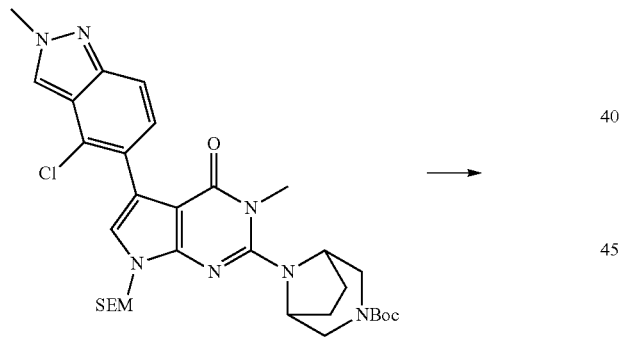

To a solution of tert-butyl 8-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-3,8-diazabicyclo[3.2.1]octane-3-carboxylate (140 mg, 0.214 mmol) in CHCl₃ (2 mL) was added TFA (2 mL) at RT. The mixture was stirred at RT for 3 h, and concentrated in vacuo. The residue was dissolved in MeOH (4 mL). 4 M NaOH (1 mL) was added at RT. The mixture was stirred at RT for 1 h, poured into water, and extracted with CHCl₃—MeOH. The organic layer was dried over anhydrous Na₂SO₄, filtered, and concentrated in vacuo. The residue was purified by column chromatography on NH silica gel (gradient elution, 0-10% MeOH/CHCl₃). The fraction was concentrated in vacuo, and purified by r-HPLC. The fraction was basified with sat. NaHCO₃, and extracted with CHCl₃—MeOH. The organic layer was dried over anhydrous Na₂SO₄, filtered, and concentrated in vacuo to give the title compound (24 mg).

Method 2: 5-(4-Chloro-2-ethyl-2H-indazol-5-yl)-3-methyl-2-((1R,2R,4S)-2-(methylamino)-7-azabicyclo[2.2.1]heptan-7-yl)-3,7-dihydro-4H-pyrrolo[2,3-d]pyrimidin-4-one

[Chem. 157]

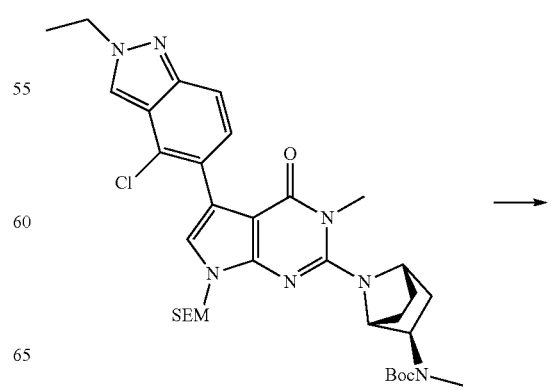

-continued

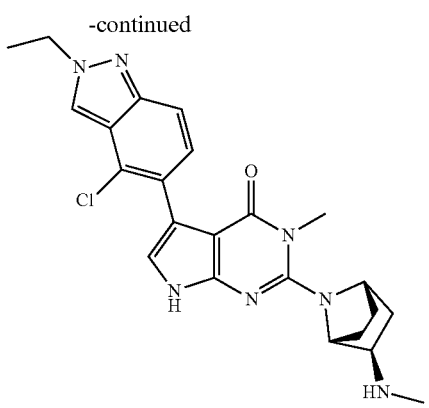

The mixture of tert-butyl ((1R,2R,4S)-7-(5-(4-chloro-2-ethyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)(methyl)carbamate (150 mg, 0.219 mmol) and TFA (3 mL) was stirred at RT for 2 h, and concentrated in vacuo. The residue was purified by column chromatography on NH silica gel (gradient elution, 0-15% MeOH/CHCl₃). The residue was dissolved in MeOH (3 mL). Ethylenediamine (0.2 mL, 2.99 mmol) was added at RT. The mixture was stirred at RT for 2 h, and concentrated in vacuo. After concentration, the residue was purified by r-HPLC. The obtained fractions were passed through Vari-Pure, and concentrated in vacuo. The obtained solid was suspended in EtOAc-hexane. The precipitate was collected and dried at 60° C. under reduced pressure to give the title compound (48 mg).

Method 3: 6-(3,9-Diazabicyclo[3.3.1]nonan-9-yl)-3-(3,4-dichloro-2-methyl-2H-indazol-5-yl)-5-methyl-1,5-dihydro-4H-pyrazolo[3,4-d]pyrimidin-4-one

[Chem. 158]

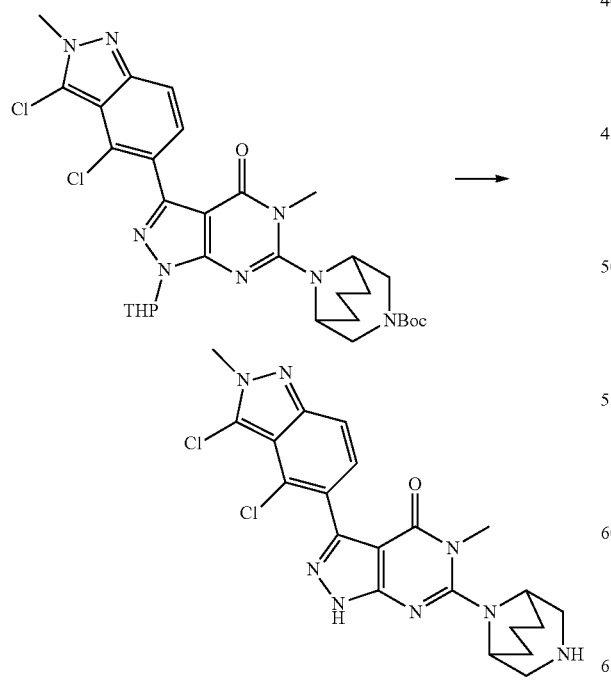

To a mixture of tert-butyl 9-(3-(3,4-dichloro-2-methyl-2H-indazol-5-yl)-5-methyl-4-oxo-1-(tetrahydro-2H-pyran-2-yl)-4,5-dihydro-1H-pyrazolo[3,4-d]pyrimidin-6-yl)-3,9-diazabicyclo[3.3.1]nonane-3-carboxylate (120 mg, 0.182 mmol) in MeOH (1 mL) was added 4 M HCl in 1,4-dioxane (2 mL, 8 mmol) at RT. The mixture was stirred at RT for 2 h, and concentrated in vacuo. The residue was purified by r-HPLC. The obtained fractions were passed through Vari-Pure, and concentrated in vacuo. The obtained solid was suspended in EtOAc-hexane. The precipitate was collected and dried at 60° C. under reduced pressure to give the title compound (38 mg).

Method 4: rac-2-((1S,2R,3R,5R)-3-Amino-2-fluoro-8-azabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one

[Chem. 159]

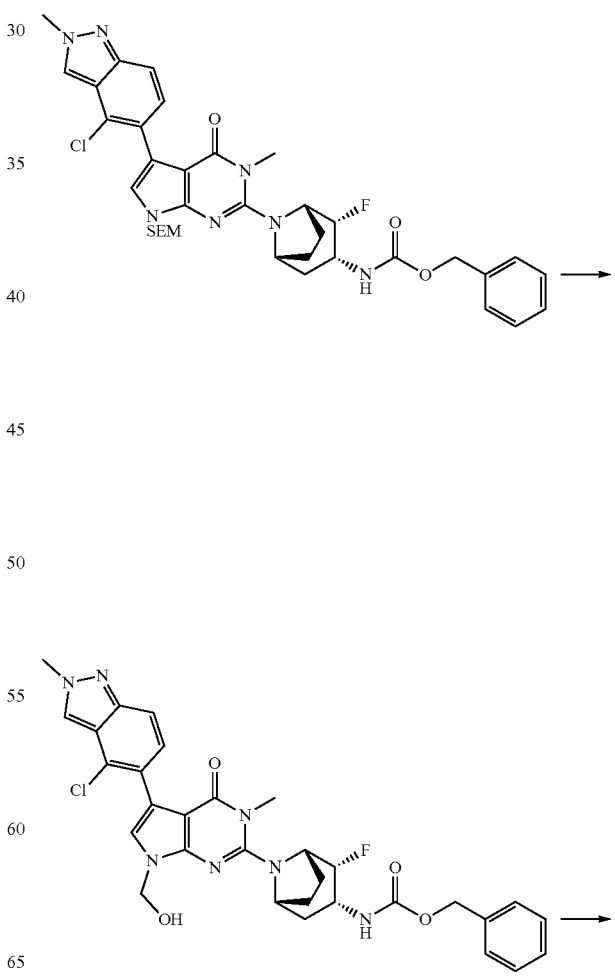

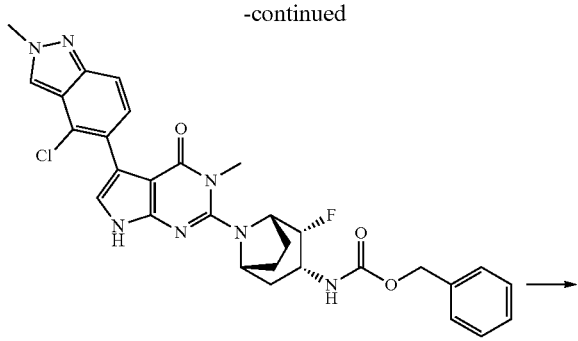

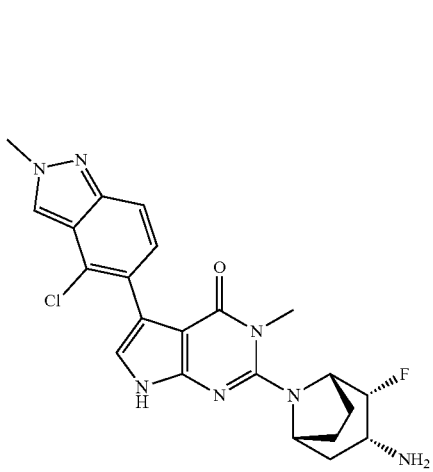

To a solution of rac-benzyl ((1S,2R,3R,5R)-8-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-2-fluoro-8-azabicyclo[3.2.1]octan-3-yl) carbamate (129 mg, 0.179 mmol) in CHCl₃ (0.5 mL) was added TFA (0.5 mL) at RT. The mixture was stirred at RT for 6 h, and concentrated in vacuo. The residue was purified by column chromatography on silica gel (gradient elution, 0-10% MeOH/CHCl₃). The fraction was concentrated in vacuo to give rac-benzyl ((1S,2R,3R,5R)-8-(5-(4-chloro-2-methyl-2H-indazol-5-yl)-7-(hydroxymethyl)-3-methyl-4-oxo-4,7-dihydro-3H-pyrrolo[2,3-d]pyrimidin-2-yl)-2-fluoro-8-azabicyclo[3.2.1]octan-3-yl)carbamate (106 mg, 0.17 mmol, 95% Yield).

The residue (106 mg, 0.17 mmol) was dissolved in MeOH (0.40 mL) and THF (0.40 mL). Ethylenediamine (0.2 mL, 2.99 mmol) was added at RT. The mixture was stirred at RT for 1 h, and concentrated in vacuo. The residue was purified by column chromatography on NH silica gel (gradient elution, 0-10% MeOH/CHCl₃). The fraction was concentrated in vacuo to give rac-benzyl ((1S,2R,3R,5R)-8-(5-(4-chloro-2-methyl-2H-indazol-5-yl)-3-methyl-4-oxo-4,7-dihydro-3H-pyrrolo[2,3-d]pyrimidin-2-yl)-2-fluoro-8-azabicyclo[3.2.1]octan-3-yl)carbamate (97 mg, 0.16 mmol, 96% Yield).

To the suspension of the residue (97 mg, 0.16 mmol), triethylsilane (0.42 mL, 2.6 mmol), triethylamine (0.073 mL, 0.52 mmol) in CH₂Cl₂ (2.0 mL) was added Palladium (II) acetate (18 mg, 0.082 mmol) at RT under N2 atmosphere and the suspension was stirred at RT for 2.5 h. The solid was removed by filteration using a pad of celite. The filterate was concentrated to give the crude oil-solid, which was purified by column chromatography on NH silica gel (gradient elution, 0-15% MeOH/CHCl₃) to give the crude solid-oil. The crude oil-solid was purified by r-HPLC. The obtained fractions were concentrated and almost concentrated residue was basified with 1 N NaOH and extracted with CHCl₃ to give the title compound (27 mg, 0.059 mmol, 36% Yield).

Method 5: 2-((1R,2S,3R,5S)-3-Amino-2-fluoro-8-azabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one

[Chem. 160]

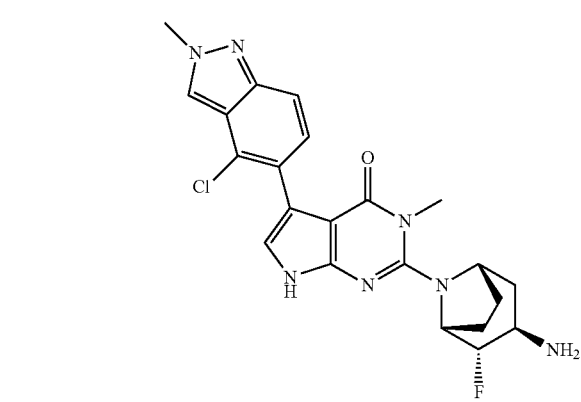

Benzyl ((1R,2S,3R,5S)-8-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-2-fluoro-8-azabicyclo[3.2.1]octan-3-yl)carbamate (61 mg, 0.085 mmol) was dissolved in methanesulfonic acid (1.0 mL) and stirred for 3 h at RT. The mixture was poured into saturated NaHCO₃ aq. at 0° C., and extracted with CHCl₃. The organic layer was concentrated in vacuo. The residue was dissolved in THF (1 mL). To the mixture was added 5 M NaOH aq. (0.085 mL, 0.43 mmol) at 0° C., and stirred for 1 h at RT. The mixture was evaporated in vacuo. The residue was purified by column chromatography on NH silica gel (gradient elution, 0-10% MeOH/CHCl₃) to give the title compound (35 mg).

TABLE 10

| Example | Structure | Name | NMR data | MS: [M + H]+ m/z | Method |
|---|---|---|---|---|---|
| 1 | 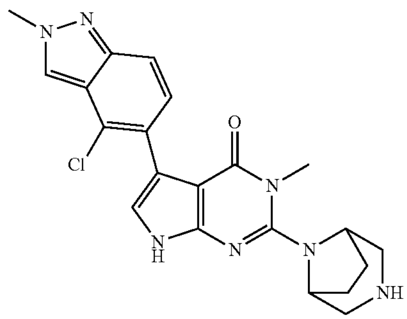 [SMILES: Cn1cc2c(Cl)c(-c3c[nH]c4nc(N5C6CCC5CNC6)n(C)c(=O)c34)ccc2n1] | 2-(3,8-diazabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one | ¹H-NMR (DMSO-d₆) δ: 11.64 (1H, br s), 8.40 (1H, s), 7.48 (1H, d, J = 8.8 Hz), 7.32 (1H, d, J = 8.8 Hz), 6.96 (1H, d, J = 2.2 Hz), 4.19 (3H, s), 3.98 (2H, br s), 3.46 (3H, s), 2.99-2.96 (2H, m), 2.66-2.63 (2H, m), 1.97-1.80 (4H, m). | 424, 426 | 1 |
| 2 | 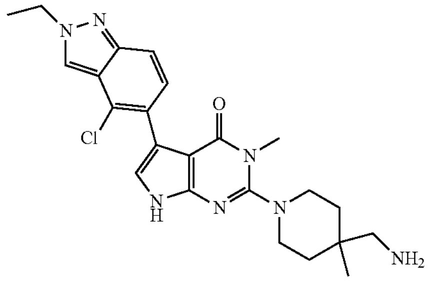 [SMILES: CCn1cc2c(Cl)c(-c3c[nH]c4nc(N5CCC(C)(CN)CC5)n(C)c(=O)c34)ccc2n1] | 2-(4-(aminomethyl)-4-methyl-piperidin-1-yl)-5-(4-chloro-2-ethyl-2H-indazol-5-yl)-3-methyl-3,7-dihydro-4H-pyrrolo[2,3-d]pyrimidin-4-one | ¹H-NMR (DMSO-d₆) δ: 8.52 (1H, s), 7.57 (1H, d, J = 8.8 Hz), 7.37 (1H, d, J = 8.8 Hz), 7.06 (1H, s), 4.54 (2H, q, J = 7.3 Hz), 3.43 (3H, s), 3.24-3.17 (2H, m), 3.08-2.99 (2H, m), 1.66-1.56 (5H, m), 1.46-1.39 (2H, m), 1.09 (2H, d, J = 6.1 Hz), 0.98 (3H, s). | 454, 456 | 2 |
| 3 | 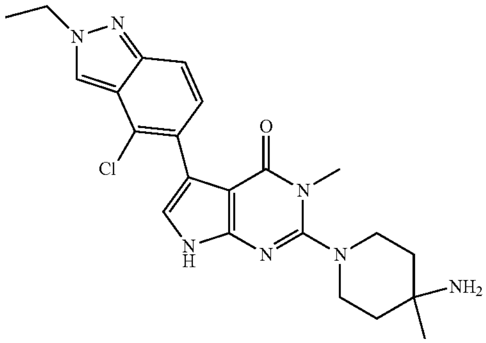 [SMILES: CCn1cc2c(Cl)c(-c3c[nH]c4nc(N5CCC(C)(N)CC5)n(C)c(=O)c34)ccc2n1] | 2-(4-amino-4-methyl-piperidin-1-yl)-5-(4-chloro-2-ethyl-2H-indazol-5-yl)-3-methyl-3,7-dihydro-4H-pyrrolo[2,3-d]pyrimidin-4-one | ¹H-NMR (DMSO-d₆) δ: 11.75 (1H, br s), 8.45 (1H, s), 7.50 (1H, d, J = 8.8 Hz), 7.31 (1H, d, J = 8.8 Hz), 7.00 (1H, s), 4.48 (2H, q, J = 7.3 Hz), 3.37 (3H, s), 3.21-3.16 (2H, m), 3.11-3.05 (2H, m), 1.63-1.43 (7H, m), 1.11 (3H, s). | 440, 442 | 2 |
| 4 | 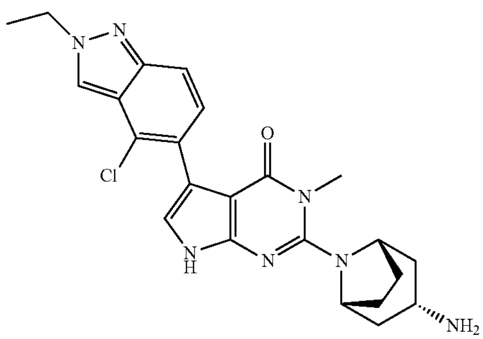 [SMILES: CCn1cc2c(Cl)c(-c3c[nH]c4nc(N5[C@@H]6CC[C@H]5C[C@H](N)C6)n(C)c(=O)c34)ccc2n1] | 2-(exo-3-amino-8-azabicyclo[3.2.1]octan-8-yl)-5-(4-chloro-2-ethyl-2H-indazol-5-yl)-3-methyl-3,7-dihydro-4H-pyrrolo[2,3-d]pyrimidin-4-one | ¹H-NMR (DMSO-d₆) δ: 11.64 (1H, br s), 8.45 (1H, s), 7.49 (1H, d, J = 8.9 Hz), 7.31 (1H, d, J = 8.9 Hz), 6.94 (1H, s), 4.48 (2H, q, J = 7.2 Hz), 4.11 (2H, br s), 3.43 (3H, s), 3.06-2.94 (1H, m), 2.04-1.92 (2H, m), 1.85-1.78 (2H, m), 1.71-1.63 (2H, m), 1.56-1.46 (6H, m). | 452, 454 | 1 |

TABLE 10-continued

| Example | Structure | Name | NMR data | MS: [M + H]⁺ m/z | Method |
|---|---|---|---|---|---|
| 5 | 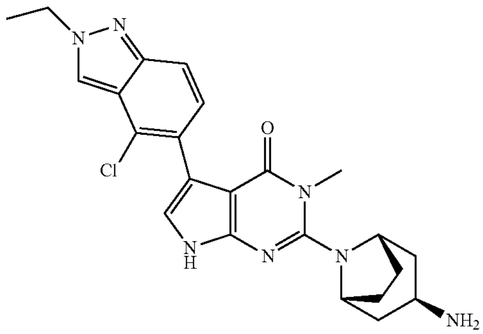 [SMILES: CCn1cc2c(Cl)c(-c3c[nH]c4nc(N5[C@@H]6CC[C@H]5C[C@@H](N)C6)n(C)c(=O)c34)ccc2n1] | 2-(endo-3-amino-8-azabicyclo[3.2.1]octan-8-yl)-5-(4-chloro-2-ethyl-2H-indazol-5-yl)-3-methyl-3,7-dihydro-4H-pyrrolo[2,3-d]pyrimidin-4-one | 1H-NMR (DMSO-d₆) δ: 11.61 (1H, br s), 8.44 (1H, s), 7.49 (1H, d, J = 8.8 Hz), 7.31 (1H, d, J = 8.8 Hz), 6.94 (1H, s), 4.48 (2H, q, J = 7.3 Hz), 4.12-4.05 (2H, m), 3.41 (3H, s), 2.27-2.22 (2H, m), 2.17-2.09 (2H, m), 2.00-1.92 (2H, m), 1.59-1.50 (7H, m). | 452, 454 | 1 |
| 6 | 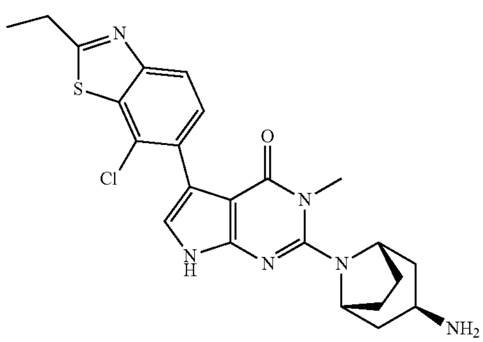 [SMILES: CCc1nc2ccc(-c3c[nH]c4nc(N5[C@@H]6CC[C@H]5C[C@@H](N)C6)n(C)c(=O)c34)c(Cl)c2s1] | 2-(endo-3-amino-8-azabicyclo[3.2.1]octan-8-yl)-5-(7-chloro-2-ethylbenzo[d]thiazol-6-yl)-3-methyl-3,7-dihydro-4H-pyrrolo[2,3-d]pyrimidin-4-one | ¹H-NMR (DMSO-d₆) δ: 11.67 (1H, s), 7.82 (1H, d, J = 8.4 Hz), 7.54 (1H, d, J = 8.4 Hz), 6.98 (1H, s), 4.06 (2H, br s), 3.38 (3H, s), 3.13 (2H, q, J = 7.6 Hz), 2.24-2.19 (2H, m), 2.13-2.08 (2H, m), 1.93-1.92 (3H, m), 1.56-1.52 (3H, m), 1.37 (3H, t, J = 7.6 Hz). | 469, 471 | 1 |
| 7 | 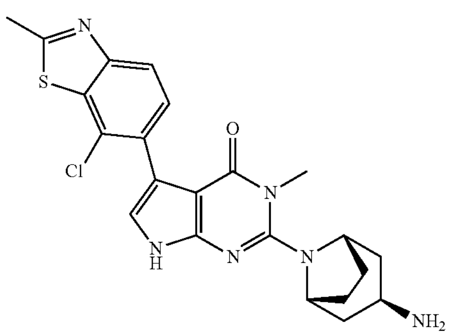 [SMILES: Cc1nc2ccc(-c3c[nH]c4nc(N5[C@@H]6CC[C@H]5C[C@@H](N)C6)n(C)c(=O)c34)c(Cl)c2s1] | 2-(endo-3-amino-8-azabicyclo[3.2.1]octan-8-yl)-5-(7-chloro-2-methylbenzo[d]thiazol-6-yl)-3-methyl-3,7-dihydro-4H-pyrrolo[2,3-d]pyrimidin-4-one | ¹H-NMR (DMSO-d₆) δ: 7.81 (1H, d, J = 8.2 Hz), 7.56 (1H, d, J = 8.4 Hz), 6.99 (1H, s), 4.16-4.03 (1H, m), 3.42-3.32 (5H, m), 2.82 (3H, s), 2.29-2.19 (1H, m), 2.18-2.07 (2H, m), 2.02-1.89 (2H, m), 1.65-1.50 (2H, m). | 455, 457 | 1 |
| 8 | 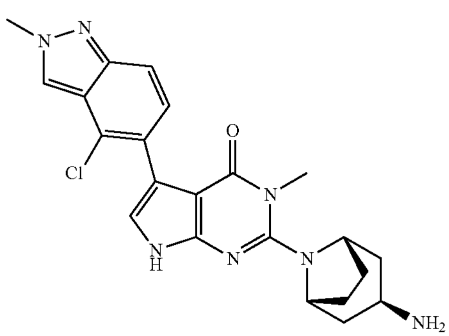 [SMILES: Cn1cc2c(Cl)c(-c3c[nH]c4nc(N5[C@@H]6CC[C@H]5C[C@@H](N)C6)n(C)c(=O)c34)ccc2n1] | 2-(endo-3-amino-8-azabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one | ¹H-NMR (DMSO-d₆) δ: 11.63 (1H, br s), 8.40 (1H, s), 7.49 (1H, d, J = 8.8 Hz), 7.32 (1H, d, J = 8.8 Hz), 6.96 (1H, s), 4.19 (3H, s), 4.08-4.00 (2H, br s), 3.41 (3H, s), 2.24-2.19 (2H, m), 2.15-2.06 (2H, m), 2.05-1.97 (3H, m), 1.61-1.55 (3H, m). | 438, 440 | 1 |

TABLE 10-continued

| Example | Structure | Name | NMR data | MS: [M + H]+ m/z | Method |
|---|---|---|---|---|---|
| 9 | 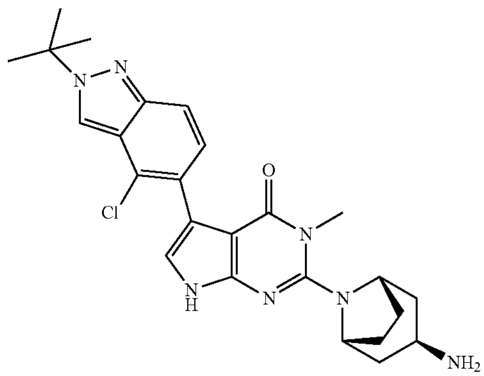 [SMILES: Cn1c(N2[C@@H]3CC[C@H]2C[C@@H](N)C3)nc2[nH]cc(-c3ccc4nn(C(C)(C)C)cc4c3Cl)c2c1=O] | 2-(endo-3-amino-8-azabicyclo[3.2.1]octan-8-yl)-5-(2-(tert-butyl)-4-chloro-2H-indazol-5-yl)-3-methyl-3,7-dihydro-4H-pyrrolo[2,3-d]pyrimidin-4-one | ¹H-NMR (CDCl₃) δ: 8.58 (1H, br s), 8.09 (1H, s), 7.64 (1H, d, J = 8.8 Hz), 7.45 (1H, d, J = 8.8 Hz), 6.89 (1H, br s), 4.09 (2H, br s), 3.54 (3H, s), 3.44 (1H, br s), 2.40-2.25 (2H, m), 2.20-2.06 (4H, m), 1.73 (9H, s), 1.62 (2H, br d, J = 13.9 Hz). | 480, 482 | 1 |
| 10 | 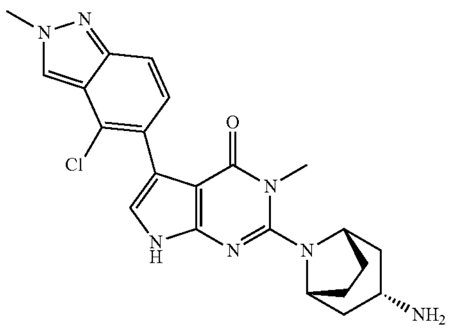 [SMILES: Cn1cc2c(Cl)c(-c3c[nH]c4nc(N5[C@@H]6CC[C@H]5C[C@H](N)C6)n(C)c(=O)c34)ccc2n1] | 2-(exo-3-amino-8-azabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one | 1H-NMR (DMSO-d₆) δ: 11.74-11.56 (1H, m), 8.38 (1H, s), 7.47 (1H, d, J = 8.7 Hz), 7.30 (1H, d, J = 8.8 Hz), 6.95 (1H, s), 4.23-4.15 (6H, m), 3.42 (3H, s), 2.09-1.64 (8H, m). | 438, 440 | 1 |
| 11 | 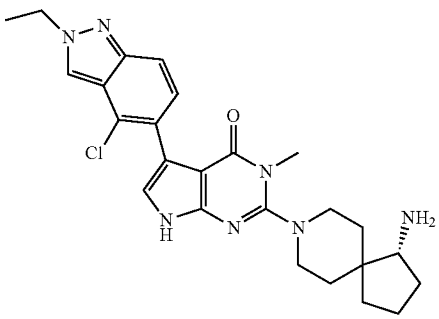 [SMILES: CCn1cc2c(Cl)c(-c3c[nH]c4nc(N5CCC6(CCC[C@H]6N)CC5)n(C)c(=O)c34)ccc2n1] | (R)-2-(1-amino-8-azaspiro[4.5]decan-8-yl)-5-(4-chloro-2-ethyl-2H-indazol-5-yl)-3-methyl-3,7-dihydro-4H-pyrrolo[2,3-d]pyrimidin-4-one | ¹H-NMR (DMSO-d₆) δ: 8.45 (1H, s), 7.50 (1H, d, J = 8.8 Hz), 7.31 (1H, d, J = 8.8 Hz), 7.01 (1H, s), 4.48 (2H, q, J = 7.2 Hz), 3.39 (3H, s), 3.35-3.27 (1H, m), 2.88-2.83 (2H, m), 2.73-2.71 (1H, m), 1.88-1.50 (10H, m), 1.39-1.15 (5H, m). | 480, 482 | 1 |
| 12 | 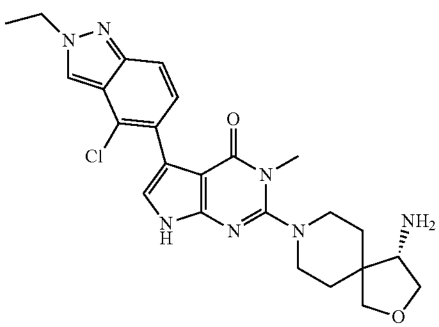 [SMILES: CCn1cc2c(Cl)c(-c3c[nH]c4nc(N5CCC6(CC5)COC[C@H]6N)n(C)c(=O)c34)ccc2n1] | (S)-2-(4-amino-2-oxa-8-azaspiro[4.5]decan-8-yl)-5-(4-chloro-2-ethyl-2H-indazol-5-yl)-3-methyl-3,7-dihydro-4H-pyrrolo[2,3-d]pyrimidin-4-one | ¹H-NMR (DMSO-d₆) δ: 11.77 (1H, br s), 8.45 (1H, s), 7.50 (1H, d, J = 9.0 Hz), 7.31 (1H, d, J = 9.0 Hz), 7.01 (1H, s), 4.48 (2H, q, J = 7.2 Hz), 3.97-3.93 (1H, m), 3.70-3.68 (1H, m), 3.60-3.58 (1H, m), 3.40 (3H, s), 3.32-3.24 (1H, m), 3.18-3.13 (1H, m), 3.09-3.06 (1H, m), 2.90-2.83 (2H, m), 1.84-1.69 (4H, m), 1.60-1.45 (5H, m). | 482, 484 | 1 |

TABLE 10-continued

| Example | Structure | Name | NMR data | MS: [M + H]⁺ m/z | Method |
|---|---|---|---|---|---|
| 13 | 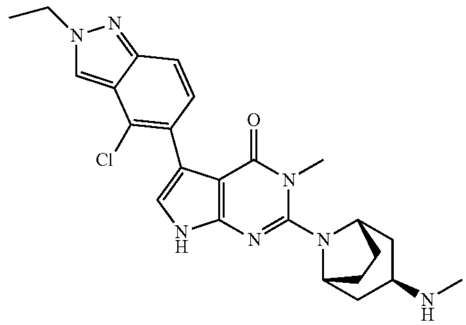 [SMILES: CCn1cc2c(Cl)c(-c3c[nH]c4nc(N5[C@@H]6CC[C@H]5C[C@@H](NC)C6)n(C)c(=O)c34)ccc2n1] | 5-(4-chloro-2-ethyl-2H-indazol-5-yl)-3-methyl-2-(endo-3-(methylamino)-8-azabicyclo[3.2.1]octan-8-yl)-3,7-dihydro-4H-pyrrolo[2,3-d]pyrimidin-4-one | ¹H-NMR (DMSO-d₆) δ: 11.61 (1H, br s), 8.44 (1H, s), 7.49 (1H, d, J = 8.8 Hz), 7.31 (1H, d, J = 8.8 Hz), 6.94 (1H, s), 4.48 (2H, q, J = 7.3 Hz), 4.07 (2H, br s), 3.42 (3H, s), 2.78-2.74 (1H, m), 2.29 (3H, s), 2.11-2.03 (4H, m), 1.93-1.92 (2H, m), 1.75-1.71 (2H, m), 1.52 (3H, t, J = 7.3 Hz). | 466, 468 | 1 |
| 14 | 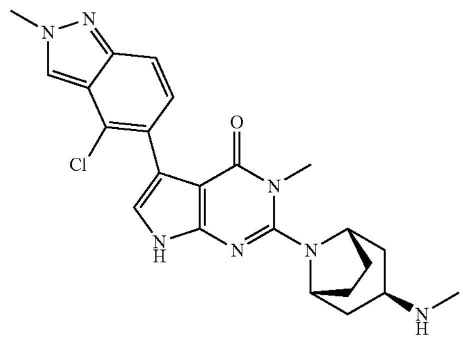 | 5-(4-chloro-2-methyl-2H-indazol-5-yl)-3-methyl-2-(endo-3-(methylamino)-8-azabicyclo[3.2.1]octan-8-yl)-3,7-dihydro-4H-pyrrolo[2,3-d]pyrimidin-4-one | ¹H-NMR (DMSO-d₆) δ: 11.61 (1H, br s), 8.40 (1H, s), 7.48 (1H, d, J = 4.9 Hz), 7.32 (1H, d, J = 9.2 Hz), 6.95 (1H, s), 4.19 (3H, s), 4.08 (2H, br s), 3.42 (3H, s), 2.82-2.80 (1H, m), 2.31 (3H, s), 2.14-2.03 (4H, m), 1.97-1.89 (2H, m), 1.77-1.70 (2H, m). | 452, 454 | 1 |
| 15 | 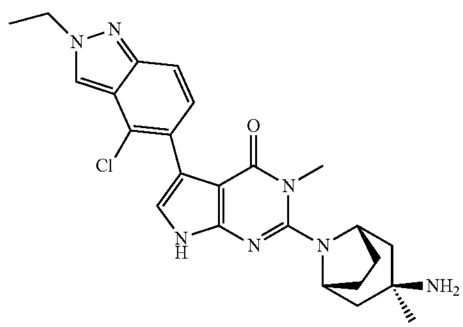 [SMILES: CCn1cc2c(Cl)c(-c3c[nH]c4nc(N5[C@@H]6CC[C@H]5C[C@@](C)(N)C6)n(C)c(=O)c34)ccc2n1] | 2-(endo-3-amino-3-methyl-8-azabicyclo[3.2.1]octan-8-yl)-5-(4-chloro-2-ethyl-2H-indazol-5-yl)-3-methyl-3,7-dihydro-4H-pyrrolo[2,3-d]pyrimidin-4-one | ¹H-NMR (DMSO-d₆) δ: 11.57 (1H, s), 8.42 (1H, s), 7.48 (1H, d, J = 8.8 Hz), 7.31 (1H, d, J = 8.8 Hz), 6.92 (1H, s), 4.47 (2H, q, J = 7.2 Hz), 4.08 (2H, br s), 3.40 (3H, s), 2.29-2.23 (2H, m), 1.94-1.85 (4H, m), 1.64-1.58 (2H, m), 1.51 (3H, t, J = 7.2 Hz), 1.09 (3H, s). | 466, 468 | 1 |
| 16 | 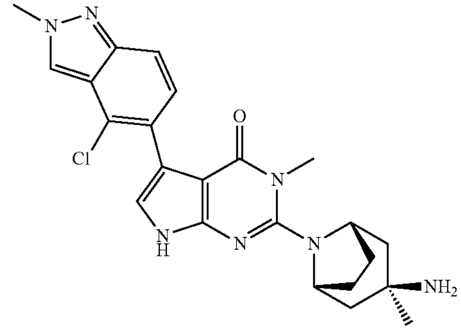 [SMILES: Cn1cc2c(Cl)c(-c3c[nH]c4nc(N5[C@@H]6CC[C@H]5C[C@@](C)(N)C6)n(C)c(=O)c34)ccc2n1] | 2-(endo-3-amino-3-methyl-8-azabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one | ¹H-NMR (DMSO-d₆) δ: 11.57 (1H, br s), 8.39 (1H, s), 7.48 (1H, d, J = 8.8 Hz), 7.33 (1H, d, J = 8.8 Hz), 6.94 (1H, s), 4.19 (3H, s), 4.09 (2H, br s), 3.41 (3H, s), 2.34-2.27 (2H, m), 1.93-1.86 (4H, m), 1.67-1.59 (2H, m), 1.47-1.35 (1H, m), 1.09 (3H, s). | 452, 454 | 1 |

TABLE 10-continued

| Example | Structure | Name | NMR data | MS: [M + H]+ m/z | Method |
|---|---|---|---|---|---|
| 17 | 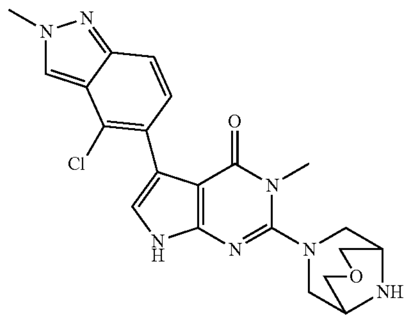 | 2-(3-oxa-7,9-diazabicyclo[3.3.1]nonan-7-yl)-5-(4-chloro-2-methyl-2H-indazol-5-yl)-3-methyl-3,7-dihydro-4H-pyrrolo[2,3-d]pyrimidin-4-one | ¹H-NMR (DMSO-d₆) δ: 11.77 (1H, br s), 8.41 (1H, s), 7.49 (1H, d, J = 8.8 Hz), 7.33 (1H, d, J = 8.8 Hz), 7.01 (1H, s), 4.19 (3H, s), 3.96-3.79 (4H, m), 3.54-3.43 (5H, m), 3.23-3.14 (2H, m), 2.87-2.80 (2H, m). | 440, 442 | 1 |
| 18 | 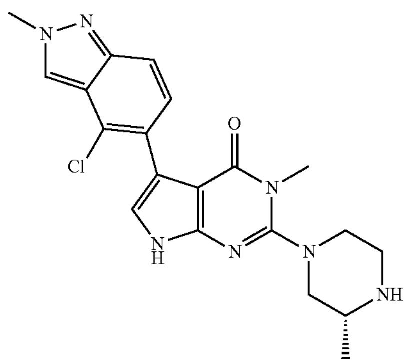 [SMILES: C[C@@H]1CN(c2nc3[nH]cc(-c4ccc5nn(C)cc5c4Cl)c3c(=O)n2C)CCN1] | (R)-5-(4-chloro-2-methyl-2H-indazol-5-yl)-3-methyl-2-(3-methyl-piperazin-1-yl)-3,7-dihydro-4H-pyrrolo[2,3-d]pyrimidin-4-one | ¹H-NMR (DMSO-d₆) δ: 11.80 (1H, br s), 8.40 (1H, s), 7.49 (1H, d, J = 8.8 Hz), 7.32 (1H, d, J = 8.8 Hz), 7.02 (1H, s), 4.19 (3H, s), 3.41-3.22 (5H, m), 2.97-2.65 (4H, m), 2.46-2.36 (1H, m), 1.01 (3H, d, J = 6.0 Hz). | 412, 414 | 1 |
| 19 | 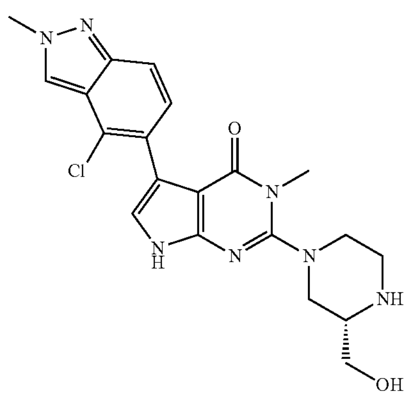 [SMILES: Cn1cc2c(Cl)c(-c3c[nH]c4nc(N5CCN[C@H](CO)C5)n(C)c(=O)c34)ccc2n1] | (S)-5-(4-chloro-2-methyl-2H-indazol-5-yl)-2-(3-(hydroxymethyl)piperazin-1-yl)-3-methyl-3,7-dihydro-4H-pyrrolo[2,3-d]pyrimidin-4-one | ¹H-NMR (DMSO-d₆) δ: 11.77 (1H, br s), 8.39 (1H, s), 7.48 (1H, d, J = 8.8 Hz), 7.31 (1H, d, J = 8.8 Hz), 7.01 (1H, s), 4.18 (3H, s), 3.39 (3H, s), 3.39-3.21 (4H, m), 3.06-2.72 (4H, m), 2.65-2.52 (1H, m). | 428, 430 | 2 |
| 20 | 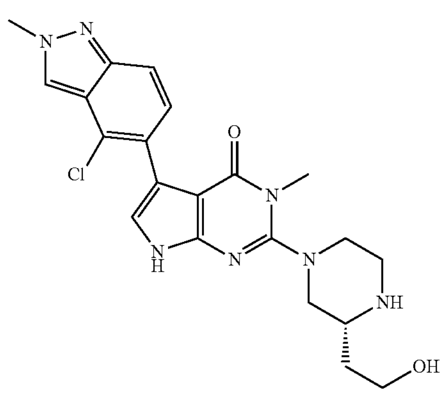 [SMILES: Cn1cc2c(Cl)c(-c3c[nH]c4nc(N5CCN[C@H](CCO)C5)n(C)c(=O)c34)ccc2n1] | (R)-5-(4-chloro-2-methyl-2H-indazol-5-yl)-2-(3-(2-hydroxyethyl)piperazin-1-yl)-3-methyl-3,7-dihydro-4H-pyrrolo[2,3-d]pyrimidin-4-one | ¹H-NMR (DMSO-d₆) δ: 11.79 (1H, br s), 8.39 (1H, s), 7.48 (1H, d, J = 8.8 Hz), 7.31 (1H, d, J = 8.8 Hz), 7.02 (1H, s), 4.18 (3H, s), 3.39 (3H, s), 3.39-3.21 (4H, m), 3.07-2.98 (2H, m), 2.94 (1H, t, J = 10.8 Hz), 2.81 (1H, t, J = 10.4 Hz), 2.58 (1H, t, J = 11.5 Hz), 1.63-1.51 (2H, m). | 442, 444 | 2 |

TABLE 10-continued

| Example | Structure | Name | NMR data | MS: [M + H]+ m/z | Method |
|---|---|---|---|---|---|
| 21 | 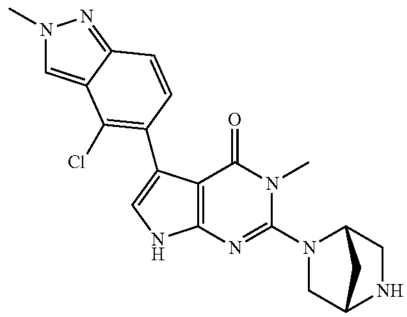 [SMILES: Cn1cc2c(Cl)c(-c3c[nH]c4nc(N5C[C@@H]6C[C@H]5CN6)n(C)c(=O)c34)ccc2n1] | 2-((1S,4S)-2,5-diazabicyclo[2.2.1]heptan-2-yl)-5-(4-chloro-2-methyl-2H-indazol-5-yl)-3-methyl-3,7-dihydro-4H-pyrrolo[2,3-d]pyrimidin-4-one | ¹H-NMR (DMSO-d₆) δ: 11.54 (1H, br s), 8.39 (1H, s), 7.48 (1H, d, J = 8.8 Hz), 7.33 (1H, d, J = 8.8 Hz), 6.91 (1H, s), 4.43 (1H, br s), 4.20 (3H, s), 3.67-3.61 (2H, m), 3.33-3.30 (4H, m), 3.19-3.14 (1H, m), 2.91-2.85 (1H, m), 1.77-1.73 (1H, m), 1.65-1.62 (1H, m). | 410, 412 | 1 |
| 22 | 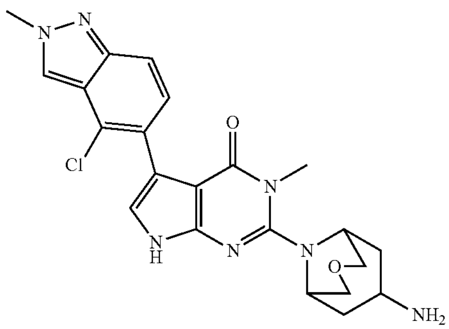 [SMILES: Cn1cc2c(Cl)c(-c3c[nH]c4nc(N5C6COCC5CC(N)C6)n(C)c(=O)c34)ccc2n1] | 2-(7-amino-3-oxa-9-azabicyclo[3.3.1]nonan-9-yl)-5-(4-chloro-2-methyl-2H-indazol-5-yl)-3-methyl-3,7-dihydro-4H-pyrrolo[2,3-d]pyrimidin-4-one | ¹H-NMR (DMSO-d₆) δ: 11.74 (1H, br s), 8.38 (1H, s), 7.52-7.26 (2H, m), 6.97 (1H, s), 4.18 (3H, s), 4.01-3.08 (9H, m), 2.18-2.01 (4H, m). | 454, 456 | 2 |
| 23 | 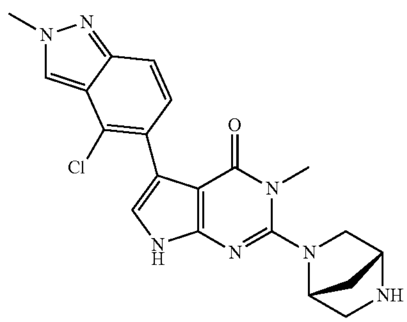 [SMILES: Cn1cc2c(Cl)c(-c3c[nH]c4nc(N5C[C@H]6C[C@@H]5CN6)n(C)c(=O)c34)ccc2n1] | 2-((1R,4R)-2,5-diazabicyclo[2.2.1]heptan-2-yl)-5-(4-chloro-2-methyl-2H-indazol-5-yl)-3-methyl-3,7-dihydro-4H-pyrrolo[2,3-d]pyrimidin-4-one | ¹H-NMR (DMSO-d₆) δ: 11.54 (1H, br s), 8.39 (1H, s), 7.48 (1H, d, J = 8.8 Hz), 7.33 (1H, d, J = 8.8 Hz), 6.91 (1H, s), 4.43 (1H, br s), 4.20 (3H, s), 3.67-3.61 (2H, m), 3.33-3.30 (4H, m), 3.19-3.14 (1H, m), 2.91-2.85 (1H, m), 1.77-1.73 (1H, m), 1.65-1.62 (1H, m). | 410, 412 | 1 |
| 24 | 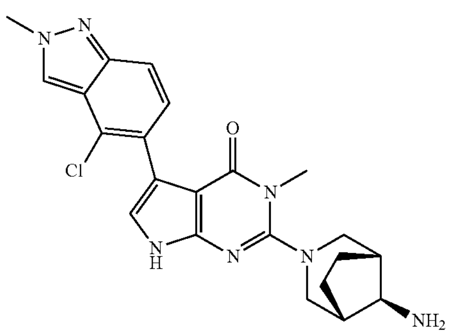 [SMILES: Cn1cc2c(Cl)c(-c3c[nH]c4nc(N5C[C@H]6CC[C@@H](C5)[C@@H]6N)n(C)c(=O)c34)ccc2n1] | 2-(exo-8-amino-3-azabicyclo[3.2.1]octan-3-yl)-5-(4-chloro-2-methyl-2H-indazol-5-yl)-3-methyl-3,7-dihydro-4H-pyrrolo[2,3-d]pyrimidin-4-one | ¹H-NMR (DMSO-d₆) δ: 8.38 (1H, s), 7.48 (1H, d, J = 8.8 Hz), 7.30 (1H, d, J = 8.8 Hz), 7.01 (1H, s), 4.18 (3H, s), 3.43 (3H, s), 3.43-3.39 (1H, m), 3.31-3.17 (4H, m), 2.95 (2H, d, J = 11.6 Hz), 2.29-2.23 (2H, m), 1.94-1.74 (4H, m). | 438, 440 | 2 |

TABLE 10-continued

| Example | Structure | Name | NMR data | MS: [M + H]+ m/z | Method |
|---|---|---|---|---|---|
| 25 | 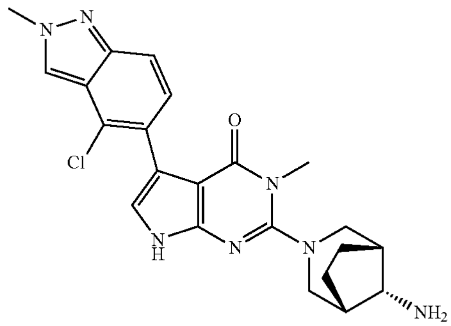 [SMILES: Cn1cc2c(Cl)c(-c3c[nH]c4nc(N5C[C@H]6CC[C@@H](C5)[C@H]6N)n(C)c(=O)c34)ccc2n1] | 2-(endo-8-amino-3-azabicyclo[3.2.1]octan-3-yl)-5-(4-chloro-2-methyl-2H-indazol-5-yl)-3-methyl-3,7-dihydro-4H-pyrrolo[2,3-d]pyrimidin-4-one | $^1$H-NMR (DMSO-$d_6$) δ: 11.69 (1H, br s), 8.38 (1H, s), 7.48 (1H, d, J = 8.8 Hz), 7.31 (1H, d, J = 8.8 Hz), 7.00 (1H, s), 4.18 (3H, s), 3.42 (3H, s), 3.42-3.36 (1H, m), 3.15-3.00 (4H, m), 2.13-2.06 (2H, br s), 1.85-1.70 (4H, m). | 438, 440 | 1 |
| 26 | 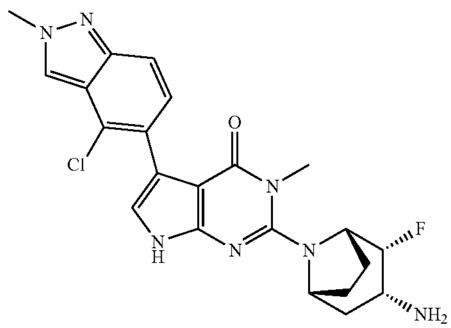 [SMILES: Cn1cc2c(Cl)c(-c3c[nH]c4nc(N5[C@@H]6CC[C@H]5[C@H](F)[C@H](N)C6)n(C)c(=O)c34)ccc2n1] | rac-2-((1S,2R,3R,5R)-3-amino-2-fluoro-8-azabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one | $^1$H-NMR (DMSO-$d_6$) δ: 11.60 (1H, s), 8.38 (1H, s), 7.47 (1H, dd, J = 8.8, 0.9 Hz), 7.31 (1H, d, J = 8.8 Hz), 6.96-6.94 (1H, m), 4.56-4.38 (2H, m), 4.18 (3H, s), 4.14-4.09 (1H, m), 3.44 (3H, s), 3.06-2.89 (1H, m), 2.07-1.92 (2H, m), 1.89-1.79 (1H, m), 1.77-1.57 (5H, m). | 456, 458 | 4 |
| 27 | 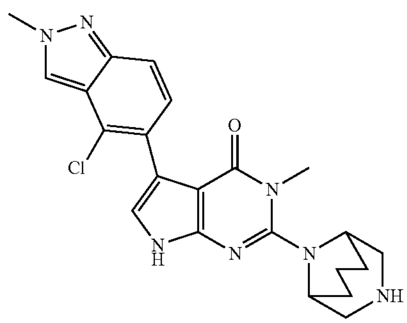 | 2-(3,9-diazabicyclo[3.3.1]nonan-9-yl)-5-(4-chloro-2-methyl-2H-indazol-5-yl)-3-methyl-3,7-dihydro-4H-pyrrolo[2,3-d]pyrimidin-4-one | $^1$H-NMR (DMSO-$d_6$) δ: 11.56 (1H, br s), 8.39 (1H, s), 7.48 (1H, d, J = 8.8 Hz), 7.33 (1H, d, J = 8.8 Hz), 6.94 (1H, s), 4.19 (3H, s), 3.65 (2H, br s), 3.34-3.32 (4H, m), 3.27-3.25 (1H, m), 2.92-2.88 (2H, m), 2.80-2.70 (1H, m), 2.16-2.10 (2H, m), 1.76-1.71 (2H, m), 1.62-1.55 (1H, m). | 438, 440 | 1 |
| 28 | 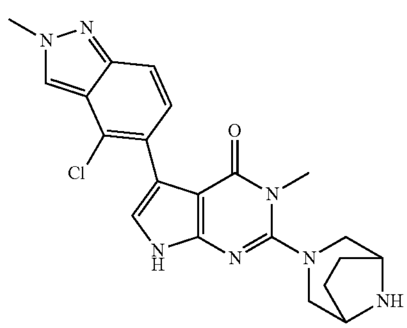 [SMILES: Cn1cc2c(Cl)c(-c3c[nH]c4nc(N5CC6CCC(C5)N6)n(C)c(=O)c34)ccc2n1] | 2-(3,8-diazabicyclo[3.2.1]octan-3-yl)-5-(4-chloro-2-methyl-2H-indazol-5-yl)-3-methyl-3,7-dihydro-4H-pyrrolo[2,3-d]pyrimidin-4-one | $^1$H-NMR (DMSO-$d_6$) δ: 11.81 (1H, br s), 8.39 (1H, s), 7.48 (1H, d, J = 8.7 Hz), 7.30 (1H, d, J = 8.8 Hz), 7.02 (1H, s), 4.18 (3H, s), 3.72 (2H, br s), 3.42 (3H, s), 3.21 (2H, d, J = 12.3 Hz), 3.09 (2H, d, J = 12.1 Hz), 2.02-1.95 (2H, m), 1.86-1.78 (2H, m). | 424, 426 | 1 |

TABLE 10-continued

| Example | Structure | Name | NMR data | MS: [M + H]+ m/z | Method |
|---|---|---|---|---|---|
| 29 | 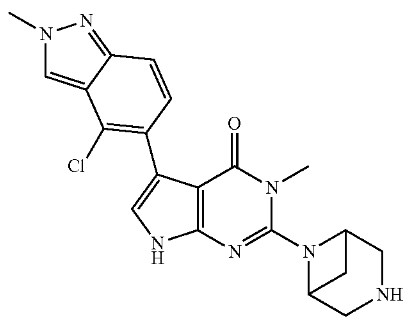 [SMILES: Cn1cc2c(Cl)c(-c3c[nH]c4nc(N5C6CNCC5C6)n(C)c(=O)c34)ccc2n1] | 2-(3,6-diazabicyclo[3.1.1]heptan-6-yl)-5-(4-chloro-2-methyl-2H-indazol-5-yl)-3-methyl-3,7-dihydro-4H-pyrrolo[2,3-d]pyrimidin-4-one | 1H-NMR (DMSO-$d_6$) δ: 11.55 (1H, br s), 8.39 (1H, s), 7.48 (1H, d, J = 8.8 Hz), 7.32 (1H, d, J = 8.8 Hz), 6.93 (1H, s), 4.48 (2H, d, J = 6.2 Hz), 4.19 (3H, s), 3.68-3.41 (2H, m), 3.28 (3H, s), 3.08 (2H, d, J = 12.1 Hz), 2.79-2.72 (1H, m), 1.84 (1H, d, J = 8.8 Hz). | 410, 412 | 1 |
| 30 | 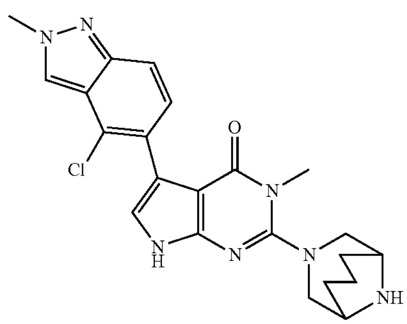 [SMILES: Cn1cc2c(Cl)c(-c3c[nH]c4nc(N5CC6CCCC(C5)N6)n(C)c(=O)c34)ccc2n1] | 2-(3,9-diazabicyclo[3.3.1]nonan-3-yl)-5-(4-chloro-2-methyl-2H-indazol-5-yl)-3-methyl-3,7-dihydro-4H-pyrrolo[2,3-d]pyrimidin-4-one | $^1$H-NMR (DMSO-$d_6$) δ: 11.77 (1H, br s), 8.40 (1H, s), 7.49 (1H, d, J = 8.8 Hz), 7.33 (1H, d, J = 8.8 Hz), 7.02 (1H, s), 4.19 (3H, s), 3.46 (3H, s), 3.39-3.36 (2H, m), 3.14-3.11 (2H, m), 3.05-3.03 (2H, m), 2.51-2.49 (1H, m), 1.89-1.76 (4H, m), 1.65-1.58 (1H, m). | 438, 440 | 1 |
| 31 | 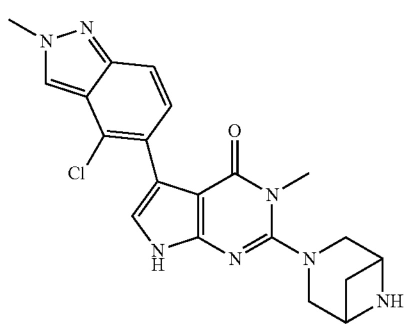 [SMILES: Cn1cc2c(Cl)c(-c3c[nH]c4nc(N5CC6CC(C5)N6)n(C)c(=O)c34)ccc2n1] | 2-(3,6-diazabicyclo[3.1.1]heptan-3-yl)-5-(4-chloro-2-methyl-2H-indazol-5-yl)-3-methyl-3,7-dihydro-4H-pyrrolo[2,3-d]pyrimidin-4-one | $^1$H-NMR (DMSO-$d_6$) δ: 11.69 (1H, br s), 8.39 (1H, s), 7.48 (1H, d, J = 8.8 Hz), 7.32 (1H, d, J = 8.8 Hz), 7.00 (1H, s), 4.19 (3H, s), 3.90 (2H, d, J = 5.6 Hz), 3.83-3.73 (4H, m), 3.39 (3H, s), 2.63-2.56 (1H, m), 1.84 (1H, d, J = 8.7 Hz). | 410, 412 | 1 |
| 32 | 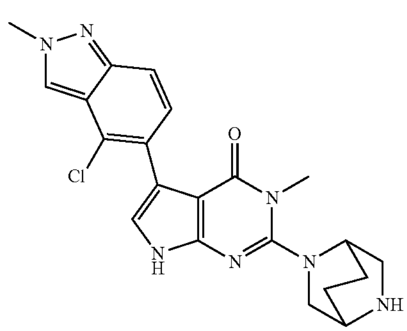 [SMILES: Cn1cc2c(Cl)c(-c3c[nH]c4nc(N5CC6CCC5CN6)n(C)c(=O)c34)ccc2n1] | 2-(2,5-diazabicyclo[2.2.2]octan-2-yl)-5-(4-chloro-2-methyl-2H-indazol-5-yl)-3-methyl-3,7-dihydro-4H-pyrrolo[2,3-d]pyrimidin-4-one | $^1$H-NMR (DMSO-$d_6$) δ: 11.56 (1H, br s), 8.38 (1H, s), 7.47 (1H, d, J = 8.8 Hz), 7.32 (1H, d, J = 8.3 Hz), 6.93 (1H, s), 4.18 (3H, s), 3.78-3.74 (1H, m), 3.65 (1H, d, J = 10.1 Hz), 3.53-3.45 (3H, m), 3.32 (1H, s), 3.30-3.27 (1H, m), 3.08 (1H, br s), 2.98 (1H, d, J = 10.9 Hz), 2.28-2.13 (1H, m), 1.94-1.67 (3H, m). | 424, 426 | 1 |

TABLE 10-continued

| Example | Structure | Name | NMR data | MS: [M + H]+ m/z | Method |
|---|---|---|---|---|---|
| 33 | 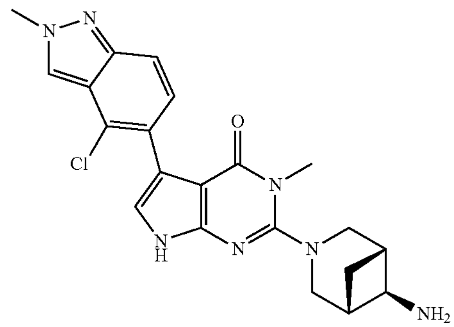 [SMILES: Cn1cc2c(Cl)c(-c3c[nH]c4nc(N5C[C@H]6C[C@@H](C5)[C@@H]6N)n(C)c(=O)c34)ccc2n1] | 2-(exo-6-amino-3-azabicyclo[3.1.1]heptan-3-yl)-5-(4-chloro-2-methyl-2H-indazol-5-yl)-3-methyl-3,7-dihydro-4H-pyrrolo[2,3-d]pyrimidin-4-one | $^1$H-NMR (DMSO-$d_6$) δ: 11.63 (1H, br s), 8.38 (1H, s), 7.47 (1H, d, J = 8.9 Hz), 7.32 (1H, d, J = 8.9 Hz), 6.97 (1H, s), 4.18 (3H, s), 3.84 (2H, d, J = 11.3 Hz), 3.62-3.59 (2H, m), 3.37 (3H, s), 3.18-3.15 (1H, m), 2.67-2.59 (1H, m), 2.34-2.29 (2H, m), 1.66-1.60 (1H, m). | 424, 426 | 1 |
| 34 | 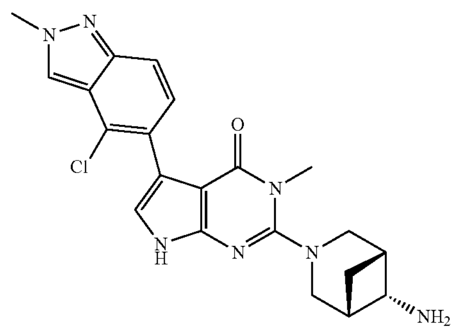 [SMILES: Cn1cc2c(Cl)c(-c3c[nH]c4nc(N5C[C@H]6C[C@@H](C5)[C@H]6N)n(C)c(=O)c34)ccc2n1] | 2-(endo-6-amino-3-azabicyclo[3.1.1]heptan-3-yl)-5-(4-chloro-2-methyl-2H-indazol-5-yl)-3-methyl-3,7-dihydro-4H-pyrrolo[2,3-d]pyrimidin-4-one | $^1$H-NMR (DMSO-$d_6$) δ: 11.62 (1H, br s), 8.39 (1H, s), 7.48 (1H, d, J = 8.8 Hz), 7.32 (1H, d, J = 8.9 Hz), 6.96 (1H, s), 4.18 (3H, s), 3.80-3.27 (7H, m), 2.44-2.39 (2H, m), 1.75-1.61 (1H, m), 1.46 (1H, d, J = 9.0 Hz). | 424, 426 | 1 |
| 35 | 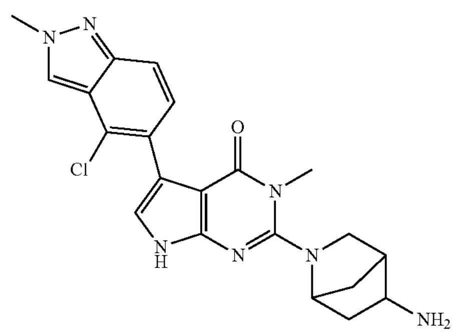 [SMILES: Cn1cc2c(Cl)c(-c3c[nH]c4nc(N5CC6CC5CC6N)n(C)c(=O)c34)ccc2n1] | 2-(5-amino-2-azabicyclo[2.2.1]heptan-2-yl)-5-(4-chloro-2-methyl-2H-indazol-5-yl)-3-methyl-3,7-dihydro-4H-pyrrolo[2,3-d]pyrimidin-4-one | $^1$H-NMR (DMSO-$d_6$) δ: 11.53 (1H, br s), 8.37 (1H, s), 7.48-7.45 (1H, m), 7.32 (1H, d, J = 8.7 Hz), 6.88 (1H, s), 4.23-4.14 (5H, m), 3.39-3.21 (5H, m), 2.65-2.60 (1H, m), 2.09-2.00 (1H, m), 1.82-1.59 (2H, m). | 424, 426 | 1 |
| 36 | 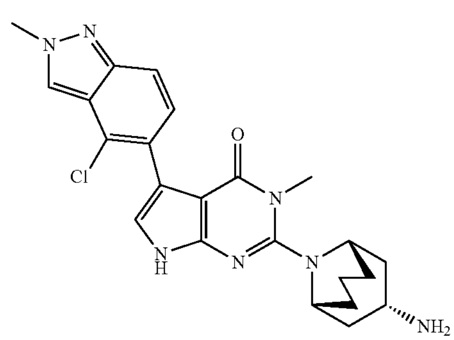 [SMILES: Cn1cc2c(Cl)c(-c3c[nH]c4nc(N5[C@@H]6CCC[C@H]5C[C@H](N)C6)n(C)c(=O)c34)ccc2n1] | 2-(exo-3-amino-9-azabicyclo[3.3.1]nonan-9-yl)-5-(4-chloro-2-methyl-2H-indazol-5-yl)-3-methyl-3,7-dihydro-4H-pyrrolo[2,3-d]pyrimidin-4-one | $^1$H-NMR (DMSO-$d_6$) δ: 11.64 (1H, br s), 8.38 (1H, s), 7.52-7.28 (2H, m), 6.94 (1H, s), 4.18 (3H, s), 4.00-3.87 (3H, m), 3.33 (3H, s), 2.17-1.59 (10H, m). | 452, 454 | 2 |

TABLE 10-continued

| Example | Structure | Name | NMR data | MS: [M + H]+ m/z | Method |
|---|---|---|---|---|---|
| 37 | 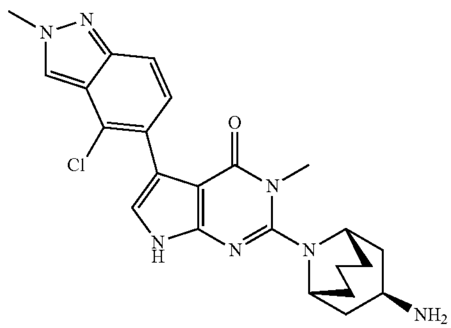 [SMILES: Cn1cc2c(Cl)c(-c3c[nH]c4nc(N5[C@@H]6CCC[C@H]5C[C@@H](N)C6)n(C)c(=O)c34)ccc2n1] | 2-(endo-3-amino-9-azabicyclo[3.3.1]nonan-9-yl)-5-(4-chloro-2-methyl-2H-indazol-5-yl)-3-methyl-3,7-dihydro-4H-pyrrolo[2,3-d]pyrimidin-4-one | ¹H-NMR (DMSO-$d_6$) δ: 11.60 (1H, br s), 8.38 (1H, s), 7.47 (1H, d, J = 8.7 Hz), 7.31 (1H, d, J = 8.8 Hz), 6.94 (1H, s), 4.18 (3H, s), 4.11-4.04 (2H, m), 3.31 (3H, s), 2.55-2.36 (1H, m), 2.12-1.76 (2H, m), 1.61-1.37 (6H, m). | 452, 454 | 1 |
| 38 | 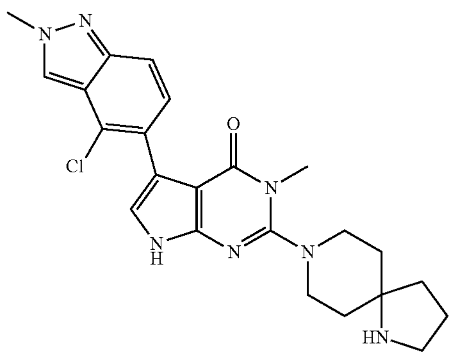 [SMILES: Cn1cc2c(Cl)c(-c3c[nH]c4nc(N5CCC6(CCCN6)CC5)n(C)c(=O)c34)ccc2n1] | 5-(4-chloro-2-methyl-2H-indazol-5-yl)-3-methyl-2-(1,8-diazaspiro[4.5]decan-8-yl)-3,7-dihydro-4H-pyrrolo[2,3-d]pyrimidin-4-one | ¹H-NMR (DMSO-$d_6$) δ: 11.71 (1H, br s), 8.38 (1H, s), 7.47 (1H, d, J = 8.7 Hz), 7.31 (1H, d, J = 8.9 Hz), 6.99 (1H, s), 4.18 (3H, s), 3.37 (3H, s), 3.21-3.14 (2H, m), 3.08-3.00 (2H, m), 2.85-2.81 (2H, m), 1.80-1.49 (8H, m). | 452, 454 | 1 |
| 39 | 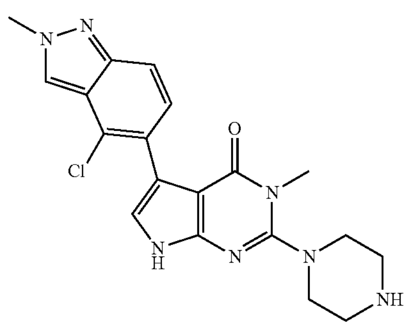 [SMILES: Cn1cc2c(Cl)c(-c3c[nH]c4nc(N5CCNCC5)n(C)c(=O)c34)ccc2n1] | 5-(4-chloro-2-methyl-2H-indazol-5-yl)-3-methyl-2-(piperazin-1-yl)-3,7-dihydro-4H-pyrrolo[2,3-d]pyrimidin-4-one | 1H-NMR (DMSO-$d_6$) δ: 11.78 (1H, s), 8.38 (1H, s), 7.46 (1H, d, J = 8.8 Hz), 7.29 (1H, d, J = 8.8 Hz), 6.99 (1H, s), 4.17 (3H, s), 3.36 (3H, s), 3.02-2.96 (4H, m), 2.86-2.78 (4H, m). | 398, 400 | 2, After purifying by r-HPLC, obtained fractions were basified with sat. NaHCO₃ and extracted with CHCl₃—MeOH. The organic layer was dried over anhydrous Na₂SO₄, filtered, and concentrated in vacuo. The residue was suspended in EtOAc-hexane. |

TABLE 10-continued

| Example | Structure | Name | NMR data | MS: [M + H]⁺ m/z | Method |
|---|---|---|---|---|---|
| 40 | 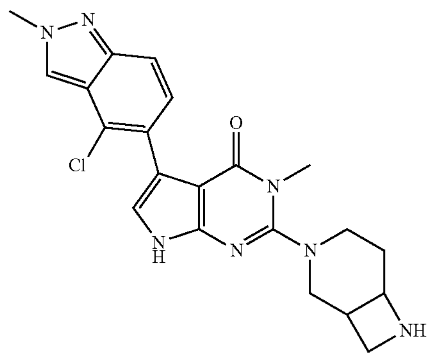 [SMILES: Cn1cc2c(Cl)c(-c3c[nH]c4nc(N5CCC6NCC6C5)n(C)c(=O)c34)ccc2n1] | 2-(3,7-diazabicyclo[4.2.0]octan-3-yl)-5-(4-chloro-2-methyl-2H-indazol-5-yl)-3-methyl-3,7-dihydro-4H-pyrrolo[2,3-d]pyrimidin-4-one | ¹H-NMR (DMSO-d₆) δ: 11.74 (1H, br s), 8.39 (1H, s), 7.48 (1H, d, J = 8.8 Hz), 7.31 (1H, d, J = 8.9 Hz), 7.01 (1H, d, J = 2.7 Hz), 4.23-4.14 (4H, m), 3.75-3.66 (2H, m), 3.36 (3H, s), 3.21-3.01 (2H, m), 2.94-2.87 (2H, m), 2.53-2.50 (1H, m), 1.81-1.73 (2H, m). | 424, 426 | 1 |
| 41 | 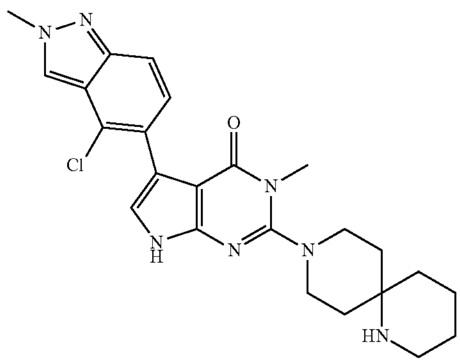 [SMILES: Cn1cc2c(Cl)c(-c3c[nH]c4nc(N5CCC6(CCCCN6)CC5)n(C)c(=O)c34)ccc2n1] | 5-(4-chloro-2-methyl-2H-indazol-5-yl)-3-methyl-2-(1,9-diazaspiro[5.5]undecan-9-yl)-3,7-dihydro-4H-pyrrolo[2,3-d]pyrimidin-4-one | ¹H-NMR (DMSO-d₆) δ: 11.77 (1H, br s), 8.40 (1H, s), 7.55-7.30 (2H, m), 7.03-7.01 (1H, m), 4.19 (3H, s), 3.37 (3H, s), 3.09-2.86 (4H, m), 1.95-1.76 (4H, m), 1.68-1.48 (6H, m). | 466, 468 | 1 |
| 42 | 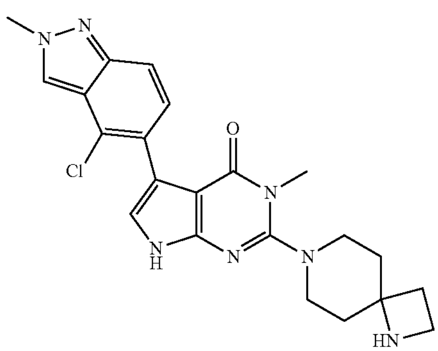 [SMILES: Cn1cc2c(Cl)c(-c3c[nH]c4nc(N5CCC6(CCN6)CC5)n(C)c(=O)c34)ccc2n1] | 5-(4-chloro-2-methyl-2H-indazol-5-yl)-3-methyl-2-(1,7-diazaspiro[3.5]nonan-7-yl)-3,7-dihydro-4H-pyrrolo[2,3-d]pyrimidin-4-one | ¹H-NMR (DMSO-d₆) δ: 11.82 (1H, br s), 8.40 (1H, s), 7.49 (1H, d, J = 9.2 Hz), 7.32 (1H, d, J = 8.8 Hz), 7.01 (1H, s), 4.19 (3H, s), 3.78-3.14 (9H, m), 2.95-2.89 (2H, m), 2.35-2.20 (4H, m). | 438, 440 | 1, using 4 M HCl in dioxane instead of TFA and CHCl₃ |
| 43 | 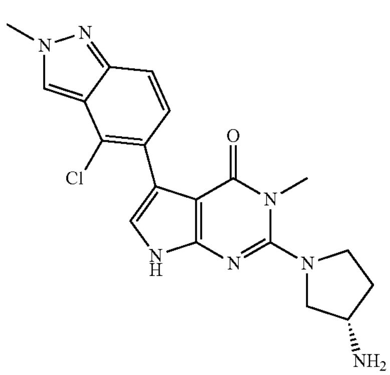 [SMILES: Cn1cc2c(Cl)c(-c3c[nH]c4nc(N5CC[C@H](N)C5)n(C)c(=O)c34)ccc2n1] | (S)-2-(3-aminopyrrolidin-1-yl)-5-(4-chloro-2-methyl-2H-indazol-5-yl)-3-methyl-3,7-dihydro-4H-pyrrolo[2,3-d]pyrimidin-4-one | ¹H-NMR (DMSO-d₆) δ: 11.51 (1H, br s), 8.39 (1H, s), 7.48 (1H, d, J = 8.8 Hz), 7.33 (1H, d, J = 8.8 Hz), 6.90 (1H, s), 4.19 (3H, s), 3.66-3.41 (4H, m), 3.33 (3H, s), 3.13-3.06 (1H, m), 2.04-1.58 (4H, m). | 398, 400 | 1 |

TABLE 10-continued

| Example | Structure | Name | NMR data | MS: [M + H]⁺ m/z | Method |
|---|---|---|---|---|---|
| 44 | 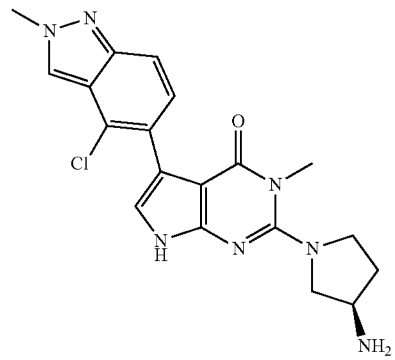 [SMILES: Cn1cc2c(Cl)c(-c3c[nH]c4nc(N5CC[C@@H](N)C5)n(C)c(=O)c34)ccc2n1] | (R)-2-(3-amino-pyrrolidin-1-yl)-5-(4-chloro-2-methyl-2H-indazol-5-yl)-3-methyl-3,7-dihydro-4H-pyrrolo[2,3-d]pyrimidin-4-one | 1H-NMR (DMSO-$d_6$) δ: 11.51 (1H, br s), 8.39 (1H, s), 7.48 (1H, d, J = 8.8 Hz), 7.33 (1H, d, J = 8.8 Hz), 6.90 (1H, s), 4.19 (3H, s), 3.66-3.39 (4H, m), 3.33 (3H, s), 3.13-3.07 (1H, m), 2.05-1.59 (4H, m). | 398, 400 | 1 |
| 45 | 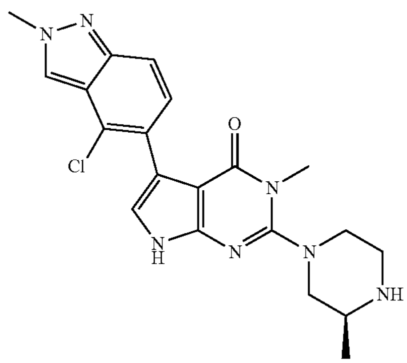 [SMILES: C[C@H]1CN(c2nc3[nH]cc(-c4ccc5nn(C)cc5c4Cl)c3c(=O)n2C)CCN1] | (S)-5-(4-chloro-2-methyl-2H-indazol-5-yl)-3-methyl-2-(3-methyl-piperazin-1-yl)-3,7-dihydro-4H-pyrrolo[2,3-d]pyrimidin-4-one | ¹H-NMR (DMSO-$d_6$) δ: 11.77 (1H, br s), 8.39 (1H, s), 7.48 (1H, d, J = 8.8 Hz), 7.31 (1H, d, J = 8.8 Hz), 7.00 (1H, s), 4.19 (3H, s), 3.51-3.45 (1H, m), 3.38 (3H, s), 2.96-2.79 (3H, m), 2.74-2.65 (1H, m), 2.42-2.35 (2H, m), 1.00 (3H, d, J = 6.6 Hz). | 412, 414 | 1 |
| 46 | 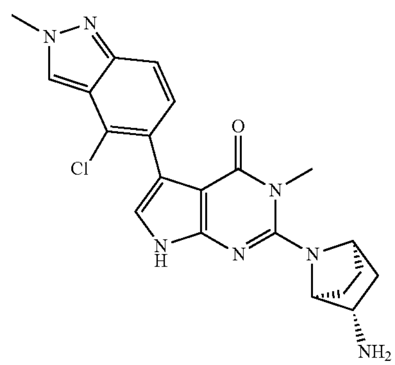 [SMILES: Cn1cc2c(Cl)c(-c3c[nH]c4nc(N5[C@@H]6CC[C@H]5[C@@H](N)C6)n(C)c(=O)c34)ccc2n1] | 2-((1S,2S,4R)-2-amino-7-azabicyclo[2.2.1]heptan-7-yl)-5-(4-chloro-2-methyl-2H-indazol-5-yl)-3-methyl-3,7-dihydro-4H-pyrrolo[2,3-d]pyrimidin-4-one | ¹H-NMR (DMSO-$d_6$) δ: 11.62 (1H, br s), 8.39 (1H, s), 7.48 (1H, d, J = 9.0 Hz), 7.32 (1H, d, J = 9.0 Hz), 6.94 (1H, s), 4.19 (3H, s), 4.15-4.12 (1H, m), 4.01-3.98 (1H, m), 3.49-3.42 (1H, m), 3.39 (3H, s), 2.30-2.24 (1H, m), 2.19-2.14 (1H, m), 2.00-1.79 (2H, m), 1.72-1.64 (1H, m), 1.54-1.45 (1H, m), 0.90-0.85 (1H, m). | 424, 426 | 1 |
| 47 | 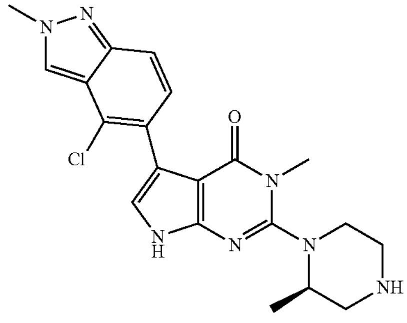 [SMILES: C[C@@H]1CNCCN1c1nc2[nH]cc(-c3ccc4nn(C)cc4c3Cl)c2c(=O)n1C] | (R)-5-(4-chloro-2-methyl-2H-indazol-5-yl)-3-methyl-2-(2-methyl-piperazin-1-yl)-3,7-dihydro-4H-pyrrolo[2,3-d]pyrimidin-4-one | ¹H-NMR (DMSO-$d_6$) δ: 11.88 (1H, br s), 8.39 (1H, s), 7.48 (1H, d, J = 9.0 Hz), 7.32 (1H, d, J = 8.8 Hz), 7.06 (1H, s), 4.19 (3H, s), 3.48-3.43 (1H, m), 3.42 (3H, s), 3.23-3.15 (1H, m), 3.10-3.02 (1H, m), 3.00-2.87 (2H, m), 2.85-2.77 (1H, m), 2.70-2.61 (1H, m), 1.04 (3H, d, J = 6.2 Hz). | 412, 414 | 1 |

TABLE 10-continued

| Example | Structure | Name | NMR data | MS: [M + H]+ m/z | Method |
|---|---|---|---|---|---|
| 48 | 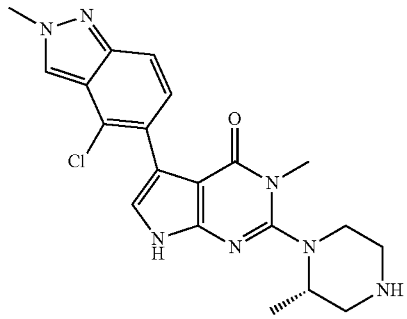 [SMILES: C[C@H]1CNCCN1c1nc2[nH]cc(-c3ccc4nn(C)cc4c3Cl)c2c(=O)n1C] | (S)-5-(4-chloro-2-methyl-2H-indazol-5-yl)-3-methyl-2-(2-methyl-piperazin-1-yl)-3,7-dihydro-4H-pyrrolo[2,3-d]pyrimidin-4-one | $^1$H-NMR (DMSO-$d_6$) δ: 11.84 (1H, br s), 8.39 (1H, s), 7.48 (1H, d, J = 8.8 Hz), 7.32 (1H, d, J = 8.9 Hz), 7.05 (1H, s), 4.18 (3H, s), 3.42 (3H, s), 3.42-3.35 (1H, m), 3.17-3.09 (1H, m), 2.99-2.93 (1H, m), 2.86-2.80 (1H, m), 2.77-2.69 (2H, m), 2.58-2.51 (1H, m), 1.02 (3H, d, J = 6.1 Hz). | 412, 414 | 1 |
| 49 | 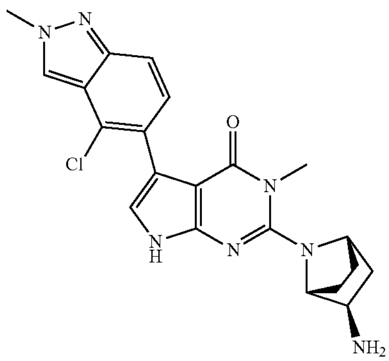 [SMILES: Cn1cc2c(Cl)c(-c3c[nH]c4nc(N5[C@H]6CC[C@@H]5[C@H](N)C6)n(C)c(=O)c34)ccc2n1] | 2-((1R,2R,4S)-2-amino-7-azabicyclo[2.2.1]heptan-7-yl)-5-(4-chloro-2-methyl-2H-indazol-5-yl)-3-methyl-3,7-dihydro-4H-pyrrolo[2,3-d]pyrimidin-4-one | $^1$H-NMR (DMSO-$d_6$) δ: 11.62 (1H, br s), 8.38 (1H, s), 7.47 (1H, d, J = 8.8 Hz), 7.31 (1H, d, J = 8.7 Hz), 6.93 (1H, s), 4.18 (3H, s), 4.15-4.10 (1H, m), 4.02-3.97 (1H, m), 3.50-3.42 (1H, m), 3.38 (3H, s), 2.34-2.07 (2H, m), 1.97-1.79 (1H, m), 1.78-1.60 (1H, m), 1.57-1.40 (1H, m), 0.91-0.83 (1H, m). | 424, 426 | 1 |
| 50 | 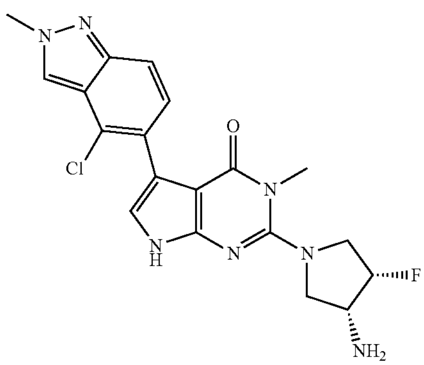 [SMILES: Cn1cc2c(Cl)c(-c3c[nH]c4nc(N5C[C@@H](N)[C@@H](F)C5)n(C)c(=O)c34)ccc2n1] | 2-((3R,4S)-3-amino-4-fluoro-pyrrolidin-1-yl)-5-(4-chloro-2-methyl-2H-indazol-5-yl)-3-methyl-3,7-dihydro-4H-pyrrolo[2,3-d]pyrimidin-4-one | $^1$H-NMR (DMSO-$d_6$) δ: 11.52 (1H, br s), 8.38 (1H, s), 7.47 (1H, d, J = 8.8 Hz), 7.31 (1H, d, J = 8.9 Hz), 6.91 (1H, d, J = 2.3 Hz), 5.05-4.88 (1H, m), 4.18 (3H, s), 4.07-3.90 (1H, m), 3.56-3.35 (4H, m), 3.32 (3H, s), 1.77 (2H, br s). | 416, 418 | 1 |
| 51 | 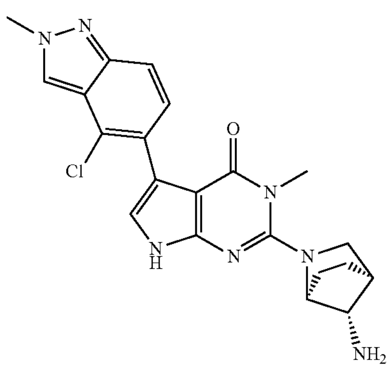 [SMILES: Cn1cc2c(Cl)c(-c3c[nH]c4nc(N5C[C@@H]6CC[C@H]5[C@H]6N)n(C)c(=O)c34)ccc2n1] | rac-2-((1S,4S,7S)-7-amino-2-azabicyclo[2.2.1]heptan-2-yl)-5-(4-chloro-2-methyl-2H-indazol-5-yl)-3-methyl-3,7-dihydro-4H-pyrrolo[2,3-d]pyrimidin-4-one | $^1$H-NMR (DMSO-$d_6$) δ: 11.49 (1H, br s), 8.37 (1H, s), 7.46 (1H, d, J = 8.9 Hz), 7.31 (1H, d, J = 8.9 Hz), 6.88 (1H, s), 4.18 (3H, s), 3.84 (1H, s), 3.73-3.65 (1H, m), 3.28-3.23 (4H, m), 3.02 (1H, d, J = 8.8 Hz), 2.15 (1H, s), 2.01-1.83 (3H, m), 1.74-1.49 (2H, m), 1.42-1.31 (1H, m). | 424, 426 | 1 |

TABLE 10-continued

| Example | Structure | Name | NMR data | MS: [M + H]+ m/z | Method |
|---|---|---|---|---|---|
| 52 | 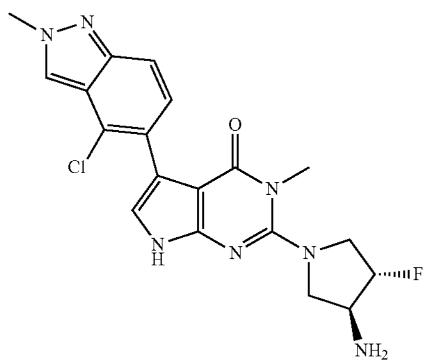 [SMILES: Cn1cc2c(Cl)c(-c3c[nH]c4nc(N5C[C@H](N)[C@@H](F)C5)n(C)c(=O)c34)ccc2n1] | 2-((3S,4S)-3-amino-4-fluoro-pyrrolidin-1-yl)-5-(4-chloro-2-methyl-2H-indazol-5-yl)-3-methyl-3,7-dihydro-4H-pyrrolo[2,3-d]pyrimidin-4-one | ¹H-NMR (DMSO-d₆) δ: 11.52 (1H, br s), 8.38 (1H, s), 7.47 (1H, d, J = 8.7 Hz), 7.32 (1H, d, J = 8.8 Hz), 6.92 (1H, d, J = 2.2 Hz), 5.07-4.87 (1H, m), 4.22-3.99 (4H, m), 3.90-3.84 (1H, m), 3.62-3.40 (2H, m), 3.36 (3H, s), 3.16 (1H, d, J = 10.7 Hz). | 416, 418 | 1 |
| 53 | 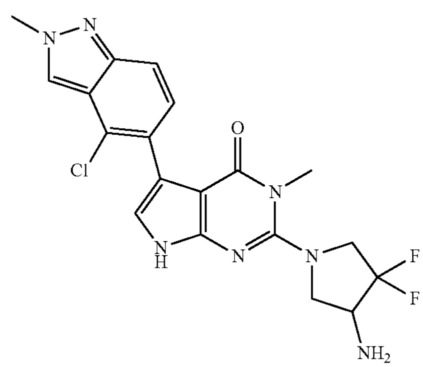 [SMILES: Cn1cc2c(Cl)c(-c3c[nH]c4nc(N5CC(N)C(F)(F)C5)n(C)c(=O)c34)ccc2n1] | 2-(4-amino-3,3-difluoro-pyrrolidin-1-yl)-5-(4-chloro-2-methyl-2H-indazol-5-yl)-3-methyl-3,7-dihydro-4H-pyrrolo[2,3-d]pyrimidin-4-one | 1H-NMR (DMSO-d₆) δ: 11.66 (1H, br s), 8.41 (1H, s), 7.50 (1H, d, J = 8.9 Hz), 7.33 (1H, d, J = 8.9 Hz), 6.98 (1H, d, J = 2.4 Hz), 4.21 (3H, s), 3.98-3.88 (2H, m), 3.82-3.76 (1H, m), 3.69-3.59 (1H, m), 3.36 (3H, s), 3.33-3.27 (1H, m), 2.09-1.93 (2H, br s). | 434, 436 | 1 |
| 54 | 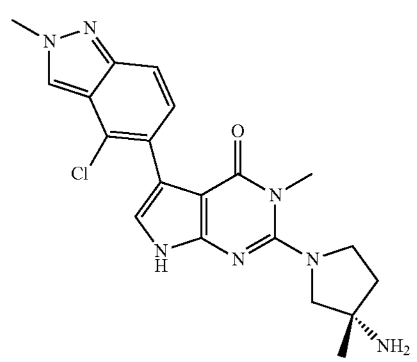 [SMILES: Cn1cc2c(Cl)c(-c3c[nH]c4nc(N5CC[C@](C)(N)C5)n(C)c(=O)c34)ccc2n1] | (S)-2-(3-amino-3-methyl-pyrrolidin-1-yl)-5-(4-chloro-2-methyl-2H-indazol-5-yl)-3-methyl-3,7-dihydro-4H-pyrrolo[2,3-d]pyrimidin-4-one | ¹H-NMR (DMSO-d₆) δ: 11.47 (1H, br s), 8.38 (1H, s), 7.47 (1H, d, J = 8.7 Hz), 7.32 (1H, d, J = 8.7 Hz), 6.89 (1H, s), 4.20-4.16 (3H, m), 3.75-3.65 (2H, m), 3.53-3.43 (2H, m), 3.33 (3H, s), 3.30-3.13 (2H, m), 2.02-1.76 (4H, m), 1.22 (3H, s). | 412, 414 | 1 |
| 55 | 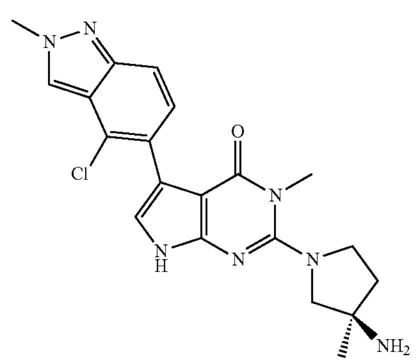 [SMILES: Cn1cc2c(Cl)c(-c3c[nH]c4nc(N5CC[C@@](C)(N)C5)n(C)c(=O)c34)ccc2n1] | (R)-2-(3-amino-3-methyl-pyrrolidin-1-yl)-5-(4-chloro-2-methyl-2H-indazol-5-yl)-3-methyl-3,7-dihydro-4H-pyrrolo[2,3-d]pyrimidin-4-one | ¹H-NMR (DMSO-d₆) δ: 11.50 (1H, br s), 8.40 (1H, s), 7.50 (1H, d, J = 8.7 Hz), 7.35 (1H, d, J = 8.8 Hz), 6.92 (1H, s), 4.21 (3H, s), 3.78-3.67 (1H, m), 3.56-3.45 (1H, m), 3.39-3.29 (4H, m), 3.20 (1H, d, J = 10.1 Hz), 1.83-1.75 (4H, m), 1.25 (3H, s). | 412, 414 | 1 |

TABLE 10-continued

| Example | Structure | Name | NMR data | MS: [M + H]+ m/z | Method |
|---|---|---|---|---|---|
| 56 | 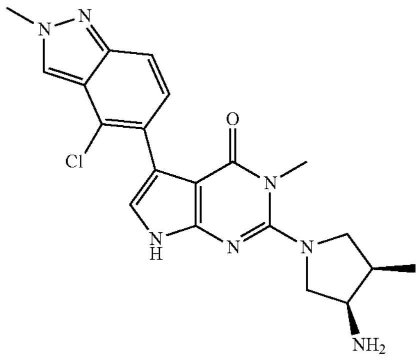 | 2-((3R,4R)-3-amino-4-methyl-pyrrolidin-1-yl)-5-(4-chloro-2-methyl-2H-indazol-5-yl)-3-methyl-3,7-dihydro-4H-pyrrolo[2,3-d]pyrimidin-4-one | $^1$H-NMR (DMSO-$d_6$) δ: 11.48 (1H, br s), 8.40 (1H, s), 7.49 (1H, d, J = 8.8 Hz), 7.35 (1H, d, J = 8.8 Hz), 6.91 (1H, s), 4.21 (3H, s), 3.69 (1H, q, J = 5.2 Hz), 3.47-3.28 (5H, m), 3.20-3.12 (2H, m), 2.26-2.13 (1H, m), 1.01 (1H, d, J = 7.0 Hz). | 412, 414 | 1 |
| 57 | 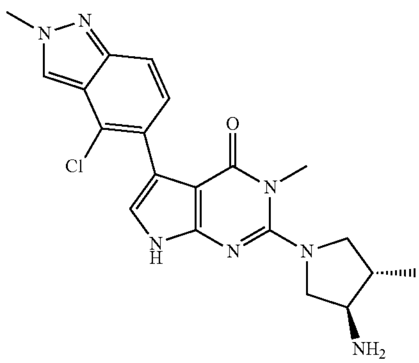 | 2-((3R,4S)-3-amino-4-methyl-pyrrolidin-1-yl)-5-(4-chloro-2-methyl-2H-indazol-5-yl)-3-methyl-3,7-dihydro-4H-pyrrolo[2,3-d]pyrimidin-4-one | $^1$H-NMR (DMSO-$d_6$) δ: 11.55 (1H, br s), 8.40 (1H, s), 7.49 (1H, d, J = 8.8 Hz), 7.34 (1H, d, J = 8.8 Hz), 6.92 (1H, s), 4.21 (3H, s), 3.61-3.51 (2H, m), 3.34 (3H, s), 3.28-3.17 (2H, m), 2.95-2.87 (1H, m), 1.92-1.76 (1H, m), 1.05 (3H, d, J = 6.6 Hz). | 412, 414 | 1 |
| 58 | 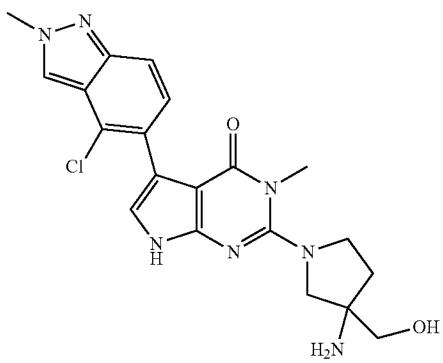 [SMILES: Cn1cc2c(Cl)c(-c3c[nH]c4nc(N5CCC(N)(CO)C5)n(C)c(=O)c34)ccc2n1] | 2-(3-amino-3-(hydroxymethyl)pyrrolidin-1-yl)-5-(4-chloro-2-methyl-2H-indazol-5-yl)-3-methyl-3,7-dihydro-4H-pyrrolo[2,3-d]pyrimidin-4-one | $^1$H-NMR (DMSO-$d_6$) δ: 11.47 (1H, br s), 8.37 (1H, s), 7.47 (1H, d, J = 8.7 Hz), 7.32 (1H, d, J = 8.7 Hz), 6.89 (1H, s), 4.86 (1H, br s), 4.18 (3H, s), 3.76-3.67 (1H, m), 3.51-3.01 (8H, m), 1.93-1.83 (1H, m), 1.67-1.54 (1H, m). | 428, 430 | 1 |
| 59 | 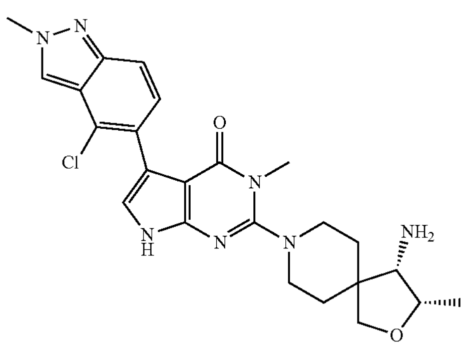 | 2-((3S,4S)-4-amino-3-methyl-2-oxa-8-azaspiro[4.5]decan-8-yl)-5-(4-chloro-2-methyl-2H-indazol-5-yl)-3-methyl-3,7-dihydro-4H-pyrrolo[2,3-d]pyrimidin-4-one | $^1$H-NMR (DMSO-$d_6$) δ: 11.74 (1H, br s), 8.40 (1H, s), 7.49 (1H, d, J = 8.8 Hz), 7.32 (1H, d, J = 8.8 Hz), 7.01 (1H, d, J = 2.0 Hz), 4.19 (3H, s), 4.09-4.02 (1H, m), 3.66 (1H, d, J = 8.3 Hz), 3.49 (1H, d, J = 8.5 Hz), 3.40 (3H, s), 3.27-3.19 (1H, m), 3.00-2.85 (3H, m), 1.90-1.84 (1H, m), 1.80-1.73 (1H, m), 1.66-1.55 (2H, m), 1.36-1.24 (2H, m), 1.09 (3H, d, J = 6.3 Hz). | 482, 484 | 1 |

TABLE 10-continued

| Example | Structure | Name | NMR data | MS: [M + H]⁺ m/z | Method |
|---|---|---|---|---|---|
| 60 | 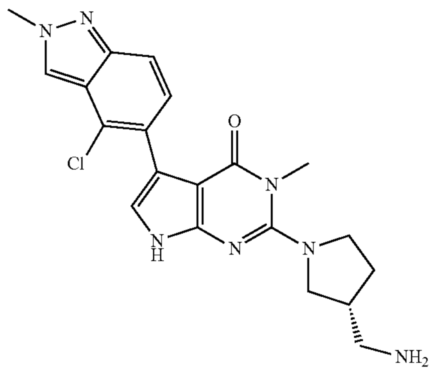 [SMILES: Cn1cc2c(Cl)c(-c3c[nH]c4nc(N5CC[C@H](CN)C5)n(C)c(=O)c34)ccc2n1] | (R)-2-(3-(aminomethyl)pyrrolidin-1-yl)-5-(4-chloro-2-methyl-2H-indazol-5-yl)-3-methyl-3,7-dihydro-4H-pyrrolo[2,3-d]pyrimidin-4-one | $^1$H-NMR (DMSO-$d_6$) δ: 11.64 (1H, br s), 8.38 (1H, s), 7.47 (1H, d, J = 8.7 Hz), 7.32 (1H, d, J = 8.9 Hz), 6.91 (1H, s), 4.18 (3H, s), 3.55-3.26 (7H, m), 2.87-2.76 (2H, m), 2.45-2.36 (1H, m), 2.13-2.00 (1H, m), 1.76-1.61 (1H, m). | 412, 414 | 1 |
| 61 | 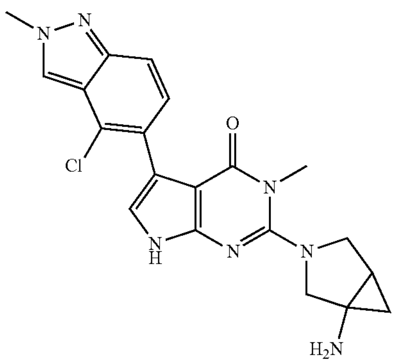 [SMILES: Cn1cc2c(Cl)c(-c3c[nH]c4nc(N5CC6CC6(N)C5)n(C)c(=O)c34)ccc2n1] | 2-(1-amino-3-azabicyclo[3.1.0]hexan-3-yl)-5-(4-chloro-2-methyl-2H-indazol-5-yl)-3-methyl-3,7-dihydro-4H-pyrrolo[2,3-d]pyrimidin-4-one | $^1$H-NMR (DMSO-$d_6$) δ: 11.68 (1H, br s), 8.38 (1H, s), 7.47 (1H, d, J = 8.8 Hz), 7.31 (1H, d, J = 8.9 Hz), 6.94 (1H, d, J = 2.3 Hz), 4.18 (3H, s), 3.73 (1H, d, J = 9.9 Hz), 3.58-3.46 (2H, m), 3.36-3.25 (4H, m), 1.39-1.31 (1H, m), 0.81-0.74 (1H, m), 0.69-0.62 (1H, m). | 410, 412 | 1 |
| 62 | 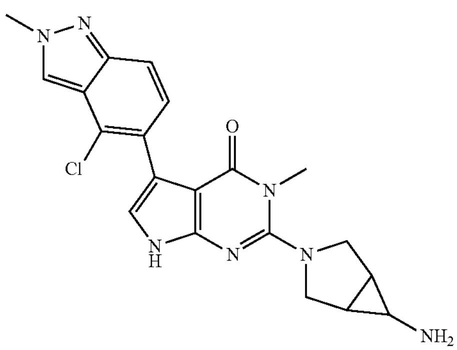 [SMILES: Cn1cc2c(Cl)c(-c3c[nH]c4nc(N5CC6C(N)C6C5)n(C)c(=O)c34)ccc2n1] | 2-(6-amino-3-azabicyclo[3.1.0]hexan-3-yl)-5-(4-chloro-2-methyl-2H-indazol-5-yl)-3-methyl-3,7-dihydro-4H-pyrrolo[2,3-d]pyrimidin-4-one | $^1$H-NMR (DMSO-$d_6$) δ: 11.59 (1H, br s), 8.38 (1H, s), 7.47 (1H, d, J = 8.8 Hz), 7.31 (1H, d, J = 8.9 Hz), 6.94 (1H, d, J = 2.3 Hz), 4.18 (3H, s), 3.73 (1H, d, J = 9.9 Hz), 3.58-3.46 (2H, m), 3.36-3.25 (4H, m), 1.39-1.31 (1H, m), 0.81-0.74 (1H, m), 0.69-0.62 (1H, m). | 410, 412 | 1 |
| 63 | 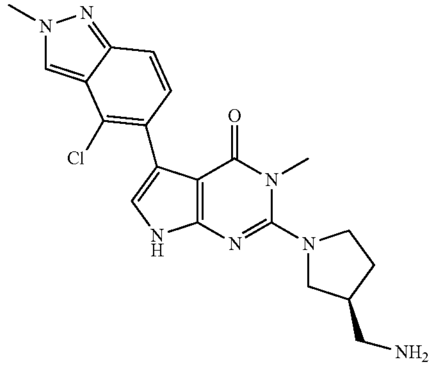 [SMILES: Cn1cc2c(Cl)c(-c3c[nH]c4nc(N5CC[C@@H](CN)C5)n(C)c(=O)c34)ccc2n1] | (S)-2-(3-(aminomethyl)pyrrolidin-1-yl)-5-(4-chloro-2-methyl-2H-indazol-5-yl)-3-methyl-3,7-dihydro-4H-pyrrolo[2,3-d]pyrimidin-4-one | $^1$H-NMR (DMSO-$d_6$) δ: 8.38 (1H, s), 7.47 (1H, d, J = 8.9 Hz), 7.32 (1H, d, J = 8.8 Hz), 6.90 (1H, s), 4.18 (3H, s), 3.51-3.22 (7H, m), 2.64-2.53 (2H, m), 2.26-2.12 (1H, m), 2.03-1.92 (1H, m), 1.68-1.54 (1H, m). | 412, 414 | 2 |

TABLE 10-continued

| Example | Structure | Name | NMR data | MS: [M + H]+ m/z | Method |
|---|---|---|---|---|---|
| 64 | 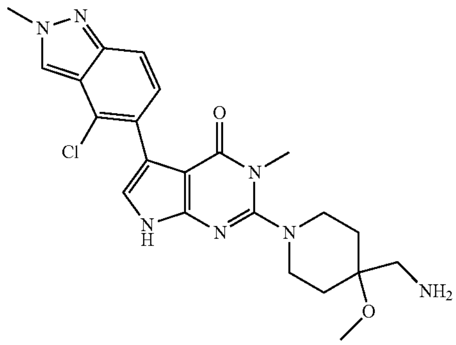 [SMILES: COC1(CN)CCN(c2nc3[nH]cc(-c4ccc5nn(C)cc5c4Cl)c3c(=O)n2C)CC1] | 2-(4-(aminomethyl)-4-methoxypiperidin-1-yl)-5-(4-chloro-2-methyl-2H-indazol-5-yl)-3-methyl-3,7-dihydro-4H-pyrrolo[2,3-d]pyrimidin-4-one | 1H-NMR (DMSO-d6) δ: 8.40 (1H, s), 7.48 (1H, d, J = 8.8 Hz), 7.32 (1H, d, J = 8.8 Hz), 7.01 (1H, s), 4.19 (3H, s), 3.39 (3H, s), 3.17-3.14 (5H, m), 3.01-2.98 (2H, m), 2.60 (2H, s), 1.83-1.80 (2H, m), 1.65-1.59 (2H, m). | 456, 458 | 2 |
| 65 | 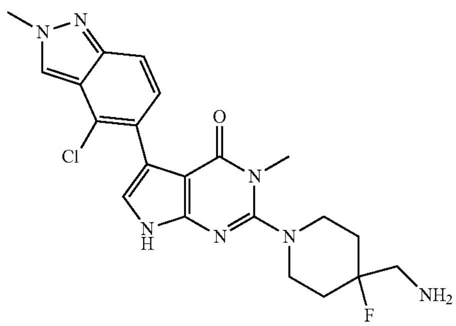 [SMILES: Cn1cc2c(Cl)c(-c3c[nH]c4nc(N5CCC(F)(CN)CC5)n(C)c(=O)c34)ccc2n1] | 2-(4-(aminomethyl)-4-fluoropiperidin-1-yl)-5-(4-chloro-2-methyl-2H-indazol-5-yl)-3-methyl-3,7-dihydro-4H-pyrrolo[2,3-d]pyrimidin-4-one | 1H-NMR (DMSO-d6) δ: 8.40 (1H, s), 7.48 (1H, d, J = 8.9 Hz), 7.32 (1H, d, J = 8.9 Hz), 7.02 (1H, s), 4.19 (3H, s), 3.40 (3H, s), 3.01-2.99 (2H, m), 2.72 (2H, d, J = 19.8 Hz), 2.54 (2H, s), 1.90-1.80 (4H, m). | 444, 446 | 2 |
| 66 | 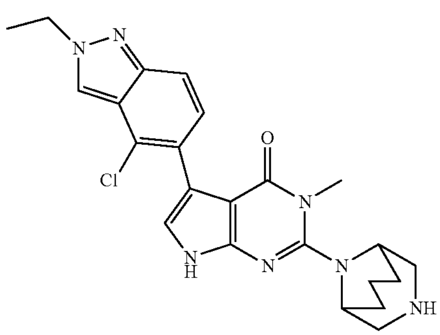 [SMILES: CCn1cc2c(Cl)c(-c3c[nH]c4nc(N5C6CCCC5CNC6)n(C)c(=O)c34)ccc2n1] | 2-(3,9-diazabicyclo[3.3.1]nonan-9-yl)-5-(4-chloro-2-ethyl-2H-indazol-5-yl)-3-methyl-3,7-dihydro-4H-pyrrolo[2,3-d]pyrimidin-4-one | 1H-NMR (DMSO-d6) δ: 11.56 (1H, br s), 8.43 (1H, s), 7.49 (1H, d, J = 8.8 Hz), 7.33 (1H, d, J = 8.8 Hz), 6.93 (1H, d, J = 2.4 Hz), 4.48 (2H, q, J = 7.2 Hz), 3.65 (2H, br s), 3.37-3.33 (4H, m), 3.28-3.25 (1H, m), 2.92-2.89 (2H, m), 2.79-2.67 (1H, m), 2.20-2.07 (2H, m), 1.76-1.70 (2H, m), 1.63-1.56 (1H, m), 1.52 (3H, t, J = 7.2 Hz). | 452, 454 | 1 |
| 67 | 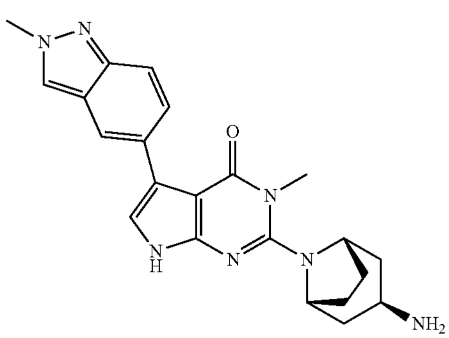 [SMILES: Cn1cc2cc(-c3c[nH]c4nc(N5[C@@H]6CC[C@H]5C[C@@H](N)C6)n(C)c(=O)c34)ccc2n1] | 2-(endo-3-amino-8-azabicyclo[3.2.1]octan-8-yl)-3-methyl-5-(2-methyl-2H-indazol-5-yl)-3,7-dihydro-4H-pyrrolo[2,3-d]pyrimidin-4-one | 1H-NMR (DMSO-d6) δ: 11.50 (1H, br s), 8.26 (1H, s), 7.75-7.46 (2H, m), 7.14 (1H, s), 4.16-4.06 (5H, m), 3.51-3.40 (4H, m), 2.27-2.10 (4H, m), 2.00-1.90 (2H, m), 1.58 (2H, d, J = 13.6 Hz). | 404 | 1 |

TABLE 10-continued

| Example | Structure | Name | NMR data | MS: [M + H]+ m/z | Method |
|---|---|---|---|---|---|
| 68 | 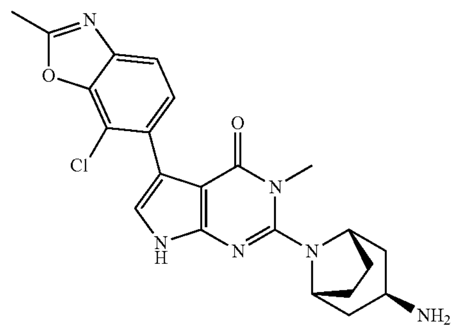 | 2-(endo-3-amino-8-azabicyclo[3.2.1]octan-8-yl)-5-(7-chloro-2-methylbenzo[d]oxazol-6-yl)-3-methyl-3,7-dihydro-4H-pyrrolo[2,3-d]pyrimidin-4-one | $^1$H-NMR (DMSO-$d_6$) δ: 11.65 (1H, br s), 7.55 (1H, d, J = 8.3 Hz), 7.40 (1H, d, J = 8.3 Hz), 6.96 (1H, s), 4.08 (2H, br s), 3.40 (3H, s), 3.35-3.31 (1H, m), 2.65 (3H, s), 2.26-2.20 (2H, m), 2.17-2.09 (2H, m), 1.98-1.90 (2H, m), 1.60-1.53 (2H, m). | 439, 441 | 2 |
| 69 | 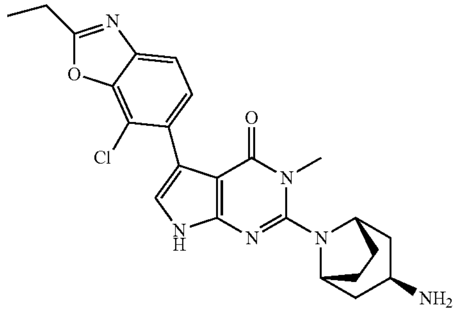 | 2-(endo-3-amino-8-azabicyclo[3.2.1]octan-8-yl)-5-(7-chloro-2-ethylbenzo[d]oxazol-6-yl)-3-methyl-3,7-dihydro-4H-pyrrolo[2,3-d]pyrimidin-4-one | $^1$H-NMR (CD$_3$OD) δ: 7.52 (1H, d, J = 8.4 Hz), 7.46 (1H, d, J = 8.4 Hz), 6.96 (1H, s), 4.22 (2H, br s), 3.55 (3H, s), 3.37-3.33 (1H, m), 3.03 (2H, q, J = 7.7 Hz), 2.56-2.44 (2H, m), 2.27-2.17 (2H, m), 2.06-1.98 (2H, m), 1.68 (2H, br d, J = 13.6 Hz), 1.46 (3H, t, J = 7.7 Hz). | 453, 455 | 1 |
| 70 | 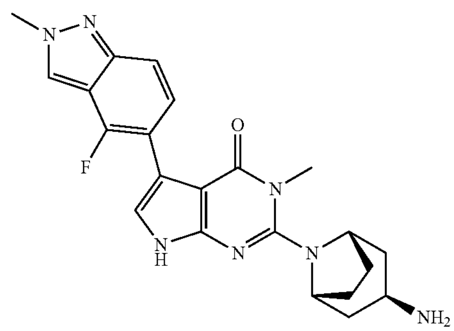 [SMILES: Cn1cc2c(F)c(-c3c[nH]c4nc(N5[C@@H]6CC[C@H]5C[C@@H](N)C6)n(C)c(=O)c34)ccc2n1] | 2-(endo-3-amino-8-azabicyclo[3.2.1]octan-8-yl)-5-(4-fluoro-2-methyl-2H-indazol-5-yl)-3-methyl-3,7-dihydro-4H-pyrrolo[2,3-d]pyrimidin-4-one | $^1$H-NMR (DMSO-$d_6$) δ: 11.61 (1H, br s), 8.44 (1H, s), 7.60-7.31 (2H, m), 6.99 (1H, s), 4.19-4.09 (5H, m), 3.55-3.32 (4H, m), 2.33-2.19 (2H, m), 2.13-1.95 (4H, m), 1.67-1.55 (2H, m). | 422 | 2 |
| 71 | 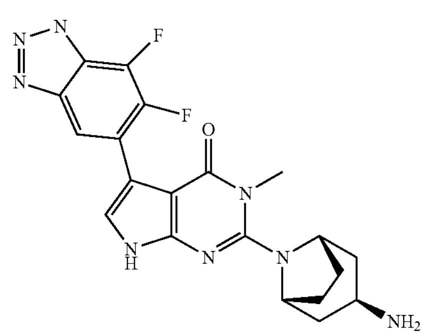 [SMILES: Cn1c(N2[C@@H]3CC[C@H]2C[C@@H](N)C3)nc2[nH]cc(-c3cc4nn[nH]c4c(F)c3F)c2c1=O] | 2-(endo-3-amino-8-azabicyclo[3.2.1]octan-8-yl)-5-(6,7-difluoro-1-methyl-1H-benzo[d][1,2,3]triazol-5-yl)-3-methyl-3,7-dihydro-4H-pyrrolo[2,3-d]pyrimidin-4-one | $^1$H-NMR (DMSO-$d_6$) δ: 11.78 (1H, s), 8.29 (1H, d, J = 4.6 Hz), 7.16 (1H, d, J = 1.8 Hz), 4.42 (3H, s), 4.17-4.03 (2H, m), 3.45 (3H, s), 2.63-2.61 (1H, m), 2.27-2.21 (2H, m), 2.18-2.12 (2H, m), 1.98-1.92 (2H, m), 1.61-1.56 (2H, m). | 441 | 2 |

TABLE 10-continued

| Example | Name | NMR data | MS: [M + H]+ m/z | Method |
|---|---|---|---|---|
| 72 | 2-(endo-3-amino-8-azabicyclo[3.2.1]octan-8-yl)-5-(6-fluoro-2-methyl-2H-indazol-5-yl)-3-methyl-3,7-dihydro-4H-pyrrolo[2,3-d]pyrimidin-4-one | 1H-NMR (DMSO-d6) δ: 11.57 (1H, s), 8.34 (1H, s), 8.06 (1H, d, J = 7.9 Hz), 7.28 (1H, d, J = 11.9 Hz), 6.97 (1H, d, J = 2.4 Hz), 4.14 (3H, s), 4.11-4.06 (2H, m), 3.44 (3H, s), 2.63-2.59 (1H, m), 2.25-2.21 (2H, m), 2.17-2.11 (2H, m), 1.98-1.92 (2H, m), 1.61-1.54 (2H, m). | 422 | 2 |
| 73 | 2-(endo-3-amino-8-azabicyclo[3.2.1]octan-8-yl)-5-(4-methoxy-2-methyl-2H-indazol-5-yl)-3-methyl-3,7-dihydro-4H-pyrrolo[2,3-d]pyrimidin-4-one | 1H-NMR (DMSO-d6) δ: 11.43 (1H, s), 8.51 (1H, s), 7.42 (1H, d, J = 8.9 Hz), 7.17 (1H, dd, J = 8.7, 1.1 Hz), 6.90 (1H, d, J = 2.4 Hz), 4.15 (3H, s), 4.11-4.07 (2H, m), 3.89 (3H, s), 3.43 (3H, s), 2.55-2.53 (1H, m), 2.23-2.12 (4H, m), 2.00-1.93 (2H, m), 1.61-1.55 (2H, m). | 434 | 2 |
| 74 | 2-(endo-3-amino-8-azabicyclo[3.2.1]octan-8-yl)-5-(7-chloro-1-methyl-1H-benzo[d][1,2,3]triazol-6-yl)-3-methyl-3,7-dihydro-4H-pyrrolo[2,3-d]pyrimidin-4-one | 1H-NMR (DMSO-d6) δ: 11.73 (1H, s), 7.92 (1H, d, J = 8.5 Hz), 7.44 (1H, d, J = 8.5 Hz), 7.02 (1H, d, J = 1.5 Hz), 4.53 (3H, s), 4.11-4.08 (2H, m), 3.41 (3H, s), 2.53-2.51 (1H, m), 2.27-2.22 (2H, m), 2.16-2.10 (2H, m), 1.99-1.92 (2H, m), 1.60-1.55 (2H, m). | 439, 441 | 2 |
| 75 | 2-(endo-3-amino-8-azabicyclo[3.2.1]octan-8-yl)-5-(4-chloro-2-(2-hydroxy-2-methylpropyl)-2H-indazol-5-yl)-3-methyl-3,7-dihydro-4H-pyrrolo[2,3-d]pyrimidin-4-one | 1H-NMR (DMSO-d6) δ: 11.60 (1H, s), 8.30 (1H, d, J = 0.9 Hz), 7.51 (1H, dd, J = 8.9, 0.9 Hz), 7.31 (1H, d, J = 8.9 Hz), 6.94 (1H, s), 4.88 (1H, s), 4.36 (2H, s), 4.11-4.07 (2H, m), 3.41 (3H, s), 2.69-2.65 (1H, m), 2.25-2.20 (2H, m), 2.18-2.11 (2H, m), 1.99-1.92 (2H, m), 1.60-1.55 (2H, m), 1.13 (6H, s). | 496, 498 | 2 |

TABLE 10-continued

| Example | Structure | Name | NMR data | MS: [M + H]+ m/z | Method |
|---|---|---|---|---|---|
| 76 | 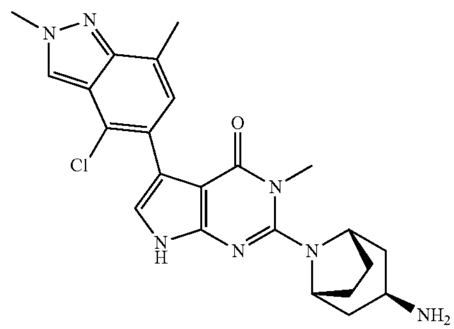 [SMILES: Cc1cc(-c2c[nH]c3nc(N4[C@@H]5CC[C@H]4C[C@@H](N)C5)n(C)c(=O)c23)c(Cl)c2cn(C)nc12] | 2-(endo-3-amino-8-azabicyclo[3.2.1]octan-8-yl)-5-(4-chloro-2,7-dimethyl-2H-indazol-5-yl)-3-methyl-3,7-dihydro-4H-pyrrolo[2,3-d]pyrimidin-4-one | ¹H-NMR (CDCl₃) δ: 8.46 (1H, br s), 7.93 (1H, s), 7.25 (1H, s), 6.90 (1H, d, J = 2.2 Hz), 4.23 (3H, s), 4.10 (2H, br s), 3.55 (3H, s), 3.43 (1H, br t, J = 6.1 Hz), 2.60 (3H, s), 2.38-2.26 (2H, m), 2.23-2.13 (2H, m), 2.13-2.04 (2H, m), 1.60 (2H, br d, J = 13.9 Hz). | 452, 454 | 1 |
| 77 | 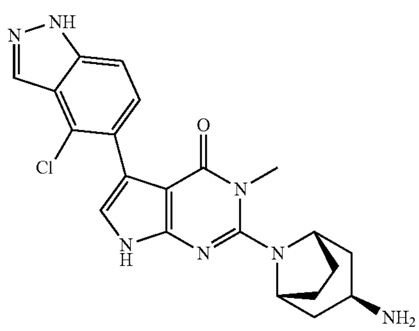 [SMILES: Cn1c(N2[C@@H]3CC[C@H]2C[C@@H](N)C3)nc2[nH]cc(-c3ccc4[nH]ncc4c3Cl)c2c1=O] | 2-(endo-3-amino-8-azabicyclo[3.2.1]octan-8-yl)-5-(1H-indazol-5-yl)-3-methyl-3,7-dihydro-4H-pyrrolo[2,3-d]pyrimidin-4-one | ¹H-NMR (DMSO-d₆) δ: 13.32 (1H, s), 11.58 (1H, s), 8.07 (1H, s), 7.45-7.42 (2H, m), 6.93 (1H, d, J = 1.5 Hz), 4.11-4.05 (2H, m), 3.28 (3H, s), 2.47-2.43 (1H, m), 2.25-2.20 (2H, m), 2.16-2.09 (2H, m), 1.98-1.91 (2H, m), 1.59-1.54 (2H, m). | 424, 426 | 2 |
| 78 | 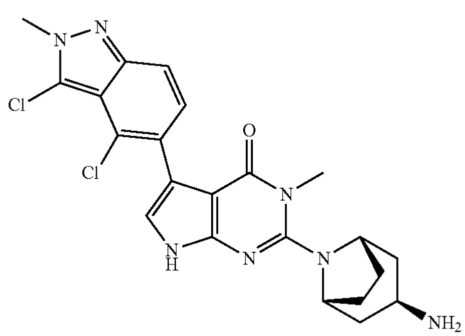 [SMILES: Cn1nc2ccc(-c3c[nH]c4nc(N5[C@@H]6CC[C@H]5C[C@@H](N)C6)n(C)c(=O)c34)c(Cl)c2c1Cl] | 2-(endo-3-amino-8-azabicyclo[3.2.1]octan-8-yl)-5-(3,4-dichloro-2-methyl-2H-indazol-5-yl)-3-methyl-3,7-dihydro-4H-pyrrolo[2,3-d]pyrimidin-4-one | ¹H-NMR (CDCl₃) δ: 8.37 (1H, br s), 7.53 (1H, d, J = 8.8 Hz), 7.46 (1H, d, J = 8.8 Hz), 6.94 (1H, d, J = 2.2 Hz), 4.14 (3H, s), 4.13-4.07 (2H, m), 3.55 (3H, s), 3.48-3.38 (1H, m), 2.39-2.25 (2H, m), 2.25-2.07 (4H, m), 1.61 (2H, br d, J = 13.9 Hz). | 472, 474 | 1 |
| 79 | 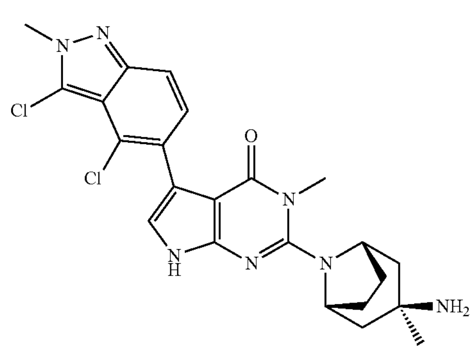 [SMILES: Cn1nc2ccc(-c3c[nH]c4nc(N5[C@@H]6CC[C@H]5C[C@@](C)(N)C6)n(C)c(=O)c34)c(Cl)c2c1Cl] | 2-(endo-3-amino-3-methyl-8-azabicyclo[3.2.1]octan-8-yl)-5-(3,4-dichloro-2-methyl-2H-indazol-5-yl)-3-methyl-3,7-dihydro-4H-pyrrolo[2,3-d]pyrimidin-4-one | ¹H-NMR (DMSO-d₆) δ: 11.63 (1H, br s), 7.50 (1H, d, J = 8.8 Hz), 7.33 (1H, d, J = 8.8 Hz), 6.97 (1H, s), 4.14 (3H, s), 4.09 (2H, br s), 3.41 (3H, s), 2.35-2.23 (2H, m), 1.96-1.81 (4H, m), 1.61 (2H, br d, J = 13.6 Hz), 1.09 (3H, s). | 486, 488 | 1 |

TABLE 10-continued

| Example | Structure | Name | NMR data | MS: [M + H]+ m/z | Method |
|---|---|---|---|---|---|
| 80 | 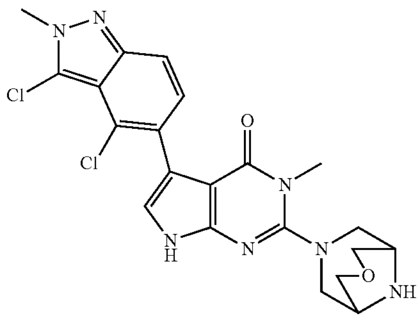 [SMILES: Cn1nc2ccc(-c3c[nH]c4nc(N5CC6COCC(C5)N6)n(C)c(=O)c34)c(Cl)c2c1Cl] | 2-(3-oxa-7,9-diazabicyclo[3.3.1]nonan-7-yl)-5-(3,4-dichloro-2-methyl-2H-indazol-5-yl)-3-methyl-3,7-dihydro-4H-pyrrolo[2,3-d]pyrimidin-4-one | $^1$H-NMR (CDCl$_3$) δ: 8.45 (1H, br s), 7.54 (1H, d, J = 8.8 Hz), 7.46 (1H, d, J = 8.8 Hz), 7.00 (1H, d, J = 1.8 Hz), 4.15 (3H, s), 4.03 (4H, s), 3.67 (3H, s), 3.57 (2H, br d, J = 12.1 Hz), 3.37 (2H, br d, J = 12.1 Hz), 3.01 (2H, br s). | 474, 476 | 1 |
| 81 | 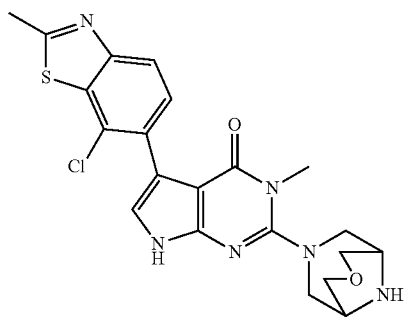 [SMILES: Cc1nc2ccc(-c3c[nH]c4nc(N5CC6COCC(C5)N6)n(C)c(=O)c34)c(Cl)c2s1] | 2-(3-oxa-7,9-diazabicyclo[3.3.1]nonan-7-yl)-5-(7-chloro-2-methylbenzo[d]thiazol-6-yl)-3-methyl-3,7-dihydro-4H-pyrrolo[2,3-d]pyrimidin-4-one | $^1$H-NMR (DMSO-d$_6$) δ: 11.86 (1H, br s), 7.84 (1H, d, J = 8.4 Hz), 7.57 (1H, d, J = 8.4 Hz), 7.07 (1H, d, J = 2.6 Hz), 3.91 (2H, d, J = 11.0 Hz), 3.83 (2H, br d, J = 11.0 Hz), 3.51 (3H, s), 3.48 (2H, br d, J = 11.7 Hz), 3.20 (2H, br d, J = 11.7 Hz), 2.88-2.81 (5H, m). | 457, 459 | 1 |
| 82 | 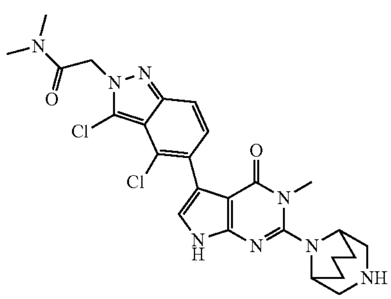 [SMILES: CN(C)C(=O)Cn1nc2ccc(-c3c[nH]c4nc(N5C6CCCC5CNC6)n(C)c(=O)c34)c(Cl)c2c1Cl] | 2-(5-(2-(3,9-diazabicyclo[3.3.1]nonan-9-yl)-3-methyl-4-oxo-4,7-dihydro-3H-pyrrolo[2,3-d]pyrimidin-5-yl)-3,4-dichloro-2H-indazol-2-yl)-N,N-dimethylacetamide | $^1$H-NMR (DMSO-d$_6$) δ: 11.62 (1H, s), 7.51-7.48 (1H, m), 7.36-7.33 (1H, m), 6.97 (1H, d, J = 2.4 Hz), 5.52 (2H, s), 3.67-3.65 (2H, m), 3.28-3.24 (5H, m), 3.12 (3H, s), 2.93-2.88 (5H, m), 2.78-2.71 (1H, m), 2.17-2.06 (2H, m), 1.75-1.70 (2H, m), 1.61-1.54 (1H, m). | 543, 545 | 2 |
| 83 | 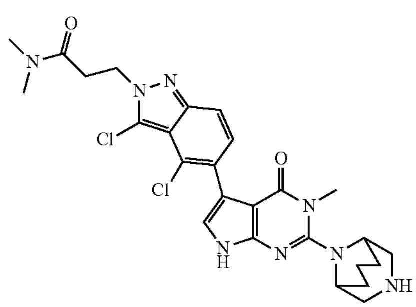 [SMILES: CN(C)C(=O)CCn1nc2ccc(-c3c[nH]c4nc(N5C6CCCC5CNC6)n(C)c(=O)c34)c(Cl)c2c1Cl] | 3-(5-(2-(3,9-diazabicyclo[3.3.1]nonan-9-yl)-3-methyl-4-oxo-4,7-dihydro-3H-pyrrolo[2,3-d]pyrimidin-5-yl)-3,4-dichloro-2H-indazol-2-yl)-N,N-dimethylpropanamide | $^1$H-NMR (DMSO-d$_6$) δ: 11.61 (1H, s), 7.50 (1H, d, J = 8.9 Hz), 7.33 (1H, d, J = 8.9 Hz), 6.96 (1H, d, J = 2.4 Hz), 4.63 (2H, t, J = 7.0 Hz), 3.68-3.63 (2H, m), 3.30-3.26 (5H, m), 3.07 (2H, t, J = 7.0 Hz), 2.96 (3H, s), 2.91 (2H, d, J = 11.3 Hz), 2.81 (3H, s), 2.76-2.70 (1H, m), 2.15-2.10 (2H, m), 1.75-1.71 (2H, m), 1.62-1.56 (1H, m). | 557, 559 | 2 |

TABLE 10-continued

| Example | Structure | Name | NMR data | MS: [M + H]+ m/z | Method |
|---|---|---|---|---|---|
| 84 | 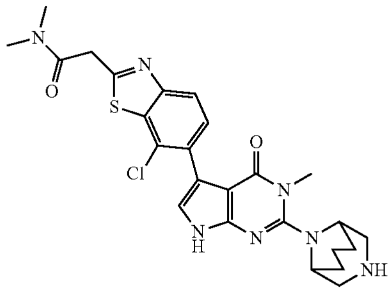 [SMILES: CN(C)C(=O)Cc1nc2ccc(-c3c[nH]c4nc(N5C6CCCC5CNC6)n(C)c(=O)c34)c(Cl)c2s1] | 2-(6-(2-(3,9-diazabicyclo[3.3.1]nonan-9-yl)-3-methyl-4-oxo-4,7-dihydro-3H-pyrrolo[2,3-d]pyrimidin-5-yl)-7-chlorobenzo[d]thiazol-2-yl)-N,N-dimethylacetamide | | 526, 528 | 2 |
| 85 | 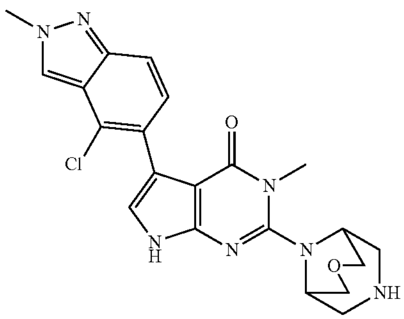 | 2-(3-oxa-7,9-diazabicyclo[3.3.1]nonan-9-yl)-5-(4-chloro-2-methyl-2H-indazol-5-yl)-3-methyl-3,7-dihydro-4H-pyrrolo[2,3-d]pyrimidin-4-one | $^1$H-NMR (DMSO-$d_6$) δ: 11.63 (1H, br s), 8.38 (1H, s), 7.47 (1H, d, J = 8.8 Hz), 7.32 (1H, d, J = 9.6 Hz), 6.97 (1H, s), 4.18 (3H, s), 4.12 (2H, d, J = 11.3 Hz), 3.96 (2H, d, J = 10.9 Hz), 3.51-3.43 (2H, m), 3.33-3.24 (2H, m), 3.33 (3H, s), 3.09 (2H, d, J = 13.9 Hz). | 440, 442 | 1 |
| 86 | 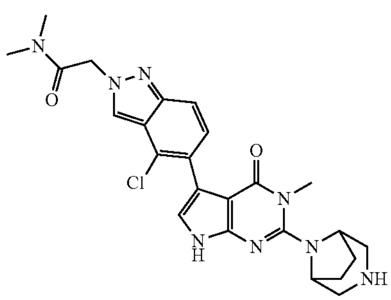 [SMILES: CN(C)C(=O)Cn1cc2c(Cl)c(-c3c[nH]c4nc(N5C6CCC5CNC6)n(C)c(=O)c34)ccc2n1] | 2-(5-(2-(3,8-diazabicyclo[3.2.1]octan-8-yl)-3-methyl-4-oxo-4,7-dihydro-3H-pyrrolo[2,3-d]pyrimidin-5-yl)-4-chloro-2H-indazol-2-yl)-N,N-dimethylacetamide | 1H-NMR (DMSO-$d_6$) δ: 11.64 (1H, s), 8.32 (1H, d, J = 0.9 Hz), 7.47 (1H, dd, J = 8.9, 0.9 Hz), 7.33 (1H, d, J = 8.9 Hz), 6.96 (1H, d, J = 2.4 Hz), 5.47 (2H, s), 3.99-3.96 (2H, m), 3.45 (3H, s), 3.10 (3H, s), 3.01-2.96 (2H, m), 2.88 (3H, s), 2.66-2.63 (2H, m), 1.97-1.90 (2H, m), 1.86-1.82 (2H, m). | 495, 497 | 2 |
| 87 | 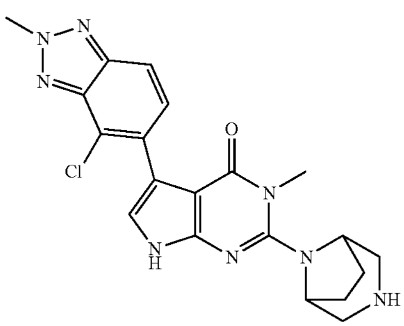 | 2-(3,8-diazabicyclo[3.2.1]octan-8-yl)-5-(4-chloro-2-methyl-2H-benzo[d][1,2,3]triazol-5-yl)-3-methyl-3,7-dihydro-4H-pyrrolo[2,3-d]pyrimidin-4-one | $^1$H-NMR (DMSO-$d_6$) δ: 11.76 (1H, s), 7.79 (1H, d, J = 8.9 Hz), 7.53 (1H, d, J = 8.9 Hz), 7.07 (1H, d, J = 2.1 Hz), 4.53 (3H, s), 4.00-3.97 (2H, m), 3.46 (3H, s), 3.00-2.95 (2H, m), 2.67-2.63 (2H, m), 1.96-1.91 (2H, m), 1.86-1.82 (2H, m). | 425, 427 | 2 |

TABLE 10-continued

| Example | Structure | Name | NMR data | MS: [M + H]+ m/z | Method |
|---|---|---|---|---|---|
| 88 | 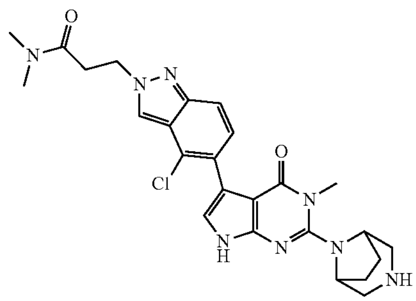 [SMILES: CN(C)C(=O)CCn1cc2c(Cl)c(-c3c[nH]c4nc(N5C6CCC5CNC6)n(C)c(=O)c34)ccc2n1] | 3-(5-(2-(3,8-diazabicyclo[3.2.1]octan-8-yl)-3-methyl-4-oxo-4,7-dihydro-3H-pyrrolo[2,3-d]pyrimidin-5-yl)-4-chloro-2H-indazol-2-yl)-N,N-dimethylpropanamide | ¹H-NMR (DMSO-d₆) δ: 11.63 (1H, s), 8.42 (1H, d, J = 0.9 Hz), 7.48 (1H, dd, J = 8.5, 0.9 Hz), 7.31 (1H, d, J = 8.9 Hz), 6.94 (1H, d, J = 2.1 Hz), 4.66 (2H, t, J = 6.9 Hz), 3.99-3.95 (2H, m), 3.45 (3H, s), 3.05 (2H, t, J = 6.9 Hz), 2.99-2.95 (2H, m), 2.94 (3H, s), 2.82 (3H, s), 2.66-2.63 (2H, m), 1.96-1.90 (2H, m), 1.86-1.82 (2H, m). | 509, 511 | 2 |
| 89 | 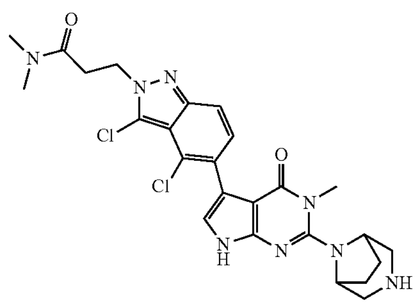 [SMILES: CN(C)C(=O)CCn1nc2ccc(-c3c[nH]c4nc(N5C6CCC5CNC6)n(C)c(=O)c34)c(Cl)c2c1Cl] | 3-(5-(2-(3,8-diazabicyclo[3.2.1]octan-8-yl)-3-methyl-4-oxo-4,7-dihydro-3H-pyrrolo[2,3-d]pyrimidin-5-yl)-3,4-dichloro-2H-indazol-2-yl)-N,N-dimethylpropanamide | ¹H-NMR (DMSO-d₆) δ: 11.66 (1H, s), 7.50 (1H, d, J = 8.9 Hz), 7.32 (1H, d, J = 8.9 Hz), 6.96 (1H, d, J = 2.4 Hz), 4.63 (2H, t, J = 7.0 Hz), 3.99-3.95 (2H, m), 3.45 (3H, s), 3.07 (2H, t, J = 7.0 Hz), 2.99-2.96 (5H, m), 2.81 (3H, s), 2.67-2.63 (2H, m), 1.96-1.90 (2H, m), 1.86-1.80 (2H, m). | 543, 545 | 2 |
| 90 | 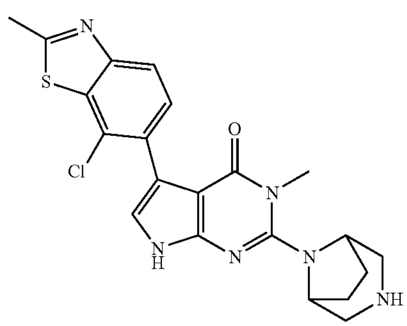 [SMILES: Cc1nc2ccc(-c3c[nH]c4nc(N5C6CCC5CNC6)n(C)c(=O)c34)c(Cl)c2s1] | 2-(3,8-diazabicyclo[3.2.1]octan-8-yl)-5-(7-chloro-2-methylbenzo[d]thiazol-6-yl)-3-methyl-3,7-dihydro-4H-pyrrolo[2,3-d]pyrimidin-4-one | ¹H-NMR (DMSO-d₆) δ: 11.74 (1H, br s), 7.83 (1H, d, J = 8.5 Hz), 7.57 (1H, d, J = 8.5 Hz), 7.02 (1H, s), 3.98 (2H, br s), 3.45 (3H, s), 2.99-2.96 (2H, m), 2.83 (3H, s), 2.65-2.62 (2H, m), 1.94-1.82 (4H, m). | 441, 443 | 1 |
| 91 | 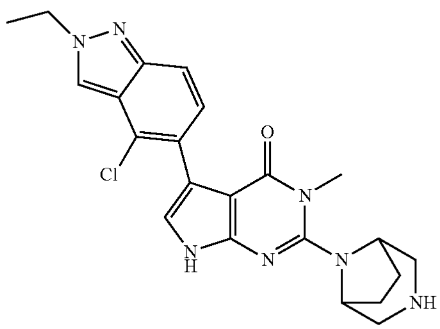 [SMILES: CCn1cc2c(Cl)c(-c3c[nH]c4nc(N5C6CCC5CNC6)n(C)c(=O)c34)ccc2n1] | 2-(3,8-diazabicyclo[3.2.1]octan-8-yl)-5-(4-chloro-2-ethyl-2H-indazol-5-yl)-3-methyl-3,7-dihydro-4H-pyrrolo[2,3-d]pyrimidin-4-one | ¹H-NMR (DMSO-d₆) δ: 11.61 (1H, br s), 8.43 (1H, s), 7.49 (1H, d, J = 8.8 Hz), 7.32 (1H, d, J = 8.8 Hz), 6.94 (1H, d, J = 2.4 Hz), 4.48 (2H, q, J = 7.2 Hz), 3.98 (2H, br s), 3.45 (3H, s), 3.00-2.96 (2H, m), 2.68-2.64 (2H, m), 1.97-1.81 (4H, m), 1.52 (3H, t, J = 7.2 Hz). | 438, 440 | 1 |

TABLE 10-continued

| Example | Structure | Name | NMR data | MS: [M + H]⁺ m/z | Method |
|---|---|---|---|---|---|
| 92 | 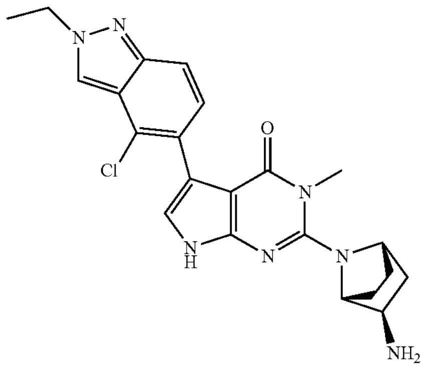 [SMILES: CCn1cc2c(Cl)c(-c3c[nH]c4nc(N5[C@H]6CC[C@@H]5[C@H](N)C6)n(C)c(=O)c34)ccc2n1] | 2-((1R,2R,4S)-2-amino-7-azabicyclo[2.2.1]heptan-7-yl)-5-(4-chloro-2-ethyl-2H-indazol-5-yl)-3-methyl-3,7-dihydro-4H-pyrrolo[2,3-d]pyrimidin-4-one | $^1$H-NMR (DMSO-$d_6$) δ: 11.61 (1H, br s), 8.44 (1H, s), 7.49 (1H, d, J = 8.8 Hz), 7.32 (1H, d, J = 8.8 Hz), 6.93 (1H, s), 4.48 (2H, q, J = 7.2 Hz), 4.14-4.12 (1H, m), 4.00-3.98 (1H, m), 3.48-3.43 (1H, m), 3.39 (3H, s), 2.30-2.22 (1H, m), 2.21-2.14 (1H, m), 1.96-1.88 (1H, m), 1.71-1.63 (2H, m), 1.54-1.46 (5H, m), 0.89-0.84 (1H, m). | 438, 440 | 1 |
| 93 | 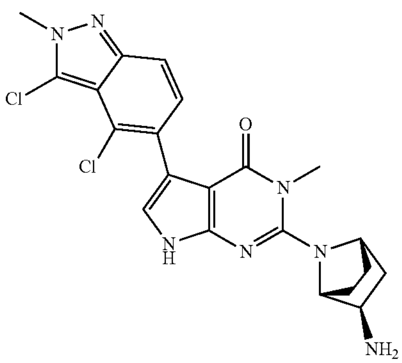 | 2-((1R,2R,4S)-2-amino-7-azabicyclo[2.2.1]heptan-7-yl)-5-(3,4-dichloro-2-methyl-2H-indazol-5-yl)-3-methyl-3,7-dihydro-4H-pyrrolo[2,3-d]pyrimidin-4-one | $^1$H-NMR (DMSO-$d_6$) δ: 11.67 (1H, br s), 7.50 (1H, d, J = 8.8 Hz), 7.33 (1H, d, J = 8.8 Hz), 6.97 (1H, s), 4.20-4.09 (4H, m), 4.01 (1H, br t, J = 4.0 Hz), 3.54-3.44 (1H, m), 3.39 (3H, s), 2.33-2.21 (1H, m), 2.20-2.07 (1H, m), 1.98-1.84 (1H, m), 1.80-1.61 (1H, m), 1.56-1.41 (1H, m), 0.90 (1H, br dd, J = 12.1, 4.0 Hz). | 458, 460 | 1 |
| 94 | 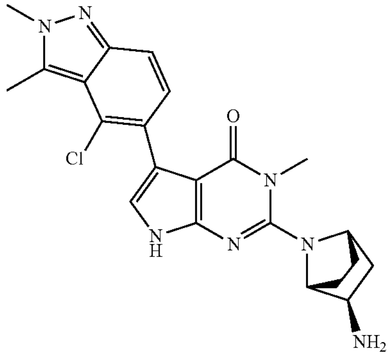 [SMILES: Cc1c2c(Cl)c(-c3c[nH]c4nc(N5[C@H]6CC[C@@H]5[C@H](N)C6)n(C)c(=O)c34)ccc2nn1C] | 2-((1R,2R,4S)-2-amino-7-azabicyclo[2.2.1]heptan-7-yl)-5-(4-chloro-2,3-dimethyl-2H-indazol-5-yl)-3-methyl-3,7-dihydro-4H-pyrrolo[2,3-d]pyrimidin-4-one | $^1$H-NMR (DMSO-$d_6$) δ: 11.58 (1H, s), 7.38 (1H, d, J = 8.9 Hz), 7.20 (1H, d, J = 8.9 Hz), 6.88 (1H, d, J = 2.4 Hz), 4.15-4.12 (1H, m), 4.06 (3H, s), 4.02-3.98 (1H, m), 3.49-3.44 (1H, m), 3.38 (3H, s), 2.82 (3H, s), 2.29-2.23 (1H, m), 2.19-2.13 (1H, m), 1.94-1.86 (1H, m), 1.72-1.63 (1H, m), 1.52-1.46 (1H, m), 0.91-0.85 (1H, m). | 438, 440 | 2 |

TABLE 10-continued

| Example | Structure | Name | NMR data | MS: [M + H]+ m/z | Method |
|---|---|---|---|---|---|
| 95 | 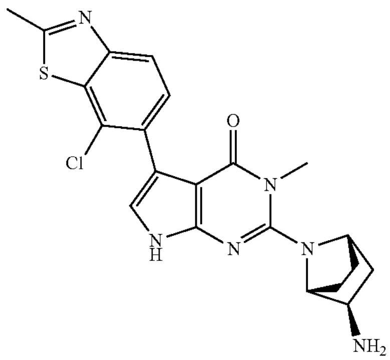 | 2-((1R,2R,4S)-2-amino-7-azabicyclo[2.2.1]heptan-7-yl)-5-(7-chloro-2-methylbenzo[d]thiazol-6-yl)-3-methyl-3,7-dihydro-4H-pyrrolo[2,3-d]pyrimidin-4-one | $^1$H-NMR (DMSO-$d_6$) δ: 7.83 (1H, d, J = 8.3 Hz), 7.57 (1H, d, J = 8.3 Hz), 7.01 (1H, s), 4.16-4.14 (1H, m), 4.05-4.02 (1H, m), 3.52-3.48 (2H, m), 3.39 (3H, s), 2.83 (3H, s), 2.32-2.21 (1H, m), 2.17-2.10 (1H, m), 1.94-1.85 (1H, m), 1.74-1.65 (1H, m), 1.54-1.47 (1H, m), 0.94-0.90 (1H, m). | 441, 443 | 2 |
| 96 | 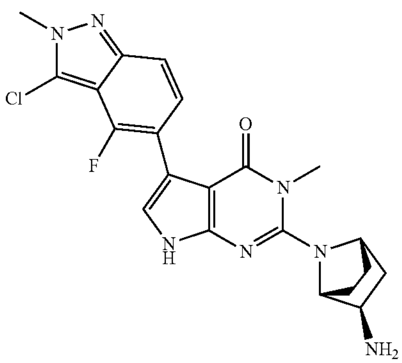 [SMILES: Cn1nc2ccc(-c3c[nH]c4nc(N5[C@H]6CC[C@@H]5[C@H](N)C6)n(C)c(=O)c34)c(F)c2c1Cl] | 2-((1R,2R,4S)-2-amino-7-azabicyclo[2.2.1]heptan-7-yl)-5-(3-chloro-4-fluoro-2-methyl-2H-indazol-5-yl)-3-methyl-3,7-dihydro-4H-pyrrolo[2,3-d]pyrimidin-4-one | $^1$H-NMR (DMSO-$d_6$) δ: 11.67 (1H, br s), 7.66-7.60 (1H, m), 7.35 (1H, d, J = 8.9 Hz), 7.02 (1H, s), 4.14-4.09 (4H, m), 4.01-3.97 (1H, m), 3.48-3.39 (4H, m), 2.33-2.10 (2H, m), 1.95-1.83 (2H, m), 1.74-1.60 (1H, m), 1.53-1.43 (1H, m), 0.91-0.80 (1H, m). | 442, 444 | 2 |
| 97 | 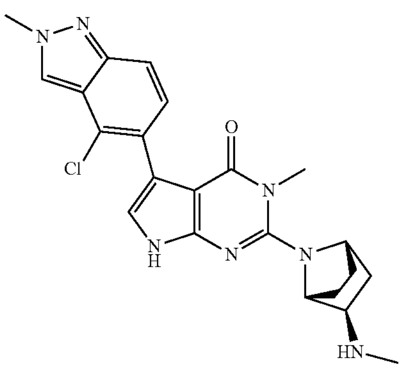 | 5-(4-chloro-2-methyl-2H-indazol-5-yl)-3-methyl-2-((1R,2R,4S)-2-(methylamino)-7-azabicyclo[2.2.1]heptan-7-yl)-3,7-dihydro-4H-pyrrolo[2,3-d]pyrimidin-4-one | $^1$H-NMR (DMSO-$d_6$) δ: 11.64 (1H, s), 8.40 (1H, s), 7.48 (1H, d, J = 8.7 Hz), 7.32 (1H, d, J = 8.7 Hz), 6.95 (1H, s), 4.23-4.15 (5H, m), 3.40 (3H, s), 3.15-3.11 (1H, m), 2.26-2.19 (4H, m), 2.09-2.03 (1H, m), 1.92-1.86 (1H, m), 1.71-1.65 (1H, m), 1.47-1.42 (1H, m), 0.95-0.90 (1H, m). | 438, 440 | 2 |
| 98 | 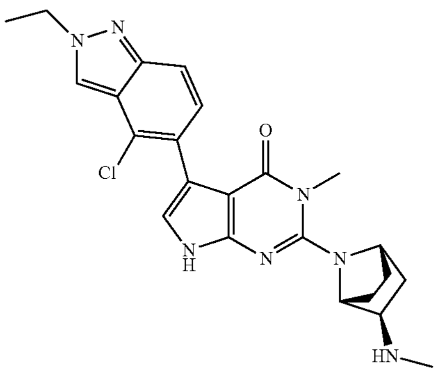 [SMILES: CCn1cc2c(Cl)c(-c3c[nH]c4nc(N5[C@H]6CC[C@@H]5[C@H](NC)C6)n(C)c(=O)c34)ccc2n1] | 5-(4-chloro-2-ethyl-2H-indazol-5-yl)-3-methyl-2-((1R,2R,4S)-2-(methylamino)-7-azabicyclo[2.2.1]heptan-7-yl)-3,7-dihydro-4H-pyrrolo[2,3-d]pyrimidin-4-one | $^1$H-NMR (DMSO-$d_6$) δ: 11.64 (1H, s), 8.44 (1H, s), 7.49 (1H, d, J = 8.9 Hz), 7.31 (1H, d, J = 8.9 Hz), 6.94 (1H, d, J = 2.4 Hz), 4.48 (2H, q, J = 7.3 Hz), 4.24-4.20 (1H, m), 4.18-4.14 (1H, m), 3.40 (3H, s), 3.16-3.12 (1H, m), 2.27-2.19 (4H, m), 2.08-2.03 (1H, m), 1.91-1.85 (1H, m), 1.72-1.65 (1H, m), 1.52 (3H, t, | 452, 454 | 2 |

TABLE 10-continued

| Example | Structure | Name | NMR data | MS: [M + H]+ m/z | Method |
|---|---|---|---|---|---|
| | | midin-4-one | J = 7.3 Hz), 1.48-1.42 (1H, m), 0.95-0.90 (1H, m). | | |
| 99 | 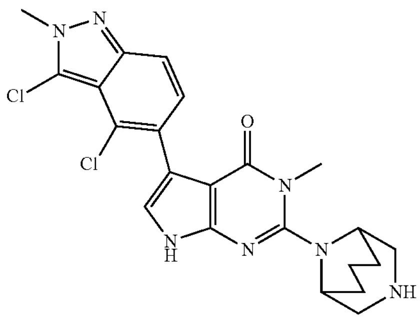 [SMILES: Cn1nc2ccc(-c3c[nH]c4nc(N5C6CCCC5CNC6)n(C)c(=O)c34)c(Cl)c2c1Cl] | 2-(3,9-diazabicyclo[3.3.1]nonan-9-yl)-5-(3,4-dichloro-2-methyl-2H-indazol-5-yl)-3-methyl-3,7-dihydro-4H-pyrrolo[2,3-d]pyrimidin-4-one | ¹H-NMR (DMSO-d₆) δ: 11.65-11.59 (1H, m), 7.50 (1H, br d, J = 8.8 Hz), 7.34 (1H, d, J = 8.8 Hz), 7.01-6.95 (1H, m), 4.14 (3H, s), 3.65 (2H, br s), 2.90 (2H, d, J = 12.1 Hz), 2.84-2.70 (1H, m), 2.21-2.05 (2H, m), 1.80-1.68 (2H, m), 1.65-1.51 (1H, m). | 472, 474 | 1 |
| 100 | 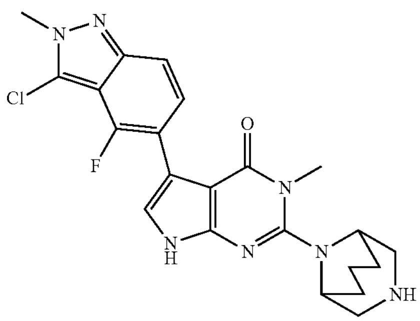 [SMILES: Cn1nc2ccc(-c3c[nH]c4nc(N5C6CCCC5CNC6)n(C)c(=O)c34)c(F)c2c1Cl] | 2-(3,9-diazabicyclo[3.3.1]nonan-9-yl)-5-(3-chloro-4-fluoro-2-methyl-2H-indazol-5-yl)-3-methyl-3,7-dihydro-4H-pyrrolo[2,3-d]pyrimidin-4-one | ¹H-NMR (DMSO-d₆) δ: 11.64 (1H, br s), 7.68-7.62 (1H, m), 7.37 (1H, d, J = 8.8 Hz), 7.05 (1H, s), 4.12 (3H, s), 3.66 (2H, br s), 3.52-3.14 (4H, m), 2.97-2.88 (2H, m), 2.18-2.06 (2H, m), 1.78-1.69 (2H, m), 1.64-1.54 (1H, m). | 456, 458 | 1 |
| 101 | 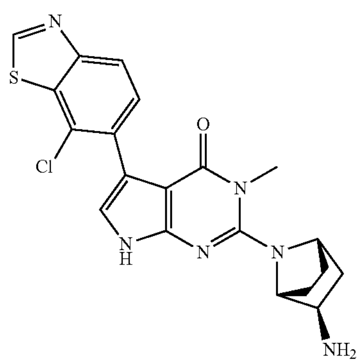 [SMILES: Cn1c(N2[C@H]3CC[C@@H]2[C@H](N)C3)nc2[nH]cc(-c3ccc4ncsc4c3Cl)c2c1=O] | 2-((1R,2R,4S)-2-amino-7-azabicyclo[2.2.1]heptan-7-yl)-5-(7-chlorobenzo[d]thiazol-6-yl)-3-methyl-3,7-dihydro-4H-pyrrolo[2,3-d]pyrimidin-4-one | ¹H-NMR (DMSO-d₆) δ: 11.74 (1H, br s), 9.42 (1H, s), 8.00 (1H, d, J = 8.3 Hz), 7.64 (1H, d, J = 8.4 Hz), 7.03 (1H, s), 4.17-3.95 (2H, m), 3.48-3.41 (1H, m), 3.39 (3H, s), 2.34-2.09 (2H, m), 1.97-1.43 (5H, m), 0.91-0.80 (1H, m). | 428, 430 | 2 |
| 102 | 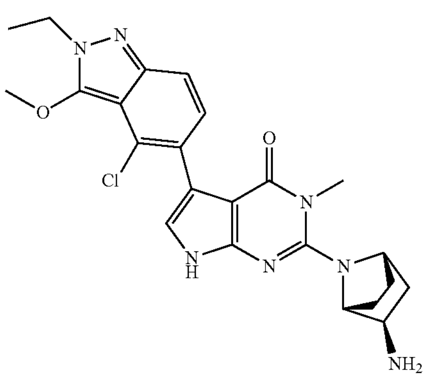 [SMILES: CCn1nc2ccc(-c3c[nH]c4nc(N5[C@H]6CC[C@@H]5[C@H](N)C6)n(C)c(=O)c34)c(Cl)c2c1OC] | 2-((1R,2R,4S)-2-amino-7-azabicyclo[2.2.1]heptan-7-yl)-5-(4-chloro-2-ethyl-3-methoxy-2H-indazol-5-yl)-3-methyl-3,7-dihydro-4H-pyrrolo[2,3-d]pyrimidin-4-one | 1H-NMR (DMSO-d₆) δ: 11.61 (1H, br s), 7.34 (1H, d, J = 8.8 Hz), 7.22 (1H, d, J = 8.8 Hz), 6.91 (1H, s), 4.30 (2H, q, J = 7.2 Hz), 4.14-4.09 (1H, m), 4.06 (3H, s), 4.01-3.96 (1H, m), 3.48-3.42 (1H, m), 3.37 (3H, s), 2.29-2.11 (2H, m), 1.94-1.85 (1H, m), 1.71-1.60 (1H, m), 1.52-1.41 (1H, m), 1.44 (3H, t, J = 7.2 Hz), 0.90-0.81 (1H, m). | 468, 470 | 1 |

TABLE 10-continued

| Example | Structure | Name | NMR data | MS: [M + H]+ m/z | Method |
|---|---|---|---|---|---|
| 103 | 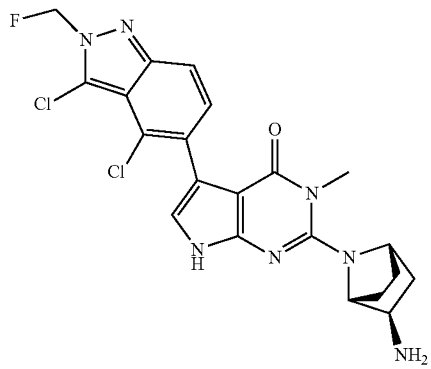 [SMILES: Cn1c(N2[C@H]3CC[C@@H]2[C@H](N)C3)nc2[nH]cc(-c3ccc4nn(CF)c(Cl)c4c3Cl)c2c1=O] | 2-((1R,2R,4S)-2-amino-7-azabicyclo[2.2.1]heptan-7-yl)-5-(3,4-dichloro-2-(fluoromethyl)-2H-indazol-5-yl)-3-methyl-3,7-dihydro-4H-pyrrolo[2,3-d]pyrimidin-4-one | $^1$H-NMR (DMSO-$d_6$) δ: 11.73 (1H, br s), 7.57 (1H, d, J = 8.8 Hz), 7.42 (1H, d, J = 8.8 Hz), 7.02 (1H, s), 6.51 (2H, d, J = 51.2 Hz), 4.15-4.10 (1H, m), 4.01-3.96 (1H, m), 3.48-3.42 (1H, m), 3.38 (3H, s), 2.28-2.13 (2H, m), 1.92-1.86 (1H, m), 1.75-1.65 (1H, m), 1.52-1.45 (1H, m), 0.89-0.82 (1H, m). | 476, 478 | 1 |
| 104 | 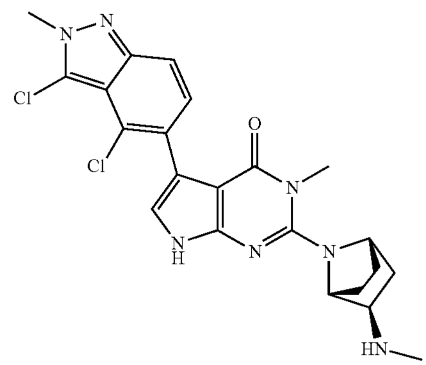 | 5-(3,4-dichloro-2-methyl-2H-indazol-5-yl)-3-methyl-2-((1R,2R,4S)-2-(methylamino)-7-azabicyclo[2.2.1]heptan-7-yl)-3,7-dihydro-4H-pyrrolo[2,3-d]pyrimidin-4-one | $^1$H-NMR (DMSO-$d_6$) δ: 11.68 (1H, br d, J = 2.2 Hz), 7.50 (1H, d, J = 8.8 Hz), 7.33 (1H, d, J = 8.8 Hz), 6.97 (1H, d, J = 2.2 Hz), 4.22 (1H, t, J = 4.4 Hz), 4.18-4.11 (4H, m), 3.40 (3H, s), 3.19-3.07 (1H, m), 2.28-2.17 (4H, m), 2.11-1.98 (1H, m), 1.95-1.79 (1H, m), 1.75-1.61 (1H, m), 1.51-1.38 (1H, m), 0.92 (1H, dd, J = 11.7, 4.4 Hz). | 472, 474 | 1 |
| 105 | 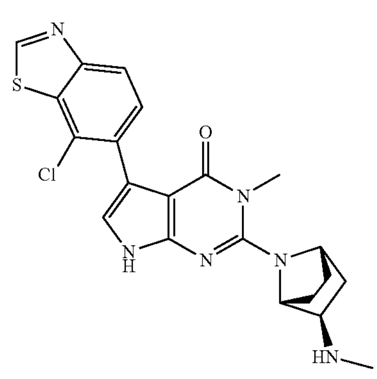 [SMILES: CN[C@@H]1C[C@@H]2CC[C@H]1N2c1nc2[nH]cc(-c3ccc4ncsc4c3Cl)c2c(=O)n1C] | 5-(7-chlorobenzo[d]thiazol-6-yl)-3-methyl-2-((1R,2R,4S)-2-(methylamino)-7-azabicyclo[2.2.1]heptan-7-yl)-3,7-dihydro-4H-pyrrolo[2,3-d]pyrimidin-4-one | $^1$H-NMR (DMSO-$d_6$) δ: 11.75 (1H, br s), 9.44 (1H, s), 8.01 (1H, d, J = 8.5 Hz), 7.65 (1H, d, J = 8.5 Hz), 7.04 (1H, d, J = 2.0 Hz), 4.24-4.22 (1H, m), 4.19-4.15 (1H, m), 3.41 (3H, s), 3.16-3.10 (1H, m), 2.24 (4H, br s), 2.10-2.03 (1H, m), 1.92-1.85 (1H, m), 1.72-1.65 (1H, m), 1.48-1.42 (1H, m), 0.95-0.90 (1H, m). | 441, 443 | 2 |

TABLE 10-continued

| Example | Structure | Name | NMR data | MS: [M + H]⁺ m/z | Method |
|---|---|---|---|---|---|
| 106 | 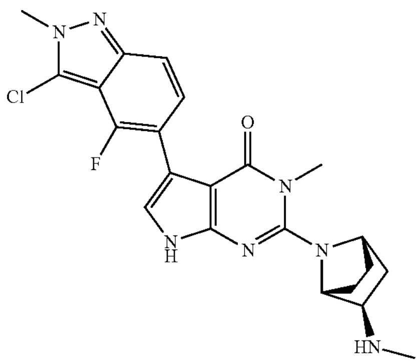 | 5-(3-chloro-4-fluoro-2-methyl-2H-indazol-5-yl)-3-methyl-2-((1R,2R,4S)-2-(methylamino)-7-azabicyclo[2.2.1]heptan-7-yl)-3,7-dihydro-4H-pyrrolo[2,3-d]pyrimidin-4-one | ¹H-NMR (DMSO-d₆) δ: 11.68 (1H, br s), 7.67-7.58 (1H, m), 7.36 (1H, d, J = 9.1 Hz), 7.06-7.00 (1H, m), 4.23-4.19 (1H, m), 4.17-4.13 (1H, m), 4.11 (3H, s), 3.43-3.42 (1H, m), 3.17-3.07 (1H, m), 2.23 (3H, s), 2.11-1.80 (3H, m), 1.73-1.60 (1H, m), 1.51-1.38 (1H, m), 0.99-0.86 (1H, m). | 456, 458 | 2 |
| 107 | 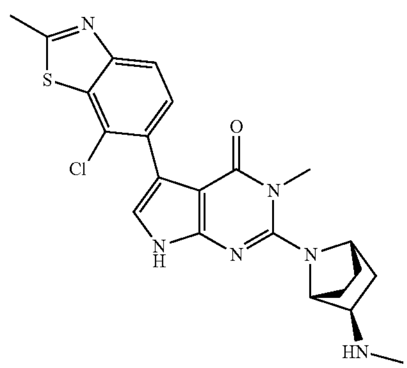 | 5-(7-chloro-2-methyl-benzo[d]thiazol-6-yl)-3-methyl-2-((1R,2R,4S)-2-(methylamino)-7-azabicyclo[2.2.1]heptan-7-yl)-3,7-dihydro-4H-pyrrolo[2,3-d]pyrimidin-4-one | ¹H-NMR (DMSO-d₆) δ: 11.73 (1H, br s), 7.82 (1H, d, J = 8.4 Hz), 7.56 (1H, d, J = 8.4 Hz), 7.01 (1H, s), 4.25-4.14 (2H, m), 3.40 (3H, s), 3.17-3.10 (1H, m), 2.82 (3H, s), 2.26-2.16 (1H, m), 2.24 (3H, s), 2.08-1.99 (1H, m), 1.93-1.81 (1H, m), 1.73-1.62 (1H, m), 1.49-1.40 (1H, m), 0.98-0.90 (1H, m). | 455, 457 | 1 |
| 108 | 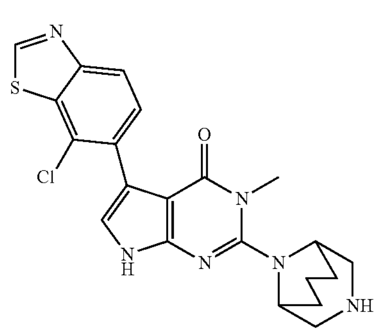 [SMILES: Cn1c(N2C3CCCC2CNC3)nc2[nH]cc(-c3ccc4ncsc4c3Cl)c2c1=O] | 2-(3,9-diazabicyclo[3.3.1]nonan-9-yl)-5-(7-chlorobenzo[d]thiazol-6-yl)-3-methyl-3,7-dihydro-4H-pyrrolo[2,3-d]pyrimidin-4-one | ¹H-NMR (DMSO-d₆) δ: 11.70 (1H, s), 9.44 (1H, s), 8.01 (1H, d, J = 8.4 Hz), 7.66 (1H, d, J = 8.4 Hz), 7.04 (1H, d, J = 2.2 Hz), 3.66 (2H, br s), 3.27 (2H, br d, J = 11.7 Hz), 2.91 (2H, d, J = 11.7 Hz), 2.81-2.63 (1H, m), 2.22-2.04 (2H, m), 1.81-1.66 (2H, m), 1.64-1.49 (1H, m). | 441, 443 | 1 |

TABLE 10-continued

| Example | Structure | Name | NMR data | MS: [M + H]+ m/z | Method |
|---|---|---|---|---|---|
| 109 | 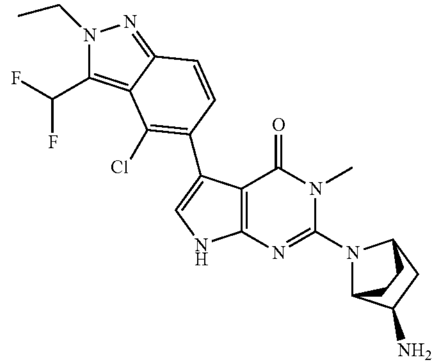 [SMILES: CCn1nc2ccc(-c3c[nH]c4nc(N5[C@H]6CC[C@@H]5[C@H](N)C6)n(C)c(=O)c34)c(Cl)c2c1C(F)F] | 2-((1R,2R,4S)-2-amino-7-azabicyclo[2.2.1]heptan-7-yl)-5-(4-chloro-3-(difluoromethyl)-2-ethyl-2H-indazol-5-yl)-3-methyl-3,7-dihydro-4H-pyrrolo[2,3-d]pyrimidin-4-one | $^1$H-NMR (CDCl$_3$) δ: 8.43 (1H, br s), 7.90 (1H, t, J = 52.8 Hz), 7.67 (1H, d, J = 8.8 Hz), 7.47 (1H, d, J = 8.8 Hz), 6.90 (1H, d, J = 2.2 Hz), 4.70 (2H, q, J = 7.3 Hz), 4.21-4.14 (1H, m), 4.06 (1H, br t, J = 4.4 Hz), 3.73-3.61 (1H, m), 3.53 (3H, s), 2.53-2.39 (1H, m), 2.19-2.09 (1H, m), 2.08-1.97 (1H, m), 1.91-1.81 (1H, m), 1.63 (3H, t, J = 7.3 Hz), 0.96 (1H, dd, J = 12.5, 4.4 Hz). | 488, 490 | 1 |
| 110 | 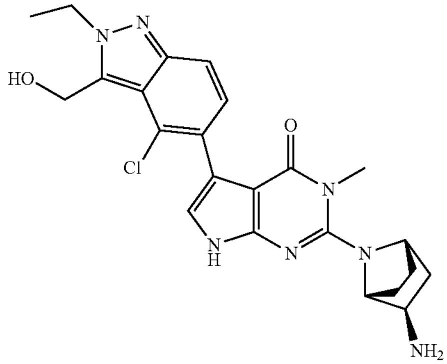 [SMILES: CCn1nc2ccc(-c3c[nH]c4nc(N5[C@H]6CC[C@@H]5[C@H](N)C6)n(C)c(=O)c34)c(Cl)c2c1CO] | 2-((1R,2R,4S)-2-amino-7-azabicyclo[2.2.1]heptan-7-yl)-5-(4-chloro-2-ethyl-3-(hydroxymethyl)-2H-indazol-5-yl)-3-methyl-3,7-dihydro-4H-pyrrolo[2,3-d]pyrimidin-4-one | $^1$H-NMR (DMSO-d$_6$) δ: 11.62 (1H, br s), 7.47 (1H, d, J = 8.8 Hz), 7.25 (1H, d, J = 8.8 Hz), 6.89 (1H, br s), 5.42 (1H, br s), 5.12 (2H, s), 4.51 (2H, q, J = 7.2 Hz), 4.14 (1H, br t, J = 4.8 Hz), 4.01 (1H, br t, J = 4.2 Hz), 3.53-3.44 (1H, m), 3.38 (3H, s), 2.33-2.21 (1H, m), 2.20-2.08 (1H, m), 1.98-1.84 (1H, m), 1.79-1.61 (1H, m), 1.57-1.44 (4H, m), 0.90 (1H, dd, J = 11.7, 4.0 Hz). | 468, 470 | 1 |
| 111 | 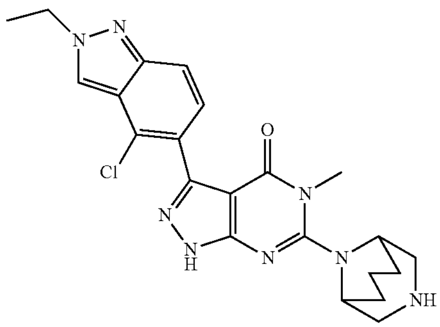 [SMILES: CCn1cc2c(Cl)c(-c3n[nH]c4nc(N5C6CCCC5CNC6)n(C)c(=O)c34)ccc2n1] | 6-(3,9-diazabicyclo[3.3.1]nonan-9-yl)-3-(4-chloro-2-ethyl-2H-indazol-5-yl)-5-methyl-1,5-dihydro-4H-pyrazolo[3,4-d]pyrimidin-4-one | $^1$H-NMR (DMSO-d$_6$) δ: 13.27 (1H, s), 8.54 (1H, s), 7.57 (1H, d, J = 8.8 Hz), 7.29 (1H, d, J = 8.8 Hz), 4.48 (2H, q, J = 7.3 Hz), 3.74-3.71 (2H, m), 3.28 (3H, s), 3.23-3.17 (2H, m), 2.89 (2H, d, J = 12.1 Hz), 2.76-2.65 (1H, m), 2.13-2.01 (2H, m), 1.76-1.69 (2H, m), 1.58-1.52 (1H, m), 1.52 (3H, t, J = 7.3 Hz). | 453, 455 | 2 |

TABLE 10-continued

| Example | Structure | Name | NMR data | MS: [M + H]+ m/z | Method |
|---|---|---|---|---|---|
| 112 | 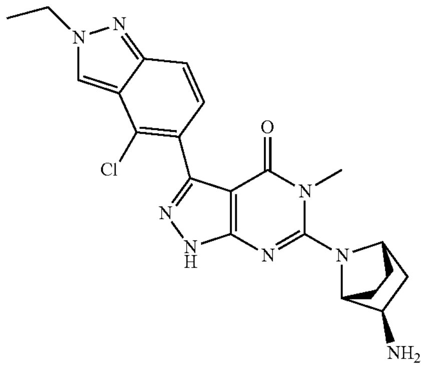 [SMILES: CCn1cc2c(Cl)c(-c3n[nH]c4nc(N5[C@H]6CC[C@@H]5[C@H](N)C6)n(C)c(=O)c34)ccc2n1] | 6-((1R,2R,4S)-2-amino-7-azabicyclo[2.2.1]heptan-7-yl)-3-(4-chloro-2-ethyl-2H-indazol-5-yl)-5-methyl-1,5-dihydro-4H-pyrazolo[3,4-d]pyrimidin-4-one | $^1$H-NMR (DMSO-$d_6$) δ: 13.36 (1H, s), 8.57 (1H, s), 7.60 (1H, d, J = 8.7 Hz), 7.31 (1H, d, J = 8.7 Hz), 4.51 (2H, q, J = 7.2 Hz), 4.24-4.19 (1H, m), 4.10-4.05 (1H, m), 3.49-3.43 (1H, m), 3.37 (3H, s), 2.30-2.23 (1H, m), 2.22-2.16 (1H, m), 1.92-1.85 (1H, m), 1.71-1.63 (1H, m), 1.57-1.49 (4H, m), 0.92-0.87 (1H, m). | 439, 441 | 3 |
| 113 | 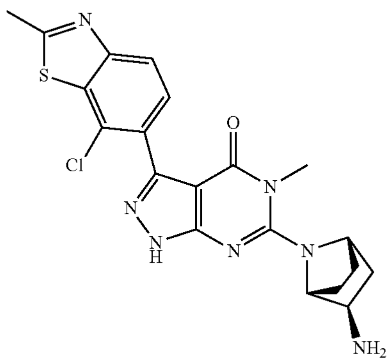 [SMILES: Cc1nc2ccc(-c3n[nH]c4nc(N5[C@H]6CC[C@@H]5[C@H](N)C6)n(C)c(=O)c34)c(Cl)c2s1] | 6-((1R,2R,4S)-2-amino-7-azabicyclo[2.2.1]heptan-7-yl)-3-(7-chloro-2-methylbenzo[d]thiazol-6-yl)-5-methyl-1,5-dihydro-4H-pyrazolo[3,4-d]pyrimidin-4-one | $^1$H-NMR (DMSO-$d_6$) δ: 7.93 (1H, d, J = 8.3 Hz), 7.63 (1H, d, J = 8.5 Hz), 4.25-4.22 (1H, m), 4.12-4.10 (1H, m), 3.49-3.48 (2H, m), 3.38 (3H, s), 2.87 (3H, s), 2.29-2.26 (1H, m), 2.19-2.16 (1H, m), 1.90-1.88 (1H, m), 1.71-1.69 (1H, m), 1.55-1.52 (1H, m), 0.95-0.92 (1H, m). | 442, 444 | 3 |
| 114 | 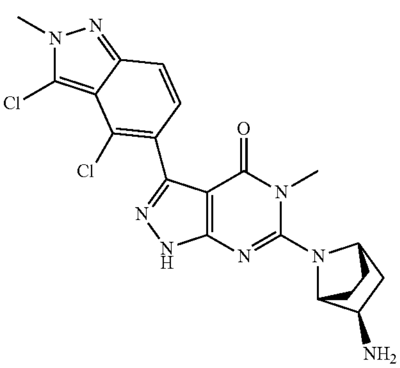 [SMILES: Cn1nc2ccc(-c3n[nH]c4nc(N5[C@H]6CC[C@@H]5[C@H](N)C6)n(C)c(=O)c34)c(Cl)c2c1Cl] | 6-((1R,2R,4S)-2-amino-7-azabicyclo[2.2.1]heptan-7-yl)-3-(3,4-dichloro-2-methyl-2H-indazol-5-yl)-5-methyl-1,5-dihydro-4H-pyrazolo[3,4-d]pyrimidin-4-one | $^1$H-NMR (DMSO-$d_6$) δ: 13.39 (1H, s), 7.61 (1H, d, J = 8.9 Hz), 7.32 (1H, d, J = 8.9 Hz), 4.24-4.20 (1H, m), 4.17 (3H, s), 4.11-4.06 (1H, m), 3.50-3.44 (1H, m), 3.38 (3H, s), 2.31-2.23 (1H, m), 2.21-2.16 (1H, m), 1.93-1.85 (1H, m), 1.73-1.65 (1H, m), 1.55-1.48 (1H, m), 0.93-0.88 (1H, m). | 459, 461 | 3 |
| 115 | 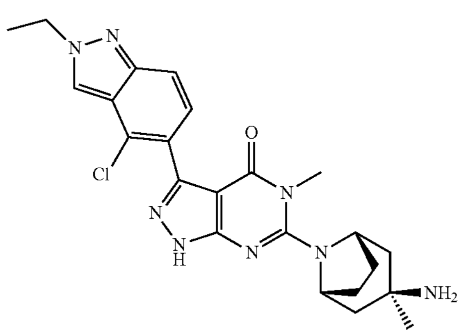 [SMILES: CCn1cc2c(Cl)c(-c3n[nH]c4nc(N5[C@@H]6CC[C@H]5C[C@@](C)(N)C6)n(C)c(=O)c34)ccc2n1] | 6-(endo-3-amino-3-methyl-8-azabicyclo[3.2.1]octan-8-yl)-3-(4-chloro-2-ethyl-2H-indazol-5-yl)-5-methyl-1,5-dihydro-4H-pyrazolo[3,4-d]pyrimidin-4-one | $^1$H-NMR (DMSO-$d_6$) δ: 8.55 (1H, s), 7.59 (1H, d, J = 8.8 Hz), 7.30 (1H, d, J = 8.8 Hz), 4.54-4.46 (2H, m), 4.18 (2H, br s), 3.38 (3H, s), 2.34-2.26 (2H, m), 1.92-1.83 (4H, m), 1.64-1.50 (5H, m), 1.08 (3H, s). | 467, 469 | 3 |

TABLE 10-continued

| Example | Structure | Name | NMR data | MS: [M + H]+ m/z | Method |
|---|---|---|---|---|---|
| 116 | 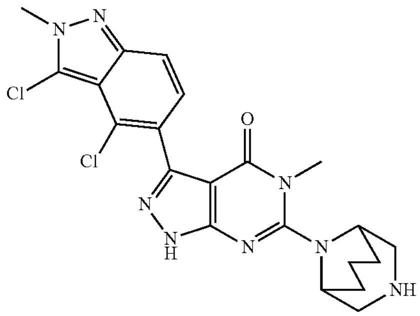 [SMILES: Cn1nc2ccc(-c3n[nH]c4nc(N5C6CCCC5CNC6)n(C)c(=O)c34)c(Cl)c2c1Cl] | 6-(3,9-diazabicyclo[3.3.1]nonan-9-yl)-3-(3,4-dichloro-2-methyl-2H-indazol-5-yl)-5-methyl-1,5-dihydro-4H-pyrazolo[3,4-d]pyrimidin-4-one | $^1$H-NMR (DMSO-$d_6$) δ: 13.31 (1H, s), 7.58 (1H, d, J = 8.5 Hz), 7.30 (1H, d, J = 8.5 Hz), 4.14 (3H, s), 3.75-3.72 (2H, m), 3.29 (3H, s), 3.24-3.17 (2H, m), 2.90 (2H, d, J = 11.7 Hz), 2.78-2.64 (1H, m), 2.10-2.04 (2H, m), 1.76-1.69 (2H, m), 1.60-1.51 (1H, m). | 473, 475 | 3 |
| 117 | 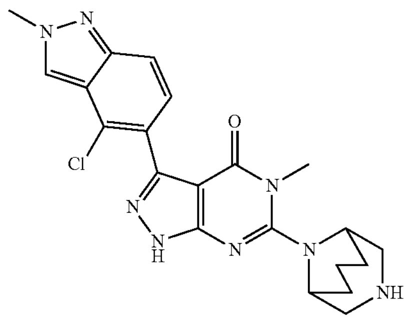 [SMILES: Cn1cc2c(Cl)c(-c3n[nH]c4nc(N5C6CCCC5CNC6)n(C)c(=O)c34)ccc2n1] | 6-(3,9-diazabicyclo[3.3.1]nonan-9-yl)-3-(4-chloro-2-methyl-2H-indazol-5-yl)-5-methyl-1,5-dihydro-4H-pyrazolo[3,4-d]pyrimidin-4-one | 1H-NMR (DMSO-$d_6$) δ: 13.27 (1H, s), 8.50 (1H, s), 7.56 (1H, d, J = 9.5 Hz), 7.29 (1H, d, J = 8.8 Hz), 4.19 (3H, s), 3.74-3.72 (2H, m), 3.29 (3H, s), 3.25-3.18 (2H, m), 2.93-2.87 (2H, br m), 2.77-2.68 (1H, m), 2.13-2.01 (2H, m), 1.78-1.69 (2H, m), 1.58-1.53 (1H, m). | 439, 441 | 3 |
| 118 | 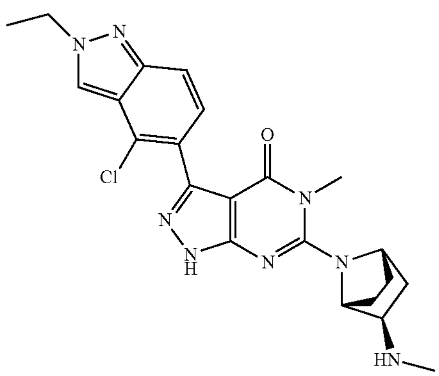 [SMILES: CCn1cc2c(Cl)c(-c3n[nH]c4nc(N5[C@H]6CC[C@@H]5[C@H](NC)C6)n(C)c(=O)c34)ccc2n1] | 3-(4-chloro-2-ethyl-2H-indazol-5-yl)-5-methyl-6-((1R,2R,4S)-2-(methylamino)-7-azabicyclo[2.2.1]heptan-7-yl)-1,5-dihydro-4H-pyrazolo[3,4-d]pyrimidin-4-one | $^1$H-NMR (DMSO-$d_6$) δ: 13.37 (1H, s), 8.58 (1H, s), 7.60 (1H, d, J = 8.9 Hz), 7.31 (1H, d, J = 8.9 Hz), 4.51 (2H, q, J = 7.2 Hz), 4.33-4.29 (1H, m), 4.27-4.23 (1H, m), 3.39 (3H, s), 3.18-3.13 (1H, m), 2.27-2.19 (4H, m), 2.10-2.04 (1H, m), 1.91-1.84 (1H, m), 1.73-1.65 (1H, m), 1.54 (3H, t, J = 7.2 Hz), 1.51-1.44 (1H, m), 0.98-0.93 (1H, m). | 453, 455 | 3 |
| 119 | 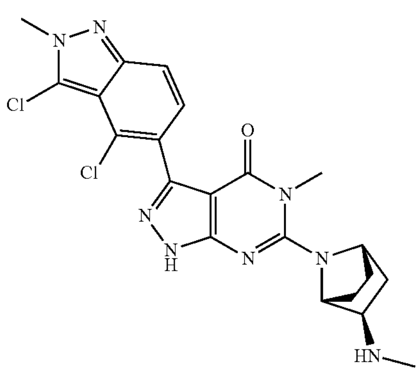 | 3-(3,4-dichloro-2-methyl-2H-indazol-5-yl)-5-methyl-6-((1R,2R,4S)-2-(methylamino)-7-azabicyclo[2.2.1]heptan-7-yl)-1,5-dihydro-4H-pyrazolo[3,4-d]pyrimidin-4-one | $^1$H-NMR (DMSO-$d_6$) δ: 13.41 (1H, s), 7.61 (1H, d, J = 8.9 Hz), 7.33 (1H, d, J = 8.9 Hz), 4.33-4.29 (1H, m), 4.28-4.23 (1H, m), 4.17 (3H, s), 3.39 (3H, s), 3.18-3.12 (1H, m), 2.28-2.19 (4H, m), 2.10-2.05 (1H, m), 1.91-1.84 (1H, m), 1.72-1.65 (1H, m), 1.51-1.43 (1H, m), 0.98-0.93 (1H, m). | 473, 475 | 3 |

TABLE 10-continued

| Example | Structure | Name | NMR data | MS: [M + H]+ m/z | Method |
|---|---|---|---|---|---|
| | | pyrazolo[3,4-d]pyrimidin-4-one | | | |
| 120 | 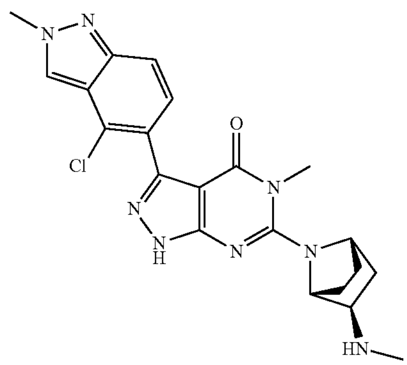 | 3-(4-chloro-2-methyl-2H-indazol-5-yl)-5-methyl-6-((1R,2R,4S)-2-(methylamino)-7-azabicyclo[2.2.1]heptan-7-yl)-1,5-dihydro-4H-pyrazolo[3,4-d]pyrimidin-4-one | $^1$H-NMR (DMSO-$d_6$) δ: 13.37 (1H, br s), 8.52 (1H, s), 7.58 (1H, d, J = 8.8 Hz), 7.32 (1H, d, J = 8.8 Hz), 4.32-4.29 (1H, m), 4.26-4.22 (4H, m), 3.39 (3H, s), 3.17-3.12 (1H, m), 2.25 (4H, br s), 2.11-2.05 (1H, m), 1.91-1.84 (1H, m), 1.72-1.64 (1H, m), 1.51-1.44 (1H, m), 0.97-0.93 (1H, m). | 439, 441 | 3 |
| 121 | 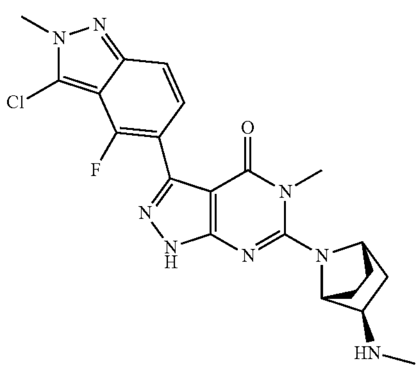 | 3-(3-chloro-4-fluoro-2-methyl-2H-indazol-5-yl)-5-methyl-6-((1R,2R,4S)-2-(methylamino)-7-azabicyclo[2.2.1]heptan-7-yl)-1,5-dihydro-4H-pyrazolo[3,4-d]pyrimidin-4-one | $^1$H-NMR (DMSO-$d_6$) δ: 7.55-7.43 (2H, m), 4.32-4.21 (2H, m), 4.14 (3H, s), 3.41 (3H, s), 3.17-3.09 (1H, m), 2.27-2.15 (4H, m), 2.11-2.03 (1H, m), 1.92-1.81 (1H, m), 1.73-1.61 (1H, m), 1.51-1.40 (1H, m), 0.98-0.90 (1H, m). | 457, 459 | 3 |
| 122 | 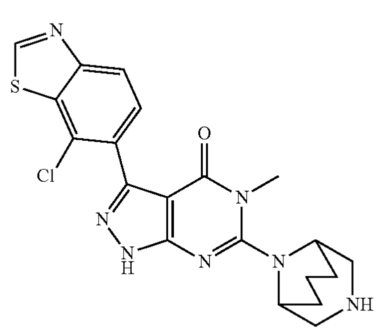 [SMILES: Cn1c(N2C3CCCC2CNC3)nc2[nH]nc(-c3ccc4ncsc4c3Cl)c2c1=O] | 6-(3,9-diazabicyclo[3.3.1]nonan-9-yl)-3-(7-chlorobenzo[d]thiazol-6-yl)-5-methyl-1,5-dihydro-4H-pyrazolo[3,4-d]pyrimidin-4-one | $^1$H-NMR (DMSO-$d_6$) δ: 13.41 (1H, br s), 9.53 (1H, s), 8.11 (1H, d, J = 8.5 Hz), 7.70 (1H, d, J = 8.5 Hz), 3.78 (2H, br s), 3.41-3.23 (5H, m), 2.94 (2H, d, J = 11.7 Hz), 2.77-2.63 (1H, m), 2.15-2.03 (2H, m), 1.81-1.71 (2H, m), 1.62-1.53 (1H, m). | 442, 444 | 3 |

TABLE 10-continued

| Example | Structure | Name | NMR data | MS: [M + H]⁺ m/z | Method |
|---|---|---|---|---|---|
| 123 | 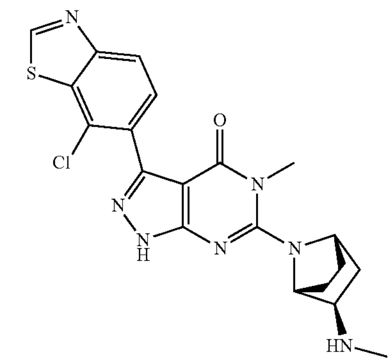 [SMILES: CN[C@@H]1C[C@@H]2CC[C@H]1N2c1nc2[nH]nc(-c3ccc4ncsc4c3Cl)c2c(=O)n1C] | 3-(7-chlorobenzo[d]thiazol-6-yl)-5-methyl-6-((1R,2R,4S)-2-(methylamino)-7-azabicyclo[2.2.1]heptan-7-yl)-1,5-dihydro-4H-pyrazolo[3,4-d]pyrimidin-4-one | $^1$H-NMR (DMSO-$d_6$) δ: 13.51 (1H, s), 9.54 (1H, s), 8.12 (1H, d, J = 8.2 Hz), 7.70 (1H, d, J = 8.2 Hz), 4.34-4.29 (1H, m), 4.28-4.24 (1H, m), 3.40 (3H, s), 3.18-3.11 (1H, m), 2.26-2.18 (4H, m), 2.11-2.05 (1H, m), 1.92-1.84 (1H, m), 1.73-1.65 (1H, m), 1.52-1.44 (1H, m), 0.98-0.93 (1H, m). | 442, 444 | 3 |
| 124 | 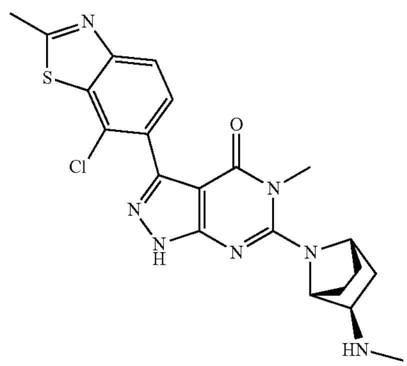 | 3-(7-chloro-2-methylbenzo[d]thiazol-6-yl)-5-methyl-6-((1R,2R,4S)-2-(methylamino)-7-azabicyclo[2.2.1]heptan-7-yl)-1,5-dihydro-4H-pyrazolo[3,4-d]pyrimidin-4-one | $^1$H-NMR (DMSO-$d_6$) δ: 13.48 (1H, s), 7.94 (1H, d, J = 8.2 Hz), 7.63 (1H, d, J = 8.2 Hz), 4.33-4.29 (1H, m), 4.28-4.23 (1H, m), 3.40 (3H, s), 3.17-3.11 (1H, m), 2.87 (3H, s), 2.24-2.18 (4H, m), 2.11-2.05 (1H, m), 1.91-1.83 (1H, m), 1.72-1.64 (1H, m), 1.51-1.44 (1H, m), 0.97-0.92 (1H, m). | 456, 458 | 3 |
| 125 | 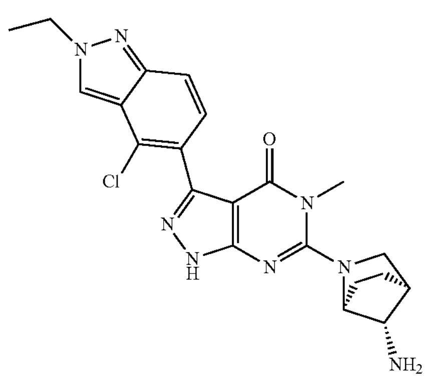 [SMILES: CCn1cc2c(Cl)c(-c3n[nH]c4nc(N5C[C@@H]6CC[C@H]5[C@H]6N)n(C)c(=O)c34)ccc2n1] | rac-6-((1S,4S,7S)-7-amino-2-azabicyclo[2.2.1]heptan-2-yl)-3-(4-chloro-2-ethyl-2H-indazol-5-yl)-5-methyl-1,5-dihydro-4H-pyrazolo[3,4-d]pyrimidin-4-one | $^1$H-NMR (DMSO-$d_6$) δ: 8.55-8.53 (1H, m), 7.58 (2H, d, J = 8.7 Hz), 7.29 (1H, d, J = 8.7 Hz), 4.54-4.45 (2H, m), 3.96-3.91 (1H, m), 3.79-3.72 (1H, m), 3.27 (3H, s), 3.07 (1H, d, J = 9.0 Hz), 2.20-2.12 (1H, m), 2.02-1.81 (4H, m), 1.53 (3H, t, J = 7.4 Hz), 1.40-1.32 (1H, m). | 439, 441 | 3 |

TABLE 10-continued

| Example | Structure | Name | NMR data | MS: [M + H]+ m/z | Method |
|---|---|---|---|---|---|
| 126 | 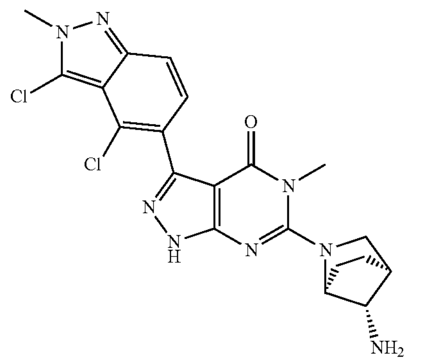 [SMILES: Cn1nc2ccc(-c3n[nH]c4nc(N5C[C@@H]6CC[C@H]5[C@H]6N)n(C)c(=O)c34)c(Cl)c2c1Cl] | rac-6-((1S,4S,7S)-7-amino-2-aza-bicyclo[2.2.1]heptan-2-yl)-3-(3,4-dichloro-2-methyl-2H-indazol-5-yl)-5-methyl-1,5-dihydro-4H-pyrazolo[3,4-d]pyrimidin-4-one | ¹H-NMR (DMSO-d₆) δ: 7.59 (1H, d, J = 9.1 Hz), 7.31 (1H, d, J = 9.0 Hz), 4.15 (3H, s), 3.96-3.93 (1H, m), 3.79-3.73 (1H, m), 3.27 (3H, s), 3.09-3.05 (1H, m), 2.21-2.11 (1H, br m), 2.03-1.82 (4H, m), 1.45-1.30 (1H, m). | 459, 461 | 3 |
| 127 | 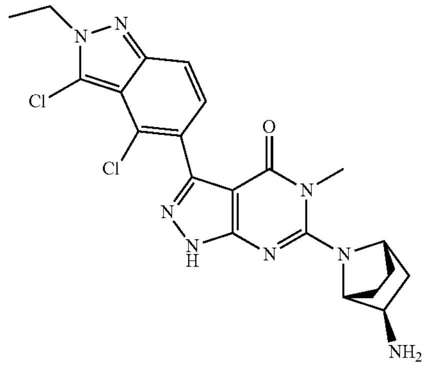 [SMILES: CCn1nc2ccc(-c3n[nH]c4nc(N5[C@H]6CC[C@@H]5[C@H](N)C6)n(C)c(=O)c34)c(Cl)c2c1Cl] | 6-((1R,2R,4S)-2-amino-7-aza-bicyclo[2.2.1]heptan-7-yl)-3-(3,4-dichloro-2-ethyl-2H-indazol-5-yl)-5-methyl-1,5-dihydro-4H-pyrazolo[3,4-d]pyrimidin-4-one | ¹H-NMR (DMSO-d₆) δ: 13.40 (1H, s), 7.63 (1H, d, J = 8.9 Hz), 7.32 (1H, d, J = 8.9 Hz), 4.52 (2H, q, J = 7.3 Hz), 4.24-4.20 (1H, m), 4.10-4.06 (1H, m), 3.49-3.44 (1H, m), 3.38 (3H, s), 2.30-2.24 (1H, m), 2.22-2.16 (1H, m), 1.93-1.86 (1H, m), 1.72-1.64 (1H, m), 1.54-1.47 (4H, m), 0.93-0.87 (1H, m). | 473, 475 | 3 |
| 128 | 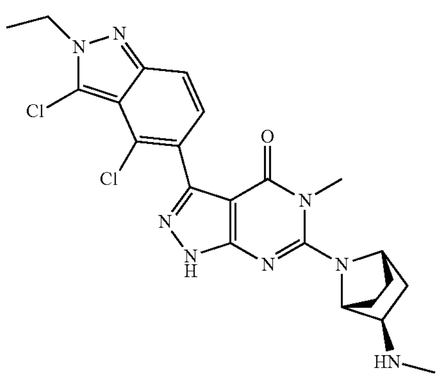 [SMILES: CCn1nc2ccc(-c3n[nH]c4nc(N5[C@H]6CC[C@@H]5[C@H](NC)C6)n(C)c(=O)c34)c(Cl)c2c1Cl] | 3-(3,4-dichloro-2-ethyl-2H-indazol-5-yl)-5-methyl-6-((1R,2R,4S)-2-(methylamino)-7-aza-bicyclo[2.2.1]heptan-7-yl)-1,5-dihydro-4H-pyrazolo[3,4-d]pyrimidin-4-one | ¹H-NMR (DMSO-d₆) δ: 13.41 (1H, s), 7.63 (1H, d, J = 8.9 Hz), 7.33 (1H, d, J = 8.9 Hz), 4.52 (2H, q, J = 7.2 Hz), 4.33-4.29 (1H, m), 4.27-4.23 (1H, m), 3.39 (3H, s), 3.16-3.12 (1H, m), 2.25-2.19 (4H, m), 2.10-2.05 (1H, m), 1.90-1.84 (1H, m), 1.72-1.65 (1H, m), 1.51-1.45 (4H, m), 0.98-0.93 (1H, m). | 487, 489 | 3 |

TABLE 10-continued

| Example | Structure | Name | NMR data | MS: [M + H]⁺ m/z | Method |
|---|---|---|---|---|---|
| 129 | 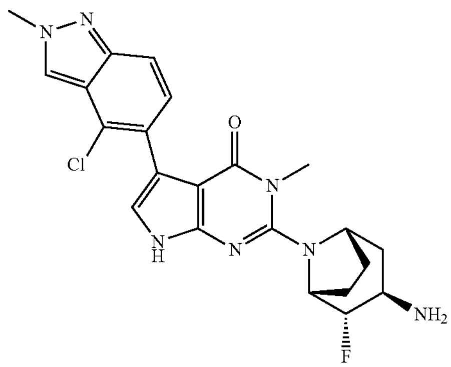 [SMILES: Cn1cc2c(Cl)c(-c3c[nH]c4nc(N5[C@H]6CC[C@@H]5[C@@H](F)[C@H](N)C6)n(C)c(=O)c34)ccc2n1] | 2-((1R,2S,3R,5S)-3-amino-2-fluoro-8-azabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one | ¹H-NMR (DMSO-d₆) δ: 11.65 (1H, br s), 8.40 (1H, s), 7.48 (1H, d, J = 8.8 Hz), 7.32 (1H, d, J = 8.8 Hz), 6.97 (1H, s), 4.50-4.31 (2H, m), 4.19 (3H, s), 4.15-4.07 (1H, m), 3.45 (3H, s), 3.28-3.17 (1H, m), 2.45-2.28 (1H, m), 2.23-1.69 (4H, m), 1.49-1.37 (1H, m). | 456, 458 | 5 |
| 130 | 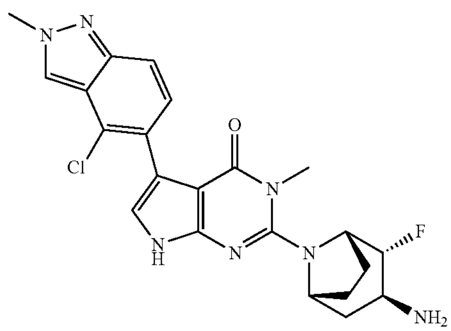 | 2-((1S,2R,3S,5R)-3-amino-2-fluoro-8-azabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one | ¹H-NMR (DMSO-d₆) δ: 11.63 (1H, br s), 8.39 (1H, s), 7.47 (1H, dd, J = 8.8, 0.8 Hz), 7.31 (1H d, J = 8.8 Hz), 6.96 (1H, s), 4.48-4.45 (1H, m), 4.39-4.32 (2H, m), 4.18 (3H, s), 4.13-4.07 (1H, m), 3.44 (3H, s), 3.28-3.19 (1H, m), 2.18-1.75 (4H, m), 1.48-1.41 (1H, m). | 456, 458 | 5 |
| 131 | 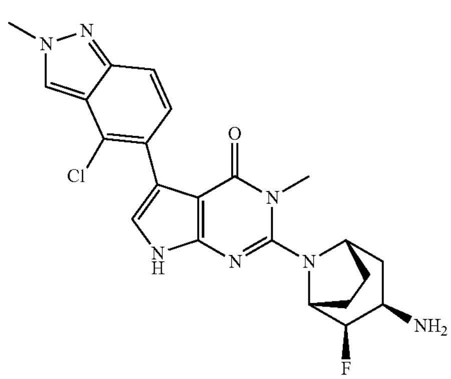 [SMILES: Cn1cc2c(Cl)c(-c3c[nH]c4nc(N5[C@H]6CC[C@@H]5[C@H](F)[C@H](N)C6)n(C)c(=O)c34)ccc2n1] | 2-((1R,2R,3R,5S)-3-amino-2-fluoro-8-azabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one | ¹H-NMR (DMSO-d₆) δ: 11.66 (1H, br s), 8.39 (1H, s), 7.47 (1H, d, J = 8.8 Hz), 7.30 (1H, d, J = 8.9 Hz), 6.97 (1H, s), 4.85 (1H, dt, J = 46.5, 5.2 Hz), 4.26-4.19 (1H, m), 4.18 (3H, s), 4.03 (1H, br s), 3.68-3.60 (1H, m), 3.40 (3H, s), 2.55-2.47 (1H, m), 2.21-2.07 (2H, m), 2.00-1.84 (2H, m), 1.75-1.66 (1H, m), 1.62-1.46 (1H, m). | 456, 458 | 5 |

TABLE 10-continued

| Example | Structure | Name | NMR data | MS: [M + H]+ m/z | Method |
|---|---|---|---|---|---|
| 132 | 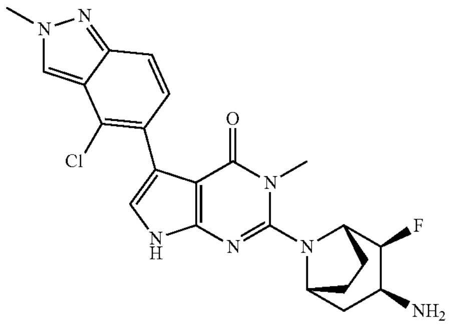 [SMILES: Cn1cc2c(Cl)c(-c3c[nH]c4nc(N5[C@@H]6CC[C@H]5[C@@H](F)[C@@H](N)C6)n(C)c(=O)c34)ccc2n1] | 2-((1S,2S,3S,5R)-3-amino-2-fluoro-8-azabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one | ¹H-NMR (DMSO-d₆) δ: 11.68 (1H, s), 8.39 (1H, s), 7.47 (1H, dd, J = 8.8, 0.9 Hz), 7.30 (1H, d, J = 8.8 Hz), 6.98-6.96 (1H, m), 4.85 (1H, ddd, J = 46.4, 5.0, 5.0 Hz), 4.25-4.20 (1H, m), 4.18 (3H, s), 4.06-4.01 (1H, m), 3.66-3.62 (1H, m), 3.40 (3H, s), 2.55-2.44 (1H, m), 2.19-2.09 (2H, m), 1.98-1.86 (2H, m), 1.74-1.67 (1H, m). | 456, 458 | 5 |
| 133 | 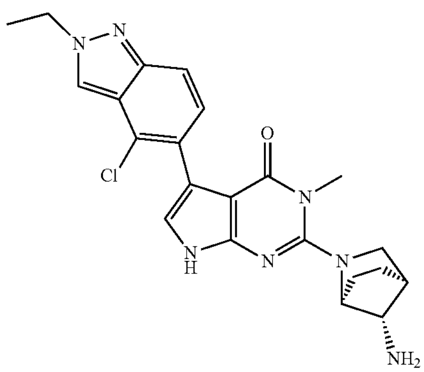 [SMILES: CCn1cc2c(Cl)c(-c3c[nH]c4nc(N5C[C@@H]6CC[C@H]5[C@H]6N)n(C)c(=O)c34)ccc2n1] | rac-2-((1S,4S,7S)-7-amino-2-azabicyclo[2.2.1]heptan-2-yl)-5-(4-chloro-2-ethyl-2H-indazol-5-yl)-3-methyl-3,7-dihydro-4H-pyrrolo[2,3-d]pyrimidin-4-one | ¹H-NMR (DMSO-d₆) δ: 11.49 (1H, br s), 8.42 (1H, s), 7.47 (1H, dd, J = 9.0, 0.7 Hz), 7.30 (1H, d, J = 9.0 Hz), 6.87 (1H, s), 4.46 (2H, q, J = 7.3 Hz), 3.86-3.66 (2H, m), 3.30-3.26 (3H, m), 3.17-3.14 (1H, m), 3.04-2.98 (1H, m), 2.18-2.11 (1H, m), 2.01-1.82 (3H, m), 1.51 (3H, t, J = 7.1 Hz), 1.40-1.31 (1H, m). | 438, 440 | 2 |
| 134 | 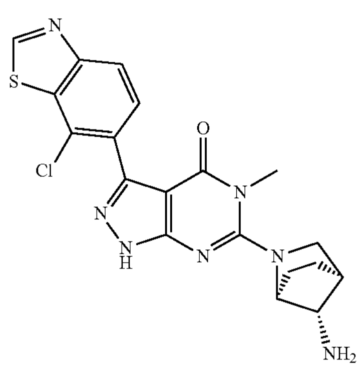 [SMILES: Cn1c(N2C[C@@H]3CC[C@H]2[C@H]3N)nc2[nH]nc(-c3ccc4ncsc4c3Cl)c2c1=O] | rac-((1S,4S,7S)-7-amino-2-azabicyclo[2.2.1]heptan-2-yl)-3-(7-chlorobenzo[d]thiazol-6-yl)-5-methyl-1,5-dihydro-4H-pyrazolo[3,4-d]pyrimidin-4-one | ¹H-NMR (DMSO-d₆) δ: 9.52 (1H, s), 8.10 (1H, d, J = 8.4 Hz), 7.68 (1H, d, J = 8.4 Hz), 3.97-3.92 (1H, br), 3.81-3.72 (1H, m), 3.28 (3H, s), 3.16 (1H, d, J = 5.2 Hz), 3.08 (1H, d, J = 9.0 Hz), 2.21-2.11 (1H, m), 2.04-1.29 (5H, m). | 428, 430 | 3 |

TABLE 10-continued

| Example | Structure | Name | NMR data | MS: [M + H]+ m/z | Method |
|---|---|---|---|---|---|
| 135 | 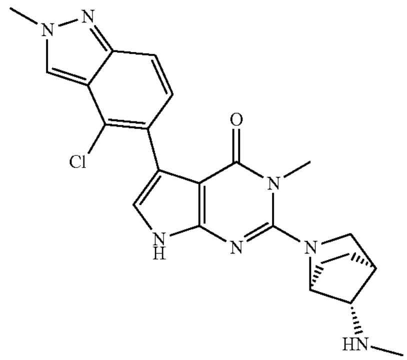 | rac-5-(4-chloro-2-methyl-2H-indazol-5-yl)-3-methyl-2-((1S,4S,7S)-7-(methylamino)-2-azabicyclo[2.2.1]heptan-2-yl)-3,7-dihydro-4H-pyrrolo[2,3-d]pyrimidin-4-one | 1H-NMR (DMSO-d6) δ: 11.50 (1H, s), 8.39 (1H, s), 7.47 (1H, dd, J = 8.9, 0.8 Hz), 7.32 (1H, d, J = 8.9 Hz), 6.89 (1H, d, J = 2.4 Hz), 4.19 (3H, s), 4.07-4.03 (1H, m), 3.77-3.72 (1H, m), 3.30 (3H, s), 3.05 (1H, d, J = 9.2 Hz), 2.94 (1H, s), 2.36-2.32 (1H, m), 2.30 (3H, s), 1.96-1.78 (3H, m), 1.38-1.33 (1H, m). | 438, 440 | 2 |

The following procedures are illustrative for general methods used in the preparation of Examples listed in Table 11 below.

Method 6: endo-6-[3-Amino-8-azabicyclo[3.2.1]octan-8-yl]-3-(4-chloro-2-methyl-2H-indazol-5-yl)-5-methyl-1H,4H,5H-pyrazolo[3,4-d]pyrimidin-4-one

[Chem. 161]

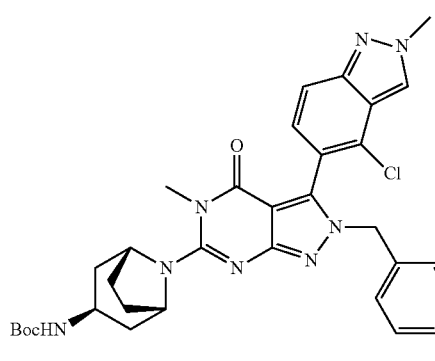

Trifluoromethanesulfonic acid (2 mL, 22.5 mmol) was added dropwise to tert-butyl N-[endo-8-[3-(4-chloro-2-methyl-2H-indazol-5-yl)-2-[(4-methoxyphenyl)methyl]-5-methyl-4-oxo-2H,4H,5H-pyrazolo[3,4-d]pyrimidin-6-yl]-8-azabicyclo[3.2.1]octan-3-yl]carbamate (100 mg, 0.15 mmol) in TFA (0.935 mL, 12.14 mmol) and DCM (10 mL). The resulting purple mixture was stirred at RT for 1 hour and 30 minutes and then evaporated in vacuo to a red liquid, which was added dropwise to saturated sodium carbonate (50 mL). The aqueous layer was extracted with DCM (2×50 mL), and the organic layer recovered through a Phase Separator and evaporated in vacuo. The crude product was purified by chromatography on silica gel (4 g cartridge, 0-10% MeOH/DCM) to afford a first crop of crude product (38 mg). The crude product was purified by preparative HPLC to afford the title compound (15 mg, 0.03 mmol, 22% yield) as a clear colourless solid.

Method 7: 6-[(1R,3S)-1-Amino-3-hydroxy-8-azaspiro[4.5]decan-8-yl]-3-(4-chloro-2-methyl-2H-indazol-5-yl)-5-methyl-1H,4H,5H-pyrazolo[3,4-d]pyrimidin-4-one

[Chem. 162]

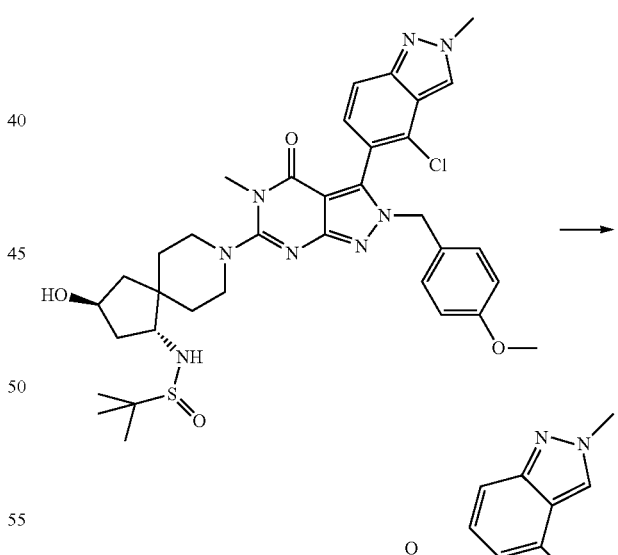

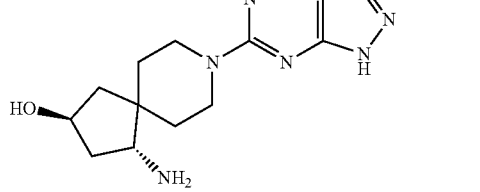

N-[(1R,3S)-8-[3-(4-Chloro-2-methyl-2H-indazol-5-yl)-2-[(4-methoxyphenyl)methyl]-5-methyl-4-oxo-2H,4H,5H-pyrazolo[3,4-d]pyrimidin-6-yl]-3-hydroxy-8-azaspiro[4.5]decan-1-yl]-2-methylpropane-2-sulfinamide (123 mg, 0.17 mmol) was dissolved in methanol (0.2 mL, 4.94 mmol) and then HCl (4M in 1,4-dioxane) (0.435 mL, 1.74 mmol) was added and the reaction was stirred at 50° C. for 1 hour. The reaction mixture was concentrated to give very pale brown solid. DCM (2 mL) and trifluoromethanesulfonic acid (0.154 mL, 1.739 mmol) were added to the solid and the resultant purple solution was stirred at room temperature for 2 hours. The mixture was loaded onto SCX (~5 g) and eluted with DCM, MeOH, and then 0.7M NH₃ in MeOH. The NH₃ in MeOH fractions were concentrated to give the title compound (70 mg, 0.14 mmol, 81% yield).

Method 8: 6-[(4S)-4-Amino-2-oxa-8-azaspiro[4.5]decan-8-yl]-3-(4-chloro-2-methyl-2H-indazol-5-yl)-5-methyl-1H,4H,5H-pyrazolo[3,4-d]pyrimidin-4-one

[Chem. 163]

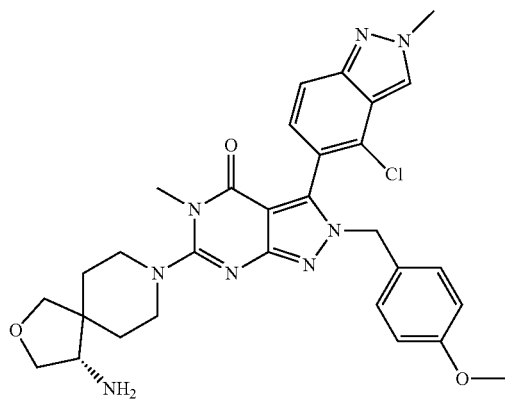  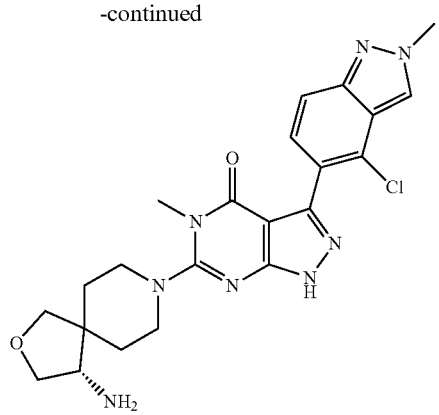

6-[(4S)-4-Amino-2-oxa-8-azaspiro[4.5]decan-8-yl]-3-(4-chloro-2-methyl-2H-indazol-5-yl)-2-[(4-methoxyphenyl)methyl]-5-methyl-2H,4H,5H-pyrazolo[3,4-d]pyrimidin-4-one (145 mg, 0.25 mmol) was dissolved in DCM (2 mL) and trifluoromethanesulfonic acid (0.22 mL, 2.46 mmol) was added. The mixture was stirred at room temperature for 2 hours. The mixture was then loaded on SCX (~5 g) and eluted with DCM, MeOH, and then 0.7 M NH₃ in MeOH. The NH₃ in MeOH fractions were concentrated to give the title compound (83 mg, 0.18 mmol, 72% yield).

By following methods similar and/or analogous to those described for method 6-8 the title compounds in Table 11 were either isolated directly as the free base or as the appropriate salt without further purification. Alternatively, compounds were purified (e.g. using mass-directed preparative HPLC, chromatography, crystallization or trituration). In some cases, the compound was isolated as the hydrochloride salt; by treating a solution of the final compound (e.g. in MeOH) with excess HCl (2N HCl in Et₂O) and then evaporating to dryness.

TABLE 11

| Example | Structure | Name | NMR Data | [M + H]⁺ m/z | Method |
|---|---|---|---|---|---|
| 136 | 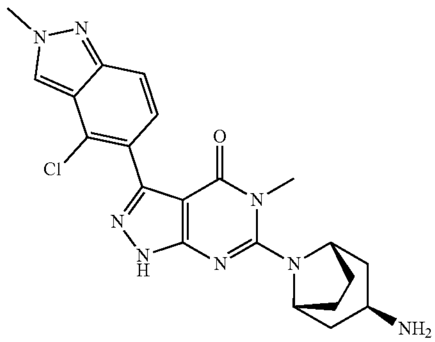 [SMILES: Cn1cc2c(Cl)c(-c3n[nH]c4nc(N5[C@@H]6CC[C@H]5C[C@@H](N)C6)n(C)c(=O)c34)ccc2n1] | endo-6-[3-amino-8-azabicyclo[3.2.1]octan-8-yl]-3-(4-chloro-2-methyl-2H-indazol-5-yl)-5-methyl-1H,4H,5H-pyrazolo[3,4-d]pyrimidin-4-one | ¹H NMR (500 MHz, DMSO-d₆) δ: 8.37 (s, 1H), 7.59 (d, J = 8.8 Hz, 1H), 7.40 (d, J = 8.8 Hz, 1H), 4.34-4.28 (m, 2H), 4.26 (s, 3H), 3.53 (s, 3H), 3.31-3.25 (m, 1H), 2.47 (app. dt, J = 12.7, 6.1 Hz, 2H), 2.23-2.16 (m, 2H), 2.11-2.03 (m, 2H), 1.67 (app. d, J = 14.4 Hz, 2H). | 439 | 6 |

TABLE 11-continued

| Example | Structure | Name | NMR Data | [M + H]+ m/z | Method |
|---|---|---|---|---|---|
| 137 | 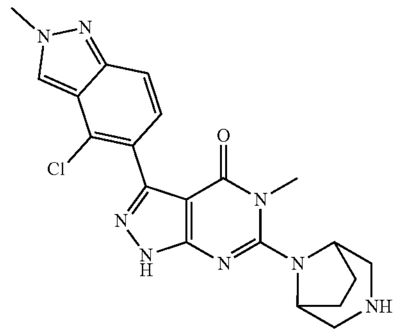 [SMILES: Cn1cc2c(Cl)c(-c3n[nH]c4nc(N5C6CCC5CNC6)n(C)c(=O)c34)ccc2n1] | 3-(4-chloro-2-methyl-2H-indazol-5-yl)-6-{3,8-diazabicyclo[3.2.1]octan-8-yl}-5-methyl-1H,4H,5H-pyrazolo[3,4-d]pyrimidin-4-one | ¹H NMR (500 MHz, DMSO-d₆) δ: 13.39 (s, 1H), 8.53 (s, 1H), 7.60 (dd, J = 8.8, 1.0 Hz, 1H), 7.32 (d, J = 8.8 Hz, 1H), 4.23 (s, 3H), 4.12 (br s, 2H), 3.44 (s, 3H), 3.04 (d, J = 11.9 Hz, 2H), 2.73 (d, J = 10.8 Hz, 2H), 2.02-1.83 (m, 4H). | 425 | 6, isolated by SCX chromatography |
| 138 | 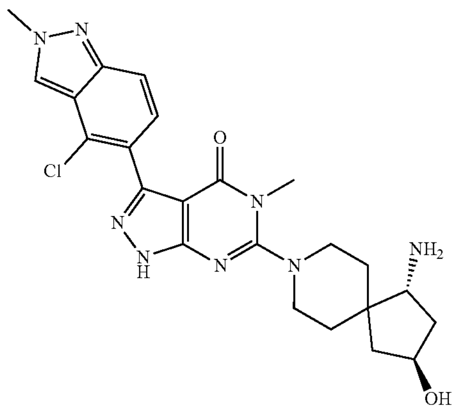 [SMILES: Cn1cc2c(Cl)c(-c3n[nH]c4nc(N5CCC6(CC5)C[C@H](O)C[C@H]6N)n(C)c(=O)c34)ccc2n1] | 6-[(1R,3S)-1-amino-3-hydroxy-8-azaspiro[4.5]decan-8-yl]-3-(4-chloro-2-methyl-2H-indazol-5-yl)-5-methyl-1H,4H,5H-pyrazolo[3,4-d]pyrimidin-4-one | ¹H NMR (500 MHz, DMSO-d₆) δ: 8.54 (s, 1H), 7.60 (dd, J = 8.8, 0.9 Hz, 1H), 7.33 (d, J = 8.8 Hz, 1H), 4.50 (br s, 1H), 4.23 (s, 3H), 4.20-4.13 (m, 1H), 3.48-3.39 (m, 2H), 3.38 (s, 3H), 3.06-2.99 (m, 1H), 2.95-2.84 (m, 2H), 2.09 (dd, J = 13.6, 7.1 Hz, 1H), 1.88-1.74 (m, 2H), 1.74-1.60 (m, 2H), 1.43-1.32 (m, 2H), 1.23 (app. d, J = 12.5 Hz, 1H). | 483 | 7 |
| 139 | 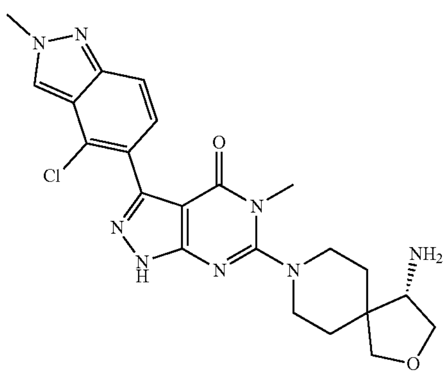 [SMILES: Cn1cc2c(Cl)c(-c3n[nH]c4nc(N5CCC6(CC5)COC[C@H]6N)n(C)c(=O)c34)ccc2n1] | 6-[(4S)-4-amino-2-oxa-8-azaspiro[4.5]decan-8-yl]-3-(4-chloro-2-methyl-2H-indazol-5-yl)-5-methyl-1H,4H,5H-pyrazolo[3,4-d]pyrimidin-4-one | ¹H NMR (500 MHz, DMSO-d₆) δ: 13.48 (br s, 1H), 8.53 (s, 1H), 7.59 (dd, J = 8.8, 0.9 Hz, 1H), 7.32 (d, J = 8.8 Hz, 1H), 4.22 (s, 3H), 3.96 (dd, J = 8.6, 6.6 Hz, 1H), 3.69 (d, J = 8.4 Hz, 1H), 3.60 (d, J = 8.4 Hz, 1H), 3.38 (s, 3H), 3.09 (t, J = 6.0 Hz, 1H), 3.00-2.90 (m, 2H), 1.81 (ddd, J = 13.5, 10.9, 3.5 Hz, 1H), 1.72 (ddd, J = 13.8, 10.8, 3.8 Hz, 1H), 1.55-1.44 (m, 2H). | 469 | 8 |
| 140 | 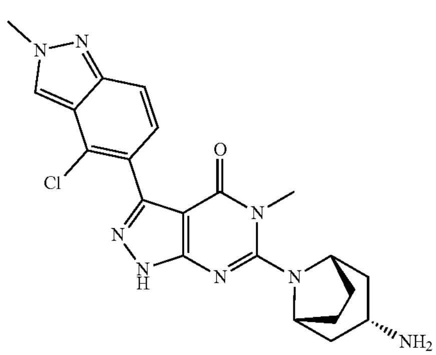 [SMILES: Cn1cc2c(Cl)c(-c3n[nH]c4nc(N5[C@@H]6CC[C@H]5C[C@H](N)C6)n(C)c(=O)c34)ccc2n1] | exo-6-[3-amino-8-azabicyclo[3.2.1]octan-8-yl]-3-(4-chloro-2-methyl-2H-indazol-5-yl)-5-methyl-1H,4H,5H-pyrazolo[3,4-d]pyrimidin-4-one | ¹H NMR (500 MHz, DMSO-d₆) δ: 8.52 (s, 1H), 7.58 (dd, J = 8.8, 0.9 Hz, 1H), 7.31 (d, J = 8.8 Hz, 1H), 4.24-4.18 (m, 2H), 4.22 (s, 3H), 3.41 (s, 3H), 3.07-2.98 (m, 1H), 2.02-1.92 (m, 2H), 1.84-1.76 (m, 2H), 1.73-1.67 (m, 2H), 1.53 (app. t, J = 11.0 Hz, 2H). | 439 | 8 |

TABLE 11-continued

| Example | Name | NMR Data | [M + H]+ m/z | Method |
|---|---|---|---|---|
| 141 | 3-(4-chloro-2-methyl-2H-indazol-5-yl)-6-{2,7-diazaspiro[3.5]nonan-7-yl}-5-methyl-1H,4H,5H-pyrazolo[3,4-d]pyrimidin-4-one | ¹H NMR (500 MHz, DMSO-d₆) δ: 8.53 (s, 1H), 7.59 (dd, J = 8.8, 0.9 Hz, 1H), 7.32 (d, J = 8.8 Hz, 1H), 4.22 (s, 3H), 3.36 (s, 3H), 3.13-3.04 (m, 4H), 1.90-1.78 (m, 4H). | 439 | 8 |
| 142 | 6-[(1R)-1-amino-8-azaspiro[4.5]decan-8-yl]-3-(4-chloro-2-methyl-2H-indazol-5-yl)-5-methyl-1H,4H,5H-pyrazolo[3,4-d]pyrimidin-4-one | ¹H NMR (500 MHz, Methanol-d₄) δ: 8.38 (s, 1H), 7.59 (dd, J = 8.8, 0.9 Hz, 1H), 7.41 (d, J = 8.8 Hz, 1H), 4.26 (s, 3H), 3.56-3.46 (m, 2H), 3.50 (s, 3H), 3.06 (dq, J = 12.6, 2.5 Hz, 2H), 2.84 (t, J = 7.4 Hz, 1H), 2.04 (dddd, J = 13.2, 9.1, 7.1, 4.5 Hz, 1H), 1.92-1.81 (m, 2H), 1.84-1.71 (m, 2H), 1.72-1.61 (m, 1 H), 1.61-1.52 (m, 1 H), 1.52-1.42 (m, 2H), 1.41-1.35 (m, 1 H). | 467 | 8 |
| 143 | 6-[(3S,4S)-4-amino-3-methyl-2-oxa-8-azaspiro[4.5]decan-8-yl]-3-(4-chloro-2-methyl-2H-indazol-5-yl)-5-methyl-1H,4H,5H-pyrazolo[3,4-d]pyrimidin-4-one | ¹H NMR (500 MHz, DMSO-d₆) δ: 13.47 (br s, 1H), 8.53 (s, 1H), 7.59 (d, J = 8.8 Hz, 1H), 7.32 (d, J = 8.8 Hz, 1H), 4.22 (s, 3H), 4.12-4.03 (m, 1H), 3.69 (d, J = 8.5 Hz, 1H), 3.51 (d, J = 8.5 Hz, 1H), 3.37 (s, 3H), 3.09-3.01 (m, 1H), 3.01-2.91 (m, 2H), 1.92-1.83 (m, 1H), 1.82-1.73 (m, 1H), 1.67-1.60 (m, 1H), 1.60-1.53 (m, 1 H), 1.10 (d, J = 6.3 Hz, 3H). | 483 | 8 |

TABLE 11-continued

| Example | Structure | Name | NMR Data | [M + H]+ m/z | Method |
|---|---|---|---|---|---|
| 144 | 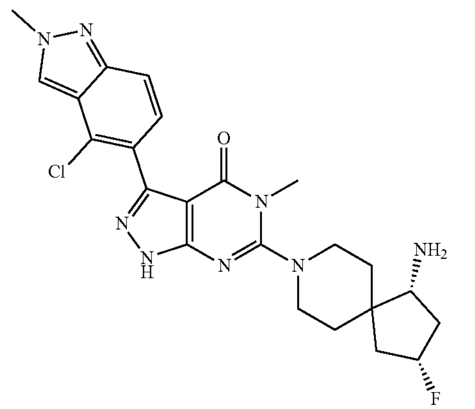 [SMILES: Cn1cc2c(Cl)c(-c3n[nH]c4nc(N5CCC6(CC5)C[C@@H](F)C[C@H]6N)n(C)c(=O)c34)ccc2n1] | 6-[(1R,3R)-1-amino-3-fluoro-8-azaspiro[4.5]decan-8-yl]-3-(4-chloro-2-methyl-2H-indazol-5-yl)-5-methyl-1H,4H,5H-pyrazolo[3,4-d]pyrimidin-4-one hydrochloride salt | 1H NMR (500 MHz, DMSO-d6) δ: 8.53 (s, 1H), 8.20 (br s, 3H), 7.60 (d, J = 8.8 Hz, 1H), 7.32 (d, J = 8.8 Hz, 1H), 5.32-5.12 (m, 1H), 4.23 (s, 3H), 3.55 (app. d, J = 12.4 Hz, 1H), 3.45 (app. d, J = 12.4 Hz, 1H), 3.39 (s, 3H), 3.31-3.24 (m, 1H), 3.04-2.89 (m, 2H), 2.27 (d, J = 14.8 Hz, 1H), 2.22 (d, J = 14.8 Hz, 1H), 2.10-1.90 (m, 3H), 1.81-1.68 (m, 2H), 1.41 (app. d, J = 12.9 Hz, 1H). | 485 | 8 |
| 145 | 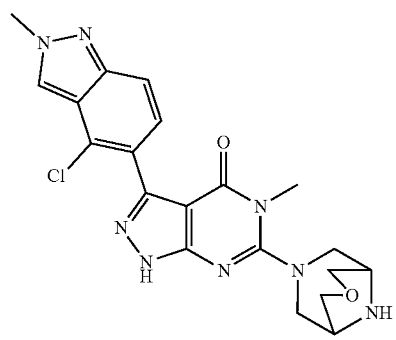 [SMILES: Cn1cc2c(Cl)c(-c3n[nH]c4nc(N5CC6COCC(C5)N6)n(C)c(=O)c34)ccc2n1] | 3-(4-chloro-2-methyl-2H-indazol-5-yl)-5-methyl-6-{3-oxa-7,9-diazabicyclo[3.3.1]nonan-7-yl}-1H,4H,5H-pyrazolo[3,4-d]pyrimidin-4-one | 1H NMR (500 MHz, DMSO-d6) δ: 13.44 (br s, 1H), 8.53 (s, 1H), 7.59 (d, J = 8.8 Hz, 1H), 7.33 (d, J = 8.8 Hz, 1H), 4.23 (s, 3H), 3.93 (app. d, J = 11.0 Hz, 2H), 3.83 (app. d, J = 11.0 Hz, 2H), 3.62 (app. d, J = 12.0 Hz, 2H), 3.48 (s, 3H), 3.26 (app. d, J = 12.0 Hz, 2H), 2.90 (br. s, 2H). | 441 | 8 |
| 146 | 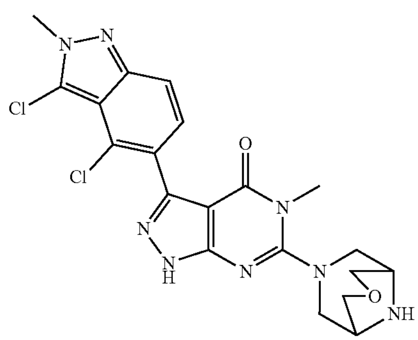 [SMILES: Cn1nc2ccc(-c3n[nH]c4nc(N5CC6COCC(C5)N6)n(C)c(=O)c34)c(Cl)c2c1Cl] | 3-(3,4-dichloro-2-methyl-2H-indazol-5-yl)-5-methyl-6-{3-oxa-7,9-diazabicyclo[3.3.1]nonan-7-yl}-1H,4H,5H-pyrazolo[3,4-d]pyrimidin-4-one hydrochloride salt | 1H NMR (500 MHz, DMSO-d6) δ: 13.59 (br s, 1H), 9.93 (br s, 1H), 9.81 (br s, 1H), 7.63 (d, J = 8.8 Hz, 1H), 7.33 (d, J = 8.8 Hz, 1H), 4.17 (s, 3H), 4.15 (app. d, J = 12.8 Hz, 2H), 4.08 (app. d, J = 12.8 Hz, 2H), 3.85 (app. d, J = 13.3 Hz, 2H), 3.67 (app. br s, 2H), 3.56 (app. d, J = 13.3 Hz, 2H), 3.48 (s, 3H). | 475 | 8 |
| 147 | 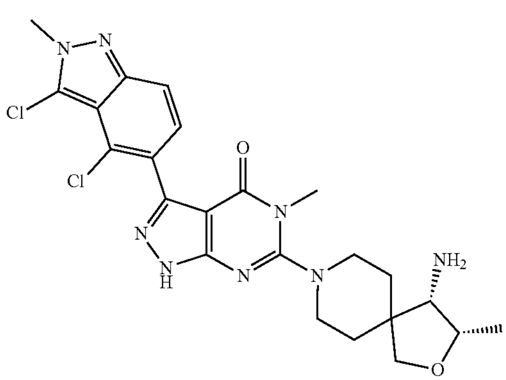 [SMILES: C[C@@H]1OCC2(CCN(c3nc4[nH]nc(-c5ccc6nn(C)c(Cl)c6c5Cl)c4c(=O)n3C)CC2)[C@@H]1N] | 6-[(3S,4S)-4-amino-3-methyl-2-oxa-8-azaspiro[4.5]decan-8-yl]-3-(3,4-dichloro-2-methyl-2H-indazol-5-yl)-5-methyl-1H,4H,5H-pyrazolo[3,4-d]pyrimidin-4-one hydrochloride salt | 1H NMR (500 MHz, DMSO-d6) δ: 8.21 (br s, 3H), 7.62 (d, J = 8.8 Hz, 1H), 7.33 (d, J = 8.8 Hz, 1H), 4.25-4.18 (m, 1H), 4.17 (s, 3H), 3.89 (d, J = 9.0 Hz, 1H), 3.65 (d, J = 9.0 Hz, 1H), 3.54-3.46 (m, 1H), 3.46-3.40 (m, 2H), 3.39 (s, 3H), 2.97-2.85 (m, 2H), 2.00-1.89 (m, 2H), 1.79-1.70 (m, 1H), 1.69-1.60 (m, 1H), 1.25 (d, J = 6.5 Hz, 3H). | 517 | 8 |

TABLE 11-continued

| Example | Structure | Name | NMR Data | [M + H]⁺ m/z | Method |
|---|---|---|---|---|---|
| 148 | 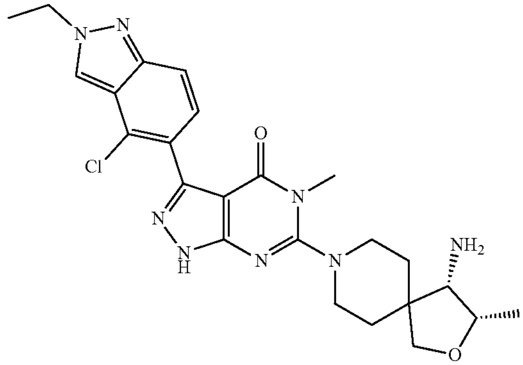 [SMILES: CCn1cc2c(Cl)c(-c3n[nH]c4nc(N5CCC6(CC5)CO[C@@H](C)[C@H]6N)n(C)c(=O)c34)ccc2n1] | 6-[(3S,4S)-4-amino-3-methyl-2-oxa-8-azaspiro[4.5]decan-8-yl]-3-(4-chloro-2-ethyl-2H-indazol-5-yl)-5-methyl-1H,4H,5H-pyrazolo[3,4-d]pyrimidin-4-one hydrochloride salt | $^1$H NMR (500 MHz, DMSO-$d_6$) δ: 13.48 (s, 1H), 8.58 (s, 1H), 8.18 (br s, 3H), 7.61 (d, J = 9.0 Hz, 1H), 7.32 (d, J = 9.0 Hz, 1H), 4.52 (q, J = 7.3 Hz, 2H), 4.25-4.18 (m, 1H), 3.89 (d, J = 9.0 Hz, 1H), 3.66 (d, J = 9.0 Hz, 1H), 3.54-3.46 (m, 1H), 3.46-3.40 (m, 2H), 3.39 (s, 3H), 2.91 (app. q, J = 11.6 Hz, 2H), 2.00-1.89 (m, 2H), 1.75 (app. d, J = 13.6 Hz, 1H), 1.65 (app. d, J = 12.8 Hz, 1H), 1.54 (t, J = 7.3 Hz, 3H), 1.24 (d, J = 6.5 Hz, 3H). | 497 | 8 |

2H-indazol-5-yl)-5-methyl-1H,4H,5H-pyrazolo[3,4-d]pyrimidin-4-one

Step 1: Benzyl N-[(1S,2R,3S,5R)-8-[3-bromo-5-methyl-1-(oxan-2-yl)-4-oxo-1H,4H,5H-pyrazolo[3,4-d]pyrimidin-6-yl]-2-fluoro-8-azabicyclo[3.2.1]octan-3-yl]carbamate

[Chem. 164]

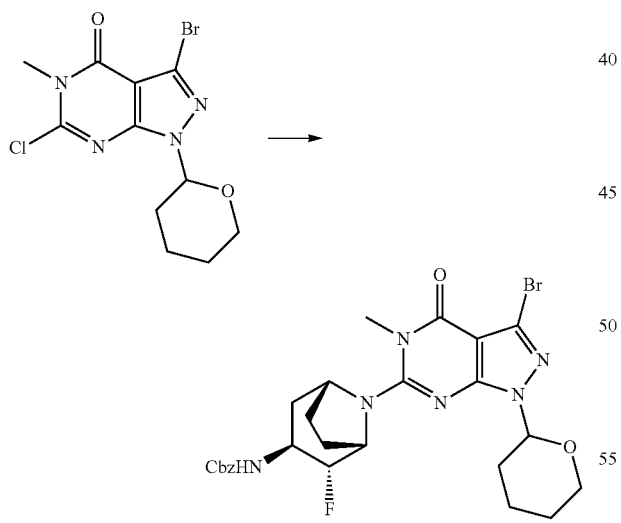

A mixture of 3-bromo-6-chloro-5-methyl-1-(oxan-2-yl)-1H,4H,5H-pyrazolo[3,4-d]pyrimidin-4-one (0.15 g, 0.43 mmol), benzyl N-[(1S,2S,3S,5R)-2-fluoro-8-azabicyclo[3.2.1]octan-3-yl]carbamate (0.144 g, 0.52 mmol) and diisopropylethylamine (0.38 mL, 2.16 mmol) in NMP (10 mL) was heated to 130° C. for 30 min. The reaction was cooled to ambient temperature, diluted in TBME/DCM 1:1 (20 mL) and washed with aqueous 1M LiCl (2×10 mL). Aqueous layers were combined and extracted with 10 mL DCM. The combined organic extracts were washed with HCl (1 M, 10 mL), dried (MgSO$_4$) and concentrated under reduced pressure to afford benzyl N-[(1S,2R,3S,5R)-8-[3-bromo-5-methyl-1-(oxan-2-yl)-4-oxo-1H,4H,5H-pyrazolo[3,4-d]pyrimidin-6-yl]-2-fluoro-8-azabicyclo[3.2.1]octan-3-yl]carbamate (310 mg, 0.40 mmol, 94% yield) as an off white solid. MS: [M+H]⁺=591.

Step 2: Benzyl N-[(1S,2R,3S,5R)-8-[3-(4-chloro-2-methyl-2H-indazol-5-yl)-5-methyl-1-(oxan-2-yl)-4-oxo-1H,4H,5H-pyrazolo[3,4-d]pyrimidin-6-yl]-2-fluoro-8-azabicyclo[3.2.1]octan-3-yl]carbamate

[Chem. 165]

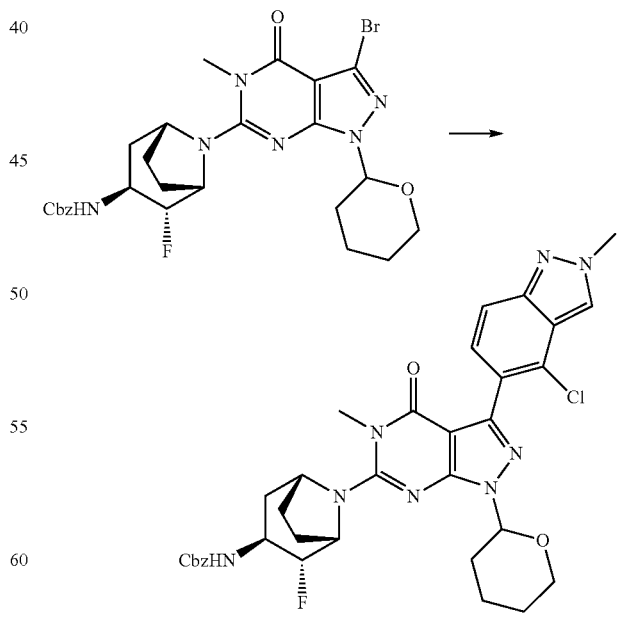

A mixture of benzyl N-[(1S,2R,3S,5R)-8-[3-bromo-5-methyl-1-(oxan-2-yl)-4-oxo-1H,4H,5H-pyrazolo[3,4-d]pyrimidin-6-yl]-2-fluoro-8-azabicyclo[3.2.1]octan-3-yl]carbamate (0.3 g, 0.51 mmol), 4-chloro-2-methyl-5-(4,4,5,5- tetramethyl-1,3,2-dioxaborolan-2-yl)-2H-indazole (0.18 g, 0.61 mmol), Na₂CO₃ (0.16 g, 1.53 mmol) and PdCl₂(dppf).DCM (0.042 g, 0.05 mmol) in 1,4-dioxane (5 mL) and water (0.6 mL) was degassed under a flow of N2. The reaction was heated to 100° C. for 2 h. Once cooled to ambient temperature, the reaction mixture was partitioned with 2 mL water and 10 mL DCM, the organic layer separated, dried over MgSO₄ and concentrated under reduced pressure. The crude product was purified by chromatography on silica gel (12 g cartridge, 0-10% MeOH/DCM) to afford product as a brown solid. The crude product was purified by chromatography on silica gel (12 g gold cartridge, 2-4% (0.7 M Ammonia/MeOH)/DCM) to afford benzyl N-[(1S,2R,3S,5R)-8-[3-(4-chloro-2-methyl-2H-indazol-5-yl)-5-methyl-1-(oxan-2-yl)-4-oxo-1H,4H,5H-pyrazolo[3,4-d]pyrimidin-6-yl]-2-fluoro-8-azabicyclo[3.2.1]octan-3-yl]carbamate (0.07 g, 0.10 mmol, 20% yield) as a white powder. MS: [M+H]⁺=675.

Step 3: 6-[(1S,2R,3S,5R)-3-Amino-2-fluoro-8-azabicyclo[3.2.1]octan-8-yl]-3-(4-chloro-2-methyl-2H-indazol-5-yl)-5-methyl-1H,4H,5H-pyrazolo[3,4-d]pyrimidin-4-one

[Chem. 166]

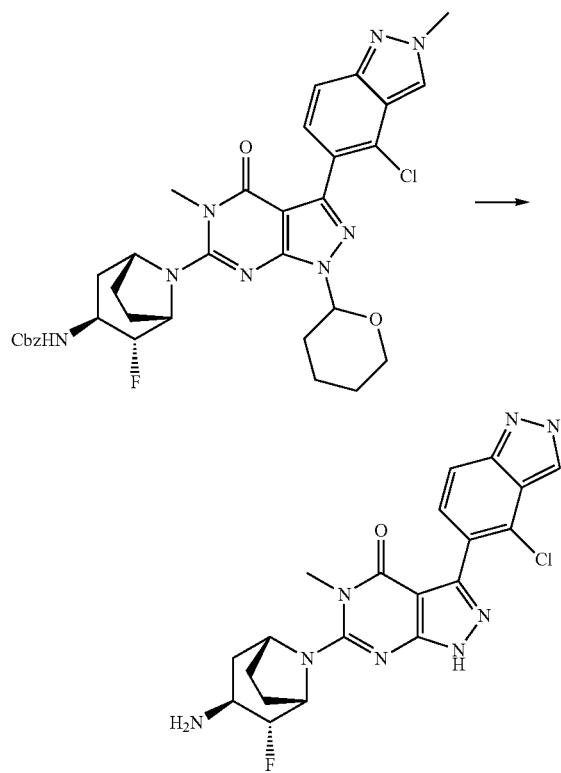

A solution of benzyl N-[(1S,2R,3S,5R)-8-[3-(4-chloro-2-methyl-2H-indazol-5-yl)-5-methyl-1-(oxan-2-yl)-4-oxo-1H,4H,5H-pyrazolo[3,4-d]pyrimidin-6-yl]-2-fluoro-8-azabicyclo[3.2.1]octan-3-yl]carbamate (0.07 g, 0.10 mmol) in TFA (1.04 mL, 13.5 mmol) was treated with trifluoromethanesulfonic acid (0.11 mL, 1.24 mmol) and stirred at RT for 5 minutes. The reaction mixture was quenched by adding it dropwise to saturated aqueous sodium carbonate (10 mL), then it was diluted with LiCl 0.1 M (50 mL), and extracted with DCM (3×20 mL). The organic layers were combined, dried over MgSO₄, filtered and concentrated under reduced pressure to afford crude material. The crude product was purified by chromatography on silica gel (4 g gold cartridge, 0-10% (0.7 M Ammonia/MeOH)/DCM) to afford 6-[(1S,2R,3S,5R)-3-amino-2-fluoro-8-azabicyclo[3.2.1]octan-8-yl]-3-(4-chloro-2-methyl-2H-indazol-5-yl)-5-methyl-1H,4H,5H-pyrazolo[3,4-d]pyrimidin-4-one as a colourless glass. Product was treated with 5 mL 2M HCl in ether, sonicated for 10 min and filtered to afford 6-[(1S,2R,3S,5R)-3-amino-2-fluoro-8-azabicyclo[3.2.1]octan-8-yl]-3-(4-chloro-2-methyl-2H-indazol-5-yl)-5-methyl-1H,4H,5H-pyrazolo[3,4-d]pyrimidin-4-one hydrochloride (10 mg, 0.02 mmol, 19% yield) as a white powder. MS: [M+H]⁺=457.

¹H NMR (500 MHz, Methanol-d₄) δ: 8.48 (s, 1H), 7.64 (dd, J=8.8, 0.9 Hz, 1H), 7.47 (d, J=8.8 Hz, 1H), 4.75-4.68 (m, 1H), 4.64 (dd, J=16.7, 7.7 Hz, 1H), 4.49 (t, J=7.8 Hz, 1H), 4.30 (s, 3H), 3.75-3.65 (m, 1H), 3.60 (s, 3H), 2.91 (q, J=11.5, 11.1 Hz, 1H), 2.48 (d, J=11.8 Hz, 1H), 2.12 (dq, J=12.5, 6.4 Hz, 1H), 1.91 (dt, J=14.4, 8.0 Hz, 1H), 1.68 (t, J=10.0 Hz, 1H), 1.44-1.35 (m, 1H).

Method 9: 2-[(3S,4S)-4-Amino-3-methyl-2-oxa-8-azaspiro[4.5]decan-8-yl]-5-(4-chloro-2-ethyl-2H-indazol-5-yl)-3-methyl-3H,4H,7H-pyrrolo[2,3-d]pyrimidin-4-one

[Chem. 167]

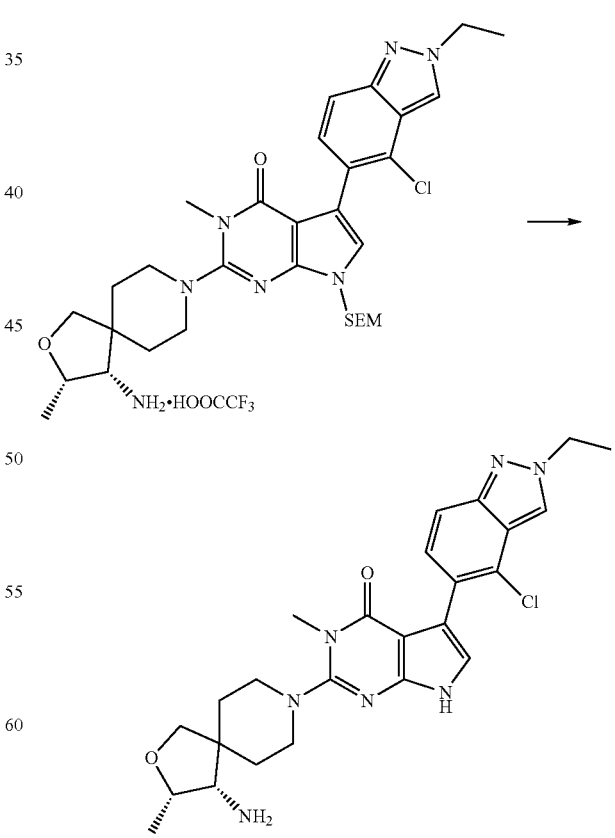

TFA (1 mL) was added to a solution of 2-[(3S,4S)-4-amino-3-methyl-2-oxa-8-azaspiro[4.5]decan-8-yl]-5-(4-chloro-2-ethyl-2H-indazol-5-yl)-3-methyl-7-{[2-(trimethylsilyl)ethoxy]methyl}-3H,4H,7H-pyrrolo[2,3-d]pyrimidin-4-one (256 mg, 1.82 mmol) in DCM (1 mL) and the mixture was stirred at RT for 18 h. The mixture was concentrated and azeotroped with toluene twice, MeOH (2 mL) and ethylenediamine (0.23 mL, 3.46 mmol) were added to the residue and it was stirred at RT for 5 h. The reaction mixture was concentrated, suspended in MeOH and the solid collected by filtration to afford the title compound (24 mg, 0.048 mmol, 14%).

The compounds shown in Table 12 were prepared using methods similar to those described in method 9. The compounds could be isolated directly, by trituration/precipitation from solution, or were purified (e.g. using mass-directed preparative HPLC, chromatography, crystallization). In some cases, the compound was isolated as the hydrochloride salt; by treating a solution of the final compound (e.g. in MeOH) with excess HCl (2N HCl in Et$_2$O) and then evaporating to dryness.

TABLE 12

| Example | Structure | Name | NMR Data | [M + H]$^+$ m/z | Method |
| --- | --- | --- | --- | --- | --- |
| 150 | 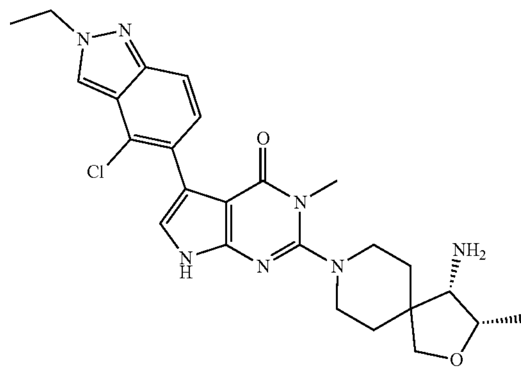 [SMILES: CCn1cc2c(Cl)c(-c3c[nH]c4nc(N5CCC6(CC5)CO[C@@H](C)[C@H]6N)n(C)c(=O)c34)ccc2n1] | 2-[(3S,4S)-4-amino-3-methyl-2-oxa-8-azaspiro[4.5]decan-8-yl]-5-(4-chloro-2-ethyl-2H-indazol-5-yl)-3-methyl-3H,4H,7H-pyrrolo[2,3-d]pyrimidin-4-one | $^1$H NMR (400 MHz, DMSO-d$_6$) δ: 11.74 (1H, s), 8.45 (1H, s), 7.50 (1H, dd), 7.32 (1H, d), 7.01 (1H, s), 4.49 (2H, q), 4.12-4.03 (1H, m), 3.67 (1H, d), 3.50 (1H, d), 3.40 (3H, s), 3.29-3.16 (2H, m), 3.02-2.84 (3H, m), 1.94-1.82 (1H, m), 1.82-1.71 (1H, m), 1.71-1.57 (2H, m), 1.53 (3H, t), 1.33 (2H, br s), 1.10 (3H, d). | 496 | 9 |
| 151 | 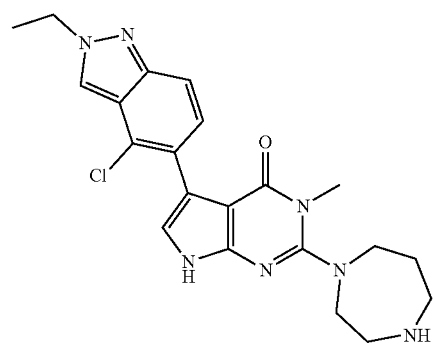 [SMILES: CCn1cc2c(Cl)c(-c3c[nH]c4nc(N5CCCNCC5)n(C)c(=O)c34)ccc2n1] | 5-(4-chloro-2-ethyl-2H-indazol-5-yl)-2-(1,4-diazepan-1-yl)-3-methyl-3H,4H,7H-pyrrolo[2,3-d]pyrimidin-4-one hydrochloride | $^1$H NMR (400 MHz, DMSO-d$_6$) δ: 8.38 (1H, s), 7.54 (1H, dd), 7.48 (1H, d), 7.06 (1H, s), 4.55 (2H, q), 3.80 (2H, t), 3.65-3.52 (7H, m), 3.46 (2H, t), 2.26-2.17 (2H, m), 1.65 (3H, t). | 426 | 9 |
| 152 | 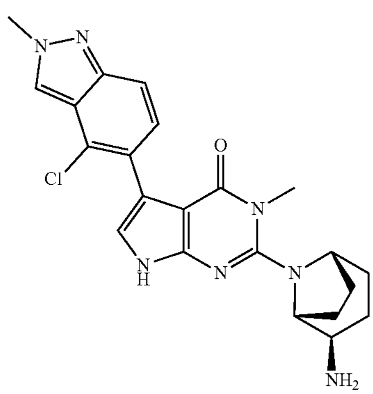 [SMILES: Cn1cc2c(Cl)c(-c3c[nH]c4nc(N5[C@@H]6CC[C@@H](N)[C@H]5CC6)n(C)c(=O)c34)ccc2n1] | rac-2-[(1R,2R,5R)-2-amino-8-azabicyclo[3.2.1]octan-8-yl]-5-(4-chloro-2-methyl-2H-indazol-5-yl)-3-methyl-3H,4H,7H-pyrrolo[2,3-d]pyrimidin-4-one | $^1$H NMR (400 MHz, DMSO-d$_6$) δ: 12.26-10.98 (1H, m), 8.40 (1H, s), 7.49 (1H, dd), 7.34 (1H, d), 6.96 (1H, s), 4.20 (3H, s), 4.11-4.04 (1H, m), 3.87-3.80 (1H, m), 3.44 (3H, s), 3.05-2.98 (1H, m), 2.04-1.92 (2H, m), 1.89-1.74 (2H, m), 1.71-1.64 (1H, m), 1.57-1.47 (2H, m), 1.28-1.14 (1H, m). | 438 | 9 |

TABLE 12-continued

| Example | Structure | Name | NMR Data | [M + H]+ m/z | Method |
|---|---|---|---|---|---|
| 153 | 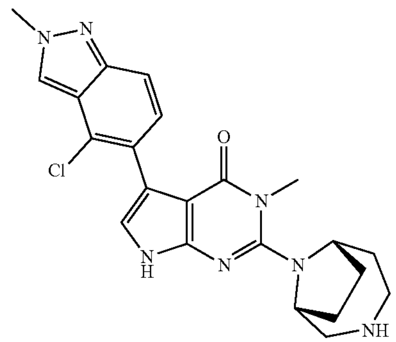 [SMILES: Cn1cc2c(Cl)c(-c3c[nH]c4nc(N5[C@@H]6CCNC[C@H]5CC6)n(C)c(=O)c34)ccc2n1] | rac-5-(4-chloro-2-methyl-2H-indazol-5-yl)-2-[(1R,6S)-3,9-diazabicyclo[4.2.1]nonan-9-yl]-3-methyl-3H,4H,7H-pyrrolo[2,3-d]pyrimidin-4-one | ¹H NMR (400 MHz, DMSO-d₆) δ: 12.25-10.77 (1H, m), 8.40 (1H, s), 7.49 (1H, dd), 7.33 (1H, d), 6.96 (1H, s), 4.46-4.40 (1H, m), 4.28 (1H, t), 4.20 (3H, s), 3.44 (3H, s), 3.02-2.94 (1H, m), 2.87-2.69 (3H, m), 2.18-1.97 (3H, m), 1.84-1.74 (2H, m), 1.53-1.43 (1H, m). | 438 | 9 |
| 154 | 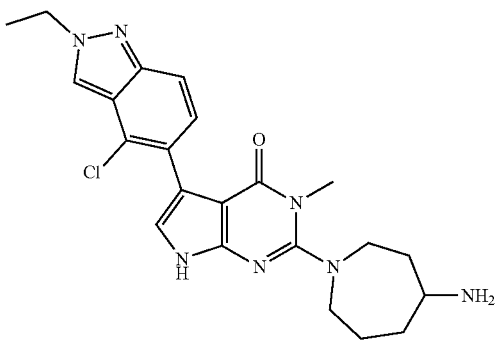 [SMILES: CCn1cc2c(Cl)c(-c3c[nH]c4nc(N5CCCC(N)CC5)n(C)c(=O)c34)ccc2n1] | rac-2-(4-aminoazepan-1-yl)-5-(4-chloro-2-ethyl-2H-indazol-5-yl)-3-methyl-3H,4H,7H-pyrrolo[2,3-d]pyrimidin-4-one hydrochloride | ¹H NMR (400 MHz, DMSO-d₆) δ: 11.65 (1H, d), 8.45 (1H, d), 8.02 (3H, br s), 7.51 (1H, dd), 7.32 (1H, d), 6.99 (1H, d), 4.49 (2H, q), 3.56-3.45 (1H, m), 3.45-3.24 (7H, m), 2.22-2.11 (1H, m), 2.10-2.00 (1H, m), 2.00-1.84 (2H, m), 1.84-1.67 (2H, m), 1.53 (3H, t). | 440 | 9 |

Example 155 and 156 rel-2-((1R,4R,7R)-7-amino-2-azabicyclo[2.2.1]heptan-2-yl)-5-(4-chloro-2-ethyl-2H-indazol-5-yl)-3-methyl-3,7-dihydro-4H-pyrrolo[2,3-d]pyrimidin-4-one (Example 155) and rel-2-((1S,4S,7S)-7-Amino-2-azabicyclo[2.2.1]heptan-2-yl)-5-(4-chloro-2-ethyl-2H-indazol-5-yl)-3-methyl-3,7-dihydro-4H-pyrrolo[2,3-d]pyrimidin-4-one (Example 156)

[Chem. 168]

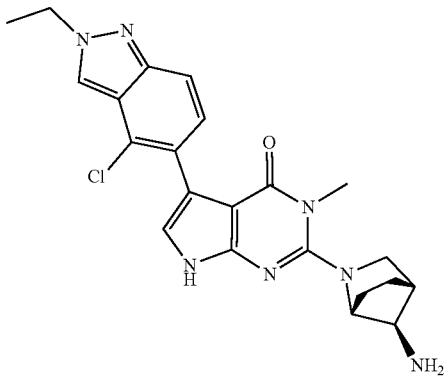

rac-2-((1S,4S,7S)-7-Amino-2-azabicyclo[2.2.1]heptan-2-yl)-5-(4-chloro-2-ethyl-2H-indazol-5-yl)-3-methyl-3,7-dihydro-4H-pyrrolo[2,3-d]pyrimidin-4-one was dissolved as a 2.0 mg/mL ethanol/DMSO/CHCl₃=1/1/3 solution, and separation was performed under the following conditions.

Column: Daicel CHIRALPAK IG 2×25 cm
Mobile phase:hexane/2-propanol=40/60
Flow rate: 25 mL/min
Retention Time of Each Isomer:
rel-2-((1R,4R,7R)-7-Amino-2-azabicyclo[2.2.1]heptan-2-yl)-5-(4-chloro-2-ethyl-2H-indazol-5-yl)-3-methyl-3,7-dihydro-4H-pyrrolo[2,3-d]pyrimidin-4-one: 8.15 minutes
rel-2-((1S,4S,7S)-7-Amino-2-azabicyclo[2.2.1]heptan-2-yl)-5-(4-chloro-2-ethyl-2H-indazol-5-yl)-3-methyl-3,7-dihydro-4H-pyrrolo[2,3-d]pyrimidin-4-one: 13.5 minutes.

Chiral Analysis Conditions:
Column: CHIRALPAK IG 4.6×150 mm
Mobile phase:hexane/2-propanol=40/60
Flow rate: 1.0 mL/min
Retention Time of Each Isomer:
rel-2-((1R,4R,7R)-7-Amino-2-azabicyclo[2.2.1]heptan-2-yl)-5-(4-chloro-2-ethyl-2H-indazol-5-yl)-3-methyl-3,7-dihydro-4H-pyrrolo[2,3-d]pyrimidin-4-one: 7.406 minutes. MS: [M+H]$^+$=438, 440. $^1$H-NMR (DMSO-d$_6$) δ: 11.49 (1H, br s), 8.42 (1H, s), 7.47 (1H, dd, J=9.0, 0.7 Hz), 7.30 (1H, d, J=9.0 Hz), 6.87 (1H, s), 4.46 (2H, q, J=7.3 Hz), 3.86-3.66 (2H, m), 3.30-3.26 (3H, m), 3.17-3.14 (1H, m), 3.04-2.98 (1H, m), 2.18-2.11 (1H, m), 2.01-1.82 (3H, m), 1.51 (3H, t, J=7.1 Hz), 1.40-1.31 (1H, m).

rel-2-((1S,4S,7S)-7-Amino-2-azabicyclo[2.2.1]heptan-2-yl)-5-(4-chloro-2-ethyl-2H-indazol-5-yl)-3-methyl-3,7-dihydro-4H-pyrrolo[2,3-d]pyrimidin-4-one: 11.246 minutes. MS: [M+H]$^+$=438, 440. $^1$H-NMR (DMSO-d$_6$) δ: 11.49 (1H, br s), 8.42 (1H, s), 7.47 (1H, dd, J=9.0, 0.7 Hz), 7.30 (1H, d, J=9.0 Hz), 6.87 (1H, s), 4.46 (2H, q, J=7.3 Hz), 3.86-3.66 (2H, m), 3.30-3.26 (3H, m), 3.17-3.14 (1H, m), 3.04-2.98 (1H, m), 2.18-2.11 (1H, m), 2.01-1.82 (3H, m), 1.51 (3H, t, J=7.1 Hz), 1.40-1.31 (1H, m).

Example 157: rel-2-((1R,4R,7R)-7-Amino-2-azabicyclo[2.2.1]heptan-2-yl)-5-(4-chloro-2-methyl-2H-indazol-5-yl)-3-methyl-3,7-dihydro-4H-pyrrolo[2,3-d]pyrimidin-4-one

[Chem. 169]

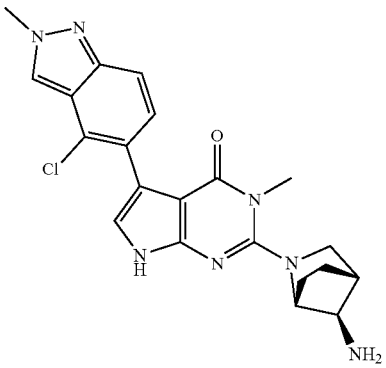

Step 1 rac-2-((1S,4S,7S)-7-Amino-2-azabicyclo[2.2.1]heptan-2-yl)-5-(4-chloro-2-methyl-2H-indazol-5-yl)-3-methyl-3,7-dihydro-4H-pyrrolo[2,3-d]pyrimidin-4-one (200 mg, 0.472 mmol) was dissolved in CHCl$_3$/MeOH=4/1 (5.0 mL). Di-tert-butyl dicarbonate (206 mg, 0.944 mmol) dissolved in CHCl$_3$ (1.0 mL) was added thereto at 0° C., followed by stirring at RT for 3 h. The solvent was distilled off, and the residue was purified by column chromatography on NH silica gel (gradient elution, 0-10% MeOH/EtOAc) to give rac-tert-butyl ((1S,4S,7S)-2-(5-(4-chloro-2-methyl-2H-indazol-5-yl)-3-methyl-4-oxo-4,7-dihydro-3H-pyrrolo[2,3-d]pyrimidin-2-yl)-2-azabicyclo[2.2.1]heptan-7-yl)carbamate. rac-tert-Butyl ((1S,4S,7S)-2-(5-(4-chloro-2-methyl-2H-indazol-5-yl)-3-methyl-4-oxo-4,7-dihydro-3H-pyrrolo[2,3-d]pyrimidin-2-yl)-2-azabicyclo[2.2.1]heptan-7-yl)carbamate was dissolved as a 25 mg/mL ethanol/CHCl$_3$=1/1 solution, and separation was performed under the following conditions.

Column: Daicel CHIRALPAK IG 2×25 cm
Mobile phase:hexane/2-propanol=45/55
Flow rate: 25 mL/min
Retention Time of Each Isomer:
rel-tert-Butyl ((1R,4R,7R)-2-(5-(4-chloro-2-methyl-2H-indazol-5-yl)-3-methyl-4-oxo-4,7-dihydro-3H-pyrrolo[2,3-d]pyrimidin-2-yl)-2-azabicyclo[2.2.1]heptan-7-yl)carbamate: 7.5 minutes
rel-tert-Butyl ((1S,4S,7S)-2-(5-(4-chloro-2-methyl-2H-indazol-5-yl)-3-methyl-4-oxo-4,7-dihydro-3H-pyrrolo[2,3-d]pyrimidin-2-yl)-2-azabicyclo[2.2.1]heptan-7-yl)carbamate: 12.5 minutes.

Chiral Analysis Conditions:
Column: CHIRALPAK IG 4.6×150 mm
Mobile phase:hexane/2-propanol=40/60
Flow rate: 1.0 mL/min
Retention Time of Each Isomer:
rel-tert-Butyl ((1R,4R,7R)-2-(5-(4-chloro-2-methyl-2H-indazol-5-yl)-3-methyl-4-oxo-4,7-dihydro-3H-pyrrolo[2,3-d]pyrimidin-2-yl)-2-azabicyclo[2.2.1]heptan-7-yl)carbamate: 5.668 minutes
rel-tert-Butyl ((1S,4S,7S)-2-(5-(4-chloro-2-methyl-2H-indazol-5-yl)-3-methyl-4-oxo-4,7-dihydro-3H-pyrrolo[2,3-d]pyrimidin-2-yl)-2-azabicyclo[2.2.1]heptan-7-yl)carbamate: 9.407 minutes.

Step 2 rel-tert-Butyl ((1R,4R,7R)-2-(5-(4-chloro-2-methyl-2H-indazol-5-yl)-3-methyl-4-oxo-4,7-dihydro-3H-pyrrolo[2,3-d]pyrimidin-2-yl)-2-azabicyclo[2.2.1]heptan-7-yl)carbamate (81.5 mg, 0.155 mmol) and TFA (1.0 mL) were dissolved in methanol (1.0 mL). The mixture was stirred at RT for 30 minutes. The solvent was distilled off, and the residue was purified by column chromatography on NH silica gel (gradient elution, 0-10% MeOH/EtOAc) to give the title compound. MS: [M+H]$^+$=424, 426. $^1$H-NMR (DMSO-d$_6$) δ: 11.49 (1H, br s), 8.37 (1H, s), 7.46 (1H, d, J=8.9 Hz), 7.31 (1H, d, J=8.9 Hz), 6.88 (1H, s), 4.18 (3H, s), 3.84 (1H, s), 3.73-3.65 (1H, m), 3.28-3.23 (4H, m), 3.02 (1H, d, J=8.8 Hz), 2.15 (1H, s), 2.01-1.83 (3H, m), 1.74-1.49 (2H, m), 1.42-1.31 (1H, m).

Example 158: rel-2-((1S,4S,7S)-7-Amino-2-azabicyclo[2.2.1]heptan-2-yl)-5-(4-chloro-2-methyl-2H-indazol-5-yl)-3-methyl-3,7-dihydro-4H-pyrrolo[2,3-d]pyrimidin-4-one

[Chem. 170]

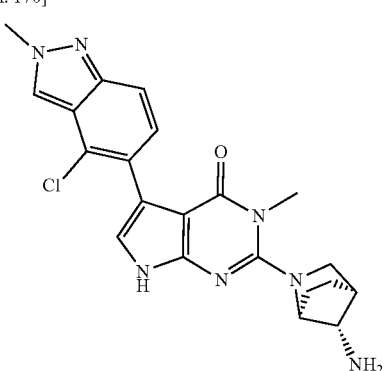

In accordance with Step 2 of Example 157, except that rel-tert-butyl ((1S,4S,7S)-2-(5-(4-chloro-2-methyl-2H-indazol-5-yl)-3-methyl-4-oxo-4,7-dihydro-3H-pyrrolo[2,3-d]pyrimidin-2-yl)-2-azabicyclo[2.2.1]heptan-7-yl)carbamate obtained in Step 1 of Example 157 was used in place of rel-tert-butyl ((1R,4R,7R)-2-(5-(4-chloro-2-methyl-2H-indazol-5-yl)-3-methyl-4-oxo-4,7-dihydro-3H-pyrrolo[2,3-d]pyrimidin-2-yl)-2-azabicyclo[2.2.1]heptan-7-yl)carbamate, the title compound was obtained. MS: [M+H]⁺=424, 426. ¹H-NMR (DMSO-d₆) δ: 11.49 (1H, br s), 8.37 (1H, s), 7.46 (1H, d, J=8.9 Hz), 7.31 (1H, d, J=8.9 Hz), 6.88 (1H, s), 4.18 (3H, s), 3.84 (1H, s), 3.73-3.65 (1H, m), 3.28-3.23 (4H, m), 3.02 (1H, d, J=8.8 Hz), 2.15 (1H, s), 2.01-1.83 (3H, m), 1.74-1.49 (2H, m), 1.42-1.31 (1H, m).

Example 159: 5-(2-((1R,2R,4S)-2-Amino-7-azabicyclo[2.2.1]heptan-7-yl)-3-methyl-4-oxo-4,7-dihydro-3H-pyrrolo[2,3-d]pyrimidin-5-yl)-4-chloro-2-ethyl-2H-indazole-3-carbonitrile

[Chem. 171]

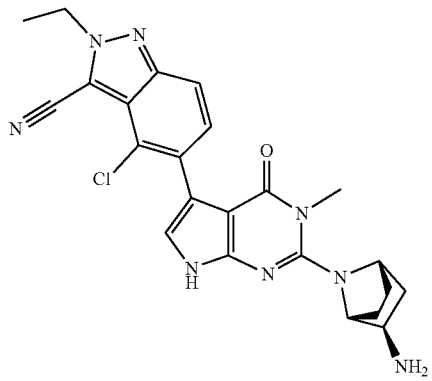

tert-Butyl ((1R,2R,4S)-7-(5-(4-chloro-3-cyano-2-ethyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)carbamate (50 mg, 0.072 mmol) was dissolved in N,N-dimethylformamide (0.5 mL). To the solution was added tetrabutylammonium fluoride (1 M in THF, 0.22 mL, 0.22 mmol) and stirred at 80° C. for 1 d. To the mixture was added 5 M NaOH aq. (0.072 mL, 0.36 mmol, 5 mol/L), and stirred at RT for 1 h. The mixture was concentrated in vacuo and the residue was purified by r-HPLC. The obtained fractions were concentrated in vacuo, and the residue was dissolved in acetonitrile (1.0 mL). To the solution was added sodium iodide (5.8 mg, 0.039 mmol) and chlorotrimethylsilane (0.0031 mL, 0.024 mmol), and the mixture was stirred at RT for 2 h. The mixture was concentrated in vacuo, and the residue was purified by column chromatography on NH silica gel (gradient elution, 0-10% MeOH/CHCl₃) to give the title compound (4.9 mg). MS: [M+H]⁺=463, 465. ¹H-NMR (DMSO-d₆) δ: 11.78 (1H, br s), 7.79 (1H, d, J=8.8 Hz), 7.53 (1H, d, J=8.8 Hz), 7.07 (1H, s), 4.68 (2H, q, J=7.2 Hz), 4.15 (1H, br t, J=4.8 Hz), 4.02 (1H, br t, J=4.4 Hz), 3.53-3.45 (1H, m), 3.40 (3H, s), 2.36-2.21 (1H, m), 2.20-2.09 (1H, m), 1.96-1.84 (1H, m), 1.75-1.64 (1H, m), 1.58 (3H, t, J=7.2 Hz), 1.54-1.44 (1H, m), 0.97-0.87 (1H, m).

Preparation 117: tert-Butyl N-[(1R,2R,3S,5S)-2-fluoro-8-azabicyclo[3.2.1]octan-3-yl]carbamate

[Chem. 172]

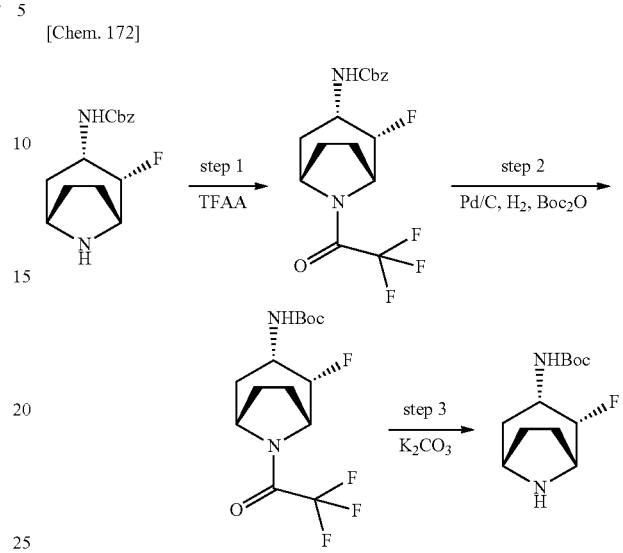

Step 1: Benzyl N-[(1R,2S,3S,5S)-2-fluoro-8-(2,2,2-trifluoroacetyl)-8-azabicyclo[3.2.1]octan-3-yl]carbamate To a solution of benzyl N-[(1R,2R,3S,5S)-2-fluoro-8-azabicyclo[3.2.1]octan-3-yl]carbamate (1.0 g, 3.6 mmol) and Et₃N (1.0 mL, 7.2 mmol) in DCM (15 mL) was added trifluoroacetic anhydride (0.53 mL, 3.78 mmol) and the reaction mixture was stirred at RT for 1 h. The reaction was diluted with DCM and sat. aq. NaHCO₃ was added. The aqueous layer was extracted with DCM, the organic phase was dried (MgSO₄), filtered and concentrated. The crude product was purified by column chromatography on silica gel (gradient elution, 0-60%, EtOAc/petrol), to give the title compound (1.32 g). ¹H NMR (400 MHz, DMSO-d₆) δ: 7.47 (1H, d), 7.42-7.25 (5H, m), 5.05 (2H, s), 4.88-4.60 (2H, m), 4.59-4.33 (1H, m), 4.01-3.85 (1H, m), 3.35 (1H, s), 2.13-2.01 (1H, m), 1.99-1.68 (5H, m).

Step 2: tert-Butyl N-[(1R,2S,3S,5S)-2-fluoro-8-(2,2,2-trifluoroacetyl)-8-azabicyclo[3.2.1]octan-3-yl] carbamate To a solution of benzyl N-[(1R,2S,3S,5S)-2-fluoro-8-(2,2,2-trifluoroacetyl)-8-azabicyclo[3.2.1]octan-3-yl]carbamate (1.32 g, 3.53 mmol) in ethanol (15 mL) were added di-tert-butyl dicarbonate (1.0 g, 4.58 mmol) and Pd/C (10%, 0.13 g) and the mixture was hydrogenated for 6 h. The reaction was filtered and the filtrate evaporated. The residue was purified by column chromatography on silica gel (gradient elution, 0-40%, EtOAc/petrol), to give the title compound (1.04 g). ¹H NMR (400 MHz, DMSO-d₆) δ: 6.98 (1H, d), 4.89-4.21 (3H, m), 3.86 (1H, d), 2.19-1.53 (6H, m), 1.39 (9H, s).

Step 3: tert-Butyl N-[(1R,2R,3S,5S)-2-fluoro-8-azabicyclo[3.2.1]octan-3-yl]carbamate To a solution of tert-butyl N-[(1R,2S,3S,5S)-2-fluoro-8-(2,2,2-trifluoroacetyl)-8-azabicyclo[3.2.1]octan-3-yl]carbamate (1.04 g, 3.07 mmol) in MeOH (15 mL) and H₂O (3 mL) was added K₂CO₃ (2.11 g, 15.35 mmol) and the mixture was stirred overnight. The MeOH was evaporated, H₂O was added and the product was extracted with DCM. The organic phase was dried (MgSO₄), filtered and evaporated, to give the title compound (0.733 g). $^1$H NMR (400 MHz, DMSO-d₆) δ: 6.75 (1H, d), 4.34 (1H, d), 3.72-3.52 (1H, m), 3.46 (1H, s), 3.35 (1H, s), 2.14 (1H, s), 1.69 (2H, d), 1.60-1.25 (13H, m).

Preparation 118: tert-Butyl N-[(1S,2R,3S,5R)-2-fluoro-8-azabicyclo[3.2.1]octan-3-yl]carbamate

[Chem. 173]

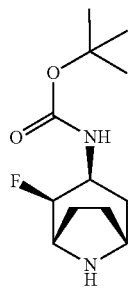

The title compound was prepared using similar method as in preparation 117 using benzyl N-[(1S,2R,3S,5R)-2-fluoro-8-azabicyclo[3.2.1]octan-3-yl]carbamate instead of benzyl N-[(1R,2R,3S,5S)-2-fluoro-8-azabicyclo[3.2.1]octan-3-yl] carbamate, to give the title compound, $^1$H NMR (400 MHz, DMSO-d₆) δ: 6.02 (1H, s), 4.96-4.44 (1H, m), 4.11-3.85 (1H, m), 3.40 (1H, q), 3.27 (1H, d), 2.35 (1H, s), 2.18-1.97 (1H, m), 1.97-1.83 (1H, m), 1.83-1.68 (1H, m), 1.68-1.48 (3H, m), 1.39 (9H, s).

Preparation 119: N-[(endo)-3-(Difluoromethyl)-8-azabicyclo[3.2.1]octan-3-yl]-2-methylpropane-2-sulfinamide

[Chem. 174]

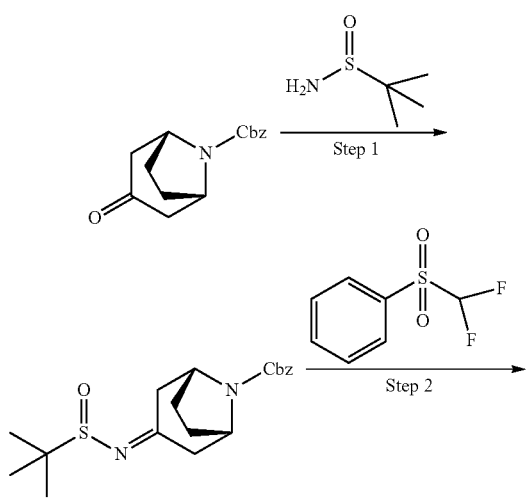

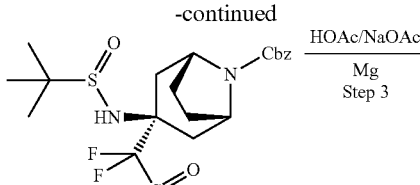

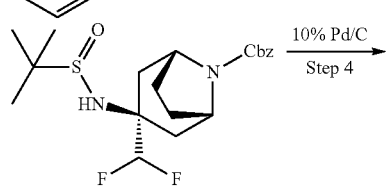

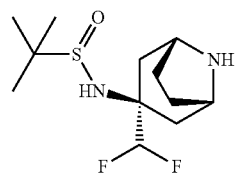

Step 1. Benzyl-3-[(2-methylpropane-2-sulfinyl)imino]-8-azabicyclo[3.2.1]octane-8-carboxylate To a stirred solution of benzyl-3-oxo-8-azabicyclo[3.2.1]octane-8-carboxylate (75.0 g, 289.2 mmol, 1.0 eq) in THF (1.5 L) was added 2-methyl-2-propanesulfinamide (43.0 g, 354.8 mmol, 1.2 eq) and Ti(OEt)₄ (200.0 g, 876.8 mmol, 3.0 eq). The reaction was heated to reflux for 3 hours and cooled to r. The mixture was quenched by adding H₂ (550 ml) slowly and stirred for 1 h. The solid was removed by filtration and the filtrate was diluted with EtOAc and washed with saturated brine and dried (Na₂SO₄). The solvent was removed under reduced pressure to afford the crude product (103 g) as a yellow powder. It was recrystallized from pet.ether/EtOAc=4:1 to afford the pure product (36 g, 34%) as a white solid. LC-MS: [M+H]⁺=363.

Step 2. Benzyl (endo)-3-[(benzenesulfonyl)difluoromethyl]-3-[(2-methylpropane-2-sulfinyl)amino]-8-azabicyclo[3.2.1]octane-8-carboxylate To the mixture of benzyl-3-[(2-methylpropane-2-sulfinyl)imino]-8-azabicyclo[3.2.1]octane-8-carboxylate (75.1 g, 207.0 mmol, 1.0 eq) and difluoromethanesulfonylbenzene (47.8 g, 248.0 mmol, 1.2 eq) in toluene (750 ml) was added KHMDS (269 ml, 269.0 mmol, 1.3 eq) at −78° C. drop wise under N₂. After the addition was complete, the reaction was stirred for another 2 hours at the same temperature and then quenched by adding H₂O (280 mL). The organic layer separated and dried over Na₂SO₄. The solvent was removed in vacuo and the residue was purified by silica gel column (EtOAc in pet.ether 0-30%, v/v) to afford the product (30.0 g, yield 26%) as yellow solid. LC-MS: [M+H]⁺=555.

Step 3. Benzyl (endo)-3-(difluoromethyl)-3-[(2-methylpropane-2-sulfinyl)amino]-8-azabicyclo[3.2.1]octane-8-carboxylate To the solution of benzyl (endo)-3-[(benzenesulfonyl)difluoromethyl]-3-[(2-methylpropane-2-sulfinyl)amino]-8-azabicyclo[3.2.1]octane-8-carboxylate (56.6 g, 102 mmol, 1.0 eq) in DMF (1050 mL) and HOAc/NaOAc (8 mol/L) (1:1, 1050 mL), Mg (50.9 g, 2.09 mol, 20.5 eq) was added portionwise at r.t. After the addition complete, the reaction was stirred for another 4 hours at r.t. LC-MS showed the reaction completed. The reaction mixture was diluted with water and extracted with EtOAc (1000 mL×2). The combined extracts were washed with water, dried over $Na_2SO_4$ and concentrated in vacuo to give the crude product, which was purified using reverse phase column (Eluant: MeOH in $H_2O$/TFA) to give the pure product (24.5 g, 58% yield) as a white solid. LC-MS: $[M+H]^+=415$.

Step 4. N-[(endo)-3-(Difluoromethyl)-8-azabicyclo[3.2.1]octan-3-yl]-2-methylpropane-2-sulfinamide The mixture of benzyl (endo)-3-(difluoromethyl)-3-[(2-methylpropane-2-sulfinyl)amino]-8-azabicyclo[3.2.1]octane-8-carboxylate (24.5 g, 59.0 mmol, 1.0 eq) and Pd/C (10%, 3.0 g) in MeOH (100 mL) was stirred at 50° C. for about 20 h under $H_2$. The Pd/C was removed by filtration and the filtrate was concentrated in vacuo to give the crude product, which was purified by silica gel column (MeOH in DCM 0-10% $NH_4OH$) to afford the title compound (10.8 g, 65% yield) as a colorless oil. LC-MS: $[M+H]^+=281$. $^1H$ NMR ($CDCl_3$) δ: 5.79 (1H, t), 3.65 (3H, br s), 2.22 (2H, m), 1.94 (2H, m), 1.83 (3H, m), 1.54 (1H, d), 1.28 (9H, s).

Preparation 120: 4-Bromo-3-chloro-2-nitroaniline and 6-bromo-3-chloro-2-nitroaniline

[Chem. 175]

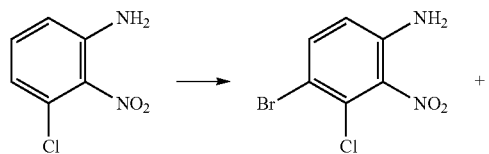

A solution of 3-chloro-2-nitroaniline (25 g, 145 mmol) and N-bromosuccinimide (25.5 g, 143 mmol) in AcOH (600 mL) was refluxed for 45 min. After cooling to RT, the reaction mixture was poured into ice-cold water (2 L). The precipitate was collected by filtration, washed with ice-cold water (2×200 mL) and dried in a vacuum oven overnight, to give the title compounds (36 g) as a mixture of isomers (4-bromo/6-bromo in 9:1 ratio). $^1H$ NMR (500 MHz, DMSO-$d_6$) δ: 7.56 (1H, d), 6.84 (1H, d), 6.40 (2H, s).

Preparation 121: Ethyl 2-[(4-bromo-3-chloro-2-nitrophenyl)amino]acetate and ethyl 2-[(6-bromo-3-chloro-2-nitrophenyl)amino]acetate

[Chem. 176]

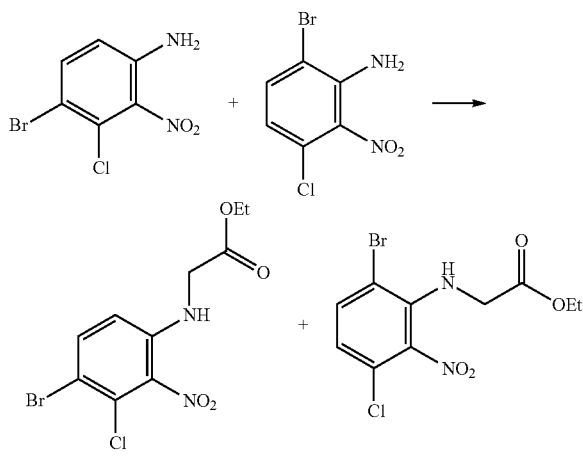

A mixture of 4-bromo-3-chloro-2-nitroaniline and 6-bromo-3-chloro-2-nitroaniline in a 9:1 ratio (30 g, 119 mmol), ethyl bromoacetate (133 mL, 119 mmol) and $K_2CO_3$ (26.4 g, 191 mmol) was heated at 140° C. under nitrogen for 30 h. The mixture was cooled to RT, then 1M aq. NaOH solution (250 mL) was added over 10 min. The mixture was stirred for a further 10 min, then extracted with DCM (3×30 mL). The combined organic layers were dried over $MgSO_4$, filtered and concentrated under vacuum. The crude product was purified by column chromatography on silica gel (gradient elution, 5-30%, EtOAc/isohexane). The purified mixture was recrystallised from boiling IPA (70 mL). The solid was filtered, washed with cyclohexane (2×50 mL), and dried in a vacuum oven overnight, to give the title compounds (4 g) as a mixture of isomers (4-bromo/6-bromo in 9:1 ratio). MS: $[M+H]^+=337$.

Preparation 122: 7-Bromo-8-chloro-1,2,3,4-tetrahydroquinoxalin-2-one and 8-bromo-5-chloro-1,2,3,4-tetrahydroquinoxalin-2-one

[Chem. 177]

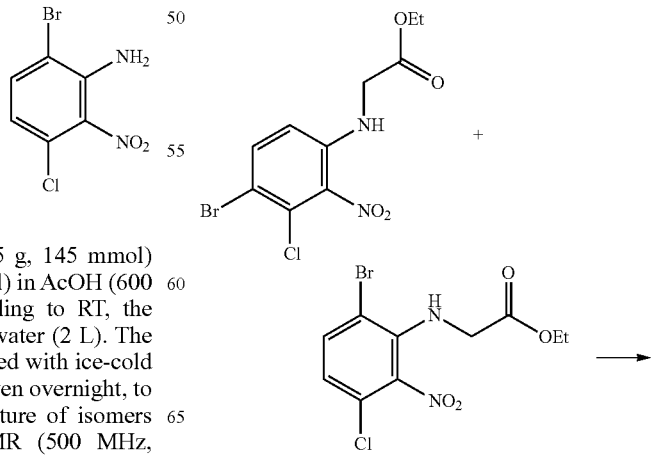

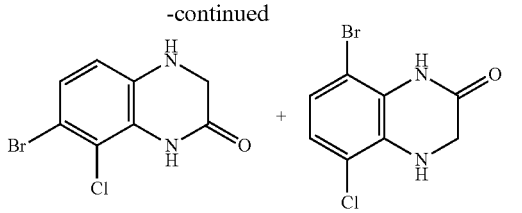

A mixture of ethyl 2-[(4-bromo-3-chloro-2-nitrophenyl)amino]acetate and ethyl 2-[(6-bromo-3-chloro-2-nitrophenyl)amino]acetate in a 9:1 ratio (3.5 g, 10.4 mmol), iron (3.5 g, 62.7 mmol) and $NH_4Cl$ (0.555 g, 10.4 mmol) in EtOH (75 mL) was refluxed for 30 min. AcOH (30 mL) was added and heating was continued for 30 min. The reaction mixture was diluted with water (300 mL) and extracted with DCM (3×100 mL). The combined organic layers were dried over $MgSO_4$, filtered and concentrated under vacuum, to give the title compounds (2.8 g) as a mixture of isomers (7-bromo/8-bromo in 9:1 ratio).

MS: $[M+H]^+=261$.

Preparation 123: 7-Bromo-8-chloroquinoxalin-2-ol

[Chem. 178]

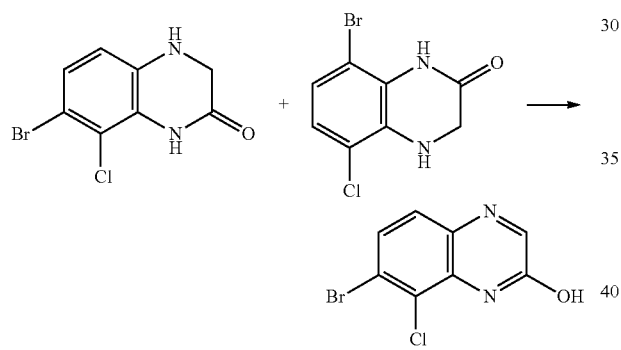

7-Bromo-8-chloro-1,2,3,4-tetrahydroquinoxalin-2-one and 8-bromo-5-chloro-1,2,3,4-tetrahydroquinoxalin-2-one in a 9:1 ratio (3.2 g, 12.2 mmol) were suspended in 50 wt % aq. NaOH (1.5 mL, 29.3 mmol) and 3 wt % aq. $H_2O_2$ (32 mL, 28.1 mmol). The reaction mixture was refluxed for 3 h. The mixture was cooled to RT, causing product to precipitate. AcOH (1.6 mL) was added. The precipitate was collected by filtration, washing with water (2×5 mL). The solid was azeotroped with acetonitrile (2×20 mL), to give the title compound (2.8 g). MS: $[M+H]^+=259$.

Preparation 124: 7-Bromo-2,8-dichloroquinoxaline

[Chem. 179]

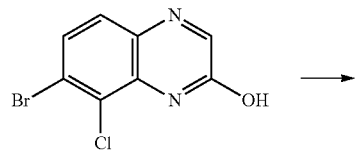

To a solution of 7-bromo-8-chloroquinoxalin-2-ol (3 g, 11.6 mmol) in toluene (23 mL) was added phosphorus(V) oxychloride (4.85 mL, 52.0 mmol) and the reaction mixture was stirred overnight at 70° C. The reaction mixture was quenched by dropwise addition into ice-cold sat. aq. $NaHCO_3$ (200 mL) and stirred for 2 h at RT. The mixture was then extracted with DCM (3×80 mL) and the combined organic layers were dried over $MgSO_4$, filtered and concentrated under reduced pressure, to give the title compound (2.5 g). $^1H$ NMR (500 MHz, DMSO-$d_6$): δ: 9.13 (1H, s), 8.22 (1H, d), 8.07 (1H, d).

Preparation 125:
7-Bromo-8-chloro-2-methoxyquinoxaline

[Chem. 180]

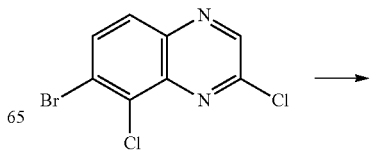

7-Bromo-2,8-dichloroquinoxaline (2 g, 7.12 mmol) and potassium carbonate (3.94 g, 28.5 mmol) were combined in a 100 mL three necked flask in MeOH (40 mL). The resultant colourless suspension was heated at 65° C. (internal temperature) for 18 h. The reaction mixture was cooled to RT. Water (150 mL) was added and the precipitate was filtered to give 7-bromo-8-chloro-2-methoxyquinoxaline (1.79 g, 6.48 mmol, 91% yield) as a light colourless solid. MS: $[M+H]^+=275$. $^1H$ NMR (DMSO-$d_6$) δ: 8.69 (1H, s), 8.00-7.89 (2H, m), 4.10 (3H, s).

Preparation 126:
7-Bromo-8-chloro-N,N-dimethylquinoxalin-2-amine

[Chem. 181]

-continued

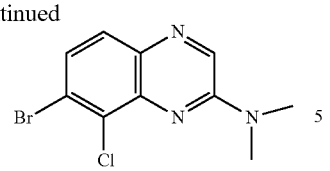

In a 100 mL three necked flask, dimethylamine, 2M in THF solution (22 mL, 44.0 mmol) was treated with 7-bromo-2,8-dichloroquinoxaline (2.01 g, 7.16 mmol) at 0° C. (internal temperature, ice bath). The resultant yellow solution was warmed to RT and stirred for 3 h. The reaction mixture was concentrated in vacuo and was partitioned between EtOAc (50 mL) and saturated aqueous NaHCO$_3$ (50 mL). The layers were separated and the aqueous phase was extracted with EtOAc (2×50 mL). The organic extracts were combined and washed with saturated brine (1×50 mL) and then dried over MgSO4, filtered and concentrated in vacuo to afford 7-bromo-8-chloro-N,N-dimethylquinoxalin-2-amine (1.98 g, 6.77 mmol, 95% yield) as a light yellow solid. MS: [M+H]$^+$=288.

$^1$H NMR (500 MHz, DMSO-d$_6$) δ: 8.76 (s, 1H), 7.72 (d, J=8.8 Hz, 1H), 7.63 (d, J=8.8 Hz, 1H), 3.29 (s, 6H).

Preparation 127:
7-Bromo-8-chloro-N,N-dimethylquinolin-2-amine

[Chem. 182]

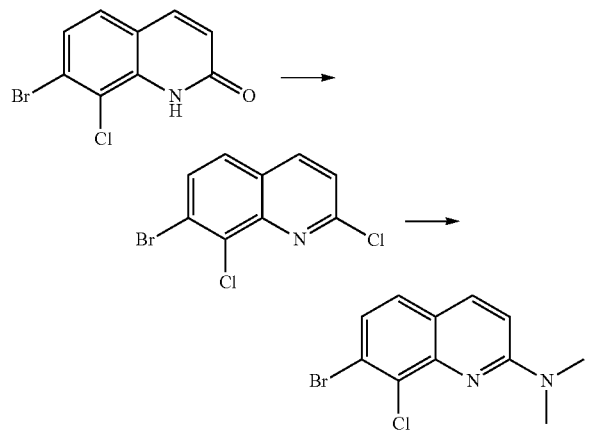

A solution of 7-bromo-8-chloro-1,2-dihydroquinolin-2-one (1.0 g, 3.87 mmol) in POCl$_3$ was heated at reflux for 1 h. After cooling, most of the POCl$_3$ was evaporated, ice and NH$_4$OH were added and the product extracted with EtOAc. The organic phase was dried (MgSO$_4$), filtered and evaporated to afford 7-bromo-2,8-dichloroquinoline (0.79 g), MS: [M+H]$^+$=278. 7-Bromo-2,8-dichloroquinoline (250 mg, 0.9 mmol) was dissolved in pyridine (1.5 mL), dimethylamine (40% solution in water, 1.5 mL) was added and the reaction mixture was heated in a sealed tube for 3 h. After cooling, water (10 ml) was added and the product extracted with EtOAc (2×15 mL). The organic phase was dried (MgSO$_4$), filtered and evaporated. The residue was purified by column chromatography on silica gel (gradient elution, 0-50%, EtOAc/petrol), to give the title compound (220 mg), MS: [M+H]$^+$=287.

Preparation 128:
7-Bromo-8-chloro-N-methylquinolin-2-amine

[Chem. 183]

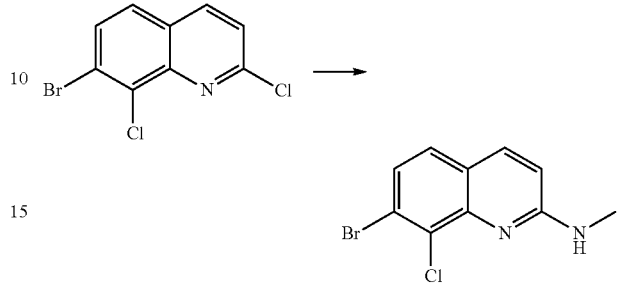

7-Bromo-2,8-dichloroquinoline (500 mg, 1.8 mmol) was dissolved in pyridine (3.0 mL), methylamine (40% solution in water, 3.0 mL) was added and the reaction mixture was heated in a sealed tube for 3 h. After cooling, water (20 ml) was added and the product extracted with EtOAc (2×20 mL). The organic phase was dried (MgSO$_4$), filtered and evaporated. The residue was purified by column chromatography on silica gel (gradient elution, 0-50%, EtOAc/petrol), to give the title compound (360 mg), MS: [M+H]$^+$=271.

Preparation 129: 8-Chloro-2-methoxy-7-(4,4,5,5-tetramethyl-1,3,2-dioxaborolan-2-yl)quinoxaline

[Chem. 184]

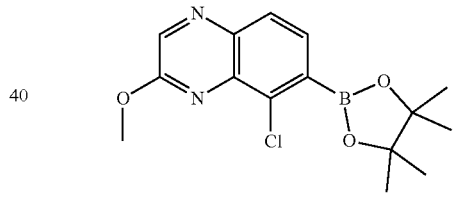

8-Chloro-2-methoxy-7-(4,4,5,5-tetramethyl-1,3,2-dioxaborolan-2-yl)quinoxaline was prepared as preparation 82 above using 7-bromo-8-chloro-2-methoxyquinoxaline. MS: [M+H]$^+$=321, 323.

Preparation 130:
3-Bromo-2-chloro-5,6-difluorobenzaldehyde

[Chem. 185]

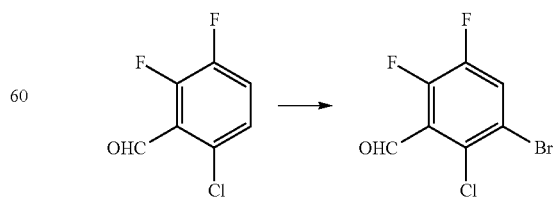

To a mixture of 2-chloro-5,6-difluorobenzaldehyde (5.3 g, 30 mmol) and sulfuric acid (15 mL) was added N-bromosuccinimide (6.6 g, 37 mmol) at 60° C. The resulting mixture was stirred at the same temperature for 5 h. The mixture was poured onto crushed ice, and then extracted with EtOAc. The organic phase was washed with brine and concentrated in vacuo. The residue was purified by column chromatography on silica gel (gradient elution, 0-20%, EtOAc/hexane), to give the title compound (6.5 g), $^1$H-NMR (400 MHz, CDCl$_3$) δ: 10.37 (1H, s), 7.72 (1H, dd).

Preparation 131:
3-Bromo-2-chloro-5,6-difluorobenzaldehyde O-methyl oxime

[Chem. 186]

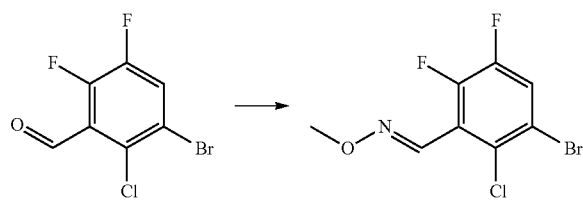

A mixture of 3-bromo-2-chloro-5,6-difluorobenzaldehyde (6.5 g, 26 mmol), O-methylhydroxylamine hydrochloride (2.4 g, 29 mmol), potassium carbonate (4.6 g, 33 mmol) and 1,2-dimethoxyethane (26 mL) was stirred at 60° C. overnight. The mixture was filtered and concentrated in vacuo. The residue was purified by column chromatography on silica gel (gradient elution, 0-20%, EtOAc/hexane), to give the title compound (7.2 g), MS: [M+H]$^+$=284.

Preparation 132:
5-Bromo-4-chloro-7-fluoro-1H-indazole

[Chem. 187]

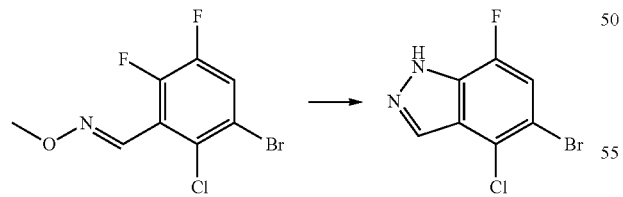

A mixture of 3-bromo-2-chloro-5,6-difluorobenzaldehyde O-methyl oxime (7.1 g, 25 mmol), tetrahydrofuran (25 mL) and hydrazine monohydrate (25 mL) was stirred under reflux for 30 h. To the cooled mixture was added EtOAc (120 mL) and water (50 mL). The separated organic layer was concentrated in vacuo. The residue was suspended in EtOAc and hexane. The precipitate was collected and dried at 50° C. under reduced pressure, to give the title compound (4.4 g), MS: [M+H]$^+$=249.

Preparation 133:
5-Bromo-4-chloro-7-fluoro-2-methyl-2H-indazole

[Chem. 188]

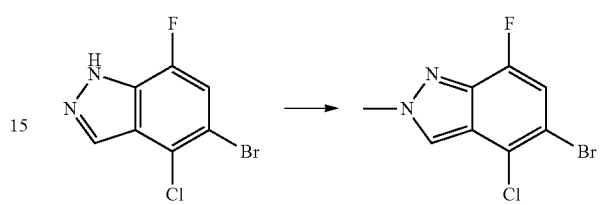

To a solution of 5-bromo-4-chloro-7-fluoro-1H-indazole (1.8 g, 7.4 mmol) in EtOAc (40 mL) was added trimethyloxonium tetrafluoroborate (1.7 g, 12 mmol) and the resulting mixture was stirred at RT overnight. The reaction mixture was diluted with EtOAc, quenched with sat. aq. NaHCO$_3$ and the phases were separated. The organic phase was washed with brine and concentrated in vacuo. The residue was purified by column chromatography on silica gel (gradient elution, 0-60%, EtOAc/hexane), to give the title compound (0.76 g), MS: [M+H]$^+$=263.

Preparation 134: 4-Chloro-7-fluoro-2-methyl-5-(4,4,5,5-tetramethyl-1,3,2-dioxaborolan-2-yl)-2H-indazole

[Chem. 189]

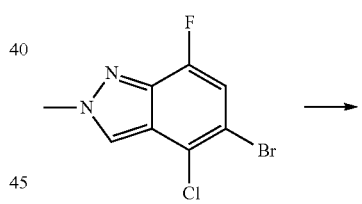

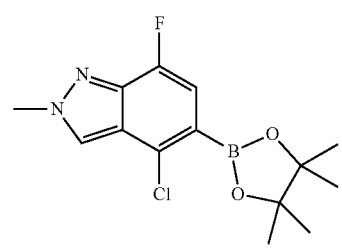

Prepared as preparation 82, except using 5-bromo-4-chloro-7-fluoro-2-methyl-2H-indazole, to give the title compound. MS: [M+H]$^+$=311.

Preparation 135: 3-Chloro-2-methyl-5-(4,4,5,5-tetramethyl-1,3,2-dioxaborolan-2-yl)-2H-indazole

[Chem. 190]

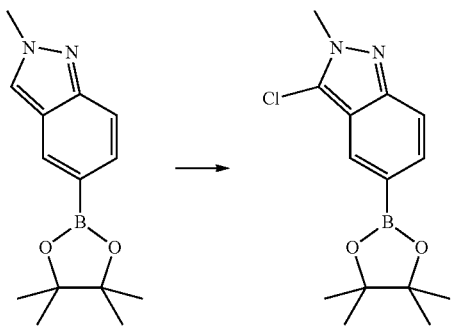

2-Methyl-5-(4,4,5,5-tetramethyl-1,3,2-dioxaborolan-2-yl)-2H-indazole (190.8 mg, 0.7392 mmol) was dissolved into THF (10 mL). To the solution was added N-chlorosuccinimide (109.2 mg, 0.8178 mmol) at RT under stirring. After stirring at RT for 2 hours, DMF (5 mL) was added. And the mixture was heated to 60° C. under stirring. After further stirring for 1 hour, the mixture was cooled to RT. The mixture was poured into 5% aq. of NaHCO₃ and extracted with EtOAc. The extract was washed by water, dried over Na₂SO₄ and concentrated. The residue was purified with silica gel column chromatography (Biotage SNAP Ultra HP-Sphere, 25 g), eluting with hexane/EtOAc to give the titled compound (142.9 mg) as a off-white wax. MS: [M+H]⁺=292.

Preparation 136: 5-Bromo-3,4,7-trichloro-2-methyl-2H-indazole

[Chem. 191]

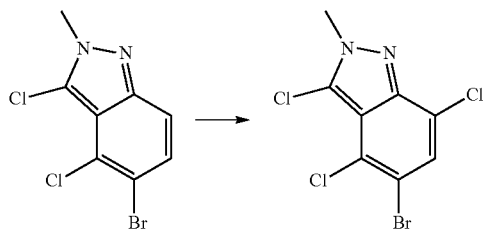

5-Bromo-3,4-dichloro-2-methyl-2H-indazole (5.001 g, 17.863 mmol) was suspended into DMF (50 mL). The suspension was heated to 65° C. under stirring to give a solution. To the hot solution was added N-chlorosuccinimide (3.578 g, 26.80 mmol) in some portions. After stirring at 65° C. for 1.5 hours, the mixture was cooled to RT. The mixture was poured into 9% aq. of NaHCO₃ and extracted with EtOAc. The extract was washed by water, dried over Na₂SO₄ and concentrated. The residue was purified with silica gel column chromatography (Biotage SNAP Ultra HP-Sphere, 100 g), eluting with hexane/EtOAc to give the titled compound (2.037 g) as a colourless solid. MS: [M+H]⁺= 313.

Preparation 137: (3,4,7-Trichloro-2-methyl-2H-indazol-5-yl)boronic acid

[Chem. 192]

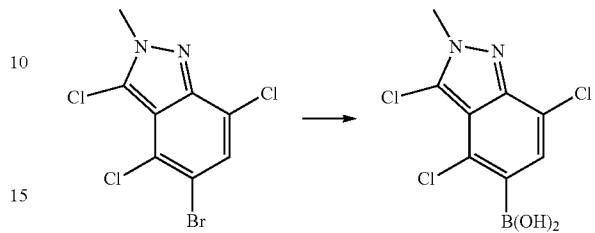

5-Bromo-3,4,7-trichloro-2-methyl-2H-indazole (2.037 g, 6.479 mmol) was dissolved into THF (40 mL). The solution was degassed under reduced pressure, purged with N₂ gas, and cooled to 0° C. under stirring. To the cooled solution was added dropwise THF solution of i-PrMgCl·LiCl complex (2.0 M, 7.75 mL, 15.5 mmol) at 0° C. under stirring. After 1 hour stirring, triisopropyl borate (7.50 ml, 32.7 mmol) was added at 0° C. And the mixture was allowed to be RT under stirring. After 1.5 hours stirring, acetic acid (5.60 mL, 97.80 mmol) was added for quenching the reaction. The resulting mixture was diluted with 2-methyltetrahydrofuran. And then, the titled compound was extracted to 3 M aq. of NaOH (300 mL). The pH value of aqueous layer was adjusted to around 2 to 3. The precipitate was collected by filtration, washed by H₂O, and dried in vacuo at 70° C. to give the titled compound (1.340 g, 74%) as a colourless solid. MS: [M+H]⁺=279.

Preparation 138: (5-Chloroquinoxalin-6-yl)boronic acid

[Chem. 193]

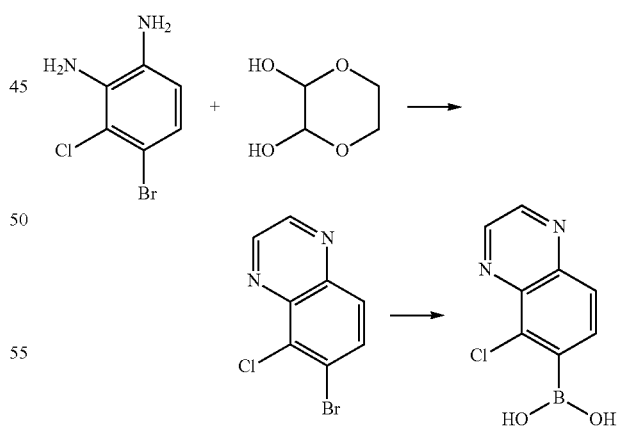

To a solution of 4-bromo-3-chloro-benzene-1,2-diamine (500 mg, 2.26 mmol) in EtOH (20.0 mL), 1,4-dioxane-2,3-diol (380 mg, 3.16 mmol) was added at r.t. The mixture was stirred at r.t. for 18 h. The reaction mixture was then vacuum-concentrated, and the residue was purified by column chromatography on silica gel (gradient elution, 20-40% EtOAc/hexane) to give 6-bromo-5-chloroquinoxaline (269 mg). MS: [M+H]⁺=243, 245.

To a solution of 6-bromo-5-chloroquinoxaline (200 mg, 0.823 mmol) in 1,4-dioxane (2.00 mL), bis(pinacolato)diboron (313 mg, 1.23 mmol), KOAc (161 mg, 1.64 mmol) and bis(diphenylphosphino)ferrocene]dichloropalladium(II) complex with dichloromethane (53.7 mg, 0.0657 mmol) were added at r.t. The mixture was stirred at 100° C. for 18h, diluted with MTBE and added 2M NaOH. The aqueous layer was added 6M HCl and extracted with $CHCl_3$ three times. The organic layer was washed with brine, dried over anhydrous $Na_2SO_4$, filtered, and concentrated in vacuo to give the title compound (108 mg). MS: $[M+H]^+=209$.

Preparation 139: 4-Chloro-2-(2-methoxyethyl)-5-(4,4,5,5-tetramethyl-1,3,2-dioxaborolan-2-yl)-2H-indazole

[Chem. 194]

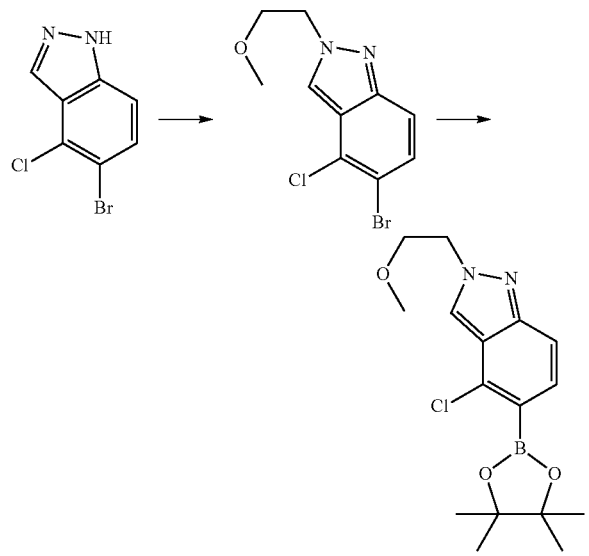

Step 1.
5-Bromo-4-chloro-2-(2-methoxyethyl)-2H-indazole

To a suspension of 5-bromo-4-chloro-1H-indazole (1.0 g, 4.7 mmol) and potassium carbonate (1.79 g, 13 mmol) in DMSO (5 ml) was added 1-bromo-2-methoxy-ethane (0.83 ml, 8.6401 mmol) at room temperature. After stirring at the same temperature over weekend, the mixture was diluted with EtOAc and washed with water. The organic phase was washed with brine, dried over $Na_2SO_4$, filtered, and concentrated in vacuo. Column chromatography (SNAP Ultra 50 g, gradient elution, 0-100% EtOAc in hexane) gave the title compound (0.45 g, 1.5 mmol, 36%) as a brown solid. MS: $[M+H]^+=289, 291, 293$.

Step 2. 4-Chloro-2-(2-methoxyethyl)-5-(4,4,5,5-tetramethyl-1,3,2-dioxaborolan-2-yl)-2H-indazole To a suspension of 5-bromo-4-chloro-2-(2-methoxyethyl)-2H-indazole (0.45 g, 1.5 mmol) in 1,4-dioxane (10 mL) was added potassium acetate (0.30 g, 3.13 mmol), 4,4,4',4',5,5,5',5'-octamethyl-2,2'-bi(1,3,2-dioxaborolane) (0.59 g, 2.3 mmol) and 1,1'-bis(diphenylphosphino)ferrocene-palladium(II)dichloride dichloromethane complex (0.12 g, 0.15 mmol) at room temperature. After stirring at 120° C. for 4 h, the mixture was diluted with EtOAc and filtered through a pad of Hyflo Super-Cel. The filtrate was concentrated in vacuo. Column chromatography (SNAP Ultra 25 g, gradient elution, 0-100% EtOAc in hexane) gave the title compound (0.68 g) as a pale brown oil. The material was not pure but was used without further purification. MS: $[M+H]^+=337, 339$.

Preparation 140: 2-chloro-5-(7-chlorobenzo[d]thiazol-6-yl)-3-methyl-7-((2-(trimethylsilyl)ethoxy)methyl)-3,7-dihydro-4H-pyrrolo[2,3-d]pyrimidin-4-one

[Chem. 195]

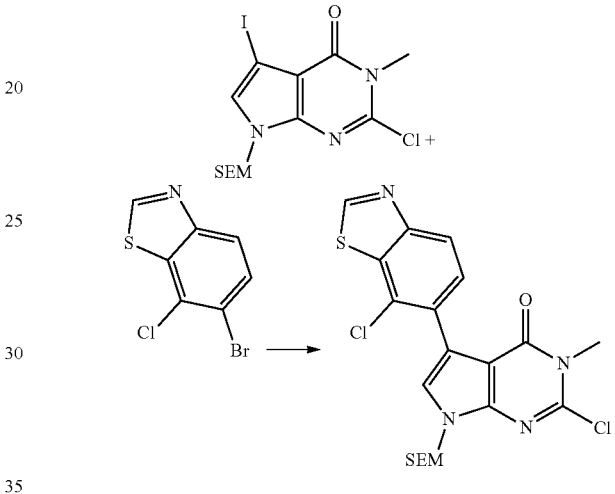

A mixture of 6-bromo-7-chloro-1,3-benzothiazole (300 mg, 1.21 mmol), bis(pinacolato)diboron (460 mg, 1.81 mmol), $Pd(dppf)Cl_2$ (177 mg, 0.24 mmol) and potassium acetate (592 mg, 6.04 mmol) in 1,4-dioxane (6 mL) was heated at 100° C. for 2 h and then allowed to cool. To the mixture was added 2-chloro-5-iodo-3-methyl-7-((2-(trimethylsilyl)ethoxy)methyl)-3,7-dihydro-4H-pyrrolo[2,3-d]pyrimidin-4-one (350 mg, 0.8 mmol), $Pd(dppf)Cl_2$ (114 mg, 0.16 mmol), $K_2CO_3$ (667 mg, 4.83 mmol) and water (3 mL). The mixture was then heated at 70° C. for a further 2 h. The mixture was cooled and then partitioned between EtOAc and water. The organic layer was washed with brine, dried ($MgSO_4$) and then evaporated in vacuo. The residue was purified by $SiO_2$ chromatography (eluting with 0-40% acetone/pet. ether) to provide the product (220 mg). MS: $[M+H]^+=481$.

Preparation 141: 4,6-Dichloro-3-iodo-1-(tetrahydro-2H-pyran-2-yl)-1H-pyrazolo[3,4-d]pyrimidine

[Chem. 196]

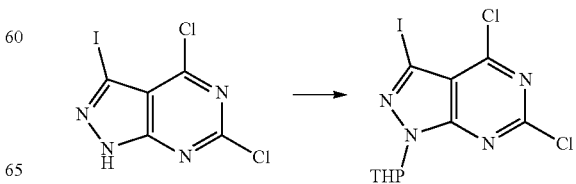

4,6-Dichloro-3-iodo-1H-pyrazolo[3,4-d]pyrimidine (4.0 g, 13 mmol), 3,4-dihydro-2H-pyran (3.5 mL, 38 mmol) and p-toluenesulfonic acid monohydrate (0.48 g, 2.5 mmol) were dissolved in THF (60 mL) and heated at 70° C. for 1.5 h. The solvent was removed under vacuum and the solid residue was purified by column chromatography on silica gel (gradient elution, 0-100%, EtOAc/hexane) to give the title compound (3.47 g). MS: [M+H]$^+$=399.

Preparation 142: 6-Chloro-3-iodo-1-(tetrahydro-2H-pyran-2-yl)-1,5-dihydro-4H-pyrazolo[3,4-d]pyrimidin-4-one

[Chem. 197]

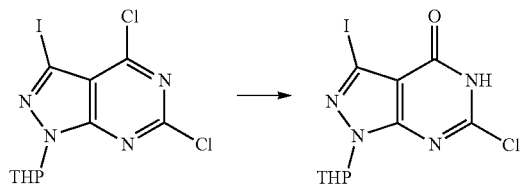

To a solution of 4,6-dichloro-3-iodo-1-(tetrahydro-2H-pyran-2-yl)-1H-pyrazolo[3,4-d]pyrimidine (2.0 g, 5.0 mmol) in THE (20 mL) was added 5 M NaOH (9.0 mL) at r.t. The mixture was stirred at the same temperature for 5 hrs, then THE (10 ml) was added to the mixture. The mixture was stirred at RT overnight. The mixture was acidified with 6 M HCl, and extracted with EtOAc. The organic layer was washed with brine, dried over Na$_2$SO$_4$, filtered, and concentrated in vacuo to give the the title compound (1.87 g). MS: [M+H]$^+$=381.

Preparation 143: 6-Chloro-3-iodo-5-methyl-1-(tetrahydro-2H-pyran-2-yl)-1,5-dihydro-4H-pyrazolo[3,4-d]pyrimidin-4-one

[Chem. 198]

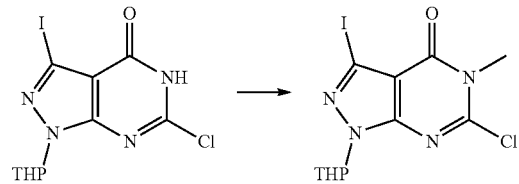

To a mixture of 6-chloro-3-iodo-1-(tetrahydro-2H-pyran-2-yl)-1,5-dihydro-4H-pyrazolo[3,4-d]pyrimidin-4-one (28.5 g, 74.9 mmol) and K$_2$CO$_3$ (12.4 g, 90.0 mmol) in DMF (270 mL) was added iodomethane (11.7 g, 82.4 mmol) in DMF (15 ml) at RT. The mixture was stirred at RT for 4 h, then diluted with water. After stirring for 4 h, The precipitate was collected by filtration and dried in vacuo to give the title compound (27.8 g). MS: [M+H]$^+$=395.

Preparation 144: 2-Chloro-5-(3,4-dichloro-2-methyl-indazol-5-yl)-3-methyl-7-(2-trimethylsilylethoxymethyl)pyrrolo[2,3-d]pyrimidin-4-one

[Chem. 199]

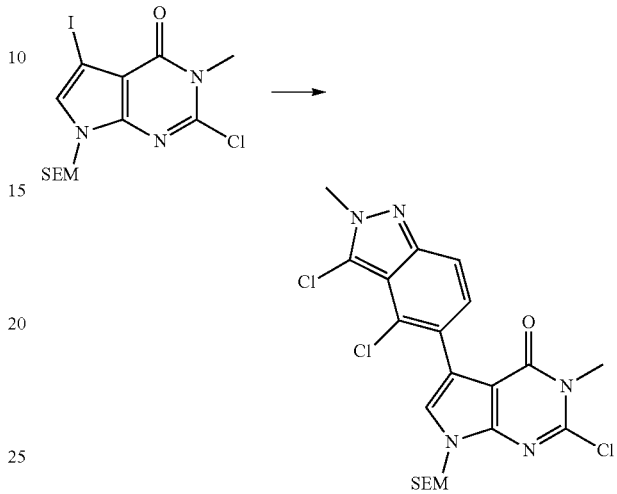

A mixture of 2-chloro-5-iodo-3-methyl-7-(2-trimethylsilylethoxymethyl)pyrrolo[2,3-d]pyrimidin-4-one (107 mg, 0.244 mmol), 3,4-dichloro-2-methyl-5-(4,4,5,5-tetramethyl-1,3,2-dioxaborolan-2-yl)indazole (107 mg, 0.326 mmol), K$_3$PO$_4$ (108 mg, 0.506 mmol), bis(di-tert-butyl(4-dimethylaminophenyl)phosphine)dichloropalladium(II) (18 mg, 0.026 mmol), 1,4-dioxane (1.2 mL) and water (0.24 mL) was stirred at 70° C. for 5 h and cooled to RT. The mixture was purified by column chromatography on silica gel (gradient elution, 0-60% EtOAc/hexane) to give the title compound (113 mg). MS: [M+H]$^+$=514, 516.

Preparation 145: 6-Chloro-3-(3,4-dichloro-2-methyl-2H-indazol-5-yl)-5-methyl-1-(tetrahydro-2H-pyran-2-yl)-1,5-dihydro-4H-pyrazolo[3,4-d]pyrimidin-4-one

[Chem. 200]

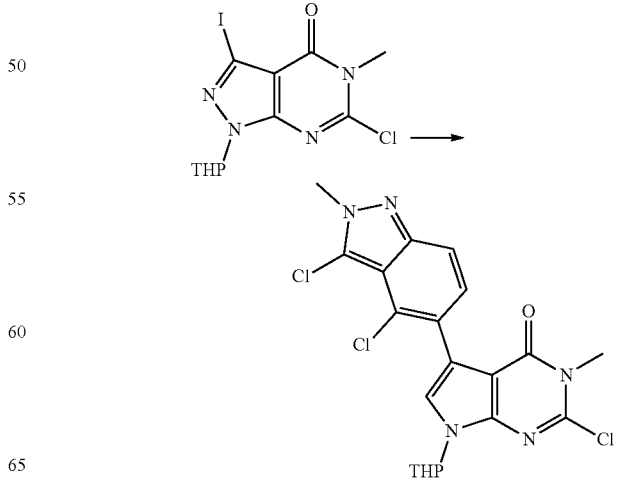

A mixture of 6-chloro-3-iodo-5-methyl-1-(tetrahydro-2H-pyran-2-yl)-1,5-dihydro-4H-pyrazolo[3,4-d]pyrimidin-4-one (500 mg, 1.27 mmol), 3,4-dichloro-2-methyl-5-(4,4,5,5-tetramethyl-1,3,2-dioxaborolan-2-yl)-2H-indazole (497 mg, 1.52 mmol), K$_3$PO$_4$ (806 mg, 3.80 mmol), [1,1'-bis(diphenylphosphino)ferrocene]dichloropalladium(II) complex with dichloromethane (103 mg, 0.127 mmol), 1,4-dioxane (5.0 mL) and water (1.25 mL) was stirred at 90° C. for 2 h, cooled to RT, poured into water, and extracted with EtOAc. The organic layer was washed with brine, dried over anhydrous Na$_2$SO$_4$, filtered, and concentrated in vacuo. The residue was purified by column chromatography on silica gel (gradient elution, 0-100% EtOAc/hexane) to give the title compound (413 mg). MS: [M+H]$^+$=467, 469.

Preparation 146: 2-Chloro-5-(3-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one

[Chem. 201]

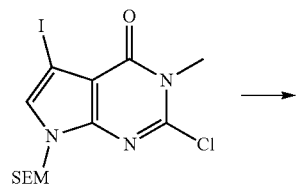

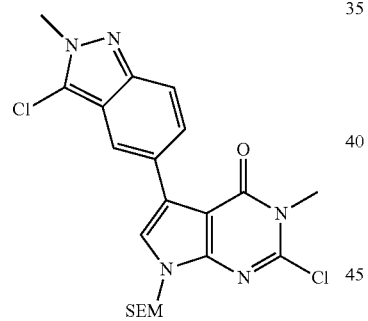

2-Chloro-5-iodo-3-methyl-7-((2-(trimethylsilyl)ethoxy)methyl)-3,7-dihydro-4H-pyrrolo[2,3-d]pyrimidin-4-one (362.7 mg, 0.8248 mmol), 3-chloro-2-methyl-5-(4,4,5,5-tetramethyl-1,3,2-dioxaborolan-2-yl)-2H-indazole (289.1 mg, 0.9881 mmol), Pd(Amphos)$_2$Cl$_2$ (34.7 mg, 0.0490 mmol) and K$_3$PO$_4$ (263.3 mg, 1.240 mmol) were mixed in vessel. To the mixture was added THF (10 mL) and Water (1 mL). The mixture was degassed under reduced pressure and purged with N$_2$ gas. After stirring for 5 hours at 75° C., the mixture was cooled to RT. The mixture was poured into water and extracted with EtOAc. The extract was washed by 9% aq. of NaHCO$_3$. To the extract was added Na$_2$SO$_4$ and SH-silica gel (Fuji Silysia). After stirring at RT for 1 hour, the solid was removed by filtration, and the filtrate was concentrated. The residue was purified with silica gel column chromatography (Biotage SNAP Ultra HP-Sphere, 25 g), eluting with hexane/EtOAc to give the titled compound (279.8 mg) as an off-white solid. MS: [M+H]$^+$=478.

Preparation 147: 2-Chloro-3-methyl-5-(3,4,7-trichloro-2-methyl-2H-indazol-5-yl)-7-((2-(trimethylsilyl)ethoxy)methyl)-3,7-dihydro-4H-pyrrolo[2,3-d]pyrimidin-4-one

[Chem. 202]

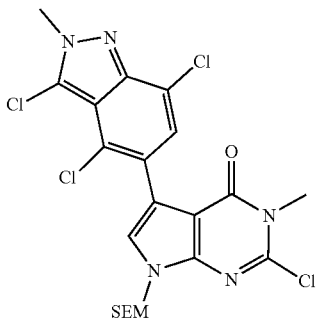

2-Chloro-3-methyl-5-(3,4,7-trichloro-2-methyl-2H-indazol-5-yl)-7-((2-(trimethylsilyl)ethoxy)methyl)-3,7-dihydro-4H-pyrrolo[2,3-d]pyrimidin-4-one was prepared in the manner similar to preparation 146, except using (3,4,7-trichloro-2-methyl-2H-indazol-5-yl)boronic acid instead of 3-chloro-2-methyl-5-(4,4,5,5-tetramethyl-1,3,2-dioxaborolan-2-yl)-2H-indazole. MS: [M+H]$^+$=546.

Preparation 148: 2-Chloro-5-[8-chloro-2-(dimethylamino)quinolin-7-yl]-3-methyl-7-{[2-(trimethylsilyl)ethoxy]methyl}-3H,4H,7H-pyrrolo[2,3-d]pyrimidin-4-one

[Chem. 203]

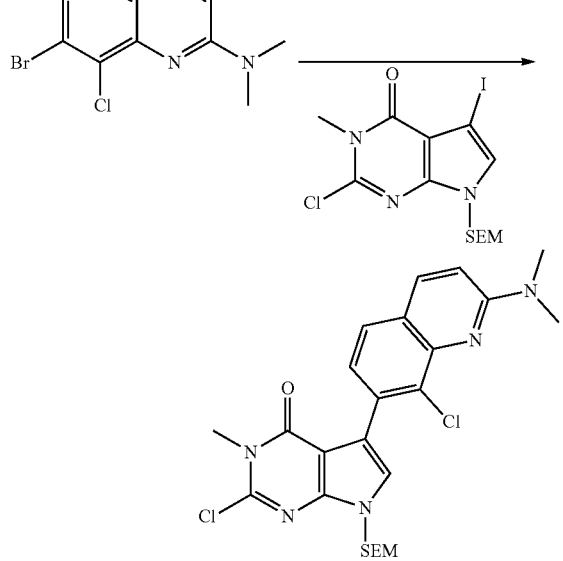

7-Bromo-8-chloro-N,N-dimethylquinolin-2-amine (390 mg, 1.36 mmol), bis(pinacolato)diboron (520 mg, 2.04 mmol), [1,1'-bis(diphenylphosphino)ferrocene]dichloropalladium(II) (150 mg, 0.2 mmol) and potassium acetate (650 mg, 6.8 mmol) were combined in a 30 mL microwave tube, sealed, evacuated and backfilled with nitrogen (×2). 1,4-Dioxane (8 mL) was added and the tube backfilled again (×2) before heating to 90° C. for 2 h. After cooling, 2-chloro-5-iodo-3-methyl-7-{[2-(trimethylsilyl)ethoxy]methyl}-3H,4H,7H-pyrrolo[2,3-d]pyrimidin-4-one (590 mg, 1.36 mmol), bis(diphenylphosphino)ferrocene]dichloropalladium(II) (150 mg, 0.2 mmol), potassium carbonate (1.12 g, 8.16 mmol) and water (2 mL) were added. The reaction was resealed, backfilled with nitrogen (×2) and heated to 70° C. for 2 h. After cooling, the reaction was diluted with water and extracted with EtOAc (3×). Combined organics were dried over anhydrous MgSO$_4$, filtered and evaporated. The residue was purified by column chromatography on silica gel (gradient elution, 0-100%, EtOAc/petrol), to give the title compound (426 mg). MS: [M+H]$^+$=518.

Preparation 149: 2-Chloro-5-[8-chloro-2-(methylamino)quinolin-7-yl]-3-methyl-7-{[2-(trimethylsilyl)ethoxy]methyl}-3H,4H,7H-pyrrolo[2,3-d]pyrimidin-4-one

[Chem. 204]

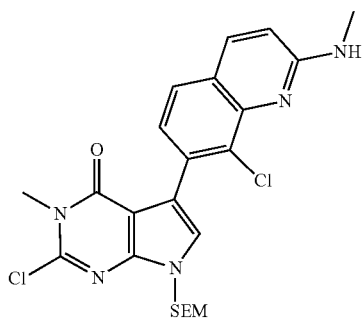

Starting with 7-bromo-8-chloro-N-methylquinolin-2-amine, the title compound was prepared using procedures similar to those described 2-chloro-5-[8-chloro-2-(dimethylamino)quinolin-7-yl]-3-methyl-7-{[2-(trimethylsilyl)ethoxy]methyl}-3H,4H,7H-pyrrolo[2,3-d]pyrimidin-4-one. MS: [M+H]$^+$=504.

Preparation 150: tert-Butyl ((1R,2R,4S)-7-(3-bromo-5-methyl-4-oxo-1-(tetrahydro-2H-pyran-2-yl)-4,5-dihydro-1H-pyrazolo[3,4-d]pyrimidin-6-yl)-7-azabicyclo[2.2.1]heptan-2-yl)(ethyl)carbamate

[Chem. 205]

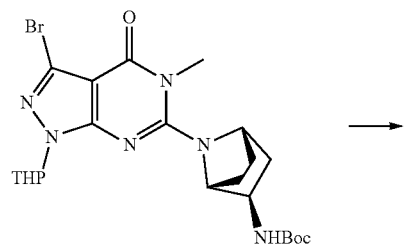

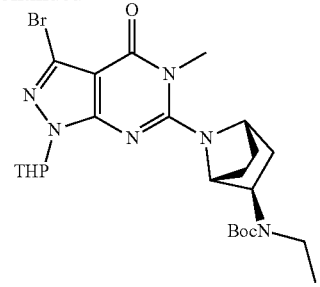

To a solution of tert-butyl ((1R,2R,4S)-7-(3-bromo-5-methyl-4-oxo-1-(tetrahydro-2H-pyran-2-yl)-4,5-dihydro-1H-pyrazolo[3,4-d]pyrimidin-6-yl)-7-azabicyclo[2.2.1]heptan-2-yl)carbamate (500 mg, 0.955 mmol) in THF (5.00 mL), NaH (60% in mineral oil, 76.4 mg, 1.91 mmol) was added at 0° C. The mixture was stirred at 0° C. for 15 min. To the mixture, iodoethane (0.153 mL, 1.91 mmol) was added at 0° C. The mixture was stirred at r.t. overnight. To the mixture, NaH (60% in mineral oil, 57.3 mg, 1.43 mmol) and iodoethane (0.115 mL, 1.43 mmol) were added at 0° C. The mixture was stirred at r.t. for 6 h. The mixture was poured into sat. NH$_4$Cl, and extracted with EtOAc. The organic layer was washed with water and brine, dried over anhydrous Na$_2$SO$_4$, filtered, and concentrated in vacuo. The residue was purified by column chromatography on silica gel (gradient elution, 10-40% EtOAc/hexane) to give the title compound (335 mg). MS: [M+H]$^+$=551, 553.

General procedure 6: tert-Butyl ((1R,2R,4S)-7-(5-(5-chloro-3-methoxyquinoxalin-6-yl)-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)carbamate

[Chem. 206]

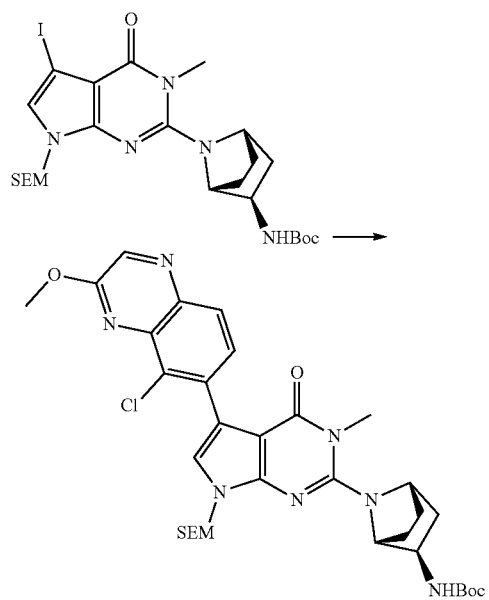

The mixture of tert-butyl ((1R,2R,4S)-7-(5-iodo-3-methyl-4-oxo-7-((2-trimethylsilyl)ethoxy)methyl)-4,7-dihydro-3H-pyrrolo[2,3-d]pyrimidin-2-yl)-7-azabicyclo [2.2.1]heptan-2-yl)carbamate (75.0 mg, 0.122 mmol), 8-chloro-2-methoxy-7-(4,4,5,5-tetramethyl-1,3,2-dioxaborolan-2-yl)quinoxaline (46.9 mg, 0.146 mmol), K$_3$PO$_4$ (38.8 mg, 0.183 mmol), bis(di-tert-butyl(4-dimethylaminophenyl)phosphine)dichloropalladium(II) (64.8 mg, 0.0794 mmol), 1,4-dioxane (1.5 mL) and water (0.15 mL) was stirred at 80° C. for 2 h, cooled to RT, poured into water, and extracted with EtOAc. The organic layer was washed with brine, dried over anhydrous Na$_2$SO$_4$, filtered, and concentrated in vacuo. The residue was purified by column chromatography on silica gel (gradient elution, 0-100% EtOAc/hexane) to give the title compound (58.0 mg). MS: [M+H]$^+$= 682, 684.

General procedure 7: tert-Butyl ((1R,2R,4S)-7-(5-(5-chloro-3-(dimethylamino)quinoxalin-6-yl)-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)carbamate

[Chem. 207]

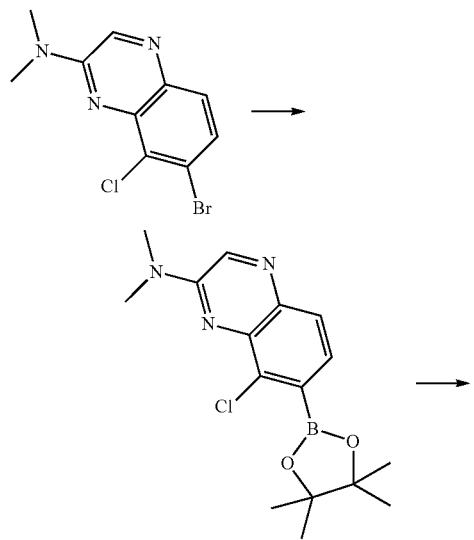

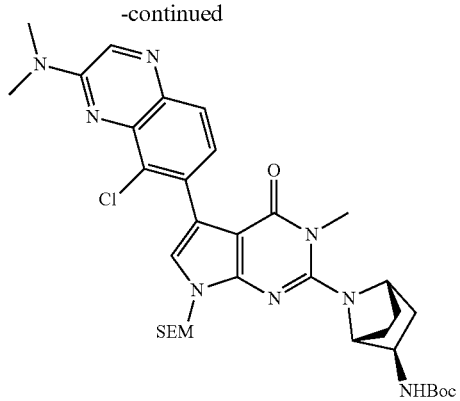

The mixture of 7-bromo-8-chloro-N,N-dimethylquinoxalin-2-amine (200 mg, 0.698 mmol), bis(pinacolato)diboron (354 mg, 1.40 mmol), [1,1'-bis(diphenylphosphino)ferrocene]dichloropalladium(II) complex with dichloromethane (57.0 mg, 0.0698 mmol) and potassium acetate (137 mg, 1.40 mmol) in 1,4-dioxane (2.0 mL) was degassed, purged with nitrogen, and stirred at 100° C. for 6 h. The reaction was cooled to RT, filtered through a pad of Celite, and washed with EtOAc. The filtrate was concentrated in vacuo. The crude residue was used in the next step without further purification. MS: [M+H]$^+$=334, 336.

The mixture of tert-butyl ((1R,2R,4S)-7-(5-iodo-3-methyl-4-oxo-7-((2-trimethylsilyl)ethoxy)methyl)-4,7-dihydro-3H-pyrrolo[2,3-d]pyrimidin-2-yl)-7-azabicyclo [2.2.1]heptan-2-yl)carbamate (75.0 mg, 0.122 mmol), 8-chloro-N,N-dimethyl-7-(4,4,5,5-tetramethyl-1,3,2-dioxaborolan-2-yl)quinoxaline-2-amine (48.8 mg, 0.146 mmol), K$_3$PO$_4$ (38.8 mg, 0.183 mmol), bis(di-tert-butyl(4-dimethylaminophenyl)phosphine)dichloropalladium(II) (64.8 mg, 0.0794 mmol), 1,4-dioxane (1.5 mL) and water (0.15 mL) was stirred at 80° C. for 2 h, cooled to RT, poured into water, and extracted with EtOAc. The organic layer was washed with brine, dried over anhydrous Na$_2$SO$_4$, filtered, and concentrated in vacuo. The residue was purified by column chromatography on silica gel (gradient elution, 0-100% EtOAc/hexane) to give the title compound (60.3 mg). MS: [M+H]$^+$=695, 697.

Compounds of Table 13 below were prepared using procedures analogous to that described in general procedure 1 starting from the appropriate substituted protected pyrrolopyrimidinone or pyrazolopyrimidinone and varying the amine (synthesised as described above with any significant variations indicated below.

TABLE 13

| Compound | Compound name | MS: [M + H]$^+$ m/z | Procedure |
|---|---|---|---|
| (structure shown) | tert-butyl (endo-8-(3-(3,4-dichloro-2-methyl-2H-indazol-5-yl)-5-methyl-4-oxo-1-(tetrahydro-2H-pyran-2-yl)-4,5-dihydro-1H-pyrazolo[3,4-d]pyrimidin-6-yl)-8-azabicyclo[3.2.1]octan-3-yl)carbamate | 657, 659 | Prepared as general procedure 1 above using 6-chloro-3-(3,4-dichloro-2-methyl-2H-indazol-5-yl)-5-methyl-1-(tetrahydro-2H-pyran-2-yl)-1,5-dihydro-4H-pyrazolo[3,4-d]pyrimidin-4-one and tert-butyl (endo-8-azabicyclo[3.2.1]octan-3-yl) carbamate |

TABLE 13-continued

| Compound | Compound name | MS: [M + H]+ m/z | Procedure |
| --- | --- | --- | --- |
|  | tert-butyl (endo-8-(3-(3,4-dichloro-2-methyl-2H-indazol-5-yl)-5-methyl-4-oxo-1-(tetrahydro-2H-pyran-2-yl)-4,5-dihydro-1H-pyrazolo[3,4-d]pyrimidin-6-yl)-3-methyl-8-azabicyclo[3.2.1]octan-3-yl)carbamate | 671, 673 | Prepared as general procedure 1 above using 6-chloro-3-(3,4-dichloro-2-methyl-2H-indazol-5-yl)-5-methyl-1-(tetrahydro-2H-pyran-2-yl)-1,5-dihydro-4H-pyrazolo[3,4-d]pyrimidin-4-one and tert-butyl N-(endo-3-methyl-8-azabicyclo[3.2.1]octan-3-yl)carbamate |
|  | tert-butyl ((3R,4S)-1-(3-(3,4-dichloro-2-methyl-2H-indazol-5-yl)-5-methyl-4-oxo-1-(tetrahydro-2H-pyran-2-yl)-4,5-dihydro-1H-pyrazolo[3,4-d]pyrimidin-6-yl)-3-fluoropiperidin-4-yl)carbamate | 649, 651 | Prepared as general procedure 1 above using 6-chloro-3-(3,4-dichloro-2-methyl-2H-indazol-5-yl)-5-methyl-1-(tetrahydro-2H-pyran-2-yl)-1,5-dihydro-4H-pyrazolo[3,4-d]pyrimidin-4-one and tert-butyl N-[(3R,4S)-3-fluoropiperidin-4-yl]carbamate |
|  | tert-butyl ((1R,2S,3S,5S)-8-(5-(3,4-dichloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-2-fluoro-8-azabicyclo[3.2.1]octan-3-yl)carbamate | 720, 722 | Prepared as general procedure 1 above using 2-chloro-5-(3,4-dichloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl N-[(1S,2R,3S,5R)-2-fluoro-8-azabicyclo[3.2.1]octan-3-yl]carbamate |
|  | tert-butyl (rac-(1R,2S,4S)-7-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)carbamate | 654, 656 | Prepared as general procedure 1 above using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl rac-(1S,2R,4R)-7-azabicyclo[2.2.1]hept-2-ylcarbamate hydrochloride |

TABLE 13-continued

| Compound | Compound name | MS: [M + H]+ m/z | Procedure |
|---|---|---|---|
| | tert-butyl (rac-7-(5-(3,4-dichloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)carbamate | 688, 690 | Prepared as general procedure 1 above using 2-chloro-5-(3,4-dichloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl rac-1S,2R,4R)-7-azabicyclo[2.2.1]hept-2-yl-carbamate hydrochloride |
| | tert-butyl ((1R,2R,4S)-7-(5-(3-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)carbamate | 654 | Prepared as general procedure 1 above using 2-chloro-5-(3-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl ((1R,2R,4S)-7-azabicyclo[2.2.1]heptan-2-yl)carbamate |
| | tert-butyl ((1R,2R,4S)-7-(3-methyl-4-oxo-5-(3,4,7-trichloro-2-methyl-2H-indazol-5-yl)-7-((2-(trimethylsilyl)ethoxy)methyl)-4,7-dihydro-3H-pyrrolo[2,3-d]pyrimidin-2-yl)-7-azabicyclo[2.2.1]heptan-2-yl)carbamate | 722, 724 | Prepared as general procedure 1 above using 2-chloro-3-methyl-5-(3,4,7-trichloro-2-methyl-2H-indazol-5-yl)-7-((2-(trimethylsilyl)ethoxy)methyl)-3,7-dihydro-4H-pyrrolo[2,3-d]pyrimidin-4-one and tert-butyl ((1R,2R,4S)-7-azabicyclo[2.2.1]heptan-2-yl)carbamate |
| | tert-butyl ((1R,4R,7R)-2-(3-(3,4-dichloro-2-methyl-2H-indazol-5-yl)-5-methyl-4-oxo-1-(tetrahydro-2H-pyran-2-yl)-4,5-dihydro-1H-pyrazolo[3,4-d]pyrimidin-6-yl)-2-azabicyclo[2.2.1]heptan-7-yl)carbamate | 643, 645 | Prepared as general procedure 1 above using 6-chloro-3-(3,4-dichloro-2-methyl-2H-indazol-5-yl)-5-methyl-1-(tetrahydro-2H-pyran-2-yl)-1,5-dihydro-4H-pyrazolo[3,4-d]pyrimidin-4-one and tert-butyl ((1R,4R,7R)-2-azabicyclo[2.2.1]heptan-7-yl)carbamate |

TABLE 13-continued

| Compound | Compound name | MS: [M + H]+ m/z | Procedure |
|---|---|---|---|
|  | tert-butyl ((1R,4R,7R)-2-(5-(3,4-dichloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-2-azabicyclo[2.2.1]heptan-7-yl)carbamate | 688, 690 | Prepared as general procedure 1 above using 2-chloro-5-(3,4-dichloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl ((1R,4R,7R)-2-azabicyclo[2.2.1]heptan-7-yl) carbamate |
|  | rac-tert-butyl ((1R,2R,4S)-7-(5-(3,4-dichloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-2-methyl-7-azabicyclo[2.2.1]heptan-2-yl)carbamate | 702, 704 | Prepared as general procedure 1 above using 2-chloro-5-(3,4-dichloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and rac-tert-butyl ((1R,2R,4S)-2-methyl-7-azabicyclo[2.2.1]heptan-2-yl) carbamate oxalate |
|  | tert-butyl ((1R,4R,7R)-2-(5-(3-chloro-4-fluoro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-2-azabicyclo[2.2.1]heptan-7-yl)carbamate | 672, 674 | Prepared as general procedure 1 above using 2-chloro-5-(3-chloro-4-fluoro-2-methyl-2H-indazol-5-yl)-3-methyl-7-((2-(trimethylsilyl)ethoxy)methyl)-3,7-dihydro-4H-pyrrolo[2,3-d]pyrimidin-4-one and tert-butyl ((1R,4R,7R)-2-azabicyclo[2.2.1]heptan-7-yl) carbamate |
|  | rac-tert-butyl ((1R,2R,4S)-7-(3-(3,4-dichloro-2-methyl-2H-indazol-5-yl)-5-methyl-4-oxo-1-(tetrahydro-2H-pyran-2-yl)-4,5-dihydro-1H-pyrazolo[3,4-d]pyrimidin-6-yl)-2-methyl-7-azabicyclo[2.2.1]heptan-2-yl)carbamate | 657, 659 | Prepared as general procedure 1 above using 6-chloro-3-(3,4-dichloro-2-methyl-2H-indazol-5-yl)-5-methyl-1-(tetrahydro-2H-pyran-2-yl)-1,5-dihydro-4H-pyrazolo[3,4-d]pyrimidin-4-one and rac-tert-butyl ((1R,2R,4S)-2-methyl-7-azabicyclo[2.2.1]heptan-2-yl) carbamate oxalate |

TABLE 13-continued

| Compound | Compound name | MS: [M + H]+ m/z | Procedure |
|---|---|---|---|
| | rac-tert-butyl 3-[5-(4-chloro-2-ethyl-2H-indazol-5-yl)-3-methyl-4-oxo-7-{[2-(trimethylsilyl)ethoxy]methyl}-3H,4H,7H-pyrrolo[2,3-d]pyrimidin-2-yl]-3,6-diazabicyclo[3.2.1]octane-6-carboxylate | 668 | Prepared using general procedure 1 using 2-chloro-5-(4-chloro-2-ethyl-2H-indazol-5-yl)-3-methyl-7-((2-(trimethylsilyl)ethoxy)methyl)-3,7-dihydro-4H-pyrrolo[2,3-d]pyrimidin-4-one and rac-tert-butyl 3,6-diazabicyclo[3.2.1]octane-6-carboxylate. purified by normal phase chromatography on silica gel. |
| | rac-tert-butyl 6-[5-(4-chloro-2-ethyl-2H-indazol-5-yl)-3-methyl-4-oxo-7-{[2-(trimethylsilyl)ethoxy]methyl}-3H,4H,7H-pyrrolo[2,3-d]pyrimidin-2-yl]-3,6-diazabicyclo[3.2.1]octane-3-carboxylate | 669 | Prepared using general procedure 1 using 2-chloro-5-(4-chloro-2-ethyl-2H-indazol-5-yl)-3-methyl-7-((2-(trimethylsilyl)ethoxy)methyl)-3,7-dihydro-4H-pyrrolo[2,3-d]pyrimidin-4-one and rac-tert-butyl 3,6-diazabicyclo[3.2.1]octane-3-carboxylate, purified by normal phase chromatography on silica gel. |
| | 2-[(3S,4S)-4-amino-3-methyl-2-oxa-8-azaspiro[4.5]decan-8-yl]-5-(4-chloro-7-fluoro-2-methyl-2H-indazol-5-yl)-3-methyl-7-{[2-(trimethylsilyl)ethoxy]methyl}-3H,4H,7H-pyrrolo[2,3-d]pyrimidin-4-one; trifluoroacetate | 630 | Starting from 4-chloro-7-fluoro-2-methyl-5-(4,4,5,5-tetramethyl-1,3,2-dioxaborolan-2-yl)-2H-indazole, the title compounds was prepared using methods similar to those described for Example 72. Purified by reverse phase chromatography on C18 silica gel. |
| | rac-tert-butyl N-[endo-7-[5-(4-chloro-2-methyl-2H-indazol-5-yl)-3-methyl-4-oxo-7-{[2-(trimethylsilyl)ethoxy]methyl}-3H,4H,7H-pyrrolo[2,3-d]pyrimidin-2-yl]-2-methyl-7-azabicyclo[2.2.1]heptan-2-yl]carbamate | 668 | Prepared as general procedure 1 using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and rac-tert-butyl N-[endo-2-methyl-7-azabicyclo[2.2.1]heptan-2-yl]carbamate (ChemExpress HY-23145). Purified by normal phase chromatography on NH silica gel. |

TABLE 13-continued

| Compound | Compound name | MS: [M + H]+ m/z | Procedure |
|---|---|---|---|
| | rac-tert-butyl 6-[5-(4-chloro-2-ethyl-2H-indazol-5-yl)-3-methyl-4-oxo-7-{[2-(trimethylsilyl)ethoxy]methyl}-3H,4H,7H-pyrrolo[2,3-d]pyrimidin-2-yl]-2,6-diazaspiro[3.4]octane-2-carboxylate | 668.7 | Prepared using general procedure 1 using 2-Chloro-5-(4-chloro-2-ethyl-2H-indazol-5-yl)-3-methyl-7-((2-(trimethylsilyl)ethoxy)methyl)-3,7-dihydro-4H-pyrrolo[2,3-d]pyrimidin-4-one and rac-tert-butyl 2,6-diazaspiro[3.4]octane-2-carboxylate, purified by normal phase chromatography on silica gel. |
| | benzyl N-[(1R,2S,3S,5S)-8-[5-(4-chloro-2-ethyl-2H-indazol-5-yl)-3-methyl-4-oxo-7-{[2-(trimethylsilyl)ethoxy]methyl}-3H,4H,7H-pyrrolo[2,3-d]pyrimidin-2-yl]-2-fluoro-8-azabicyclo[3.2.1]octan-3-yl]carbamate | 734 | Prepared using general procedure 1 using 2-chloro-5-(4-chloro-2-ethyl-2H-indazol-5-yl)-3-methyl-7-((2-(trimethylsilyl)ethoxy)methyl)-3,7-dihydro-4H-pyrrolo[2,3-d]pyrimidin-4-one and benzyl N-[(1R,2R,3S,5S)-2-fluoro-8-azabicyclo[3.2.1]octan-3-yl]carbamate hydrochloride, purified by normal phase chromatography on silica gel. |
| | tert-butyl N-[(1R,2R,4S)-7-{5-[8-chloro-2-(dimethylamino)quinolin-7-yl]-3-methyl-4-oxo-7-{[2-(trimethylsilyl)ethoxy]methyl}-3H,4H,7H-pyrrolo[2,3-d]pyrimidin-2-yl)-7-azabicyclo[2.2.1]heptan-2-yl]carbamate | 694 | Prepared as general procedure 1, using 2-chloro-5-[8-chloro-2-(dimethylamino)quinolin-7-yl]-3-methyl-7-{[2-(trimethylsilyl)ethoxy]methyl}-3H,4H,7H-pyrrolo[2,3-d]pyrimidin-4-one and tert-butyl N-[(1R,2R,4S)-7-azabicyclo[2.2.1]heptan-2-yl]carbamate heating at 120° C. for 7 h, purified on KP-NH column. |

TABLE 13-continued

| Compound | Compound name | MS: [M + H]+ m/z | Procedure |
|---|---|---|---|
|  | tert-butyl N-[(1R,2R,4S)-7-{5-[8-chloro-2-(methylamino)quinolin-7-yl]-3-methyl-4-oxo-7-{[2-(trimethylsilyl)ethoxy]methyl}-3H,4H,7H-pyrrolo[2,3-d]pyrimidin-2-yl}-7-azabicyclo[2.2.1]heptan-2-yl]carbamate | 694 | Prepared as general procedure 1, using 2-chloro-5-[8-chloro-2-(methylamino)quinolin-7-yl]-3-methyl-7-{[2-(trimethylsilyl)ethoxy]methyl}-3H,4H,7H-pyrrolo[2,3-d]pyrimidin-4-one and tert-butyl N-[(1R,2R,4S)-7-azabicyclo[2.2.1]heptan-2-yl]carbamate heating at 120° C. for 7 h, purified on KP-NH column. |
|  | 2-((3R,4S)-4-amino-3-fluoropiperidin-1-yl)-5-(7-chlorobenzo[d]thiazol-6-yl)-3-methyl-7-((2-(trimethylsilyl)ethoxy)methyl)-3,7-dihydro-4H-pyrrolo[2,3-d]pyrimidin-4-one | 663 | Prepared using general procedure 1 using 2-chloro-5-(7-chloro-1,3-benzothiazol-6-yl)-3-methyl-7-{[2-(trimethylsilyl)ethoxy]methyl}-3H,4H,7H-pyrrolo[2,3-d]pyrimidin-4-one and tert-butyl N-[(3R,4S)-3-fluoropiperidin-4-yl]carbamate |
|  | rac-tert-butyl 9-[5-(4-chloro-2-methyl-2H-indazol-5-yl)-3-methyl-4-oxo-7-{[2-(trimethylsilyl)ethoxy]methyl}-3H,4H,7H-pyrrolo[2,3-d]pyrimidin-2-yl]-3,9-diazabicyclo[4.2.1]nonane-3-carboxylate | 668 | Prepared using general procedure 1 using 2-chloro-5-(4-chloro-2-methyl-2H-indazol-5-yl)-3-methyl-7-((2-(trimethylsilyl)ethoxy)methyl)-3,7-dihydro-4H-pyrrolo[2,3-d]pyrimidin-4-one and rac-tert-butyl 3,9-diazabicyclo[4.2.1]nonane-3-carboxylate |

Preparation 151: tert-Butyl ((1S,2S,4R)-7-(5-iodo-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)(methyl)carbamate

[Chem. 208]

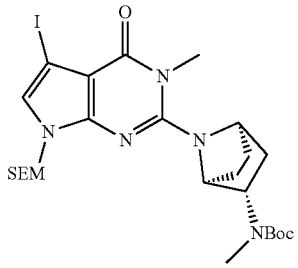

tert-Butyl ((1S,2S,4R)-7-(5-iodo-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)(methyl)carbamate was prepared in the manner similar to preparation 93 and 94, except using tert-butyl ((1S,2S,4R)-7-azabicyclo[2.2.1]heptan-2-yl)carbamate instead of tert-butyl ((1R,2R,4S)-7-azabicyclo[2.2.1]heptan-2-yl)carbamate. MS: [M+H]$^+$=630.

Preparation 152: tert-Butyl ((1S,2S,4R)-7-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)(methyl)carbamate

[Chem. 209]

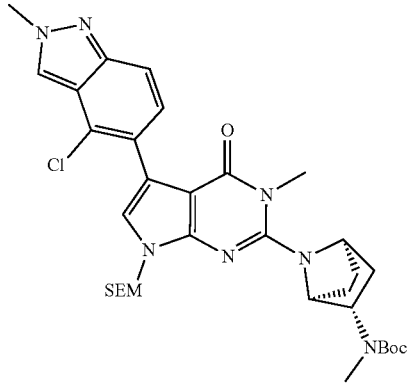

tert-Butyl ((1S,2S,4R)-7-(5-(4-chloro-2-methyl-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)(methyl)carbamate was prepared in the manner similar to general procedure 2, except using tert-butyl ((1S,2S,4R)-7-(5-iodo-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)(methyl)carbamate and 4-chloro-2-methyl-5-(4,4,5,5-tetramethyl-1,3,2-dioxaborolan-2-yl)-2H-indazole, MS: [M+H]$^+$=668, 670.

Preparation 153: tert-Butyl (endo-8-(5-(5-chloroquinoxalin-6-yl)-3-methyl-4-oxo-7-((2-(trimethylsilyl)ethoxy)methyl)-4,7-dihydro-3H-pyrrolo[2,3-d]pyrimidin-2-yl)-8-azabicyclo[3.2.1]octan-3-yl)carbamate

[Chem. 210]

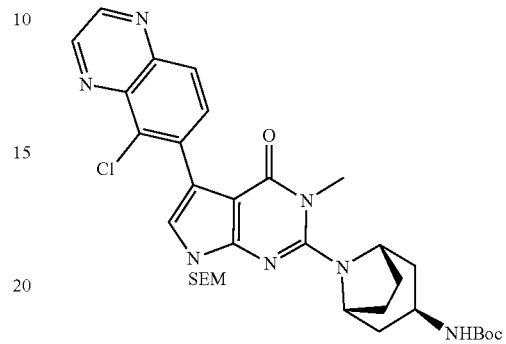

tert-Butyl (endo-8-(5-(5-chloroquinoxalin-6-yl)-3-methyl-4-oxo-7-((2-(trimethylsilyl)ethoxy)methyl)-4,7-dihydro-3H-pyrrolo[2,3-d]pyrimidin-2-yl)-8-azabicyclo[3.2.1]octan-3-yl)carbamate was prepared in the manner similar to general procedure 2, except using tert-butyl (endo-8-(5-iodo-3-methyl-4-oxo-7-((2-(trimethylsilyl)ethoxy)methyl)-4,7-dihydro-3H-pyrrolo[2,3-d]pyrimidin-2-yl)-8-azabicyclo[3.2.1]octan-3-yl)carbamate and (5-chloroquinoxalin-6-yl)boronic acid and MS: [M+H]$^+$= 666, 668.

Preparation 154: tert-Butyl ((1R,2R,4S)-7-(3-(3,4-dichloro-2-methyl-2H-indazol-5-yl)-5-methyl-4-oxo-1-(tetrahydro-2H-pyran-2-yl)-4,5-dihydro-1H-pyrazolo[3,4-d]pyrimidin-6-yl)-7-azabicyclo[2.2.1]heptan-2-yl)(ethyl)carbamate

[Chem. 211]

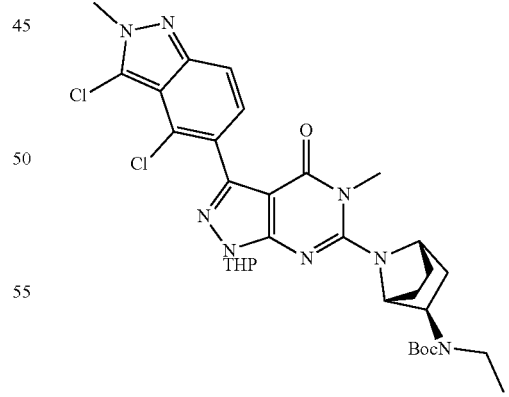

tert-Butyl ((1R,2R,4S)-7-(3-(3,4-dichloro-2-methyl-2H-indazol-5-yl)-5-methyl-4-oxo-1-(tetrahydro-2H-pyran-2-yl)-4,5-dihydro-1H-pyrazolo[3,4-d]pyrimidin-6-yl)-7-azabicyclo[2.2.1]heptan-2-yl)(ethyl)carbamate was prepared in a similar manner to general procedure 3 except using tert-butyl ((1R,2R,4S)-7-(3-bromo-5-methyl-4-oxo-1-(tetrahydro-2H-pyran-2-yl)-4,5-dihydro-1H-pyrazolo[3,4- d]pyrimidin-6-yl)-7-azabicyclo[2.2.1]heptan-2-yl)(ethyl) carbamate and 3,4-dichloro-2-methyl-5-(4,4,5,5-tetramethyl-1,3,2-dioxaborolan-2-yl)-2H-indazole, MS: [M+H]⁺=671, 673.

Compounds of Table 14 below were prepared using procedures analogous to that described in general procedure 2 starting from the appropriate substituted protected pyrrolopyrimidinone and varying the boronate or boronic acid (synthesised as described above with any significant variations indicated below).

TABLE 14

| Compound | Compound name | MS: [M + H]⁺ m/z | Procedure |
|---|---|---|---|
| 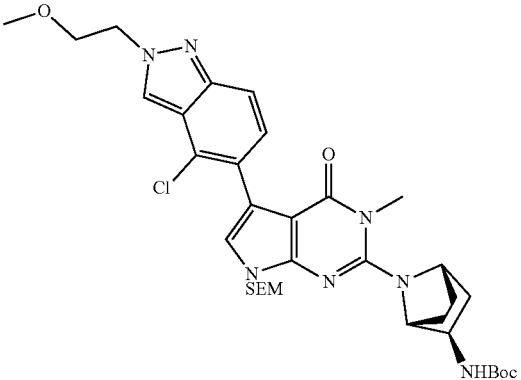 [SMILES: COCCn1cc2c(Cl)c(-c3cn(COCC[Si](C)(C)C)c4nc(N5[C@H]6CC[C@@H]5[C@H](NC(=O)OC(C)(C)C)C6)n(C)c(=O)c34)ccc2n1] | tert-butyl ((1R,2R,4S)-7-(5-(4-chloro-2-(2-methoxyethyl)-2H-indazol-5-yl)-3-methyl-4-oxo-7-((2-(trimethylsilyl)ethoxy)methyl)-4,7-dihydro-3H-pyrrolo[2,3-d]pyrimidin-2-yl)-7-azabicyclo[2.2.1]heptan-2-yl)carbamate | 698, 700 | Prepared as general procedure 2 above using tert-butyl ((1R,2R,4S)-7-(5-iodo-3-methyl-4-oxo-7-((2-trimethylsilyl)ethoxy)methyl)-4,7-dihydro-3H-pyrrolo[2,3-d]pyrimidin-2-yl)-7-azabicyclo[2.2.1]heptan-2-yl)carbamate and 4-chloro-2-(2-methoxyethyl)-5-(4,4,5,5-tetramethyl-1,3,2-dioxaborolan-2-yl)-2H-indazole |

TABLE 15

Examples 160-178

By following methods similar and/or analogous to those described for general procedures for preparations of compounds of Formula (I) (methods 1-3), the compounds set out in Table 15 were prepared, with any significant variations indicated. The title compounds were either isolated directly as the free base or as the appropriate salt without further purification, or purified for example using mass-directed preparative HPLC, chromatography, crystallization or trituration and converted to the appropriate salt.

| Example | Structure | Name | NMR data | MS: [M + H]⁺ m/z | Method |
|---|---|---|---|---|---|
| 160 | 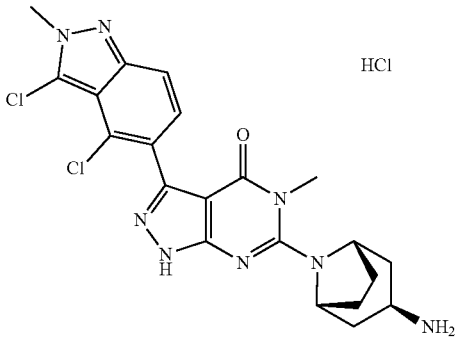 [SMILES: Cn1nc2ccc(-c3n[nH]c4nc(N5[C@@H]6CC[C@H]5C[C@@H](N)C6)n(C)c(=O)c34)c(Cl)c2c1Cl ; Cl] | 6-(endo-3-amino-8-azabicyclo[3.2.1]octan-8-yl)-3-(3,4-dichloro-2-methyl-2H-indazol-5-yl)-5-methyl-1,5-dihydro-4H-pyrazolo[3,4-d]pyrimidin-4-one, hydrochloride salt | ¹H-NMR (DMSO-d₆) δ: 13.40 (1H, s), 7.95 (3H, s), 7.59 (1H, J = 9.2 Hz, d), 7.29 (1H, J = 9.2 Hz, d), 4.28 (2H, s), 4.14 (3H, s), 3.48-3.40 (1H, m), 3.37 (3H, s), 2.53-2.48 (2H, m), 2.12-2.06 (2H, m), 1.84-1.78 (2H, m), 1.72-1.65 (2H, m). | 473, 475 | 3 (given without purification) |

TABLE 15-continued

Examples 160-178

By following methods similar and/or analogous to those described for general procedures for preparations of compounds of Formula (I) (methods 1-3), the compounds set out in Table 15 were prepared, with any significant variations indicated. The title compounds were either isolated directly as the free base or as the appropriate salt without further purification, or purified for example using mass-directed preparative HPLC, chromatography, crystallization or trituration and converted to the appropriate salt.

| Example | Structure | Name | NMR data | MS: [M + H]+ m/z | Method |
|---|---|---|---|---|---|
| 161 | 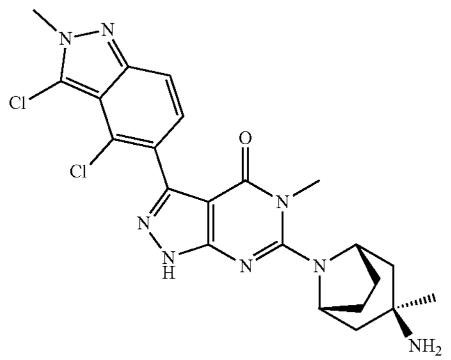 [SMILES: Cn1nc2ccc(-c3n[nH]c4nc(N5[C@@H]6CC[C@H]5C[C@@](C)(N)C6)n(C)c(=O)c34)c(Cl)c2c1Cl] | 6-(endo-3-amino-3-methyl-8-azabicyclo[3.2.1]octan-8-yl)-3-(3,4-dichloro-2-methyl-2H-indazol-5-yl)-5-methyl-1,5-dihydro-4H-pyrazolo[3,4-d]pyrimidin-4-one | $^1$H-NMR (DMSO-d$_6$) δ: 7.58 (1H, J = 8.8 Hz, d), 7.29 (1H, J = 8.8 Hz, d), 4.18-4.13 (2H, m), 4.14 (3H, s), 3.36 (3H, s), 2.31-2.25 (2H, m), 1.89-1.82 (4H, m), 1.62-1.55 (2H, m), 1.06 (3H, s). | 487, 489 | 3 |
| 162 | 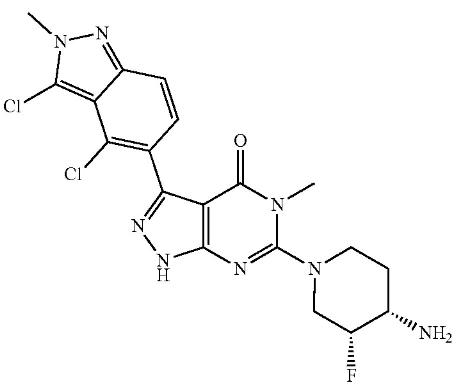 [SMILES: Cn1nc2ccc(-c3n[nH]c4nc(N5CC[C@H](N)[C@H](F)C5)n(C)c(=O)c34)c(Cl)c2c1Cl] | 6-((3R,4S)-4-amino-3-fluoropiperidin-1-yl)-3-(3,4-dichloro-2-methyl-2H-indazol-5-yl)-5-methyl-1,5-dihydro-1H-pyrazolo[3,4-d]pyrimidin-4-one | $^1$H-NMR (DMSO-d$_6$) δ: 8.45 (3H, s), 7.60 (1H, J = 8.8 Hz, d), 7.30 (1H, J = 8.8 Hz, d), 5.05 (1H, J = 48.8 Hz, d), 4.14 (3H, s), 3.92-3.81 (1H, m), 3.72-3.64 (1H, m), 3.35 (3H, s), 3.32-3.16 (1H, m), 3.01-2.93 (1H, m), 2.13-2.01 (1H, m), 1.59-1.58 (1H, m). | 465, 467 | 3 |
| 163 | 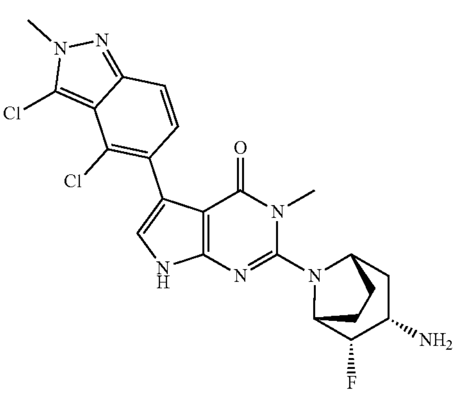 [SMILES: Cn1nc2ccc(-c3c[nH]c4nc(N5[C@H]6CC[C@@H]5[C@@H](F)[C@@H](N)C6)n(C)c(=O)c34)c(Cl)c2c1Cl] | 2-((1R,2S,3S,5S)-3-amino-2-fluoro-8-azabicyclo[3.2.1]octan-8-yl)-5-(3,4-dichloro-2-methyl-2H-indazol-5-yl)-3-methyl-3,7-dihydro-4H-pyrrolo[2,3-d]pyrimidin-4-one | $^1$H-NMR (DMSO-d$_6$) δ: 11.67 (1H, s), 7.51 (1H, J = 8.8 Hz, d), 7.33 (1H, J = 8.8 Hz, d), 6.99 (1H, s), 4.57-4.39 (2H, m), 4.15 (3H, s), 3.45 (3H, s), 3.04-2.92 (1H, m), 2.09-1.94 (2H, m), 1.90-1.80 (1H, m), 1.75-1.56 (4H, m). | 490, 492 | 2 |

TABLE 15-continued

Examples 160-178
By following methods similar and/or analogous to those described for general procedures for preparations of compounds of Formula (I) (methods 1-3), the compounds set out in Table 15 were prepared, with any significant variations indicated. The title compounds were either isolated directly as the free base or as the appropriate salt without further purification, or purified for example using mass-directed preparative HPLC, chromatography, crystallization or trituration and converted to the appropriate salt.

| Example | Structure | Name | NMR data | MS: [M + H]+ m/z | Method |
|---|---|---|---|---|---|
| 164 | 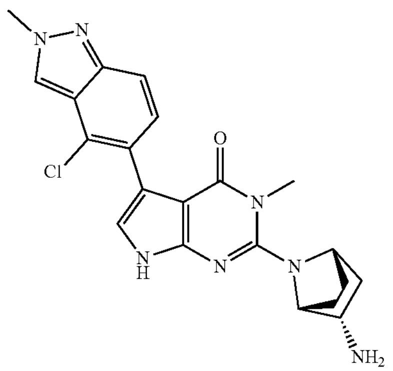 [SMILES: Cn1cc2c(Cl)c(-c3c[nH]c4nc(N5[C@H]6CC[C@@H]5[C@@H](N)C6)n(C)c(=O)c34)ccc2n1] | 2-(rac-(1R,2S,4S)-2-amino-7-azabicyclo[2.2.1]heptan-7-yl)-5-(4-chloro-2-methyl-2H-indazol-5-yl)-3-methyl-3,7-dihydro-4H-pyrrolo[2,3-d]pyrimidin-4-one | $^1$H-NMR (DMSO-d$_6$) δ: 11.59 (1H, s), 8.38 (1H, s), 7.47 (1H, J = 8.8 Hz, d), 7.32 (1H, J = 8.8 Hz, d), 6.92 (1H, s), 4.24-4.21 (1H, m), 4.18 (3H, s), 3.95 (1H, J = 4.6 Hz, d), 3.46 (3H, s), 2.98-2.91 (1H, m), 1.91-1.54 (5H, m), 1.52-1.44 (1H, m), 1.38-1.28 (2H, m). | 424, 426 | 2 |
| 165 | 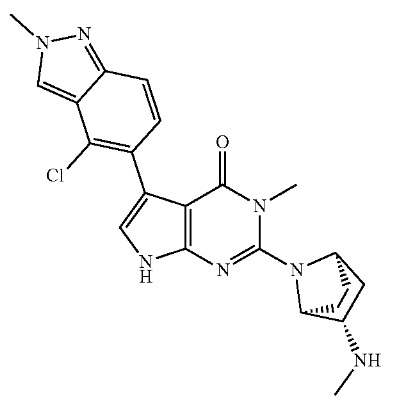 [SMILES: CN[C@H]1C[C@H]2CC[C@@H]1N2c1nc2[nH]cc(-c3ccc4nn(C)cc4c3Cl)c2c(=O)n1C] | 5-(4-chloro-2-methyl-2H-indazol-5-yl)-3-methyl-2-((1S,2S,4R)-2-(methylamino)-7-azabicyclo[2.2.1]heptan-7-yl)-3,7-dihydro-4H-pyrrolo[2,3-d]pyrimidin-4-one | $^1$H-NMR (DMSO-d$_6$) δ: 11.62 (1H, s), 8.38 (1H, s), 7.47 (1H, J = 8.8 Hz, d), 7.31 (1H, J = 8.8 Hz, d), 6.94 (1H, J = 2.2 Hz, d), 4.25-4.14 (2H, m), 4.18 (3H, s), 3.40 (3H, s), 3.16-3.09 (1H, m), 2.27-2.19 (1H, m), 2.24 (3H, s), 2.08-2.01 (1H, m), 1.93-1.85 (1H, m), 1.74-1.64 (1H, m), 1.48-1.41 (1H, m), 0.96-0.89 (1H, m). | 438, 440 | 2 |
| 166 | 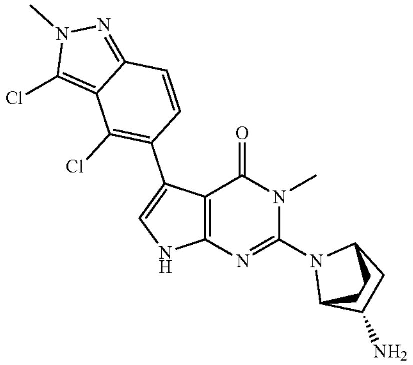 [SMILES: Cn1nc2ccc(-c3c[nH]c4nc(N5[C@H]6CC[C@@H]5[C@@H](N)C6)n(C)c(=O)c34)c(Cl)c2c1Cl] | 2-((1R,2S,4S)-2-amino-7-azabicyclo[2.2.1]heptan-7-yl)-5-(3,4-dichloro-2-methyl-2H-indazol-5-yl)-3-methyl-3,7-dihydro-4H-pyrrolo[2,3-d]pyrimidin-4-one | $^1$H-NMR (DMSO-d$_6$) δ: 11.64 (1H, s), 7.49 (1H, J = 8.8 Hz, d), 7.32 (1H, J = 8.8 Hz, d), 6.95 (1H, s), 4.26-4.19 (1H, m), 4.13 (3H, s), 3.97-3.92 (1H, m), 3.46 (3H, s), 2.99-2.91 (1H, m), 1.90-1.70 (5H, m), 1.52-1.43 (1H, m), 1.37-1.26 (2H, m). | 458, 460 | 2 |

TABLE 15-continued

Examples 160-178

By following methods similar and/or analogous to those described for general procedures for preparations of compounds of Formula (I) (methods 1-3), the compounds set out in Table 15 were prepared, with any significant variations indicated. The title compounds were either isolated directly as the free base or as the appropriate salt without further purification, or purified for example using mass-directed preparative HPLC, chromatography, crystallization or trituration and converted to the appropriate salt.

| Example | Structure | Name | NMR data | MS: [M + H]+ m/z | Method |
|---|---|---|---|---|---|
| 167 | 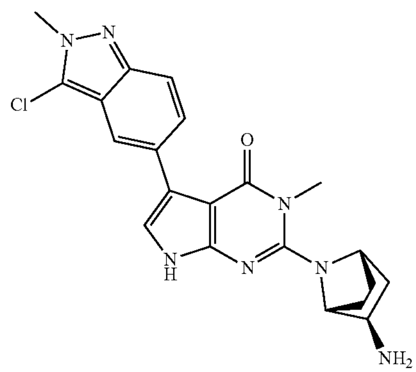 [SMILES: Cn1nc2ccc(-c3c[nH]c4nc(N5[C@H]6CC[C@@H]5[C@H](N)C6)n(C)c(=O)c34)cc2c1Cl] | 2-((1R,2R,4S)-2-amino-7-aza-bicyclo[2.2.1]heptan-7-yl)-5-(3-chloro-2-methyl-2H-indazol-5-yl)-3-methyl-3,7-dihydro-4H-pyrrolo[2,3-d]pyrimidin-4-one | $^1$H-NMR (DMSO-d$_6$) δ: 11.61 (1H, s), 8.44 (1H, s), 7.74 (1H, J = 9.3, 1.2 Hz, dd), 7.50 (1H, J = 9.3 Hz, d), 7.25 (1H, s), 4.13-4.08 (1H, m), 4.12 (3H, s), 4.02-3.99 (1H, m), 3.46 (3H, s), 2.31-2.04 (3H, m), 1.95-1.85 (1H, m), 1.71-1.62 (1H, m), 1.52-1.44 (1H, m), 0.92-0.84 (1H, m). | 424, 426 | 2 |
| 168 | 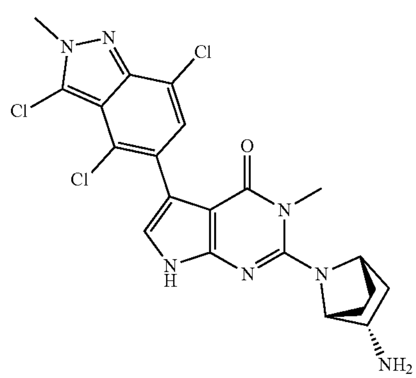 [SMILES: Cn1nc2c(Cl)cc(-c3c[nH]c4nc(N5[C@H]6CC[C@@H]5[C@@H](N)C6)n(C)c(=O)c34)c(Cl)c2c1Cl] | 2-((1R,2S,4S)-2-amino-7-aza-bicyclo[2.2.1]heptan-7-yl)-3-methyl-5-(3,4,7-trichloro-2-methyl-2H-indazol-5-yl)-3,7-dihydro-4H-pyrrolo[2,3-d]pyrimidin-4-one | $^1$H-NMR (DMSO-d$_6$) δ: 11.74 (1H, s), 7.47 (1H, s), 7.04 (1H, s), 4.17 (3H, s), 4.14-4.10 (1H, m), 4.03-3.96 (1H, m), 3.50-3.42 (2H, m), 3.39 (3H, s), 2.30-2.21 (1H, m), 2.20-2.10 (1H, m), 1.92-1.84 (1H, m), 1.71-1.60 (1H, m), 1.51-1.44 (1H, m), 0.92-0.83 (1H, m). | 492, 494 | 2 |
| 169 | 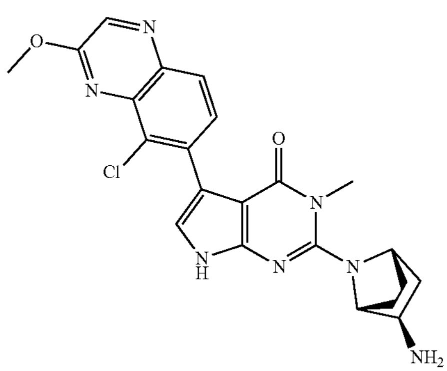 [SMILES: COc1cnc2ccc(-c3c[nH]c4nc(N5[C@H]6CC[C@@H]5[C@H](N)C6)n(C)c(=O)c34)c(Cl)c2n1] | 2-((1R,2R,4S)-2-amino-7-aza-bicyclo[2.2.1]heptan-7-yl)-5-(5-chloro-3-methoxy-quinoxalin-6-yl)-3-methyl-3,7-dihydro-4H-pyrrolo[2,3-d]pyrimidin-4-one | $^1$H-NMR (DMSO-d$_6$) δ: 11.84 (1H, br s), 8.66 (1H, s), 7.94 (1H, d, J = 8.6 Hz), 7.76 (1H, d, J = 8.6 Hz), 7.17 (1H, s), 4.19-4.17 (1H, m), 4.13 (3H, s), 4.05-4.03 (1H, m), 3.52-3.47 (1H, m), 3.43 (3H, s), 2.34-2.26 (1H, m), 2.24-2.18 (1H, m), 2.05-1.68 (3H, m), 1.56-1.50 (1H, m), 0.93-0.88 (1H, m). | 452, 454 | 2 |

TABLE 15-continued

Examples 160-178
By following methods similar and/or analogous to those described for general procedures for preparations of compounds of Formula (I) (methods 1-3), the compounds set out in Table 15 were prepared, with any significant variations indicated. The title compounds were either isolated directly as the free base or as the appropriate salt without further purification, or purified for example using mass-directed preparative HPLC, chromatography, crystallization or trituration and converted to the appropriate salt.

| Example | Structure | Name | NMR data | MS: [M + H]+ m/z | Method |
|---|---|---|---|---|---|
| 170 | 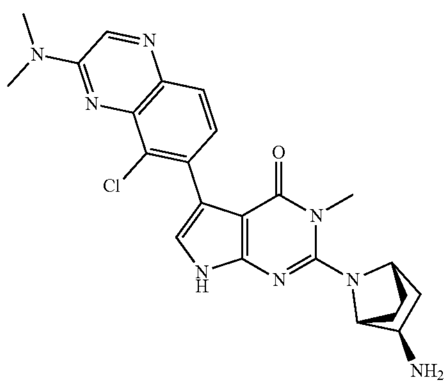 [SMILES: CN(C)c1cnc2ccc(-c3c[nH]c4nc(N5[C@H]6CC[C@@H]5[C@H](N)C6)n(C)c(=O)c34)c(Cl)c2n1] | 2-((1R,2R,4S)-2-amino-7-azabicyclo[2.2.1]heptan-7-yl)-5-(5-chloro-3-(dimethylamino)quinoxalin-6-yl)-3-methyl-3,7-dihydro-4H-pyrrolo[2,3-d]pyrimidin-4-one | $^1$H-NMR (DMSO-$d_6$) δ: 11.72 (1H, br s), 8.69 (1H, s), 7.69 (1H, d, J = 8.5 Hz), 7.42 (1H, d, J = 8.5 Hz), 7.06 (1H, s), 4.15-4.13 (1H, m), 4.01-3.99 (1H, m), 3.48-3.43 (1H, m), 3.40 (3H, s), 3.32 (3H, s), 3.28 (3H, s), 2.30-2.23 (1H, m), 2.21-2.15 (1H, m), 1.94-1.88 (1H, m), 1.70-1.64 (2H, m), 1.52-1.46 (1H, m), 0.89-0.83 (1H, m). | 465, 467 | 2 |
| 171 | 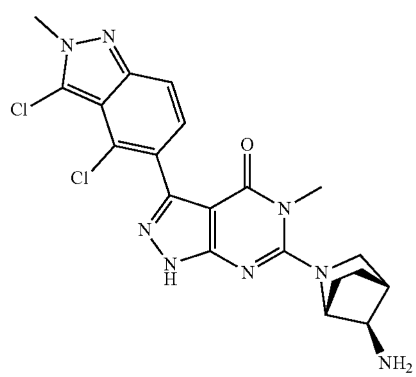 [SMILES: Cn1nc2ccc(-c3n[nH]c4nc(N5C[C@H]6CC[C@@H]5[C@@H]6N)n(C)c(=O)c34)c(Cl)c2c1Cl] | 6-((1R,4R,7R)-7-amino-2-azabicyclo[2.2.1]heptan-2-yl)-3-(3,4-dichloro-2-methyl-2H-indazol-5-yl)-5-methyl-1,5-dihydro-4H-pyrazolo[3,4-d]pyrimidin-4-one | $^1$H-NMR (DMSO-$d_6$) δ: 13.20 (1H, br s), 7.60 (1H, d, J = 8.8 Hz), 7.31 (1H, d, J = 8.8 Hz), 4.16 (3H, s), 3.95-3.93 (1H, m), 3.79-3.75 (1H, m), 3.28 (3H, s), 3.26-3.24 (1H, m), 3.07 (1H, d, J = 9.2 Hz), 2.19-2.14 (1H, m), 2.02-1.84 (3H, m), 1.40-1.33 (1H, m). | 459, 461 | 3 |
| 172 | 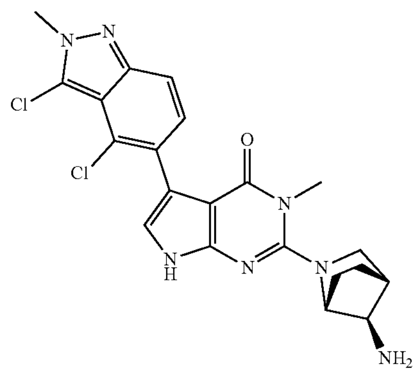 [SMILES: Cn1nc2ccc(-c3c[nH]c4nc(N5C[C@H]6CC[C@@H]5[C@@H]6N)n(C)c(=O)c34)c(Cl)c2c1Cl] | 2-((1R,4R,7R)-7-amino-2-azabicyclo[2.2.1]heptan-2-yl)-5-(3,4-dichloro-2-methyl-2H-indazol-5-yl)-3-methyl-3,7-dihydro-4H-pyrrolo[2,3-d]pyrimidin-4-one | $^1$H-NMR (DMSO-$d_6$) δ: 11.51 (1H, br s), 7.49 (1H, d, J = 9.0 Hz), 7.32 (1H, d, J = 9.0 Hz), 6.90 (1H, s), 4.13 (3H, s), 3.85-3.83 (1H, m), 3.73-3.68 (1H, m), 3.28 (3H, s), 3.25-3.22 (1H, m), 3.01 (1H, d, J = 9.0 Hz), 2.18-2.14 (1H, m), 2.00-1.84 (3H, m), 1.40-1.33 (1H, m). | 458, 460 | 2 |

TABLE 15-continued

Examples 160-178

By following methods similar and/or analogous to those described for general procedures for preparations of compounds of Formula (I) (methods 1-3), the compounds set out in Table 15 were prepared, with any significant variations indicated. The title compounds were either isolated directly as the free base or as the appropriate salt without further purification, or purified for example using mass-directed preparative HPLC, chromatography, crystallization or trituration and converted to the appropriate salt.

| Example | Structure | Name | NMR data | MS: [M + H]+ m/z | Method |
|---|---|---|---|---|---|
| 173 | 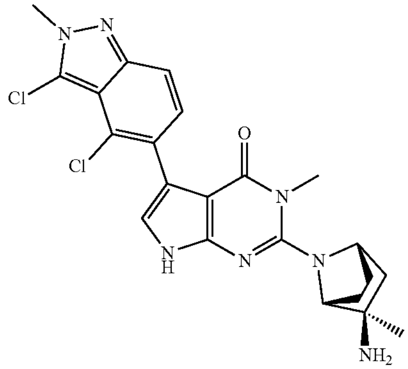 [SMILES: Cn1nc2ccc(-c3c[nH]c4nc(N5[C@H]6CC[C@@H]5[C@](C)(N)C6)n(C)c(=O)c34)c(Cl)c2c1Cl] | rac-2-((1R,2R,4S)-2-amino-2-methyl-7-azabicyclo[2.2.1]heptan-7-yl)-5-(3,4-dichloro-2-methyl-2H-indazol-5-yl)-3-methyl-3,7-dihydro-4H-pyrrolo[2,3-d]pyrimidin-4-one | $^1$H-NMR (DMSO-$d_6$) δ: 11.63 (1H, br s), 7.49 (1H, d, J = 9.3 Hz), 7.32 (1H, d, J = 9.2 Hz), 6.95 (1H, s), 4.20-4.17 (1H, m), 4.13 (6H, s), 3.78-3.75 (1H, m), 3.41 (3H, s), 2.24-2.17 (1H, m), 1.90-1.81 (2H, m), 1.75-1.66 (1H, m), 1.53-1.46 (1H, m), 1.23 (3H, s), 1.18-1.14 (1H, m). | 472, 474 | 2 |
| 174 | 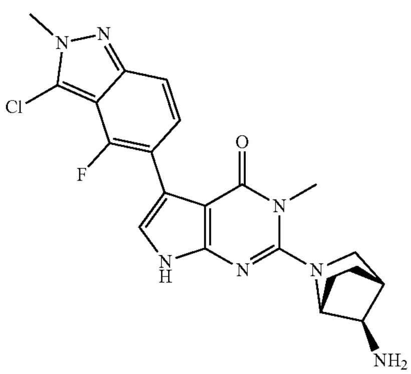 [SMILES: Cn1nc2ccc(-c3c[nH]c4nc(N5C[C@H]6CC[C@@H]5[C@@H]6N)n(C)c(=O)c34)c(F)c2c1Cl] | 2-((1R,4R,7R)-7-amino-2-azabicyclo[2.2.1]heptan-2-yl)-5-(3-chloro-4-fluoro-2-methyl-2H-indazol-5-yl)-3-methyl-3,7-dihydro-4H-pyrrolo[2,3-d]pyrimidin-4-one | $^1$H-NMR (DMSO-$d_6$) δ: 11.56 (1H, br s), 7.66-7.62 (1H, m), 7.36 (1H, d, J = 9.0 Hz), 6.98 (1H, s), 4.12 (3H, s), 3.87-3.84 (1H, m), 3.73-3.68 (1H, m), 3.32 (3H, s), 3.26-3.23 (1H, m), 3.05-3.03 (1H, m), 2.18-2.13 (1H, m), 1.99-1.85 (3H, m), 1.42-1.32 (1H, m). | 442, 444 | 2 |
| 175 | 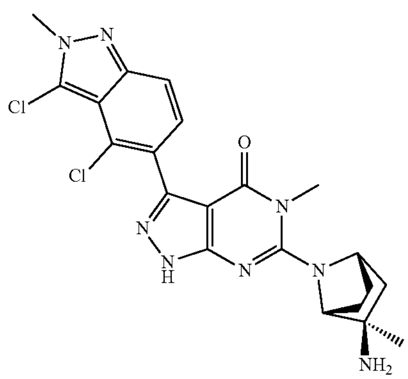 [SMILES: Cn1nc2ccc(-c3n[nH]c4nc(N5[C@H]6CC[C@@H]5[C@](C)(N)C6)n(C)c(=O)c34)c(Cl)c2c1Cl] | rac-6-((1R,2R,4S)-2-amino-2-methyl-7-azabicyclo[2.2.1]heptan-7-yl)-3-(3,4-dichloro-2-methyl-2H-indazol-5-yl)-5-methyl-1,5-dihydro-4H-pyrazolo[3,4-d]pyrimidin-4-one | $^1$H-NMR (DMSO-$d_6$) δ: 13.38 (1H, br s), 7.61 (1H, d, J = 8.8 Hz), 7.32 (1H, d, J = 8.8 Hz), 4.31-4.27 (1H, m), 4.17 (3H, s), 3.88-3.84 (1H, m), 3.41 (3H, s), 2.28-2.20 (1H, m), 1.91-1.69 (3H, m), 1.57-1.49 (1H, m), 1.26-1.18 (4H, m). | 473, 475 | 3 |

TABLE 15-continued

Examples 160-178

By following methods similar and/or analogous to those described for general procedures for preparations of compounds of Formula (I) (methods 1-3), the compounds set out in Table 15 were prepared, with any significant variations indicated. The title compounds were either isolated directly as the free base or as the appropriate salt without further purification, or purified for example using mass-directed preparative HPLC, chromatography, crystallization or trituration and converted to the appropriate salt.

| Example | Structure | Name | NMR data | MS: [M + H]+ m/z | Method |
|---|---|---|---|---|---|
| 176 | 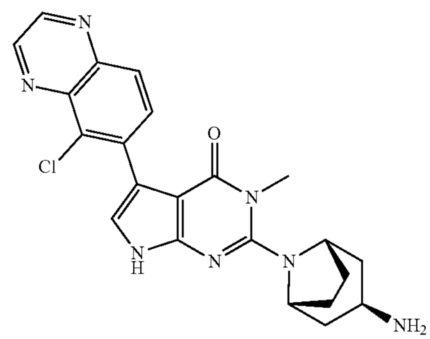 [SMILES: Cn1c(N2[C@@H]3CC[C@H]2C[C@@H](N)C3)nc2[nH]cc(-c3ccc4nccnc4c3Cl)c2c1=O] | 2-(endo-3-amino-8-azabicyclo[3.2.1]octan-8-yl)-5-(5-chloroquinoxalin-6-yl)-3-methyl-3,7-dihydro-4H-pyrrolo[2,3-d]pyrimidin-4-one | $^1$H-NMR (DMSO-$d_6$) δ: 11.76 (1H, s), 9.06 (1H, d, J = 1.8 Hz), 9.00 (1H, d, J = 1.8 Hz), 8.03-7.94 (2H, m), 7.22 (1H, s), 4.12 (2H, s), 3.43 (3H, s), 2.34-2.21 (3H, m), 2.18-2.10 (2H, m), 2.00-1.92 (2H, m), 1.58 (2H, d, J = 13.2 Hz). | 436, 438 | 2 |
| 177 | 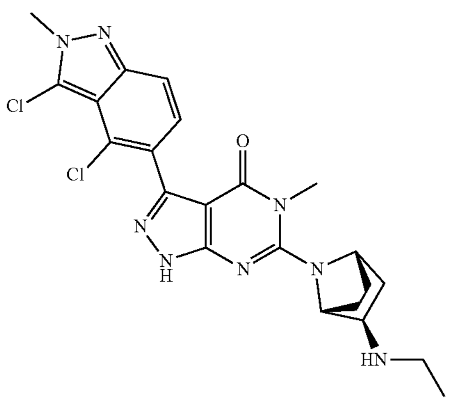 [SMILES: CCN[C@@H]1C[C@@H]2CC[C@H]1N2c1nc2[nH]nc(-c3ccc4nn(C)c(Cl)c4c3Cl)c2c(=O)n1C] | 3-(3,4-dichloro-2-methyl-2H-indazol-5-yl)-6-((1R,2R,4S)-2-(ethylamino)-7-azabicyclo[2.2.1]heptan-7-yl)-5-methyl-1,5-dihydro-4H-pyrazolo[3,4-d]pyrimidin-4-one | $^1$H-NMR (DMSO-$d_6$) δ: 13.41 (1H, s), 7.61 (1H, d, J = 8.9 Hz), 7.33 (1H, d, J = 8.9 Hz), 4.29-4.23 (2H, m), 4.17 (3H, s), 3.39 (3H, s), 3.27-3.23 (1H, m), 2.48-2.44 (2H, m), 2.26-2.20 (1H, m), 2.12-2.07 (1H, m), 1.90-1.84 (1H, m), 1.72-1.65 (1H, m), 1.52-1.46 (1H, m), 1.02 (3H, t, J = 7.2 Hz), 0.98-0.93 (1H, m). | 487, 489 | 3 |
| 178 | 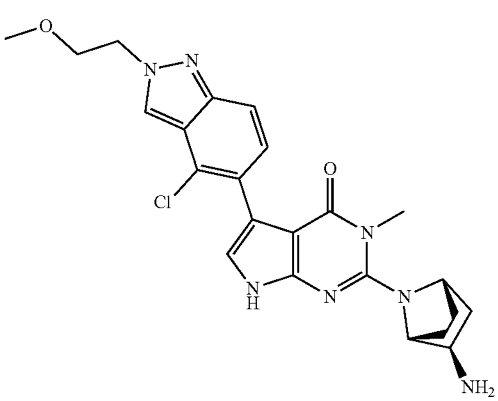 [SMILES: COCCn1cc2c(Cl)c(-c3c[nH]c4nc(N5[C@H]6CC[C@@H]5[C@H](N)C6)n(C)c(=O)c34)ccc2n1] | 2-((1R,2R,4S)-2-amino-7-azabicyclo[2.2.1]heptan-7-yl)-5-(4-chloro-2-(2-methoxyethyl)-2H-indazol-5-yl)-3-methyl-3,7-dihydro-4H-pyrrolo[2,3-d]pyrimidin-4-one | $^1$H-NMR (DMSO-$d_6$) δ: 11.63 (1H, br s), 8.40 (1H, d, J = 0.6 Hz), 7.49 (1H, dd, J = 8.9, 0.9 Hz), 7.32 (1H, d, J = 8.9 Hz), 6.94 (1H, s), 4.61 (2H, t, J = 5.2 Hz), 4.13 (1H, t, J = 4.9 Hz), 4.00 (1H, t, J = 4.4 Hz), 3.84 (2H, t, J = 5.3 Hz), 3.48-3.44 (1H, m), 3.39 (3H, s), 3.24 (3H, s), 2.29-2.23 (1H, m), 2.19-2.14 (1H, m), 1.94-1.87 (1H, m), 1.71-1.64 (1H, m), 1.52-1.46 (1H, m), 0.88 (1H, dd, J = 11.9, 4.6 Hz). | 468, 470 | 2 |

Example 179: 3-(3,4-Dichloro-2-methyl-2H-indazol-5-yl)-6-((1R,2R,4S)-2-(isopropylamino)-7-azabicyclo[2.2.1]heptan-7-yl)-5-methyl-1,5-dihydro-4H-pyrazolo[3,4-d]pyrimidin-4-one

[Chem. 212]

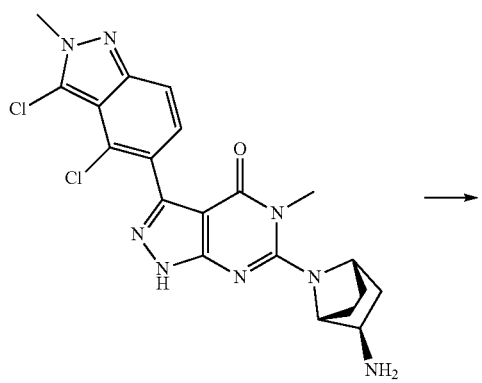

→

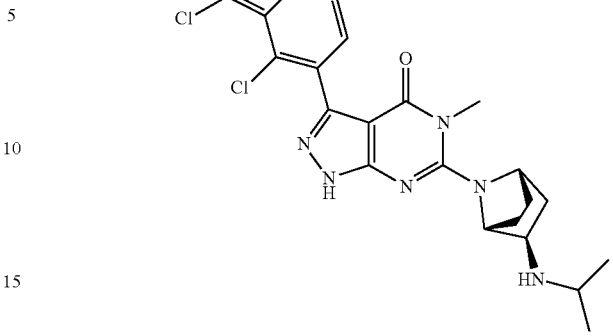

To a solution of 6-[(1S,3R,4R)-3-amino-7-azabicyclo[2.2.1]heptan-7-yl]-3-(3,4-dichloro-2-methyl-indazol-5-yl)-5-methyl-1H-pyrazolo[3,4-d]pyrimidin-4-one (20.0 mg, 0.0435 mmol) in DCM (0.400 mL), acetone (0.0320 mL, 0.435 mmol) and NaBH(OAc)$_3$ (27.7 mg, 0.131 mmol) were added at r.t. The mixture was stirred at r.t. for 18h. The reaction solution was then vacuum-concentrated, and the residue was purified by column chromatography on silica gel (gradient elution, 0-10% MeOH/CHCl$_3$) to give the title compound (14.1 mg). MS: [M+H]$^+$=501, 503. $^1$H-NMR (DMSO-d$_6$) δ: 13.39 (1H, s), 7.61 (1H, d, J=8.9 Hz), 7.33 (1H, d, J=8.9 Hz), 4.26-4.22 (2H, m), 4.17 (3H, s), 3.39 (3H, s), 2.72-2.66 (1H, m), 2.30-2.23 (1H, m), 2.13-2.06 (1H, m), 1.89-1.67 (3H, m), 1.54-1.48 (1H, m), 1.02-0.92 (7H, m).

Compounds of Table 16 below were prepared using procedures similar to those described for Example 150. The prerequisite substituted indazoles required were prepared using methods similar to those described above.

TABLE 16

| Example | Structure | Name | NMR Data | MS: [M + H]$^+$ m/z | Comment |
|---|---|---|---|---|---|
| 180 | HCl (structure shown) | 2-[(4S)-4-amino-2-oxa-8-azaspiro[4.5]decan-8-yl]-5-(2-ethyl-2H-indazol-5-yl)-3-methyl-3H,4H,7H-pyrrolo[2,3-d]pyrimidin-4-one hydrochloride | $^1$H NMR (500 MHz, DMSO-d$_6$) δ: 11.69-11.65 (m, 1H), 8.39 (s, 1H), 8.32 (s, 1H), 7.67 (dd, J = 9.0, 1.6 Hz, 1H), 7.56-7.27 (m, 4H), 7.22 (d, J = 2.1 Hz, 1H), 4.43 (q, J = 7.3 Hz, 2H), 4.07 (dd, J = 10.0, 6.0 Hz, 1H), 3.81-3.73 (m, 2H), 3.68 (dd, J = 10.1, 3.6 Hz, 1H), 3.47 (s, 4H), 3.37 (d, J = 13.2 Hz, 1H), 3.29 (s, 1H), 2.92 (t, J = 11.2 Hz, 1H), 2.82 (t, J = 11.6 Hz, 1H), 1.92-1.78 (m, 2H), 1.66 (t, J = 14.2 Hz, 2H), 1.51 (t, J = 7.3 Hz, 3H). | 448 | Prepared using 5-bromo-1H-indazole |

TABLE 16-continued

| Example | Structure | Name | NMR Data | MS: [M + H]+ m/z | Comment |
|---|---|---|---|---|---|
| 181 | 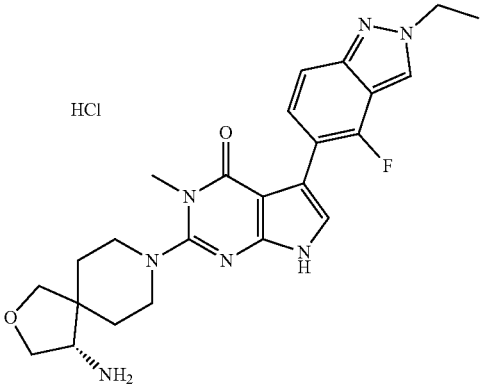 [SMILES: CCn1cc2c(F)c(-c3c[nH]c4nc(N5CCC6(CC5)COC[C@H]6N)n(C)c(=O)c34)ccc2n1 ; Cl] | 2-[(4S)-4-amino-2-oxa-8-azaspiro[4.5]decan-8-yl]-5-(2-ethyl-4-fluoro-2H-indazol-5-yl)-3-methyl-3H,4H,7H-pyrrolo[2,3-d]pyrimidin-4-one hydrochloride | $^1$H NMR (500 MHz, DMSO-$d_6$) δ: 11.76 (br s, 1H), 8.52 (s, 1H), 7.72 (br s, 3H), 7.56 (dd, J = 8.9, 7.3 Hz, 1H), 7.38 (dd, J = 8.8, 0.9 Hz, 1H), 7.07 (s, 1H), 4.47 (q, J = 7.3 Hz, 2H), 4.09 (dd, J = 10.2, 5.9 Hz, 1H), 3.86-3.69 (m, 3H), 3.55 (dd, J = 6.0, 3.4 Hz, 1H), 3.41-3.31 (m, 2H), 3.33 (s, 3H), 2.93 (t, J = 11.6 Hz, 1H), 2.82 (t, J = 11.7 Hz, 1H), 1.86 (m, 2H), 1.68 (t, J = 13.9 Hz, 2H), 1.52 (t, J = 7.3 Hz, 3H). | 466 | prepred starting from 5-bromo-4-fluoro-1H-indazole |
| 182 | 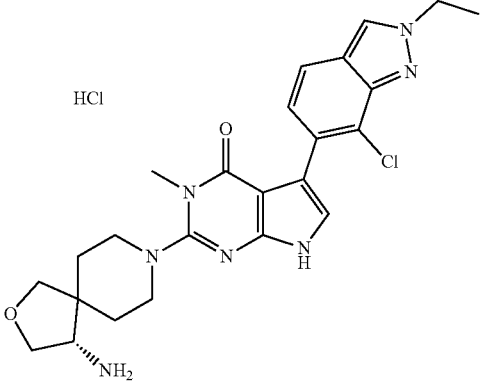 [SMILES: CCn1cc2ccc(-c3c[nH]c4nc(N5CCC6(CC5)COC[C@H]6N)n(C)c(=O)c34)c(Cl)c2n1 ; Cl] | 2-[(4S)-4-amino-2-oxa-8-azaspiro[4.5]decan-8-yl]-5-(7-chloro-2-ethyl-2H-indazol-6-yl)-3-methyl-3H,4H,7H-pyrrolo[2,3-d]pyrimidin-4-one hydrochloride | $^1$H NMR (500 MHz, DMSO-$d_6$) δ: 11.78 (d, J = 2.4 Hz, 1H), 8.47 (s, 1H), 8.41 (d, J = 5.5 Hz, 3H), 7.57 (d, J = 8.6 Hz, 1H), 7.10 (d, J = 8.5 Hz, 1H), 7.03 (d, J = 2.4 Hz, 1H), 4.49 (q, J = 7.3 Hz, 2H), 4.09 (dd, J = 10.3, 6.0 Hz, 1H), 3.86-3.75 (m, 3H), 3.60-3.52 (m, 4H), 3.40-3.36 (m, 1H), 3.34-3.27 (m, 1H), 2.93 (t, J = 11.8 Hz, 1H), 2.81 (t, J = 11.8 Hz, 1H), 1.95-1.82 (m, 2H), 1.75-1.64 (m, 2H), 1.52 (t, J = 7.3 Hz, 3H). | 482 | Using 4-bromo-3-chloro-2-fluoro-benzaldehyde as starting material |
| 183 | 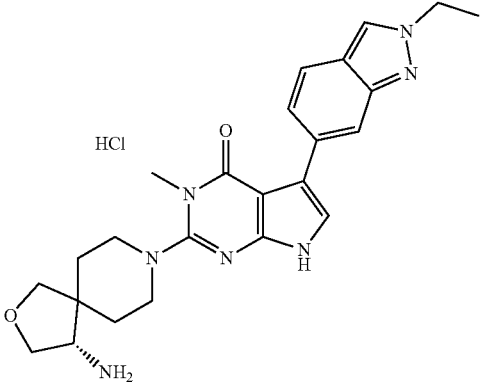 [SMILES: CCn1cc2ccc(-c3c[nH]c4nc(N5CCC6(CC5)COC[C@H]6N)n(C)c(=O)c34)cc2n1 ; Cl] | 2-[(4S)-4-amino-2-oxa-8-azaspiro[4.5]decan-8-yl]-5-(2-ethyl-2H-indazol-6-yl)-3-methyl-3H,4H,7H-pyrrolo[2,3-d]pyrimidin-4-one hydrochloride | $^1$H NMR (500 MHz, DMSO-$d_6$) δ: 11.76 (d, J = 2.6 Hz, 1H), 8.50-8.38 (m, 4H), 8.33 (s, 1H), 7.61 (dd, J = 8.8, 0.9 Hz, 1H), 7.52 (dd, J = 8.7, 1.5 Hz, 1H), 7.31 (d, J = 2.5 Hz, 1H), 4.44 (q, J = 7.3 Hz, 2H), 4.09 (dd, J = 10.3, 6.0 Hz, 1H), 3.86-3.76 (m, 3H), 3.55 (m, 1H), 3.48 (s, 3H), 3.43-3.37 (m, 1H), 3.36-3.30 (m, 1H), 2.93 (t, J = 11.8 Hz, 1H), 2.81 (t, J = 11.8 Hz, 1H), 1.85-1.65 (m, 2H), 1.50-1.25 (m, 2H), 1.52 (t, J = 7.3 Hz, 3H). | 448 | Prepared using 6-bromo-1H-indazole |

TABLE 16-continued

| Example | Structure | Name | NMR Data | MS: [M + H]+ m/z | Comment |
|---|---|---|---|---|---|
| 184 | 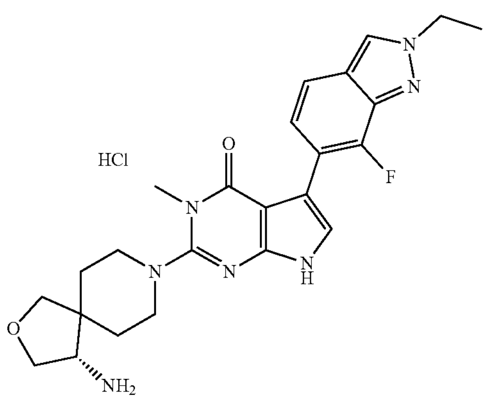 [SMILES: CCn1cc2ccc(-c3c[nH]c4nc(N5CCC6(CC5)COC[C@H]6N)n(C)c(=O)c34)c(F)c2n1 ; Cl] | 2-[(4S)-4-amino-2-oxa-8-azaspiro[4.5]decan-8-yl]-5-(2-ethyl-7-fluoro-2H-indazol-6-yl)-3-methyl-3H,4H,7H-pyrrolo[2,3-d]pyrimidin-4-one hydrochloride | ¹H NMR (500 MHz, Methanol-d₄) δ: 8.36 (d, J = 2.8 Hz, 1H), 7.49 (s, 1H), 7.48 (d, J = 2.3 Hz, 1H), 7.16 (d, J = 1.6 Hz, 1H), 4.54 (q, J = 7.3 Hz, 2H), 4.20 (dd, J = 10.7, 5.5 Hz, 1H), 3.96 (d, J = 9.2 Hz, 1H), 3.89 (d, J = 9.2 Hz, 1H), 3.85 (dd, J = 10.7, 2.6 Hz, 1H), 3.66-3.61 (m, 1H), 3.57 (s, 3H), 3.52-3.42 (m, 2H), 3.10-3.01 (m, 1H), 3.01-2.93 (m, 1H), 2.03-1.94 (m, 2H), 1.89-1.76 (m, 2H), 1.63 (t, J = 7.3 Hz, 3H). The 4 exchangeable protons of the salt were not observed. | 466 | Using 4-bromo-2,3-difluoro-benzaldehyde as starting material |
| 185 | 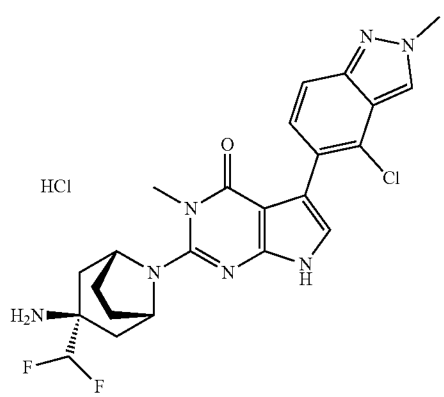 | 2-[(endo)-3-amino-3-(difluoromethyl)-8-azabicyclo[3.2.1]octan-8-yl]-5-(4-chloro-2-methyl-2H-indazol-5-yl)-3-methyl-3H,4H,7H-pyrrolo[2,3-d]pyrimidin-4-one hydrochloride | ¹H NMR (500 MHz, DMSO-d₆) δ: 12.56 (s, 1H), 8.16 (s, 1H), 7.33 (br s, 2H), 7.03 (d, J = 8.7 Hz, 2H), 6.89 (t, J = 6.9 Hz, 1H), 6.69 (td, J = 7.3, 1.1 Hz, 1H), 4.68 (d, J = 6.3 Hz, 2H), 3.96-3.83 (m, 2H), 3.19 (dq, J = 7.2, 3.6 Hz, 1H), 2.81 (t, J = 6.4 Hz, 2H), 2.33 (m, 2H), 2.22-1.90 (m, 6H), 1.67 (m, 2H). | 488 | Using N-[(endo)-3-(difluoromethyl)-8-azabicyclo[3.2.1]octan-3-yl]-2-methyl-propane-2-sulfinamide as the required amine |
| 186 | 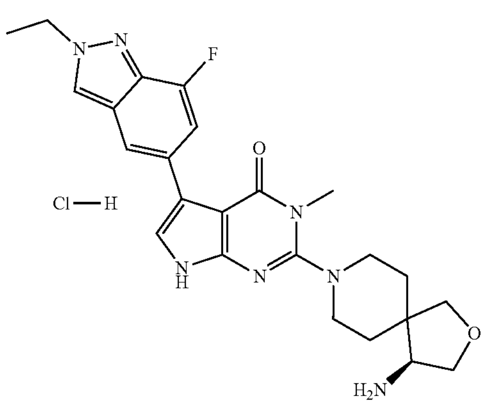 | 2-[(4S)-4-amino-2-oxa-8-azaspiro[4.5]decan-8-yl]-5-(2-ethyl-7-fluoro-2H-indazol-5-yl)-3-methyl-3H,4H,7H-pyrrolo[2,3-d]pyrimidin-4-one hydrochloride | ¹H NMR (500 MHz, DMSO-d₆) δ: 12.56 (s, 1H), 8.16 (s, 1H), 7.33 (br s, 2H), 7.03 (d, J = 8.7 Hz, 2H), 6.89 (t, J = 6.9 Hz, 1H), 6.69 (td, J = 7.3, 1.1 Hz, 1H), 4.68 (d, J = 6.3 Hz, 2H), 3.96-3.83 (m, 2H), 3.19 (dq, J = 7.2, 3.6 Hz, 1H), 2.81 (t, J = 6.4 Hz, 2H), 2.33 (m, 2H), 2.22-1.90 (m, 6H), 1.67 (m, 2H). | 466 | Using from 5-bromo-2,3-difluoro-benzaldehyde as starting material. |

The compounds shown in Table 17 were prepared using methods similar to those described in Method 1-9. The compounds could be isolated directly, by trituration/precipitation from solution, or were purified (e.g. using mass-directed preparative HPLC, chromatography, crystallization). In some cases, the compound was isolated as the hydrochloride salt; by treating a solution of the final compound (e.g. in MeOH) with excess HCl (2N HCl in Et$_2$O) and then evaporating to dryness.

TABLE 17

| Example | Structure | Name | NMR Data | MS: [M + H]+ m/z | Comment |
|---|---|---|---|---|---|
| 187 | 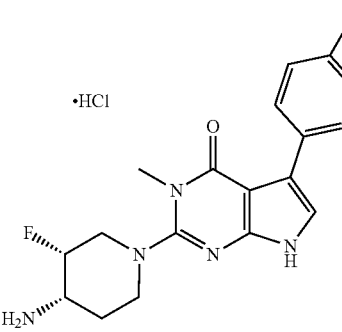 | 2-[(3R,4S)-4-amino-3-fluoropiperidin-1-yl]-5-(7-chloro-1,3-benzothiazol-6-yl)-3-methyl-3H,4H,7H-pyrrolo[2,3-d]pyrimidin-4-one hydrochloride | $^1$H NMR (400 MHz, DMSO-d$_6$) δ: 11.92 (1H, d), 9.46 (1H, s), 8.38 (3H, d), 8.04 (1H, d), 7.65 (1H, d), 7.14 (1H, d), 5.07 (1H, d), 3.86-3.76 (1H, m), 3.67-3.50 (2H, m), 3.42 (3H, s), 3.27-3.13 (1H, m), 3.00-2.89 (1H, m), 2.13-2.04 (1H, m), 1.98-1.90 (1H, m). | 433 | Method 9 |
| 188 | 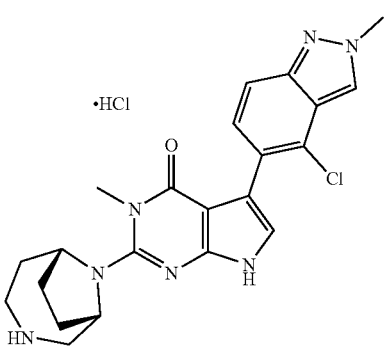 [SMILES: Cn1cc2c(Cl)c(-c3c[nH]c4nc(N5[C@H]6CCNC[C@@H]5CC6)n(C)c(=O)c34)ccc2n1 ; Cl] | 5-(4-chloro-2-methyl-2H-indazol-5-yl)-2-[(1S,6R)-3,9-diazabicyclo[4.2.1]nonan-9-yl]-3-methyl-3H,4H,7H-pyrrolo[2,3-d]pyrimidin-4-one hydrochloride | $^1$H NMR (400 MHz, DMSO-d$_6$) δ: 11.72 (1H, d), 9.63-9.52 (1H, m), 9.13-9.01 (1H, m), 8.41 (1H, s), 7.50 (1H, dd), 7.32 (1H, d), 7.02 (1H, d), 4.85-4.77 (1H, m), 4.32-4.24 (1H, m), 4.20 (3H, s), 3.50 (3H, s), 3.44-3.28 (2H, m), 3.20-3.04 (2H, m), 2.38-2.27 (2H, m), 2.11-1.95 (2H, m), 1.80-1.71 (2H, m). | 438 | Method 9 |
| 189 | 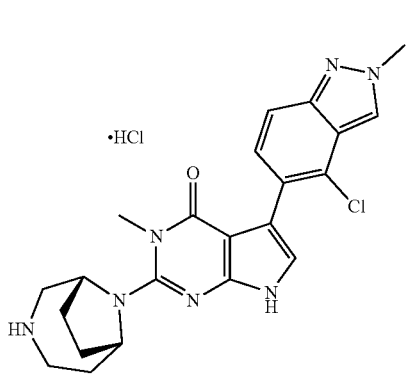 [SMILES: Cn1cc2c(Cl)c(-c3c[nH]c4nc(N5[C@@H]6CCNC[C@H]5CC6)n(C)c(=O)c34)ccc2n1 ; Cl] | 5-(4-chloro-2-methyl-2H-indazol-5-yl)-2-[(1R,6S)-3,9-diazabicyclo[4.2.1]nonan-9-yl]-3-methyl-3H,4H,7H-pyrrolo[2,3-d]pyrimidin-4-one hydrochloride | $^1$H NMR (400 MHz, DMSO-d$_6$) δ: 11.72 (1H, d), 9.64-9.53 (1H, m), 9.15-9.01 (1H, m), 8.41 (1H, s), 7.50 (1H, dd), 7.32 (1H, d), 7.02 (1H, d), 4.85-4.77 (1H, m), 4.33-4.25 (1H, m), 4.20 (3H, s), 3.50 (3H, s), 3.45-3.24 (2H, m), 3.20-3.04 (2H, m), 2.38-2.27 (2H, m), 2.10-1.91 (2H, m), 1.83-1.67 (2H, m). | 438 | Method 9 |

The compounds shown in Table 18 were prepared using methods similar to those described in Method 1-9. The compounds could be isolated directly, by trituration/precipitation from solution, or were purified (e.g. using mass-directed preparative HPLC, chromatography, crystallization). In some cases, the compound was isolated as the hydrochloride salt; by treating a solution of the final compound (e.g. in MeOH) with excess HCl (2N HCl in Et$_2$O) and then evaporating to dryness.

TABLE 18

| Example | Structure | Name | NMR Data | MS: [M + H]+ m/z | Comment |
|---|---|---|---|---|---|
| 190 | 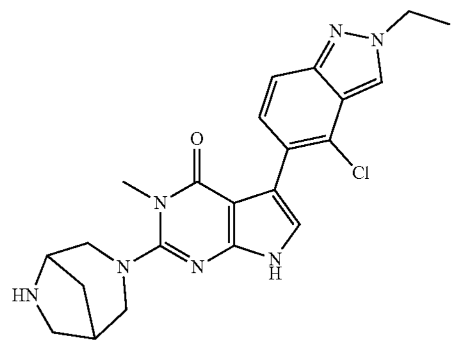 [SMILES: CCn1cc2c(Cl)c(-c3c[nH]c4nc(N5CC6CNC(C6)C5)n(C)c(=O)c34)ccc2n1] | 5-(4-chloro-2-ethyl-2H-indazol-5-yl)-2-{3,6-diazabicyclo[3.2.1]octan-3-yl}-3-methyl-3H,4H,7H-pyrrolo[2,3-d]pyrimidin-4-one hydrochloride | $^1$H NMR (400 MHz, DMSO-d$_6$) δ: 11.84 (1H, d), 9.66 (1H, s), 9.07 (1H, s), 8.46 (1H, s), 7.52 (1H, dd), 7.32 (1H, d), 7.07 (1H, d), 4.49 (2H, q), 4.15-4.07 (1H, m), 3.55-3.48 (5H, m), 3.43-3.35 (1H, m), 3.34-3.16 (2H, m), 2.81 (1H, d), 2.75-2.69 (1H, m), 1.98 (1H, d), 1.94-1.86 (1H, m), 1.53 (3H, t). | 438 | Method 2, then purified by reverse phase chromatography on C18 silica gel. Further purification by chiral SFC (45% isocratic MeOH + 0.1% DEA, AD column, gave the title compound as the faster eluting enantiomer |
| 191 | 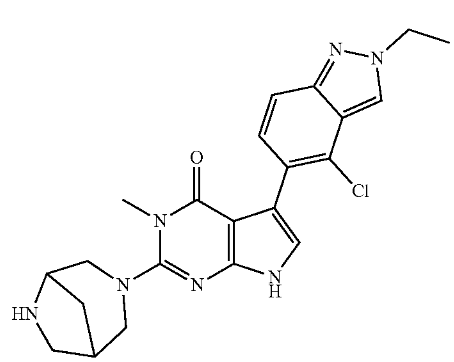 [SMILES: CCn1cc2c(Cl)c(-c3c[nH]c4nc(N5CC6CNC(C6)C5)n(C)c(=O)c34)ccc2n1] | 5-(4-chloro-2-ethyl-2H-indazol-5-yl)-2-{3,6-diazabicyclo[3.2.1]octan-3-yl}-3-methyl-3H,4H,7H-pyrrolo[2,3-d]pyrimidin-4-one hydrochloride | $^1$H NMR (400 MHz, DMSO-d$_6$) δ: 11.85 (1H, d), 9.84 (1H, s), 9.16 (1H, s), 8.46 (1H, s), 7.51 (1H, d), 7.32 (1H, d), 7.06 (1H, d), 4.49 (2H, q), 4.14-4.07 (1H, m), 3.56-3.45 (5H, m), 3.45-3.34 (1H, m), 3.34-3.17 (2H, m), 2.81 (1H, d), 2.75-2.69 (1H, m), 1.97 (1H, d), 1.95-1.85 (1H, m), 1.53 (3H, t). | 438. | Method 2, then purified by reverse phase chromatography on C18 silica gel. Further purification by chiral SFC (45% isocratic MeOH + 0.1% DEA, AD column, gave the title compound as the slower eluting enantiomer |
| 192 | 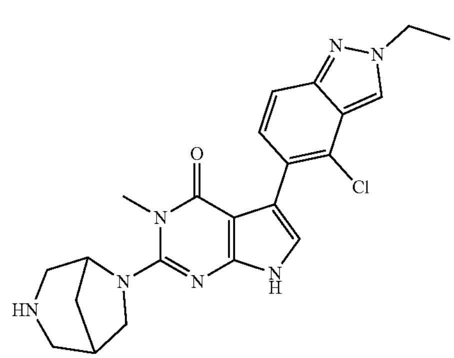 [SMILES: CCn1cc2c(Cl)c(-c3c[nH]c4nc(N5CC6CNCC5C6)n(C)c(=O)c34)ccc2n1] | 5-(4-chloro-2-ethyl-2H-indazol-5-yl)-2-{3,6-diazabicyclo[3.2.1]octan-6-yl}-3-methyl-3H,4H,7H-pyrrolo[2,3-d]pyrimidin-4-one hydrochloride | $^1$H NMR (400 MHz, DMSO-d$_6$) δ: 11.52 (1H, d), 9.79 (1H, d), 8.76 (1H, br. s), 8.45 (1H, s), 7.51 (1H, dd), 7.32 (1H, d), 6.95 (1H, d), 4.65-4.58 (1H, m), 4.49 (2H, q), 3.75-3.60 (3H, m), 3.47 (3H, s), 3.17 (2H, s), 3.11-3.01 (1H, m), 2.72 (1H, s), 1.95 (1H, d), 1.93-1.84 (1H, m), 1.53 (3H, t). | 438 | Method 2, then purified by reverse phase chromatography on C18 silica gel. Further purification by chiral SFC (40% isocratic EtOH + 0.1% DEA, AD column provided the title compound as the faster eluting enantiomer. |

TABLE 18-continued

| Example | Structure | Name | NMR Data | MS: [M + H]+ m/z | Comment |
|---|---|---|---|---|---|
| 193 | 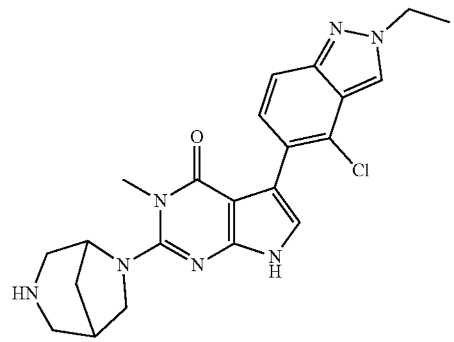 [SMILES: CCn1cc2c(Cl)c(-c3c[nH]c4nc(N5CC6CNCC5C6)n(C)c(=O)c34)ccc2n1] | 5-(4-chloro-2-ethyl-2H-indazol-5-yl)-2-{3,6-diazabicyclo[3.2.1]octan-6-yl}-3-methyl-3H,4H,7H-pyrrolo[2,3-d]pyrimidin-4-one hydrochloride | $^1$H NMR (400 MHz, DMSO-$d_6$) δ: 11.51 (1H, d), 9.57 (1H, d), 8.67 (1H, br. s), 8.45 (1H, s), 7.51 (1H, dd), 7.32 (1H, d), 6.96 (1H, d), 4.63-4.59 (2H, m), 4.52-4.46 (2H, m), 3.79-3.66 (2H, m), 3.61 (1H, d), 3.47 (3H, s), 3.21-3.18 (1H, m), 3.13-2.99 (1H, m), 2.74 (1H, s), 2.00-1.85 (2H, m), 1.54 (3H, t). | 438 | Method 2, then purified by reverse phase chromatography on C18 silica gel. Further purification by chiral SFC (40% isocratic EtOH + 0.1% DEA, AD column provided the title compound as the slower eluting enantiomer. |
| 194 | 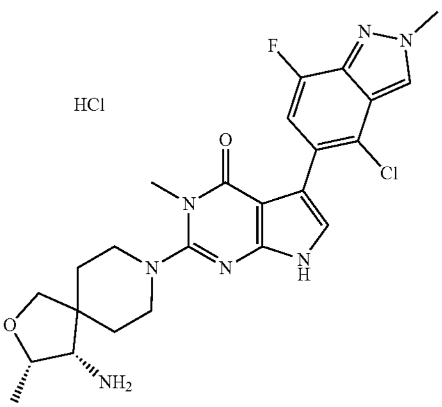 [SMILES: C[C@@H]1OCC2(CCN(c3nc4[nH]cc(-c5cc(F)c6nn(C)cc6c5Cl)c4c(=O)n3C)CC2)[C@@H]1N ; Cl] | 2-[(3S,4S)-4-amino-3-methyl-2-oxa-8-azaspiro[4.5]decan-8-yl]-5-(4-chloro-7-fluoro-2-methyl-2H-indazol-5-yl)-3-methyl-3H,4H,7H-pyrrolo[2,3-d]pyrimidin-4-one hydrochloride | $^1$H NMR (400 MHz, DMSO-$d_6$) δ: 11.82 (1H, d), 8.56 (1H, d), 8.09 (3H, br. s), 7.18 (1H, d), 7.12 (1H, d), 4.26-4.20 (4H, m), 3.88 (1H, d), 3.67 (1H, d), 3.53-3.42 (4H, m), 3.42-3.28 (2H, m), 2.94-2.77 (2H, m), 2.00-1.87 (2H, m), 1.78 (1H, d), 1.66 (1H, d), 1.25 (3H, d) | 500 | Method 2, purified by reverse phase chromatography on C18 silica gel. |
| 195 | 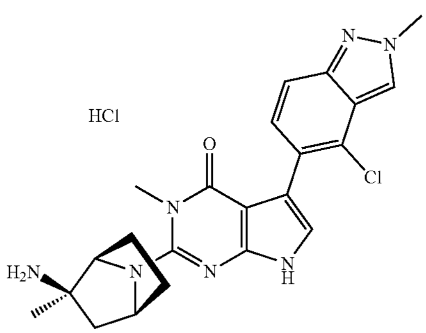 | 2-[(endo)-2-amino-2-methyl-7-azabicyclo[2.2.1]heptan-7-yl]-5-(4-chloro-2-methyl-2H-indazol-5-yl)-3-methyl-3H,4H,7H-pyrrolo[2,3-d]pyrimidin-4-one hydrochloride | $^1$H NMR (400 MHz, DMSO-$d_6$) δ: 11.73 (1H, d), 8.51 (3H, s), 8.40 (1H, s), 7.49 (1H, dd), 7.32 (1H, d), 6.99 (1H, d), 4.34 (1H, t), 4.20 (3H, s), 4.14 (1H, d), 3.43 (3H, s), 2.21-2.10 (1H, m), 2.05-1.98 (1H, m), 1.96-1.87 (1H, m), 1.86-1.76 (1H, m), 1.75-1.69 (1H, m), 1.65 (1H, d), 1.46 (3H, s). | 438 | Method 9, purified by prep SFC (50% MeOH + 0.1% diethylamine) |
| 196 | 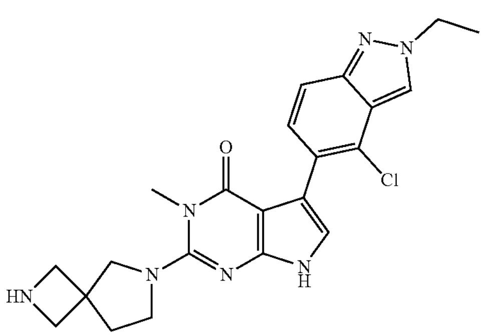 [SMILES: CCn1cc2c(Cl)c(-c3c[nH]c4nc(N5CCC6(CNC6)C5)n(C)c(=O)c34)ccc2n1] | rac-5-(4-chloro-2-ethyl-2H-indazol-5-yl)-2-{2,6-diazaspiro[3.4]octan-6-yl}-3-methyl-3H,4H,7H-pyrrolo[2,3-d]pyrimidin-4-one | $^1$H NMR (400 MHz, Me-d3-OD) δ: 8.31 (1H, s), 7.52 (1H, dd), 7.45 (1H, d), 6.95 (1H, s), 4.53 (2H, q), 3.80 (2H, d), 3.76-3.61 (4H, m), 3.58 (2H, t), 3.50 (3H, s), 2.24 (2H, t), 1.64 (3H, t). | 438 | Method 2. Purified by reverse phase chromatography on C18 silica gel and then by preparative HPLC. |

TABLE 18-continued

| Example | Structure | Name | NMR Data | MS: [M + H]+ m/z | Comment |
|---|---|---|---|---|---|
| 197 | HCl structure | 2-[(1R,2S,3S,5S)-3-amino-2-fluoro-8-azabicyclo[3.2.1]octan-8-yl]-5-(4-chloro-2-ethyl-2H-indazol-5-yl)-3-methyl-3H,4H,7H-pyrrolo[2,3-d]pyrimidin-4-one hydrochloride | ¹H NMR (400 MHz, DMSO-d₆) δ: 11.68 (1H, d), 8.45 (1H, s), 8.30 (3H, br s), 7.51 (1H, dd), 7.31 (1H, d), 6.98 (1H, d), 4.96-4.79 (1H, m), 4.60-4.53 (1H, m), 4.49 (2H, q), 4.31-4.23 (1H, m), 3.76-3.60 (1H, m), 3.46 (3H, s), 2.29-2.19 (1H, m), 2.14-2.00 (2H, m), 1.97-1.88 (1H, m), 1.78-1.67 (2H, m), 1.53 (3H, t). | 470 | Method 2 followed by Method 5. Purified by reverse phase chromatography on C18 silica gel and then by preparative HPLC. |
| 198 | HCl structure | 2-[(1R,2R,4S)-2-amino-7-azabicyclo[2.2.1]heptan-7-yl]-5-[8-chloro-2-(dimethylamino)quinolin-7-yl]-3-methyl-3H,4H,7H-pyrrolo[2,3-d]pyrimidin-4-one hydrochloride | ¹H NMR (400 MHz, DMSO-d₆) δ: 8.22 (1H, d), 7.72 (1H, d), 7.40 (1H, d), 7.27 (1H, d), 7.11 (1H, s), 4.37 (1H, s), 4.28 (1H, s), 3.83-3.67 (1H, m), 3.40 (3H, s), 3.31 (7H, s), 1.95 (2H, s), 1.88-1.71 (1H, m), 1.65 (1H, d), 1.36 (1H, dd). | 464 | Method 9 |
| 199 | HCl structure | 2-[(1R,2R,4S)-2-amino-7-azabicyclo[2.2.1]heptan-7-yl]-5-[8-chloro-2-(methylamino)quinolin-7-yl]-3-methyl-3H,4H,7H-pyrrolo[2,3-d]pyrimidin-4-one hydrochloride | ¹H NMR (400 MHz, DMSO-d₆) δ: 11.86 (1H, s), 8.53-8.32 (1H, m), 7.84 (1H, s), 7.53 (1H, d), 7.23 (2H, s), 4.39 (1H, s), 4.30 (1H, s), 3.41 (3H, s), 3.13 (3H, s), 1.96 (2H, s), 1.83 (1H, d), 1.66 (1H, s), 1.38 (1H, dd). | 450 | Method 9 |

SHP2 Biochemical Assay

SHP2 activity was monitored by measuring the conversion of the surrogate substrate 6,8-difluoromethylumbelliferyl phosphate (DiFMUP) to the fluorescent product, 6,8-difluoromethylumbelliferone (DiFMU).

SHP2 was pre-incubated with test compounds and the activating peptide pIRS1 (H₂N-LN(pY)IDLDLV-(PEG)₈-LST(pY)ASINFQK-amide) for 30 min, prior to addition of the 6,8-difluoromethylumbelliferyl phosphate (DiFMUP), (Thermo Fisher D6567). Final assay concentrations were 10 pM SHP2, 0.25 g M pIRS1 peptide, 50 μM DiFMUP, 25 mM Bis-Tris propane, pH 7.0, 150 mM NaCl, 0.05% (v/v) Tween-20, 0.5 mM TCEP and 5% (v/v) DMSO. Rates of reaction were then measured over 30 min by monitoring fluorescence on a BMG Pherastar reader at excitation 360 nm/emission 450 nm. IC$_{50}$ values were calculated in singlicate from the normalized dose-response plots using four parameter logistic curve fit. The Experiment for each compound was carried out in one time or multiple times, and the IC$_{50}$ values were shown as a single value (for a compound measured in a single experiment) or an average value (for a compound measured in multiple experiments).

Results were shown in the Table 19 and 20.

Cellular pERK Inhibition Assay

Method A:

pERK levels were determined using the In-Cell Western assay. HCC827 cells (ATCC, Manassas, USA) were seeded into 384-well plates at a density of 1×10⁴ cells/well in RPMI1640 medium supplemented with 10% FBS and incubated 24h. Compounds were diluted first in DMSO and then into serum-free medium, before being added to cells in quadruplicate to give a final concentration of 0.2% DMSO. Plates were incubated at 37° C. for the indicated time in a humidified atmosphere of 5% CO₂ in air.

Following compound treatment, cells were fixed with formalin neutral buffer solution for 20 minutes at room temperature. Plates were washed three times with 0.1% Triton-X in PBS and cells were blocked for 1 hour with Odyssey blocking buffer (LI-COR, #927-40000). After shaking out blocking buffer, cells were incubated with phospho-p44/42 ERK antibody (Cell Signalling Technology, #4370, 1:200) diluted in Odyssey blocking buffer at 4° C. overnight. Plates were washed again and cells were incubated for 1 hour with Goat anti-Rabbit IR Dye 8000 W (LI-COR, #926-32211, 1:800) diluted in Odyssey blocking buffer. After washing and removing wash solution completely using a centrifuge machine, cells were scanned on the Odyssey (LI-COR), following the manufacturer's instructions. The average signal from blank wells (no cells added) was subtracted from the signals from each sample well. Levels of pERK were then expressed as percent of control, using DMSO treated samples as control. The relative $IC_{50}$ values were calculated in quadruplicate from the normalized dose-response plots using four parameter logistic curve fit. The Experiment for each compound was carried out in one time or multiple times, and the $IC_{50}$ values were shown as a single value (for a compound measured in a single experiment) or an average value (for a compound measured in multiple experiments).

Results were shown in the Table 19 and 20.

Method B:

HCC827 cells (ATCC, Manassas, USA) were seeded into 96-well plates at a density of $1 \times 10^5$ cells/well in RPMI medium supplemented with 10% FBS and incubated 24h. Compounds were diluted first in DMSO and then into serum-free medium, before being added to cells in triplicate to give a final concentration of 0.1% DMSO. Plates were incubated at 37° C. for the indicated time in a humidified atmosphere of 5% $CO_2$ in air.

Following compound treatment, medium was removed and cells were lysed by adding 50 μL of lysis buffer (Cell Signalling Technology, Beverly, USA) to each well. Plates were then incubated at room temperature for 25 minutes with shaking. pERK levels were measured in lysates using the PathScan(Registered Trademark) phospho-p44/42 MAPK (Thr202/Tyr204) sandwich ELISA (Cell Signalling Technology, Beverly, USA) as per kit instructions. Briefly, 50 μL of cell lysate was added to 50 μL of ELISA sample diluent in a 96-well ELISA plate and incubated overnight at 4° C. Following washing, 100 μL of detection antibody was added per well and the plates incubated for 1 hour at 37° C. Plates were washed again and incubated at 37° C. for 30 minutes with 100 μl of HRP-linked secondary antibody per well. After final washing, 100 μL per well of TMB substrate was added and plates incubated at 37° C. to develop colour. Colour development was stopped by the addition of 100 μL per well of stop solution. Plates were read at 450 nm on a SpectraMax Gemini reader (Molecular Devices, Uckfield, UK).

The average signal from blank wells (no cells added) was subtracted from the signals from each sample well. Levels of pERK were then expressed as "percent of control", using DMSO treated samples as control. Dose response curves were generated using GraphPad Prism Version 6 (GraphPad Software, La Jolla, USA) and fitted using the four parameter logistic curve fit.

Results were shown in the Table 19 and 20.

TABLE 19

| Example | SHP2 (IC50, -M) | pERK (IC50, -M) Method A | pERK (IC50, -M) Method B |
|---|---|---|---|
| 1 | 0.014 | 0.14 | |
| 2 | 0.014 | 0.13 | |
| 3 | 0.015 | 0.21 | |
| 4 | 0.0075 | 0.12 | |
| 5 | 0.0075 | 0.16 | |
| 6 | 0.0065 | 0.58 | |
| 7 | 0.0090 | 0.17 | |
| 8 | 0.011 | 0.095 | |
| 9 | 0.094 | 1.2 | |
| 10 | 0.0085 | 0.17 | |
| 11 | 0.0063 | 0.053 | |
| 12 | 0.011 | 0.12 | |
| 13 | 0.019 | 0.34 | |
| 14 | 0.024 | 0.31 | |
| 15 | 0.017 | 0.50 | |
| 16 | 0.011 | 0.11 | |
| 17 | 0.043 | 0.80 | |
| 18 | 0.23 | | |
| 19 | 0.35 | | |
| 20 | 0.76 | | |
| 21 | 0.011 | 0.32 | |
| 22 | 0.014 | 2.2 | |
| 23 | 0.12 | 4.1 | |
| 24 | 0.018 | 0.14 | |
| 25 | 0.035 | 0.43 | |
| 26 | 0.011 | 0.088 | |
| 27 | 0.0070 | 0.046 | |
| 28 | 0.019 | 0.68 | |
| 29 | 0.22 | 2.4 | |
| 30 | 0.0097 | 0.22 | |
| 31 | 0.040 | 1.0 | |
| 32 | 0.017 | 0.92 | |
| 33 | 0.047 | 0.48 | |
| 34 | 0.16 | 2.3 | |
| 35 | 0.038 | 1.0 | |
| 36 | 0.0055 | 0.35 | |
| 37 | 0.012 | 0.97 | |
| 38 | 0.074 | 1.4 | |
| 39 | 0.066 | 0.70 | |
| 40 | 0.096 | 4.5 | |
| 41 | 0.057 | 1.8 | |
| 42 | 0.078 | | |
| 43 | 0.035 | 0.72 | |
| 44 | 0.055 | 1.5 | |
| 45 | 0.11 | 1.5 | |
| 46 | 0.033 | 0.42 | |
| 47 | 0.032 | 0.38 | |
| 48 | 0.085 | 1.0 | |
| 49 | 0.0045 | 0.021 | |
| 50 | 0.25 | 4.7 | |
| 51 | 0.012 | 0.061 | |
| 52 | 0.18 | 1.9 | |
| 53 | 0.33 | 3.1 | |
| 54 | 0.11 | 1.8 | |
| 55 | 0.074 | 1.1 | |
| 56 | 0.073 | 1.1 | |
| 57 | 0.12 | 2.9 | |
| 58 | 0.099 | >10 | |
| 59 | 0.0055 | 0.048 | |
| 60 | 0.082 | 3.8 | |
| 61 | 0.098 | 1.8 | |
| 62 | 0.023 | 0.36 | |
| 63 | 0.11 | 4.3 | |
| 64 | 0.042 | 1.5 | |
| 65 | 0.033 | 0.43 | |
| 66 | 0.0082 | 0.082 | |
| 67 | 0.34 | 3.4 | |
| 68 | 0.041 | 0.67 | |
| 69 | 0.12 | 3.0 | |
| 70 | 0.029 | 0.19 | |
| 71 | 0.26 | 5.0 | |
| 72 | 0.099 | 1.9 | |
| 73 | 0.87 | >10 | |
| 74 | 0.17 | 5.4 | |
| 75 | 0.028 | 2.1 | |
| 76 | 0.031 | 0.18 | |
| 77 | 0.040 | 1.9 | |
| 78 | 0.0060 | 0.13 | |
| 79 | 0.0055 | 0.16 | |

TABLE 19-continued

| Example | SHP2 (IC50, -M) | pERK (IC50, -M) Method A | pERK (IC50, -M) Method B |
|---|---|---|---|
| 80 | 0.011 | 0.27 | |
| 81 | 0.014 | 0.78 | |
| 82 | 0.014 | 0.91 | |
| 83 | 0.011 | 0.19 | |
| 84 | 0.018 | 0.55 | |
| 85 | 0.013 | 0.64 | |
| 86 | 0.059 | 5.2 | |
| 87 | 0.068 | 0.58 | |
| 88 | 0.052 | 4.5 | |
| 89 | 0.014 | 0.54 | |
| 90 | 0.012 | 0.74 | |
| 91 | 0.012 | 0.34 | |
| 92 | 0.0033 | 0.032 | |
| 93 | 0.0020 | 0.021 | |
| 94 | 0.0050 | 0.072 | |
| 95 | 0.0025 | 0.068 | |
| 96 | 0.0028 | 0.030 | |
| 97 | 0.0077 | 0.082 | |
| 98 | 0.010 | 0.19 | |
| 99 | 0.0045 | 0.057 | |
| 100 | 0.0060 | 0.095 | |
| 101 | 0.0015 | 0.046 | |
| 102 | 0.0090 | 0.088 | |
| 103 | 0.0020 | 0.026 | |
| 104 | 0.0027 | 0.084 | |
| 105 | 0.0050 | 0.16 | |
| 106 | 0.0050 | 0.10 | |
| 107 | 0.0070 | 0.27 | |
| 108 | 0.0040 | 0.090 | |
| 109 | 0.0065 | 0.12 | |
| 110 | 0.014 | 1.7 | |
| 111 | 0.026 | 0.41 | |
| 112 | 0.013 | 0.26 | |
| 113 | 0.0045 | 0.078 | |
| 114 | 0.0055 | 0.073 | |
| 115 | 0.046 | 0.49 | |
| 116 | 0.0090 | 0.10 | |
| 117 | 0.025 | 0.64 | |
| 118 | 0.049 | 1.1 | |
| 119 | 0.017 | 0.29 | |
| 120 | 0.029 | 0.55 | |
| 121 | 0.016 | 0.21 | |
| 122 | 0.0080 | 0.14 | |
| 123 | 0.018 | 0.17 | |
| 124 | 0.019 | 0.43 | |
| 125 | 0.017 | 0.26 | |
| 126 | 0.013 | 0.084 | |
| 127 | 0.0037 | 0.063 | |
| 128 | 0.011 | 0.16 | |
| 129 | 0.069 | 0.98 | |
| 130 | 0.063 | 0.80 | |
| 131 | 0.028 | 0.46 | |
| 132 | 0.015 | 0.25 | |
| 133 | 0.0067 | 0.046 | |
| 134 | 0.0040 | 0.083 | |
| 135 | 0.048 | 0.95 | |
| 136 | 0.03 | | 2.7 |
| 137 | 0.059 | | 45% at 3.0 μM |
| 138 | 0.019 | | 1.6 |
| 139 | 0.02 | | 0.097 |
| 140 | 0.017 | | 0.48 |
| 141 | 0.043 | | 64% at 10 μM |
| 142 | 0.017 | | 0.11 |
| 143 | 0.022 | | 0.081 |
| 144 | 0.019 | | 0.21 |
| 145 | 0.15 | | |
| 146 | 0.057 | | 3.8 |
| 147 | 0.012 | | 0.034 |
| 148 | 0.024 | | 0.025 |
| 149 | 0.29 | | |
| 150 | 0.012 | | 0.013 |
| 151 | 0.023 | | 0.52 |
| 152 | 0.029 | | 0.66 |
| 153 | 0.026 | | 0.52 |
| 154 | 0.021 | | 0.92 |
| 155 | 0.0040 | | |
| 156 | 0.25 | | |
| 157 | 0.0037 | 0.022 | |
| 158 | 0.25 | 2.0 | |
| 159 | 0.0035 | 0.15 | |

TABLE 20

| Example | SHP2 (IC50, μM) | pERK (IC50, μM) Method A | pERK (IC50, μM) Method B |
|---|---|---|---|
| 160 | 0.0085 | 0.23 | |
| 161 | 0.012 | 0.26 | |
| 162 | 0.042 | 0.81 | |
| 163 | 0.002 | 0.012 | |
| 164 | 0.17 | 6.3 | |
| 165 | 0.084 | 1.4 | |
| 166 | 0.053 | | |
| 167 | 0.013 | | |
| 168 | 0.007 | | |
| 169 | 0.0033 | 0.073 | |
| 170 | 0.003 | 0.016 | |
| 171 | 0.0026 | 0.02 | |
| 172 | 0.0015 | 0.016 | |
| 173 | 0.0025 | 0.14 | |
| 174 | 0.003 | 0.021 | |
| 175 | 0.012 | 0.22 | |
| 176 | 0.077 | 0.66 | |
| 177 | 0.095 | 1.4 | |
| 178 | 0.005 | 0.071 | |
| 179 | 0.15 | 2.1 | |
| 180 | 0.034 | | 0.85 |
| 181 | 0.023 | | 0.21 |
| 182 | 0.036 | | 2.2 |
| 183 | 0.14 | | |
| 184 | 0.07 | | 1.1 |
| 185 | 0.18 | | |
| 186 | 0.036 | | |
| 187 | 0.051 | | 0.8 |
| 188 | 0.041 | | 0.56 |
| 189 | 0.019 | | 0.23 |
| 190 | 0.045 | | 3.3 |
| 191 | 0.092 | | 60% at 10 uM |
| 192 | 0.067 | | 0.99 |
| 193 | 0.26 | | |
| 194 | 0.016 | | 0.043 |
| 195 | 0.016 | | 0.045 |
| 196 | 0.032 | | |
| 197 | 0.012 | | 0.032 |
| 198 | 0.013 | | 0.066 |
| 199 | 0.014 | | 0.11 |

The invention claimed is:
1. A compound of formula (I):

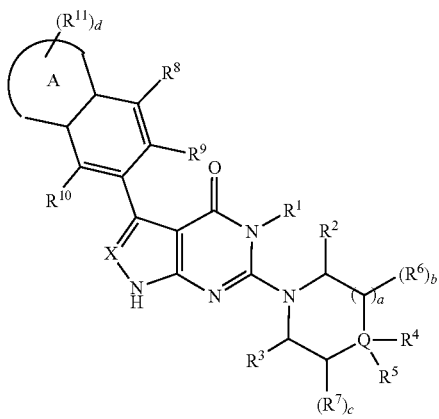

or a tautomer or a solvate or a pharmaceutically acceptable salt thereof, wherein:
X is CH or N;
$R^1$ is —$CH_3$;
$R^2$ and $R^3$ are independently selected from hydrogen and $C_{1-4}$alkyl;
Q is C or N;
wherein when Q is C then either:
  (i) $R^4$ is amino, amino$C_{1-4}$alkyl or mono$C_{1-4}$alkylamino;
    $R^5$ is hydrogen, $C_{1-4}$alkyl, halogen, hydroxy$C_{1-4}$alkyl, $C_{1-4}$alkoxy, halo$C_{1-4}$alkyl or $C_{1-4}$alkoxy$C_{1-4}$alkyl;
    or
  (ii) $R^4$ and $R^5$ together with Q form a four- to six-membered ring that can optionally contain 1 to 3 heteroatoms or groups independently selected from N, O, S, NH, C(O) and $S(O)_m$, and said ring formed by $R^4$ and $R^5$ can be unsubstituted or substituted with 1 to 4 groups independently selected from amino, halogen, halo$C_{1-4}$alkyl, hydroxyl, methoxy, methylamino, and $C_{1-4}$alkyl, and m is selected from 1 and 2; and
wherein when Q is N then:
  $R^4$ is absent; and
  $R^5$ is hydrogen;
$R^6$ and $R^7$ are independently selected from halogen, $C_{1-4}$alkyl, hydroxy$C_{1-4}$alkyl and hydroxyl provided that when Q is N then $R^6$ or $R^7$ are not halogen or hydroxyl;
Or, any two groups selected from $R^2$, $R^3$, $R^6$ and $R^7$ together form a one- to three-membered bridge group selected from $C_{1-3}$alkylene, $C_{2-3}$alkenylene, methylene-$NR^q$-methylene and methylene-O-methylene, wherein the bridge group is optionally substituted by a group selected from $C_{1-4}$alkyl, hydroxyl and halogen and $R^q$ is selected from hydrogen and $C_{1-4}$alkyl;
Or, $R^4$ and $R^7$ form a four- to six-membered ring containing a N atom;
Or, $R^5$ and $R^7$ form a three- to six-membered ring;
Or, $R^6$ and $R^7$ form a direct bond;
a is selected from 0, 1 and 2;
b is selected from 0, 1 and 2;
c is selected from 0, 1 and 2;
Or, Q is C, c is 2, $R^4$ is hydrogen and the two $R^7$ join to form a 4 to 6 membered nitrogen containing ring;
Ring A is either:
  (i) a five-membered nitrogen-containing heterocyclic ring wherein the heterocyclic ring optionally contains one or two additional heteroatoms selected from N, O and S, or
  (ii) a six-membered aromatic nitrogen-containing heterocyclic ring, wherein the heterocyclic ring optionally contains one or two additional heteroatoms selected from N, O and S; or
  (iii) a six-membered non-aromatic nitrogen-containing heterocyclic ring, wherein the heterocyclic ring optionally contains one or two additional heteroatoms selected from N and S;
$R^8$ is selected from hydrogen, $C_{1-4}$alkyl, halo$C_{1-4}$alkyl and halogen;
$R^9$ is selected from hydrogen and halogen;
$R^{10}$ is selected from halo$C_{1-4}$alkyl, $C_{1-4}$alkyl, halogen, hydrogen and $C_{1-4}$alkoxy;
$R^{11}$ are independently selected from halogen, cyano, cyano$C_{1-4}$alkyl, hydroxyl, oxo (=O), $C_{1-4}$alkyl optionally substituted with five- or six-membered heterocyclic group containing 1 or 2 heteroatoms selected from O, N, and S, halo$C_{1-4}$alkyl, $C_{1-4}$alkoxy, hydroxyl$C_{1-4}$alkyl, $C_{1-4}$alkoxy$C_{1-4}$alkyl, $C_{1-4}$alkylsulfone, amino, mono$C_{1-4}$alkylamino, di$C_{1-4}$alkylamino, amino$C_{1-4}$alkyl, —$C_{1-4}$alkylene-C(=O)$NH_{(2-q)}(C_{1-6}alkyl)_q$), —$C_{1-4}$alkylene-NHC(=O)$C_{1-6}$alkyl, sulfonamide, sulfonamide$C_{1-4}$alkyl, 3 to 6 membered cycloalkyl, $C_{1-4}$alkyl substituted with 3 to 6 membered cycloalkyl, five- or six-membered unsaturated heterocyclic group containing 1, 2, 3 or 4 heteroatoms selected from O, N, and S, and optionally substituted four- to six-membered saturated heterocyclic group containing 1 or 2 heteroatoms selected from O, N, and S where the optional substituent is selected from $C_{1-4}$alkyl;
q is selected from 0, 1 and 2; and
d is selected from 0, 1 and 2.

2. A compound according to claim 1 or a tautomer or a solvate or a pharmaceutically acceptable salt thereof, wherein Ring A is a five-membered or six-membered nitrogen-containing heteroaromatic ring wherein the ring optionally contains one or two additional heteroatoms selected from N, O and S.

3. A compound according to claim 1, or a tautomer or a solvate or a pharmaceutically acceptable salt thereof, wherein any two groups selected from $R^2$, $R^3$, $R^6$ and $R^7$ together form a one- to three-membered bridge group selected from $C_{1-3}$alkylene, $C_{2-3}$alkenylene, methylene-$NR^q$-methylene and methylene-O-methylene, wherein the bridge group is optionally substituted by a group selected from $C_{1-4}$alkyl, hydroxyl and halogen and $R^q$ is selected from hydrogen and $C_{1-4}$alkyl.

4. A compound according to claim 1, or a tautomer or a solvate or a pharmaceutically acceptable salt thereof, wherein Q is C.

5. A compound according to claim 1, or a tautomer or a solvate or a pharmaceutically acceptable salt thereof, wherein
$R^4$ is amino, amino$C_{1-4}$alkyl or mono$C_{1-4}$alkylamino; and
$R^5$ is hydrogen, $C_{1-4}$alkyl, halogen, hydroxy$C_{1-4}$alkyl, $C_{1-4}$alkoxy, halo$C_{1-4}$alkyl or $C_{1-4}$alkoxy$C_{1-4}$alkyl.

6. A compound according to claim 1, or a tautomer or a solvate or a pharmaceutically acceptable salt thereof, wherein R⁴ and R⁵ together with Q form a four- to six-membered ring that can optionally contain 1 to 3 heteroatoms or groups independently selected from N, O, S, NH, C(O) and S(O)$_m$, and said ring formed by R⁴ and R⁵ can be unsubstituted or substituted with 1 to 4 groups independently selected from amino, halogen, halo$_{C1-4}$alkyl, hydroxyl, methoxy, methylamino, and C$_{1-4}$alkyl, and m is selected from 1 and 2.

7. A compound according to claim 1, or a tautomer or a solvate or a pharmaceutically acceptable salt thereof, wherein Q is N.

8. A compound according to claim 1, or a tautomer or a solvate or a pharmaceutically acceptable salt thereof, wherein X is CH.

9. A compound according to claim 1, or a tautomer or a solvate or a pharmaceutically acceptable salt thereof, wherein X is N.

10. A compound according to claim 1, or a tautomer or a solvate or a pharmaceutically acceptable salt thereof, wherein the compound is selected from:
- 2-(3,8-diazabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one,
- 2-(4-(aminomethyl)-4-methylpiperidin-1-yl)-5-(4-chloro-2-ethyl-2H-indazol-5-yl)-3-methyl-3,7-dihydro-4H-pyrrolo[2,3-d]pyrimidin-4-one,
- 2-(4-amino-4-methylpiperidin-1-yl)-5-(4-chloro-2-ethyl-2H-indazol-5-yl)-3-methyl-3,7-dihydro-4H-pyrrolo[2,3-d]pyrimidin-4-one,
- 2-(exo-3-amino-8-azabicyclo[3.2.1]octan-8-yl)-5-(4-chloro-2-ethyl-2H-indazol-5-yl)-3-methyl-3,7-dihydro-4H-pyrrolo[2,3-d]pyrimidin-4-one,
- 2-(endo-3-amino-8-azabicyclo[3.2.1]octan-8-yl)-5-(4-chloro-2-ethyl-2H-indazol-5-yl)-3-methyl-3,7-dihydro-4H-pyrrolo[2,3-d]pyrimidin-4-one,
- 2-(endo-3-amino-8-azabicyclo[3.2.1]octan-8-yl)-5-(7-chloro-2-ethylbenzo[d]thiazol-6-yl)-3-methyl-3,7-dihydro-4H-pyrrolo[2,3-d]pyrimidin-4-one,
- 2-(endo-3-amino-8-azabicyclo[3.2.1]octan-8-yl)-5-(7-chloro-2-methylbenzo[d]thiazol-6-yl)-3-methyl-3,7-dihydro-4H-pyrrolo[2,3-d]pyrimidin-4-one,
- 2-(endo-3-amino-8-azabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one,
- 2-(endo-3-amino-8-azabicyclo[3.2.1]octan-8-yl)-5-(2-(tert-butyl)-4-chloro-2H-indazol-5-yl)-3-methyl-3,7-dihydro-4H-pyrrolo[2,3-d]pyrimidin-4-one,
- 2-(exo-3-amino-8-azabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one,
- (R)-2-(1-amino-8-azaspiro[4.5]decan-8-yl)-5-(4-chloro-2-ethyl-2H-indazol-5-yl)-3-methyl-3,7-dihydro-4H-pyrrolo[2,3-d]pyrimidin-4-one,
- (S)-2-(4-amino-2-oxa-8-azaspiro[4.5]decan-8-yl)-5-(4-chloro-2-ethyl-2H-indazol-5-yl)-3-methyl-3,7-dihydro-4H-pyrrolo[2,3-d]pyrimidin-4-one,
- 5-(4-chloro-2-ethyl-2H-indazol-5-yl)-3-methyl-2-(endo-3-(methylamino)-8-azabicyclo[3.2.1]octan-8-yl)-3,7-dihydro-4H-pyrrolo[2,3-d]pyrimidin-4-one,
- 5-(4-chloro-2-methyl-2H-indazol-5-yl)-3-methyl-2-(endo-3-(methylamino)-8-azabicyclo[3.2.1]octan-8-yl)-3,7-dihydro-4H-pyrrolo[2,3-d]pyrimidin-4-one,
- 2-(endo-3-amino-3-methyl-8-azabicyclo[3.2.1]octan-8-yl)-5-(4-chloro-2-ethyl-2H-indazol-5-yl)-3-methyl-3,7-dihydro-4H-pyrrolo[2,3-d]pyrimidin-4-one,
- 2-(endo-3-amino-3-methyl-8-azabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one,
- 2-(3-oxa-7,9-diazabicyclo[3.3.1]nonan-7-yl)-5-(4-chloro-2-methyl-2H-indazol-5-yl)-3-methyl-3,7-dihydro-4H-pyrrolo[2,3-d]pyrimidin-4-one,
- (R)-5-(4-chloro-2-methyl-2H-indazol-5-yl)-3-methyl-2-(3-methylpiperazin-1-yl)-3,7-dihydro-4H-pyrrolo[2,3-d]pyrimidin-4-one,
- (S)-5-(4-chloro-2-methyl-2H-indazol-5-yl)-2-(3-(hydroxymethyl)piperazin-1-yl)-3-methyl-3,7-dihydro-4H-pyrrolo[2,3-d]pyrimidin-4-one,
- (R)-5-(4-chloro-2-methyl-2H-indazol-5-yl)-2-(3-(2-hydroxyethyl)piperazin-1-yl)-3-methyl-3,7-dihydro-4H-pyrrolo[2,3-d]pyrimidin-4-one,
- 2-((1S,4S)-2,5-diazabicyclo[2.2.1]heptan-2-yl)-5-(4-chloro-2-methyl-2H-indazol-5-yl)-3-methyl-3,7-dihydro-4H-pyrrolo[2,3-d]pyrimidin-4-one,
- 2-(7-amino-3-oxa-9-azabicyclo[3.3.1]nonan-9-yl)-5-(4-chloro-2-methyl-2H-indazol-5-yl)-3-methyl-3,7-dihydro-4H-pyrrolo[2,3-d]pyrimidin-4-one,
- 2-((1R,4R)-2,5-diazabicyclo[2.2.1]heptan-2-yl)-5-(4-chloro-2-methyl-2H-indazol-5-yl)-3-methyl-3,7-dihydro-4H-pyrrolo[2,3-d]pyrimidin-4-one,
- 2-(exo-8-amino-3-azabicyclo[3.2.1]octan-3-yl)-5-(4-chloro-2-methyl-2H-indazol-5-yl)-3-methyl-3,7-dihydro-4H-pyrrolo[2,3-d]pyrimidin-4-one,
- 2-(endo-8-amino-3-azabicyclo[3.2.1]octan-3-yl)-5-(4-chloro-2-methyl-2H-indazol-5-yl)-3-methyl-3,7-dihydro-4H-pyrrolo[2,3-d]pyrimidin-4-one,
- rac-2-((1S,2R,3R,5R)-3-amino-2-fluoro-8-azabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one,
- 2-(3,9-diazabicyclo[3.3.1]nonan-9-yl)-5-(4-chloro-2-methyl-2H-indazol-5-yl)-3-methyl-3,7-dihydro-4H-pyrrolo[2,3-d]pyrimidin-4-one,
- 2-(3,8-diazabicyclo[3.2.1]octan-3-yl)-5-(4-chloro-2-methyl-2H-indazol-5-yl)-3-methyl-3,7-dihydro-4H-pyrrolo[2,3-d]pyrimidin-4-one,
- 2-(3,6-diazabicyclo[3.1.1]heptan-6-yl)-5-(4-chloro-2-methyl-2H-indazol-5-yl)-3-methyl-3,7-dihydro-4H-pyrrolo[2,3-d]pyrimidin-4-one,
- 2-(3,9-diazabicyclo[3.3.1]nonan-3-yl)-5-(4-chloro-2-methyl-2H-indazol-5-yl)-3-methyl-3,7-dihydro-4H-pyrrolo[2,3-d]pyrimidin-4-one,
- 2-(3,6-diazabicyclo[3.1.1]heptan-3-yl)-5-(4-chloro-2-methyl-2H-indazol-5-yl)-3-methyl-3,7-dihydro-4H-pyrrolo[2,3-d]pyrimidin-4-one,
- 2-(2,5-diazabicyclo[2.2.2]octan-2-yl)-5-(4-chloro-2-methyl-2H-indazol-5-yl)-3-methyl-3,7-dihydro-4H-pyrrolo[2,3-d]pyrimidin-4-one,
- 2-(exo-6-amino-3-azabicyclo[3.1.1]heptan-3-yl)-5-(4-chloro-2-methyl-2H-indazol-5-yl)-3-methyl-3,7-dihydro-4H-pyrrolo[2,3-d]pyrimidin-4-one,
- 2-(endo-6-amino-3-azabicyclo[3.1.1]heptan-3-yl)-5-(4-chloro-2-methyl-2H-indazol-5-yl)-3-methyl-3,7-dihydro-4H-pyrrolo[2,3-d]pyrimidin-4-one,
- 2-(5-amino-2-azabicyclo[2.2.1]heptan-2-yl)-5-(4-chloro-2-methyl-2H-indazol-5-yl)-3-methyl-3,7-dihydro-4H-pyrrolo[2,3-d]pyrimidin-4-one,
- 2-(exo-3-amino-9-azabicyclo[3.3.1]nonan-9-yl)-5-(4-chloro-2-methyl-2H-indazol-5-yl)-3-methyl-3,7-dihydro-4H-pyrrolo[2,3-d]pyrimidin-4-one,
- 2-(endo-3-amino-9-azabicyclo[3.3.1]nonan-9-yl)-5-(4-chloro-2-methyl-2H-indazol-5-yl)-3-methyl-3,7-dihydro-4H-pyrrolo[2,3-d]pyrimidin-4-one, 5-(4-chloro-2-methyl-2H-indazol-5-yl)-3-methyl-2-(1,8-diazaspiro[4.5]decan-8-yl)-3,7-dihydro-4H-pyrrolo[2,3-d]pyrimidin-4-one, 5-(4-chloro-2-methyl-2H-indazol-5-yl)-3-methyl-2-(piperazin-1-yl)-3,7-dihydro-4H-pyrrolo[2,3-d]pyrimidin-4-one, 2-(3,7-diazabicyclo[4.2.0]octan-3-yl)-5-(4-chloro-2-methyl-2H-indazol-5-yl)-3-methyl-3,7-dihydro-4H-pyrrolo[2,3-d]pyrimidin-4-one, 5-(4-chloro-2-methyl-2H-indazol-5-yl)-3-methyl-2-(1,9-diazaspiro[5.5]undecan-9-yl)-3,7-dihydro-4H-pyrrolo[2,3-d]pyrimidin-4-one, 5-(4-chloro-2-methyl-2H-indazol-5-yl)-3-methyl-2-(1,7-diazaspiro[3.5]nonan-7-yl)-3,7-dihydro-4H-pyrrolo[2,3-d]pyrimidin-4-one, (S)-2-(3-aminopyrrolidin-1-yl)-5-(4-chloro-2-methyl-2H-indazol-5-yl)-3-methyl-3,7-dihydro-4H-pyrrolo[2,3-d]pyrimidin-4-one, (R)-2-(3-aminopyrrolidin-1-yl)-5-(4-chloro-2-methyl-2H-indazol-5-yl)-3-methyl-3,7-dihydro-4H-pyrrolo[2,3-d]pyrimidin-4-one, (S)-5-(4-chloro-2-methyl-2H-indazol-5-yl)-3-methyl-2-(3-methylpiperazin-1-yl)-3,7-dihydro-4H-pyrrolo[2,3-d]pyrimidin-4-one, 2-((1S,2S,4R)-2-amino-7-azabicyclo[2.2.1]heptan-7-yl)-5-(4-chloro-2-methyl-2H-indazol-5-yl)-3-methyl-3,7-dihydro-4H-pyrrolo[2,3-d]pyrimidin-4-one, (R)-5-(4-chloro-2-methyl-2H-indazol-5-yl)-3-methyl-2-(2-methylpiperazin-1-yl)-3,7-dihydro-4H-pyrrolo[2,3-d]pyrimidin-4-one, (S)-5-(4-chloro-2-methyl-2H-indazol-5-yl)-3-methyl-2-(2-methylpiperazin-1-yl)-3,7-dihydro-4H-pyrrolo[2,3-d]pyrimidin-4-one, 2-((1R,2R,4S)-2-amino-7-azabicyclo[2.2.1]heptan-7-yl)-5-(4-chloro-2-methyl-2H-indazol-5-yl)-3-methyl-3,7-dihydro-4H-pyrrolo[2,3-d]pyrimidin-4-one, 2-((3R,4S)-3-amino-4-fluoropyrrolidin-1-yl)-5-(4-chloro-2-methyl-2H-indazol-5-yl)-3-methyl-3,7-dihydro-4H-pyrrolo[2,3-d]pyrimidin-4-one, rac-2-((1S,4S,7S)-7-amino-2-azabicyclo[2.2.1]heptan-2-yl)-5-(4-chloro-2-methyl-2H-indazol-5-yl)-3-methyl-3,7-dihydro-4H-pyrrolo[2,3-d]pyrimidin-4-one, 2-((3S,4S)-3-amino-4-fluoropyrrolidin-1-yl)-5-(4-chloro-2-methyl-2H-indazol-5-yl)-3-methyl-3,7-dihydro-4H-pyrrolo[2,3-d]pyrimidin-4-one, 2-(4-amino-3,3-difluoropyrrolidin-1-yl)-5-(4-chloro-2-methyl-2H-indazol-5-yl)-3-methyl-3,7-dihydro-4H-pyrrolo[2,3-d]pyrimidin-4-one, (S)-2-(3-amino-3-methylpyrrolidin-1-yl)-5-(4-chloro-2-methyl-2H-indazol-5-yl)-3-methyl-3,7-dihydro-4H-pyrrolo[2,3-d]pyrimidin-4-one, (R)-2-(3-amino-3-methylpyrrolidin-1-yl)-5-(4-chloro-2-methyl-2H-indazol-5-yl)-3-methyl-3,7-dihydro-4H-pyrrolo[2,3-d]pyrimidin-4-one, 2-((3R,4R)-3-amino-4-methylpyrrolidin-1-yl)-5-(4-chloro-2-methyl-2H-indazol-5-yl)-3-methyl-3,7-dihydro-4H-pyrrolo[2,3-d]pyrimidin-4-one, 2-((3R,4S)-3-amino-4-methylpyrrolidin-1-yl)-5-(4-chloro-2-methyl-2H-indazol-5-yl)-3-methyl-3,7-dihydro-4H-pyrrolo[2,3-d]pyrimidin-4-one, 2-(3-amino-3-(hydroxymethyl)pyrrolidin-1-yl)-5-(4-chloro-2-methyl-2H-indazol-5-yl)-3-methyl-3,7-dihydro-4H-pyrrolo[2,3-d]pyrimidin-4-one, 2-((3S,4S)-4-amino-3-methyl-2-oxa-8-azaspiro[4.5]decan-8-yl)-5-(4-chloro-2-methyl-2H-indazol-5-yl)-3-methyl-3,7-dihydro-4H-pyrrolo[2,3-d]pyrimidin-4-one, (R)-2-(3-(aminomethyl)pyrrolidin-1-yl)-5-(4-chloro-2-methyl-2H-indazol-5-yl)-3-methyl-3,7-dihydro-4H-pyrrolo[2,3-d]pyrimidin-4-one, 2-(1-amino-3-azabicyclo[3.1.0]hexan-3-yl)-5-(4-chloro-2-methyl-2H-indazol-5-yl)-3-methyl-3,7-dihydro-4H-pyrrolo[2,3-d]pyrimidin-4-one, 2-(6-amino-3-azabicyclo[3.1.0]hexan-3-yl)-5-(4-chloro-2-methyl-2H-indazol-5-yl)-3-methyl-3,7-dihydro-4H-pyrrolo[2,3-d]pyrimidin-4-one, (S)-2-(3-(aminomethyl)pyrrolidin-1-yl)-5-(4-chloro-2-methyl-2H-indazol-5-yl)-3-methyl-3,7-dihydro-4H-pyrrolo[2,3-d]pyrimidin-4-one, 2-(4-(aminomethyl)-4-methoxypiperidin-1-yl)-5-(4-chloro-2-methyl-2H-indazol-5-yl)-3-methyl-3,7-dihydro-4H-pyrrolo[2,3-d]pyrimidin-4-one, 2-(4-(aminomethyl)-4-fluoropiperidin-1-yl)-5-(4-chloro-2-methyl-2H-indazol-5-yl)-3-methyl-3,7-dihydro-4H-pyrrolo[2,3-d]pyrimidin-4-one, 2-(3,9-diazabicyclo[3.3.1]nonan-9-yl)-5-(4-chloro-2-ethyl-2H-indazol-5-yl)-3-methyl-3,7-dihydro-4H-pyrrolo[2,3-d]pyrimidin-4-one, 2-(endo-3-amino-8-azabicyclo[3.2.1]octan-8-yl)-3-methyl-5-(2-methyl-2H-indazol-5-yl)-3,7-dihydro-4H-pyrrolo[2,3-d]pyrimidin-4-one, 2-(endo-3-amino-8-azabicyclo[3.2.1]octan-8-yl)-5-(7-chloro-2-methylbenzo[d]oxazol-6-yl)-3-methyl-3,7-dihydro-4H-pyrrolo[2,3-d]pyrimidin-4-one, 2-(endo-3-amino-8-azabicyclo[3.2.1]octan-8-yl)-5-(7-chloro-2-ethylbenzo[d]oxazol-6-yl)-3-methyl-3,7-dihydro-4H-pyrrolo[2,3-d]pyrimidin-4-one, 2-(endo-3-amino-8-azabicyclo[3.2.1]octan-8-yl)-5-(4-fluoro-2-methyl-2H-indazol-5-yl)-3-methyl-3,7-dihydro-4H-pyrrolo[2,3-d]pyrimidin-4-one, 2-(endo-3-amino-8-azabicyclo[3.2.1]octan-8-yl)-5-(6,7-difluoro-1-methyl-1H-benzo[d][1,2,3]triazol-5-yl)-3-methyl-3,7-dihydro-4H-pyrrolo[2,3-d]pyrimidin-4-one, 2-(endo-3-amino-8-azabicyclo[3.2.1]octan-8-yl)-5-(6-fluoro-2-methyl-2H-indazol-5-yl)-3-methyl-3,7-dihydro-4H-pyrrolo[2,3-d]pyrimidin-4-one, 2-(endo-3-amino-8-azabicyclo[3.2.1]octan-8-yl)-5-(4-methoxy-2-methyl-2H-indazol-5-yl)-3-methyl-3,7-dihydro-4H-pyrrolo[2,3-d]pyrimidin-4-one, 2-(endo-3-amino-8-azabicyclo[3.2.1]octan-8-yl)-5-(7-chloro-1-methyl-1H-benzo[d][1,2,3]triazol-6-yl)-3-methyl-3,7-dihydro-4H-pyrrolo[2,3-d]pyrimidin-4-one, 2-(endo-3-amino-8-azabicyclo[3.2.1]octan-8-yl)-5-(4-chloro-2-(2-hydroxy-2-methylpropyl)-2H-indazol-5-yl)-3-methyl-3,7-dihydro-4H-pyrrolo[2,3-d]pyrimidin-4-one, 2-(endo-3-amino-8-azabicyclo[3.2.1]octan-8-yl)-5-(4-chloro-2,7-dimethyl-2H-indazol-5-yl)-3-methyl-3,7-dihydro-4H-pyrrolo[2,3-d]pyrimidin-4-one, 2-(endo-3-amino-8-azabicyclo[3.2.1]octan-8-yl)-5-(1H-indazol-5-yl)-3-methyl-3,7-dihydro-4H-pyrrolo[2,3-d]pyrimidin-4-one, 2-(endo-3-amino-8-azabicyclo[3.2.1]octan-8-yl)-5-(3,4-dichloro-2-methyl-2H-indazol-5-yl)-3-methyl-3,7-dihydro-4H-pyrrolo[2,3-d]pyrimidin-4-one, 2-(endo-3-amino-3-methyl-8-azabicyclo[3.2.1]octan-8-yl)-5-(3,4-dichloro-2-methyl-2H-indazol-5-yl)-3-methyl-3,7-dihydro-4H-pyrrolo[2,3-d]pyrimidin-4-one, 2-(3-oxa-7,9-diazabicyclo[3.3.1]nonan-7-yl)-5-(3,4-dichloro-2-methyl-2H-indazol-5-yl)-3-methyl-3,7-dihydro-4H-pyrrolo[2,3-d]pyrimidin-4-one, 2-(3-oxa-7,9-diazabicyclo[3.3.1]nonan-7-yl)-5-(7-chloro-2-methylbenzo[d]thiazol-6-yl)-3-methyl-3,7-dihydro-4H-pyrrolo[2,3-d]pyrimidin-4-one, 2-(5-(2-(3,9-diazabicyclo[3.3.1]nonan-9-yl)-3-methyl-4-oxo-4,7-dihydro-3H-pyrrolo[2,3-d]pyrimidin-5-yl)-3,4-dichloro-2H-indazol-2-yl)-N,N-dimethylacetamide, 3-(5-(2-(3,9-diazabicyclo[3.3.1]nonan-9-yl)-3-methyl-4-oxo-4,7-dihydro-3H-pyrrolo[2,3-d]pyrimidin-5-yl)-3,4-dichloro-2H-indazol-2-yl)-N,N-dimethylpropanamide, 2-(6-(2-(3,9-diazabicyclo[3.3.1]nonan-9-yl)-3-methyl-4-oxo-4,7-dihydro-3H-pyrrolo[2,3-d]pyrimidin-5-yl)-7-chlorobenzo[d]thiazol-2-yl)-N,N-dimethylacetamide, 2-(3-oxa-7,9-diazabicyclo[3.3.1]nonan-9-yl)-5-(4-chloro-2-methyl-2H-indazol-5-yl)-3-methyl-3,7-dihydro-4H-pyrrolo[2,3-d]pyrimidin-4-one, 2-(5-(2-(3,8-diazabicyclo[3.2.1]octan-8-yl)-3-methyl-4-oxo-4,7-dihydro-3H-pyrrolo[2,3-d]pyrimidin-5-yl)-4-chloro-2H-indazol-2-yl)-N,N-dimethylacetamide, 2-(3,8-diazabicyclo[3.2.1]octan-8-yl)-5-(4-chloro-2-methyl-2H-benzo[d][1,2,3]triazol-5-yl)-3-methyl-3,7-dihydro-4H-pyrrolo[2,3-d]pyrimidin-4-one, 3-(5-(2-(3,8-diazabicyclo[3.2.1]octan-8-yl)-3-methyl-4-oxo-4,7-dihydro-3H-pyrrolo[2,3-d]pyrimidin-5-yl)-4-chloro-2H-indazol-2-yl)-N,N-dimethylpropanamide, 3-(5-(2-(3,8-diazabicyclo[3.2.1]octan-8-yl)-3-methyl-4-oxo-4,7-dihydro-3H-pyrrolo[2,3-d]pyrimidin-5-yl)-3,4-dichloro-2H-indazol-2-yl)-N,N-dimethylpropanamide, 2-(3,8-diazabicyclo[3.2.1]octan-8-yl)-5-(7-chloro-2-methylbenzo[d]thiazol-6-yl)-3-methyl-3,7-dihydro-4H-pyrrolo[2,3-d]pyrimidin-4-one, 2-(3,8-diazabicyclo[3.2.1]octan-8-yl)-5-(4-chloro-2-ethyl-2H-indazol-5-yl)-3-methyl-3,7-dihydro-4H-pyrrolo[2,3-d]pyrimidin-4-one, 2-((1R,2R,4S)-2-amino-7-azabicyclo[2.2.1]heptan-7-yl)-5-(4-chloro-2-ethyl-2H-indazol-5-yl)-3-methyl-3,7-dihydro-4H-pyrrolo[2,3-d]pyrimidin-4-one, 2-((1R,2R,4S)-2-amino-7-azabicyclo[2.2.1]heptan-7-yl)-5-(3,4-dichloro-2-methyl-2H-indazol-5-yl)-3-methyl-3,7-dihydro-4H-pyrrolo[2,3-d]pyrimidin-4-one, 2-((1R,2R,4S)-2-amino-7-azabicyclo[2.2.1]heptan-7-yl)-5-(4-chloro-2,3-dimethyl-2H-indazol-5-yl)-3-methyl-3,7-dihydro-4H-pyrrolo[2,3-d]pyrimidin-4-one, 2-((1R,2R,4S)-2-amino-7-azabicyclo[2.2.1]heptan-7-yl)-5-(7-chloro-2-methylbenzo[d]thiazol-6-yl)-3-methyl-3,7-dihydro-4H-pyrrolo[2,3-d]pyrimidin-4-one, 2-((1R,2R,4S)-2-amino-7-azabicyclo[2.2.1]heptan-7-yl)-5-(3-chloro-4-fluoro-2-methyl-2H-indazol-5-yl)-3-methyl-3,7-dihydro-4H-pyrrolo[2,3-d]pyrimidin-4-one, 5-(4-chloro-2-methyl-2H-indazol-5-yl)-3-methyl-2-((1R,2R,4S)-2-(methylamino)-7-azabicyclo[2.2.1]heptan-7-yl)-3,7-dihydro-4H-pyrrolo[2,3-d]pyrimidin-4-one, 5-(4-chloro-2-ethyl-2H-indazol-5-yl)-3-methyl-2-((1R,2R,4S)-2-(methylamino)-7-azabicyclo[2.2.1]heptan-7-yl)-3,7-dihydro-4H-pyrrolo[2,3-d]pyrimidin-4-one, 2-(3,9-diazabicyclo[3.3.1]nonan-9-yl)-5-(3,4-dichloro-2-methyl-2H-indazol-5-yl)-3-methyl-3,7-dihydro-4H-pyrrolo[2,3-d]pyrimidin-4-one, 2-(3,9-diazabicyclo[3.3.1]nonan-9-yl)-5-(3-chloro-4-fluoro-2-methyl-2H-indazol-5-yl)-3-methyl-3,7-dihydro-4H-pyrrolo[2,3-d]pyrimidin-4-one, 2-((1R,2R,4S)-2-amino-7-azabicyclo[2.2.1]heptan-7-yl)-5-(7-chlorobenzo[d]thiazol-6-yl)-3-methyl-3,7-dihydro-4H-pyrrolo[2,3-d]pyrimidin-4-one, 2-((1R,2R,4S)-2-amino-7-azabicyclo[2.2.1]heptan-7-yl)-5-(4-chloro-2-ethyl-3-methoxy-2H-indazol-5-yl)-3-methyl-3,7-dihydro-4H-pyrrolo[2,3-d]pyrimidin-4-one, 2-((1R,2R,4S)-2-amino-7-azabicyclo[2.2.1]heptan-7-yl)-5-(3,4-dichloro-2-(fluoromethyl)-2H-indazol-5-yl)-3-methyl-3,7-dihydro-4H-pyrrolo[2,3-d]pyrimidin-4-one, 5-(3,4-dichloro-2-methyl-2H-indazol-5-yl)-3-methyl-2-((1R,2R,4S)-2-(methylamino)-7-azabicyclo[2.2.1]heptan-7-yl)-3,7-dihydro-4H-pyrrolo[2,3-d]pyrimidin-4-one, 5-(7-chlorobenzo[d]thiazol-6-yl)-3-methyl-2-((1R,2R,4S)-2-(methylamino)-7-azabicyclo[2.2.1]heptan-7-yl)-3,7-dihydro-4H-pyrrolo[2,3-d]pyrimidin-4-one, 5-(3-chloro-4-fluoro-2-methyl-2H-indazol-5-yl)-3-methyl-2-((1R,2R,4S)-2-(methylamino)-7-azabicyclo[2.2.1]heptan-7-yl)-3,7-dihydro-4H-pyrrolo[2,3-d]pyrimidin-4-one, 5-(7-chloro-2-methylbenzo[d]thiazol-6-yl)-3-methyl-2-((1R,2R,4S)-2-(methylamino)-7-azabicyclo[2.2.1]heptan-7-yl)-3,7-dihydro-4H-pyrrolo[2,3-d]pyrimidin-4-one, 2-(3,9-diazabicyclo[3.3.1]nonan-9-yl)-5-(7-chlorobenzo[d]thiazol-6-yl)-3-methyl-3,7-dihydro-4H-pyrrolo[2,3-d]pyrimidin-4-one, 2-((1R,2R,4S)-2-amino-7-azabicyclo[2.2.1]heptan-7-yl)-5-(4-chloro-3-(difluoromethyl)-2-ethyl-2H-indazol-5-yl)-3-methyl-3,7-dihydro-4H-pyrrolo[2,3-d]pyrimidin-4-one, 2-((1R,2R,4S)-2-amino-7-azabicyclo[2.2.1]heptan-7-yl)-5-(4-chloro-2-ethyl-3-(hydroxymethyl)-2H-indazol-5-yl)-3-methyl-3,7-dihydro-4H-pyrrolo[2,3-d]pyrimidin-4-one, 6-(3,9-diazabicyclo[3.3.1]nonan-9-yl)-3-(4-chloro-2-ethyl-2H-indazol-5-yl)-5-methyl-1,5-dihydro-4H-pyrazolo[3,4-d]pyrimidin-4-one, 6-((1R,2R,4S)-2-amino-7-azabicyclo[2.2.1]heptan-7-yl)-3-(4-chloro-2-ethyl-2H-indazol-5-yl)-5-methyl-1,5-dihydro-4H-pyrazolo[3,4-d]pyrimidin-4-one, 6-((1R,2R,4S)-2-amino-7-azabicyclo[2.2.1]heptan-7-yl)-3-(7-chloro-2-methylbenzo[d]thiazol-6-yl)-5-methyl-1,5-dihydro-4H-pyrazolo[3,4-d]pyrimidin-4-one, 6-((1R,2R,4S)-2-amino-7-azabicyclo[2.2.1]heptan-7-yl)-3-(3,4-dichloro-2-methyl-2H-indazol-5-yl)-5-methyl-1,5-dihydro-4H-pyrazolo[3,4-d]pyrimidin-4-one, 6-(endo-3-amino-3-methyl-8-azabicyclo[3.2.1]octan-8-yl)-3-(4-chloro-2-ethyl-2H-indazol-5-yl)-5-methyl-1,5-dihydro-4H-pyrazolo[3,4-d]pyrimidin-4-one, 6-(3,9-diazabicyclo[3.3.1]nonan-9-yl)-3-(3,4-dichloro-2-methyl-2H-indazol-5-yl)-5-methyl-1,5-dihydro-4H-pyrazolo[3,4-d]pyrimidin-4-one, 6-(3,9-diazabicyclo[3.3.1]nonan-9-yl)-3-(4-chloro-2-methyl-2H-indazol-5-yl)-5-methyl-1,5-dihydro-4H-pyrazolo[3,4-d]pyrimidin-4-one, 3-(4-chloro-2-ethyl-2H-indazol-5-yl)-5-methyl-6-((1R,2R,4S)-2-(methylamino)-7-azabicyclo[2.2.1]heptan-7-yl)-1,5-dihydro-4H-pyrazolo[3,4-d]pyrimidin-4-one, 3-(3,4-dichloro-2-methyl-2H-indazol-5-yl)-5-methyl-6-((1R,2R,4S)-2-(methylamino)-7-azabicyclo[2.2.1]heptan-7-yl)-1,5-dihydro-4H-pyrazolo[3,4-d]pyrimidin-4-one, 3-(4-chloro-2-methyl-2H-indazol-5-yl)-5-methyl-6-((1R,2R,4S)-2-(methylamino)-7-azabicyclo[2.2.1]heptan-7-yl)-1,5-dihydro-4H-pyrazolo[3,4-d]pyrimidin-4-one, 3-(3-chloro-4-fluoro-2-methyl-2H-indazol-5-yl)-5-methyl-6-((1R,2R,4S)-2-(methylamino)-7-azabicyclo[2.2.1]heptan-7-yl)-1,5-dihydro-4H-pyrazolo[3,4-d]pyrimidin-4-one, 6-(3,9-diazabicyclo[3.3.1]nonan-9-yl)-3-(7-chlorobenzo[d]thiazol-6-yl)-5-methyl-1,5-dihydro-4H-pyrazolo[3,4-d]pyrimidin-4-one, 3-(7-chlorobenzo[d]thiazol-6-yl)-5-methyl-6-((1R,2R,4S)-2-(methylamino)-7-azabicyclo[2.2.1]heptan-7-yl)-1,5-dihydro-4H-pyrazolo[3,4-d]pyrimidin-4-one, 3-(7-chloro-2-methylbenzo[d]thiazol-6-yl)-5-methyl-6-((1R,2R,4S)-2-(methylamino)-7-azabicyclo[2.2.1]heptan-7-yl)-1,5-dihydro-4H-pyrazolo[3,4-d]pyrimidin-4-one, rac-6-((1S,4S,7S)-7-amino-2-azabicyclo[2.2.1]heptan-2-yl)-3-(4-chloro-2-ethyl-2H-indazol-5-yl)-5-methyl-1,5-dihydro-4H-pyrazolo[3,4-d]pyrimidin-4-one, rac-6-((1S,4S,7S)-7-amino-2-azabicyclo[2.2.1]heptan-2-yl)-3-(3,4-dichloro-2-methyl-2H-indazol-5-yl)-5-methyl-1,5-dihydro-4H-pyrazolo[3,4-d]pyrimidin-4-one, 6-((1R,2R,4S)-2-amino-7-azabicyclo[2.2.1]heptan-7-yl)-3-(3,4-dichloro-2-ethyl-2H-indazol-5-yl)-5-methyl-1,5-dihydro-4H-pyrazolo[3,4-d]pyrimidin-4-one, 3-(3,4-dichloro-2-ethyl-2H-indazol-5-yl)-5-methyl-6-((1R,2R,4S)-2-(methylamino)-7-azabicyclo[2.2.1]heptan-7-yl)-1,5-dihydro-4H-pyrazolo[3,4-d]pyrimidin-4-one, 2-((1R,2S,3R,5S)-3-amino-2-fluoro-8-azabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one, 2-((1S,2R,3S,5R)-3-amino-2-fluoro-8-azabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one, 2-((1R,2R,3R,5S)-3-amino-2-fluoro-8-azabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one, 2-((1S,2S,3S,5R)-3-amino-2-fluoro-8-azabicyclo[3.2.1]octan-8-yl)-5-(4-chloro-2-methyl-2H-indazol-5-yl)-3-methyl-3,7-dihydro-4H-pyrrolo[2,3-d]pyrimidin-4-one, rac-2-((1S,4S,7S)-7-amino-2-azabicyclo[2.2.1]heptan-2-yl)-5-(4-chloro-2-ethyl-2H-indazol-5-yl)-3-methyl-3,7-dihydro-4H-pyrrolo[2,3-d]pyrimidin-4-one, rac-((1S,4S,7S)-7-amino-2-azabicyclo[2.2.1]heptan-2-yl)-3-(7-chlorobenzo[d]thiazol-6-yl)-5-methyl-1,5-dihydro-4H-pyrazolo[3,4-d]pyrimidin-4-one, rac-5-(4-chloro-2-methyl-2H-indazol-5-yl)-3-methyl-2-((1S,4S,7S)-7-(methylamino)-2-azabicyclo[2.2.1]heptan-2-yl)-3,7-dihydro-4H-pyrrolo[2,3-d]pyrimidin-4-one, endo-6-[3-amino-8-azabicyclo[3.2.1]octan-8-yl]-3-(4-chloro-2-methyl-2H-indazol-5-yl)-5-methyl-1H,4H,5H-pyrazolo[3,4-d]pyrimidin-4-one, 3-(4-chloro-2-methyl-2H-indazol-5-yl)-6-{3,8-diazabicyclo[3.2.1]octan-8-yl}-5-methyl-1H,4H,5H-pyrazolo[3,4-d]pyrimidin-4-one, 6-[(1R,3S)-1-amino-3-hydroxy-8-azaspiro[4.5]decan-8-yl]-3-(4-chloro-2-methyl-2H-indazol-5-yl)-5-methyl-1H,4H,5H-pyrazolo[3,4-d]pyrimidin-4-one, 6-[(4S)-4-amino-2-oxa-8-azaspiro[4.5]decan-8-yl]-3-(4-chloro-2-methyl-2H-indazol-5-yl)-5-methyl-1H,4H,5H-pyrazolo[3,4-d]pyrimidin-4-one, exo-6-[3-amino-8-azabicyclo[3.2.1]octan-8-yl]-3-(4-chloro-2-methyl-2H-indazol-5-yl)-5-methyl-1H,4H,5H-pyrazolo[3,4-d]pyrimidin-4-one, 3-(4-chloro-2-methyl-2H-indazol-5-yl)-6-{2,7-diazaspiro[3.5]nonan-7-yl}-5-methyl-1H,4H,5H-pyrazolo[3,4-d]pyrimidin-4-one, 6-[(1R)-1-amino-8-azaspiro[4.5]decan-8-yl]-3-(4-chloro-2-methyl-2H-indazol-5-yl)-5-methyl-1H,4H,5H-pyrazolo[3,4-d]pyrimidin-4-one, 6-[(3S,4S)-4-amino-3-methyl-2-oxa-8-azaspiro[4.5]decan-8-yl]-3-(4-chloro-2-methyl-2H-indazol-5-yl)-5-methyl-1H,4H,5H-pyrazolo[3,4-d]pyrimidin-4-one, 6-[(1R,3R)-1-amino-3-fluoro-8-azaspiro[4.5]decan-8-yl]-3-(4-chloro-2-methyl-2H-indazol-5-yl)-5-methyl-1H,4H,5H-pyrazolo[3,4-d]pyrimidin-4-one, 3-(4-chloro-2-methyl-2H-indazol-5-yl)-5-methyl-6-{3-oxa-7,9-diazabicyclo[3.3.1]nonan-7-yl}-1H,4H,5H-pyrazolo[3,4-d]pyrimidin-4-one, 3-(3,4-dichloro-2-methyl-2H-indazol-5-yl)-5-methyl-6-{3-oxa-7,9-diazabicyclo[3.3.1]nonan-7-yl}-1H,4H,5H-pyrazolo[3,4-d]pyrimidin-4-one, 6-[(3S,4S)-4-amino-3-methyl-2-oxa-8-azaspiro[4.5]decan-8-yl]-3-(3,4-dichloro-2-methyl-2H-indazol-5-yl)-5-methyl-1H,4H,5H-pyrazolo[3,4-d]pyrimidin-4-one, 6-[(3S,4S)-4-amino-3-methyl-2-oxa-8-azaspiro[4.5]decan-8-yl]-3-(4-chloro-2-ethyl-2H-indazol-5-yl)-5-methyl-1H,4H,5H-pyrazolo[3,4-d]pyrimidin-4-one, 6-[(1S,2R,3S,5R)-3-amino-2-fluoro-8-azabicyclo[3.2.1]octan-8-yl]-3-(4-chloro-2-methyl-2H-indazol-5-yl)-5-methyl-1H,4H,5H-pyrazolo[3,4-d]pyrimidin-4-one, 2-[(3S,4S)-4-amino-3-methyl-2-oxa-8-azaspiro[4.5]decan-8-yl]-5-(4-chloro-2-ethyl-2H-indazol-5-yl)-3-methyl-3H,4H,7H-pyrrolo[2,3-d]pyrimidin-4-one, 5-(4-chloro-2-ethyl-2H-indazol-5-yl)-2-(1,4-diazepan-1-yl)-3-methyl-3H,4H,7H-pyrrolo[2,3-d]pyrimidin-4-one, rac-2-[(1R,2R,5R)-2-amino-8-azabicyclo[3.2.1]octan-8-yl]-5-(4-chloro-2-methyl-2H-indazol-5-yl)-3-methyl-3H,4H,7H-pyrrolo[2,3-d]pyrimidin-4-one, rac-5-(4-chloro-2-methyl-2H-indazol-5-yl)-2-[(1R,6S)-3,9-diazabicyclo[4.2.1]nonan-9-yl]-3-methyl-3H,4H,7H-pyrrolo[2,3-d]pyrimidin-4-one, rac-2-(4-aminoazepan-1-yl)-5-(4-chloro-2-ethyl-2H-indazol-5-yl)-3-methyl-3H,4H,7H-pyrrolo[2,3-d]pyrimidin-4-one, rel-2-((1R,4R,7R)-7-amino-2-azabicyclo[2.2.1]heptan-2-yl)-5-(4-chloro-2-ethyl-2H-indazol-5-yl)-3-methyl-3,7-dihydro-4H-pyrrolo[2,3-d]pyrimidin-4-one, rel-2-((1S,4S,7S)-7-amino-2-azabicyclo[2.2.1]heptan-2-yl)-5-(4-chloro-2-ethyl-2H-indazol-5-yl)-3-methyl-3,7-dihydro-4H-pyrrolo[2,3-d]pyrimidin-4-one, rel-2-((1R,4R,7R)-7-amino-2-azabicyclo[2.2.1]heptan-2-yl)-5-(4-chloro-2-methyl-2H-indazol-5-yl)-3-methyl-3,7-dihydro-4H-pyrrolo[2,3-d]pyrimidin-4-one, rel-2-((1S,4S,7S)-7-Amino-2-azabicyclo[2.2.1]heptan-2-yl)-5-(4-chloro-2-methyl-2H-indazol-5-yl)-3-methyl-3,7-dihydro-4H-pyrrolo[2,3-d]pyrimidin-4-one, 5-(2-((1R,2R,4S)-2-amino-7-azabicyclo[2.2.1]heptan-7-yl)-3-methyl-4-oxo-4,7-dihydro-3H-pyrrolo[2,3-d]pyrimidin-5-yl)-4-chloro-2-ethyl-2H-indazole-3-carbonitrile, 6-(endo-3-amino-8-azabicyclo[3.2.1]octan-8-yl)-3-(3,4-dichloro-2-methyl-2H-indazol-5-yl)-5-methyl-1,5-dihydro-4H-pyrazolo[3,4-d]pyrimidin-4-one, 6-(endo-3-amino-3-methyl-8-azabicyclo[3.2.1]octan-8-yl)-3-(3,4-dichloro-2-methyl-2H-indazol-5-yl)-5-methyl-1,5-dihydro-4H-pyrazolo[3,4-d]pyrimidin-4-one, 6-((3R,4S)-4-amino-3-fluoropiperidin-1-yl)-3-(3,4-dichloro-2-methyl-2H-indazol-5-yl)-5-methyl-1,5-dihydro-4H-pyrazolo[3,4-d]pyrimidin-4-one, 2-((1R,2S,3S,5S)-3-amino-2-fluoro-8-azabicyclo[3.2.1]octan-8-yl)-5-(3,4-dichloro-2-methyl-2H-indazol-5-yl)-3-methyl-3,7-dihydro-4H-pyrrolo[2,3-d]pyrimidin-4-one, 2-(rac-(1R,2S,4S)-2-amino-7-azabicyclo[2.2.1]heptan-7-yl)-5-(4-chloro-2-methyl-2H-indazol-5-yl)-3-methyl-3,7-dihydro-4H-pyrrolo[2,3-d]pyrimidin-4-one, 5-(4-chloro-2-methyl-2H-indazol-5-yl)-3-methyl-2-((1S,2S,4R)-2-(methylamino)-7-azabicyclo[2.2.1]heptan-7-yl)-3,7-dihydro-4H-pyrrolo[2,3-d]pyrimidin-4-one, 2-((1R,2S,4S)-2-amino-7-azabicyclo[2.2.1]heptan-7-yl)-5-(3,4-dichloro-2-methyl-2H-indazol-5-yl)-3-methyl-3,7-dihydro-4H-pyrrolo[2,3-d]pyrimidin-4-one, 2-((1R,2R,4S)-2-amino-7-azabicyclo[2.2.1]heptan-7-yl)-5-(3-chloro-2-methyl-2H-indazol-5-yl)-3-methyl-3,7-dihydro-4H-pyrrolo[2,3-d]pyrimidin-4-one, 2-((1R,2S,4S)-2-amino-7-azabicyclo[2.2.1]heptan-7-yl)-3-methyl-5-(3,4,7-trichloro-2-methyl-2H-indazol-5-yl)-3,7-dihydro-4H-pyrrolo[2,3-d]pyrimidin-4-one, 2-((1R,2R,4S)-2-amino-7-azabicyclo[2.2.1]heptan-7-yl)-5-(5-chloro-3-methoxyquinoxalin-6-yl)-3-methyl-3,7-dihydro-4H-pyrrolo[2,3-d]pyrimidin-4-one, 2-((1R,2R,4S)-2-amino-7-azabicyclo[2.2.1]heptan-7-yl)-5-(5-chloro-3-(dimethylamino)quinoxalin-6-yl)-3-methyl-3,7-dihydro-4H-pyrrolo[2,3-d]pyrimidin-4-one, 6-((1R,4R,7R)-7-amino-2-azabicyclo[2.2.1]heptan-2-yl)-3-(3,4-dichloro-2-methyl-2H-indazol-5-yl)-5-methyl-1,5-dihydro-4H-pyrazolo[3,4-d]pyrimidin-4-one, 2-((1R,4R,7R)-7-amino-2-azabicyclo[2.2.1]heptan-2-yl)-5-(3,4-dichloro-2-methyl-2H-indazol-5-yl)-3-methyl-3,7-dihydro-4H-pyrrolo[2,3-d]pyrimidin-4-one, rac-2-((1R,2R,4S)-2-amino-2-methyl-7-azabicyclo[2.2.1]heptan-7-yl)-5-(3,4-dichloro-2-methyl-2H-indazol-5-yl)-3-methyl-3,7-dihydro-4H-pyrrolo[2,3-d]pyrimidin-4-one, 2-((1R,4R,7R)-7-amino-2-azabicyclo[2.2.1]heptan-2-yl)-5-(3-chloro-4-fluoro-2-methyl-2H-indazol-5-yl)-3-methyl-3,7-dihydro-4H-pyrrolo[2,3-d]pyrimidin-4-one, rac-6-((1R,2R,4S)-2-amino-2-methyl-7-azabicyclo[2.2.1]heptan-7-yl)-3-(3,4-dichloro-2-methyl-2H-indazol-5-yl)-5-methyl-1,5-dihydro-4H-pyrazolo[3,4-d]pyrimidin-4-one, 2-(endo-3-amino-8-azabicyclo[3.2.1]octan-8-yl)-5-(5-chloroquinoxalin-6-yl)-3-methyl-3,7-dihydro-4H-pyrrolo[2,3-d]pyrimidin-4-one, 3-(3,4-dichloro-2-methyl-2H-indazol-5-yl)-6-((1R,2R,4S)-2-(ethylamino)-7-azabicyclo[2.2.1]heptan-7-yl)-5-methyl-1,5-dihydro-4H-pyrazolo[3,4-d]pyrimidin-4-one, 2-((1R,2R,4S)-2-amino-7-azabicyclo[2.2.1]heptan-7-yl)-5-(4-chloro-2-(2-methoxyethyl)-2H-indazol-5-yl)-3-methyl-3,7-dihydro-4H-pyrrolo[2,3-d]pyrimidin-4-one, 3-(3,4-dichloro-2-methyl-2H-indazol-5-yl)-6-((1R,2R,4S)-2-(isopropylamino)-7-azabicyclo[2.2.1]heptan-7-yl)-5-methyl-1,5-dihydro-4H-pyrazolo[3,4-d]pyrimidin-4-one, 2-[(4S)-4-amino-2-oxa-8-azaspiro[4.5]decan-8-yl]-5-(2-ethyl-2H-indazol-5-yl)-3-methyl-3H,4H,7H-pyrrolo[2,3-d]pyrimidin-4-one, 2-[(4S)-4-amino-2-oxa-8-azaspiro[4.5]decan-8-yl]-5-(2-ethyl-4-fluoro-2H-indazol-5-yl)-3-methyl-3H,4H,7H-pyrrolo[2,3-d]pyrimidin-4-one, 2-[(4S)-4-amino-2-oxa-8-azaspiro[4.5]decan-8-yl]-5-(7-chloro-2-ethyl-2H-indazol-6-yl)-3-methyl-3H,4H,7H-pyrrolo[2,3-d]pyrimidin-4-one, 2-[(4S)-4-amino-2-oxa-8-azaspiro[4.5]decan-8-yl]-5-(2-ethyl-2H-indazol-6-yl)-3-methyl-3H,4H,7H-pyrrolo[2,3-d]pyrimidin-4-one, 2-[(4S)-4-amino-2-oxa-8-azaspiro[4.5]decan-8-yl]-5-(2-ethyl-7-fluoro-2H-indazol-6-yl)-3-methyl-3H,4H,7H-pyrrolo[2,3-d]pyrimidin-4-one, 2-[(endo)-3-amino-3-(difluoromethyl)-8-azabicyclo[3.2.1]octan-8-yl]-5-(4-chloro-2-methyl-2H-indazol-5-yl)-3-methyl-3H,4H,7H-pyrrolo[2,3-d]pyrimidin-4-one, 2-[(4S)-4-amino-2-oxa-8-azaspiro[4.5]decan-8-yl]-5-(2-ethyl-7-fluoro-2H-indazol-5-yl)-3-methyl-3H,4H,7H-pyrrolo[2,3-d]pyrimidin-4-one, 2-[(3R,4S)-4-amino-3-fluoropiperidin-1-yl]-5-(7-chloro-1,3-benzothiazol-6-yl)-3-methyl-3H,4H,7H-pyrrolo[2,3-d]pyrimidin-4-one, 5-(4-chloro-2-methyl-2H-indazol-5-yl)-2-[(1S,6R)-3,9-diazabicyclo[4.2.1]nonan-9-yl]-3-methyl-3H,4H,7H-pyrrolo[2,3-d]pyrimidin-4-one, 5-(4-chloro-2-methyl-2H-indazol-5-yl)-2-[(1R,6S)-3,9-diazabicyclo[4.2.1]nonan-9-yl]-3-methyl-3H,4H,7H-pyrrolo[2,3-d]pyrimidin-4-one, 5-(4-chloro-2-ethyl-2H-indazol-5-yl)-2-{(1R,5R)-3,6-diazabicyclo[3.2.1]octan-3-yl}-3-methyl-3H,4H,7H-pyrrolo[2,3-d]pyrimidin-4-one, 5-(4-chloro-2-ethyl-2H-indazol-5-yl)-2-{(1S,5S)-3,6-diazabicyclo[3.2.1]octan-3-yl}-3-methyl-3H,4H,7H-pyrrolo[2,3-d]pyrimidin-4-one, 5-(4-chloro-2-ethyl-2H-indazol-5-yl)-2-[(1S,5R)-3,6-diazabicyclo[3.2.1]octan-6-yl]-3-methyl-3H,4H,7H-pyrrolo[2,3-d]pyrimidin-4-one, 5-(4-chloro-2-ethyl-2H-indazol-5-yl)-2-[(1R,5S)-3,6-diazabicyclo[3.2.1]octan-6-yl]-3-methyl-3H,4H,7H-pyrrolo[2,3-d]pyrimidin-4-one, 2-[(3S,4S)-4-amino-3-methyl-2-oxa-8-azaspiro[4.5]decan-8-yl]-5-(4-chloro-7-fluoro-2-methyl-2H-indazol-5-yl)-3-methyl-3H,4H,7H-pyrrolo[2,3-d]pyrimidin-4-one, 2-[(endo)-2-amino-2-methyl-7-azabicyclo[2.2.1]heptan-7-yl]-5-(4-chloro-2-methyl-2H-indazol-5-yl)-3-methyl-3H,4H,7H-pyrrolo[2,3-d]pyrimidin-4-one, rac-5-(4-chloro-2-ethyl-2H-indazol-5-yl)-2-{2,6-diazaspiro[3.4]octan-6-yl}-3-methyl-3H,4H,7H-pyrrolo[2,3-d]pyrimidin-4-one, 2-[(1R,2S,3S,5S)-3-amino-2-fluoro-8-azabicyclo[3.2.1]octan-8-yl]-5-(4-chloro-2-ethyl-2H-indazol-5-yl)-3-methyl-3H,4H,7H-pyrrolo[2,3-d]pyrimidin-4-one, 2-[(1R,2R,4S)-2-amino-7-azabicyclo[2.2.1]heptan-7-yl]-5-[8-chloro-2-(dimethylamino)quinolin-7-yl]-3-methyl-3H,4H,7H-pyrrolo[2,3-d]pyrimidin-4-one, and 2-[(1R,2R,4S)-2-amino-7-azabicyclo[2.2.1]heptan-7-yl]-5-[8-chloro-2-(methylamino)quinolin-7-yl]-3-methyl-3H,4H,7H-pyrrolo[2,3-d]pyrimidin-4-one.

11. A pharmaceutical composition comprising a compound according to claim 1, or a tautomer or a solvate or a pharmaceutically acceptable salt thereof, and a pharmaceutically acceptable carrier.

12. A method for treating a disease or condition mediated by SHP2, comprising administering to a patient in need thereof the pharmaceutical composition according to claim 11.

13. A method of claim 12, wherein the disease or condition mediated by SHP2 is cancer.

14. A method of claim 12, wherein the disease or condition mediated by SHP2 is head and neck cancers, esophagus cancer, gastric cancer, colon cancer, rectum cancer, liver cancer, gallbladder cancer, cholangiocarcinoma, biliary tract cancer, pancreatic cancer, lung cancer, breast cancer, ovarian cancer, cervical cancer, endometrial cancer, renal cancer, bladder cancer, prostate cancer, testicular tumor, osteosarcoma, soft-tissue sarcoma, leukemia, myelodysplastic syndrome, chronic myeloproliferative disease, malignant lymphoma, multiple myeloma, skin cancer, brain tumor, or mesothelioma.

15. A method for treating a disease or condition mediated by SHP2, comprising administering to a patient in need thereof a compound according to claim 1 or a tautomer or a solvate or a pharmaceutically acceptable salt thereof.

16. A method of claim 15, wherein the disease or condition mediated by SHP2 is cancer.

17. A method of claim 15, wherein the disease or condition mediated by SHP2 is head and neck cancers, esophagus cancer, gastric cancer, colon cancer, rectum cancer, liver cancer, gallbladder cancer, cholangiocarcinoma, biliary tract cancer, pancreatic cancer, lung cancer, breast cancer, ovarian cancer, cervical cancer, endometrial cancer, renal cancer, bladder cancer, prostate cancer, testicular tumor, osteosarcoma, soft-tissue sarcoma, leukemia, myelodysplastic syndrome, chronic myeloproliferative disease, malignant lymphoma, multiple myeloma, skin cancer, brain tumor, or mesothelioma.

18. A method for inhibiting activity of SHP2 comprising contacting the SHP2 with a compound of formula (I) according to claim 1 or a tautomer or a solvate or a pharmaceutically acceptable salt thereof.

19. A method for inhibiting activity of SHP2 comprising contacting the SHP2 with a pharmaceutical composition according to claim 11.

* * * * *